US007065452B1

(12) United States Patent
Armistead et al.

(10) Patent No.: US 7,065,452 B1
(45) Date of Patent: Jun. 20, 2006

(54) MOLECULES COMPRISING A CALCINEURIN-LIKE BINDING POCKET AND ENCODED DATA STORAGE MEDIUM CAPABLE OF GRAPHICALLY DISPLAYING THEM

(75) Inventors: David M. Armistead, Maynard, MA (US); Matthew James Fitzgibbon, Millis, MA (US); Mark Andrew Fleming, Cambridge, MA (US); James P. Griffith, Weston, MA (US); Eunice E. Kim, Framingham, MA (US); Joseph L. Kim, Natick, MA (US); Michael D. Sintchak, Winchester, MA (US); John Allan Thomson, Belmont, MA (US); Keith P. Wilson, Hopkinton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/431,469

(22) Filed: Nov. 1, 1999

Related U.S. Application Data

(62) Division of application No. 08/512,815, filed on Aug. 9, 1995, now Pat. No. 5,978,740.

(51) Int. Cl.
  G06G 7/48 (2006.01)
  G06N 7/06 (2006.01)
(52) U.S. Cl. ............................................. 702/27; 703/2
(58) Field of Classification Search ................. 702/27, 702/153; 435/21, 194, 7.1; 345/419; 703/2, 703/11
See application file for complete search history.

(56) References Cited

U.S. PATENT DOCUMENTS

| 4,833,233 A | 5/1989 | Carter | 530/363 |
| 5,025,388 A | 6/1991 | Cramer, III | 364/496 |
| 5,331,573 A | 7/1994 | Balaji | 364/496 |
| 5,353,236 A | 10/1994 | Subbiah | 364/499 |
| 5,705,335 A * | 1/1998 | Hendry | |

FOREIGN PATENT DOCUMENTS

WO    WO94/25860    11/1994

OTHER PUBLICATIONS

Griffith et al., "X-ray Structure of Calcineurin Inhibited by the Immunophilin-Immunosuppressant FKBP12-FK506 Complex", Cell Press vol. 82 Aug. 11, 1995 pp. 507-522.*
Kissinger et al., "Crystal structure of human calcineurin and the human FKBP12-FK506-calcineurin complex", NATURE vol. 378, Dec. 7, 1995, pp. 641-644.*
Barford et al., "Co-crystallization of the Catalytic Subunit of the Serin/Threonine Specific Protein Phosphatase 1 from Human in Complex eit Microcystin LR", J. Mol. Biol. (1994) vol. 235, pp. 763-766.*
Cheng et al., "Biochemistry", vol. 33 No. 14, Apr. 12, 1994, pp. 4093-4100.*
Anglister et al., "1H, 13C, 15N Nuclear Magnetic Resonance Backbone Assignments and Secondary Structure of Human Calcineurin B", Biochemistry 1994, vol. 33 pp. 3540-3547.*
Milan et al., "The Latch Region of Calcineurin B Is Involved in Both Immunosuppressant-Immunophilin Complex docking and Phosphatase Activation", Cell Press Nov. 4, 1994, pp. 437-447.*
Andrus, M.B. and Schreiber, S.L., "Structure-Based Design of an Acyclic Ligand That Bridges FKBP12 and Calcineurin" *J. Am. Chem. Soc.*, 115, pp. 10420-10421 (1993).
Barford, D. and Keller, J.C., "Co-crystallization of the Catalytic Subunit of the Serine/Threonine Specific Protein Phosphatase 1 from Human in Complex with Microcystin LR", *J. Mol. Biol.*, 235, pp. 763-766 (1994).
Bierer, B.E. et al., "Cyclosporin A and FK506: Molecular Mechanisms of Immunosuppression and Probes for Transplantation Biology" *Curr. Opinion in Immunology*, 5, pp. 763-773 (1993).
Caffrey, M.V. et al. "Synthesis And Evaluation Of Dual Domain Macrocyclic FKBP12 Ligands" *Bioorg. Med. Chem. Lett.*, 4, pp. 2507-2510 (Nov., 1994).
Campbell, I.D. and Dwek, R.A., "Diffraction" in *Biological Spectroscopy*, The Benjamin/Cummings Publishing Company, Menlo Park, CA, pp. 299-326 (1984).
Griffith, J.P. et al., "X-Ray Structure of Calcineurin Inhibited by the Immunophilin-Immunosuppressant FKBP12-FK506 Complex", *Cell*, 82, pp. 507-522 (1995).

(Continued)

*Primary Examiner*—Marjorie A. Moran
(74) *Attorney, Agent, or Firm*—James F. Haley, Jr.; Fish & Neave IP Group Ropes & Gray LLP

(57) ABSTRACT

The present invention relates to crystallized molecules and molecular complexes which comprise the active site binding pocket or the FKBP12/FK506 binding pocket of calcineurin or close structural homologues to either binding pocket. This invention also relates to a data storage material encoded with the corresponding structure coordinates of those crystallized molecules or molecular complexes. Such data storage material is capable of displaying such molecules and molecular complexes as a graphical three-dimensional representation on a computer screen. In addition, this invention relates to methods of using the structure coordinates of those molecules or molecular complexes to solve the structure of homologous proteins. This invention also relates to methods of using the structure coordinates to screen and design compounds that bind to calcineurin or homologues thereof.

8 Claims, 109 Drawing Sheets

OTHER PUBLICATIONS

Guerini, D. and Klee, C.B., "Cloning of Human Calcineurin A: Evidence for Two Isozymes and Identification of a Polyproline Structural Domain", *Proc. Natl. Acad. Sci. USA*, 86, pp. 9183-9187 (1989).

Holt, D.A. et al., "Design, Synthesis, and Kinetic Evaluation of High-Affinity FKBP Ligands and the X-ray Crystal Structures of Their Complexes with FKBP12" *J. Am. Chem. Soc.*, 115, pp. 9925-9938 (1993).

Hubbard, M.J. and Klee, C.B., "Functional Domain Structure of Calcineurin A: Mapping by Limited Proteolysis", *Biochemistry*, 28, pp. 1868-1874 (1989).

Kajihara, A. et al., "Protein Modelling Using a Chimera Reference Protein Derived From Exons" *Protein Eng.*, 6, pp. 615-620 (1993).

Kissinger, C.R. et al., "Crystal Structures of Human Calcineurin and the Human FKBP12-FK506-Calcineurin Complex", *Nature*, 378, pp. 641-644 (1995).

Kunz, J. and Hall, M.N. "Cyclosporin A, FK506 and Rapamycin: More Than Just Immunosuppression" *TIBS*, 18, pp. 334-338 (1993).

Sharma, R.K. and Wang, J.H., "Calmodulin and $Ca^{2+}$-Dependent Phosphorylation and Dephosphorylation of 63-kDa Subunit-Containing Bovine Brain Calmodulin-Stimulated Cyclic Nucleotide Phosphodiesterase Isozyme" *J. Biol. Chem.*, 261, pp. 1322-1328 (1986).

Sträter, N. et al., "Crystal Structure of a Purple Acid Phosphatase Containing a Dinuclear Fe(III)-Zn(II) Active Site", *Science*, 268, pp. 1489-1492 (1995).

Uhlin, U. et al., "Crystallization and Crystallographic Investigations of Ribonucleotide Reductase Protein R1 from *Escherichia coli*" *FEBS Lett.*, 336, pp. 148-152 (1993).

Villafranca, J.E. et al., "Protein Serine/Threonine Phosphatases", *Current Opinion in Biotech.*, 7, pp. 387-402 (1996).

Wilson, K.P. et al., "Comparative X-ray Strucutres of the Major Binding Protein for the Immunosuppressant FK506 (*Tacrolimus*) in Unliganded Form and in Complex with FK506 and Rapamycin" *Acta Cryst.*, D51, pp. 511-521 (Ju., 1995).

Balbes, L.M., et al., "A Perspective of Modern Methods in Computer-Aided Drug Design," in "*Reviews in Computational Chemistry*," K.B. Lipkowitz and D.B. Boyd, Eds., VCH Publishers, New York, 5: 337-379 (1994).

Bartlett, P.A., et al., "CAVEAT: A Program to Facilitate the Structure-Derived Design of Biologically Active Molecules," in "*Molecular Recognition in Chemical and Biological Problems*," S.M. Roberts, Ed., Royal Society of Chemistry, Special Publication No. 78: 182-196 (1989).

Böhm, H.-J., "The Computer Program LUDI: A New Method for the De Novo Design of Enzyme Inhibitors," *J. Comp. Aid. Molec. Design*, 6: 61-78 (1992).

Cohen, N.C., et al., "Molecular Modeling Software and Methods for Medicinal Chemistry," *J. Med. Chem.*, 33: 883-894 (1990).

Eisen, M.B., et al., "HOOK: A Program for Finding Novel Molecular Architectures that Satisfy the Chemical and Steric Requirements of a Macromolecule Binding Site," *Proteins Struct. Funct. Genet.*, 19: 199-221 (1994).

Gillet, V., et al., "SPROUT: A Program for Structure Generation," *J. Comp. Aid. Molec. Design*, 7: 127-153 (1993).

Goodford, P.J., "A Computational Procedure for Determining Energetically Favorable Binding Sites on Biologically Important Macromolecules," *J. Med. Chem.*, 28: 849-857 (1985).

Goodsell, D.S., and Olson, A.J., "Automated Docking of Substrates to Proteins by Simulated Annealing," *Proteins Struct. Funct. Genet.*, 8: 195-202 (1990).

Guida, W.C., "Software for Structure-Based Drug Design," *Curr. Opin. Struct. Biology*, 4: 777-781 (1994).

Kuntz, I.D., et al., "A Geometric Approach to Macromolecule-Ligand Interactions," *J. Mol. Biol.*, 161: 269-288 (1982).

Lauri, G. and Bartlett, P.A., "CAVEAT: A Program to Facilitate the Design of Organic Molecules," *J. Comp. Aid. Molec. Design*, 8: 51-66 (1994).

Martin, Y.C., "3D Database Searching in Drug Design," *J. Med. Chem.*, 35: 2145-2154 (1992).

Miranker, A., and Karplus, M., "Functionality Maps of Binding Sites: A Multiple Copy Simultaneous Search Method," *Proteins Struct. Funct. Genet.*, 11: 29-34 (1991).

Meng, E.C., et al., "Automated Docking with Grid-Based Energy Evaluation," *Journal of Computational Chemistry*, 13: 505-524 (1992).

Navia, M.A. and Murcho, M.A., "Use of Structural Information in Drug Design," *Current Opinion in Structural Biology*, 2: 202-210 (1992).

Nishibata, Y., and Itai, A., "Automatic Creation of Drug Candidate Structures Based on Receptor Structure. Starting Point for Artificial Lead Generation." *Tetrahedron*, 47: 8985-8990 (1991).

* cited by examiner

FIG. 1: A-1

FKBP12 COORDINATES

| | | Atom Type | Residue | # | X | Y | Z | OCC | B |
|---|---|---|---|---|---|---|---|---|---|
| ATOM | 1 | C | GLY | 1 | 42.069 | 47.090 | 53.319 | 1.00 | 41.82 |
| ATOM | 2 | O | GLY | 1 | 42.192 | 48.313 | 53.390 | 1.00 | 43.35 |
| ATOM | 3 | HT1 | GLY | 1 | 41.201 | 48.096 | 55.578 | 1.00 | 0.00 |
| ATOM | 4 | HT2 | GLY | 1 | 40.002 | 46.972 | 56.021 | 1.00 | 0.00 |
| ATOM | 5 | N | GLY | 1 | 40.527 | 47.383 | 55.225 | 1.00 | 42.06 |
| ATOM | 6 | HT3 | GLY | 1 | 39.884 | 47.885 | 54.576 | 1.00 | 0.00 |
| ATOM | 7 | CA | GLY | 1 | 41.301 | 46.401 | 54.465 | 1.00 | 41.76 |
| ATOM | 8 | N | VAL | 2 | 42.600 | 46.396 | 52.305 | 1.00 | 38.51 |
| ATOM | 9 | H | VAL | 2 | 42.552 | 45.423 | 52.352 | 1.00 | 0.00 |
| ATOM | 10 | CA | VAL | 2 | 43.257 | 47.052 | 51.168 | 1.00 | 36.15 |
| ATOM | 11 | CB | VAL | 2 | 44.072 | 45.930 | 50.446 | 1.00 | 35.20 |
| ATOM | 12 | CG1 | VAL | 2 | 43.160 | 44.784 | 50.162 | 1.00 | 36.74 |
| ATOM | 13 | CG2 | VAL | 2 | 44.661 | 46.365 | 49.109 | 1.00 | 33.68 |
| ATOM | 14 | C | VAL | 2 | 42.327 | 47.815 | 50.219 | 1.00 | 36.38 |
| ATOM | 15 | O | VAL | 2 | 41.121 | 47.775 | 50.382 | 1.00 | 39.17 |
| ATOM | 16 | N | GLN | 3 | 42.780 | 48.580 | 49.247 | 1.00 | 35.98 |
| ATOM | 17 | H | GLN | 3 | 43.706 | 48.879 | 49.318 | 1.00 | 0.00 |
| ATOM | 18 | CA | GLN | 3 | 41.905 | 49.201 | 48.276 | 1.00 | 34.49 |
| ATOM | 19 | CB | GLN | 3 | 41.521 | 50.543 | 48.810 | 1.00 | 33.04 |
| ATOM | 20 | CG | GLN | 3 | 40.565 | 51.283 | 47.925 | 1.00 | 36.48 |
| ATOM | 21 | CD | GLN | 3 | 40.481 | 52.766 | 48.248 | 1.00 | 37.58 |
| ATOM | 22 | OE1 | GLN | 3 | 41.243 | 53.348 | 49.007 | 1.00 | 39.56 |
| ATOM | 23 | NE2 | GLN | 3 | 39.588 | 53.526 | 47.665 | 1.00 | 38.51 |
| ATOM | 24 | HE21 | GLN | 3 | 39.638 | 54.450 | 47.971 | 1.00 | 0.00 |
| ATOM | 25 | HE22 | GLN | 3 | 38.980 | 53.155 | 47.002 | 1.00 | 0.00 |
| ATOM | 26 | C | GLN | 3 | 42.622 | 49.341 | 46.933 | 1.00 | 35.68 |
| ATOM | 27 | O | GLN | 3 | 43.488 | 50.208 | 46.802 | 1.00 | 36.78 |
| ATOM | 28 | N | VAL | 4 | 42.383 | 48.542 | 45.895 | 1.00 | 35.37 |
| ATOM | 29 | H | VAL | 4 | 41.698 | 47.845 | 45.965 | 1.00 | 0.00 |
| ATOM | 30 | CA | VAL | 4 | 43.090 | 48.778 | 44.637 | 1.00 | 36.52 |
| ATOM | 31 | CB | VAL | 4 | 43.088 | 47.481 | 43.779 | 1.00 | 37.20 |
| ATOM | 32 | CG1 | VAL | 4 | 43.757 | 46.372 | 44.574 | 1.00 | 37.93 |
| ATOM | 33 | CG2 | VAL | 4 | 41.679 | 47.004 | 43.446 | 1.00 | 38.64 |
| ATOM | 34 | C | VAL | 4 | 42.561 | 49.958 | 43.799 | 1.00 | 37.11 |
| ATOM | 35 | O | VAL | 4 | 41.453 | 49.956 | 43.272 | 1.00 | 37.77 |
| ATOM | 36 | N | GLU | 5 | 43.247 | 51.096 | 43.769 | 1.00 | 38.01 |
| ATOM | 37 | H | GLU | 5 | 43.922 | 51.237 | 44.467 | 1.00 | 0.00 |
| ATOM | 38 | CA | GLU | 5 | 42.900 | 52.179 | 42.850 | 1.00 | 38.19 |
| ATOM | 39 | CB | GLU | 5 | 42.971 | 53.497 | 43.620 | 1.00 | 41.44 |
| ATOM | 40 | CG | GLU | 5 | 41.899 | 53.624 | 44.721 | 1.00 | 47.00 |
| ATOM | 41 | CD | GLU | 5 | 42.112 | 54.827 | 45.661 | 1.00 | 52.99 |
| ATOM | 42 | OE1 | GLU | 5 | 42.618 | 54.659 | 46.786 | 1.00 | 55.30 |
| ATOM | 43 | OE2 | GLU | 5 | 41.773 | 55.949 | 45.274 | 1.00 | 54.87 |
| ATOM | 44 | C | GLU | 5 | 43.892 | 52.149 | 41.668 | 1.00 | 37.89 |
| ATOM | 45 | O | GLU | 5 | 45.087 | 52.367 | 41.866 | 1.00 | 38.08 |
| ATOM | 46 | N | THR | 6 | 43.586 | 51.840 | 40.396 | 1.00 | 37.45 |
| ATOM | 47 | H | THR | 6 | 42.645 | 51.760 | 40.135 | 1.00 | 0.00 |
| ATOM | 48 | CA | THR | 6 | 44.662 | 51.769 | 39.388 | 1.00 | 36.36 |
| ATOM | 49 | CB | THR | 6 | 44.306 | 51.055 | 38.091 | 1.00 | 35.22 |
| ATOM | 50 | OG1 | THR | 6 | 43.348 | 51.821 | 37.361 | 1.00 | 34.96 |
| ATOM | 51 | HG1 | THR | 6 | 43.544 | 52.769 | 37.301 | 1.00 | 0.00 |
| ATOM | 52 | CG2 | THR | 6 | 43.783 | 49.683 | 38.407 | 1.00 | 34.83 |
| ATOM | 53 | C | THR | 6 | 45.242 | 53.070 | 38.883 | 1.00 | 36.03 |
| ATOM | 54 | O | THR | 6 | 44.588 | 54.102 | 38.779 | 1.00 | 34.37 |
| ATOM | 55 | N | ILE | 7 | 46.499 | 52.948 | 38.513 | 1.00 | 36.48 |
| ATOM | 56 | H | ILE | 7 | 46.960 | 52.142 | 38.779 | 1.00 | 0.00 |

FIG. 1: A-2

| | | | | | | | | |
|---|---|---|---|---|---|---|---|---|
| ATOM | 57 | CA | ILE | 7 | 47.244 | 54.056 | 37.929 | 1.00 | 37.99 |
| ATOM | 58 | CB | ILE | 7 | 48.602 | 54.186 | 38.696 | 1.00 | 37.09 |
| ATOM | 59 | CG2 | ILE | 7 | 49.467 | 55.319 | 38.135 | 1.00 | 38.38 |
| ATOM | 60 | CG1 | ILE | 7 | 48.261 | 54.424 | 40.161 | 1.00 | 35.33 |
| ATOM | 61 | CD1 | ILE | 7 | 49.400 | 54.804 | 41.082 | 1.00 | 34.52 |
| ATOM | 62 | C | ILE | 7 | 47.459 | 53.888 | 36.424 | 1.00 | 37.49 |
| ATOM | 63 | O | ILE | 7 | 47.305 | 54.830 | 35.638 | 1.00 | 38.48 |
| ATOM | 64 | N | SER | 8 | 47.833 | 52.670 | 36.033 | 1.00 | 36.45 |
| ATOM | 65 | H | SER | 8 | 48.045 | 52.009 | 36.725 | 1.00 | 0.00 |
| ATOM | 66 | CA | SER | 8 | 48.013 | 52.366 | 34.625 | 1.00 | 36.97 |
| ATOM | 67 | CB | SER | 8 | 49.397 | 52.794 | 34.130 | 1.00 | 37.72 |
| ATOM | 68 | OG | SER | 8 | 50.501 | 52.013 | 34.581 | 1.00 | 40.69 |
| ATOM | 69 | HG | SER | 8 | 50.341 | 51.065 | 34.470 | 1.00 | 0.00 |
| ATOM | 70 | C | SER | 8 | 47.844 | 50.886 | 34.314 | 1.00 | 38.32 |
| ATOM | 71 | O | SER | 8 | 48.604 | 50.034 | 34.790 | 1.00 | 38.56 |
| ATOM | 72 | N | PRO | 9 | 46.890 | 50.543 | 33.438 | 1.00 | 38.11 |
| ATOM | 73 | CD | PRO | 9 | 46.866 | 50.980 | 32.051 | 1.00 | 37.29 |
| ATOM | 74 | CA | PRO | 9 | 45.961 | 49.429 | 33.579 | 1.00 | 36.59 |
| ATOM | 75 | CB | PRO | 9 | 44.831 | 49.866 | 32.701 | 1.00 | 37.13 |
| ATOM | 76 | CG | PRO | 9 | 45.389 | 50.912 | 31.735 | 1.00 | 37.10 |
| ATOM | 77 | C | PRO | 9 | 46.385 | 47.984 | 33.321 | 1.00 | 35.28 |
| ATOM | 78 | O | PRO | 9 | 45.867 | 47.090 | 33.970 | 1.00 | 36.36 |
| ATOM | 79 | N | GLY | 10 | 47.273 | 47.625 | 32.421 | 1.00 | 34.47 |
| ATOM | 80 | H | GLY | 10 | 47.711 | 48.307 | 31.881 | 1.00 | 0.00 |
| ATOM | 81 | CA | GLY | 10 | 47.651 | 46.211 | 32.284 | 1.00 | 35.42 |
| ATOM | 82 | C | GLY | 10 | 46.639 | 45.294 | 31.618 | 1.00 | 35.67 |
| ATOM | 83 | O | GLY | 10 | 45.510 | 45.768 | 31.475 | 1.00 | 36.52 |
| ATOM | 84 | N | ASP | 11 | 46.914 | 44.030 | 31.177 | 1.00 | 34.34 |
| ATOM | 85 | H | ASP | 11 | 47.784 | 43.636 | 31.398 | 1.00 | 0.00 |
| ATOM | 86 | CA | ASP | 11 | 45.867 | 43.287 | 30.451 | 1.00 | 32.77 |
| ATOM | 87 | CB | ASP | 11 | 46.513 | 42.108 | 29.677 | 1.00 | 30.21 |
| ATOM | 88 | CG | ASP | 11 | 47.046 | 40.838 | 30.335 | 1.00 | 31.55 |
| ATOM | 89 | OD1 | ASP | 11 | 46.983 | 40.669 | 31.539 | 1.00 | 32.36 |
| ATOM | 90 | OD2 | ASP | 11 | 47.554 | 39.968 | 29.637 | 1.00 | 32.01 |
| ATOM | 91 | C | ASP | 11 | 44.654 | 42.778 | 31.246 | 1.00 | 33.67 |
| ATOM | 92 | O | ASP | 11 | 44.786 | 41.802 | 31.975 | 1.00 | 35.19 |
| ATOM | 93 | N | GLY | 12 | 43.433 | 43.342 | 31.200 | 1.00 | 33.12 |
| ATOM | 94 | H | GLY | 12 | 43.375 | 44.219 | 30.771 | 1.00 | 0.00 |
| ATOM | 95 | CA | GLY | 12 | 42.266 | 42.803 | 31.947 | 1.00 | 34.13 |
| ATOM | 96 | C | GLY | 12 | 41.949 | 41.274 | 31.936 | 1.00 | 34.14 |
| ATOM | 97 | O | GLY | 12 | 40.937 | 40.858 | 32.478 | 1.00 | 33.16 |
| ATOM | 98 | N | ARG | 13 | 42.796 | 40.420 | 31.334 | 1.00 | 34.05 |
| ATOM | 99 | H | ARG | 13 | 43.551 | 40.821 | 30.882 | 1.00 | 0.00 |
| ATOM | 100 | CA | ARG | 13 | 42.712 | 38.977 | 31.239 | 1.00 | 35.99 |
| ATOM | 101 | CB | ARG | 13 | 42.524 | 38.606 | 29.760 | 1.00 | 34.93 |
| ATOM | 102 | CG | ARG | 13 | 42.456 | 39.627 | 28.611 | 1.00 | 33.77 |
| ATOM | 103 | CD | ARG | 13 | 43.730 | 39.644 | 27.772 | 1.00 | 32.76 |
| ATOM | 104 | NE | ARG | 13 | 44.211 | 38.299 | 27.561 | 1.00 | 34.61 |
| ATOM | 105 | HE | ARG | 13 | 43.573 | 37.556 | 27.533 | 1.00 | 0.00 |
| ATOM | 106 | CZ | ARG | 13 | 45.501 | 38.029 | 27.382 | 1.00 | 38.10 |
| ATOM | 107 | NH1 | ARG | 13 | 45.864 | 36.745 | 27.291 | 1.00 | 38.67 |
| ATOM | 108 | HH11 | ARG | 13 | 45.168 | 36.028 | 27.331 | 1.00 | 0.00 |
| ATOM | 109 | HH12 | ARG | 13 | 46.819 | 36.503 | 27.122 | 1.00 | 0.00 |
| ATOM | 110 | NH2 | ARG | 13 | 46.427 | 38.995 | 27.254 | 1.00 | 38.28 |
| ATOM | 111 | HH21 | ARG | 13 | 46.176 | 39.959 | 27.310 | 1.00 | 0.00 |
| ATOM | 112 | HH22 | ARG | 13 | 47.382 | 38.735 | 27.112 | 1.00 | 0.00 |
| ATOM | 113 | C | ARG | 13 | 43.877 | 38.115 | 31.819 | 1.00 | 38.59 |
| ATOM | 114 | O | ARG | 13 | 44.115 | 36.954 | 31.409 | 1.00 | 41.28 |
| ATOM | 115 | N | THR | 14 | 44.731 | 38.612 | 32.722 | 1.00 | 38.83 |
| ATOM | 116 | H | THR | 14 | 44.706 | 39.581 | 32.876 | 1.00 | 0.00 |

FIG. 1: A-3

| ATOM | 117 | CA   | THR | 14 | 45.771 | 37.752 | 33.328 | 1.00 | 39.77 |
|------|-----|------|-----|----|--------|--------|--------|------|-------|
| ATOM | 118 | CB   | THR | 14 | 47.090 | 37.720 | 32.545 | 1.00 | 39.64 |
| ATOM | 119 | OG1  | THR | 14 | 46.838 | 37.843 | 31.156 | 1.00 | 39.49 |
| ATOM | 120 | HG1  | THR | 14 | 46.165 | 37.205 | 30.877 | 1.00 | 0.00  |
| ATOM | 121 | CG2  | THR | 14 | 47.796 | 36.419 | 32.791 | 1.00 | 40.29 |
| ATOM | 122 | C    | THR | 14 | 46.182 | 38.103 | 34.763 | 1.00 | 40.74 |
| ATOM | 123 | O    | THR | 14 | 47.022 | 38.936 | 35.124 | 1.00 | 40.39 |
| ATOM | 124 | N    | PHE | 15 | 45.513 | 37.341 | 35.604 | 1.00 | 40.86 |
| ATOM | 125 | H    | PHE | 15 | 44.954 | 36.630 | 35.237 | 1.00 | 0.00  |
| ATOM | 126 | CA   | PHE | 15 | 45.598 | 37.474 | 37.049 | 1.00 | 39.72 |
| ATOM | 127 | CB   | PHE | 15 | 44.169 | 37.443 | 37.576 | 1.00 | 36.40 |
| ATOM | 128 | CG   | PHE | 15 | 43.358 | 38.645 | 37.143 | 1.00 | 35.33 |
| ATOM | 129 | CD1  | PHE | 15 | 43.197 | 39.701 | 38.029 | 1.00 | 34.10 |
| ATOM | 130 | CD2  | PHE | 15 | 42.730 | 38.664 | 35.889 | 1.00 | 37.08 |
| ATOM | 131 | CE1  | PHE | 15 | 42.396 | 40.784 | 37.666 | 1.00 | 35.93 |
| ATOM | 132 | CE2  | PHE | 15 | 41.930 | 39.752 | 35.540 | 1.00 | 35.56 |
| ATOM | 133 | CZ   | PHE | 15 | 41.762 | 40.810 | 36.428 | 1.00 | 34.80 |
| ATOM | 134 | C    | PHE | 15 | 46.469 | 36.454 | 37.814 | 1.00 | 39.79 |
| ATOM | 135 | O    | PHE | 15 | 46.649 | 35.294 | 37.382 | 1.00 | 39.27 |
| ATOM | 136 | N    | PRO | 16 | 47.039 | 36.846 | 38.966 | 1.00 | 39.55 |
| ATOM | 137 | CD   | PRO | 16 | 46.973 | 38.189 | 39.561 | 1.00 | 38.77 |
| ATOM | 138 | CA   | PRO | 16 | 47.804 | 35.929 | 39.788 | 1.00 | 39.65 |
| ATOM | 139 | CB   | PRO | 16 | 48.632 | 36.893 | 40.614 | 1.00 | 39.12 |
| ATOM | 140 | CG   | PRO | 16 | 47.675 | 38.043 | 40.892 | 1.00 | 38.01 |
| ATOM | 141 | C    | PRO | 16 | 46.862 | 34.996 | 40.562 | 1.00 | 40.78 |
| ATOM | 142 | O    | PRO | 16 | 45.770 | 35.371 | 41.072 | 1.00 | 38.94 |
| ATOM | 143 | N    | LYS | 17 | 47.239 | 33.714 | 40.554 | 1.00 | 38.87 |
| ATOM | 144 | H    | LYS | 17 | 47.937 | 33.411 | 39.941 | 1.00 | 0.00  |
| ATOM | 145 | CA   | LYS | 17 | 46.461 | 32.820 | 41.394 | 1.00 | 40.02 |
| ATOM | 146 | CB   | LYS | 17 | 45.761 | 31.810 | 40.478 | 1.00 | 41.97 |
| ATOM | 147 | CG   | LYS | 17 | 46.634 | 30.839 | 39.712 | 1.00 | 42.19 |
| ATOM | 148 | CD   | LYS | 17 | 45.801 | 29.939 | 38.819 | 1.00 | 42.73 |
| ATOM | 149 | CE   | LYS | 17 | 46.535 | 28.596 | 38.652 | 1.00 | 45.69 |
| ATOM | 150 | NZ   | LYS | 17 | 47.837 | 28.725 | 37.991 | 1.00 | 45.59 |
| ATOM | 151 | HZ1  | LYS | 17 | 48.255 | 27.785 | 37.851 | 1.00 | 0.00  |
| ATOM | 152 | HZ2  | LYS | 17 | 48.464 | 29.300 | 38.588 | 1.00 | 0.00  |
| ATOM | 153 | HZ3  | LYS | 17 | 47.711 | 29.192 | 37.070 | 1.00 | 0.00  |
| ATOM | 154 | C    | LYS | 17 | 47.300 | 32.143 | 42.488 | 1.00 | 41.12 |
| ATOM | 155 | O    | LYS | 17 | 48.536 | 32.184 | 42.447 | 1.00 | 42.33 |
| ATOM | 156 | N    | ARG | 18 | 46.723 | 31.543 | 43.535 | 1.00 | 40.99 |
| ATOM | 157 | H    | ARG | 18 | 45.748 | 31.490 | 43.555 | 1.00 | 0.00  |
| ATOM | 158 | CA   | ARG | 18 | 47.526 | 30.951 | 44.600 | 1.00 | 39.94 |
| ATOM | 159 | CB   | ARG | 18 | 46.614 | 30.325 | 45.605 | 1.00 | 39.82 |
| ATOM | 160 | CG   | ARG | 18 | 46.198 | 28.894 | 45.299 | 1.00 | 43.90 |
| ATOM | 161 | CD   | ARG | 18 | 45.130 | 28.438 | 46.280 | 1.00 | 46.69 |
| ATOM | 162 | NE   | ARG | 18 | 45.626 | 28.253 | 47.631 | 1.00 | 46.26 |
| ATOM | 163 | HE   | ARG | 18 | 46.008 | 27.385 | 47.874 | 1.00 | 0.00  |
| ATOM | 164 | CZ   | ARG | 18 | 45.589 | 29.215 | 48.554 | 1.00 | 47.53 |
| ATOM | 165 | NH1  | ARG | 18 | 46.054 | 28.912 | 49.759 | 1.00 | 48.01 |
| ATOM | 166 | HH11 | ARG | 18 | 46.414 | 27.999 | 49.943 | 1.00 | 0.00  |
| ATOM | 167 | HH12 | ARG | 18 | 46.050 | 29.606 | 50.479 | 1.00 | 0.00  |
| ATOM | 168 | NH2  | ARG | 18 | 45.128 | 30.452 | 48.294 | 1.00 | 48.91 |
| ATOM | 169 | HH21 | ARG | 18 | 44.781 | 30.688 | 47.387 | 1.00 | 0.00  |
| ATOM | 170 | HH22 | ARG | 18 | 45.121 | 31.140 | 49.020 | 1.00 | 0.00  |
| ATOM | 171 | C    | ARG | 18 | 48.566 | 29.924 | 44.142 | 1.00 | 39.96 |
| ATOM | 172 | O    | ARG | 18 | 48.407 | 29.161 | 43.181 | 1.00 | 38.95 |
| ATOM | 173 | N    | GLY | 19 | 49.714 | 30.133 | 44.789 | 1.00 | 39.66 |
| ATOM | 174 | H    | GLY | 19 | 49.729 | 30.840 | 45.455 | 1.00 | 0.00  |
| ATOM | 175 | CA   | GLY | 19 | 50.931 | 29.369 | 44.547 | 1.00 | 37.93 |
| ATOM | 176 | C    | GLY | 19 | 51.777 | 30.013 | 43.461 | 1.00 | 37.60 |

FIG. 1: A-4

| ATOM | 177 | O    | GLY | 19 | 52.922 | 29.611 | 43.225 | 1.00 | 38.81 |
|------|-----|------|-----|----|--------|--------|--------|------|-------|
| ATOM | 178 | N    | GLN | 20 | 51.199 | 31.031 | 42.792 | 1.00 | 35.56 |
| ATOM | 179 | H    | GLN | 20 | 50.274 | 31.263 | 42.998 | 1.00 | 0.00  |
| ATOM | 180 | CA   | GLN | 20 | 51.869 | 31.780 | 41.735 | 1.00 | 32.71 |
| ATOM | 181 | CB   | GLN | 20 | 50.882 | 32.504 | 40.865 | 1.00 | 33.74 |
| ATOM | 182 | CG   | GLN | 20 | 51.338 | 32.512 | 39.434 | 1.00 | 36.20 |
| ATOM | 183 | CD   | GLN | 20 | 50.326 | 31.797 | 38.574 | 1.00 | 35.51 |
| ATOM | 184 | OE1  | GLN | 20 | 49.681 | 32.411 | 37.739 | 1.00 | 36.56 |
| ATOM | 185 | NE2  | GLN | 20 | 50.075 | 30.509 | 38.749 | 1.00 | 34.62 |
| ATOM | 186 | HE21 | GLN | 20 | 50.536 | 29.998 | 39.437 | 1.00 | 0.00  |
| ATOM | 187 | HE22 | GLN | 20 | 49.407 | 30.171 | 38.127 | 1.00 | 0.00  |
| ATOM | 188 | C    | GLN | 20 | 52.832 | 32.830 | 42.204 | 1.00 | 30.13 |
| ATOM | 189 | O    | GLN | 20 | 52.399 | 33.714 | 42.960 | 1.00 | 28.75 |
| ATOM | 190 | N    | THR | 21 | 54.076 | 32.784 | 41.704 | 1.00 | 28.40 |
| ATOM | 191 | H    | THR | 21 | 54.316 | 32.069 | 41.073 | 1.00 | 0.00  |
| ATOM | 192 | CA   | THR | 21 | 55.067 | 33.801 | 42.075 | 1.00 | 26.74 |
| ATOM | 193 | CB   | THR | 21 | 56.514 | 33.354 | 41.670 | 1.00 | 29.08 |
| ATOM | 194 | OG1  | THR | 21 | 56.762 | 32.109 | 42.319 | 1.00 | 28.19 |
| ATOM | 195 | HG1  | THR | 21 | 56.664 | 31.409 | 41.657 | 1.00 | 0.00  |
| ATOM | 196 | CG2  | THR | 21 | 57.609 | 34.331 | 42.100 | 1.00 | 27.45 |
| ATOM | 197 | C    | THR | 21 | 54.797 | 35.186 | 41.470 | 1.00 | 25.93 |
| ATOM | 198 | O    | THR | 21 | 55.098 | 35.430 | 40.304 | 1.00 | 23.14 |
| ATOM | 199 | N    | CYS | 22 | 54.154 | 36.112 | 42.202 | 1.00 | 27.31 |
| ATOM | 200 | H    | CYS | 22 | 53.779 | 35.806 | 43.055 | 1.00 | 0.00  |
| ATOM | 201 | CA   | CYS | 22 | 53.937 | 37.501 | 41.753 | 1.00 | 29.39 |
| ATOM | 202 | CB   | CYS | 22 | 52.899 | 38.281 | 42.549 | 1.00 | 28.95 |
| ATOM | 203 | SG   | CYS | 22 | 51.357 | 37.402 | 42.845 | 1.00 | 31.42 |
| ATOM | 204 | C    | CYS | 22 | 55.162 | 38.426 | 41.811 | 1.00 | 30.45 |
| ATOM | 205 | O    | CYS | 22 | 55.578 | 38.922 | 42.871 | 1.00 | 29.88 |
| ATOM | 206 | N    | VAL | 23 | 55.774 | 38.632 | 40.634 | 1.00 | 30.12 |
| ATOM | 207 | H    | VAL | 23 | 55.413 | 38.174 | 39.846 | 1.00 | 0.00  |
| ATOM | 208 | CA   | VAL | 23 | 56.898 | 39.547 | 40.507 | 1.00 | 27.94 |
| ATOM | 209 | CB   | VAL | 23 | 57.733 | 39.242 | 39.268 | 1.00 | 26.58 |
| ATOM | 210 | CG1  | VAL | 23 | 59.047 | 39.982 | 39.453 | 1.00 | 23.51 |
| ATOM | 211 | CG2  | VAL | 23 | 57.989 | 37.753 | 39.067 | 1.00 | 25.36 |
| ATOM | 212 | C    | VAL | 23 | 56.359 | 40.980 | 40.389 | 1.00 | 27.94 |
| ATOM | 213 | O    | VAL | 23 | 55.593 | 41.279 | 39.485 | 1.00 | 29.74 |
| ATOM | 214 | N    | VAL | 24 | 56.635 | 41.873 | 41.322 | 1.00 | 26.11 |
| ATOM | 215 | H    | VAL | 24 | 57.138 | 41.554 | 42.101 | 1.00 | 0.00  |
| ATOM | 216 | CA   | VAL | 24 | 56.212 | 43.262 | 41.279 | 1.00 | 25.02 |
| ATOM | 217 | CB   | VAL | 24 | 55.146 | 43.661 | 42.348 | 1.00 | 26.06 |
| ATOM | 218 | CG1  | VAL | 24 | 53.762 | 43.087 | 42.093 | 1.00 | 25.35 |
| ATOM | 219 | CG2  | VAL | 24 | 55.665 | 43.142 | 43.688 | 1.00 | 28.24 |
| ATOM | 220 | C    | VAL | 24 | 57.393 | 44.185 | 41.569 | 1.00 | 25.29 |
| ATOM | 221 | O    | VAL | 24 | 58.481 | 43.812 | 42.037 | 1.00 | 25.98 |
| ATOM | 222 | N    | HIS | 25 | 57.197 | 45.454 | 41.276 | 1.00 | 21.24 |
| ATOM | 223 | H    | HIS | 25 | 56.376 | 45.706 | 40.791 | 1.00 | 0.00  |
| ATOM | 224 | CA   | HIS | 25 | 58.146 | 46.421 | 41.707 | 1.00 | 21.30 |
| ATOM | 225 | CB   | HIS | 25 | 58.736 | 47.210 | 40.563 | 1.00 | 26.13 |
| ATOM | 226 | CG   | HIS | 25 | 60.271 | 47.203 | 40.531 | 1.00 | 28.07 |
| ATOM | 227 | CD2  | HIS | 25 | 60.974 | 47.708 | 39.475 | 1.00 | 29.42 |
| ATOM | 228 | ND1  | HIS | 25 | 61.198 | 46.773 | 41.390 | 1.00 | 29.32 |
| ATOM | 229 | HD1  | HIS | 25 | 61.047 | 46.384 | 42.281 | 1.00 | 0.00  |
| ATOM | 230 | CE1  | HIS | 25 | 62.384 | 46.994 | 40.915 | 1.00 | 27.59 |
| ATOM | 231 | NE2  | HIS | 25 | 62.239 | 47.559 | 39.760 | 1.00 | 28.50 |
| ATOM | 232 | HE2  | HIS | 25 | 62.985 | 47.893 | 39.210 | 1.00 | 0.00  |
| ATOM | 233 | C    | HIS | 25 | 57.236 | 47.303 | 42.508 | 1.00 | 23.00 |
| ATOM | 234 | O    | HIS | 25 | 56.236 | 47.738 | 41.970 | 1.00 | 26.21 |
| ATOM | 235 | N    | TYR | 26 | 57.454 | 47.566 | 43.784 | 1.00 | 20.88 |
| ATOM | 236 | H    | TYR | 26 | 58.222 | 47.138 | 44.208 | 1.00 | 0.00  |

FIG. 1: A-5

| ATOM | 237 | CA | TYR | 26 | 56.544 | 48.416 | 44.538 | 1.00 | 18.89 |
| --- | --- | --- | --- | --- | --- | --- | --- | --- | --- |
| ATOM | 238 | CB | TYR | 26 | 56.068 | 47.697 | 45.797 | 1.00 | 17.38 |
| ATOM | 239 | CG | TYR | 26 | 57.155 | 47.348 | 46.802 | 1.00 | 15.80 |
| ATOM | 240 | CD1 | TYR | 26 | 57.447 | 48.208 | 47.877 | 1.00 | 14.23 |
| ATOM | 241 | CE1 | TYR | 26 | 58.468 | 47.879 | 48.774 | 1.00 | 11.98 |
| ATOM | 242 | CD2 | TYR | 26 | 57.886 | 46.157 | 46.621 | 1.00 | 16.82 |
| ATOM | 243 | CE2 | TYR | 26 | 58.917 | 45.840 | 47.511 | 1.00 | 15.75 |
| ATOM | 244 | CZ | TYR | 26 | 59.187 | 46.706 | 48.582 | 1.00 | 14.95 |
| ATOM | 245 | OH | TYR | 26 | 60.174 | 46.341 | 49.466 | 1.00 | 20.01 |
| ATOM | 246 | HH | TYR | 26 | 59.987 | 46.721 | 50.340 | 1.00 | 0.00 |
| ATOM | 247 | C | TYR | 26 | 57.152 | 49.730 | 44.979 | 1.00 | 19.71 |
| ATOM | 248 | O | TYR | 26 | 58.355 | 49.948 | 44.830 | 1.00 | 23.57 |
| ATOM | 249 | N | THR | 27 | 56.347 | 50.586 | 45.567 | 1.00 | 19.61 |
| ATOM | 250 | H | THR | 27 | 55.385 | 50.494 | 45.384 | 1.00 | 0.00 |
| ATOM | 251 | CA | THR | 27 | 56.823 | 51.753 | 46.301 | 1.00 | 20.40 |
| ATOM | 252 | CB | THR | 27 | 57.006 | 53.035 | 45.434 | 1.00 | 21.63 |
| ATOM | 253 | OG1 | THR | 27 | 58.193 | 52.798 | 44.677 | 1.00 | 20.88 |
| ATOM | 254 | HG1 | THR | 27 | 57.901 | 52.431 | 43.834 | 1.00 | 0.00 |
| ATOM | 255 | CG2 | THR | 27 | 57.186 | 54.335 | 46.231 | 1.00 | 18.41 |
| ATOM | 256 | C | THR | 27 | 55.834 | 52.083 | 47.404 | 1.00 | 19.02 |
| ATOM | 257 | O | THR | 27 | 54.721 | 52.526 | 47.190 | 1.00 | 19.18 |
| ATOM | 258 | N | GLY | 28 | 56.236 | 51.771 | 48.612 | 1.00 | 20.92 |
| ATOM | 259 | H | GLY | 28 | 57.161 | 51.471 | 48.732 | 1.00 | 0.00 |
| ATOM | 260 | CA | GLY | 28 | 55.436 | 52.035 | 49.785 | 1.00 | 23.65 |
| ATOM | 261 | C | GLY | 28 | 55.701 | 53.389 | 50.432 | 1.00 | 26.52 |
| ATOM | 262 | O | GLY | 28 | 56.822 | 53.926 | 50.550 | 1.00 | 27.81 |
| ATOM | 263 | N | MET | 29 | 54.567 | 53.921 | 50.871 | 1.00 | 27.75 |
| ATOM | 264 | H | MET | 29 | 53.725 | 53.435 | 50.718 | 1.00 | 0.00 |
| ATOM | 265 | CA | MET | 29 | 54.491 | 55.225 | 51.510 | 1.00 | 27.83 |
| ATOM | 266 | CB | MET | 29 | 53.905 | 56.309 | 50.650 | 1.00 | 30.08 |
| ATOM | 267 | CG | MET | 29 | 54.666 | 56.679 | 49.419 | 1.00 | 32.75 |
| ATOM | 268 | SD | MET | 29 | 53.495 | 56.923 | 48.087 | 1.00 | 34.24 |
| ATOM | 269 | CE | MET | 29 | 54.295 | 55.650 | 47.175 | 1.00 | 35.09 |
| ATOM | 270 | C | MET | 29 | 53.538 | 55.177 | 52.658 | 1.00 | 27.17 |
| ATOM | 271 | O | MET | 29 | 52.720 | 54.267 | 52.817 | 1.00 | 26.91 |
| ATOM | 272 | N | LEU | 30 | 53.677 | 56.181 | 53.490 | 1.00 | 27.89 |
| ATOM | 273 | H | LEU | 30 | 54.483 | 56.732 | 53.446 | 1.00 | 0.00 |
| ATOM | 274 | CA | LEU | 30 | 52.667 | 56.356 | 54.516 | 1.00 | 30.48 |
| ATOM | 275 | CB | LEU | 30 | 53.298 | 57.017 | 55.777 | 1.00 | 27.96 |
| ATOM | 276 | CG | LEU | 30 | 54.527 | 56.394 | 56.423 | 1.00 | 25.12 |
| ATOM | 277 | CD1 | LEU | 30 | 55.041 | 57.364 | 57.456 | 1.00 | 23.11 |
| ATOM | 278 | CD2 | LEU | 30 | 54.204 | 55.058 | 57.065 | 1.00 | 21.88 |
| ATOM | 279 | C | LEU | 30 | 51.524 | 57.228 | 53.941 | 1.00 | 31.36 |
| ATOM | 280 | O | LEU | 30 | 51.602 | 57.856 | 52.863 | 1.00 | 29.62 |
| ATOM | 281 | N | GLU | 31 | 50.441 | 57.323 | 54.702 | 1.00 | 31.29 |
| ATOM | 282 | H | GLU | 31 | 50.378 | 56.747 | 55.493 | 1.00 | 0.00 |
| ATOM | 283 | CA | GLU | 31 | 49.262 | 58.044 | 54.236 | 1.00 | 32.84 |
| ATOM | 284 | CB | GLU | 31 | 48.178 | 57.796 | 55.298 | 1.00 | 32.44 |
| ATOM | 285 | CG | GLU | 31 | 46.770 | 58.072 | 54.796 | 1.00 | 31.53 |
| ATOM | 286 | CD | GLU | 31 | 45.698 | 57.826 | 55.833 | 1.00 | 34.07 |
| ATOM | 287 | OE1 | GLU | 31 | 44.549 | 57.608 | 55.422 | 1.00 | 34.66 |
| ATOM | 288 | OE2 | GLU | 31 | 46.013 | 57.857 | 57.036 | 1.00 | 33.21 |
| ATOM | 289 | C | GLU | 31 | 49.441 | 59.535 | 53.905 | 1.00 | 32.14 |
| ATOM | 290 | O | GLU | 31 | 48.616 | 60.173 | 53.260 | 1.00 | 33.96 |
| ATOM | 291 | N | ASP | 32 | 50.540 | 60.143 | 54.310 | 1.00 | 31.59 |
| ATOM | 292 | H | ASP | 32 | 51.134 | 59.673 | 54.927 | 1.00 | 0.00 |
| ATOM | 293 | CA | ASP | 32 | 50.783 | 61.517 | 53.895 | 1.00 | 31.09 |
| ATOM | 294 | CB | ASP | 32 | 51.608 | 62.280 | 54.938 | 1.00 | 32.37 |
| ATOM | 295 | CG | ASP | 32 | 52.895 | 61.673 | 55.492 | 1.00 | 33.17 |
| ATOM | 296 | OD1 | ASP | 32 | 53.434 | 62.267 | 56.421 | 1.00 | 35.90 |

FIG. 1: A-6

| ATOM | 297 | OD2 | ASP | 32 | 53.350 | 60.626 | 55.044 | 1.00 | 33.02 |
|---|---|---|---|---|---|---|---|---|---|
| ATOM | 298 | C | ASP | 32 | 51.496 | 61.601 | 52.570 | 1.00 | 31.07 |
| ATOM | 299 | O | ASP | 32 | 51.721 | 62.674 | 52.022 | 1.00 | 34.08 |
| ATOM | 300 | N | GLY | 33 | 51.843 | 60.432 | 52.042 | 1.00 | 31.65 |
| ATOM | 301 | H | GLY | 33 | 51.444 | 59.632 | 52.417 | 1.00 | 0.00 |
| ATOM | 302 | CA | GLY | 33 | 52.607 | 60.313 | 50.802 | 1.00 | 30.10 |
| ATOM | 303 | C | GLY | 33 | 54.090 | 60.071 | 51.065 | 1.00 | 29.11 |
| ATOM | 304 | O | GLY | 33 | 54.873 | 59.762 | 50.168 | 1.00 | 30.34 |
| ATOM | 305 | N | LYS | 34 | 54.563 | 60.167 | 52.305 | 1.00 | 28.54 |
| ATOM | 306 | H | LYS | 34 | 53.959 | 60.458 | 53.009 | 1.00 | 0.00 |
| ATOM | 307 | CA | LYS | 34 | 55.984 | 59.971 | 52.538 | 1.00 | 28.12 |
| ATOM | 308 | CB | LYS | 34 | 56.360 | 60.398 | 53.936 | 1.00 | 28.68 |
| ATOM | 309 | CG | LYS | 34 | 57.865 | 60.568 | 54.117 | 1.00 | 27.68 |
| ATOM | 310 | CD | LYS | 34 | 58.081 | 61.183 | 55.479 | 1.00 | 28.13 |
| ATOM | 311 | CE | LYS | 34 | 57.705 | 60.187 | 56.545 | 1.00 | 27.71 |
| ATOM | 312 | NZ | LYS | 34 | 58.191 | 60.672 | 57.813 | 1.00 | 29.87 |
| ATOM | 313 | HZ1 | LYS | 34 | 57.696 | 61.553 | 58.056 | 1.00 | 0.00 |
| ATOM | 314 | HZ2 | LYS | 34 | 59.213 | 60.854 | 57.752 | 1.00 | 0.00 |
| ATOM | 315 | HZ3 | LYS | 34 | 58.008 | 59.959 | 58.547 | 1.00 | 0.00 |
| ATOM | 316 | C | LYS | 34 | 56.496 | 58.555 | 52.335 | 1.00 | 27.80 |
| ATOM | 317 | O | LYS | 34 | 56.101 | 57.581 | 52.991 | 1.00 | 30.02 |
| ATOM | 318 | N | LYS | 35 | 57.347 | 58.486 | 51.323 | 1.00 | 25.28 |
| ATOM | 319 | H | LYS | 35 | 57.412 | 59.266 | 50.737 | 1.00 | 0.00 |
| ATOM | 320 | CA | LYS | 35 | 58.062 | 57.274 | 51.007 | 1.00 | 23.24 |
| ATOM | 321 | CB | LYS | 35 | 59.032 | 57.523 | 49.855 | 1.00 | 18.81 |
| ATOM | 322 | CG | LYS | 35 | 59.361 | 56.174 | 49.209 | 1.00 | 18.77 |
| ATOM | 323 | CD | LYS | 35 | 60.466 | 56.193 | 48.143 | 1.00 | 17.00 |
| ATOM | 324 | CE | LYS | 35 | 61.856 | 56.062 | 48.750 | 1.00 | 16.60 |
| ATOM | 325 | NZ | LYS | 35 | 62.806 | 55.735 | 47.710 | 1.00 | 18.86 |
| ATOM | 326 | HZ1 | LYS | 35 | 62.765 | 56.447 | 46.952 | 1.00 | 0.00 |
| ATOM | 327 | HZ2 | LYS | 35 | 62.576 | 54.799 | 47.323 | 1.00 | 0.00 |
| ATOM | 328 | HZ3 | LYS | 35 | 63.760 | 55.721 | 48.122 | 1.00 | 0.00 |
| ATOM | 329 | C | LYS | 35 | 58.841 | 56.759 | 52.214 | 1.00 | 23.19 |
| ATOM | 330 | O | LYS | 35 | 59.441 | 57.506 | 52.993 | 1.00 | 25.70 |
| ATOM | 331 | N | PHE | 36 | 58.677 | 55.471 | 52.433 | 1.00 | 21.46 |
| ATOM | 332 | H | PHE | 36 | 57.956 | 55.019 | 51.940 | 1.00 | 0.00 |
| ATOM | 333 | CA | PHE | 36 | 59.442 | 54.770 | 53.439 | 1.00 | 18.53 |
| ATOM | 334 | CB | PHE | 36 | 58.557 | 54.038 | 54.487 | 1.00 | 15.06 |
| ATOM | 335 | CG | PHE | 36 | 57.485 | 53.000 | 54.092 | 1.00 | 15.47 |
| ATOM | 336 | CD1 | PHE | 36 | 56.127 | 53.322 | 54.281 | 1.00 | 11.31 |
| ATOM | 337 | CD2 | PHE | 36 | 57.829 | 51.703 | 53.619 | 1.00 | 15.12 |
| ATOM | 338 | CE1 | PHE | 36 | 55.134 | 52.362 | 54.006 | 1.00 | 12.76 |
| ATOM | 339 | CE2 | PHE | 36 | 56.820 | 50.760 | 53.346 | 1.00 | 15.65 |
| ATOM | 340 | CZ | PHE | 36 | 55.466 | 51.083 | 53.543 | 1.00 | 9.65 |
| ATOM | 341 | C | PHE | 36 | 60.288 | 53.752 | 52.720 | 1.00 | 20.38 |
| ATOM | 342 | O | PHE | 36 | 61.377 | 53.520 | 53.205 | 1.00 | 24.97 |
| ATOM | 343 | N | ASP | 37 | 59.909 | 53.117 | 51.594 | 1.00 | 19.98 |
| ATOM | 344 | H | ASP | 37 | 59.015 | 53.280 | 51.221 | 1.00 | 0.00 |
| ATOM | 345 | CA | ASP | 37 | 60.786 | 52.151 | 50.924 | 1.00 | 19.12 |
| ATOM | 346 | CB | ASP | 37 | 60.755 | 50.796 | 51.671 | 1.00 | 21.95 |
| ATOM | 347 | CG | ASP | 37 | 61.641 | 49.636 | 51.198 | 1.00 | 21.09 |
| ATOM | 348 | OD1 | ASP | 37 | 61.238 | 48.497 | 51.386 | 1.00 | 22.65 |
| ATOM | 349 | OD2 | ASP | 37 | 62.722 | 49.847 | 50.660 | 1.00 | 22.17 |
| ATOM | 350 | C | ASP | 37 | 60.350 | 51.925 | 49.495 | 1.00 | 17.87 |
| ATOM | 351 | O | ASP | 37 | 59.294 | 52.376 | 49.117 | 1.00 | 17.69 |
| ATOM | 352 | N | SER | 38 | 61.118 | 51.231 | 48.678 | 1.00 | 17.89 |
| ATOM | 353 | H | SER | 38 | 62.003 | 50.983 | 49.010 | 1.00 | 0.00 |
| ATOM | 354 | CA | SER | 38 | 60.779 | 50.896 | 47.310 | 1.00 | 17.18 |
| ATOM | 355 | CB | SER | 38 | 60.908 | 52.048 | 46.328 | 1.00 | 18.01 |
| ATOM | 356 | OG | SER | 38 | 60.771 | 51.662 | 44.958 | 1.00 | 19.28 |

FIG. 1: A-7

| ATOM | 357 | HG | SER | 38 | 59.971 | 52.126 | 44.651 | 1.00 | 0.00 |
|------|-----|------|-----|----|--------|--------|--------|------|-------|
| ATOM | 358 | C | SER | 38 | 61.705 | 49.845 | 46.765 | 1.00 | 17.77 |
| ATOM | 359 | O | SER | 38 | 62.911 | 49.958 | 46.948 | 1.00 | 20.48 |
| ATOM | 360 | N | SER | 39 | 61.213 | 48.833 | 46.051 | 1.00 | 16.66 |
| ATOM | 361 | H | SER | 39 | 60.238 | 48.777 | 46.012 | 1.00 | 0.00 |
| ATOM | 362 | CA | SER | 39 | 62.071 | 47.849 | 45.366 | 1.00 | 17.42 |
| ATOM | 363 | CB | SER | 39 | 61.223 | 46.796 | 44.704 | 1.00 | 15.25 |
| ATOM | 364 | OG | SER | 39 | 60.344 | 47.446 | 43.781 | 1.00 | 16.64 |
| ATOM | 365 | HG | SER | 39 | 59.996 | 48.275 | 44.158 | 1.00 | 0.00 |
| ATOM | 366 | C | SER | 39 | 62.986 | 48.430 | 44.279 | 1.00 | 20.01 |
| ATOM | 367 | O | SER | 39 | 63.897 | 47.810 | 43.721 | 1.00 | 19.70 |
| ATOM | 368 | N | ARG | 40 | 62.679 | 49.672 | 43.907 | 1.00 | 23.62 |
| ATOM | 369 | H | ARG | 40 | 61.914 | 50.125 | 44.324 | 1.00 | 0.00 |
| ATOM | 370 | CA | ARG | 40 | 63.425 | 50.443 | 42.916 | 1.00 | 25.92 |
| ATOM | 371 | CB | ARG | 40 | 62.541 | 51.567 | 42.399 | 1.00 | 22.84 |
| ATOM | 372 | CG | ARG | 40 | 61.420 | 51.048 | 41.552 | 1.00 | 22.60 |
| ATOM | 373 | CD | ARG | 40 | 60.536 | 52.150 | 40.979 | 1.00 | 25.68 |
| ATOM | 374 | NE | ARG | 40 | 59.457 | 51.564 | 40.188 | 1.00 | 31.06 |
| ATOM | 375 | HE | ARG | 40 | 58.539 | 51.609 | 40.524 | 1.00 | 0.00 |
| ATOM | 376 | CZ | ARG | 40 | 59.704 | 50.930 | 39.010 | 1.00 | 34.77 |
| ATOM | 377 | NH1 | ARG | 40 | 58.669 | 50.342 | 38.376 | 1.00 | 31.00 |
| ATOM | 378 | HH11 | ARG | 40 | 57.759 | 50.363 | 38.788 | 1.00 | 0.00 |
| ATOM | 379 | HH12 | ARG | 40 | 58.825 | 49.854 | 37.517 | 1.00 | 0.00 |
| ATOM | 380 | NH2 | ARG | 40 | 60.955 | 50.885 | 38.457 | 1.00 | 32.96 |
| ATOM | 381 | HH21 | ARG | 40 | 61.724 | 51.332 | 38.913 | 1.00 | 0.00 |
| ATOM | 382 | HH22 | ARG | 40 | 61.098 | 50.408 | 37.590 | 1.00 | 0.00 |
| ATOM | 383 | C | ARG | 40 | 64.724 | 51.018 | 43.469 | 1.00 | 27.43 |
| ATOM | 384 | O | ARG | 40 | 65.693 | 51.163 | 42.728 | 1.00 | 29.93 |
| ATOM | 385 | N | ASP | 41 | 64.764 | 51.230 | 44.800 | 1.00 | 27.19 |
| ATOM | 386 | H | ASP | 41 | 63.924 | 51.110 | 45.289 | 1.00 | 0.00 |
| ATOM | 387 | CA | ASP | 41 | 65.928 | 51.717 | 45.559 | 1.00 | 24.84 |
| ATOM | 388 | CB | ASP | 41 | 65.696 | 51.745 | 47.061 | 1.00 | 21.53 |
| ATOM | 389 | CG | ASP | 41 | 64.640 | 52.675 | 47.624 | 1.00 | 21.05 |
| ATOM | 390 | OD1 | ASP | 41 | 64.413 | 52.612 | 48.832 | 1.00 | 20.59 |
| ATOM | 391 | OD2 | ASP | 41 | 64.051 | 53.459 | 46.880 | 1.00 | 23.80 |
| ATOM | 392 | C | ASP | 41 | 67.177 | 50.870 | 45.400 | 1.00 | 24.97 |
| ATOM | 393 | O | ASP | 41 | 68.345 | 51.283 | 45.514 | 1.00 | 25.61 |
| ATOM | 394 | N | ARG | 42 | 66.830 | 49.603 | 45.245 | 1.00 | 22.10 |
| ATOM | 395 | H | ARG | 42 | 65.887 | 49.361 | 45.318 | 1.00 | 0.00 |
| ATOM | 396 | CA | ARG | 42 | 67.850 | 48.604 | 45.080 | 1.00 | 22.23 |
| ATOM | 397 | CB | ARG | 42 | 67.791 | 47.652 | 46.309 | 1.00 | 21.91 |
| ATOM | 398 | CG | ARG | 42 | 66.432 | 47.150 | 46.667 | 1.00 | 23.04 |
| ATOM | 399 | CD | ARG | 42 | 66.300 | 46.343 | 47.924 | 1.00 | 20.28 |
| ATOM | 400 | NE | ARG | 42 | 64.947 | 45.806 | 47.920 | 1.00 | 14.87 |
| ATOM | 401 | HE | ARG | 42 | 64.807 | 44.872 | 47.657 | 1.00 | 0.00 |
| ATOM | 402 | CZ | ARG | 42 | 63.895 | 46.531 | 48.275 | 1.00 | 13.69 |
| ATOM | 403 | NH1 | ARG | 42 | 62.703 | 45.970 | 48.215 | 1.00 | 17.94 |
| ATOM | 404 | HH11 | ARG | 42 | 62.607 | 45.021 | 47.917 | 1.00 | 0.00 |
| ATOM | 405 | HH12 | ARG | 42 | 61.894 | 46.497 | 48.472 | 1.00 | 0.00 |
| ATOM | 406 | NH2 | ARG | 42 | 63.992 | 47.759 | 48.747 | 1.00 | 12.98 |
| ATOM | 407 | HH21 | ARG | 42 | 64.888 | 48.190 | 48.860 | 1.00 | 0.00 |
| ATOM | 408 | HH22 | ARG | 42 | 63.166 | 48.265 | 48.999 | 1.00 | 0.00 |
| ATOM | 409 | C | ARG | 42 | 67.706 | 47.882 | 43.758 | 1.00 | 21.35 |
| ATOM | 410 | O | ARG | 42 | 68.304 | 46.846 | 43.489 | 1.00 | 21.41 |
| ATOM | 411 | N | ASN | 43 | 66.954 | 48.520 | 42.872 | 1.00 | 22.88 |
| ATOM | 412 | H | ASN | 43 | 66.681 | 49.440 | 43.070 | 1.00 | 0.00 |
| ATOM | 413 | CA | ASN | 43 | 66.663 | 47.970 | 41.559 | 1.00 | 24.51 |
| ATOM | 414 | CB | ASN | 43 | 67.796 | 48.385 | 40.679 | 1.00 | 24.48 |
| ATOM | 415 | CG | ASN | 43 | 67.440 | 49.794 | 40.271 | 1.00 | 29.50 |
| ATOM | 416 | OD1 | ASN | 43 | 66.386 | 49.982 | 39.670 | 1.00 | 33.59 |

FIG. 1: A-8

| | | | | | | | | |
|---|---|---|---|---|---|---|---|---|
| ATOM | 417 | ND2 | ASN | 43 | 68.178 | 50.852 | 40.553 | 1.00 | 27.08 |
| ATOM | 418 | HD21 | ASN | 43 | 67.776 | 51.686 | 40.250 | 1.00 | 0.00 |
| ATOM | 419 | HD22 | ASN | 43 | 69.016 | 50.738 | 41.032 | 1.00 | 0.00 |
| ATOM | 420 | C | ASN | 43 | 66.390 | 46.479 | 41.424 | 1.00 | 24.85 |
| ATOM | 421 | O | ASN | 43 | 66.762 | 45.855 | 40.438 | 1.00 | 27.39 |
| ATOM | 422 | N | LYS | 44 | 65.709 | 45.900 | 42.419 | 1.00 | 24.30 |
| ATOM | 423 | H | LYS | 44 | 65.401 | 46.462 | 43.161 | 1.00 | 0.00 |
| ATOM | 424 | CA | LYS | 44 | 65.426 | 44.470 | 42.473 | 1.00 | 23.99 |
| ATOM | 425 | CB | LYS | 44 | 65.808 | 43.933 | 43.792 | 1.00 | 20.96 |
| ATOM | 426 | CG | LYS | 44 | 66.506 | 42.628 | 43.684 | 1.00 | 23.46 |
| ATOM | 427 | CD | LYS | 44 | 67.863 | 42.872 | 43.144 | 1.00 | 23.83 |
| ATOM | 428 | CE | LYS | 44 | 68.256 | 41.581 | 42.481 | 1.00 | 27.20 |
| ATOM | 429 | NZ | LYS | 44 | 68.729 | 40.675 | 43.507 | 1.00 | 36.28 |
| ATOM | 430 | HZ1 | LYS | 44 | 69.086 | 39.801 | 43.071 | 1.00 | 0.00 |
| ATOM | 431 | HZ2 | LYS | 44 | 67.963 | 40.456 | 44.175 | 1.00 | 0.00 |
| ATOM | 432 | HZ3 | LYS | 44 | 69.502 | 41.148 | 44.020 | 1.00 | 0.00 |
| ATOM | 433 | C | LYS | 44 | 63.941 | 44.274 | 42.312 | 1.00 | 27.07 |
| ATOM | 434 | O | LYS | 44 | 63.200 | 44.934 | 43.055 | 1.00 | 31.31 |
| ATOM | 435 | N | PRO | 45 | 63.332 | 43.560 | 41.365 | 1.00 | 28.67 |
| ATOM | 436 | CD | PRO | 45 | 63.807 | 43.335 | 40.005 | 1.00 | 28.62 |
| ATOM | 437 | CA | PRO | 45 | 61.909 | 43.224 | 41.470 | 1.00 | 28.69 |
| ATOM | 438 | CB | PRO | 45 | 61.624 | 42.545 | 40.166 | 1.00 | 26.52 |
| ATOM | 439 | CG | PRO | 45 | 62.484 | 43.360 | 39.229 | 1.00 | 27.83 |
| ATOM | 440 | C | PRO | 45 | 61.617 | 42.379 | 42.708 | 1.00 | 27.51 |
| ATOM | 441 | O | PRO | 45 | 62.368 | 41.468 | 43.045 | 1.00 | 29.13 |
| ATOM | 442 | N | PHE | 46 | 60.597 | 42.725 | 43.452 | 1.00 | 26.12 |
| ATOM | 443 | H | PHE | 46 | 60.007 | 43.450 | 43.168 | 1.00 | 0.00 |
| ATOM | 444 | CA | PHE | 46 | 60.248 | 41.920 | 44.597 | 1.00 | 31.28 |
| ATOM | 445 | CB | PHE | 46 | 59.465 | 42.716 | 45.650 | 1.00 | 32.61 |
| ATOM | 446 | CG | PHE | 46 | 59.120 | 41.920 | 46.901 | 1.00 | 33.87 |
| ATOM | 447 | CD1 | PHE | 46 | 57.828 | 41.384 | 47.059 | 1.00 | 37.56 |
| ATOM | 448 | CD2 | PHE | 46 | 60.082 | 41.724 | 47.893 | 1.00 | 33.24 |
| ATOM | 449 | CE1 | PHE | 46 | 57.510 | 40.654 | 48.212 | 1.00 | 35.56 |
| ATOM | 450 | CE2 | PHE | 46 | 59.752 | 40.996 | 49.036 | 1.00 | 31.96 |
| ATOM | 451 | CZ | PHE | 46 | 58.479 | 40.465 | 49.195 | 1.00 | 34.08 |
| ATOM | 452 | C | PHE | 46 | 59.359 | 40.785 | 44.127 | 1.00 | 34.32 |
| ATOM | 453 | O | PHE | 46 | 58.313 | 41.026 | 43.503 | 1.00 | 36.16 |
| ATOM | 454 | N | LYS | 47 | 59.737 | 39.552 | 44.453 | 1.00 | 33.97 |
| ATOM | 455 | H | LYS | 47 | 60.573 | 39.430 | 44.943 | 1.00 | 0.00 |
| ATOM | 456 | CA | LYS | 47 | 58.898 | 38.431 | 44.081 | 1.00 | 33.67 |
| ATOM | 457 | CB | LYS | 47 | 59.676 | 37.387 | 43.326 | 1.00 | 32.98 |
| ATOM | 458 | CG | LYS | 47 | 60.550 | 37.818 | 42.159 | 1.00 | 33.56 |
| ATOM | 459 | CD | LYS | 47 | 61.116 | 36.562 | 41.503 | 1.00 | 36.93 |
| ATOM | 460 | CE | LYS | 47 | 61.795 | 35.672 | 42.568 | 1.00 | 42.30 |
| ATOM | 461 | NZ | LYS | 47 | 61.538 | 34.243 | 42.355 | 1.00 | 47.07 |
| ATOM | 462 | HZ1 | LYS | 47 | 62.041 | 33.696 | 43.081 | 1.00 | 0.00 |
| ATOM | 463 | HZ2 | LYS | 47 | 61.876 | 33.968 | 41.411 | 1.00 | 0.00 |
| ATOM | 464 | HZ3 | LYS | 47 | 60.517 | 34.060 | 42.431 | 1.00 | 0.00 |
| ATOM | 465 | C | LYS | 47 | 58.297 | 37.745 | 45.295 | 1.00 | 34.78 |
| ATOM | 466 | O | LYS | 47 | 58.927 | 37.710 | 46.354 | 1.00 | 35.77 |
| ATOM | 467 | N | PHE | 48 | 57.064 | 37.230 | 45.188 | 1.00 | 36.45 |
| ATOM | 468 | H | PHE | 48 | 56.529 | 37.505 | 44.412 | 1.00 | 0.00 |
| ATOM | 469 | CA | PHE | 48 | 56.428 | 36.398 | 46.226 | 1.00 | 34.29 |
| ATOM | 470 | CB | PHE | 48 | 55.710 | 37.268 | 47.252 | 1.00 | 30.97 |
| ATOM | 471 | CG | PHE | 48 | 54.509 | 38.048 | 46.766 | 1.00 | 31.16 |
| ATOM | 472 | CD1 | PHE | 48 | 54.679 | 39.206 | 46.001 | 1.00 | 30.30 |
| ATOM | 473 | CD2 | PHE | 48 | 53.212 | 37.643 | 47.146 | 1.00 | 32.81 |
| ATOM | 474 | CE1 | PHE | 48 | 53.545 | 39.949 | 45.634 | 1.00 | 31.75 |
| ATOM | 475 | CE2 | PHE | 48 | 52.085 | 38.402 | 46.770 | 1.00 | 29.93 |
| ATOM | 476 | CZ | PHE | 48 | 52.254 | 39.557 | 46.016 | 1.00 | 29.15 |

FIG. 1: A-9

| ATOM | 477 | C | PHE | 48 | 55.414 | 35.364 | 45.707 | 1.00 | 34.91 |
| --- | --- | --- | --- | --- | --- | --- | --- | --- | --- |
| ATOM | 478 | O | PHE | 48 | 54.771 | 35.615 | 44.697 | 1.00 | 35.21 |
| ATOM | 479 | N | MET | 49 | 55.293 | 34.189 | 46.341 | 1.00 | 35.75 |
| ATOM | 480 | H | MET | 49 | 55.922 | 34.053 | 47.077 | 1.00 | 0.00 |
| ATOM | 481 | CA | MET | 49 | 54.326 | 33.108 | 46.087 | 1.00 | 35.33 |
| ATOM | 482 | CB | MET | 49 | 54.925 | 31.803 | 46.679 | 1.00 | 38.16 |
| ATOM | 483 | CG | MET | 49 | 54.063 | 30.523 | 46.688 | 1.00 | 45.74 |
| ATOM | 484 | SD | MET | 49 | 54.317 | 29.195 | 47.950 | 1.00 | 53.12 |
| ATOM | 485 | CE | MET | 49 | 55.717 | 28.211 | 47.465 | 1.00 | 47.62 |
| ATOM | 486 | C | MET | 49 | 52.951 | 33.437 | 46.718 | 1.00 | 34.27 |
| ATOM | 487 | O | MET | 49 | 52.802 | 33.406 | 47.946 | 1.00 | 35.14 |
| ATOM | 488 | N | LEU | 50 | 51.906 | 33.818 | 45.956 | 1.00 | 33.74 |
| ATOM | 489 | H | LEU | 50 | 52.087 | 33.902 | 44.992 | 1.00 | 0.00 |
| ATOM | 490 | CA | LEU | 50 | 50.544 | 34.145 | 46.466 | 1.00 | 30.96 |
| ATOM | 491 | CB | LEU | 50 | 49.704 | 34.589 | 45.273 | 1.00 | 28.85 |
| ATOM | 492 | CG | LEU | 50 | 48.364 | 35.276 | 45.440 | 1.00 | 26.99 |
| ATOM | 493 | CD1 | LEU | 50 | 48.504 | 36.547 | 46.254 | 1.00 | 27.85 |
| ATOM | 494 | CD2 | LEU | 50 | 47.842 | 35.636 | 44.088 | 1.00 | 22.86 |
| ATOM | 495 | C | LEU | 50 | 49.808 | 33.018 | 47.226 | 1.00 | 32.10 |
| ATOM | 496 | O | LEU | 50 | 50.064 | 31.831 | 46.968 | 1.00 | 33.28 |
| ATOM | 497 | N | GLY | 51 | 48.875 | 33.204 | 48.170 | 1.00 | 32.19 |
| ATOM | 498 | H | GLY | 51 | 48.557 | 34.116 | 48.321 | 1.00 | 0.00 |
| ATOM | 499 | CA | GLY | 51 | 48.310 | 32.048 | 48.914 | 1.00 | 32.20 |
| ATOM | 500 | C | GLY | 51 | 49.144 | 31.575 | 50.118 | 1.00 | 32.53 |
| ATOM | 501 | O | GLY | 51 | 48.692 | 31.520 | 51.253 | 1.00 | 30.27 |
| ATOM | 502 | N | LYS | 52 | 50.419 | 31.279 | 49.905 | 1.00 | 35.99 |
| ATOM | 503 | H | LYS | 52 | 50.712 | 31.268 | 48.971 | 1.00 | 0.00 |
| ATOM | 504 | CA | LYS | 52 | 51.397 | 30.935 | 50.944 | 1.00 | 37.12 |
| ATOM | 505 | CB | LYS | 52 | 52.654 | 30.449 | 50.251 | 1.00 | 41.85 |
| ATOM | 506 | CG | LYS | 52 | 53.557 | 29.560 | 51.117 | 1.00 | 47.92 |
| ATOM | 507 | CD | LYS | 52 | 55.001 | 30.068 | 51.090 | 1.00 | 50.14 |
| ATOM | 508 | CE | LYS | 52 | 55.671 | 29.809 | 52.438 | 1.00 | 52.41 |
| ATOM | 509 | NZ | LYS | 52 | 57.050 | 30.246 | 52.362 | 1.00 | 55.15 |
| ATOM | 510 | HZ1 | LYS | 52 | 57.521 | 30.087 | 53.275 | 1.00 | 0.00 |
| ATOM | 511 | HZ2 | LYS | 52 | 57.050 | 31.264 | 52.148 | 1.00 | 0.00 |
| ATOM | 512 | HZ3 | LYS | 52 | 57.555 | 29.735 | 51.612 | 1.00 | 0.00 |
| ATOM | 513 | C | LYS | 52 | 51.786 | 32.005 | 51.974 | 1.00 | 35.55 |
| ATOM | 514 | O | LYS | 52 | 52.895 | 32.040 | 52.474 | 1.00 | 35.47 |
| ATOM | 515 | N | GLN | 53 | 50.965 | 32.970 | 52.378 | 1.00 | 36.40 |
| ATOM | 516 | H | GLN | 53 | 50.055 | 32.946 | 52.017 | 1.00 | 0.00 |
| ATOM | 517 | CA | GLN | 53 | 51.294 | 33.898 | 53.479 | 1.00 | 37.96 |
| ATOM | 518 | CB | GLN | 53 | 51.170 | 33.090 | 54.792 | 1.00 | 40.53 |
| ATOM | 519 | CG | GLN | 53 | 50.001 | 32.088 | 54.980 | 1.00 | 44.03 |
| ATOM | 520 | CD | GLN | 53 | 50.479 | 30.689 | 55.421 | 1.00 | 43.54 |
| ATOM | 521 | OE1 | GLN | 53 | 50.412 | 29.683 | 54.711 | 1.00 | 41.92 |
| ATOM | 522 | NE2 | GLN | 53 | 51.030 | 30.534 | 56.611 | 1.00 | 43.08 |
| ATOM | 523 | HE21 | GLN | 53 | 51.286 | 29.611 | 56.795 | 1.00 | 0.00 |
| ATOM | 524 | HE22 | GLN | 53 | 51.156 | 31.307 | 57.188 | 1.00 | 0.00 |
| ATOM | 525 | C | GLN | 53 | 52.624 | 34.715 | 53.523 | 1.00 | 38.13 |
| ATOM | 526 | O | GLN | 53 | 52.994 | 35.274 | 54.560 | 1.00 | 39.71 |
| ATOM | 527 | N | GLU | 54 | 53.443 | 34.841 | 52.474 | 1.00 | 37.00 |
| ATOM | 528 | H | GLU | 54 | 53.262 | 34.222 | 51.741 | 1.00 | 0.00 |
| ATOM | 529 | CA | GLU | 54 | 54.709 | 35.618 | 52.489 | 1.00 | 36.22 |
| ATOM | 530 | CB | GLU | 54 | 55.472 | 35.223 | 51.222 | 1.00 | 36.71 |
| ATOM | 531 | CG | GLU | 54 | 55.891 | 33.753 | 51.070 | 1.00 | 36.14 |
| ATOM | 532 | CD | GLU | 54 | 56.704 | 33.442 | 49.817 | 1.00 | 38.51 |
| ATOM | 533 | OE1 | GLU | 54 | 57.119 | 34.382 | 49.126 | 1.00 | 38.90 |
| ATOM | 534 | OE2 | GLU | 54 | 56.928 | 32.258 | 49.523 | 1.00 | 39.98 |
| ATOM | 535 | C | GLU | 54 | 54.741 | 37.184 | 52.627 | 1.00 | 35.40 |
| ATOM | 536 | O | GLU | 54 | 55.771 | 37.873 | 52.686 | 1.00 | 35.37 |

FIG. 1: A-10

| ATOM | 537 | N | VAL | 55 | 53.587 | 37.844 | 52.632 | 1.00 | 33.24 |
|---|---|---|---|---|---|---|---|---|---|
| ATOM | 538 | H | VAL | 55 | 52.773 | 37.305 | 52.699 | 1.00 | 0.00 |
| ATOM | 539 | CA | VAL | 55 | 53.478 | 39.291 | 52.675 | 1.00 | 29.96 |
| ATOM | 540 | CB | VAL | 55 | 53.299 | 39.801 | 51.193 | 1.00 | 30.84 |
| ATOM | 541 | CG1 | VAL | 55 | 54.436 | 39.323 | 50.303 | 1.00 | 29.50 |
| ATOM | 542 | CG2 | VAL | 55 | 52.000 | 39.285 | 50.598 | 1.00 | 29.78 |
| ATOM | 543 | C | VAL | 55 | 52.303 | 39.761 | 53.570 | 1.00 | 29.32 |
| ATOM | 544 | O | VAL | 55 | 51.381 | 38.981 | 53.886 | 1.00 | 29.24 |
| ATOM | 545 | N | ILE | 56 | 52.244 | 41.021 | 54.005 | 1.00 | 28.85 |
| ATOM | 546 | H | ILE | 56 | 53.060 | 41.556 | 53.927 | 1.00 | 0.00 |
| ATOM | 547 | CA | ILE | 56 | 51.082 | 41.525 | 54.744 | 1.00 | 28.81 |
| ATOM | 548 | CB | ILE | 56 | 51.242 | 43.048 | 55.091 | 1.00 | 28.00 |
| ATOM | 549 | CG2 | ILE | 56 | 52.228 | 43.047 | 56.234 | 1.00 | 28.05 |
| ATOM | 550 | CG1 | ILE | 56 | 51.662 | 43.961 | 53.956 | 1.00 | 24.01 |
| ATOM | 551 | CD1 | ILE | 56 | 51.316 | 45.414 | 54.287 | 1.00 | 17.23 |
| ATOM | 552 | C | ILE | 56 | 49.738 | 41.318 | 54.006 | 1.00 | 29.72 |
| ATOM | 553 | O | ILE | 56 | 49.735 | 41.387 | 52.769 | 1.00 | 30.04 |
| ATOM | 554 | N | ARG | 57 | 48.579 | 41.114 | 54.675 | 1.00 | 30.29 |
| ATOM | 555 | H | ARG | 57 | 48.601 | 41.193 | 55.657 | 1.00 | 0.00 |
| ATOM | 556 | CA | ARG | 57 | 47.371 | 40.689 | 53.974 | 1.00 | 31.47 |
| ATOM | 557 | CB | ARG | 57 | 46.365 | 40.215 | 54.974 | 1.00 | 32.72 |
| ATOM | 558 | CG | ARG | 57 | 45.411 | 39.104 | 54.490 | 1.00 | 38.09 |
| ATOM | 559 | CD | ARG | 57 | 45.981 | 37.653 | 54.488 | 1.00 | 41.25 |
| ATOM | 560 | NE | ARG | 57 | 44.951 | 36.602 | 54.311 | 1.00 | 45.34 |
| ATOM | 561 | HE | ARG | 57 | 44.950 | 36.114 | 53.462 | 1.00 | 0.00 |
| ATOM | 562 | CZ | ARG | 57 | 44.012 | 36.222 | 55.255 | 1.00 | 48.44 |
| ATOM | 563 | NH1 | ARG | 57 | 43.125 | 35.237 | 54.974 | 1.00 | 44.33 |
| ATOM | 564 | HH11 | ARG | 57 | 43.170 | 34.768 | 54.091 | 1.00 | 0.00 |
| ATOM | 565 | HH12 | ARG | 57 | 42.458 | 34.951 | 55.662 | 1.00 | 0.00 |
| ATOM | 566 | NH2 | ARG | 57 | 43.923 | 36.770 | 56.494 | 1.00 | 46.09 |
| ATOM | 567 | HH21 | ARG | 57 | 43.215 | 36.452 | 57.124 | 1.00 | 0.00 |
| ATOM | 568 | HH22 | ARG | 57 | 44.547 | 37.502 | 56.763 | 1.00 | 0.00 |
| ATOM | 569 | C | ARG | 57 | 46.754 | 41.751 | 53.093 | 1.00 | 32.82 |
| ATOM | 570 | O | ARG | 57 | 45.949 | 41.493 | 52.191 | 1.00 | 36.68 |
| ATOM | 571 | N | GLY | 58 | 47.191 | 42.983 | 53.321 | 1.00 | 32.92 |
| ATOM | 572 | H | GLY | 58 | 47.709 | 43.132 | 54.137 | 1.00 | 0.00 |
| ATOM | 573 | CA | GLY | 58 | 46.891 | 44.102 | 52.445 | 1.00 | 29.68 |
| ATOM | 574 | C | GLY | 58 | 47.551 | 43.795 | 51.119 | 1.00 | 29.05 |
| ATOM | 575 | O | GLY | 58 | 46.937 | 43.991 | 50.074 | 1.00 | 31.35 |
| ATOM | 576 | N | TRP | 59 | 48.765 | 43.241 | 51.093 | 1.00 | 28.03 |
| ATOM | 577 | H | TRP | 59 | 49.243 | 43.102 | 51.934 | 1.00 | 0.00 |
| ATOM | 578 | CA | TRP | 59 | 49.332 | 42.816 | 49.818 | 1.00 | 28.52 |
| ATOM | 579 | CB | TRP | 59 | 50.821 | 42.548 | 49.847 | 1.00 | 26.34 |
| ATOM | 580 | CG | TRP | 59 | 51.689 | 43.718 | 49.340 | 1.00 | 23.30 |
| ATOM | 581 | CD2 | TRP | 59 | 52.739 | 43.650 | 48.445 | 1.00 | 17.27 |
| ATOM | 582 | CE2 | TRP | 59 | 53.247 | 44.928 | 48.520 | 1.00 | 15.62 |
| ATOM | 583 | CE3 | TRP | 59 | 53.353 | 42.732 | 47.610 | 1.00 | 18.23 |
| ATOM | 584 | CD1 | TRP | 59 | 51.551 | 44.963 | 49.887 | 1.00 | 20.47 |
| ATOM | 585 | NE1 | TRP | 59 | 52.526 | 45.656 | 49.369 | 1.00 | 20.44 |
| ATOM | 586 | HE1 | TRP | 59 | 52.604 | 46.626 | 49.499 | 1.00 | 0.00 |
| ATOM | 587 | CZ2 | TRP | 59 | 54.356 | 45.312 | 47.792 | 1.00 | 14.10 |
| ATOM | 588 | CZ3 | TRP | 59 | 54.476 | 43.104 | 46.865 | 1.00 | 16.40 |
| ATOM | 589 | CH2 | TRP | 59 | 54.981 | 44.393 | 46.958 | 1.00 | 14.34 |
| ATOM | 590 | C | TRP | 59 | 48.745 | 41.555 | 49.240 | 1.00 | 29.75 |
| ATOM | 591 | O | TRP | 59 | 48.380 | 41.568 | 48.075 | 1.00 | 30.98 |
| ATOM | 592 | N | GLU | 60 | 48.575 | 40.458 | 49.963 | 1.00 | 33.00 |
| ATOM | 593 | H | GLU | 60 | 48.885 | 40.486 | 50.893 | 1.00 | 0.00 |
| ATOM | 594 | CA | GLU | 60 | 47.988 | 39.243 | 49.364 | 1.00 | 36.15 |
| ATOM | 595 | CB | GLU | 60 | 47.851 | 38.104 | 50.380 | 1.00 | 38.46 |
| ATOM | 596 | CG | GLU | 60 | 48.122 | 36.774 | 49.652 | 1.00 | 41.72 |

FIG. 1: A-11

| | | | | | | | | |
|---|---|---|---|---|---|---|---|---|
| ATOM | 597 | CD | GLU | 60 | 49.291 | 35.928 | 50.149 | 1.00 | 44.26 |
| ATOM | 598 | OE1 | GLU | 60 | 49.063 | 34.762 | 50.479 | 1.00 | 45.57 |
| ATOM | 599 | OE2 | GLU | 60 | 50.426 | 36.406 | 50.194 | 1.00 | 47.14 |
| ATOM | 600 | C | GLU | 60 | 46.616 | 39.443 | 48.744 | 1.00 | 37.17 |
| ATOM | 601 | O | GLU | 60 | 46.388 | 39.068 | 47.590 | 1.00 | 35.88 |
| ATOM | 602 | N | GLU | 61 | 45.721 | 40.094 | 49.492 | 1.00 | 38.28 |
| ATOM | 603 | H | GLU | 61 | 45.949 | 40.334 | 50.415 | 1.00 | 0.00 |
| ATOM | 604 | CA | GLU | 61 | 44.428 | 40.455 | 48.946 | 1.00 | 40.12 |
| ATOM | 605 | CB | GLU | 61 | 43.541 | 40.997 | 50.079 | 1.00 | 41.82 |
| ATOM | 606 | CG | GLU | 61 | 42.032 | 41.132 | 49.685 | 1.00 | 45.70 |
| ATOM | 607 | CD | GLU | 61 | 41.126 | 41.860 | 50.681 | 1.00 | 46.57 |
| ATOM | 608 | OE1 | GLU | 61 | 41.018 | 41.378 | 51.816 | 1.00 | 48.32 |
| ATOM | 609 | OE2 | GLU | 61 | 40.546 | 42.897 | 50.326 | 1.00 | 42.68 |
| ATOM | 610 | C | GLU | 61 | 44.545 | 41.513 | 47.806 | 1.00 | 40.85 |
| ATOM | 611 | O | GLU | 61 | 44.018 | 41.302 | 46.700 | 1.00 | 43.70 |
| ATOM | 612 | N | GLY | 62 | 45.256 | 42.643 | 47.983 | 1.00 | 38.17 |
| ATOM | 613 | H | GLY | 62 | 45.724 | 42.757 | 48.837 | 1.00 | 0.00 |
| ATOM | 614 | CA | GLY | 62 | 45.362 | 43.702 | 46.988 | 1.00 | 33.48 |
| ATOM | 615 | C | GLY | 62 | 45.998 | 43.311 | 45.661 | 1.00 | 32.00 |
| ATOM | 616 | O | GLY | 62 | 45.474 | 43.556 | 44.567 | 1.00 | 31.30 |
| ATOM | 617 | N | VAL | 63 | 47.154 | 42.680 | 45.733 | 1.00 | 30.37 |
| ATOM | 618 | H | VAL | 63 | 47.564 | 42.533 | 46.611 | 1.00 | 0.00 |
| ATOM | 619 | CA | VAL | 63 | 47.809 | 42.229 | 44.516 | 1.00 | 31.68 |
| ATOM | 620 | CB | VAL | 63 | 49.253 | 41.782 | 44.854 | 1.00 | 27.55 |
| ATOM | 621 | CG1 | VAL | 63 | 49.949 | 41.351 | 43.592 | 1.00 | 25.68 |
| ATOM | 622 | CG2 | VAL | 63 | 50.042 | 42.918 | 45.473 | 1.00 | 24.53 |
| ATOM | 623 | C | VAL | 63 | 46.983 | 41.081 | 43.886 | 1.00 | 35.52 |
| ATOM | 624 | O | VAL | 63 | 47.022 | 40.853 | 42.669 | 1.00 | 37.20 |
| ATOM | 625 | N | ALA | 64 | 46.171 | 40.335 | 44.662 | 1.00 | 37.43 |
| ATOM | 626 | H | ALA | 64 | 46.264 | 40.394 | 45.637 | 1.00 | 0.00 |
| ATOM | 627 | CA | ALA | 64 | 45.242 | 39.338 | 44.082 | 1.00 | 37.26 |
| ATOM | 628 | CB | ALA | 64 | 44.284 | 38.795 | 45.135 | 1.00 | 37.48 |
| ATOM | 629 | C | ALA | 64 | 44.359 | 39.907 | 42.962 | 1.00 | 36.85 |
| ATOM | 630 | O | ALA | 64 | 44.159 | 39.339 | 41.882 | 1.00 | 35.68 |
| ATOM | 631 | N | GLN | 65 | 43.917 | 41.131 | 43.280 | 1.00 | 35.68 |
| ATOM | 632 | H | GLN | 65 | 44.228 | 41.501 | 44.132 | 1.00 | 0.00 |
| ATOM | 633 | CA | GLN | 65 | 43.084 | 41.953 | 42.426 | 1.00 | 33.82 |
| ATOM | 634 | CB | GLN | 65 | 42.387 | 42.998 | 43.320 | 1.00 | 31.98 |
| ATOM | 635 | CG | GLN | 65 | 41.413 | 42.339 | 44.271 | 1.00 | 32.72 |
| ATOM | 636 | CD | GLN | 65 | 41.089 | 43.076 | 45.562 | 1.00 | 36.64 |
| ATOM | 637 | OE1 | GLN | 65 | 40.593 | 44.193 | 45.593 | 1.00 | 39.18 |
| ATOM | 638 | NE2 | GLN | 65 | 41.327 | 42.544 | 46.749 | 1.00 | 37.45 |
| ATOM | 639 | HE21 | GLN | 65 | 41.804 | 41.694 | 46.796 | 1.00 | 0.00 |
| ATOM | 640 | HE22 | GLN | 65 | 40.981 | 43.069 | 47.492 | 1.00 | 0.00 |
| ATOM | 641 | C | GLN | 65 | 43.850 | 42.630 | 41.287 | 1.00 | 34.72 |
| ATOM | 642 | O | GLN | 65 | 43.338 | 43.597 | 40.716 | 1.00 | 39.31 |
| ATOM | 643 | N | MET | 66 | 45.030 | 42.187 | 40.841 | 1.00 | 33.73 |
| ATOM | 644 | H | MET | 66 | 45.401 | 41.357 | 41.212 | 1.00 | 0.00 |
| ATOM | 645 | CA | MET | 66 | 45.773 | 42.902 | 39.790 | 1.00 | 32.72 |
| ATOM | 646 | CB | MET | 66 | 47.164 | 43.337 | 40.337 | 1.00 | 30.79 |
| ATOM | 647 | CG | MET | 66 | 47.055 | 44.645 | 41.125 | 1.00 | 33.02 |
| ATOM | 648 | SD | MET | 66 | 48.593 | 45.437 | 41.680 | 1.00 | 30.39 |
| ATOM | 649 | CE | MET | 66 | 49.703 | 44.956 | 40.404 | 1.00 | 34.75 |
| ATOM | 650 | C | MET | 66 | 45.992 | 42.217 | 38.441 | 1.00 | 33.11 |
| ATOM | 651 | O | MET | 66 | 46.232 | 41.002 | 38.381 | 1.00 | 32.31 |
| ATOM | 652 | N | SER | 67 | 45.910 | 42.951 | 37.311 | 1.00 | 33.02 |
| ATOM | 653 | H | SER | 67 | 45.580 | 43.859 | 37.394 | 1.00 | 0.00 |
| ATOM | 654 | CA | SER | 67 | 46.184 | 42.362 | 35.973 | 1.00 | 34.10 |
| ATOM | 655 | CB | SER | 67 | 45.507 | 43.030 | 34.764 | 1.00 | 33.83 |
| ATOM | 656 | OG | SER | 67 | 44.178 | 43.505 | 34.864 | 1.00 | 37.19 |

FIG. 1: A-12

| | | | | | | | | |
|---|---|---|---|---|---|---|---|---|
| ATOM | 657 | HG | SER | 67 | 44.119 | 44.205 | 35.528 | 1.00 | 0.00 |
| ATOM | 658 | C | SER | 67 | 47.653 | 42.496 | 35.597 | 1.00 | 32.59 |
| ATOM | 659 | O | SER | 67 | 48.275 | 43.464 | 35.991 | 1.00 | 30.48 |
| ATOM | 660 | N | VAL | 68 | 48.316 | 41.628 | 34.838 | 1.00 | 34.29 |
| ATOM | 661 | H | VAL | 68 | 47.840 | 40.800 | 34.613 | 1.00 | 0.00 |
| ATOM | 662 | CA | VAL | 68 | 49.722 | 41.820 | 34.422 | 1.00 | 32.97 |
| ATOM | 663 | CB | VAL | 68 | 50.157 | 40.543 | 33.651 | 1.00 | 34.46 |
| ATOM | 664 | CG1 | VAL | 68 | 51.591 | 40.603 | 33.168 | 1.00 | 35.72 |
| ATOM | 665 | CG2 | VAL | 68 | 50.084 | 39.361 | 34.615 | 1.00 | 34.40 |
| ATOM | 666 | C | VAL | 68 | 49.952 | 43.104 | 33.603 | 1.00 | 31.72 |
| ATOM | 667 | O | VAL | 68 | 49.329 | 43.415 | 32.581 | 1.00 | 31.58 |
| ATOM | 668 | N | GLY | 69 | 50.873 | 43.873 | 34.175 | 1.00 | 29.96 |
| ATOM | 669 | H | GLY | 69 | 51.430 | 43.484 | 34.882 | 1.00 | 0.00 |
| ATOM | 670 | CA | GLY | 69 | 51.150 | 45.221 | 33.737 | 1.00 | 29.11 |
| ATOM | 671 | C | GLY | 69 | 50.294 | 46.253 | 34.477 | 1.00 | 30.32 |
| ATOM | 672 | O | GLY | 69 | 50.373 | 47.467 | 34.256 | 1.00 | 31.12 |
| ATOM | 673 | N | GLN | 70 | 49.372 | 45.806 | 35.326 | 1.00 | 30.54 |
| ATOM | 674 | H | GLN | 70 | 49.253 | 44.849 | 35.388 | 1.00 | 0.00 |
| ATOM | 675 | CA | GLN | 70 | 48.557 | 46.721 | 36.102 | 1.00 | 31.29 |
| ATOM | 676 | CB | GLN | 70 | 47.329 | 46.059 | 36.732 | 1.00 | 32.00 |
| ATOM | 677 | CG | GLN | 70 | 46.186 | 47.013 | 37.104 | 1.00 | 33.97 |
| ATOM | 678 | CD | GLN | 70 | 44.926 | 46.303 | 37.579 | 1.00 | 36.12 |
| ATOM | 679 | OE1 | GLN | 70 | 44.442 | 45.295 | 37.062 | 1.00 | 40.80 |
| ATOM | 680 | NE2 | GLN | 70 | 44.305 | 46.714 | 38.648 | 1.00 | 37.28 |
| ATOM | 681 | HE21 | GLN | 70 | 43.501 | 46.189 | 38.841 | 1.00 | 0.00 |
| ATOM | 682 | HE22 | GLN | 70 | 44.665 | 47.431 | 39.193 | 1.00 | 0.00 |
| ATOM | 683 | C | GLN | 70 | 49.414 | 47.258 | 37.236 | 1.00 | 32.86 |
| ATOM | 684 | O | GLN | 70 | 50.041 | 46.527 | 38.012 | 1.00 | 31.95 |
| ATOM | 685 | N | ARG | 71 | 49.491 | 48.585 | 37.152 | 1.00 | 32.49 |
| ATOM | 686 | H | ARG | 71 | 49.202 | 48.957 | 36.292 | 1.00 | 0.00 |
| ATOM | 687 | CA | ARG | 71 | 50.099 | 49.470 | 38.132 | 1.00 | 31.24 |
| ATOM | 688 | CB | ARG | 71 | 50.891 | 50.555 | 37.374 | 1.00 | 33.82 |
| ATOM | 689 | CG | ARG | 71 | 51.417 | 51.583 | 38.328 | 1.00 | 40.25 |
| ATOM | 690 | CD | ARG | 71 | 52.293 | 52.658 | 37.744 | 1.00 | 46.99 |
| ATOM | 691 | NE | ARG | 71 | 51.645 | 53.546 | 36.778 | 1.00 | 50.72 |
| ATOM | 692 | HE | ARG | 71 | 50.723 | 53.375 | 36.497 | 1.00 | 0.00 |
| ATOM | 693 | CZ | ARG | 71 | 52.315 | 54.601 | 36.262 | 1.00 | 51.22 |
| ATOM | 694 | NH1 | ARG | 71 | 51.719 | 55.352 | 35.326 | 1.00 | 48.94 |
| ATOM | 695 | HH11 | ARG | 71 | 50.799 | 55.118 | 35.012 | 1.00 | 0.00 |
| ATOM | 696 | HH12 | ARG | 71 | 52.204 | 56.132 | 34.928 | 1.00 | 0.00 |
| ATOM | 697 | NH2 | ARG | 71 | 53.552 | 54.931 | 36.692 | 1.00 | 49.74 |
| ATOM | 698 | HH21 | ARG | 71 | 53.996 | 54.400 | 37.413 | 1.00 | 0.00 |
| ATOM | 699 | HH22 | ARG | 71 | 54.022 | 55.720 | 36.296 | 1.00 | 0.00 |
| ATOM | 700 | C | ARG | 71 | 48.963 | 50.061 | 38.970 | 1.00 | 28.83 |
| ATOM | 701 | O | ARG | 71 | 48.120 | 50.804 | 38.454 | 1.00 | 28.36 |
| ATOM | 702 | N | ALA | 72 | 48.888 | 49.750 | 40.256 | 1.00 | 27.78 |
| ATOM | 703 | H | ALA | 72 | 49.604 | 49.197 | 40.635 | 1.00 | 0.00 |
| ATOM | 704 | CA | ALA | 72 | 47.806 | 50.195 | 41.123 | 1.00 | 27.48 |
| ATOM | 705 | CB | ALA | 72 | 46.778 | 49.108 | 41.359 | 1.00 | 28.71 |
| ATOM | 706 | C | ALA | 72 | 48.226 | 50.619 | 42.507 | 1.00 | 27.52 |
| ATOM | 707 | O | ALA | 72 | 49.211 | 50.140 | 43.033 | 1.00 | 30.60 |
| ATOM | 708 | N | LYS | 73 | 47.444 | 51.491 | 43.110 | 1.00 | 27.01 |
| ATOM | 709 | H | LYS | 73 | 46.705 | 51.845 | 42.584 | 1.00 | 0.00 |
| ATOM | 710 | CA | LYS | 73 | 47.578 | 51.987 | 44.470 | 1.00 | 25.46 |
| ATOM | 711 | CB | LYS | 73 | 47.274 | 53.480 | 44.495 | 1.00 | 24.08 |
| ATOM | 712 | CG | LYS | 73 | 46.995 | 54.164 | 45.817 | 1.00 | 23.30 |
| ATOM | 713 | CD | LYS | 73 | 47.096 | 55.658 | 45.582 | 1.00 | 25.76 |
| ATOM | 714 | CE | LYS | 73 | 46.470 | 56.399 | 46.760 | 1.00 | 30.11 |
| ATOM | 715 | NZ | LYS | 73 | 46.525 | 57.846 | 46.563 | 1.00 | 33.42 |
| ATOM | 716 | HZ1 | LYS | 73 | 45.930 | 58.104 | 45.750 | 1.00 | 0.00 |

FIG. 1: A-13

| ATOM | 717 | HZ2 | LYS | 73 | 47.506 | 58.142 | 46.377 | 1.00 | 0.00 |
|---|---|---|---|---|---|---|---|---|---|
| ATOM | 718 | HZ3 | LYS | 73 | 46.176 | 58.328 | 47.415 | 1.00 | 0.00 |
| ATOM | 719 | C | LYS | 73 | 46.673 | 51.282 | 45.465 | 1.00 | 26.41 |
| ATOM | 720 | O | LYS | 73 | 45.451 | 51.469 | 45.536 | 1.00 | 24.57 |
| ATOM | 721 | N | LEU | 74 | 47.354 | 50.437 | 46.231 | 1.00 | 28.26 |
| ATOM | 722 | H | LEU | 74 | 48.315 | 50.348 | 46.050 | 1.00 | 0.00 |
| ATOM | 723 | CA | LEU | 74 | 46.744 | 49.689 | 47.337 | 1.00 | 27.51 |
| ATOM | 724 | CB | LEU | 74 | 47.476 | 48.406 | 47.689 | 1.00 | 24.45 |
| ATOM | 725 | CG | LEU | 74 | 48.142 | 47.654 | 46.592 | 1.00 | 23.35 |
| ATOM | 726 | CD1 | LEU | 74 | 48.902 | 46.472 | 47.145 | 1.00 | 25.32 |
| ATOM | 727 | CD2 | LEU | 74 | 47.099 | 47.184 | 45.657 | 1.00 | 20.90 |
| ATOM | 728 | C | LEU | 74 | 46.826 | 50.539 | 48.591 | 1.00 | 28.08 |
| ATOM | 729 | O | LEU | 74 | 47.908 | 50.660 | 49.169 | 1.00 | 30.35 |
| ATOM | 730 | N | THR | 75 | 45.760 | 51.225 | 48.992 | 1.00 | 27.67 |
| ATOM | 731 | H | THR | 75 | 45.015 | 51.343 | 48.362 | 1.00 | 0.00 |
| ATOM | 732 | CA | THR | 75 | 45.749 | 51.891 | 50.286 | 1.00 | 25.75 |
| ATOM | 733 | CB | THR | 75 | 44.785 | 53.034 | 50.323 | 1.00 | 24.20 |
| ATOM | 734 | OG1 | THR | 75 | 45.017 | 53.894 | 49.214 | 1.00 | 25.23 |
| ATOM | 735 | HG1 | THR | 75 | 44.150 | 54.174 | 48.886 | 1.00 | 0.00 |
| ATOM | 736 | CG2 | THR | 75 | 45.003 | 53.828 | 51.565 | 1.00 | 26.72 |
| ATOM | 737 | C | THR | 75 | 45.307 | 50.848 | 51.304 | 1.00 | 28.10 |
| ATOM | 738 | O | THR | 75 | 44.208 | 50.287 | 51.324 | 1.00 | 30.18 |
| ATOM | 739 | N | ILE | 76 | 46.261 | 50.457 | 52.125 | 1.00 | 29.77 |
| ATOM | 740 | H | ILE | 76 | 47.151 | 50.869 | 52.049 | 1.00 | 0.00 |
| ATOM | 741 | CA | ILE | 76 | 46.029 | 49.433 | 53.125 | 1.00 | 29.87 |
| ATOM | 742 | CB | ILE | 76 | 47.209 | 48.529 | 53.200 | 1.00 | 26.82 |
| ATOM | 743 | CG2 | ILE | 76 | 46.897 | 47.388 | 54.152 | 1.00 | 23.97 |
| ATOM | 744 | CG1 | ILE | 76 | 47.539 | 48.069 | 51.802 | 1.00 | 23.51 |
| ATOM | 745 | CD1 | ILE | 76 | 48.881 | 47.377 | 51.662 | 1.00 | 25.59 |
| ATOM | 746 | C | ILE | 76 | 45.775 | 50.004 | 54.505 | 1.00 | 33.06 |
| ATOM | 747 | O | ILE | 76 | 46.367 | 50.991 | 54.937 | 1.00 | 34.29 |
| ATOM | 748 | N | SER | 77 | 44.836 | 49.364 | 55.187 | 1.00 | 34.85 |
| ATOM | 749 | H | SER | 77 | 44.324 | 48.700 | 54.684 | 1.00 | 0.00 |
| ATOM | 750 | CA | SER | 77 | 44.452 | 49.714 | 56.553 | 1.00 | 34.94 |
| ATOM | 751 | CB | SER | 77 | 42.973 | 49.458 | 56.706 | 1.00 | 32.22 |
| ATOM | 752 | OG | SER | 77 | 42.697 | 48.094 | 56.374 | 1.00 | 30.43 |
| ATOM | 753 | HG | SER | 77 | 43.342 | 47.549 | 56.862 | 1.00 | 0.00 |
| ATOM | 754 | C | SER | 77 | 45.198 | 48.960 | 57.668 | 1.00 | 36.01 |
| ATOM | 755 | O | SER | 77 | 45.059 | 47.728 | 57.699 | 1.00 | 35.63 |
| ATOM | 756 | N | PRO | 78 | 45.870 | 49.574 | 58.665 | 1.00 | 36.58 |
| ATOM | 757 | CD | PRO | 78 | 45.484 | 50.863 | 59.233 | 1.00 | 36.06 |
| ATOM | 758 | CA | PRO | 78 | 46.872 | 48.931 | 59.528 | 1.00 | 37.13 |
| ATOM | 759 | CB | PRO | 78 | 46.992 | 49.820 | 60.742 | 1.00 | 36.00 |
| ATOM | 760 | CG | PRO | 78 | 45.692 | 50.610 | 60.723 | 1.00 | 37.95 |
| ATOM | 761 | C | PRO | 78 | 46.633 | 47.494 | 59.941 | 1.00 | 37.64 |
| ATOM | 762 | O | PRO | 78 | 47.578 | 46.732 | 60.008 | 1.00 | 38.53 |
| ATOM | 763 | N | ASP | 79 | 45.408 | 47.034 | 60.163 | 1.00 | 39.49 |
| ATOM | 764 | H | ASP | 79 | 44.663 | 47.656 | 60.065 | 1.00 | 0.00 |
| ATOM | 765 | CA | ASP | 79 | 45.177 | 45.645 | 60.564 | 1.00 | 41.87 |
| ATOM | 766 | CB | ASP | 79 | 43.712 | 45.491 | 60.999 | 1.00 | 43.28 |
| ATOM | 767 | CG | ASP | 79 | 42.701 | 45.788 | 59.902 | 1.00 | 42.93 |
| ATOM | 768 | OD1 | ASP | 79 | 41.995 | 44.845 | 59.498 | 1.00 | 43.41 |
| ATOM | 769 | OD2 | ASP | 79 | 42.655 | 46.944 | 59.469 | 1.00 | 38.42 |
| ATOM | 770 | C | ASP | 79 | 45.513 | 44.630 | 59.472 | 1.00 | 41.98 |
| ATOM | 771 | O | ASP | 79 | 45.844 | 43.466 | 59.696 | 1.00 | 44.22 |
| ATOM | 772 | N | TYR | 80 | 45.429 | 45.108 | 58.235 | 1.00 | 41.78 |
| ATOM | 773 | H | TYR | 80 | 45.037 | 45.983 | 58.138 | 1.00 | 0.00 |
| ATOM | 774 | CA | TYR | 80 | 45.856 | 44.334 | 57.068 | 1.00 | 40.72 |
| ATOM | 775 | CB | TYR | 80 | 44.710 | 44.529 | 55.976 | 1.00 | 40.86 |
| ATOM | 776 | CG | TYR | 80 | 43.773 | 43.307 | 55.929 | 1.00 | 42.68 |

FIG. 1: A-14

| ATOM | 777 | CD1 | TYR | 80 | 44.106 | 42.202 | 56.747 | 1.00 | 46.71 |
|------|-----|-----|-----|----|--------|--------|--------|------|-------|
| ATOM | 778 | CE1 | TYR | 80 | 43.461 | 40.963 | 56.672 | 1.00 | 45.23 |
| ATOM | 779 | CD2 | TYR | 80 | 42.715 | 43.157 | 55.020 | 1.00 | 42.41 |
| ATOM | 780 | CE2 | TYR | 80 | 42.056 | 41.899 | 54.939 | 1.00 | 44.31 |
| ATOM | 781 | CZ | TYR | 80 | 42.447 | 40.803 | 55.756 | 1.00 | 44.01 |
| ATOM | 782 | OH | TYR | 80 | 41.969 | 39.510 | 55.638 | 1.00 | 41.07 |
| ATOM | 783 | HH | TYR | 80 | 41.329 | 39.467 | 54.920 | 1.00 | 0.00 |
| ATOM | 784 | C | TYR | 80 | 47.294 | 44.681 | 56.595 | 1.00 | 39.44 |
| ATOM | 785 | O | TYR | 80 | 47.716 | 44.474 | 55.458 | 1.00 | 38.04 |
| ATOM | 786 | N | ALA | 81 | 48.055 | 45.151 | 57.604 | 1.00 | 37.51 |
| ATOM | 787 | H | ALA | 81 | 47.627 | 45.151 | 58.481 | 1.00 | 0.00 |
| ATOM | 788 | CA | ALA | 81 | 49.438 | 45.627 | 57.590 | 1.00 | 34.06 |
| ATOM | 789 | CB | ALA | 81 | 49.453 | 47.121 | 57.265 | 1.00 | 30.75 |
| ATOM | 790 | C | ALA | 81 | 50.075 | 45.394 | 58.987 | 1.00 | 33.78 |
| ATOM | 791 | O | ALA | 81 | 50.153 | 44.241 | 59.419 | 1.00 | 33.43 |
| ATOM | 792 | N | TYR | 82 | 50.478 | 46.396 | 59.797 | 1.00 | 32.85 |
| ATOM | 793 | H | TYR | 82 | 50.267 | 47.306 | 59.519 | 1.00 | 0.00 |
| ATOM | 794 | CA | TYR | 82 | 51.169 | 46.176 | 61.081 | 1.00 | 34.87 |
| ATOM | 795 | CB | TYR | 82 | 52.405 | 47.096 | 61.027 | 1.00 | 28.44 |
| ATOM | 796 | CG | TYR | 82 | 53.289 | 46.636 | 59.863 | 1.00 | 24.90 |
| ATOM | 797 | CD1 | TYR | 82 | 53.328 | 47.357 | 58.674 | 1.00 | 25.10 |
| ATOM | 798 | CE1 | TYR | 82 | 53.986 | 46.866 | 57.544 | 1.00 | 21.45 |
| ATOM | 799 | CD2 | TYR | 82 | 53.948 | 45.409 | 59.913 | 1.00 | 24.80 |
| ATOM | 800 | CE2 | TYR | 82 | 54.599 | 44.910 | 58.794 | 1.00 | 22.97 |
| ATOM | 801 | CZ | TYR | 82 | 54.609 | 45.645 | 57.621 | 1.00 | 21.85 |
| ATOM | 802 | OH | TYR | 82 | 55.259 | 45.136 | 56.533 | 1.00 | 24.65 |
| ATOM | 803 | HH | TYR | 82 | 55.256 | 45.782 | 55.814 | 1.00 | 0.00 |
| ATOM | 804 | C | TYR | 82 | 50.379 | 46.316 | 62.413 | 1.00 | 40.53 |
| ATOM | 805 | O | TYR | 82 | 50.766 | 45.858 | 63.501 | 1.00 | 42.10 |
| ATOM | 806 | N | GLY | 83 | 49.197 | 46.954 | 62.321 | 1.00 | 45.31 |
| ATOM | 807 | H | GLY | 83 | 48.945 | 47.208 | 61.412 | 1.00 | 0.00 |
| ATOM | 808 | CA | GLY | 83 | 48.187 | 47.156 | 63.377 | 1.00 | 47.72 |
| ATOM | 809 | C | GLY | 83 | 48.507 | 47.941 | 64.651 | 1.00 | 50.23 |
| ATOM | 810 | O | GLY | 83 | 48.115 | 49.101 | 64.910 | 1.00 | 52.47 |
| ATOM | 811 | N | ALA | 84 | 49.195 | 47.183 | 65.493 | 1.00 | 49.36 |
| ATOM | 812 | H | ALA | 84 | 49.431 | 46.273 | 65.210 | 1.00 | 0.00 |
| ATOM | 813 | CA | ALA | 84 | 49.556 | 47.712 | 66.797 | 1.00 | 47.15 |
| ATOM | 814 | CB | ALA | 84 | 49.196 | 46.683 | 67.890 | 1.00 | 50.91 |
| ATOM | 815 | C | ALA | 84 | 51.029 | 48.053 | 66.918 | 1.00 | 43.75 |
| ATOM | 816 | O | ALA | 84 | 51.408 | 49.202 | 67.136 | 1.00 | 38.36 |
| ATOM | 817 | N | THR | 85 | 51.811 | 46.998 | 66.682 | 1.00 | 40.44 |
| ATOM | 818 | H | THR | 85 | 51.398 | 46.173 | 66.357 | 1.00 | 0.00 |
| ATOM | 819 | CA | THR | 85 | 53.258 | 47.031 | 66.838 | 1.00 | 40.70 |
| ATOM | 820 | CB | THR | 85 | 53.831 | 45.608 | 66.953 | 1.00 | 38.80 |
| ATOM | 821 | OG1 | THR | 85 | 53.559 | 44.877 | 65.764 | 1.00 | 39.70 |
| ATOM | 822 | HG1 | THR | 85 | 54.155 | 45.179 | 65.057 | 1.00 | 0.00 |
| ATOM | 823 | CG2 | THR | 85 | 53.186 | 44.871 | 68.096 | 1.00 | 40.87 |
| ATOM | 824 | C | THR | 85 | 54.089 | 47.729 | 65.773 | 1.00 | 41.15 |
| ATOM | 825 | O | THR | 85 | 55.298 | 47.904 | 65.936 | 1.00 | 43.48 |
| ATOM | 826 | N | GLY | 86 | 53.468 | 48.113 | 64.652 | 1.00 | 40.17 |
| ATOM | 827 | H | GLY | 86 | 52.514 | 47.924 | 64.589 | 1.00 | 0.00 |
| ATOM | 828 | CA | GLY | 86 | 54.191 | 48.689 | 63.524 | 1.00 | 37.20 |
| ATOM | 829 | C | GLY | 86 | 55.336 | 47.771 | 63.059 | 1.00 | 35.37 |
| ATOM | 830 | O | GLY | 86 | 55.296 | 46.539 | 63.204 | 1.00 | 35.07 |
| ATOM | 831 | N | HIS | 87 | 56.406 | 48.357 | 62.517 | 1.00 | 33.89 |
| ATOM | 832 | H | HIS | 87 | 56.406 | 49.342 | 62.482 | 1.00 | 0.00 |
| ATOM | 833 | CA | HIS | 87 | 57.582 | 47.577 | 62.181 | 1.00 | 30.63 |
| ATOM | 834 | CB | HIS | 87 | 57.718 | 47.423 | 60.705 | 1.00 | 28.30 |
| ATOM | 835 | CG | HIS | 87 | 58.358 | 46.073 | 60.452 | 1.00 | 29.42 |
| ATOM | 836 | CD2 | HIS | 87 | 59.654 | 45.893 | 60.034 | 1.00 | 27.09 |

FIG. 1: A-15

| | | | | | | | | |
|---|---|---|---|---|---|---|---|---|
| ATOM | 837 | ND1 | HIS | 87 | 57.798 | 44.851 | 60.608 | 1.00 | 31.65 |
| ATOM | 838 | HD1 | HIS | 87 | 56.875 | 44.656 | 60.899 | 1.00 | 0.00 |
| ATOM | 839 | CE1 | HIS | 87 | 58.702 | 43.948 | 60.300 | 1.00 | 26.74 |
| ATOM | 840 | NE2 | HIS | 87 | 59.798 | 44.597 | 59.962 | 1.00 | 26.86 |
| ATOM | 841 | HE2 | HIS | 87 | 60.664 | 44.175 | 59.760 | 1.00 | 0.00 |
| ATOM | 842 | C | HIS | 87 | 58.797 | 48.303 | 62.709 | 1.00 | 30.65 |
| ATOM | 843 | O | HIS | 87 | 58.973 | 49.463 | 62.304 | 1.00 | 33.14 |
| ATOM | 844 | N | PRO | 88 | 59.629 | 47.719 | 63.592 | 1.00 | 31.15 |
| ATOM | 845 | CD | PRO | 88 | 59.379 | 46.404 | 64.186 | 1.00 | 29.92 |
| ATOM | 846 | CA | PRO | 88 | 60.857 | 48.346 | 64.178 | 1.00 | 30.23 |
| ATOM | 847 | CB | PRO | 88 | 61.619 | 47.176 | 64.798 | 1.00 | 32.28 |
| ATOM | 848 | CG | PRO | 88 | 60.512 | 46.225 | 65.232 | 1.00 | 32.35 |
| ATOM | 849 | C | PRO | 88 | 61.689 | 49.092 | 63.144 | 1.00 | 28.69 |
| ATOM | 850 | O | PRO | 88 | 62.099 | 48.464 | 62.172 | 1.00 | 30.18 |
| ATOM | 851 | N | GLY | 89 | 61.838 | 50.407 | 63.215 | 1.00 | 26.86 |
| ATOM | 852 | H | GLY | 89 | 61.438 | 50.886 | 63.968 | 1.00 | 0.00 |
| ATOM | 853 | CA | GLY | 89 | 62.569 | 51.145 | 62.197 | 1.00 | 24.90 |
| ATOM | 854 | C | GLY | 89 | 61.784 | 51.826 | 61.062 | 1.00 | 28.34 |
| ATOM | 855 | O | GLY | 89 | 62.070 | 52.967 | 60.706 | 1.00 | 29.67 |
| ATOM | 856 | N | ILE | 90 | 60.765 | 51.249 | 60.426 | 1.00 | 28.41 |
| ATOM | 857 | H | ILE | 90 | 60.449 | 50.406 | 60.808 | 1.00 | 0.00 |
| ATOM | 858 | CA | ILE | 90 | 60.139 | 51.885 | 59.261 | 1.00 | 26.38 |
| ATOM | 859 | CB | ILE | 90 | 59.941 | 50.996 | 58.017 | 1.00 | 26.93 |
| ATOM | 860 | CG2 | ILE | 90 | 60.961 | 51.343 | 56.962 | 1.00 | 28.43 |
| ATOM | 861 | CG1 | ILE | 90 | 59.893 | 49.551 | 58.430 | 1.00 | 27.14 |
| ATOM | 862 | CD1 | ILE | 90 | 61.188 | 48.805 | 58.717 | 1.00 | 30.53 |
| ATOM | 863 | C | ILE | 90 | 58.743 | 52.431 | 59.451 | 1.00 | 28.97 |
| ATOM | 864 | O | ILE | 90 | 58.472 | 53.597 | 59.139 | 1.00 | 31.50 |
| ATOM | 865 | N | ILE | 91 | 57.858 | 51.568 | 59.983 | 1.00 | 28.96 |
| ATOM | 866 | H | ILE | 91 | 58.227 | 50.776 | 60.415 | 1.00 | 0.00 |
| ATOM | 867 | CA | ILE | 91 | 56.408 | 51.819 | 60.100 | 1.00 | 27.73 |
| ATOM | 868 | CB | ILE | 91 | 55.616 | 50.558 | 59.655 | 1.00 | 26.34 |
| ATOM | 869 | CG2 | ILE | 91 | 54.099 | 50.804 | 59.799 | 1.00 | 21.54 |
| ATOM | 870 | CG1 | ILE | 91 | 56.016 | 50.183 | 58.232 | 1.00 | 22.37 |
| ATOM | 871 | CD1 | ILE | 91 | 55.607 | 51.244 | 57.237 | 1.00 | 22.51 |
| ATOM | 872 | C | ILE | 91 | 55.936 | 52.198 | 61.507 | 1.00 | 29.11 |
| ATOM | 873 | O | ILE | 91 | 55.934 | 51.311 | 62.387 | 1.00 | 30.82 |
| ATOM | 874 | N | PRO | 92 | 55.529 | 53.451 | 61.774 | 1.00 | 28.57 |
| ATOM | 875 | CD | PRO | 92 | 55.492 | 54.537 | 60.803 | 1.00 | 28.83 |
| ATOM | 876 | CA | PRO | 92 | 54.980 | 53.862 | 63.063 | 1.00 | 31.00 |
| ATOM | 877 | CB | PRO | 92 | 54.698 | 55.328 | 62.808 | 1.00 | 30.11 |
| ATOM | 878 | CG | PRO | 92 | 54.379 | 55.401 | 61.332 | 1.00 | 29.05 |
| ATOM | 879 | C | PRO | 92 | 53.767 | 53.013 | 63.522 | 1.00 | 33.43 |
| ATOM | 880 | O | PRO | 92 | 53.078 | 52.465 | 62.653 | 1.00 | 35.46 |
| ATOM | 881 | N | PRO | 93 | 53.421 | 52.766 | 64.793 | 1.00 | 34.10 |
| ATOM | 882 | CD | PRO | 93 | 54.236 | 53.010 | 65.975 | 1.00 | 35.74 |
| ATOM | 883 | CA | PRO | 93 | 52.225 | 52.023 | 65.158 | 1.00 | 35.34 |
| ATOM | 884 | CB | PRO | 93 | 52.246 | 52.021 | 66.698 | 1.00 | 35.19 |
| ATOM | 885 | CG | PRO | 93 | 53.200 | 53.099 | 67.090 | 1.00 | 34.66 |
| ATOM | 886 | C | PRO | 93 | 50.921 | 52.554 | 64.557 | 1.00 | 36.07 |
| ATOM | 887 | O | PRO | 93 | 50.777 | 53.728 | 64.200 | 1.00 | 36.07 |
| ATOM | 888 | N | HIS | 94 | 49.951 | 51.664 | 64.364 | 1.00 | 38.60 |
| ATOM | 889 | H | HIS | 94 | 50.112 | 50.752 | 64.681 | 1.00 | 0.00 |
| ATOM | 890 | CA | HIS | 94 | 48.654 | 52.037 | 63.807 | 1.00 | 40.88 |
| ATOM | 891 | CB | HIS | 94 | 47.973 | 52.797 | 64.945 | 1.00 | 43.90 |
| ATOM | 892 | CG | HIS | 94 | 46.506 | 53.091 | 64.765 | 1.00 | 47.81 |
| ATOM | 893 | CD2 | HIS | 94 | 45.980 | 54.366 | 64.651 | 1.00 | 50.92 |
| ATOM | 894 | ND1 | HIS | 94 | 45.514 | 52.220 | 64.697 | 1.00 | 50.10 |
| ATOM | 895 | HD1 | HIS | 94 | 45.559 | 51.268 | 64.927 | 1.00 | 0.00 |
| ATOM | 896 | CE1 | HIS | 94 | 44.405 | 52.916 | 64.540 | 1.00 | 52.77 |

FIG. 1: A-16

| | | | | | | | | |
|---|---|---|---|---|---|---|---|---|
| ATOM | 897 | NE2 | HIS | 94 | 44.689 | 54.203 | 64.513 | 1.00 | 51.50 |
| ATOM | 898 | HE2 | HIS | 94 | 44.047 | 54.925 | 64.360 | 1.00 | 0.00 |
| ATOM | 899 | C | HIS | 94 | 48.652 | 52.805 | 62.461 | 1.00 | 39.67 |
| ATOM | 900 | O | HIS | 94 | 47.983 | 53.828 | 62.267 | 1.00 | 39.97 |
| ATOM | 901 | N | ALA | 95 | 49.370 | 52.224 | 61.490 | 1.00 | 37.99 |
| ATOM | 902 | H | ALA | 95 | 49.906 | 51.451 | 61.740 | 1.00 | 0.00 |
| ATOM | 903 | CA | ALA | 95 | 49.546 | 52.796 | 60.144 | 1.00 | 35.23 |
| ATOM | 904 | CB | ALA | 95 | 51.037 | 52.985 | 59.887 | 1.00 | 35.82 |
| ATOM | 905 | C | ALA | 95 | 48.975 | 52.194 | 58.850 | 1.00 | 32.11 |
| ATOM | 906 | O | ALA | 95 | 49.143 | 51.039 | 58.480 | 1.00 | 32.00 |
| ATOM | 907 | N | THR | 96 | 48.259 | 53.094 | 58.214 | 1.00 | 30.85 |
| ATOM | 908 | H | THR | 96 | 48.116 | 53.929 | 58.707 | 1.00 | 0.00 |
| ATOM | 909 | CA | THR | 96 | 47.609 | 52.990 | 56.922 | 1.00 | 31.08 |
| ATOM | 910 | CB | THR | 96 | 46.473 | 54.017 | 56.729 | 1.00 | 33.73 |
| ATOM | 911 | OG1 | THR | 96 | 45.609 | 53.994 | 57.882 | 1.00 | 35.36 |
| ATOM | 912 | HG1 | THR | 96 | 45.030 | 54.760 | 57.848 | 1.00 | 0.00 |
| ATOM | 913 | CG2 | THR | 96 | 45.728 | 53.738 | 55.425 | 1.00 | 32.78 |
| ATOM | 914 | C | THR | 96 | 48.677 | 53.368 | 55.918 | 1.00 | 31.50 |
| ATOM | 915 | O | THR | 96 | 49.117 | 54.515 | 55.833 | 1.00 | 32.50 |
| ATOM | 916 | N | LEU | 97 | 49.022 | 52.411 | 55.090 | 1.00 | 32.18 |
| ATOM | 917 | H | LEU | 97 | 48.454 | 51.611 | 55.101 | 1.00 | 0.00 |
| ATOM | 918 | CA | LEU | 97 | 50.135 | 52.449 | 54.142 | 1.00 | 30.94 |
| ATOM | 919 | CB | LEU | 97 | 50.987 | 51.207 | 54.306 | 1.00 | 31.46 |
| ATOM | 920 | CG | LEU | 97 | 51.258 | 50.762 | 55.748 | 1.00 | 33.64 |
| ATOM | 921 | CD1 | LEU | 97 | 51.834 | 49.363 | 55.688 | 1.00 | 34.90 |
| ATOM | 922 | CD2 | LEU | 97 | 52.152 | 51.778 | 56.484 | 1.00 | 32.11 |
| ATOM | 923 | C | LEU | 97 | 49.683 | 52.486 | 52.701 | 1.00 | 30.16 |
| ATOM | 924 | O | LEU | 97 | 49.034 | 51.522 | 52.293 | 1.00 | 31.15 |
| ATOM | 925 | N | VAL | 98 | 49.966 | 53.506 | 51.881 | 1.00 | 29.23 |
| ATOM | 926 | H | VAL | 98 | 50.622 | 54.176 | 52.168 | 1.00 | 0.00 |
| ATOM | 927 | CA | VAL | 98 | 49.521 | 53.445 | 50.494 | 1.00 | 25.96 |
| ATOM | 928 | CB | VAL | 98 | 49.020 | 54.858 | 49.919 | 1.00 | 24.00 |
| ATOM | 929 | CG1 | VAL | 98 | 48.545 | 55.782 | 51.069 | 1.00 | 17.45 |
| ATOM | 930 | CG2 | VAL | 98 | 50.080 | 55.498 | 49.064 | 1.00 | 25.60 |
| ATOM | 931 | C | VAL | 98 | 50.728 | 52.914 | 49.742 | 1.00 | 28.61 |
| ATOM | 932 | O | VAL | 98 | 51.906 | 53.252 | 49.955 | 1.00 | 28.41 |
| ATOM | 933 | N | PHE | 99 | 50.422 | 51.896 | 48.960 | 1.00 | 30.13 |
| ATOM | 934 | H | PHE | 99 | 49.520 | 51.533 | 49.008 | 1.00 | 0.00 |
| ATOM | 935 | CA | PHE | 99 | 51.431 | 51.242 | 48.145 | 1.00 | 28.95 |
| ATOM | 936 | CB | PHE | 99 | 51.504 | 49.755 | 48.424 | 1.00 | 27.30 |
| ATOM | 937 | CG | PHE | 99 | 52.302 | 49.292 | 49.623 | 1.00 | 28.31 |
| ATOM | 938 | CD1 | PHE | 99 | 51.689 | 49.213 | 50.885 | 1.00 | 27.04 |
| ATOM | 939 | CD2 | PHE | 99 | 53.631 | 48.894 | 49.439 | 1.00 | 26.44 |
| ATOM | 940 | CE1 | PHE | 99 | 52.418 | 48.727 | 51.968 | 1.00 | 25.08 |
| ATOM | 941 | CE2 | PHE | 99 | 54.342 | 48.413 | 50.531 | 1.00 | 25.08 |
| ATOM | 942 | CZ | PHE | 99 | 53.738 | 48.329 | 51.789 | 1.00 | 25.86 |
| ATOM | 943 | C | PHE | 99 | 51.211 | 51.366 | 46.646 | 1.00 | 29.41 |
| ATOM | 944 | O | PHE | 99 | 50.248 | 50.784 | 46.111 | 1.00 | 28.62 |
| ATOM | 945 | N | ASP | 100 | 52.066 | 52.100 | 45.923 | 1.00 | 27.90 |
| ATOM | 946 | H | ASP | 100 | 52.790 | 52.603 | 46.356 | 1.00 | 0.00 |
| ATOM | 947 | CA | ASP | 100 | 51.933 | 51.986 | 44.484 | 1.00 | 27.65 |
| ATOM | 948 | CB | ASP | 100 | 52.515 | 53.213 | 43.786 | 1.00 | 29.75 |
| ATOM | 949 | CG | ASP | 100 | 52.444 | 52.983 | 42.290 | 1.00 | 33.48 |
| ATOM | 950 | OD1 | ASP | 100 | 51.353 | 52.728 | 41.787 | 1.00 | 37.53 |
| ATOM | 951 | OD2 | ASP | 100 | 53.481 | 52.982 | 41.620 | 1.00 | 38.98 |
| ATOM | 952 | C | ASP | 100 | 52.653 | 50.706 | 44.034 | 1.00 | 24.82 |
| ATOM | 953 | O | ASP | 100 | 53.860 | 50.593 | 44.178 | 1.00 | 25.12 |
| ATOM | 954 | N | VAL | 101 | 51.943 | 49.696 | 43.554 | 1.00 | 23.79 |
| ATOM | 955 | H | VAL | 101 | 50.973 | 49.812 | 43.528 | 1.00 | 0.00 |
| ATOM | 956 | CA | VAL | 101 | 52.489 | 48.409 | 43.126 | 1.00 | 23.21 |

FIG. 1: A-17

| ATOM | 957 | CB | VAL | 101 | 51.826 | 47.263 | 43.990 | 1.00 | 21.54 |
|---|---|---|---|---|---|---|---|---|---|
| ATOM | 958 | CG1 | VAL | 101 | 51.996 | 45.848 | 43.456 | 1.00 | 18.74 |
| ATOM | 959 | CG2 | VAL | 101 | 52.550 | 47.246 | 45.312 | 1.00 | 17.06 |
| ATOM | 960 | C | VAL | 101 | 52.277 | 48.151 | 41.636 | 1.00 | 25.95 |
| ATOM | 961 | O | VAL | 101 | 51.190 | 48.341 | 41.120 | 1.00 | 29.28 |
| ATOM | 962 | N | GLU | 102 | 53.269 | 47.725 | 40.869 | 1.00 | 27.01 |
| ATOM | 963 | H | GLU | 102 | 54.162 | 47.669 | 41.268 | 1.00 | 0.00 |
| ATOM | 964 | CA | GLU | 102 | 53.092 | 47.385 | 39.474 | 1.00 | 28.99 |
| ATOM | 965 | CB | GLU | 102 | 54.066 | 48.215 | 38.645 | 1.00 | 33.82 |
| ATOM | 966 | CG | GLU | 102 | 54.184 | 47.980 | 37.124 | 1.00 | 37.96 |
| ATOM | 967 | CD | GLU | 102 | 55.526 | 48.447 | 36.530 | 1.00 | 43.93 |
| ATOM | 968 | OE1 | GLU | 102 | 56.546 | 48.494 | 37.239 | 1.00 | 44.49 |
| ATOM | 969 | OE2 | GLU | 102 | 55.566 | 48.761 | 35.335 | 1.00 | 46.19 |
| ATOM | 970 | C | GLU | 102 | 53.331 | 45.895 | 39.233 | 1.00 | 29.60 |
| ATOM | 971 | O | GLU | 102 | 54.370 | 45.374 | 39.647 | 1.00 | 30.02 |
| ATOM | 972 | N | LEU | 103 | 52.428 | 45.157 | 38.593 | 1.00 | 27.97 |
| ATOM | 973 | H | LEU | 103 | 51.593 | 45.582 | 38.324 | 1.00 | 0.00 |
| ATOM | 974 | CA | LEU | 103 | 52.674 | 43.754 | 38.315 | 1.00 | 28.42 |
| ATOM | 975 | CB | LEU | 103 | 51.353 | 42.980 | 38.146 | 1.00 | 27.72 |
| ATOM | 976 | CG | LEU | 103 | 51.090 | 41.665 | 38.900 | 1.00 | 29.71 |
| ATOM | 977 | CD1 | LEU | 103 | 49.805 | 41.113 | 38.317 | 1.00 | 27.63 |
| ATOM | 978 | CD2 | LEU | 103 | 52.216 | 40.615 | 38.756 | 1.00 | 27.20 |
| ATOM | 979 | C | LEU | 103 | 53.514 | 43.564 | 37.047 | 1.00 | 28.71 |
| ATOM | 980 | O | LEU | 103 | 53.080 | 43.813 | 35.922 | 1.00 | 32.25 |
| ATOM | 981 | N | LEU | 104 | 54.748 | 43.120 | 37.245 | 1.00 | 27.89 |
| ATOM | 982 | H | LEU | 104 | 55.012 | 42.922 | 38.169 | 1.00 | 0.00 |
| ATOM | 983 | CA | LEU | 104 | 55.689 | 42.876 | 36.179 | 1.00 | 25.74 |
| ATOM | 984 | CB | LEU | 104 | 57.131 | 42.886 | 36.683 | 1.00 | 23.34 |
| ATOM | 985 | CG | LEU | 104 | 57.710 | 43.912 | 37.645 | 1.00 | 23.01 |
| ATOM | 986 | CD1 | LEU | 104 | 59.188 | 43.777 | 37.513 | 1.00 | 22.54 |
| ATOM | 987 | CD2 | LEU | 104 | 57.459 | 45.337 | 37.279 | 1.00 | 23.08 |
| ATOM | 988 | C | LEU | 104 | 55.484 | 41.535 | 35.492 | 1.00 | 27.74 |
| ATOM | 989 | O | LEU | 104 | 55.166 | 41.470 | 34.317 | 1.00 | 29.64 |
| ATOM | 990 | N | LYS | 105 | 55.637 | 40.425 | 36.204 | 1.00 | 28.91 |
| ATOM | 991 | H | LYS | 105 | 55.672 | 40.516 | 37.179 | 1.00 | 0.00 |
| ATOM | 992 | CA | LYS | 105 | 55.664 | 39.089 | 35.617 | 1.00 | 28.20 |
| ATOM | 993 | CB | LYS | 105 | 57.105 | 38.601 | 35.415 | 1.00 | 27.28 |
| ATOM | 994 | CG | LYS | 105 | 57.705 | 38.570 | 34.015 | 1.00 | 29.13 |
| ATOM | 995 | CD | LYS | 105 | 58.941 | 37.649 | 33.955 | 1.00 | 28.39 |
| ATOM | 996 | CE | LYS | 105 | 58.471 | 36.191 | 34.022 | 1.00 | 31.50 |
| ATOM | 997 | NZ | LYS | 105 | 59.563 | 35.242 | 34.103 | 1.00 | 31.35 |
| ATOM | 998 | HZ1 | LYS | 105 | 59.180 | 34.287 | 34.251 | 1.00 | 0.00 |
| ATOM | 999 | HZ2 | LYS | 105 | 60.183 | 35.494 | 34.899 | 1.00 | 0.00 |
| ATOM | 1000 | HZ3 | LYS | 105 | 60.105 | 35.266 | 33.216 | 1.00 | 0.00 |
| ATOM | 1001 | C | LYS | 105 | 54.976 | 38.051 | 36.489 | 1.00 | 28.35 |
| ATOM | 1002 | O | LYS | 105 | 54.370 | 38.402 | 37.480 | 1.00 | 27.82 |
| ATOM | 1003 | N | LEU | 106 | 55.022 | 36.782 | 36.081 | 1.00 | 30.95 |
| ATOM | 1004 | H | LEU | 106 | 55.356 | 36.625 | 35.175 | 1.00 | 0.00 |
| ATOM | 1005 | CA | LEU | 106 | 54.616 | 35.586 | 36.844 | 1.00 | 35.17 |
| ATOM | 1006 | CB | LEU | 106 | 53.242 | 34.999 | 36.578 | 1.00 | 33.38 |
| ATOM | 1007 | CG | LEU | 106 | 51.952 | 35.717 | 36.750 | 1.00 | 33.64 |
| ATOM | 1008 | CD1 | LEU | 106 | 51.859 | 36.455 | 38.091 | 1.00 | 30.30 |
| ATOM | 1009 | CD2 | LEU | 106 | 51.841 | 36.587 | 35.514 | 1.00 | 37.34 |
| ATOM | 1010 | C | LEU | 106 | 55.521 | 34.414 | 36.450 | 1.00 | 36.29 |
| ATOM | 1011 | O | LEU | 106 | 56.067 | 34.339 | 35.344 | 1.00 | 37.48 |
| ATOM | 1012 | N | GLU | 107 | 55.707 | 33.475 | 37.344 | 1.00 | 37.84 |
| ATOM | 1013 | H | GLU | 107 | 55.235 | 33.508 | 38.201 | 1.00 | 0.00 |
| ATOM | 1014 | CA | GLU | 107 | 56.599 | 32.345 | 37.112 | 1.00 | 39.89 |
| ATOM | 1015 | CB | GLU | 107 | 58.043 | 32.822 | 37.214 | 1.00 | 40.97 |
| ATOM | 1016 | CG | GLU | 107 | 58.321 | 33.971 | 38.226 | 1.00 | 42.27 |

FIG. 1: A-18

| | | Atom Type | Residue | # | X | Y | Z | OCC | B |
|---|---|---|---|---|---|---|---|---|---|
| ATOM | 1017 | CD | GLU | 107 | 59.781 | 34.393 | 38.327 | 1.00 | 43.06 |
| ATOM | 1018 | OE1 | GLU | 107 | 60.436 | 33.959 | 39.285 | 1.00 | 44.20 |
| ATOM | 1019 | OE2 | GLU | 107 | 60.245 | 35.133 | 37.449 | 1.00 | 40.58 |
| ATOM | 1020 | C | GLU | 107 | 56.339 | 31.243 | 38.131 | 1.00 | 41.09 |
| ATOM | 1021 | O | GLU | 107 | 55.419 | 31.432 | 38.956 | 1.00 | 45.17 |

CALCINEURIN SUBUNIT A COORDINATES

| | | Atom Type | Residue | # | X | Y | Z | OCC | B |
|---|---|---|---|---|---|---|---|---|---|
| ATOM | 1022 | CB | ALA | 24 | 84.175 | 45.346 | 46.445 | 1.00 | 50.31 |
| ATOM | 1023 | C | ALA | 24 | 83.049 | 45.548 | 48.634 | 1.00 | 49.53 |
| ATOM | 1024 | O | ALA | 24 | 81.801 | 45.480 | 48.725 | 1.00 | 48.08 |
| ATOM | 1025 | HT1 | ALA | 24 | 83.506 | 42.768 | 46.656 | 1.00 | 0.00 |
| ATOM | 1026 | HT2 | ALA | 24 | 82.099 | 43.702 | 46.895 | 1.00 | 0.00 |
| ATOM | 1027 | N | ALA | 24 | 82.997 | 43.379 | 47.325 | 1.00 | 50.14 |
| ATOM | 1028 | HT3 | ALA | 24 | 82.743 | 42.842 | 48.181 | 1.00 | 0.00 |
| ATOM | 1029 | CA | ALA | 24 | 83.776 | 44.567 | 47.691 | 1.00 | 49.48 |
| ATOM | 1030 | N | ALA | 25 | 83.824 | 46.440 | 49.286 | 1.00 | 47.16 |
| ATOM | 1031 | H | ALA | 25 | 84.752 | 46.604 | 49.015 | 1.00 | 0.00 |
| ATOM | 1032 | CA | ALA | 25 | 83.263 | 47.330 | 50.312 | 1.00 | 46.17 |
| ATOM | 1033 | CB | ALA | 25 | 83.226 | 46.548 | 51.621 | 1.00 | 48.69 |
| ATOM | 1034 | C | ALA | 25 | 83.999 | 48.656 | 50.524 | 1.00 | 43.20 |
| ATOM | 1035 | O | ALA | 25 | 84.803 | 48.938 | 49.631 | 1.00 | 43.07 |
| ATOM | 1036 | N | ALA | 26 | 83.751 | 49.430 | 51.619 | 1.00 | 40.97 |
| ATOM | 1037 | H | ALA | 26 | 83.041 | 49.124 | 52.217 | 1.00 | 0.00 |
| ATOM | 1038 | CA | ALA | 26 | 84.374 | 50.759 | 51.934 | 1.00 | 38.77 |
| ATOM | 1039 | CB | ALA | 26 | 83.910 | 51.874 | 50.922 | 1.00 | 38.27 |
| ATOM | 1040 | C | ALA | 26 | 84.222 | 51.429 | 53.331 | 1.00 | 36.45 |
| ATOM | 1041 | O | ALA | 26 | 83.144 | 51.518 | 53.958 | 1.00 | 32.84 |
| ATOM | 1042 | N | ALA | 27 | 85.367 | 51.993 | 53.764 | 1.00 | 36.14 |
| ATOM | 1043 | H | ALA | 27 | 86.093 | 52.091 | 53.118 | 1.00 | 0.00 |
| ATOM | 1044 | CA | ALA | 27 | 85.493 | 52.548 | 55.113 | 1.00 | 35.20 |
| ATOM | 1045 | CB | ALA | 27 | 85.761 | 51.335 | 55.977 | 1.00 | 38.09 |
| ATOM | 1046 | C | ALA | 27 | 86.403 | 53.720 | 55.596 | 1.00 | 35.93 |
| ATOM | 1047 | O | ALA | 27 | 86.983 | 54.503 | 54.815 | 1.00 | 37.21 |
| ATOM | 1048 | N | ALA | 28 | 86.544 | 53.867 | 56.947 | 1.00 | 34.19 |
| ATOM | 1049 | H | ALA | 28 | 86.111 | 53.208 | 57.520 | 1.00 | 0.00 |
| ATOM | 1050 | CA | ALA | 28 | 87.237 | 54.988 | 57.578 | 1.00 | 31.95 |
| ATOM | 1051 | CB | ALA | 28 | 86.194 | 56.174 | 57.561 | 1.00 | 30.78 |
| ATOM | 1052 | C | ALA | 28 | 88.057 | 55.125 | 58.930 | 1.00 | 31.17 |
| ATOM | 1053 | O | ALA | 28 | 88.123 | 54.384 | 59.921 | 1.00 | 28.93 |
| ATOM | 1054 | N | ALA | 29 | 88.852 | 56.147 | 58.583 | 1.00 | 28.83 |
| ATOM | 1055 | H | ALA | 29 | 88.846 | 56.328 | 57.623 | 1.00 | 0.00 |
| ATOM | 1056 | CA | ALA | 29 | 89.774 | 57.001 | 59.262 | 1.00 | 23.93 |
| ATOM | 1057 | CB | ALA | 29 | 91.116 | 57.198 | 58.530 | 1.00 | 22.54 |
| ATOM | 1058 | C | ALA | 29 | 89.037 | 58.317 | 59.041 | 1.00 | 22.19 |
| ATOM | 1059 | O | ALA | 29 | 88.652 | 58.615 | 57.908 | 1.00 | 21.75 |
| ATOM | 1060 | N | ALA | 30 | 88.737 | 59.091 | 60.058 | 1.00 | 21.20 |
| ATOM | 1061 | H | ALA | 30 | 88.935 | 58.783 | 60.964 | 1.00 | 0.00 |
| ATOM | 1062 | CA | ALA | 30 | 88.135 | 60.389 | 59.851 | 1.00 | 22.28 |
| ATOM | 1063 | CB | ALA | 30 | 87.373 | 60.772 | 61.135 | 1.00 | 19.34 |
| ATOM | 1064 | C | ALA | 30 | 89.174 | 61.469 | 59.479 | 1.00 | 21.66 |
| ATOM | 1065 | O | ALA | 30 | 90.193 | 61.684 | 60.152 | 1.00 | 20.96 |
| ATOM | 1066 | N | ALA | 31 | 88.961 | 62.168 | 58.374 | 1.00 | 20.60 |
| ATOM | 1067 | H | ALA | 31 | 88.121 | 61.993 | 57.904 | 1.00 | 0.00 |
| ATOM | 1068 | CA | ALA | 31 | 89.856 | 63.258 | 57.981 | 1.00 | 20.34 |
| ATOM | 1069 | CB | ALA | 31 | 89.352 | 63.883 | 56.667 | 1.00 | 19.97 |
| ATOM | 1070 | C | ALA | 31 | 89.960 | 64.354 | 59.065 | 1.00 | 22.46 |
| ATOM | 1071 | O | ALA | 31 | 88.958 | 64.783 | 59.650 | 1.00 | 22.75 |

FIG. 1: A-19

| ATOM | 1072 | N    | ALA | 32 | 91.213 | 64.693 | 59.406 | 1.00 | 22.27 |
|------|------|------|-----|----|--------|--------|--------|------|-------|
| ATOM | 1073 | H    | ALA | 32 | 91.890 | 64.113 | 59.010 | 1.00 | 0.00  |
| ATOM | 1074 | CA   | ALA | 32 | 91.670 | 65.720 | 60.377 | 1.00 | 21.07 |
| ATOM | 1075 | CB   | ALA | 32 | 93.101 | 65.388 | 60.808 | 1.00 | 16.27 |
| ATOM | 1076 | C    | ALA | 32 | 91.687 | 67.140 | 59.809 | 1.00 | 21.01 |
| ATOM | 1077 | O    | ALA | 32 | 91.244 | 67.271 | 58.666 | 1.00 | 25.29 |
| ATOM | 1078 | N    | ALA | 33 | 92.131 | 68.275 | 60.388 | 1.00 | 19.49 |
| ATOM | 1079 | H    | ALA | 33 | 92.413 | 68.248 | 61.330 | 1.00 | 0.00  |
| ATOM | 1080 | CA   | ALA | 33 | 92.349 | 69.492 | 59.581 | 1.00 | 16.51 |
| ATOM | 1081 | CB   | ALA | 33 | 92.365 | 70.585 | 60.570 | 1.00 | 14.14 |
| ATOM | 1082 | C    | ALA | 33 | 93.659 | 69.407 | 58.724 | 1.00 | 20.57 |
| ATOM | 1083 | O    | ALA | 33 | 94.760 | 69.875 | 58.983 | 1.00 | 21.29 |
| ATOM | 1084 | N    | ALA | 34 | 93.495 | 68.469 | 57.761 | 1.00 | 25.97 |
| ATOM | 1085 | H    | ALA | 34 | 92.676 | 67.993 | 57.896 | 1.00 | 0.00  |
| ATOM | 1086 | CA   | ALA | 34 | 94.225 | 67.896 | 56.585 | 1.00 | 21.13 |
| ATOM | 1087 | CB   | ALA | 34 | 94.337 | 66.372 | 56.553 | 1.00 | 20.20 |
| ATOM | 1088 | C    | ALA | 34 | 93.277 | 68.129 | 55.374 | 1.00 | 22.53 |
| ATOM | 1089 | O    | ALA | 34 | 93.573 | 67.809 | 54.221 | 1.00 | 20.37 |
| ATOM | 1090 | N    | ALA | 35 | 92.008 | 68.505 | 55.703 | 1.00 | 21.03 |
| ATOM | 1091 | H    | ALA | 35 | 91.689 | 68.264 | 56.596 | 1.00 | 0.00  |
| ATOM | 1092 | CA   | ALA | 35 | 91.063 | 69.017 | 54.731 | 1.00 | 18.49 |
| ATOM | 1093 | CB   | ALA | 35 | 89.642 | 68.919 | 55.232 | 1.00 | 12.08 |
| ATOM | 1094 | C    | ALA | 35 | 91.405 | 70.485 | 54.559 | 1.00 | 19.12 |
| ATOM | 1095 | O    | ALA | 35 | 91.393 | 70.975 | 53.451 | 1.00 | 21.45 |
| ATOM | 1096 | N    | ASP | 36 | 91.749 | 71.272 | 55.574 | 1.00 | 21.28 |
| ATOM | 1097 | H    | ASP | 36 | 91.824 | 70.881 | 56.463 | 1.00 | 0.00  |
| ATOM | 1098 | CA   | ASP | 36 | 91.997 | 72.703 | 55.380 | 1.00 | 24.10 |
| ATOM | 1099 | CB   | ASP | 36 | 91.440 | 73.596 | 56.538 | 1.00 | 21.58 |
| ATOM | 1100 | CG   | ASP | 36 | 89.912 | 73.763 | 56.542 | 1.00 | 29.14 |
| ATOM | 1101 | OD1  | ASP | 36 | 89.223 | 72.967 | 57.218 | 1.00 | 32.83 |
| ATOM | 1102 | OD2  | ASP | 36 | 89.398 | 74.679 | 55.881 | 1.00 | 24.50 |
| ATOM | 1103 | C    | ASP | 36 | 93.474 | 72.946 | 55.291 | 1.00 | 27.46 |
| ATOM | 1104 | O    | ASP | 36 | 94.204 | 72.675 | 56.231 | 1.00 | 30.17 |
| ATOM | 1105 | N    | ASN | 37 | 94.039 | 73.366 | 54.193 | 1.00 | 31.18 |
| ATOM | 1106 | H    | ASN | 37 | 93.499 | 73.442 | 53.376 | 1.00 | 0.00  |
| ATOM | 1107 | CA   | ASN | 37 | 95.450 | 73.691 | 54.202 | 1.00 | 35.64 |
| ATOM | 1108 | CB   | ASN | 37 | 96.184 | 72.664 | 53.350 | 1.00 | 40.99 |
| ATOM | 1109 | CG   | ASN | 37 | 96.431 | 71.306 | 54.057 | 1.00 | 45.60 |
| ATOM | 1110 | OD1  | ASN | 37 | 96.734 | 70.305 | 53.428 | 1.00 | 43.54 |
| ATOM | 1111 | ND2  | ASN | 37 | 96.345 | 71.049 | 55.354 | 1.00 | 49.10 |
| ATOM | 1112 | HD21 | ASN | 37 | 96.016 | 71.721 | 55.981 | 1.00 | 0.00  |
| ATOM | 1113 | HD22 | ASN | 37 | 96.632 | 70.143 | 55.576 | 1.00 | 0.00  |
| ATOM | 1114 | C    | ASN | 37 | 95.738 | 75.122 | 53.752 | 1.00 | 37.92 |
| ATOM | 1115 | O    | ASN | 37 | 95.672 | 75.514 | 52.566 | 1.00 | 35.92 |
| ATOM | 1116 | N    | ASP | 38 | 95.901 | 75.830 | 54.903 | 1.00 | 37.29 |
| ATOM | 1117 | H    | ASP | 38 | 95.865 | 75.291 | 55.717 | 1.00 | 0.00  |
| ATOM | 1118 | CA   | ASP | 38 | 96.180 | 77.278 | 55.073 | 1.00 | 38.07 |
| ATOM | 1119 | CB   | ASP | 38 | 97.561 | 77.498 | 54.509 | 1.00 | 40.31 |
| ATOM | 1120 | CG   | ASP | 38 | 98.541 | 77.179 | 55.609 | 1.00 | 42.81 |
| ATOM | 1121 | OD1  | ASP | 38 | 98.514 | 77.971 | 56.566 | 1.00 | 45.63 |
| ATOM | 1122 | OD2  | ASP | 38 | 99.282 | 76.179 | 55.509 | 1.00 | 42.77 |
| ATOM | 1123 | C    | ASP | 38 | 95.245 | 78.437 | 54.637 | 1.00 | 36.72 |
| ATOM | 1124 | O    | ASP | 38 | 95.488 | 79.528 | 54.093 | 1.00 | 33.25 |
| ATOM | 1125 | N    | GLY | 39 | 94.109 | 78.096 | 55.211 | 1.00 | 33.60 |
| ATOM | 1126 | H    | GLY | 39 | 94.089 | 77.333 | 55.821 | 1.00 | 0.00  |
| ATOM | 1127 | CA   | GLY | 39 | 92.908 | 78.825 | 55.000 | 1.00 | 32.50 |
| ATOM | 1128 | C    | GLY | 39 | 91.939 | 77.938 | 54.218 | 1.00 | 31.26 |
| ATOM | 1129 | O    | GLY | 39 | 90.868 | 77.557 | 54.671 | 1.00 | 32.03 |
| ATOM | 1130 | N    | LYS | 40 | 92.432 | 77.520 | 53.067 | 1.00 | 28.47 |
| ATOM | 1131 | H    | LYS | 40 | 93.384 | 77.673 | 52.895 | 1.00 | 0.00  |

FIG. 1: A-20

| ATOM | 1132 | CA | LYS | 40 | 91.641 | 76.900 | 52.026 | 1.00 | 25.84 |
|------|------|------|-----|----|--------|--------|--------|------|-------|
| ATOM | 1133 | CB | LYS | 40 | 92.323 | 77.223 | 50.677 | 1.00 | 30.80 |
| ATOM | 1134 | CG | LYS | 40 | 92.335 | 78.723 | 50.414 | 1.00 | 34.55 |
| ATOM | 1135 | CD | LYS | 40 | 92.946 | 79.268 | 49.119 | 1.00 | 37.54 |
| ATOM | 1136 | CE | LYS | 40 | 92.708 | 80.799 | 49.207 | 1.00 | 37.03 |
| ATOM | 1137 | NZ | LYS | 40 | 92.761 | 81.447 | 47.916 | 1.00 | 36.90 |
| ATOM | 1138 | HZ1 | LYS | 40 | 93.684 | 81.256 | 47.478 | 1.00 | 0.00 |
| ATOM | 1139 | HZ2 | LYS | 40 | 92.636 | 82.474 | 48.035 | 1.00 | 0.00 |
| ATOM | 1140 | HZ3 | LYS | 40 | 92.003 | 81.076 | 47.308 | 1.00 | 0.00 |
| ATOM | 1141 | C | LYS | 40 | 91.353 | 75.423 | 52.119 | 1.00 | 22.41 |
| ATOM | 1142 | O | LYS | 40 | 92.213 | 74.623 | 52.481 | 1.00 | 19.83 |
| ATOM | 1143 | N | PRO | 41 | 90.123 | 75.002 | 51.861 | 1.00 | 22.00 |
| ATOM | 1144 | CD | PRO | 41 | 88.926 | 75.859 | 51.854 | 1.00 | 19.73 |
| ATOM | 1145 | CA | PRO | 41 | 89.793 | 73.581 | 51.904 | 1.00 | 20.61 |
| ATOM | 1146 | CB | PRO | 41 | 88.280 | 73.591 | 52.007 | 1.00 | 23.55 |
| ATOM | 1147 | CG | PRO | 41 | 87.929 | 74.975 | 52.564 | 1.00 | 21.04 |
| ATOM | 1148 | C | PRO | 41 | 90.364 | 72.866 | 50.704 | 1.00 | 20.28 |
| ATOM | 1149 | O | PRO | 41 | 90.512 | 73.429 | 49.616 | 1.00 | 21.97 |
| ATOM | 1150 | N | ARG | 42 | 90.801 | 71.625 | 50.873 | 1.00 | 21.79 |
| ATOM | 1151 | H | ARG | 42 | 90.765 | 71.246 | 51.768 | 1.00 | 0.00 |
| ATOM | 1152 | CA | ARG | 42 | 91.398 | 70.848 | 49.779 | 1.00 | 21.51 |
| ATOM | 1153 | CB | ARG | 42 | 92.578 | 69.977 | 50.301 | 1.00 | 20.84 |
| ATOM | 1154 | CG | ARG | 42 | 93.682 | 70.713 | 51.061 | 1.00 | 23.19 |
| ATOM | 1155 | CD | ARG | 42 | 94.970 | 69.950 | 51.308 | 1.00 | 26.44 |
| ATOM | 1156 | NE | ARG | 42 | 95.806 | 70.089 | 50.136 | 1.00 | 35.33 |
| ATOM | 1157 | HE | ARG | 42 | 95.464 | 69.665 | 49.322 | 1.00 | 0.00 |
| ATOM | 1158 | CZ | ARG | 42 | 97.001 | 70.731 | 50.007 | 1.00 | 40.01 |
| ATOM | 1159 | NH1 | ARG | 42 | 97.498 | 70.823 | 48.761 | 1.00 | 41.01 |
| ATOM | 1160 | HH11 | ARG | 42 | 96.993 | 70.432 | 47.990 | 1.00 | 0.00 |
| ATOM | 1161 | HH12 | ARG | 42 | 98.371 | 71.286 | 48.603 | 1.00 | 0.00 |
| ATOM | 1162 | NH2 | ARG | 42 | 97.756 | 71.227 | 51.010 | 1.00 | 37.84 |
| ATOM | 1163 | HH21 | ARG | 42 | 97.445 | 71.136 | 51.949 | 1.00 | 0.00 |
| ATOM | 1164 | HH22 | ARG | 42 | 98.621 | 71.688 | 50.806 | 1.00 | 0.00 |
| ATOM | 1165 | C | ARG | 42 | 90.270 | 69.979 | 49.240 | 1.00 | 21.01 |
| ATOM | 1166 | O | ARG | 42 | 90.199 | 68.772 | 49.507 | 1.00 | 20.20 |
| ATOM | 1167 | N | VAL | 43 | 89.354 | 70.611 | 48.466 | 1.00 | 19.35 |
| ATOM | 1168 | H | VAL | 43 | 89.519 | 71.557 | 48.259 | 1.00 | 0.00 |
| ATOM | 1169 | CA | VAL | 43 | 88.113 | 69.934 | 48.037 | 1.00 | 17.98 |
| ATOM | 1170 | CB | VAL | 43 | 87.211 | 70.888 | 47.239 | 1.00 | 16.82 |
| ATOM | 1171 | CG1 | VAL | 43 | 86.790 | 72.072 | 48.100 | 1.00 | 9.06 |
| ATOM | 1172 | CG2 | VAL | 43 | 87.967 | 71.399 | 46.047 | 1.00 | 15.82 |
| ATOM | 1173 | C | VAL | 43 | 88.295 | 68.645 | 47.251 | 1.00 | 19.52 |
| ATOM | 1174 | O | VAL | 43 | 87.458 | 67.765 | 47.322 | 1.00 | 21.60 |
| ATOM | 1175 | N | ASP | 44 | 89.413 | 68.437 | 46.565 | 1.00 | 21.12 |
| ATOM | 1176 | H | ASP | 44 | 89.968 | 69.219 | 46.391 | 1.00 | 0.00 |
| ATOM | 1177 | CA | ASP | 44 | 89.822 | 67.148 | 46.006 | 1.00 | 21.78 |
| ATOM | 1178 | CB | ASP | 44 | 91.124 | 67.383 | 45.206 | 1.00 | 28.20 |
| ATOM | 1179 | CG | ASP | 44 | 92.394 | 67.906 | 45.944 | 1.00 | 35.44 |
| ATOM | 1180 | OD1 | ASP | 44 | 92.327 | 68.730 | 46.878 | 1.00 | 35.94 |
| ATOM | 1181 | OD2 | ASP | 44 | 93.489 | 67.474 | 45.559 | 1.00 | 39.50 |
| ATOM | 1182 | C | ASP | 44 | 90.011 | 66.084 | 47.106 | 1.00 | 20.71 |
| ATOM | 1183 | O | ASP | 44 | 89.446 | 64.998 | 47.028 | 1.00 | 21.62 |
| ATOM | 1184 | N | ILE | 45 | 90.691 | 66.359 | 48.234 | 1.00 | 21.23 |
| ATOM | 1185 | H | ILE | 45 | 91.069 | 67.256 | 48.333 | 1.00 | 0.00 |
| ATOM | 1186 | CA | ILE | 45 | 90.837 | 65.385 | 49.344 | 1.00 | 20.46 |
| ATOM | 1187 | CB | ILE | 45 | 91.637 | 66.032 | 50.521 | 1.00 | 17.75 |
| ATOM | 1188 | CG2 | ILE | 45 | 91.674 | 65.154 | 51.789 | 1.00 | 10.96 |
| ATOM | 1189 | CG1 | ILE | 45 | 93.043 | 66.299 | 49.992 | 1.00 | 17.65 |
| ATOM | 1190 | CD1 | ILE | 45 | 93.781 | 65.018 | 49.525 | 1.00 | 19.86 |
| ATOM | 1191 | C | ILE | 45 | 89.500 | 64.868 | 49.879 | 1.00 | 22.50 |

FIG. 1: A-21

| | | | | | | | | | |
|---|---|---|---|---|---|---|---|---|---|
| ATOM | 1192 | O | ILE | 45 | 89.252 | 63.664 | 50.079 | 1.00 | 25.21 |
| ATOM | 1193 | N | LEU | 46 | 88.674 | 65.900 | 50.097 | 1.00 | 21.62 |
| ATOM | 1194 | H | LEU | 46 | 89.068 | 66.785 | 49.955 | 1.00 | 0.00 |
| ATOM | 1195 | CA | LEU | 46 | 87.283 | 65.821 | 50.520 | 1.00 | 20.02 |
| ATOM | 1196 | CB | LEU | 46 | 86.814 | 67.258 | 50.794 | 1.00 | 18.61 |
| ATOM | 1197 | CG | LEU | 46 | 85.669 | 67.549 | 51.755 | 1.00 | 19.28 |
| ATOM | 1198 | CD1 | LEU | 46 | 86.153 | 67.416 | 53.190 | 1.00 | 16.09 |
| ATOM | 1199 | CD2 | LEU | 46 | 85.147 | 68.945 | 51.502 | 1.00 | 14.88 |
| ATOM | 1200 | C | LEU | 46 | 86.377 | 65.114 | 49.492 | 1.00 | 20.87 |
| ATOM | 1201 | O | LEU | 46 | 85.737 | 64.147 | 49.904 | 1.00 | 24.45 |
| ATOM | 1202 | N | LYS | 47 | 86.287 | 65.425 | 48.190 | 1.00 | 18.62 |
| ATOM | 1203 | H | LYS | 47 | 86.795 | 66.192 | 47.888 | 1.00 | 0.00 |
| ATOM | 1204 | CA | LYS | 47 | 85.448 | 64.708 | 47.224 | 1.00 | 17.99 |
| ATOM | 1205 | CB | LYS | 47 | 85.711 | 65.121 | 45.779 | 1.00 | 19.77 |
| ATOM | 1206 | CG | LYS | 47 | 84.841 | 64.479 | 44.680 | 1.00 | 18.97 |
| ATOM | 1207 | CD | LYS | 47 | 85.448 | 64.900 | 43.349 | 1.00 | 20.85 |
| ATOM | 1208 | CE | LYS | 47 | 84.708 | 64.428 | 42.109 | 1.00 | 22.34 |
| ATOM | 1209 | NZ | LYS | 47 | 84.686 | 62.976 | 42.045 | 1.00 | 26.53 |
| ATOM | 1210 | HZ1 | LYS | 47 | 84.238 | 62.670 | 41.157 | 1.00 | 0.00 |
| ATOM | 1211 | HZ2 | LYS | 47 | 84.136 | 62.618 | 42.853 | 1.00 | 0.00 |
| ATOM | 1212 | HZ3 | LYS | 47 | 85.658 | 62.608 | 42.097 | 1.00 | 0.00 |
| ATOM | 1213 | C | LYS | 47 | 85.708 | 63.234 | 47.258 | 1.00 | 17.49 |
| ATOM | 1214 | O | LYS | 47 | 84.814 | 62.412 | 47.436 | 1.00 | 20.23 |
| ATOM | 1215 | N | ALA | 48 | 86.986 | 62.898 | 47.182 | 1.00 | 17.49 |
| ATOM | 1216 | H | ALA | 48 | 87.658 | 63.615 | 47.118 | 1.00 | 0.00 |
| ATOM | 1217 | CA | ALA | 48 | 87.388 | 61.501 | 47.122 | 1.00 | 15.01 |
| ATOM | 1218 | CB | ALA | 48 | 88.817 | 61.460 | 46.795 | 1.00 | 12.93 |
| ATOM | 1219 | C | ALA | 48 | 87.166 | 60.656 | 48.356 | 1.00 | 15.68 |
| ATOM | 1220 | O | ALA | 48 | 86.875 | 59.466 | 48.294 | 1.00 | 19.82 |
| ATOM | 1221 | N | HIS | 49 | 87.337 | 61.267 | 49.525 | 1.00 | 16.17 |
| ATOM | 1222 | H | HIS | 49 | 87.713 | 62.175 | 49.481 | 1.00 | 0.00 |
| ATOM | 1223 | CA | HIS | 49 | 87.067 | 60.632 | 50.831 | 1.00 | 15.92 |
| ATOM | 1224 | CB | HIS | 49 | 87.526 | 61.488 | 52.023 | 1.00 | 16.45 |
| ATOM | 1225 | CG | HIS | 49 | 87.730 | 60.679 | 53.296 | 1.00 | 15.80 |
| ATOM | 1226 | CD2 | HIS | 49 | 88.480 | 59.519 | 53.333 | 1.00 | 13.49 |
| ATOM | 1227 | ND1 | HIS | 49 | 87.210 | 60.878 | 54.507 | 1.00 | 14.45 |
| ATOM | 1228 | HD1 | HIS | 49 | 86.663 | 61.625 | 54.832 | 1.00 | 0.00 |
| ATOM | 1229 | CE1 | HIS | 49 | 87.597 | 59.883 | 55.250 | 1.00 | 13.40 |
| ATOM | 1230 | NE2 | HIS | 49 | 88.349 | 59.081 | 54.546 | 1.00 | 12.56 |
| ATOM | 1231 | HE2 | HIS | 49 | 88.745 | 58.254 | 54.895 | 1.00 | 0.00 |
| ATOM | 1232 | C | HIS | 49 | 85.574 | 60.422 | 51.048 | 1.00 | 15.41 |
| ATOM | 1233 | O | HIS | 49 | 85.171 | 59.358 | 51.494 | 1.00 | 15.46 |
| ATOM | 1234 | N | LEU | 50 | 84.766 | 61.446 | 50.764 | 1.00 | 13.37 |
| ATOM | 1235 | H | LEU | 50 | 85.161 | 62.287 | 50.438 | 1.00 | 0.00 |
| ATOM | 1236 | CA | LEU | 50 | 83.323 | 61.347 | 50.836 | 1.00 | 13.25 |
| ATOM | 1237 | CB | LEU | 50 | 82.782 | 62.733 | 50.536 | 1.00 | 13.30 |
| ATOM | 1238 | CG | LEU | 50 | 83.158 | 63.821 | 51.521 | 1.00 | 14.86 |
| ATOM | 1239 | CD1 | LEU | 50 | 82.473 | 65.084 | 51.124 | 1.00 | 15.86 |
| ATOM | 1240 | CD2 | LEU | 50 | 82.678 | 63.496 | 52.928 | 1.00 | 18.66 |
| ATOM | 1241 | C | LEU | 50 | 82.780 | 60.271 | 49.884 | 1.00 | 13.94 |
| ATOM | 1242 | O | LEU | 50 | 82.019 | 59.406 | 50.317 | 1.00 | 14.16 |
| ATOM | 1243 | N | MET | 51 | 83.239 | 60.159 | 48.630 | 1.00 | 14.34 |
| ATOM | 1244 | H | MET | 51 | 83.854 | 60.847 | 48.296 | 1.00 | 0.00 |
| ATOM | 1245 | CA | MET | 51 | 82.741 | 59.112 | 47.734 | 1.00 | 15.28 |
| ATOM | 1246 | CB | MET | 51 | 83.320 | 59.254 | 46.318 | 1.00 | 16.58 |
| ATOM | 1247 | CG | MET | 51 | 82.625 | 60.245 | 45.394 | 1.00 | 17.87 |
| ATOM | 1248 | SD | MET | 51 | 83.380 | 60.334 | 43.748 | 1.00 | 26.04 |
| ATOM | 1249 | CE | MET | 51 | 82.325 | 59.123 | 43.021 | 1.00 | 15.44 |
| ATOM | 1250 | C | MET | 51 | 83.006 | 57.683 | 48.187 | 1.00 | 16.78 |
| ATOM | 1251 | O | MET | 51 | 82.349 | 56.713 | 47.782 | 1.00 | 20.27 |

FIG. 1: A-22

| ATOM | 1252 | N | LYS | 52 | 83.989 | 57.498 | 49.059 | 1.00 | 18.56 |
|---|---|---|---|---|---|---|---|---|---|
| ATOM | 1253 | H | LYS | 52 | 84.567 | 58.250 | 49.291 | 1.00 | 0.00 |
| ATOM | 1254 | CA | LYS | 52 | 84.259 | 56.168 | 49.608 | 1.00 | 18.69 |
| ATOM | 1255 | CB | LYS | 52 | 85.758 | 56.063 | 49.944 | 1.00 | 21.08 |
| ATOM | 1256 | CG | LYS | 52 | 86.754 | 56.437 | 48.817 | 1.00 | 20.81 |
| ATOM | 1257 | CD | LYS | 52 | 88.145 | 55.963 | 49.204 | 1.00 | 23.37 |
| ATOM | 1258 | CE | LYS | 52 | 89.286 | 56.611 | 48.391 | 1.00 | 30.03 |
| ATOM | 1259 | NZ | LYS | 52 | 89.767 | 57.894 | 48.945 | 1.00 | 31.58 |
| ATOM | 1260 | HZ1 | LYS | 52 | 90.162 | 57.740 | 49.895 | 1.00 | 0.00 |
| ATOM | 1261 | HZ2 | LYS | 52 | 88.976 | 58.568 | 48.999 | 1.00 | 0.00 |
| ATOM | 1262 | HZ3 | LYS | 52 | 90.505 | 58.273 | 48.320 | 1.00 | 0.00 |
| ATOM | 1263 | C | LYS | 52 | 83.392 | 55.950 | 50.859 | 1.00 | 20.01 |
| ATOM | 1264 | O | LYS | 52 | 83.512 | 54.951 | 51.549 | 1.00 | 19.77 |
| ATOM | 1265 | N | GLU | 53 | 82.422 | 56.858 | 51.127 | 1.00 | 20.59 |
| ATOM | 1266 | H | GLU | 53 | 82.217 | 57.503 | 50.430 | 1.00 | 0.00 |
| ATOM | 1267 | CA | GLU | 53 | 81.601 | 56.903 | 52.322 | 1.00 | 19.86 |
| ATOM | 1268 | CB | GLU | 53 | 80.708 | 55.661 | 52.470 | 1.00 | 19.53 |
| ATOM | 1269 | CG | GLU | 53 | 79.683 | 55.436 | 51.403 | 1.00 | 17.55 |
| ATOM | 1270 | CD | GLU | 53 | 78.605 | 54.451 | 51.821 | 1.00 | 21.15 |
| ATOM | 1271 | OE1 | GLU | 53 | 77.552 | 54.898 | 52.272 | 1.00 | 22.75 |
| ATOM | 1272 | OE2 | GLU | 53 | 78.787 | 53.241 | 51.666 | 1.00 | 21.64 |
| ATOM | 1273 | C | GLU | 53 | 82.473 | 57.026 | 53.572 | 1.00 | 20.93 |
| ATOM | 1274 | O | GLU | 53 | 82.272 | 56.456 | 54.646 | 1.00 | 23.12 |
| ATOM | 1275 | N | GLY | 54 | 83.493 | 57.861 | 53.409 | 1.00 | 21.41 |
| ATOM | 1276 | H | GLY | 54 | 83.624 | 58.248 | 52.518 | 1.00 | 0.00 |
| ATOM | 1277 | CA | GLY | 54 | 84.414 | 58.189 | 54.467 | 1.00 | 17.93 |
| ATOM | 1278 | C | GLY | 54 | 83.902 | 59.384 | 55.263 | 1.00 | 19.98 |
| ATOM | 1279 | O | GLY | 54 | 83.184 | 60.289 | 54.791 | 1.00 | 16.56 |
| ATOM | 1280 | N | ARG | 55 | 84.290 | 59.363 | 56.539 | 1.00 | 20.47 |
| ATOM | 1281 | H | ARG | 55 | 84.651 | 58.538 | 56.911 | 1.00 | 0.00 |
| ATOM | 1282 | CA | ARG | 55 | 83.904 | 60.469 | 57.380 | 1.00 | 20.06 |
| ATOM | 1283 | CB | ARG | 55 | 83.234 | 59.873 | 58.603 | 1.00 | 22.16 |
| ATOM | 1284 | CG | ARG | 55 | 81.747 | 60.194 | 58.663 | 1.00 | 23.41 |
| ATOM | 1285 | CD | ARG | 55 | 81.109 | 59.524 | 59.839 | 1.00 | 25.27 |
| ATOM | 1286 | NE | ARG | 55 | 81.235 | 58.091 | 59.705 | 1.00 | 28.71 |
| ATOM | 1287 | HE | ARG | 55 | 81.595 | 57.717 | 58.874 | 1.00 | 0.00 |
| ATOM | 1288 | CZ | ARG | 55 | 80.864 | 57.233 | 60.672 | 1.00 | 33.66 |
| ATOM | 1289 | NH1 | ARG | 55 | 81.053 | 55.913 | 60.461 | 1.00 | 34.62 |
| ATOM | 1290 | HH11 | ARG | 55 | 81.455 | 55.597 | 59.602 | 1.00 | 0.00 |
| ATOM | 1291 | HH12 | ARG | 55 | 80.781 | 55.251 | 61.160 | 1.00 | 0.00 |
| ATOM | 1292 | NH2 | ARG | 55 | 80.310 | 57.645 | 61.833 | 1.00 | 31.92 |
| ATOM | 1293 | HH21 | ARG | 55 | 80.186 | 58.617 | 62.012 | 1.00 | 0.00 |
| ATOM | 1294 | HH22 | ARG | 55 | 80.044 | 56.969 | 62.520 | 1.00 | 0.00 |
| ATOM | 1295 | C | ARG | 55 | 84.971 | 61.486 | 57.786 | 1.00 | 21.37 |
| ATOM | 1296 | O | ARG | 55 | 86.184 | 61.265 | 57.626 | 1.00 | 21.45 |
| ATOM | 1297 | N | LEU | 56 | 84.513 | 62.675 | 58.174 | 1.00 | 19.72 |
| ATOM | 1298 | H | LEU | 56 | 83.550 | 62.852 | 58.128 | 1.00 | 0.00 |
| ATOM | 1299 | CA | LEU | 56 | 85.407 | 63.670 | 58.705 | 1.00 | 20.97 |
| ATOM | 1300 | CB | LEU | 56 | 84.932 | 65.036 | 58.355 | 1.00 | 20.35 |
| ATOM | 1301 | CG | LEU | 56 | 85.412 | 65.653 | 57.071 | 1.00 | 20.05 |
| ATOM | 1302 | CD1 | LEU | 56 | 85.363 | 64.655 | 55.919 | 1.00 | 24.78 |
| ATOM | 1303 | CD2 | LEU | 56 | 84.515 | 66.833 | 56.775 | 1.00 | 20.80 |
| ATOM | 1304 | C | LEU | 56 | 85.518 | 63.574 | 60.204 | 1.00 | 21.58 |
| ATOM | 1305 | O | LEU | 56 | 84.787 | 62.817 | 60.842 | 1.00 | 21.68 |
| ATOM | 1306 | N | GLU | 57 | 86.478 | 64.249 | 60.811 | 1.00 | 23.10 |
| ATOM | 1307 | H | GLU | 57 | 87.164 | 64.703 | 60.282 | 1.00 | 0.00 |
| ATOM | 1308 | CA | GLU | 57 | 86.518 | 64.252 | 62.258 | 1.00 | 22.49 |
| ATOM | 1309 | CB | GLU | 57 | 87.942 | 64.672 | 62.604 | 1.00 | 21.78 |
| ATOM | 1310 | CG | GLU | 57 | 88.522 | 64.140 | 63.909 | 1.00 | 26.48 |
| ATOM | 1311 | CD | GLU | 57 | 88.742 | 62.624 | 64.078 | 1.00 | 31.32 |

FIG. 1: A-23

| ATOM | 1312 | OE1 | GLU | 57 | 87.880 | 61.995 | 64.703 | 1.00 | 33.93 |
|---|---|---|---|---|---|---|---|---|---|
| ATOM | 1313 | OE2 | GLU | 57 | 89.770 | 62.070 | 63.640 | 1.00 | 29.95 |
| ATOM | 1314 | C | GLU | 57 | 85.387 | 65.216 | 62.675 | 1.00 | 22.20 |
| ATOM | 1315 | O | GLU | 57 | 85.268 | 66.287 | 62.059 | 1.00 | 25.00 |
| ATOM | 1316 | N | GLU | 58 | 84.464 | 64.910 | 63.603 | 1.00 | 21.96 |
| ATOM | 1317 | H | GLU | 58 | 84.481 | 64.003 | 63.973 | 1.00 | 0.00 |
| ATOM | 1318 | CA | GLU | 58 | 83.372 | 65.823 | 63.976 | 1.00 | 23.99 |
| ATOM | 1319 | CB | GLU | 58 | 82.860 | 65.433 | 65.384 | 1.00 | 25.99 |
| ATOM | 1320 | CG | GLU | 58 | 81.990 | 66.526 | 66.056 | 1.00 | 28.21 |
| ATOM | 1321 | CD | GLU | 58 | 80.680 | 66.059 | 66.652 | 1.00 | 30.88 |
| ATOM | 1322 | OE1 | GLU | 58 | 79.740 | 65.727 | 65.915 | 1.00 | 30.11 |
| ATOM | 1323 | OE2 | GLU | 58 | 80.615 | 66.045 | 67.874 | 1.00 | 32.71 |
| ATOM | 1324 | C | GLU | 58 | 83.642 | 67.348 | 63.952 | 1.00 | 22.49 |
| ATOM | 1325 | O | GLU | 58 | 82.883 | 68.194 | 63.491 | 1.00 | 23.84 |
| ATOM | 1326 | N | THR | 59 | 84.787 | 67.723 | 64.474 | 1.00 | 20.98 |
| ATOM | 1327 | H | THR | 59 | 85.363 | 67.037 | 64.870 | 1.00 | 0.00 |
| ATOM | 1328 | CA | THR | 59 | 85.198 | 69.118 | 64.558 | 1.00 | 18.39 |
| ATOM | 1329 | CB | THR | 59 | 86.334 | 69.142 | 65.624 | 1.00 | 14.67 |
| ATOM | 1330 | OG1 | THR | 59 | 86.920 | 67.842 | 65.836 | 1.00 | 16.86 |
| ATOM | 1331 | HG1 | THR | 59 | 87.274 | 67.850 | 66.735 | 1.00 | 0.00 |
| ATOM | 1332 | CG2 | THR | 59 | 85.717 | 69.534 | 66.935 | 1.00 | 14.19 |
| ATOM | 1333 | C | THR | 59 | 85.564 | 69.758 | 63.222 | 1.00 | 16.68 |
| ATOM | 1334 | O | THR | 59 | 85.376 | 70.948 | 62.991 | 1.00 | 16.77 |
| ATOM | 1335 | N | VAL | 60 | 85.960 | 68.970 | 62.228 | 1.00 | 18.25 |
| ATOM | 1336 | H | VAL | 60 | 86.040 | 68.015 | 62.417 | 1.00 | 0.00 |
| ATOM | 1337 | CA | VAL | 60 | 86.306 | 69.495 | 60.898 | 1.00 | 18.64 |
| ATOM | 1338 | CB | VAL | 60 | 87.236 | 68.490 | 60.159 | 1.00 | 18.71 |
| ATOM | 1339 | CG1 | VAL | 60 | 87.773 | 69.141 | 58.907 | 1.00 | 17.41 |
| ATOM | 1340 | CG2 | VAL | 60 | 88.464 | 68.135 | 60.976 | 1.00 | 17.97 |
| ATOM | 1341 | C | VAL | 60 | 84.992 | 69.711 | 60.122 | 1.00 | 18.99 |
| ATOM | 1342 | O | VAL | 60 | 84.756 | 70.714 | 59.437 | 1.00 | 19.51 |
| ATOM | 1343 | N | ALA | 61 | 84.084 | 68.744 | 60.283 | 1.00 | 16.96 |
| ATOM | 1344 | H | ALA | 61 | 84.367 | 67.954 | 60.788 | 1.00 | 0.00 |
| ATOM | 1345 | CA | ALA | 61 | 82.737 | 68.817 | 59.744 | 1.00 | 16.08 |
| ATOM | 1346 | CB | ALA | 61 | 82.007 | 67.552 | 60.235 | 1.00 | 11.73 |
| ATOM | 1347 | C | ALA | 61 | 82.092 | 70.125 | 60.248 | 1.00 | 17.37 |
| ATOM | 1348 | O | ALA | 61 | 81.720 | 71.003 | 59.472 | 1.00 | 19.75 |
| ATOM | 1349 | N | LEU | 62 | 82.059 | 70.374 | 61.564 | 1.00 | 19.84 |
| ATOM | 1350 | H | LEU | 62 | 82.355 | 69.654 | 62.163 | 1.00 | 0.00 |
| ATOM | 1351 | CA | LEU | 62 | 81.600 | 71.624 | 62.169 | 1.00 | 19.10 |
| ATOM | 1352 | CB | LEU | 62 | 81.736 | 71.523 | 63.667 | 1.00 | 20.23 |
| ATOM | 1353 | CG | LEU | 62 | 80.761 | 70.693 | 64.460 | 1.00 | 20.88 |
| ATOM | 1354 | CD1 | LEU | 62 | 81.226 | 70.619 | 65.904 | 1.00 | 20.57 |
| ATOM | 1355 | CD2 | LEU | 62 | 79.378 | 71.318 | 64.378 | 1.00 | 18.85 |
| ATOM | 1356 | C | LEU | 62 | 82.337 | 72.881 | 61.714 | 1.00 | 20.71 |
| ATOM | 1357 | O | LEU | 62 | 81.727 | 73.947 | 61.641 | 1.00 | 21.62 |
| ATOM | 1358 | N | ARG | 63 | 83.659 | 72.827 | 61.479 | 1.00 | 22.06 |
| ATOM | 1359 | H | ARG | 63 | 84.148 | 72.053 | 61.829 | 1.00 | 0.00 |
| ATOM | 1360 | CA | ARG | 63 | 84.416 | 73.939 | 60.895 | 1.00 | 20.95 |
| ATOM | 1361 | CB | ARG | 63 | 85.907 | 73.583 | 60.909 | 1.00 | 19.41 |
| ATOM | 1362 | CG | ARG | 63 | 86.817 | 74.726 | 60.475 | 1.00 | 18.04 |
| ATOM | 1363 | CD | ARG | 63 | 88.290 | 74.445 | 60.650 | 1.00 | 18.68 |
| ATOM | 1364 | NE | ARG | 63 | 89.030 | 75.361 | 59.784 | 1.00 | 23.34 |
| ATOM | 1365 | HE | ARG | 63 | 88.516 | 75.959 | 59.216 | 1.00 | 0.00 |
| ATOM | 1366 | CZ | ARG | 63 | 90.369 | 75.342 | 59.563 | 1.00 | 25.33 |
| ATOM | 1367 | NH1 | ARG | 63 | 90.904 | 76.237 | 58.715 | 1.00 | 21.46 |
| ATOM | 1368 | HH11 | ARG | 63 | 90.319 | 76.910 | 58.262 | 1.00 | 0.00 |
| ATOM | 1369 | HH12 | ARG | 63 | 91.891 | 76.235 | 58.550 | 1.00 | 0.00 |
| ATOM | 1370 | NH2 | ARG | 63 | 91.184 | 74.406 | 60.110 | 1.00 | 29.46 |
| ATOM | 1371 | HH21 | ARG | 63 | 90.795 | 73.692 | 60.692 | 1.00 | 0.00 |

FIG. 1: A-24

| ATOM | 1372 | HH22 | ARG | 63 | 92.166 | 74.423 | 59.921 | 1.00 | 0.00 |
|---|---|---|---|---|---|---|---|---|---|
| ATOM | 1373 | C | ARG | 63 | 83.960 | 74.241 | 59.450 | 1.00 | 23.81 |
| ATOM | 1374 | O | ARG | 63 | 83.796 | 75.411 | 59.078 | 1.00 | 25.11 |
| ATOM | 1375 | N | ILE | 64 | 83.723 | 73.227 | 58.574 | 1.00 | 24.54 |
| ATOM | 1376 | H | ILE | 64 | 83.917 | 72.320 | 58.892 | 1.00 | 0.00 |
| ATOM | 1377 | CA | ILE | 64 | 83.218 | 73.436 | 57.193 | 1.00 | 22.65 |
| ATOM | 1378 | CB | ILE | 64 | 83.078 | 72.082 | 56.435 | 1.00 | 23.45 |
| ATOM | 1379 | CG2 | ILE | 64 | 82.417 | 72.295 | 55.080 | 1.00 | 23.81 |
| ATOM | 1380 | CG1 | ILE | 64 | 84.442 | 71.450 | 56.219 | 1.00 | 21.98 |
| ATOM | 1381 | CD1 | ILE | 64 | 84.372 | 70.078 | 55.522 | 1.00 | 21.05 |
| ATOM | 1382 | C | ILE | 64 | 81.852 | 74.091 | 57.301 | 1.00 | 20.24 |
| ATOM | 1383 | O | ILE | 64 | 81.587 | 75.111 | 56.663 | 1.00 | 20.59 |
| ATOM | 1384 | N | ILE | 65 | 81.024 | 73.583 | 58.226 | 1.00 | 19.00 |
| ATOM | 1385 | H | ILE | 65 | 81.308 | 72.778 | 58.712 | 1.00 | 0.00 |
| ATOM | 1386 | CA | ILE | 65 | 79.691 | 74.171 | 58.441 | 1.00 | 20.73 |
| ATOM | 1387 | CB | ILE | 65 | 78.859 | 73.225 | 59.345 | 1.00 | 17.60 |
| ATOM | 1388 | CG2 | ILE | 65 | 77.529 | 73.853 | 59.547 | 1.00 | 18.37 |
| ATOM | 1389 | CG1 | ILE | 65 | 78.564 | 71.874 | 58.708 | 1.00 | 16.25 |
| ATOM | 1390 | CD1 | ILE | 65 | 78.087 | 70.875 | 59.769 | 1.00 | 14.06 |
| ATOM | 1391 | C | ILE | 65 | 79.729 | 75.605 | 59.035 | 1.00 | 23.65 |
| ATOM | 1392 | O | ILE | 65 | 79.123 | 76.531 | 58.479 | 1.00 | 26.67 |
| ATOM | 1393 | N | THR | 66 | 80.455 | 75.899 | 60.119 | 1.00 | 23.04 |
| ATOM | 1394 | H | THR | 66 | 80.958 | 75.171 | 60.524 | 1.00 | 0.00 |
| ATOM | 1395 | CA | THR | 66 | 80.525 | 77.244 | 60.665 | 1.00 | 20.54 |
| ATOM | 1396 | CB | THR | 66 | 81.161 | 77.220 | 62.037 | 1.00 | 25.07 |
| ATOM | 1397 | OG1 | THR | 66 | 82.512 | 76.718 | 61.950 | 1.00 | 33.54 |
| ATOM | 1398 | HG1 | THR | 66 | 82.484 | 75.756 | 62.068 | 1.00 | 0.00 |
| ATOM | 1399 | CG2 | THR | 66 | 80.322 | 76.313 | 62.956 | 1.00 | 26.74 |
| ATOM | 1400 | C | THR | 66 | 81.288 | 78.206 | 59.800 | 1.00 | 18.48 |
| ATOM | 1401 | O | THR | 66 | 80.890 | 79.364 | 59.687 | 1.00 | 21.50 |
| ATOM | 1402 | N | GLU | 67 | 82.351 | 77.809 | 59.129 | 1.00 | 15.71 |
| ATOM | 1403 | H | GLU | 67 | 82.741 | 76.945 | 59.368 | 1.00 | 0.00 |
| ATOM | 1404 | CA | GLU | 67 | 83.030 | 78.705 | 58.194 | 1.00 | 18.32 |
| ATOM | 1405 | CB | GLU | 67 | 84.414 | 78.086 | 57.866 | 1.00 | 22.50 |
| ATOM | 1406 | CG | GLU | 67 | 85.487 | 78.159 | 58.970 | 1.00 | 22.14 |
| ATOM | 1407 | CD | GLU | 67 | 86.936 | 77.782 | 58.618 | 1.00 | 21.18 |
| ATOM | 1408 | OE1 | GLU | 67 | 87.281 | 77.495 | 57.480 | 1.00 | 24.37 |
| ATOM | 1409 | OE2 | GLU | 67 | 87.766 | 77.795 | 59.514 | 1.00 | 18.66 |
| ATOM | 1410 | C | GLU | 67 | 82.230 | 79.014 | 56.887 | 1.00 | 19.71 |
| ATOM | 1411 | O | GLU | 67 | 82.305 | 80.112 | 56.304 | 1.00 | 18.50 |
| ATOM | 1412 | N | GLY | 68 | 81.427 | 78.018 | 56.425 | 1.00 | 19.98 |
| ATOM | 1413 | H | GLY | 68 | 81.598 | 77.124 | 56.785 | 1.00 | 0.00 |
| ATOM | 1414 | CA | GLY | 68 | 80.445 | 78.167 | 55.361 | 1.00 | 15.48 |
| ATOM | 1415 | C | GLY | 68 | 79.330 | 79.110 | 55.764 | 1.00 | 16.79 |
| ATOM | 1416 | O | GLY | 68 | 79.045 | 80.122 | 55.117 | 1.00 | 18.82 |
| ATOM | 1417 | N | ALA | 69 | 78.715 | 78.849 | 56.912 | 1.00 | 17.97 |
| ATOM | 1418 | H | ALA | 69 | 78.984 | 78.035 | 57.380 | 1.00 | 0.00 |
| ATOM | 1419 | CA | ALA | 69 | 77.677 | 79.718 | 57.493 | 1.00 | 18.59 |
| ATOM | 1420 | CB | ALA | 69 | 77.257 | 79.215 | 58.860 | 1.00 | 14.75 |
| ATOM | 1421 | C | ALA | 69 | 78.064 | 81.190 | 57.669 | 1.00 | 21.10 |
| ATOM | 1422 | O | ALA | 69 | 77.306 | 82.107 | 57.321 | 1.00 | 24.02 |
| ATOM | 1423 | N | SER | 70 | 79.275 | 81.485 | 58.149 | 1.00 | 22.62 |
| ATOM | 1424 | H | SER | 70 | 79.829 | 80.759 | 58.508 | 1.00 | 0.00 |
| ATOM | 1425 | CA | SER | 70 | 79.694 | 82.886 | 58.246 | 1.00 | 24.11 |
| ATOM | 1426 | CB | SER | 70 | 81.028 | 83.020 | 58.932 | 1.00 | 24.37 |
| ATOM | 1427 | OG | SER | 70 | 81.017 | 82.382 | 60.209 | 1.00 | 31.83 |
| ATOM | 1428 | HG | SER | 70 | 81.056 | 81.422 | 60.109 | 1.00 | 0.00 |
| ATOM | 1429 | C | SER | 70 | 79.823 | 83.643 | 56.929 | 1.00 | 25.90 |
| ATOM | 1430 | O | SER | 70 | 79.634 | 84.861 | 56.923 | 1.00 | 28.63 |
| ATOM | 1431 | N | ILE | 71 | 80.142 | 82.978 | 55.795 | 1.00 | 24.97 |

FIG. 1: A-25

| ATOM | 1432 | H    | ILE | 71 | 80.377 | 82.030 | 55.891 | 1.00 | 0.00  |
|------|------|------|-----|----|--------|--------|--------|------|-------|
| ATOM | 1433 | CA   | ILE | 71 | 80.226 | 83.596 | 54.459 | 1.00 | 23.41 |
| ATOM | 1434 | CB   | ILE | 71 | 80.903 | 82.652 | 53.398 | 1.00 | 23.69 |
| ATOM | 1435 | CG2  | ILE | 71 | 80.890 | 83.341 | 52.047 | 1.00 | 24.89 |
| ATOM | 1436 | CG1  | ILE | 71 | 82.361 | 82.400 | 53.671 | 1.00 | 19.79 |
| ATOM | 1437 | CD1  | ILE | 71 | 82.817 | 81.196 | 52.878 | 1.00 | 19.34 |
| ATOM | 1438 | C    | ILE | 71 | 78.839 | 83.945 | 53.950 | 1.00 | 22.74 |
| ATOM | 1439 | O    | ILE | 71 | 78.606 | 85.059 | 53.484 | 1.00 | 24.70 |
| ATOM | 1440 | N    | LEU | 72 | 77.920 | 82.985 | 54.077 | 1.00 | 21.85 |
| ATOM | 1441 | H    | LEU | 72 | 78.234 | 82.112 | 54.400 | 1.00 | 0.00  |
| ATOM | 1442 | CA   | LEU | 72 | 76.496 | 83.164 | 53.743 | 1.00 | 20.98 |
| ATOM | 1443 | CB   | LEU | 72 | 75.709 | 81.895 | 54.068 | 1.00 | 19.13 |
| ATOM | 1444 | CG   | LEU | 72 | 76.266 | 80.636 | 53.324 | 1.00 | 24.67 |
| ATOM | 1445 | CD1  | LEU | 72 | 75.839 | 79.326 | 53.985 | 1.00 | 22.09 |
| ATOM | 1446 | CD2  | LEU | 72 | 75.844 | 80.751 | 51.863 | 1.00 | 21.08 |
| ATOM | 1447 | C    | LEU | 72 | 75.915 | 84.326 | 54.524 | 1.00 | 21.39 |
| ATOM | 1448 | O    | LEU | 72 | 75.463 | 85.283 | 53.923 | 1.00 | 20.39 |
| ATOM | 1449 | N    | ARG | 73 | 76.044 | 84.374 | 55.851 | 1.00 | 22.29 |
| ATOM | 1450 | H    | ARG | 73 | 76.484 | 83.618 | 56.297 | 1.00 | 0.00  |
| ATOM | 1451 | CA   | ARG | 73 | 75.549 | 85.486 | 56.674 | 1.00 | 22.78 |
| ATOM | 1452 | CB   | ARG | 73 | 76.063 | 85.251 | 58.083 | 1.00 | 25.17 |
| ATOM | 1453 | CG   | ARG | 73 | 75.622 | 86.337 | 59.052 | 1.00 | 24.03 |
| ATOM | 1454 | CD   | ARG | 73 | 76.254 | 86.153 | 60.368 | 1.00 | 22.43 |
| ATOM | 1455 | NE   | ARG | 73 | 75.660 | 85.003 | 61.003 | 1.00 | 28.78 |
| ATOM | 1456 | HE   | ARG | 73 | 74.695 | 84.984 | 61.166 | 1.00 | 0.00  |
| ATOM | 1457 | CZ   | ARG | 73 | 76.403 | 83.954 | 61.376 | 1.00 | 35.32 |
| ATOM | 1458 | NH1  | ARG | 73 | 75.743 | 82.933 | 61.937 | 1.00 | 40.90 |
| ATOM | 1459 | HH11 | ARG | 73 | 74.751 | 82.976 | 62.052 | 1.00 | 0.00  |
| ATOM | 1460 | HH12 | ARG | 73 | 76.247 | 82.118 | 62.226 | 1.00 | 0.00  |
| ATOM | 1461 | NH2  | ARG | 73 | 77.758 | 83.888 | 61.232 | 1.00 | 36.08 |
| ATOM | 1462 | HH21 | ARG | 73 | 78.266 | 84.646 | 60.824 | 1.00 | 0.00  |
| ATOM | 1463 | HH22 | ARG | 73 | 78.246 | 83.066 | 61.527 | 1.00 | 0.00  |
| ATOM | 1464 | C    | ARG | 73 | 75.880 | 86.922 | 56.232 | 1.00 | 23.51 |
| ATOM | 1465 | O    | ARG | 73 | 75.124 | 87.892 | 56.400 | 1.00 | 22.79 |
| ATOM | 1466 | N    | GLN | 74 | 77.068 | 87.086 | 55.649 | 1.00 | 24.86 |
| ATOM | 1467 | H    | GLN | 74 | 77.650 | 86.308 | 55.520 | 1.00 | 0.00  |
| ATOM | 1468 | CA   | GLN | 74 | 77.419 | 88.407 | 55.160 | 1.00 | 26.55 |
| ATOM | 1469 | CB   | GLN | 74 | 78.940 | 88.474 | 55.031 | 1.00 | 29.60 |
| ATOM | 1470 | CG   | GLN | 74 | 79.810 | 88.001 | 56.223 | 1.00 | 34.91 |
| ATOM | 1471 | CD   | GLN | 74 | 79.318 | 88.110 | 57.691 | 1.00 | 38.93 |
| ATOM | 1472 | OE1  | GLN | 74 | 79.577 | 87.200 | 58.501 | 1.00 | 39.29 |
| ATOM | 1473 | NE2  | GLN | 74 | 78.616 | 89.147 | 58.175 | 1.00 | 36.05 |
| ATOM | 1474 | HE21 | GLN | 74 | 78.369 | 89.884 | 57.589 | 1.00 | 0.00  |
| ATOM | 1475 | HE22 | GLN | 74 | 78.390 | 89.058 | 59.122 | 1.00 | 0.00  |
| ATOM | 1476 | C    | GLN | 74 | 76.719 | 88.742 | 53.830 | 1.00 | 25.84 |
| ATOM | 1477 | O    | GLN | 74 | 76.447 | 89.904 | 53.504 | 1.00 | 27.25 |
| ATOM | 1478 | N    | GLU | 75 | 76.368 | 87.719 | 53.048 | 1.00 | 25.82 |
| ATOM | 1479 | H    | GLU | 75 | 76.539 | 86.819 | 53.390 | 1.00 | 0.00  |
| ATOM | 1480 | CA   | GLU | 75 | 75.639 | 87.854 | 51.783 | 1.00 | 24.99 |
| ATOM | 1481 | CB   | GLU | 75 | 75.566 | 86.508 | 51.116 | 1.00 | 24.81 |
| ATOM | 1482 | CG   | GLU | 75 | 76.953 | 85.955 | 50.811 | 1.00 | 21.07 |
| ATOM | 1483 | CD   | GLU | 75 | 76.949 | 84.863 | 49.767 | 1.00 | 17.68 |
| ATOM | 1484 | OE1  | GLU | 75 | 77.514 | 85.124 | 48.722 | 1.00 | 23.33 |
| ATOM | 1485 | OE2  | GLU | 75 | 76.388 | 83.788 | 49.959 | 1.00 | 19.85 |
| ATOM | 1486 | C    | GLU | 75 | 74.216 | 88.435 | 51.823 | 1.00 | 26.11 |
| ATOM | 1487 | O    | GLU | 75 | 73.497 | 88.298 | 52.813 | 1.00 | 25.53 |
| ATOM | 1488 | N    | LYS | 76 | 73.782 | 89.120 | 50.756 | 1.00 | 25.59 |
| ATOM | 1489 | H    | LYS | 76 | 74.333 | 89.103 | 49.952 | 1.00 | 0.00  |
| ATOM | 1490 | CA   | LYS | 76 | 72.494 | 89.794 | 50.752 | 1.00 | 25.39 |
| ATOM | 1491 | CB   | LYS | 76 | 72.507 | 90.856 | 49.672 | 1.00 | 29.35 |

FIG. 1: A-26

| ATOM | 1492 | CG | LYS | 76 | 73.557 | 91.959 | 49.783 | 1.00 | 33.02 |
|---|---|---|---|---|---|---|---|---|---|
| ATOM | 1493 | CD | LYS | 76 | 73.713 | 92.844 | 48.515 | 1.00 | 38.84 |
| ATOM | 1494 | CE | LYS | 76 | 75.209 | 93.284 | 48.340 | 1.00 | 42.73 |
| ATOM | 1495 | NZ | LYS | 76 | 75.481 | 94.280 | 47.304 | 1.00 | 42.85 |
| ATOM | 1496 | HZ1 | LYS | 76 | 76.496 | 94.503 | 47.300 | 1.00 | 0.00 |
| ATOM | 1497 | HZ2 | LYS | 76 | 74.950 | 95.146 | 47.530 | 1.00 | 0.00 |
| ATOM | 1498 | HZ3 | LYS | 76 | 75.199 | 93.929 | 46.369 | 1.00 | 0.00 |
| ATOM | 1499 | C | LYS | 76 | 71.308 | 88.871 | 50.529 | 1.00 | 25.78 |
| ATOM | 1500 | O | LYS | 76 | 71.465 | 87.877 | 49.816 | 1.00 | 27.09 |
| ATOM | 1501 | N | ASN | 77 | 70.103 | 89.150 | 51.085 | 1.00 | 25.34 |
| ATOM | 1502 | H | ASN | 77 | 70.083 | 89.881 | 51.733 | 1.00 | 0.00 |
| ATOM | 1503 | CA | ASN | 77 | 68.868 | 88.324 | 50.899 | 1.00 | 23.86 |
| ATOM | 1504 | CB | ASN | 77 | 67.539 | 89.041 | 51.317 | 1.00 | 22.89 |
| ATOM | 1505 | CG | ASN | 77 | 67.204 | 89.284 | 52.794 | 1.00 | 21.18 |
| ATOM | 1506 | OD1 | ASN | 77 | 67.796 | 88.765 | 53.733 | 1.00 | 25.75 |
| ATOM | 1507 | ND2 | ASN | 77 | 66.222 | 90.083 | 53.123 | 1.00 | 16.83 |
| ATOM | 1508 | HD21 | ASN | 77 | 65.671 | 90.493 | 52.436 | 1.00 | 0.00 |
| ATOM | 1509 | HD22 | ASN | 77 | 66.142 | 90.275 | 54.081 | 1.00 | 0.00 |
| ATOM | 1510 | C | ASN | 77 | 68.634 | 87.908 | 49.450 | 1.00 | 22.54 |
| ATOM | 1511 | O | ASN | 77 | 68.309 | 86.774 | 49.109 | 1.00 | 23.17 |
| ATOM | 1512 | N | LEU | 78 | 68.819 | 88.919 | 48.623 | 1.00 | 21.52 |
| ATOM | 1513 | H | LEU | 78 | 69.059 | 89.780 | 49.014 | 1.00 | 0.00 |
| ATOM | 1514 | CA | LEU | 78 | 68.790 | 88.816 | 47.187 | 1.00 | 21.81 |
| ATOM | 1515 | CB | LEU | 78 | 67.827 | 89.900 | 46.711 | 1.00 | 22.02 |
| ATOM | 1516 | CG | LEU | 78 | 67.507 | 90.136 | 45.229 | 1.00 | 21.03 |
| ATOM | 1517 | CD1 | LEU | 78 | 66.754 | 88.973 | 44.588 | 1.00 | 13.83 |
| ATOM | 1518 | CD2 | LEU | 78 | 66.662 | 91.388 | 45.166 | 1.00 | 18.04 |
| ATOM | 1519 | C | LEU | 78 | 70.224 | 88.999 | 46.641 | 1.00 | 23.26 |
| ATOM | 1520 | O | LEU | 78 | 70.851 | 90.050 | 46.803 | 1.00 | 24.56 |
| ATOM | 1521 | N | LEU | 79 | 70.849 | 88.000 | 46.024 | 1.00 | 23.75 |
| ATOM | 1522 | H | LEU | 79 | 70.406 | 87.135 | 45.993 | 1.00 | 0.00 |
| ATOM | 1523 | CA | LEU | 79 | 72.204 | 88.139 | 45.495 | 1.00 | 20.55 |
| ATOM | 1524 | CB | LEU | 79 | 72.832 | 86.778 | 45.349 | 1.00 | 17.37 |
| ATOM | 1525 | CG | LEU | 79 | 72.925 | 85.918 | 46.576 | 1.00 | 17.55 |
| ATOM | 1526 | CD1 | LEU | 79 | 73.075 | 84.441 | 46.162 | 1.00 | 15.36 |
| ATOM | 1527 | CD2 | LEU | 79 | 74.032 | 86.484 | 47.462 | 1.00 | 14.33 |
| ATOM | 1528 | C | LEU | 79 | 72.199 | 88.815 | 44.141 | 1.00 | 22.27 |
| ATOM | 1529 | O | LEU | 79 | 71.171 | 88.812 | 43.472 | 1.00 | 19.98 |
| ATOM | 1530 | N | ASP | 80 | 73.287 | 89.431 | 43.694 | 1.00 | 24.45 |
| ATOM | 1531 | H | ASP | 80 | 74.051 | 89.517 | 44.303 | 1.00 | 0.00 |
| ATOM | 1532 | CA | ASP | 80 | 73.296 | 89.969 | 42.335 | 1.00 | 27.61 |
| ATOM | 1533 | CB | ASP | 80 | 73.812 | 91.361 | 42.182 | 1.00 | 30.56 |
| ATOM | 1534 | CG | ASP | 80 | 73.122 | 92.378 | 43.031 | 1.00 | 33.32 |
| ATOM | 1535 | OD1 | ASP | 80 | 72.137 | 92.957 | 42.548 | 1.00 | 37.74 |
| ATOM | 1536 | OD2 | ASP | 80 | 73.601 | 92.574 | 44.154 | 1.00 | 36.22 |
| ATOM | 1537 | C | ASP | 80 | 74.307 | 89.147 | 41.602 | 1.00 | 28.65 |
| ATOM | 1538 | O | ASP | 80 | 75.508 | 89.284 | 41.829 | 1.00 | 30.65 |
| ATOM | 1539 | N | ILE | 81 | 73.860 | 88.247 | 40.752 | 1.00 | 28.18 |
| ATOM | 1540 | H | ILE | 81 | 72.901 | 88.209 | 40.578 | 1.00 | 0.00 |
| ATOM | 1541 | CA | ILE | 81 | 74.782 | 87.359 | 40.081 | 1.00 | 26.19 |
| ATOM | 1542 | CB | ILE | 81 | 74.229 | 85.929 | 40.296 | 1.00 | 23.56 |
| ATOM | 1543 | CG2 | ILE | 81 | 75.053 | 84.895 | 39.544 | 1.00 | 23.16 |
| ATOM | 1544 | CG1 | ILE | 81 | 74.273 | 85.621 | 41.796 | 1.00 | 21.34 |
| ATOM | 1545 | CD1 | ILE | 81 | 73.918 | 84.178 | 42.198 | 1.00 | 19.01 |
| ATOM | 1546 | C | ILE | 81 | 75.040 | 87.673 | 38.613 | 1.00 | 27.80 |
| ATOM | 1547 | O | ILE | 81 | 74.062 | 87.788 | 37.873 | 1.00 | 26.93 |
| ATOM | 1548 | N | ASP | 82 | 76.286 | 87.859 | 38.137 | 1.00 | 28.35 |
| ATOM | 1549 | H | ASP | 82 | 77.040 | 87.865 | 38.759 | 1.00 | 0.00 |
| ATOM | 1550 | CA | ASP | 82 | 76.494 | 87.963 | 36.685 | 1.00 | 29.41 |
| ATOM | 1551 | CB | ASP | 82 | 77.749 | 88.658 | 36.277 | 1.00 | 33.58 |

FIG. 1: A-27

| ATOM | 1552 | CG | ASP | 82 | 77.942 | 90.007 | 36.909 | 1.00 | 39.71 |
|---|---|---|---|---|---|---|---|---|---|
| ATOM | 1553 | OD1 | ASP | 82 | 78.930 | 90.142 | 37.642 | 1.00 | 41.85 |
| ATOM | 1554 | OD2 | ASP | 82 | 77.117 | 90.892 | 36.661 | 1.00 | 43.17 |
| ATOM | 1555 | C | ASP | 82 | 76.603 | 86.657 | 35.909 | 1.00 | 26.50 |
| ATOM | 1556 | O | ASP | 82 | 77.108 | 85.669 | 36.428 | 1.00 | 25.07 |
| ATOM | 1557 | N | ALA | 83 | 76.116 | 86.636 | 34.671 | 1.00 | 24.98 |
| ATOM | 1558 | H | ALA | 83 | 75.691 | 87.443 | 34.321 | 1.00 | 0.00 |
| ATOM | 1559 | CA | ALA | 83 | 76.409 | 85.509 | 33.782 | 1.00 | 25.44 |
| ATOM | 1560 | CB | ALA | 83 | 75.552 | 85.497 | 32.544 | 1.00 | 24.97 |
| ATOM | 1561 | C | ALA | 83 | 77.854 | 85.618 | 33.272 | 1.00 | 24.70 |
| ATOM | 1562 | O | ALA | 83 | 78.350 | 86.751 | 33.257 | 1.00 | 27.83 |
| ATOM | 1563 | N | PRO | 84 | 78.614 | 84.591 | 32.857 | 1.00 | 21.31 |
| ATOM | 1564 | CD | PRO | 84 | 80.056 | 84.659 | 32.642 | 1.00 | 16.02 |
| ATOM | 1565 | CA | PRO | 84 | 78.186 | 83.225 | 32.760 | 1.00 | 19.46 |
| ATOM | 1566 | CB | PRO | 84 | 79.350 | 82.557 | 32.067 | 1.00 | 17.97 |
| ATOM | 1567 | CG | PRO | 84 | 80.203 | 83.661 | 31.539 | 1.00 | 14.28 |
| ATOM | 1568 | C | PRO | 84 | 77.826 | 82.611 | 34.112 | 1.00 | 21.27 |
| ATOM | 1569 | O | PRO | 84 | 78.535 | 82.784 | 35.097 | 1.00 | 20.14 |
| ATOM | 1570 | N | VAL | 85 | 76.651 | 81.998 | 34.206 | 1.00 | 21.17 |
| ATOM | 1571 | H | VAL | 85 | 76.043 | 82.034 | 33.438 | 1.00 | 0.00 |
| ATOM | 1572 | CA | VAL | 85 | 76.314 | 81.221 | 35.387 | 1.00 | 22.34 |
| ATOM | 1573 | CB | VAL | 85 | 75.217 | 81.749 | 36.340 | 1.00 | 22.68 |
| ATOM | 1574 | CG1 | VAL | 85 | 75.684 | 81.438 | 37.756 | 1.00 | 17.16 |
| ATOM | 1575 | CG2 | VAL | 85 | 74.898 | 83.195 | 36.092 | 1.00 | 26.12 |
| ATOM | 1576 | C | VAL | 85 | 75.718 | 79.893 | 34.952 | 1.00 | 23.60 |
| ATOM | 1577 | O | VAL | 85 | 75.008 | 79.811 | 33.942 | 1.00 | 24.19 |
| ATOM | 1578 | N | THR | 86 | 76.070 | 78.815 | 35.644 | 1.00 | 21.64 |
| ATOM | 1579 | H | THR | 86 | 76.768 | 78.890 | 36.330 | 1.00 | 0.00 |
| ATOM | 1580 | CA | THR | 86 | 75.309 | 77.614 | 35.426 | 1.00 | 22.02 |
| ATOM | 1581 | CB | THR | 86 | 76.275 | 76.374 | 35.188 | 1.00 | 24.41 |
| ATOM | 1582 | OG1 | THR | 86 | 75.561 | 75.143 | 35.421 | 1.00 | 25.18 |
| ATOM | 1583 | HG1 | THR | 86 | 76.189 | 74.445 | 35.636 | 1.00 | 0.00 |
| ATOM | 1584 | CG2 | THR | 86 | 77.472 | 76.498 | 35.984 | 1.00 | 25.54 |
| ATOM | 1585 | C | THR | 86 | 74.437 | 77.531 | 36.678 | 1.00 | 19.18 |
| ATOM | 1586 | O | THR | 86 | 74.858 | 77.803 | 37.803 | 1.00 | 19.84 |
| ATOM | 1587 | N | VAL | 87 | 73.136 | 77.465 | 36.426 | 1.00 | 15.26 |
| ATOM | 1588 | H | VAL | 87 | 72.868 | 77.494 | 35.491 | 1.00 | 0.00 |
| ATOM | 1589 | CA | VAL | 87 | 72.128 | 77.365 | 37.469 | 1.00 | 14.68 |
| ATOM | 1590 | CB | VAL | 87 | 70.931 | 78.225 | 37.064 | 1.00 | 13.83 |
| ATOM | 1591 | CG1 | VAL | 87 | 69.913 | 78.280 | 38.179 | 1.00 | 7.16 |
| ATOM | 1592 | CG2 | VAL | 87 | 71.449 | 79.597 | 36.662 | 1.00 | 8.43 |
| ATOM | 1593 | C | VAL | 87 | 71.688 | 75.916 | 37.758 | 1.00 | 16.39 |
| ATOM | 1594 | O | VAL | 87 | 71.408 | 75.110 | 36.864 | 1.00 | 18.18 |
| ATOM | 1595 | N | CYS | 88 | 71.694 | 75.525 | 39.025 | 1.00 | 16.75 |
| ATOM | 1596 | H | CYS | 88 | 71.965 | 76.173 | 39.707 | 1.00 | 0.00 |
| ATOM | 1597 | CA | CYS | 88 | 71.396 | 74.163 | 39.404 | 1.00 | 14.45 |
| ATOM | 1598 | CB | CYS | 88 | 72.513 | 73.600 | 40.152 | 1.00 | 12.05 |
| ATOM | 1599 | SG | CYS | 88 | 73.849 | 73.692 | 38.981 | 1.00 | 12.68 |
| ATOM | 1600 | C | CYS | 88 | 70.173 | 74.029 | 40.252 | 1.00 | 17.38 |
| ATOM | 1601 | O | CYS | 88 | 69.947 | 74.877 | 41.117 | 1.00 | 23.03 |
| ATOM | 1602 | N | GLY | 89 | 69.359 | 73.008 | 40.017 | 1.00 | 15.87 |
| ATOM | 1603 | H | GLY | 89 | 69.631 | 72.353 | 39.347 | 1.00 | 0.00 |
| ATOM | 1604 | CA | GLY | 89 | 68.149 | 72.819 | 40.771 | 1.00 | 12.25 |
| ATOM | 1605 | C | GLY | 89 | 68.367 | 71.846 | 41.899 | 1.00 | 13.66 |
| ATOM | 1606 | O | GLY | 89 | 69.491 | 71.552 | 42.273 | 1.00 | 17.05 |
| ATOM | 1607 | N | ASP | 90 | 67.293 | 71.289 | 42.422 | 1.00 | 13.25 |
| ATOM | 1608 | H | ASP | 90 | 66.460 | 71.482 | 41.955 | 1.00 | 0.00 |
| ATOM | 1609 | CA | ASP | 90 | 67.282 | 70.439 | 43.627 | 1.00 | 14.52 |
| ATOM | 1610 | CB | ASP | 90 | 65.905 | 69.777 | 43.814 | 1.00 | 17.28 |
| ATOM | 1611 | CG | ASP | 90 | 64.717 | 70.748 | 43.977 | 1.00 | 23.77 |

FIG. 1: A-28

| ATOM | 1612 | OD1 | ASP | 90 | 63.699 | 70.300 | 44.481 | 1.00 | 23.87 |
|---|---|---|---|---|---|---|---|---|---|
| ATOM | 1613 | OD2 | ASP | 90 | 64.786 | 71.939 | 43.625 | 1.00 | 24.07 |
| ATOM | 1614 | C | ASP | 90 | 68.295 | 69.332 | 43.670 | 1.00 | 13.73 |
| ATOM | 1615 | O | ASP | 90 | 68.330 | 68.597 | 42.702 | 1.00 | 17.62 |
| ATOM | 1616 | N | ILE | 91 | 69.067 | 69.157 | 44.731 | 1.00 | 12.91 |
| ATOM | 1617 | H | ILE | 91 | 69.034 | 69.865 | 45.407 | 1.00 | 0.00 |
| ATOM | 1618 | CA | ILE | 91 | 70.079 | 68.099 | 44.814 | 1.00 | 13.40 |
| ATOM | 1619 | CB | ILE | 91 | 71.428 | 68.756 | 45.405 | 1.00 | 11.92 |
| ATOM | 1620 | CG2 | ILE | 91 | 72.500 | 67.746 | 45.849 | 1.00 | 8.36 |
| ATOM | 1621 | CG1 | ILE | 91 | 72.027 | 69.633 | 44.297 | 1.00 | 12.03 |
| ATOM | 1622 | CD1 | ILE | 91 | 72.515 | 68.888 | 43.007 | 1.00 | 4.73 |
| ATOM | 1623 | C | ILE | 91 | 69.584 | 66.916 | 45.652 | 1.00 | 16.29 |
| ATOM | 1624 | O | ILE | 91 | 69.777 | 65.741 | 45.353 | 1.00 | 18.91 |
| ATOM | 1625 | N | HIS | 92 | 68.913 | 67.220 | 46.762 | 1.00 | 15.90 |
| ATOM | 1626 | H | HIS | 92 | 68.792 | 68.172 | 46.911 | 1.00 | 0.00 |
| ATOM | 1627 | CA | HIS | 92 | 68.393 | 66.250 | 47.715 | 1.00 | 13.28 |
| ATOM | 1628 | CB | HIS | 92 | 67.110 | 65.676 | 47.195 | 1.00 | 11.50 |
| ATOM | 1629 | CG | HIS | 92 | 65.998 | 66.657 | 47.467 | 1.00 | 12.28 |
| ATOM | 1630 | CD2 | HIS | 92 | 65.183 | 67.171 | 46.511 | 1.00 | 13.22 |
| ATOM | 1631 | ND1 | HIS | 92 | 65.643 | 67.188 | 48.616 | 1.00 | 13.26 |
| ATOM | 1632 | HD1 | HIS | 92 | 66.060 | 67.003 | 49.493 | 1.00 | 0.00 |
| ATOM | 1633 | CE1 | HIS | 92 | 64.656 | 67.998 | 48.392 | 1.00 | 12.51 |
| ATOM | 1634 | NE2 | HIS | 92 | 64.388 | 67.982 | 47.125 | 1.00 | 13.73 |
| ATOM | 1635 | HE2 | HIS | 92 | 63.547 | 68.250 | 46.715 | 1.00 | 0.00 |
| ATOM | 1636 | C | HIS | 92 | 69.266 | 65.093 | 48.170 | 1.00 | 15.16 |
| ATOM | 1637 | O | HIS | 92 | 68.983 | 63.924 | 47.918 | 1.00 | 17.65 |
| ATOM | 1638 | N | GLY | 93 | 70.383 | 65.310 | 48.837 | 1.00 | 12.61 |
| ATOM | 1639 | H | GLY | 93 | 70.746 | 66.205 | 48.938 | 1.00 | 0.00 |
| ATOM | 1640 | CA | GLY | 93 | 71.102 | 64.180 | 49.364 | 1.00 | 11.45 |
| ATOM | 1641 | C | GLY | 93 | 71.723 | 63.240 | 48.359 | 1.00 | 9.28 |
| ATOM | 1642 | O | GLY | 93 | 72.405 | 62.292 | 48.738 | 1.00 | 10.05 |
| ATOM | 1643 | N | GLN | 94 | 71.547 | 63.448 | 47.075 | 1.00 | 11.96 |
| ATOM | 1644 | H | GLN | 94 | 70.956 | 64.171 | 46.784 | 1.00 | 0.00 |
| ATOM | 1645 | CA | GLN | 94 | 72.143 | 62.570 | 46.073 | 1.00 | 14.58 |
| ATOM | 1646 | CB | GLN | 94 | 71.283 | 62.515 | 44.830 | 1.00 | 15.52 |
| ATOM | 1647 | CG | GLN | 94 | 69.825 | 62.227 | 45.107 | 1.00 | 18.07 |
| ATOM | 1648 | CD | GLN | 94 | 68.921 | 62.134 | 43.892 | 1.00 | 17.85 |
| ATOM | 1649 | OE1 | GLN | 94 | 67.731 | 62.345 | 44.020 | 1.00 | 20.75 |
| ATOM | 1650 | NE2 | GLN | 94 | 69.290 | 61.786 | 42.677 | 1.00 | 17.16 |
| ATOM | 1651 | HE21 | GLN | 94 | 70.227 | 61.615 | 42.498 | 1.00 | 0.00 |
| ATOM | 1652 | HE22 | GLN | 94 | 68.560 | 61.705 | 42.026 | 1.00 | 0.00 |
| ATOM | 1653 | C | GLN | 94 | 73.533 | 63.036 | 45.682 | 1.00 | 15.97 |
| ATOM | 1654 | O | GLN | 94 | 73.841 | 63.394 | 44.542 | 1.00 | 16.30 |
| ATOM | 1655 | N | PHE | 95 | 74.422 | 62.944 | 46.667 | 1.00 | 18.16 |
| ATOM | 1656 | H | PHE | 95 | 74.079 | 62.633 | 47.535 | 1.00 | 0.00 |
| ATOM | 1657 | CA | PHE | 95 | 75.823 | 63.340 | 46.556 | 1.00 | 18.64 |
| ATOM | 1658 | CB | PHE | 95 | 76.586 | 62.899 | 47.792 | 1.00 | 18.42 |
| ATOM | 1659 | CG | PHE | 95 | 78.090 | 63.135 | 47.750 | 1.00 | 16.62 |
| ATOM | 1660 | CD1 | PHE | 95 | 78.954 | 62.043 | 47.620 | 1.00 | 17.26 |
| ATOM | 1661 | CD2 | PHE | 95 | 78.585 | 64.430 | 47.866 | 1.00 | 15.80 |
| ATOM | 1662 | CE1 | PHE | 95 | 80.317 | 62.259 | 47.606 | 1.00 | 16.94 |
| ATOM | 1663 | CE2 | PHE | 95 | 79.951 | 64.633 | 47.854 | 1.00 | 14.48 |
| ATOM | 1664 | CZ | PHE | 95 | 80.813 | 63.556 | 47.724 | 1.00 | 14.67 |
| ATOM | 1665 | C | PHE | 95 | 76.520 | 62.771 | 45.349 | 1.00 | 19.39 |
| ATOM | 1666 | O | PHE | 95 | 77.258 | 63.472 | 44.658 | 1.00 | 20.09 |
| ATOM | 1667 | N | PHE | 96 | 76.255 | 61.498 | 45.028 | 1.00 | 19.87 |
| ATOM | 1668 | H | PHE | 96 | 75.670 | 60.957 | 45.597 | 1.00 | 0.00 |
| ATOM | 1669 | CA | PHE | 96 | 76.970 | 60.938 | 43.884 | 1.00 | 18.26 |
| ATOM | 1670 | CB | PHE | 96 | 76.895 | 59.466 | 43.968 | 1.00 | 17.59 |
| ATOM | 1671 | CG | PHE | 96 | 77.701 | 58.971 | 45.176 | 1.00 | 22.20 |

FIG. 1: A-29

| ATOM | 1672 | CD1 | PHE | 96 | 77.076 | 58.838 | 46.442 | 1.00 | 21.86 |
|---|---|---|---|---|---|---|---|---|---|
| ATOM | 1673 | CD2 | PHE | 96 | 79.040 | 58.590 | 45.010 | 1.00 | 18.55 |
| ATOM | 1674 | CE1 | PHE | 96 | 77.783 | 58.317 | 47.530 | 1.00 | 21.32 |
| ATOM | 1675 | CE2 | PHE | 96 | 79.721 | 58.070 | 46.110 | 1.00 | 20.98 |
| ATOM | 1676 | CZ | PHE | 96 | 79.108 | 57.931 | 47.359 | 1.00 | 19.11 |
| ATOM | 1677 | C | PHE | 96 | 76.502 | 61.422 | 42.534 | 1.00 | 18.25 |
| ATOM | 1678 | O | PHE | 96 | 77.204 | 61.284 | 41.537 | 1.00 | 21.63 |
| ATOM | 1679 | N | ASP | 97 | 75.339 | 62.082 | 42.545 | 1.00 | 15.89 |
| ATOM | 1680 | H | ASP | 97 | 74.828 | 62.091 | 43.378 | 1.00 | 0.00 |
| ATOM | 1681 | CA | ASP | 97 | 74.792 | 62.741 | 41.390 | 1.00 | 13.39 |
| ATOM | 1682 | CB | ASP | 97 | 73.286 | 62.676 | 41.455 | 1.00 | 14.76 |
| ATOM | 1683 | CG | ASP | 97 | 72.744 | 61.319 | 41.043 | 1.00 | 14.79 |
| ATOM | 1684 | OD1 | ASP | 97 | 73.032 | 60.917 | 39.924 | 1.00 | 19.87 |
| ATOM | 1685 | OD2 | ASP | 97 | 72.046 | 60.655 | 41.808 | 1.00 | 16.12 |
| ATOM | 1686 | C | ASP | 97 | 75.283 | 64.171 | 41.385 | 1.00 | 13.61 |
| ATOM | 1687 | O | ASP | 97 | 75.429 | 64.787 | 40.341 | 1.00 | 15.27 |
| ATOM | 1688 | N | LEU | 98 | 75.630 | 64.744 | 42.534 | 1.00 | 14.05 |
| ATOM | 1689 | H | LEU | 98 | 75.316 | 64.329 | 43.365 | 1.00 | 0.00 |
| ATOM | 1690 | CA | LEU | 98 | 76.304 | 66.052 | 42.602 | 1.00 | 12.58 |
| ATOM | 1691 | CB | LEU | 98 | 76.565 | 66.485 | 44.003 | 1.00 | 10.02 |
| ATOM | 1692 | CG | LEU | 98 | 76.303 | 67.859 | 44.588 | 1.00 | 12.48 |
| ATOM | 1693 | CD1 | LEU | 98 | 77.375 | 68.107 | 45.682 | 1.00 | 6.02 |
| ATOM | 1694 | CD2 | LEU | 98 | 76.321 | 68.923 | 43.512 | 1.00 | 9.01 |
| ATOM | 1695 | C | LEU | 98 | 77.669 | 65.954 | 41.958 | 1.00 | 13.11 |
| ATOM | 1696 | O | LEU | 98 | 78.171 | 66.880 | 41.365 | 1.00 | 15.78 |
| ATOM | 1697 | N | MET | 99 | 78.365 | 64.833 | 42.069 | 1.00 | 16.53 |
| ATOM | 1698 | H | MET | 99 | 78.009 | 64.164 | 42.690 | 1.00 | 0.00 |
| ATOM | 1699 | CA | MET | 99 | 79.672 | 64.637 | 41.418 | 1.00 | 17.92 |
| ATOM | 1700 | CB | MET | 99 | 80.226 | 63.278 | 41.863 | 1.00 | 15.18 |
| ATOM | 1701 | CG | MET | 99 | 80.244 | 63.158 | 43.369 | 1.00 | 11.83 |
| ATOM | 1702 | SD | MET | 99 | 81.362 | 64.386 | 44.042 | 1.00 | 19.23 |
| ATOM | 1703 | CE | MET | 99 | 80.423 | 65.836 | 44.411 | 1.00 | 14.17 |
| ATOM | 1704 | C | MET | 99 | 79.510 | 64.720 | 39.887 | 1.00 | 19.73 |
| ATOM | 1705 | O | MET | 99 | 80.187 | 65.485 | 39.183 | 1.00 | 20.40 |
| ATOM | 1706 | N | LYS | 100 | 78.489 | 64.022 | 39.377 | 1.00 | 19.63 |
| ATOM | 1707 | H | LYS | 100 | 78.025 | 63.371 | 39.939 | 1.00 | 0.00 |
| ATOM | 1708 | CA | LYS | 100 | 78.141 | 64.164 | 37.978 | 1.00 | 19.81 |
| ATOM | 1709 | CB | LYS | 100 | 76.978 | 63.257 | 37.699 | 1.00 | 18.14 |
| ATOM | 1710 | CG | LYS | 100 | 76.737 | 63.170 | 36.221 | 1.00 | 20.40 |
| ATOM | 1711 | CD | LYS | 100 | 77.992 | 62.690 | 35.520 | 1.00 | 24.15 |
| ATOM | 1712 | CE | LYS | 100 | 77.647 | 62.595 | 34.053 | 1.00 | 29.22 |
| ATOM | 1713 | NZ | LYS | 100 | 78.812 | 62.204 | 33.278 | 1.00 | 33.01 |
| ATOM | 1714 | HZ1 | LYS | 100 | 79.559 | 62.910 | 33.419 | 1.00 | 0.00 |
| ATOM | 1715 | HZ2 | LYS | 100 | 78.557 | 62.171 | 32.269 | 1.00 | 0.00 |
| ATOM | 1716 | HZ3 | LYS | 100 | 79.146 | 61.267 | 33.583 | 1.00 | 0.00 |
| ATOM | 1717 | C | LYS | 100 | 77.819 | 65.614 | 37.569 | 1.00 | 19.62 |
| ATOM | 1718 | O | LYS | 100 | 78.354 | 66.153 | 36.606 | 1.00 | 20.04 |
| ATOM | 1719 | N | LEU | 101 | 77.007 | 66.317 | 38.323 | 1.00 | 18.30 |
| ATOM | 1720 | H | LEU | 101 | 76.591 | 65.855 | 39.083 | 1.00 | 0.00 |
| ATOM | 1721 | CA | LEU | 101 | 76.644 | 67.687 | 38.044 | 1.00 | 18.00 |
| ATOM | 1722 | CB | LEU | 101 | 75.813 | 68.193 | 39.235 | 1.00 | 14.61 |
| ATOM | 1723 | CG | LEU | 101 | 75.272 | 69.575 | 39.169 | 1.00 | 13.38 |
| ATOM | 1724 | CD1 | LEU | 101 | 73.977 | 69.493 | 39.892 | 1.00 | 12.35 |
| ATOM | 1725 | CD2 | LEU | 101 | 76.209 | 70.632 | 39.714 | 1.00 | 8.60 |
| ATOM | 1726 | C | LEU | 101 | 77.868 | 68.575 | 37.805 | 1.00 | 20.00 |
| ATOM | 1727 | O | LEU | 101 | 77.894 | 69.293 | 36.803 | 1.00 | 21.46 |
| ATOM | 1728 | N | PHE | 102 | 78.894 | 68.563 | 38.678 | 1.00 | 18.83 |
| ATOM | 1729 | H | PHE | 102 | 78.817 | 68.004 | 39.482 | 1.00 | 0.00 |
| ATOM | 1730 | CA | PHE | 102 | 80.060 | 69.396 | 38.449 | 1.00 | 16.56 |
| ATOM | 1731 | CB | PHE | 102 | 80.866 | 69.367 | 39.696 | 1.00 | 16.41 |

FIG. 1: A-30

| ATOM | 1732 | CG | PHE | 102 | 80.301 | 70.135 | 40.878 | 1.00 | 16.22 |
| ATOM | 1733 | CD1 | PHE | 102 | 80.085 | 71.511 | 40.803 | 1.00 | 17.75 |
| ATOM | 1734 | CD2 | PHE | 102 | 80.031 | 69.471 | 42.067 | 1.00 | 18.34 |
| ATOM | 1735 | CE1 | PHE | 102 | 79.604 | 72.218 | 41.905 | 1.00 | 14.49 |
| ATOM | 1736 | CE2 | PHE | 102 | 79.547 | 70.195 | 43.178 | 1.00 | 22.31 |
| ATOM | 1737 | CZ | PHE | 102 | 79.333 | 71.568 | 43.096 | 1.00 | 18.01 |
| ATOM | 1738 | C | PHE | 102 | 80.848 | 68.883 | 37.223 | 1.00 | 19.71 |
| ATOM | 1739 | O | PHE | 102 | 81.497 | 69.681 | 36.536 | 1.00 | 21.54 |
| ATOM | 1740 | N | GLU | 103 | 80.843 | 67.572 | 36.869 | 1.00 | 19.67 |
| ATOM | 1741 | H | GLU | 103 | 80.484 | 66.921 | 37.510 | 1.00 | 0.00 |
| ATOM | 1742 | CA | GLU | 103 | 81.338 | 67.124 | 35.553 | 1.00 | 20.12 |
| ATOM | 1743 | CB | GLU | 103 | 81.128 | 65.659 | 35.285 | 1.00 | 22.22 |
| ATOM | 1744 | CG | GLU | 103 | 81.921 | 64.503 | 35.857 | 1.00 | 29.90 |
| ATOM | 1745 | CD | GLU | 103 | 81.688 | 63.175 | 35.084 | 1.00 | 33.72 |
| ATOM | 1746 | OE1 | GLU | 103 | 81.737 | 62.114 | 35.702 | 1.00 | 35.67 |
| ATOM | 1747 | OE2 | GLU | 103 | 81.459 | 63.165 | 33.865 | 1.00 | 34.36 |
| ATOM | 1748 | C | GLU | 103 | 80.537 | 67.822 | 34.423 | 1.00 | 19.59 |
| ATOM | 1749 | O | GLU | 103 | 81.074 | 68.522 | 33.594 | 1.00 | 21.84 |
| ATOM | 1750 | N | VAL | 104 | 79.214 | 67.758 | 34.336 | 1.00 | 20.28 |
| ATOM | 1751 | H | VAL | 104 | 78.769 | 67.278 | 35.065 | 1.00 | 0.00 |
| ATOM | 1752 | CA | VAL | 104 | 78.395 | 68.376 | 33.281 | 1.00 | 19.91 |
| ATOM | 1753 | CB | VAL | 104 | 76.940 | 67.814 | 33.542 | 1.00 | 18.88 |
| ATOM | 1754 | CG1 | VAL | 104 | 75.877 | 68.524 | 32.752 | 1.00 | 17.73 |
| ATOM | 1755 | CG2 | VAL | 104 | 76.911 | 66.346 | 33.129 | 1.00 | 13.28 |
| ATOM | 1756 | C | VAL | 104 | 78.470 | 69.925 | 33.222 | 1.00 | 22.25 |
| ATOM | 1757 | O | VAL | 104 | 78.621 | 70.536 | 32.152 | 1.00 | 25.12 |
| ATOM | 1758 | N | GLY | 105 | 78.342 | 70.595 | 34.375 | 1.00 | 21.92 |
| ATOM | 1759 | H | GLY | 105 | 78.239 | 70.055 | 35.175 | 1.00 | 0.00 |
| ATOM | 1760 | CA | GLY | 105 | 78.349 | 72.055 | 34.493 | 1.00 | 20.15 |
| ATOM | 1761 | C | GLY | 105 | 79.721 | 72.695 | 34.376 | 1.00 | 21.14 |
| ATOM | 1762 | O | GLY | 105 | 79.909 | 73.793 | 33.843 | 1.00 | 24.50 |
| ATOM | 1763 | N | GLY | 106 | 80.722 | 71.992 | 34.855 | 1.00 | 19.70 |
| ATOM | 1764 | H | GLY | 106 | 80.541 | 71.105 | 35.223 | 1.00 | 0.00 |
| ATOM | 1765 | CA | GLY | 106 | 82.070 | 72.477 | 34.805 | 1.00 | 20.01 |
| ATOM | 1766 | C | GLY | 106 | 82.725 | 72.532 | 36.183 | 1.00 | 23.34 |
| ATOM | 1767 | O | GLY | 106 | 82.087 | 72.343 | 37.210 | 1.00 | 25.07 |
| ATOM | 1768 | N | SER | 107 | 84.024 | 72.810 | 36.278 | 1.00 | 24.17 |
| ATOM | 1769 | H | SER | 107 | 84.500 | 72.996 | 35.447 | 1.00 | 0.00 |
| ATOM | 1770 | CA | SER | 107 | 84.702 | 72.927 | 37.569 | 1.00 | 20.74 |
| ATOM | 1771 | CB | SER | 107 | 86.199 | 73.032 | 37.430 | 1.00 | 19.20 |
| ATOM | 1772 | OG | SER | 107 | 86.814 | 72.822 | 38.691 | 1.00 | 20.71 |
| ATOM | 1773 | HG | SER | 107 | 87.753 | 72.653 | 38.534 | 1.00 | 0.00 |
| ATOM | 1774 | C | SER | 107 | 84.296 | 74.164 | 38.327 | 1.00 | 18.27 |
| ATOM | 1775 | O | SER | 107 | 84.271 | 75.218 | 37.701 | 1.00 | 18.11 |
| ATOM | 1776 | N | PRO | 108 | 84.061 | 74.158 | 39.647 | 1.00 | 17.40 |
| ATOM | 1777 | CD | PRO | 108 | 83.900 | 72.972 | 40.483 | 1.00 | 15.32 |
| ATOM | 1778 | CA | PRO | 108 | 83.954 | 75.374 | 40.440 | 1.00 | 16.47 |
| ATOM | 1779 | CB | PRO | 108 | 83.676 | 74.853 | 41.811 | 1.00 | 11.22 |
| ATOM | 1780 | CG | PRO | 108 | 83.010 | 73.558 | 41.531 | 1.00 | 11.77 |
| ATOM | 1781 | C | PRO | 108 | 85.245 | 76.206 | 40.326 | 1.00 | 20.15 |
| ATOM | 1782 | O | PRO | 108 | 85.260 | 77.421 | 40.520 | 1.00 | 24.43 |
| ATOM | 1783 | N | ALA | 109 | 86.375 | 75.558 | 39.997 | 1.00 | 20.60 |
| ATOM | 1784 | H | ALA | 109 | 86.321 | 74.582 | 39.932 | 1.00 | 0.00 |
| ATOM | 1785 | CA | ALA | 109 | 87.672 | 76.180 | 39.790 | 1.00 | 18.81 |
| ATOM | 1786 | CB | ALA | 109 | 88.676 | 75.214 | 39.285 | 1.00 | 17.25 |
| ATOM | 1787 | C | ALA | 109 | 87.642 | 77.268 | 38.759 | 1.00 | 21.06 |
| ATOM | 1788 | O | ALA | 109 | 88.407 | 78.227 | 38.825 | 1.00 | 24.57 |
| ATOM | 1789 | N | ASN | 110 | 86.749 | 77.090 | 37.796 | 1.00 | 23.02 |
| ATOM | 1790 | H | ASN | 110 | 86.217 | 76.271 | 37.802 | 1.00 | 0.00 |
| ATOM | 1791 | CA | ASN | 110 | 86.567 | 78.077 | 36.743 | 1.00 | 24.98 |

FIG. 1: A-31

| | | | | | | | | | |
|---|---|---|---|---|---|---|---|---|---|
| ATOM | 1792 | CB | ASN | 110 | 87.469 | 77.717 | 35.549 | 1.00 | 28.49 |
| ATOM | 1793 | CG | ASN | 110 | 87.074 | 76.397 | 34.963 | 1.00 | 29.08 |
| ATOM | 1794 | OD1 | ASN | 110 | 87.585 | 75.380 | 35.387 | 1.00 | 34.13 |
| ATOM | 1795 | ND2 | ASN | 110 | 86.094 | 76.283 | 34.101 | 1.00 | 29.72 |
| ATOM | 1796 | HD21 | ASN | 110 | 85.583 | 77.083 | 33.870 | 1.00 | 0.00 |
| ATOM | 1797 | HD22 | ASN | 110 | 85.952 | 75.387 | 33.757 | 1.00 | 0.00 |
| ATOM | 1798 | C | ASN | 110 | 85.154 | 78.303 | 36.217 | 1.00 | 23.35 |
| ATOM | 1799 | O | ASN | 110 | 84.974 | 78.860 | 35.138 | 1.00 | 23.53 |
| ATOM | 1800 | N | THR | 111 | 84.124 | 77.815 | 36.880 | 1.00 | 23.28 |
| ATOM | 1801 | H | THR | 111 | 84.277 | 77.273 | 37.680 | 1.00 | 0.00 |
| ATOM | 1802 | CA | THR | 111 | 82.755 | 78.005 | 36.402 | 1.00 | 20.55 |
| ATOM | 1803 | CB | THR | 111 | 82.011 | 76.687 | 36.078 | 1.00 | 17.61 |
| ATOM | 1804 | OG1 | THR | 111 | 82.877 | 75.842 | 35.325 | 1.00 | 16.07 |
| ATOM | 1805 | HG1 | THR | 111 | 82.307 | 75.264 | 34.803 | 1.00 | 0.00 |
| ATOM | 1806 | CG2 | THR | 111 | 80.752 | 76.950 | 35.283 | 1.00 | 11.55 |
| ATOM | 1807 | C | THR | 111 | 81.937 | 78.687 | 37.471 | 1.00 | 22.32 |
| ATOM | 1808 | O | THR | 111 | 81.986 | 78.286 | 38.637 | 1.00 | 25.14 |
| ATOM | 1809 | N | ARG | 112 | 81.195 | 79.737 | 37.145 | 1.00 | 23.02 |
| ATOM | 1810 | H | ARG | 112 | 81.286 | 80.143 | 36.261 | 1.00 | 0.00 |
| ATOM | 1811 | CA | ARG | 112 | 80.306 | 80.324 | 38.136 | 1.00 | 22.16 |
| ATOM | 1812 | CB | ARG | 112 | 79.817 | 81.625 | 37.622 | 1.00 | 25.25 |
| ATOM | 1813 | CG | ARG | 112 | 80.225 | 82.882 | 38.331 | 1.00 | 31.08 |
| ATOM | 1814 | CD | ARG | 112 | 80.239 | 84.030 | 37.276 | 1.00 | 33.63 |
| ATOM | 1815 | NE | ARG | 112 | 80.445 | 85.274 | 37.972 | 1.00 | 38.57 |
| ATOM | 1816 | HE | ARG | 112 | 81.298 | 85.749 | 37.885 | 1.00 | 0.00 |
| ATOM | 1817 | CZ | ARG | 112 | 79.479 | 85.769 | 38.771 | 1.00 | 43.88 |
| ATOM | 1818 | NH1 | ARG | 112 | 79.721 | 86.878 | 39.521 | 1.00 | 45.08 |
| ATOM | 1819 | HH11 | ARG | 112 | 80.632 | 87.290 | 39.514 | 1.00 | 0.00 |
| ATOM | 1820 | HH12 | ARG | 112 | 79.032 | 87.204 | 40.168 | 1.00 | 0.00 |
| ATOM | 1821 | NH2 | ARG | 112 | 78.261 | 85.187 | 38.818 | 1.00 | 40.87 |
| ATOM | 1822 | HH21 | ARG | 112 | 78.059 | 84.369 | 38.281 | 1.00 | 0.00 |
| ATOM | 1823 | HH22 | ARG | 112 | 77.583 | 85.541 | 39.462 | 1.00 | 0.00 |
| ATOM | 1824 | C | ARG | 112 | 79.108 | 79.397 | 38.378 | 1.00 | 22.37 |
| ATOM | 1825 | O | ARG | 112 | 78.500 | 78.882 | 37.426 | 1.00 | 19.09 |
| ATOM | 1826 | N | TYR | 113 | 78.756 | 79.162 | 39.645 | 1.00 | 20.28 |
| ATOM | 1827 | H | TYR | 113 | 79.331 | 79.554 | 40.332 | 1.00 | 0.00 |
| ATOM | 1828 | CA | TYR | 113 | 77.600 | 78.369 | 40.047 | 1.00 | 16.36 |
| ATOM | 1829 | CB | TYR | 113 | 78.073 | 77.219 | 40.859 | 1.00 | 15.16 |
| ATOM | 1830 | CG | TYR | 113 | 78.478 | 76.079 | 39.948 | 1.00 | 19.88 |
| ATOM | 1831 | CD1 | TYR | 113 | 77.446 | 75.310 | 39.387 | 1.00 | 17.88 |
| ATOM | 1832 | CE1 | TYR | 113 | 77.767 | 74.240 | 38.558 | 1.00 | 17.80 |
| ATOM | 1833 | CD2 | TYR | 113 | 79.830 | 75.783 | 39.679 | 1.00 | 15.86 |
| ATOM | 1834 | CE2 | TYR | 113 | 80.131 | 74.702 | 38.848 | 1.00 | 14.15 |
| ATOM | 1835 | CZ | TYR | 113 | 79.101 | 73.947 | 38.299 | 1.00 | 13.05 |
| ATOM | 1836 | OH | TYR | 113 | 79.351 | 72.878 | 37.472 | 1.00 | 16.26 |
| ATOM | 1837 | HH | TYR | 113 | 80.296 | 72.683 | 37.479 | 1.00 | 0.00 |
| ATOM | 1838 | C | TYR | 113 | 76.471 | 79.016 | 40.810 | 1.00 | 14.43 |
| ATOM | 1839 | O | TYR | 113 | 76.731 | 79.848 | 41.645 | 1.00 | 18.02 |
| ATOM | 1840 | N | LEU | 114 | 75.196 | 78.751 | 40.587 | 1.00 | 16.97 |
| ATOM | 1841 | H | LEU | 114 | 74.982 | 78.229 | 39.780 | 1.00 | 0.00 |
| ATOM | 1842 | CA | LEU | 114 | 74.086 | 79.231 | 41.427 | 1.00 | 14.11 |
| ATOM | 1843 | CB | LEU | 114 | 73.108 | 80.049 | 40.684 | 1.00 | 13.97 |
| ATOM | 1844 | CG | LEU | 114 | 72.360 | 81.262 | 41.192 | 1.00 | 16.23 |
| ATOM | 1845 | CD1 | LEU | 114 | 71.386 | 81.615 | 40.082 | 1.00 | 18.72 |
| ATOM | 1846 | CD2 | LEU | 114 | 71.585 | 81.043 | 42.451 | 1.00 | 14.39 |
| ATOM | 1847 | C | LEU | 114 | 73.349 | 77.984 | 41.810 | 1.00 | 15.05 |
| ATOM | 1848 | O | LEU | 114 | 72.980 | 77.186 | 40.945 | 1.00 | 18.40 |
| ATOM | 1849 | N | PHE | 115 | 73.120 | 77.708 | 43.071 | 1.00 | 15.74 |
| ATOM | 1850 | H | PHE | 115 | 73.433 | 78.345 | 43.737 | 1.00 | 0.00 |
| ATOM | 1851 | CA | PHE | 115 | 72.364 | 76.520 | 43.495 | 1.00 | 12.20 |

FIG. 1: A-32

| ATOM | 1852 | CB  | PHE | 115 | 73.139 | 75.702 | 44.505 | 1.00 | 9.15  |
|------|------|-----|-----|-----|--------|--------|--------|------|-------|
| ATOM | 1853 | CG  | PHE | 115 | 74.183 | 74.751 | 43.931 | 1.00 | 4.55  |
| ATOM | 1854 | CD1 | PHE | 115 | 75.449 | 75.207 | 43.588 | 1.00 | 6.18  |
| ATOM | 1855 | CD2 | PHE | 115 | 73.838 | 73.419 | 43.715 | 1.00 | 2.77  |
| ATOM | 1856 | CE1 | PHE | 115 | 76.369 | 74.322 | 43.011 | 1.00 | 5.39  |
| ATOM | 1857 | CE2 | PHE | 115 | 74.753 | 72.546 | 43.142 | 1.00 | 2.48  |
| ATOM | 1858 | CZ  | PHE | 115 | 76.021 | 72.997 | 42.786 | 1.00 | 2.34  |
| ATOM | 1859 | C   | PHE | 115 | 71.060 | 76.960 | 44.139 | 1.00 | 13.75 |
| ATOM | 1860 | O   | PHE | 115 | 71.010 | 77.730 | 45.101 | 1.00 | 16.34 |
| ATOM | 1861 | N   | LEU | 116 | 69.957 | 76.534 | 43.580 | 1.00 | 13.45 |
| ATOM | 1862 | H   | LEU | 116 | 70.039 | 75.951 | 42.791 | 1.00 | 0.00  |
| ATOM | 1863 | CA  | LEU | 116 | 68.635 | 76.929 | 44.041 | 1.00 | 15.21 |
| ATOM | 1864 | CB  | LEU | 116 | 67.786 | 76.842 | 42.757 | 1.00 | 13.18 |
| ATOM | 1865 | CG  | LEU | 116 | 67.560 | 78.096 | 41.935 | 1.00 | 11.70 |
| ATOM | 1866 | CD1 | LEU | 116 | 68.781 | 78.875 | 41.691 | 1.00 | 7.70  |
| ATOM | 1867 | CD2 | LEU | 116 | 67.062 | 77.656 | 40.587 | 1.00 | 14.61 |
| ATOM | 1868 | C   | LEU | 116 | 67.983 | 76.218 | 45.262 | 1.00 | 17.06 |
| ATOM | 1869 | O   | LEU | 116 | 66.756 | 76.024 | 45.399 | 1.00 | 19.44 |
| ATOM | 1870 | N   | GLY | 117 | 68.748 | 75.813 | 46.260 | 1.00 | 17.13 |
| ATOM | 1871 | H   | GLY | 117 | 69.704 | 76.038 | 46.230 | 1.00 | 0.00  |
| ATOM | 1872 | CA  | GLY | 117 | 68.179 | 75.124 | 47.412 | 1.00 | 13.85 |
| ATOM | 1873 | C   | GLY | 117 | 67.935 | 73.624 | 47.229 | 1.00 | 15.63 |
| ATOM | 1874 | O   | GLY | 117 | 68.087 | 72.979 | 46.193 | 1.00 | 16.84 |
| ATOM | 1875 | N   | ASP | 118 | 67.377 | 73.091 | 48.305 | 1.00 | 15.22 |
| ATOM | 1876 | H   | ASP | 118 | 67.066 | 73.755 | 48.941 | 1.00 | 0.00  |
| ATOM | 1877 | CA  | ASP | 118 | 67.129 | 71.680 | 48.533 | 1.00 | 16.20 |
| ATOM | 1878 | CB  | ASP | 118 | 65.900 | 71.239 | 47.743 | 1.00 | 15.43 |
| ATOM | 1879 | CG  | ASP | 118 | 64.573 | 71.648 | 48.382 | 1.00 | 17.15 |
| ATOM | 1880 | OD1 | ASP | 118 | 64.547 | 72.520 | 49.249 | 1.00 | 15.52 |
| ATOM | 1881 | OD2 | ASP | 118 | 63.546 | 71.092 | 47.997 | 1.00 | 18.50 |
| ATOM | 1882 | C   | ASP | 118 | 68.276 | 70.727 | 48.276 | 1.00 | 16.53 |
| ATOM | 1883 | O   | ASP | 118 | 68.290 | 69.887 | 47.380 | 1.00 | 20.09 |
| ATOM | 1884 | N   | TYR | 119 | 69.247 | 70.916 | 49.161 | 1.00 | 14.12 |
| ATOM | 1885 | H   | TYR | 119 | 69.219 | 71.743 | 49.671 | 1.00 | 0.00  |
| ATOM | 1886 | CA  | TYR | 119 | 70.481 | 70.126 | 49.203 | 1.00 | 14.00 |
| ATOM | 1887 | CB  | TYR | 119 | 71.592 | 70.963 | 49.870 | 1.00 | 13.49 |
| ATOM | 1888 | CG  | TYR | 119 | 71.721 | 72.370 | 49.313 | 1.00 | 12.23 |
| ATOM | 1889 | CD1 | TYR | 119 | 72.067 | 72.530 | 47.980 | 1.00 | 7.89  |
| ATOM | 1890 | CE1 | TYR | 119 | 72.115 | 73.800 | 47.456 | 1.00 | 11.16 |
| ATOM | 1891 | CD2 | TYR | 119 | 71.431 | 73.485 | 50.132 | 1.00 | 13.37 |
| ATOM | 1892 | CE2 | TYR | 119 | 71.472 | 74.778 | 49.603 | 1.00 | 11.79 |
| ATOM | 1893 | CZ  | TYR | 119 | 71.813 | 74.912 | 48.255 | 1.00 | 13.58 |
| ATOM | 1894 | OH  | TYR | 119 | 71.802 | 76.155 | 47.661 | 1.00 | 16.18 |
| ATOM | 1895 | HH  | TYR | 119 | 71.375 | 76.769 | 48.279 | 1.00 | 0.00  |
| ATOM | 1896 | C   | TYR | 119 | 70.360 | 68.810 | 49.963 | 1.00 | 13.10 |
| ATOM | 1897 | O   | TYR | 119 | 71.053 | 67.826 | 49.772 | 1.00 | 10.98 |
| ATOM | 1898 | N   | VAL | 120 | 69.351 | 68.879 | 50.816 | 1.00 | 14.82 |
| ATOM | 1899 | H   | VAL | 120 | 68.776 | 69.659 | 50.765 | 1.00 | 0.00  |
| ATOM | 1900 | CA  | VAL | 120 | 69.089 | 67.943 | 51.895 | 1.00 | 15.66 |
| ATOM | 1901 | CB  | VAL | 120 | 69.367 | 68.855 | 53.106 | 1.00 | 15.80 |
| ATOM | 1902 | CG1 | VAL | 120 | 68.128 | 69.002 | 53.966 | 1.00 | 16.16 |
| ATOM | 1903 | CG2 | VAL | 120 | 70.592 | 68.365 | 53.791 | 1.00 | 11.17 |
| ATOM | 1904 | C   | VAL | 120 | 67.717 | 67.241 | 51.868 | 1.00 | 18.38 |
| ATOM | 1905 | O   | VAL | 120 | 66.727 | 67.728 | 51.273 | 1.00 | 18.49 |
| ATOM | 1906 | N   | ASP | 121 | 67.695 | 66.111 | 52.586 | 1.00 | 17.33 |
| ATOM | 1907 | H   | ASP | 121 | 68.567 | 65.849 | 52.959 | 1.00 | 0.00  |
| ATOM | 1908 | CA  | ASP | 121 | 66.582 | 65.180 | 52.724 | 1.00 | 16.76 |
| ATOM | 1909 | CB  | ASP | 121 | 65.274 | 65.871 | 53.025 | 1.00 | 13.45 |
| ATOM | 1910 | CG  | ASP | 121 | 65.214 | 66.496 | 54.393 | 1.00 | 16.45 |
| ATOM | 1911 | OD1 | ASP | 121 | 64.686 | 67.603 | 54.514 | 1.00 | 18.01 |

FIG. 1: A-33

| ATOM | 1912 | OD2 | ASP | 121 | 65.666 | 65.858 | 55.339 | 1.00 | 14.32 |
|---|---|---|---|---|---|---|---|---|---|
| ATOM | 1913 | C | ASP | 121 | 66.302 | 64.279 | 51.539 | 1.00 | 18.09 |
| ATOM | 1914 | O | ASP | 121 | 66.669 | 64.591 | 50.412 | 1.00 | 22.54 |
| ATOM | 1915 | N | ARG | 122 | 65.611 | 63.165 | 51.734 | 1.00 | 18.16 |
| ATOM | 1916 | H | ARG | 122 | 65.410 | 62.918 | 52.664 | 1.00 | 0.00 |
| ATOM | 1917 | CA | ARG | 122 | 65.257 | 62.206 | 50.687 | 1.00 | 17.31 |
| ATOM | 1918 | CB | ARG | 122 | 64.570 | 62.883 | 49.448 | 1.00 | 17.39 |
| ATOM | 1919 | CG | ARG | 122 | 63.269 | 63.530 | 49.941 | 1.00 | 20.48 |
| ATOM | 1920 | CD | ARG | 122 | 61.987 | 63.209 | 49.161 | 1.00 | 24.78 |
| ATOM | 1921 | NE | ARG | 122 | 60.822 | 64.081 | 49.397 | 1.00 | 27.96 |
| ATOM | 1922 | HE | ARG | 122 | 59.951 | 63.654 | 49.526 | 1.00 | 0.00 |
| ATOM | 1923 | CZ | ARG | 122 | 60.888 | 65.436 | 49.456 | 1.00 | 26.84 |
| ATOM | 1924 | NH1 | ARG | 122 | 59.796 | 66.186 | 49.684 | 1.00 | 22.77 |
| ATOM | 1925 | HH11 | ARG | 122 | 58.908 | 65.743 | 49.816 | 1.00 | 0.00 |
| ATOM | 1926 | HH12 | ARG | 122 | 59.873 | 67.182 | 49.720 | 1.00 | 0.00 |
| ATOM | 1927 | NH2 | ARG | 122 | 62.044 | 66.089 | 49.303 | 1.00 | 25.45 |
| ATOM | 1928 | HH21 | ARG | 122 | 62.888 | 65.600 | 49.095 | 1.00 | 0.00 |
| ATOM | 1929 | HH22 | ARG | 122 | 62.060 | 67.084 | 49.366 | 1.00 | 0.00 |
| ATOM | 1930 | C | ARG | 122 | 66.459 | 61.421 | 50.234 | 1.00 | 17.09 |
| ATOM | 1931 | O | ARG | 122 | 66.411 | 60.201 | 50.375 | 1.00 | 18.20 |
| ATOM | 1932 | N | GLY | 123 | 67.560 | 61.981 | 49.737 | 1.00 | 15.89 |
| ATOM | 1933 | H | GLY | 123 | 67.578 | 62.949 | 49.574 | 1.00 | 0.00 |
| ATOM | 1934 | CA | GLY | 123 | 68.712 | 61.165 | 49.384 | 1.00 | 12.80 |
| ATOM | 1935 | C | GLY | 123 | 69.512 | 60.854 | 50.626 | 1.00 | 13.10 |
| ATOM | 1936 | O | GLY | 123 | 69.685 | 61.708 | 51.483 | 1.00 | 15.67 |
| ATOM | 1937 | N | TYR | 124 | 70.033 | 59.664 | 50.845 | 1.00 | 14.89 |
| ATOM | 1938 | H | TYR | 124 | 69.808 | 58.979 | 50.196 | 1.00 | 0.00 |
| ATOM | 1939 | CA | TYR | 124 | 70.784 | 59.334 | 52.065 | 1.00 | 16.07 |
| ATOM | 1940 | CB | TYR | 124 | 70.618 | 57.808 | 52.242 | 1.00 | 17.64 |
| ATOM | 1941 | CG | TYR | 124 | 69.255 | 57.387 | 52.810 | 1.00 | 16.47 |
| ATOM | 1942 | CD1 | TYR | 124 | 69.095 | 56.132 | 53.405 | 1.00 | 13.81 |
| ATOM | 1943 | CE1 | TYR | 124 | 67.875 | 55.763 | 53.951 | 1.00 | 14.96 |
| ATOM | 1944 | CD2 | TYR | 124 | 68.162 | 58.268 | 52.767 | 1.00 | 17.78 |
| ATOM | 1945 | CE2 | TYR | 124 | 66.931 | 57.913 | 53.305 | 1.00 | 18.15 |
| ATOM | 1946 | CZ | TYR | 124 | 66.811 | 56.665 | 53.887 | 1.00 | 18.05 |
| ATOM | 1947 | OH | TYR | 124 | 65.587 | 56.334 | 54.394 | 1.00 | 26.08 |
| ATOM | 1948 | HH | TYR | 124 | 64.934 | 56.923 | 54.001 | 1.00 | 0.00 |
| ATOM | 1949 | C | TYR | 124 | 72.263 | 59.780 | 52.199 | 1.00 | 15.51 |
| ATOM | 1950 | O | TYR | 124 | 73.017 | 59.427 | 53.095 | 1.00 | 15.09 |
| ATOM | 1951 | N | PHE | 125 | 72.696 | 60.665 | 51.320 | 1.00 | 15.38 |
| ATOM | 1952 | H | PHE | 125 | 72.099 | 60.903 | 50.581 | 1.00 | 0.00 |
| ATOM | 1953 | CA | PHE | 125 | 74.028 | 61.230 | 51.326 | 1.00 | 15.32 |
| ATOM | 1954 | CB | PHE | 125 | 74.742 | 60.831 | 50.046 | 1.00 | 14.98 |
| ATOM | 1955 | CG | PHE | 125 | 74.782 | 59.307 | 49.878 | 1.00 | 15.01 |
| ATOM | 1956 | CD1 | PHE | 125 | 75.624 | 58.531 | 50.693 | 1.00 | 16.18 |
| ATOM | 1957 | CD2 | PHE | 125 | 73.960 | 58.687 | 48.942 | 1.00 | 10.27 |
| ATOM | 1958 | CE1 | PHE | 125 | 75.646 | 57.135 | 50.573 | 1.00 | 14.84 |
| ATOM | 1959 | CE2 | PHE | 125 | 73.994 | 57.299 | 48.837 | 1.00 | 13.76 |
| ATOM | 1960 | CZ | PHE | 125 | 74.828 | 56.518 | 49.640 | 1.00 | 12.07 |
| ATOM | 1961 | C | PHE | 125 | 73.930 | 62.743 | 51.430 | 1.00 | 15.30 |
| ATOM | 1962 | O | PHE | 125 | 74.737 | 63.480 | 50.899 | 1.00 | 19.01 |
| ATOM | 1963 | N | SER | 126 | 73.001 | 63.272 | 52.222 | 1.00 | 16.48 |
| ATOM | 1964 | H | SER | 126 | 72.400 | 62.622 | 52.641 | 1.00 | 0.00 |
| ATOM | 1965 | CA | SER | 126 | 72.759 | 64.711 | 52.392 | 1.00 | 15.03 |
| ATOM | 1966 | CB | SER | 126 | 71.399 | 65.006 | 53.062 | 1.00 | 16.95 |
| ATOM | 1967 | OG | SER | 126 | 70.201 | 64.599 | 52.372 | 1.00 | 19.04 |
| ATOM | 1968 | HG | SER | 126 | 70.186 | 63.647 | 52.166 | 1.00 | 0.00 |
| ATOM | 1969 | C | SER | 126 | 73.776 | 65.476 | 53.190 | 1.00 | 15.27 |
| ATOM | 1970 | O | SER | 126 | 73.987 | 66.656 | 52.925 | 1.00 | 14.34 |
| ATOM | 1971 | N | ILE | 127 | 74.469 | 64.868 | 54.175 | 1.00 | 17.67 |

FIG. 1: A-34

| ATOM | 1972 | H | ILE | 127 | 74.196 | 63.981 | 54.462 | 1.00 | 0.00 |
|------|------|-----|-----|-----|--------|--------|--------|------|-------|
| ATOM | 1973 | CA | ILE | 127 | 75.538 | 65.608 | 54.887 | 1.00 | 15.57 |
| ATOM | 1974 | CB | ILE | 127 | 75.837 | 64.932 | 56.314 | 1.00 | 13.45 |
| ATOM | 1975 | CG2 | ILE | 127 | 76.546 | 63.605 | 56.251 | 1.00 | 10.69 |
| ATOM | 1976 | CG1 | ILE | 127 | 76.746 | 65.842 | 57.079 | 1.00 | 13.34 |
| ATOM | 1977 | CD1 | ILE | 127 | 76.262 | 67.292 | 57.232 | 1.00 | 13.82 |
| ATOM | 1978 | C | ILE | 127 | 76.788 | 65.683 | 53.996 | 1.00 | 17.31 |
| ATOM | 1979 | O | ILE | 127 | 77.476 | 66.701 | 54.067 | 1.00 | 18.98 |
| ATOM | 1980 | N | GLU | 128 | 77.089 | 64.715 | 53.084 | 1.00 | 14.23 |
| ATOM | 1981 | H | GLU | 128 | 76.523 | 63.923 | 53.046 | 1.00 | 0.00 |
| ATOM | 1982 | CA | GLU | 128 | 78.206 | 64.856 | 52.159 | 1.00 | 12.73 |
| ATOM | 1983 | CB | GLU | 128 | 78.430 | 63.547 | 51.441 | 1.00 | 15.92 |
| ATOM | 1984 | CG | GLU | 128 | 78.872 | 62.302 | 52.254 | 1.00 | 14.73 |
| ATOM | 1985 | CD | GLU | 128 | 77.809 | 61.328 | 52.806 | 1.00 | 20.61 |
| ATOM | 1986 | OE1 | GLU | 128 | 76.707 | 61.738 | 53.207 | 1.00 | 20.45 |
| ATOM | 1987 | OE2 | GLU | 128 | 78.105 | 60.128 | 52.868 | 1.00 | 22.71 |
| ATOM | 1988 | C | GLU | 128 | 77.942 | 65.975 | 51.136 | 1.00 | 16.06 |
| ATOM | 1989 | O | GLU | 128 | 78.840 | 66.702 | 50.695 | 1.00 | 17.48 |
| ATOM | 1990 | N | CYS | 129 | 76.683 | 66.190 | 50.730 | 1.00 | 17.79 |
| ATOM | 1991 | H | CYS | 129 | 76.024 | 65.486 | 50.906 | 1.00 | 0.00 |
| ATOM | 1992 | CA | CYS | 129 | 76.314 | 67.348 | 49.893 | 1.00 | 17.59 |
| ATOM | 1993 | CB | CYS | 129 | 74.874 | 67.344 | 49.351 | 1.00 | 14.57 |
| ATOM | 1994 | SG | CYS | 129 | 74.577 | 65.903 | 48.312 | 1.00 | 13.14 |
| ATOM | 1995 | C | CYS | 129 | 76.403 | 68.661 | 50.637 | 1.00 | 20.64 |
| ATOM | 1996 | O | CYS | 129 | 76.886 | 69.624 | 50.046 | 1.00 | 25.40 |
| ATOM | 1997 | N | VAL | 130 | 75.929 | 68.807 | 51.888 | 1.00 | 19.35 |
| ATOM | 1998 | H | VAL | 130 | 75.382 | 68.086 | 52.274 | 1.00 | 0.00 |
| ATOM | 1999 | CA | VAL | 130 | 76.113 | 70.046 | 52.638 | 1.00 | 16.39 |
| ATOM | 2000 | CB | VAL | 130 | 75.376 | 69.932 | 53.957 | 1.00 | 18.46 |
| ATOM | 2001 | CG1 | VAL | 130 | 75.660 | 71.129 | 54.845 | 1.00 | 19.50 |
| ATOM | 2002 | CG2 | VAL | 130 | 73.875 | 69.920 | 53.679 | 1.00 | 19.73 |
| ATOM | 2003 | C | VAL | 130 | 77.582 | 70.332 | 52.888 | 1.00 | 17.73 |
| ATOM | 2004 | O | VAL | 130 | 78.047 | 71.462 | 52.740 | 1.00 | 20.31 |
| ATOM | 2005 | N | LEU | 131 | 78.361 | 69.311 | 53.261 | 1.00 | 17.85 |
| ATOM | 2006 | H | LEU | 131 | 77.929 | 68.464 | 53.481 | 1.00 | 0.00 |
| ATOM | 2007 | CA | LEU | 131 | 79.803 | 69.458 | 53.443 | 1.00 | 17.66 |
| ATOM | 2008 | CB | LEU | 131 | 80.352 | 68.199 | 54.164 | 1.00 | 15.83 |
| ATOM | 2009 | CG | LEU | 131 | 80.033 | 67.931 | 55.628 | 1.00 | 11.91 |
| ATOM | 2010 | CD1 | LEU | 131 | 80.649 | 66.653 | 56.013 | 1.00 | 13.15 |
| ATOM | 2011 | CD2 | LEU | 131 | 80.651 | 68.918 | 56.532 | 1.00 | 8.85 |
| ATOM | 2012 | C | LEU | 131 | 80.602 | 69.733 | 52.144 | 1.00 | 18.86 |
| ATOM | 2013 | O | LEU | 131 | 81.370 | 70.711 | 52.138 | 1.00 | 22.70 |
| ATOM | 2014 | N | TYR | 132 | 80.498 | 68.981 | 51.030 | 1.00 | 16.66 |
| ATOM | 2015 | H | TYR | 132 | 79.973 | 68.158 | 51.078 | 1.00 | 0.00 |
| ATOM | 2016 | CA | TYR | 132 | 81.170 | 69.362 | 49.785 | 1.00 | 16.60 |
| ATOM | 2017 | CB | TYR | 132 | 80.875 | 68.352 | 48.691 | 1.00 | 19.58 |
| ATOM | 2018 | CG | TYR | 132 | 81.861 | 68.425 | 47.528 | 1.00 | 19.31 |
| ATOM | 2019 | CD1 | TYR | 132 | 83.194 | 68.041 | 47.710 | 1.00 | 21.49 |
| ATOM | 2020 | CE1 | TYR | 132 | 84.103 | 68.084 | 46.652 | 1.00 | 21.21 |
| ATOM | 2021 | CD2 | TYR | 132 | 81.441 | 68.858 | 46.283 | 1.00 | 20.22 |
| ATOM | 2022 | CE2 | TYR | 132 | 82.344 | 68.910 | 45.224 | 1.00 | 23.07 |
| ATOM | 2023 | CZ | TYR | 132 | 83.671 | 68.516 | 45.407 | 1.00 | 22.64 |
| ATOM | 2024 | OH | TYR | 132 | 84.548 | 68.510 | 44.336 | 1.00 | 21.77 |
| ATOM | 2025 | HH | TYR | 132 | 84.167 | 69.001 | 43.592 | 1.00 | 0.00 |
| ATOM | 2026 | C | TYR | 132 | 80.779 | 70.738 | 49.257 | 1.00 | 16.57 |
| ATOM | 2027 | O | TYR | 132 | 81.607 | 71.514 | 48.802 | 1.00 | 19.22 |
| ATOM | 2028 | N | LEU | 133 | 79.508 | 71.104 | 49.286 | 1.00 | 17.52 |
| ATOM | 2029 | H | LEU | 133 | 78.831 | 70.445 | 49.557 | 1.00 | 0.00 |
| ATOM | 2030 | CA | LEU | 133 | 79.096 | 72.425 | 48.883 | 1.00 | 15.66 |
| ATOM | 2031 | CB | LEU | 133 | 77.587 | 72.450 | 48.705 | 1.00 | 13.55 |

FIG. 1: A-35

| | | | | | | | | |
|---|---|---|---|---|---|---|---|---|
| ATOM | 2032 | CG | LEU | 133 | 77.053 | 71.740 | 47.500 | 1.00 | 10.97 |
| ATOM | 2033 | CD1 | LEU | 133 | 75.537 | 71.824 | 47.453 | 1.00 | 14.01 |
| ATOM | 2034 | CD2 | LEU | 133 | 77.668 | 72.364 | 46.279 | 1.00 | 10.16 |
| ATOM | 2035 | C | LEU | 133 | 79.512 | 73.498 | 49.883 | 1.00 | 18.62 |
| ATOM | 2036 | O | LEU | 133 | 79.889 | 74.597 | 49.456 | 1.00 | 19.81 |
| ATOM | 2037 | N | TRP | 134 | 79.498 | 73.285 | 51.215 | 1.00 | 18.98 |
| ATOM | 2038 | H | TRP | 134 | 79.091 | 72.465 | 51.555 | 1.00 | 0.00 |
| ATOM | 2039 | CA | TRP | 134 | 79.982 | 74.331 | 52.150 | 1.00 | 19.07 |
| ATOM | 2040 | CB | TRP | 134 | 79.616 | 73.874 | 53.572 | 1.00 | 17.38 |
| ATOM | 2041 | CG | TRP | 134 | 78.415 | 74.590 | 54.147 | 1.00 | 15.74 |
| ATOM | 2042 | CD2 | TRP | 134 | 77.118 | 74.595 | 53.657 | 1.00 | 15.85 |
| ATOM | 2043 | CE2 | TRP | 134 | 76.476 | 75.480 | 54.567 | 1.00 | 15.31 |
| ATOM | 2044 | CE3 | TRP | 134 | 76.386 | 74.005 | 52.611 | 1.00 | 12.41 |
| ATOM | 2045 | CD1 | TRP | 134 | 78.559 | 75.385 | 55.256 | 1.00 | 17.13 |
| ATOM | 2046 | NE1 | TRP | 134 | 77.367 | 75.920 | 55.482 | 1.00 | 19.23 |
| ATOM | 2047 | HE1 | TRP | 134 | 77.155 | 76.516 | 56.234 | 1.00 | 0.00 |
| ATOM | 2048 | CZ2 | TRP | 134 | 75.121 | 75.775 | 54.442 | 1.00 | 9.40 |
| ATOM | 2049 | CZ3 | TRP | 134 | 75.032 | 74.309 | 52.493 | 1.00 | 11.07 |
| ATOM | 2050 | CH2 | TRP | 134 | 74.413 | 75.183 | 53.400 | 1.00 | 10.22 |
| ATOM | 2051 | C | TRP | 134 | 81.504 | 74.612 | 52.000 | 1.00 | 17.80 |
| ATOM | 2052 | O | TRP | 134 | 82.014 | 75.737 | 51.964 | 1.00 | 16.50 |
| ATOM | 2053 | N | ALA | 135 | 82.270 | 73.545 | 51.816 | 1.00 | 15.91 |
| ATOM | 2054 | H | ALA | 135 | 81.845 | 72.668 | 51.947 | 1.00 | 0.00 |
| ATOM | 2055 | CA | ALA | 135 | 83.693 | 73.598 | 51.486 | 1.00 | 16.51 |
| ATOM | 2056 | CB | ALA | 135 | 84.173 | 72.184 | 51.194 | 1.00 | 15.89 |
| ATOM | 2057 | C | ALA | 135 | 84.077 | 74.469 | 50.289 | 1.00 | 15.64 |
| ATOM | 2058 | O | ALA | 135 | 85.015 | 75.248 | 50.280 | 1.00 | 18.28 |
| ATOM | 2059 | N | LEU | 136 | 83.282 | 74.283 | 49.248 | 1.00 | 16.50 |
| ATOM | 2060 | H | LEU | 136 | 82.599 | 73.584 | 49.362 | 1.00 | 0.00 |
| ATOM | 2061 | CA | LEU | 136 | 83.361 | 74.901 | 47.938 | 1.00 | 12.85 |
| ATOM | 2062 | CB | LEU | 136 | 82.445 | 74.108 | 47.021 | 1.00 | 11.26 |
| ATOM | 2063 | CG | LEU | 136 | 82.853 | 73.597 | 45.656 | 1.00 | 10.86 |
| ATOM | 2064 | CD1 | LEU | 136 | 84.213 | 72.914 | 45.701 | 1.00 | 10.28 |
| ATOM | 2065 | CD2 | LEU | 136 | 81.788 | 72.615 | 45.185 | 1.00 | 6.05 |
| ATOM | 2066 | C | LEU | 136 | 82.939 | 76.331 | 48.047 | 1.00 | 14.67 |
| ATOM | 2067 | O | LEU | 136 | 83.481 | 77.108 | 47.293 | 1.00 | 17.23 |
| ATOM | 2068 | N | LYS | 137 | 81.954 | 76.694 | 48.895 | 1.00 | 16.22 |
| ATOM | 2069 | H | LYS | 137 | 81.427 | 75.968 | 49.293 | 1.00 | 0.00 |
| ATOM | 2070 | CA | LYS | 137 | 81.558 | 78.079 | 49.181 | 1.00 | 12.85 |
| ATOM | 2071 | CB | LYS | 137 | 80.305 | 78.112 | 50.091 | 1.00 | 12.18 |
| ATOM | 2072 | CG | LYS | 137 | 79.813 | 79.510 | 50.506 | 1.00 | 10.11 |
| ATOM | 2073 | CD | LYS | 137 | 79.639 | 80.300 | 49.218 | 1.00 | 13.41 |
| ATOM | 2074 | CE | LYS | 137 | 79.199 | 81.725 | 49.386 | 1.00 | 16.00 |
| ATOM | 2075 | NZ | LYS | 137 | 78.815 | 82.254 | 48.091 | 1.00 | 17.45 |
| ATOM | 2076 | HZ1 | LYS | 137 | 78.026 | 81.703 | 47.697 | 1.00 | 0.00 |
| ATOM | 2077 | HZ2 | LYS | 137 | 79.631 | 82.194 | 47.448 | 1.00 | 0.00 |
| ATOM | 2078 | HZ3 | LYS | 137 | 78.533 | 83.249 | 48.199 | 1.00 | 0.00 |
| ATOM | 2079 | C | LYS | 137 | 82.714 | 78.796 | 49.887 | 1.00 | 16.44 |
| ATOM | 2080 | O | LYS | 137 | 82.996 | 79.954 | 49.576 | 1.00 | 15.21 |
| ATOM | 2081 | N | ILE | 138 | 83.406 | 78.082 | 50.819 | 1.00 | 19.14 |
| ATOM | 2082 | H | ILE | 138 | 83.023 | 77.219 | 51.078 | 1.00 | 0.00 |
| ATOM | 2083 | CA | ILE | 138 | 84.612 | 78.553 | 51.513 | 1.00 | 18.29 |
| ATOM | 2084 | CB | ILE | 138 | 85.110 | 77.520 | 52.563 | 1.00 | 18.94 |
| ATOM | 2085 | CG2 | ILE | 138 | 86.391 | 78.018 | 53.184 | 1.00 | 22.34 |
| ATOM | 2086 | CG1 | ILE | 138 | 84.144 | 77.374 | 53.723 | 1.00 | 17.23 |
| ATOM | 2087 | CD1 | ILE | 138 | 84.597 | 76.344 | 54.737 | 1.00 | 15.31 |
| ATOM | 2088 | C | ILE | 138 | 85.725 | 78.809 | 50.516 | 1.00 | 18.68 |
| ATOM | 2089 | O | ILE | 138 | 86.328 | 79.888 | 50.486 | 1.00 | 21.75 |
| ATOM | 2090 | N | LEU | 139 | 85.993 | 77.823 | 49.663 | 1.00 | 19.52 |
| ATOM | 2091 | H | LEU | 139 | 85.513 | 76.984 | 49.780 | 1.00 | 0.00 |

FIG. 1: A-36

| ATOM | 2092 | CA | LEU | 139 | 86.976 | 77.972 | 48.575 | 1.00 | 20.42 |
|---|---|---|---|---|---|---|---|---|---|
| ATOM | 2093 | CB | LEU | 139 | 87.204 | 76.632 | 47.979 | 1.00 | 20.12 |
| ATOM | 2094 | CG | LEU | 139 | 87.204 | 76.350 | 47.222 | 1.00 | 23.85 |
| ATOM | 2094 | CG | LEU | 139 | 88.472 | 76.350 | 47.222 | 1.00 | 23.85 |
| ATOM | 2095 | CD1 | LEU | 139 | 89.799 | 76.686 | 47.924 | 1.00 | 19.31 |
| ATOM | 2096 | CD2 | LEU | 139 | 88.368 | 74.879 | 47.014 | 1.00 | 22.70 |
| ATOM | 2097 | C | LEU | 139 | 86.638 | 78.972 | 47.452 | 1.00 | 20.73 |
| ATOM | 2098 | O | LEU | 139 | 87.469 | 79.786 | 47.016 | 1.00 | 23.33 |
| ATOM | 2099 | N | TYR | 140 | 85.394 | 79.029 | 46.986 | 1.00 | 18.86 |
| ATOM | 2100 | H | TYR | 140 | 84.748 | 78.426 | 47.387 | 1.00 | 0.00 |
| ATOM | 2101 | CA | TYR | 140 | 84.972 | 79.986 | 45.960 | 1.00 | 16.36 |
| ATOM | 2102 | CB | TYR | 140 | 84.522 | 79.222 | 44.738 | 1.00 | 10.45 |
| ATOM | 2103 | CG | TYR | 140 | 85.502 | 78.183 | 44.277 | 1.00 | 8.40 |
| ATOM | 2104 | CD1 | TYR | 140 | 86.647 | 78.554 | 43.608 | 1.00 | 8.69 |
| ATOM | 2105 | CE1 | TYR | 140 | 87.602 | 77.608 | 43.266 | 1.00 | 5.40 |
| ATOM | 2106 | CD2 | TYR | 140 | 85.297 | 76.851 | 44.599 | 1.00 | 12.87 |
| ATOM | 2107 | CE2 | TYR | 140 | 86.252 | 75.893 | 44.254 | 1.00 | 12.12 |
| ATOM | 2108 | CZ | TYR | 140 | 87.395 | 76.296 | 43.590 | 1.00 | 7.67 |
| ATOM | 2109 | OH | TYR | 140 | 88.334 | 75.367 | 43.242 | 1.00 | 13.98 |
| ATOM | 2110 | HH | TYR | 140 | 89.101 | 75.826 | 42.881 | 1.00 | 0.00 |
| ATOM | 2111 | C | TYR | 140 | 83.848 | 80.957 | 46.393 | 1.00 | 17.92 |
| ATOM | 2112 | O | TYR | 140 | 82.762 | 80.985 | 45.795 | 1.00 | 19.46 |
| ATOM | 2113 | N | PRO | 141 | 84.052 | 81.858 | 47.358 | 1.00 | 18.72 |
| ATOM | 2114 | CD | PRO | 141 | 85.184 | 81.846 | 48.281 | 1.00 | 21.66 |
| ATOM | 2115 | CA | PRO | 141 | 83.082 | 82.812 | 47.871 | 1.00 | 19.26 |
| ATOM | 2116 | CB | PRO | 141 | 83.896 | 83.677 | 48.819 | 1.00 | 17.13 |
| ATOM | 2117 | CG | PRO | 141 | 84.758 | 82.696 | 49.495 | 1.00 | 18.65 |
| ATOM | 2118 | C | PRO | 141 | 82.210 | 83.675 | 46.976 | 1.00 | 20.90 |
| ATOM | 2119 | O | PRO | 141 | 81.072 | 84.026 | 47.293 | 1.00 | 18.59 |
| ATOM | 2120 | N | LYS | 142 | 82.822 | 84.163 | 45.905 | 1.00 | 24.57 |
| ATOM | 2121 | H | LYS | 142 | 83.778 | 83.998 | 45.809 | 1.00 | 0.00 |
| ATOM | 2122 | CA | LYS | 142 | 82.090 | 84.989 | 44.935 | 1.00 | 28.34 |
| ATOM | 2123 | CB | LYS | 142 | 82.819 | 86.293 | 44.636 | 1.00 | 31.54 |
| ATOM | 2124 | CG | LYS | 142 | 82.892 | 87.374 | 45.692 | 1.00 | 37.05 |
| ATOM | 2125 | CD | LYS | 142 | 84.135 | 87.269 | 46.566 | 1.00 | 42.22 |
| ATOM | 2126 | CE | LYS | 142 | 85.451 | 87.630 | 45.863 | 1.00 | 45.21 |
| ATOM | 2127 | NZ | LYS | 142 | 86.590 | 87.571 | 46.775 | 1.00 | 46.50 |
| ATOM | 2128 | HZ1 | LYS | 142 | 87.459 | 87.787 | 46.244 | 1.00 | 0.00 |
| ATOM | 2129 | HZ2 | LYS | 142 | 86.664 | 86.614 | 47.175 | 1.00 | 0.00 |
| ATOM | 2130 | HZ3 | LYS | 142 | 86.469 | 88.262 | 47.541 | 1.00 | 0.00 |
| ATOM | 2131 | C | LYS | 142 | 81.839 | 84.324 | 43.576 | 1.00 | 29.04 |
| ATOM | 2132 | O | LYS | 142 | 81.430 | 84.989 | 42.623 | 1.00 | 32.69 |
| ATOM | 2133 | N | THR | 143 | 82.050 | 82.991 | 43.513 | 1.00 | 27.69 |
| ATOM | 2134 | H | THR | 143 | 82.216 | 82.562 | 44.377 | 1.00 | 0.00 |
| ATOM | 2135 | CA | THR | 143 | 81.988 | 82.134 | 42.309 | 1.00 | 22.07 |
| ATOM | 2136 | CB | THR | 143 | 83.303 | 81.352 | 42.140 | 1.00 | 22.81 |
| ATOM | 2137 | OG1 | THR | 143 | 84.159 | 82.384 | 41.691 | 1.00 | 22.65 |
| ATOM | 2138 | HG1 | THR | 143 | 85.030 | 82.016 | 41.523 | 1.00 | 0.00 |
| ATOM | 2139 | CG2 | THR | 143 | 83.270 | 80.030 | 41.306 | 1.00 | 21.69 |
| ATOM | 2140 | C | THR | 143 | 80.884 | 81.109 | 42.408 | 1.00 | 22.38 |
| ATOM | 2141 | O | THR | 143 | 80.322 | 80.725 | 41.396 | 1.00 | 24.04 |
| ATOM | 2142 | N | LEU | 144 | 80.665 | 80.578 | 43.611 | 1.00 | 18.57 |
| ATOM | 2143 | H | LEU | 144 | 81.201 | 80.890 | 44.371 | 1.00 | 0.00 |
| ATOM | 2144 | CA | LEU | 144 | 79.700 | 79.521 | 43.883 | 1.00 | 19.42 |
| ATOM | 2145 | CB | LEU | 144 | 80.465 | 78.339 | 44.480 | 1.00 | 17.34 |
| ATOM | 2146 | CG | LEU | 144 | 80.157 | 76.889 | 44.858 | 1.00 | 15.74 |
| ATOM | 2147 | CD1 | LEU | 144 | 79.106 | 76.767 | 45.922 | 1.00 | 16.50 |
| ATOM | 2148 | CD2 | LEU | 144 | 79.799 | 76.186 | 43.630 | 1.00 | 14.36 |
| ATOM | 2149 | C | LEU | 144 | 78.662 | 80.075 | 44.865 | 1.00 | 20.27 |
| ATOM | 2150 | O | LEU | 144 | 78.964 | 80.536 | 45.967 | 1.00 | 20.47 |
| ATOM | 2151 | N | PHE | 145 | 77.394 | 80.069 | 44.476 | 1.00 | 19.18 |

FIG. 1: A-37

| ATOM | 2152 | H | PHE | 145 | 77.179 | 79.753 | 43.573 | 1.00 | 0.00 |
|---|---|---|---|---|---|---|---|---|---|
| ATOM | 2153 | CA | PHE | 145 | 76.347 | 80.604 | 45.333 | 1.00 | 17.36 |
| ATOM | 2154 | CB | PHE | 145 | 75.652 | 81.766 | 44.676 | 1.00 | 15.43 |
| ATOM | 2155 | CG | PHE | 145 | 76.631 | 82.861 | 44.297 | 1.00 | 20.91 |
| ATOM | 2156 | CD1 | PHE | 145 | 77.256 | 82.852 | 43.028 | 1.00 | 19.52 |
| ATOM | 2157 | CD2 | PHE | 145 | 76.896 | 83.891 | 45.217 | 1.00 | 19.96 |
| ATOM | 2158 | CE1 | PHE | 145 | 78.137 | 83.886 | 42.693 | 1.00 | 18.11 |
| ATOM | 2159 | CE2 | PHE | 145 | 77.780 | 84.912 | 44.858 | 1.00 | 17.57 |
| ATOM | 2160 | CZ | PHE | 145 | 78.391 | 84.908 | 43.604 | 1.00 | 17.39 |
| ATOM | 2161 | C | PHE | 145 | 75.303 | 79.574 | 45.670 | 1.00 | 16.04 |
| ATOM | 2162 | O | PHE | 145 | 74.794 | 78.879 | 44.814 | 1.00 | 17.70 |
| ATOM | 2163 | N | LEU | 146 | 74.977 | 79.450 | 46.936 | 1.00 | 16.74 |
| ATOM | 2164 | H | LEU | 146 | 75.452 | 80.015 | 47.579 | 1.00 | 0.00 |
| ATOM | 2165 | CA | LEU | 146 | 73.952 | 78.546 | 47.416 | 1.00 | 12.62 |
| ATOM | 2166 | CB | LEU | 146 | 74.526 | 77.711 | 48.529 | 1.00 | 11.21 |
| ATOM | 2167 | CG | LEU | 146 | 75.825 | 77.017 | 48.194 | 1.00 | 9.46 |
| ATOM | 2168 | CD1 | LEU | 146 | 76.429 | 76.471 | 49.453 | 1.00 | 11.74 |
| ATOM | 2169 | CD2 | LEU | 146 | 75.572 | 75.948 | 47.175 | 1.00 | 8.82 |
| ATOM | 2170 | C | LEU | 146 | 72.780 | 79.348 | 47.918 | 1.00 | 13.23 |
| ATOM | 2171 | O | LEU | 146 | 72.948 | 80.294 | 48.672 | 1.00 | 15.41 |
| ATOM | 2172 | N | LEU | 147 | 71.575 | 79.035 | 47.472 | 1.00 | 17.20 |
| ATOM | 2173 | H | LEU | 147 | 71.527 | 78.312 | 46.813 | 1.00 | 0.00 |
| ATOM | 2174 | CA | LEU | 147 | 70.329 | 79.684 | 47.922 | 1.00 | 17.47 |
| ATOM | 2175 | CB | LEU | 147 | 69.396 | 79.876 | 46.756 | 1.00 | 15.96 |
| ATOM | 2176 | CG | LEU | 147 | 69.100 | 81.254 | 46.284 | 1.00 | 12.11 |
| ATOM | 2177 | CD1 | LEU | 147 | 70.306 | 81.993 | 45.808 | 1.00 | 8.16 |
| ATOM | 2178 | CD2 | LEU | 147 | 68.107 | 81.073 | 45.159 | 1.00 | 16.92 |
| ATOM | 2179 | C | LEU | 147 | 69.591 | 78.830 | 48.951 | 1.00 | 18.76 |
| ATOM | 2180 | O | LEU | 147 | 69.905 | 77.624 | 49.097 | 1.00 | 18.35 |
| ATOM | 2181 | N | ARG | 148 | 68.597 | 79.369 | 49.669 | 1.00 | 16.91 |
| ATOM | 2182 | H | ARG | 148 | 68.381 | 80.321 | 49.588 | 1.00 | 0.00 |
| ATOM | 2183 | CA | ARG | 148 | 67.854 | 78.482 | 50.562 | 1.00 | 16.55 |
| ATOM | 2184 | CB | ARG | 148 | 67.310 | 79.262 | 51.761 | 1.00 | 17.09 |
| ATOM | 2185 | CG | ARG | 148 | 66.916 | 78.326 | 52.915 | 1.00 | 12.47 |
| ATOM | 2186 | CD | ARG | 148 | 66.540 | 79.161 | 54.092 | 1.00 | 14.01 |
| ATOM | 2187 | NE | ARG | 148 | 66.324 | 78.285 | 55.214 | 1.00 | 16.19 |
| ATOM | 2188 | HE | ARG | 148 | 66.261 | 77.327 | 55.042 | 1.00 | 0.00 |
| ATOM | 2189 | CZ | ARG | 148 | 66.170 | 78.755 | 56.460 | 1.00 | 18.74 |
| ATOM | 2190 | NH1 | ARG | 148 | 66.047 | 77.913 | 57.488 | 1.00 | 15.67 |
| ATOM | 2191 | HH11 | ARG | 148 | 66.061 | 76.927 | 57.327 | 1.00 | 0.00 |
| ATOM | 2192 | HH12 | ARG | 148 | 65.927 | 78.271 | 58.413 | 1.00 | 0.00 |
| ATOM | 2193 | NH2 | ARG | 148 | 66.091 | 80.054 | 56.712 | 1.00 | 18.45 |
| ATOM | 2194 | HH21 | ARG | 148 | 66.131 | 80.719 | 55.969 | 1.00 | 0.00 |
| ATOM | 2195 | HH22 | ARG | 148 | 66.005 | 80.369 | 57.654 | 1.00 | 0.00 |
| ATOM | 2196 | C | ARG | 148 | 66.690 | 77.716 | 49.921 | 1.00 | 17.74 |
| ATOM | 2197 | O | ARG | 148 | 65.989 | 78.189 | 49.001 | 1.00 | 21.65 |
| ATOM | 2198 | N | GLY | 149 | 66.441 | 76.480 | 50.366 | 1.00 | 16.77 |
| ATOM | 2199 | H | GLY | 149 | 66.929 | 76.204 | 51.167 | 1.00 | 0.00 |
| ATOM | 2200 | CA | GLY | 149 | 65.327 | 75.708 | 49.820 | 1.00 | 15.53 |
| ATOM | 2201 | C | GLY | 149 | 64.263 | 75.417 | 50.851 | 1.00 | 15.88 |
| ATOM | 2202 | O | GLY | 149 | 64.584 | 75.466 | 52.018 | 1.00 | 16.06 |
| ATOM | 2203 | N | ASN | 150 | 63.005 | 75.090 | 50.551 | 1.00 | 18.25 |
| ATOM | 2204 | H | ASN | 150 | 62.665 | 75.330 | 49.670 | 1.00 | 0.00 |
| ATOM | 2205 | CA | ASN | 150 | 62.032 | 74.694 | 51.592 | 1.00 | 17.64 |
| ATOM | 2206 | CB | ASN | 150 | 60.718 | 74.270 | 50.931 | 1.00 | 15.57 |
| ATOM | 2207 | CG | ASN | 150 | 60.692 | 73.038 | 50.052 | 1.00 | 18.41 |
| ATOM | 2208 | OD1 | ASN | 150 | 61.490 | 72.851 | 49.134 | 1.00 | 22.57 |
| ATOM | 2209 | ND2 | ASN | 150 | 59.779 | 72.108 | 50.190 | 1.00 | 16.22 |
| ATOM | 2210 | HD21 | ASN | 150 | 59.824 | 71.334 | 49.615 | 1.00 | 0.00 |
| ATOM | 2211 | HD22 | ASN | 150 | 59.079 | 72.262 | 50.854 | 1.00 | 0.00 |

FIG. 1: A-38

| | | | | | | | | |
|---|---|---|---|---|---|---|---|---|
| ATOM | 2212 | C | ASN | 150 | 62.425 | 73.602 | 52.591 | 1.00 | 16.35 |
| ATOM | 2213 | O | ASN | 150 | 61.888 | 73.465 | 53.685 | 1.00 | 19.15 |
| ATOM | 2214 | N | HIS | 151 | 63.360 | 72.769 | 52.164 | 1.00 | 15.59 |
| ATOM | 2215 | H | HIS | 151 | 63.664 | 72.932 | 51.258 | 1.00 | 0.00 |
| ATOM | 2216 | CA | HIS | 151 | 63.925 | 71.686 | 52.956 | 1.00 | 16.17 |
| ATOM | 2217 | CB | HIS | 151 | 64.388 | 70.529 | 52.050 | 1.00 | 16.86 |
| ATOM | 2218 | CG | HIS | 151 | 63.324 | 69.501 | 51.694 | 1.00 | 17.72 |
| ATOM | 2219 | CD2 | HIS | 151 | 62.205 | 69.659 | 50.926 | 1.00 | 13.32 |
| ATOM | 2220 | ND1 | HIS | 151 | 63.300 | 68.256 | 52.154 | 1.00 | 18.26 |
| ATOM | 2221 | HD1 | HIS | 151 | 63.992 | 67.852 | 52.701 | 1.00 | 0.00 |
| ATOM | 2222 | CE1 | HIS | 151 | 62.248 | 67.645 | 51.733 | 1.00 | 13.78 |
| ATOM | 2223 | NE2 | HIS | 151 | 61.605 | 68.496 | 51.000 | 1.00 | 15.60 |
| ATOM | 2224 | HE2 | HIS | 151 | 60.718 | 68.268 | 50.657 | 1.00 | 0.00 |
| ATOM | 2225 | C | HIS | 151 | 65.116 | 72.104 | 53.805 | 1.00 | 16.72 |
| ATOM | 2226 | O | HIS | 151 | 65.557 | 71.342 | 54.662 | 1.00 | 20.69 |
| ATOM | 2227 | N | GLU | 152 | 65.717 | 73.268 | 53.614 | 1.00 | 15.30 |
| ATOM | 2228 | H | GLU | 152 | 65.303 | 73.948 | 53.048 | 1.00 | 0.00 |
| ATOM | 2229 | CA | GLU | 152 | 66.848 | 73.639 | 54.444 | 1.00 | 15.12 |
| ATOM | 2230 | CB | GLU | 152 | 67.780 | 74.546 | 53.689 | 1.00 | 16.74 |
| ATOM | 2231 | CG | GLU | 152 | 68.821 | 73.773 | 52.906 | 1.00 | 16.17 |
| ATOM | 2232 | CD | GLU | 152 | 68.303 | 73.183 | 51.618 | 1.00 | 18.12 |
| ATOM | 2233 | OE1 | GLU | 152 | 68.307 | 71.966 | 51.480 | 1.00 | 19.15 |
| ATOM | 2234 | OE2 | GLU | 152 | 67.893 | 73.952 | 50.760 | 1.00 | 18.61 |
| ATOM | 2235 | C | GLU | 152 | 66.325 | 74.352 | 55.666 | 1.00 | 15.54 |
| ATOM | 2236 | O | GLU | 152 | 66.391 | 75.559 | 55.844 | 1.00 | 16.27 |
| ATOM | 2237 | N | CYS | 153 | 65.688 | 73.565 | 56.504 | 1.00 | 15.65 |
| ATOM | 2238 | H | CYS | 153 | 65.705 | 72.595 | 56.336 | 1.00 | 0.00 |
| ATOM | 2239 | CA | CYS | 153 | 65.046 | 74.081 | 57.688 | 1.00 | 15.82 |
| ATOM | 2240 | CB | CYS | 153 | 63.668 | 74.671 | 57.312 | 1.00 | 15.39 |
| ATOM | 2241 | SG | CYS | 153 | 62.287 | 73.536 | 56.957 | 1.00 | 21.31 |
| ATOM | 2242 | C | CYS | 153 | 64.888 | 72.935 | 58.683 | 1.00 | 17.91 |
| ATOM | 2243 | O | CYS | 153 | 65.071 | 71.776 | 58.329 | 1.00 | 16.43 |
| ATOM | 2244 | N | ARG | 154 | 64.561 | 73.238 | 59.952 | 1.00 | 21.58 |
| ATOM | 2245 | H | ARG | 154 | 64.686 | 74.176 | 60.179 | 1.00 | 0.00 |
| ATOM | 2246 | CA | ARG | 154 | 64.279 | 72.262 | 61.028 | 1.00 | 19.93 |
| ATOM | 2247 | CB | ARG | 154 | 64.084 | 72.966 | 62.357 | 1.00 | 19.03 |
| ATOM | 2248 | CG | ARG | 154 | 65.308 | 73.852 | 62.627 | 1.00 | 20.60 |
| ATOM | 2249 | CD | ARG | 154 | 65.257 | 74.687 | 63.891 | 1.00 | 17.76 |
| ATOM | 2250 | NE | ARG | 154 | 66.423 | 75.541 | 63.914 | 1.00 | 16.58 |
| ATOM | 2251 | HE | ARG | 154 | 67.189 | 75.287 | 64.470 | 1.00 | 0.00 |
| ATOM | 2252 | CZ | ARG | 154 | 66.505 | 76.662 | 63.175 | 1.00 | 19.09 |
| ATOM | 2253 | NH1 | ARG | 154 | 67.610 | 77.373 | 63.253 | 1.00 | 18.69 |
| ATOM | 2254 | HH11 | ARG | 154 | 67.691 | 78.209 | 62.731 | 1.00 | 0.00 |
| ATOM | 2255 | HH12 | ARG | 154 | 68.357 | 77.073 | 63.846 | 1.00 | 0.00 |
| ATOM | 2256 | NH2 | ARG | 154 | 65.543 | 77.115 | 62.356 | 1.00 | 18.35 |
| ATOM | 2257 | HH21 | ARG | 154 | 64.683 | 76.615 | 62.272 | 1.00 | 0.00 |
| ATOM | 2258 | HH22 | ARG | 154 | 65.679 | 77.969 | 61.856 | 1.00 | 0.00 |
| ATOM | 2259 | C | ARG | 154 | 63.063 | 71.397 | 60.814 | 1.00 | 20.36 |
| ATOM | 2260 | O | ARG | 154 | 63.123 | 70.174 | 60.771 | 1.00 | 20.75 |
| ATOM | 2261 | N | HIS | 155 | 61.908 | 72.014 | 60.597 | 1.00 | 22.57 |
| ATOM | 2262 | H | HIS | 155 | 61.899 | 72.985 | 60.673 | 1.00 | 0.00 |
| ATOM | 2263 | CA | HIS | 155 | 60.669 | 71.239 | 60.407 | 1.00 | 22.82 |
| ATOM | 2264 | CB | HIS | 155 | 59.487 | 72.150 | 60.058 | 1.00 | 29.04 |
| ATOM | 2265 | CG | HIS | 155 | 59.315 | 72.799 | 58.665 | 1.00 | 39.10 |
| ATOM | 2266 | CD2 | HIS | 155 | 59.857 | 74.025 | 58.281 | 1.00 | 43.42 |
| ATOM | 2267 | ND1 | HIS | 155 | 58.555 | 72.402 | 57.630 | 1.00 | 42.46 |
| ATOM | 2268 | HD1 | HIS | 155 | 57.946 | 71.632 | 57.595 | 1.00 | 0.00 |
| ATOM | 2269 | CE1 | HIS | 155 | 58.629 | 73.331 | 56.681 | 1.00 | 47.02 |
| ATOM | 2270 | NE2 | HIS | 155 | 59.419 | 74.306 | 57.080 | 1.00 | 44.98 |
| ATOM | 2271 | HE2 | HIS | 155 | 59.592 | 75.130 | 56.580 | 1.00 | 0.00 |

FIG. 1: A-39

| ATOM | 2272 | C | HIS | 155 | 60.688 | 70.139 | 59.372 | 1.00 | 20.10 |
| --- | --- | --- | --- | --- | --- | --- | --- | --- | --- |
| ATOM | 2273 | O | HIS | 155 | 60.095 | 69.100 | 59.624 | 1.00 | 19.75 |
| ATOM | 2274 | N | LEU | 156 | 61.349 | 70.325 | 58.225 | 1.00 | 17.62 |
| ATOM | 2275 | H | LEU | 156 | 61.959 | 71.079 | 58.115 | 1.00 | 0.00 |
| ATOM | 2276 | CA | LEU | 156 | 61.325 | 69.268 | 57.246 | 1.00 | 17.78 |
| ATOM | 2277 | CB | LEU | 156 | 61.421 | 69.850 | 55.841 | 1.00 | 17.76 |
| ATOM | 2278 | CG | LEU | 156 | 60.160 | 70.501 | 55.256 | 1.00 | 19.31 |
| ATOM | 2279 | CD1 | LEU | 156 | 60.301 | 70.648 | 53.753 | 1.00 | 19.31 |
| ATOM | 2280 | CD2 | LEU | 156 | 58.938 | 69.612 | 55.471 | 1.00 | 20.01 |
| ATOM | 2281 | C | LEU | 156 | 62.396 | 68.184 | 57.410 | 1.00 | 20.32 |
| ATOM | 2282 | O | LEU | 156 | 62.165 | 67.016 | 57.069 | 1.00 | 19.81 |
| ATOM | 2283 | N | THR | 157 | 63.555 | 68.537 | 57.964 | 1.00 | 19.67 |
| ATOM | 2284 | H | THR | 157 | 63.698 | 69.464 | 58.247 | 1.00 | 0.00 |
| ATOM | 2285 | CA | THR | 157 | 64.658 | 67.616 | 58.209 | 1.00 | 18.19 |
| ATOM | 2286 | CB | THR | 157 | 65.948 | 68.424 | 58.305 | 1.00 | 19.00 |
| ATOM | 2287 | OG1 | THR | 157 | 65.694 | 69.404 | 59.299 | 1.00 | 20.10 |
| ATOM | 2288 | HG1 | THR | 157 | 66.504 | 69.705 | 59.728 | 1.00 | 0.00 |
| ATOM | 2289 | CG2 | THR | 157 | 66.359 | 69.095 | 56.982 | 1.00 | 16.35 |
| ATOM | 2290 | C | THR | 157 | 64.456 | 66.770 | 59.453 | 1.00 | 17.89 |
| ATOM | 2291 | O | THR | 157 | 64.950 | 65.638 | 59.536 | 1.00 | 22.22 |
| ATOM | 2292 | N | ALA | 158 | 63.770 | 67.262 | 60.464 | 1.00 | 18.27 |
| ATOM | 2293 | H | ALA | 158 | 63.693 | 68.242 | 60.521 | 1.00 | 0.00 |
| ATOM | 2294 | CA | ALA | 158 | 63.265 | 66.388 | 61.534 | 1.00 | 20.15 |
| ATOM | 2295 | CB | ALA | 158 | 62.508 | 67.184 | 62.614 | 1.00 | 20.41 |
| ATOM | 2296 | C | ALA | 158 | 62.284 | 65.310 | 61.030 | 1.00 | 21.54 |
| ATOM | 2297 | O | ALA | 158 | 62.366 | 64.138 | 61.369 | 1.00 | 22.99 |
| ATOM | 2298 | N | TYR | 159 | 61.324 | 65.721 | 60.198 | 1.00 | 23.26 |
| ATOM | 2299 | H | TYR | 159 | 61.305 | 66.679 | 60.004 | 1.00 | 0.00 |
| ATOM | 2300 | CA | TYR | 159 | 60.319 | 64.856 | 59.611 | 1.00 | 22.59 |
| ATOM | 2301 | CB | TYR | 159 | 59.238 | 65.782 | 59.161 | 1.00 | 24.56 |
| ATOM | 2302 | CG | TYR | 159 | 58.184 | 65.233 | 58.212 | 1.00 | 31.97 |
| ATOM | 2303 | CD1 | TYR | 159 | 57.414 | 64.088 | 58.495 | 1.00 | 33.28 |
| ATOM | 2304 | CE1 | TYR | 159 | 56.472 | 63.646 | 57.563 | 1.00 | 33.66 |
| ATOM | 2305 | CD2 | TYR | 159 | 57.999 | 65.922 | 57.006 | 1.00 | 34.83 |
| ATOM | 2306 | CE2 | TYR | 159 | 57.063 | 65.481 | 56.084 | 1.00 | 35.68 |
| ATOM | 2307 | CZ | TYR | 159 | 56.309 | 64.351 | 56.371 | 1.00 | 36.53 |
| ATOM | 2308 | OH | TYR | 159 | 55.356 | 63.963 | 55.436 | 1.00 | 43.54 |
| ATOM | 2309 | HH | TYR | 159 | 55.344 | 64.594 | 54.709 | 1.00 | 0.00 |
| ATOM | 2310 | C | TYR | 159 | 60.795 | 63.937 | 58.505 | 1.00 | 22.41 |
| ATOM | 2311 | O | TYR | 159 | 60.403 | 62.774 | 58.414 | 1.00 | 26.10 |
| ATOM | 2312 | N | PHE | 160 | 61.603 | 64.416 | 57.595 | 1.00 | 21.57 |
| ATOM | 2313 | H | PHE | 160 | 61.829 | 65.351 | 57.659 | 1.00 | 0.00 |
| ATOM | 2314 | CA | PHE | 160 | 62.165 | 63.538 | 56.585 | 1.00 | 21.14 |
| ATOM | 2315 | CB | PHE | 160 | 62.495 | 64.318 | 55.375 | 1.00 | 20.94 |
| ATOM | 2316 | CG | PHE | 160 | 61.285 | 64.525 | 54.519 | 1.00 | 16.06 |
| ATOM | 2317 | CD1 | PHE | 160 | 60.636 | 65.751 | 54.580 | 1.00 | 14.80 |
| ATOM | 2318 | CD2 | PHE | 160 | 60.876 | 63.498 | 53.683 | 1.00 | 12.54 |
| ATOM | 2319 | CE1 | PHE | 160 | 59.542 | 65.955 | 53.769 | 1.00 | 11.64 |
| ATOM | 2320 | CE2 | PHE | 160 | 59.775 | 63.727 | 52.880 | 1.00 | 15.40 |
| ATOM | 2321 | CZ | PHE | 160 | 59.116 | 64.956 | 52.926 | 1.00 | 14.17 |
| ATOM | 2322 | C | PHE | 160 | 63.392 | 62.762 | 56.994 | 1.00 | 22.48 |
| ATOM | 2323 | O | PHE | 160 | 63.292 | 62.052 | 57.989 | 1.00 | 27.43 |
| ATOM | 2324 | N | THR | 161 | 64.541 | 62.737 | 56.304 | 1.00 | 22.40 |
| ATOM | 2325 | H | THR | 161 | 64.555 | 62.989 | 55.363 | 1.00 | 0.00 |
| ATOM | 2326 | CA | THR | 161 | 65.678 | 61.980 | 56.837 | 1.00 | 20.17 |
| ATOM | 2327 | CB | THR | 161 | 66.190 | 60.926 | 55.800 | 1.00 | 20.42 |
| ATOM | 2328 | OG1 | THR | 161 | 66.043 | 61.425 | 54.469 | 1.00 | 24.05 |
| ATOM | 2329 | HG1 | THR | 161 | 66.128 | 60.659 | 53.882 | 1.00 | 0.00 |
| ATOM | 2330 | CG2 | THR | 161 | 65.434 | 59.629 | 55.980 | 1.00 | 19.93 |
| ATOM | 2331 | C | THR | 161 | 66.909 | 62.698 | 57.363 | 1.00 | 19.02 |

FIG. 1: A-40

| ATOM | 2332 | O | THR | 161 | 67.738 | 62.067 | 58.011 | 1.00 | 20.03 |
| --- | --- | --- | --- | --- | --- | --- | --- | --- | --- |
| ATOM | 2333 | N | PHE | 162 | 67.126 | 64.001 | 57.256 | 1.00 | 19.02 |
| ATOM | 2334 | H | PHE | 162 | 66.378 | 64.563 | 56.987 | 1.00 | 0.00 |
| ATOM | 2335 | CA | PHE | 162 | 68.425 | 64.587 | 57.627 | 1.00 | 17.61 |
| ATOM | 2336 | CB | PHE | 162 | 68.442 | 65.987 | 56.976 | 1.00 | 14.66 |
| ATOM | 2337 | CG | PHE | 162 | 69.748 | 66.734 | 57.037 | 1.00 | 11.35 |
| ATOM | 2338 | CD1 | PHE | 162 | 69.748 | 68.035 | 57.548 | 1.00 | 13.12 |
| ATOM | 2339 | CD2 | PHE | 162 | 70.934 | 66.129 | 56.586 | 1.00 | 13.59 |
| ATOM | 2340 | CE1 | PHE | 162 | 70.946 | 68.750 | 57.613 | 1.00 | 15.89 |
| ATOM | 2341 | CE2 | PHE | 162 | 72.139 | 66.839 | 56.644 | 1.00 | 12.23 |
| ATOM | 2342 | CZ | PHE | 162 | 72.137 | 68.144 | 57.156 | 1.00 | 17.84 |
| ATOM | 2343 | C | PHE | 162 | 68.793 | 64.613 | 59.138 | 1.00 | 18.83 |
| ATOM | 2344 | O | PHE | 162 | 69.971 | 64.446 | 59.456 | 1.00 | 19.27 |
| ATOM | 2345 | N | LYS | 163 | 67.882 | 64.792 | 60.119 | 1.00 | 18.70 |
| ATOM | 2346 | H | LYS | 163 | 66.970 | 65.047 | 59.854 | 1.00 | 0.00 |
| ATOM | 2347 | CA | LYS | 163 | 68.190 | 64.637 | 61.542 | 1.00 | 16.82 |
| ATOM | 2348 | CB | LYS | 163 | 66.944 | 64.677 | 62.377 | 1.00 | 17.58 |
| ATOM | 2349 | CG | LYS | 163 | 66.609 | 65.881 | 63.245 | 1.00 | 18.14 |
| ATOM | 2350 | CD | LYS | 163 | 67.416 | 65.856 | 64.512 | 1.00 | 20.78 |
| ATOM | 2351 | CE | LYS | 163 | 66.704 | 66.479 | 65.690 | 1.00 | 19.60 |
| ATOM | 2352 | NZ | LYS | 163 | 65.758 | 65.520 | 66.204 | 1.00 | 25.18 |
| ATOM | 2353 | HZ1 | LYS | 163 | 65.098 | 65.246 | 65.449 | 1.00 | 0.00 |
| ATOM | 2354 | HZ2 | LYS | 163 | 65.228 | 65.949 | 66.991 | 1.00 | 0.00 |
| ATOM | 2355 | HZ3 | LYS | 163 | 66.266 | 64.680 | 66.547 | 1.00 | 0.00 |
| ATOM | 2356 | C | LYS | 163 | 68.834 | 63.293 | 61.804 | 1.00 | 18.05 |
| ATOM | 2357 | O | LYS | 163 | 69.927 | 63.206 | 62.326 | 1.00 | 20.06 |
| ATOM | 2358 | N | GLN | 164 | 68.195 | 62.216 | 61.361 | 1.00 | 21.91 |
| ATOM | 2359 | H | GLN | 164 | 67.332 | 62.366 | 60.927 | 1.00 | 0.00 |
| ATOM | 2360 | CA | GLN | 164 | 68.650 | 60.840 | 61.537 | 1.00 | 22.85 |
| ATOM | 2361 | CB | GLN | 164 | 67.589 | 59.883 | 60.942 | 1.00 | 28.43 |
| ATOM | 2362 | CG | GLN | 164 | 67.854 | 58.355 | 60.879 | 1.00 | 34.39 |
| ATOM | 2363 | CD | GLN | 164 | 67.990 | 57.649 | 62.228 | 1.00 | 39.74 |
| ATOM | 2364 | OE1 | GLN | 164 | 67.894 | 58.236 | 63.304 | 1.00 | 42.26 |
| ATOM | 2365 | NE2 | GLN | 164 | 68.208 | 56.353 | 62.298 | 1.00 | 40.61 |
| ATOM | 2366 | HE21 | GLN | 164 | 68.330 | 56.035 | 63.210 | 1.00 | 0.00 |
| ATOM | 2367 | HE22 | GLN | 164 | 68.190 | 55.819 | 61.480 | 1.00 | 0.00 |
| ATOM | 2368 | C | GLN | 164 | 69.988 | 60.617 | 60.872 | 1.00 | 21.33 |
| ATOM | 2369 | O | GLN | 164 | 70.890 | 60.032 | 61.446 | 1.00 | 23.49 |
| ATOM | 2370 | N | GLU | 165 | 70.161 | 61.095 | 59.661 | 1.00 | 18.26 |
| ATOM | 2371 | H | GLU | 165 | 69.383 | 61.482 | 59.205 | 1.00 | 0.00 |
| ATOM | 2372 | CA | GLU | 165 | 71.428 | 61.000 | 58.984 | 1.00 | 17.32 |
| ATOM | 2373 | CB | GLU | 165 | 71.263 | 61.608 | 57.632 | 1.00 | 16.64 |
| ATOM | 2374 | CG | GLU | 165 | 72.401 | 61.201 | 56.770 | 1.00 | 20.06 |
| ATOM | 2375 | CD | GLU | 165 | 72.576 | 62.009 | 55.504 | 1.00 | 23.85 |
| ATOM | 2376 | OE1 | GLU | 165 | 73.719 | 62.114 | 55.051 | 1.00 | 27.58 |
| ATOM | 2377 | OE2 | GLU | 165 | 71.593 | 62.503 | 54.958 | 1.00 | 25.48 |
| ATOM | 2378 | C | GLU | 165 | 72.525 | 61.716 | 59.786 | 1.00 | 18.81 |
| ATOM | 2379 | O | GLU | 165 | 73.508 | 61.084 | 60.176 | 1.00 | 20.10 |
| ATOM | 2380 | N | CYS | 166 | 72.434 | 63.019 | 60.090 | 1.00 | 20.20 |
| ATOM | 2381 | H | CYS | 166 | 71.666 | 63.522 | 59.743 | 1.00 | 0.00 |
| ATOM | 2382 | CA | CYS | 166 | 73.397 | 63.684 | 60.956 | 1.00 | 19.98 |
| ATOM | 2383 | CB | CYS | 166 | 72.959 | 65.013 | 61.368 | 1.00 | 19.93 |
| ATOM | 2384 | SG | CYS | 166 | 72.991 | 66.202 | 60.036 | 1.00 | 20.30 |
| ATOM | 2385 | C | CYS | 166 | 73.668 | 62.973 | 62.276 | 1.00 | 23.22 |
| ATOM | 2386 | O | CYS | 166 | 74.768 | 63.076 | 62.799 | 1.00 | 26.79 |
| ATOM | 2387 | N | ALA | 167 | 72.717 | 62.242 | 62.865 | 1.00 | 23.64 |
| ATOM | 2388 | H | ALA | 167 | 71.809 | 62.297 | 62.491 | 1.00 | 0.00 |
| ATOM | 2389 | CA | ALA | 167 | 72.924 | 61.487 | 64.103 | 1.00 | 20.08 |
| ATOM | 2390 | CB | ALA | 167 | 71.640 | 61.229 | 64.780 | 1.00 | 20.11 |
| ATOM | 2391 | C | ALA | 167 | 73.578 | 60.139 | 63.999 | 1.00 | 22.48 |

FIG. 1: A-41

| ATOM | 2392 | O | ALA | 167 | 74.210 | 59.614 | 64.910 | 1.00 | 25.92 |
|---|---|---|---|---|---|---|---|---|---|
| ATOM | 2393 | N | ILE | 168 | 73.294 | 59.480 | 62.898 | 1.00 | 24.17 |
| ATOM | 2394 | H | ILE | 168 | 72.617 | 59.864 | 62.304 | 1.00 | 0.00 |
| ATOM | 2395 | CA | ILE | 168 | 73.892 | 58.181 | 62.576 | 1.00 | 22.74 |
| ATOM | 2396 | CB | ILE | 168 | 73.000 | 57.503 | 61.469 | 1.00 | 20.81 |
| ATOM | 2397 | CG2 | ILE | 168 | 73.675 | 56.292 | 60.907 | 1.00 | 20.17 |
| ATOM | 2398 | CG1 | ILE | 168 | 71.649 | 57.108 | 62.050 | 1.00 | 21.66 |
| ATOM | 2399 | CD1 | ILE | 168 | 71.609 | 55.993 | 63.092 | 1.00 | 18.60 |
| ATOM | 2400 | C | ILE | 168 | 75.337 | 58.368 | 62.094 | 1.00 | 21.39 |
| ATOM | 2401 | O | ILE | 168 | 76.218 | 57.544 | 62.264 | 1.00 | 23.79 |
| ATOM | 2402 | N | LYS | 169 | 75.579 | 59.411 | 61.341 | 1.00 | 20.61 |
| ATOM | 2403 | H | LYS | 169 | 74.841 | 60.022 | 61.143 | 1.00 | 0.00 |
| ATOM | 2404 | CA | LYS | 169 | 76.883 | 59.577 | 60.747 | 1.00 | 20.14 |
| ATOM | 2405 | CB | LYS | 169 | 76.739 | 60.253 | 59.380 | 1.00 | 19.11 |
| ATOM | 2406 | CG | LYS | 169 | 76.205 | 59.281 | 58.350 | 1.00 | 17.14 |
| ATOM | 2407 | CD | LYS | 169 | 75.886 | 60.011 | 57.053 | 1.00 | 20.16 |
| ATOM | 2408 | CE | LYS | 169 | 75.215 | 59.048 | 56.075 | 1.00 | 18.23 |
| ATOM | 2409 | NZ | LYS | 169 | 75.288 | 59.560 | 54.725 | 1.00 | 14.06 |
| ATOM | 2410 | HZ1 | LYS | 169 | 74.745 | 58.937 | 54.093 | 1.00 | 0.00 |
| ATOM | 2411 | HZ2 | LYS | 169 | 76.281 | 59.579 | 54.416 | 1.00 | 0.00 |
| ATOM | 2412 | HZ3 | LYS | 169 | 74.896 | 60.521 | 54.688 | 1.00 | 0.00 |
| ATOM | 2413 | C | LYS | 169 | 77.813 | 60.369 | 61.621 | 1.00 | 20.17 |
| ATOM | 2414 | O | LYS | 169 | 78.973 | 60.006 | 61.829 | 1.00 | 20.58 |
| ATOM | 2415 | N | TYR | 170 | 77.262 | 61.485 | 62.079 | 1.00 | 18.41 |
| ATOM | 2416 | H | TYR | 170 | 76.302 | 61.607 | 61.954 | 1.00 | 0.00 |
| ATOM | 2417 | CA | TYR | 170 | 78.006 | 62.434 | 62.888 | 1.00 | 20.51 |
| ATOM | 2418 | CB | TYR | 170 | 78.157 | 63.809 | 62.181 | 1.00 | 17.92 |
| ATOM | 2419 | CG | TYR | 170 | 79.151 | 63.774 | 61.026 | 1.00 | 18.40 |
| ATOM | 2420 | CD1 | TYR | 170 | 78.740 | 63.209 | 59.806 | 1.00 | 16.17 |
| ATOM | 2421 | CE1 | TYR | 170 | 79.615 | 63.131 | 58.744 | 1.00 | 14.27 |
| ATOM | 2422 | CD2 | TYR | 170 | 80.450 | 64.276 | 61.175 | 1.00 | 14.21 |
| ATOM | 2423 | CE2 | TYR | 170 | 81.334 | 64.203 | 60.099 | 1.00 | 16.01 |
| ATOM | 2424 | CZ | TYR | 170 | 80.897 | 63.625 | 58.906 | 1.00 | 14.97 |
| ATOM | 2425 | OH | TYR | 170 | 81.740 | 63.500 | 57.847 | 1.00 | 17.07 |
| ATOM | 2426 | HH | TYR | 170 | 81.237 | 63.229 | 57.070 | 1.00 | 0.00 |
| ATOM | 2427 | C | TYR | 170 | 77.256 | 62.615 | 64.189 | 1.00 | 21.99 |
| ATOM | 2428 | O | TYR | 170 | 77.031 | 61.606 | 64.846 | 1.00 | 24.17 |
| ATOM | 2429 | N | SER | 171 | 76.816 | 63.797 | 64.622 | 1.00 | 20.67 |
| ATOM | 2430 | H | SER | 171 | 76.846 | 64.576 | 64.041 | 1.00 | 0.00 |
| ATOM | 2431 | CA | SER | 171 | 76.043 | 63.858 | 65.833 | 1.00 | 19.55 |
| ATOM | 2432 | CB | SER | 171 | 76.889 | 64.244 | 66.999 | 1.00 | 23.18 |
| ATOM | 2433 | OG | SER | 171 | 77.216 | 65.638 | 67.049 | 1.00 | 26.67 |
| ATOM | 2434 | HG | SER | 171 | 78.030 | 65.697 | 67.570 | 1.00 | 0.00 |
| ATOM | 2435 | C | SER | 171 | 74.984 | 64.891 | 65.696 | 1.00 | 18.96 |
| ATOM | 2436 | O | SER | 171 | 74.840 | 65.509 | 64.663 | 1.00 | 19.86 |
| ATOM | 2437 | N | GLU | 172 | 74.205 | 65.156 | 66.722 | 1.00 | 22.06 |
| ATOM | 2438 | H | GLU | 172 | 74.182 | 64.520 | 67.465 | 1.00 | 0.00 |
| ATOM | 2439 | CA | GLU | 172 | 73.269 | 66.273 | 66.705 | 1.00 | 22.05 |
| ATOM | 2440 | CB | GLU | 172 | 72.346 | 66.189 | 67.911 | 1.00 | 25.25 |
| ATOM | 2441 | CG | GLU | 172 | 70.860 | 66.179 | 67.520 | 1.00 | 32.45 |
| ATOM | 2442 | CD | GLU | 172 | 69.977 | 67.225 | 68.201 | 1.00 | 35.10 |
| ATOM | 2443 | OE1 | GLU | 172 | 69.813 | 67.152 | 69.428 | 1.00 | 32.81 |
| ATOM | 2444 | OE2 | GLU | 172 | 69.466 | 68.102 | 67.483 | 1.00 | 37.52 |
| ATOM | 2445 | C | GLU | 172 | 73.922 | 67.649 | 66.691 | 1.00 | 21.13 |
| ATOM | 2446 | O | GLU | 172 | 73.256 | 68.596 | 66.305 | 1.00 | 21.82 |
| ATOM | 2447 | N | ALA | 173 | 75.197 | 67.805 | 67.085 | 1.00 | 20.84 |
| ATOM | 2448 | H | ALA | 173 | 75.652 | 66.995 | 67.388 | 1.00 | 0.00 |
| ATOM | 2449 | CA | ALA | 173 | 75.947 | 69.095 | 67.093 | 1.00 | 19.33 |
| ATOM | 2450 | CB | ALA | 173 | 77.308 | 68.994 | 67.846 | 1.00 | 13.85 |
| ATOM | 2451 | C | ALA | 173 | 76.249 | 69.548 | 65.669 | 1.00 | 18.52 |

FIG. 1: A-42

| | | | | | | | | | |
|---|---|---|---|---|---|---|---|---|---|
| ATOM | 2452 | O | ALA | 173 | 76.010 | 70.692 | 65.271 | 1.00 | 18.58 |
| ATOM | 2453 | N | VAL | 174 | 76.696 | 68.565 | 64.887 | 1.00 | 18.02 |
| ATOM | 2454 | H | VAL | 174 | 76.980 | 67.730 | 65.312 | 1.00 | 0.00 |
| ATOM | 2455 | CA | VAL | 174 | 76.768 | 68.719 | 63.442 | 1.00 | 18.30 |
| ATOM | 2456 | CB | VAL | 174 | 77.335 | 67.424 | 62.896 | 1.00 | 16.65 |
| ATOM | 2457 | CG1 | VAL | 174 | 77.165 | 67.291 | 61.375 | 1.00 | 12.98 |
| ATOM | 2458 | CG2 | VAL | 174 | 78.776 | 67.393 | 63.368 | 1.00 | 11.87 |
| ATOM | 2459 | C | VAL | 174 | 75.339 | 69.024 | 62.899 | 1.00 | 21.54 |
| ATOM | 2460 | O | VAL | 174 | 75.194 | 70.015 | 62.160 | 1.00 | 24.23 |
| ATOM | 2461 | N | TYR | 175 | 74.243 | 68.294 | 63.281 | 1.00 | 20.24 |
| ATOM | 2462 | H | TYR | 175 | 74.397 | 67.465 | 63.778 | 1.00 | 0.00 |
| ATOM | 2463 | CA | TYR | 175 | 72.854 | 68.655 | 62.865 | 1.00 | 19.96 |
| ATOM | 2464 | CB | TYR | 175 | 71.778 | 67.816 | 63.553 | 1.00 | 19.12 |
| ATOM | 2465 | CG | TYR | 175 | 70.387 | 68.143 | 63.032 | 1.00 | 18.62 |
| ATOM | 2466 | CD1 | TYR | 175 | 69.999 | 67.772 | 61.728 | 1.00 | 19.51 |
| ATOM | 2467 | CE1 | TYR | 175 | 68.749 | 68.125 | 61.229 | 1.00 | 17.76 |
| ATOM | 2468 | CD2 | TYR | 175 | 69.510 | 68.863 | 63.837 | 1.00 | 20.99 |
| ATOM | 2469 | CE2 | TYR | 175 | 68.249 | 69.234 | 63.347 | 1.00 | 21.28 |
| ATOM | 2470 | CZ | TYR | 175 | 67.895 | 68.860 | 62.052 | 1.00 | 22.17 |
| ATOM | 2471 | OH | TYR | 175 | 66.675 | 69.258 | 61.595 | 1.00 | 22.72 |
| ATOM | 2472 | HH | TYR | 175 | 66.192 | 69.692 | 62.305 | 1.00 | 0.00 |
| ATOM | 2473 | C | TYR | 175 | 72.464 | 70.103 | 63.161 | 1.00 | 19.51 |
| ATOM | 2474 | O | TYR | 175 | 72.014 | 70.854 | 62.308 | 1.00 | 17.87 |
| ATOM | 2475 | N | ASP | 176 | 72.684 | 70.495 | 64.412 | 1.00 | 21.61 |
| ATOM | 2476 | H | ASP | 176 | 73.072 | 69.846 | 65.019 | 1.00 | 0.00 |
| ATOM | 2477 | CA | ASP | 176 | 72.421 | 71.818 | 64.897 | 1.00 | 21.88 |
| ATOM | 2478 | CB | ASP | 176 | 72.731 | 71.904 | 66.365 | 1.00 | 25.05 |
| ATOM | 2479 | CG | ASP | 176 | 71.789 | 71.097 | 67.260 | 1.00 | 26.36 |
| ATOM | 2480 | OD1 | ASP | 176 | 70.667 | 70.780 | 66.858 | 1.00 | 26.01 |
| ATOM | 2481 | OD2 | ASP | 176 | 72.201 | 70.784 | 68.378 | 1.00 | 28.93 |
| ATOM | 2482 | C | ASP | 176 | 73.212 | 72.861 | 64.183 | 1.00 | 21.38 |
| ATOM | 2483 | O | ASP | 176 | 72.659 | 73.901 | 63.830 | 1.00 | 25.24 |
| ATOM | 2484 | N | ALA | 177 | 74.475 | 72.578 | 63.910 | 1.00 | 20.58 |
| ATOM | 2485 | H | ALA | 177 | 74.854 | 71.759 | 64.278 | 1.00 | 0.00 |
| ATOM | 2486 | CA | ALA | 177 | 75.316 | 73.478 | 63.119 | 1.00 | 17.28 |
| ATOM | 2487 | CB | ALA | 177 | 76.663 | 72.903 | 62.813 | 1.00 | 19.85 |
| ATOM | 2488 | C | ALA | 177 | 74.741 | 73.774 | 61.761 | 1.00 | 16.97 |
| ATOM | 2489 | O | ALA | 177 | 74.797 | 74.906 | 61.277 | 1.00 | 20.43 |
| ATOM | 2490 | N | CYS | 178 | 74.222 | 72.728 | 61.115 | 1.00 | 16.07 |
| ATOM | 2491 | H | CYS | 178 | 74.351 | 71.837 | 61.516 | 1.00 | 0.00 |
| ATOM | 2492 | CA | CYS | 178 | 73.591 | 72.868 | 59.812 | 1.00 | 14.26 |
| ATOM | 2493 | CB | CYS | 178 | 73.156 | 71.576 | 59.198 | 1.00 | 10.05 |
| ATOM | 2494 | SG | CYS | 178 | 74.553 | 70.547 | 58.776 | 1.00 | 14.13 |
| ATOM | 2495 | C | CYS | 178 | 72.343 | 73.679 | 60.018 | 1.00 | 15.99 |
| ATOM | 2496 | O | CYS | 178 | 72.217 | 74.648 | 59.289 | 1.00 | 19.56 |
| ATOM | 2497 | N | MET | 179 | 71.438 | 73.434 | 60.983 | 1.00 | 15.56 |
| ATOM | 2498 | H | MET | 179 | 71.620 | 72.688 | 61.593 | 1.00 | 0.00 |
| ATOM | 2499 | CA | MET | 179 | 70.262 | 74.278 | 61.153 | 1.00 | 13.62 |
| ATOM | 2500 | CB | MET | 179 | 69.510 | 73.831 | 62.322 | 1.00 | 14.95 |
| ATOM | 2501 | CG | MET | 179 | 68.889 | 72.475 | 62.095 | 1.00 | 19.31 |
| ATOM | 2502 | SD | MET | 179 | 67.878 | 72.375 | 60.600 | 1.00 | 23.01 |
| ATOM | 2503 | CE | MET | 179 | 68.802 | 71.264 | 59.570 | 1.00 | 20.89 |
| ATOM | 2504 | C | MET | 179 | 70.595 | 75.738 | 61.321 | 1.00 | 13.60 |
| ATOM | 2505 | O | MET | 179 | 70.048 | 76.556 | 60.597 | 1.00 | 17.45 |
| ATOM | 2506 | N | ASP | 180 | 71.525 | 76.123 | 62.183 | 1.00 | 13.39 |
| ATOM | 2507 | H | ASP | 180 | 71.914 | 75.461 | 62.795 | 1.00 | 0.00 |
| ATOM | 2508 | CA | ASP | 180 | 71.958 | 77.504 | 62.227 | 1.00 | 15.87 |
| ATOM | 2509 | CB | ASP | 180 | 72.909 | 77.669 | 63.354 | 1.00 | 22.40 |
| ATOM | 2510 | CG | ASP | 180 | 72.408 | 77.291 | 64.756 | 1.00 | 29.22 |
| ATOM | 2511 | OD1 | ASP | 180 | 71.467 | 76.503 | 64.903 | 1.00 | 31.24 |

FIG. 1: A-43

| ATOM | 2512 | OD2 | ASP | 180 | 73.011 | 77.788 | 65.724 | 1.00 | 33.40 |
|---|---|---|---|---|---|---|---|---|---|
| ATOM | 2513 | C | ASP | 180 | 72.634 | 77.972 | 60.927 | 1.00 | 15.47 |
| ATOM | 2514 | O | ASP | 180 | 72.475 | 79.110 | 60.504 | 1.00 | 15.20 |
| ATOM | 2515 | N | ALA | 181 | 73.374 | 77.138 | 60.190 | 1.00 | 15.40 |
| ATOM | 2516 | H | ALA | 181 | 73.552 | 76.242 | 60.540 | 1.00 | 0.00 |
| ATOM | 2517 | CA | ALA | 181 | 73.979 | 77.556 | 58.924 | 1.00 | 14.75 |
| ATOM | 2518 | CB | ALA | 181 | 74.949 | 76.496 | 58.409 | 1.00 | 14.81 |
| ATOM | 2519 | C | ALA | 181 | 72.916 | 77.793 | 57.851 | 1.00 | 16.67 |
| ATOM | 2520 | O | ALA | 181 | 72.913 | 78.833 | 57.186 | 1.00 | 18.03 |
| ATOM | 2521 | N | PHE | 182 | 71.952 | 76.868 | 57.689 | 1.00 | 15.94 |
| ATOM | 2522 | H | PHE | 182 | 72.024 | 76.069 | 58.228 | 1.00 | 0.00 |
| ATOM | 2523 | CA | PHE | 182 | 70.841 | 76.985 | 56.748 | 1.00 | 13.91 |
| ATOM | 2524 | CB | PHE | 182 | 69.858 | 75.857 | 56.896 | 1.00 | 7.67 |
| ATOM | 2525 | CG | PHE | 182 | 70.364 | 74.532 | 56.401 | 1.00 | 6.40 |
| ATOM | 2526 | CD1 | PHE | 182 | 71.603 | 74.399 | 55.759 | 1.00 | 8.30 |
| ATOM | 2527 | CD2 | PHE | 182 | 69.587 | 73.409 | 56.620 | 1.00 | 5.59 |
| ATOM | 2528 | CE1 | PHE | 182 | 72.049 | 73.139 | 55.348 | 1.00 | 5.21 |
| ATOM | 2529 | CE2 | PHE | 182 | 70.040 | 72.161 | 56.205 | 1.00 | 4.65 |
| ATOM | 2530 | CZ | PHE | 182 | 71.266 | 72.019 | 55.571 | 1.00 | 2.88 |
| ATOM | 2531 | C | PHE | 182 | 70.076 | 78.280 | 56.970 | 1.00 | 16.76 |
| ATOM | 2532 | O | PHE | 182 | 69.732 | 78.914 | 55.967 | 1.00 | 19.69 |
| ATOM | 2533 | N | ASP | 183 | 69.890 | 78.749 | 58.223 | 1.00 | 16.36 |
| ATOM | 2534 | H | ASP | 183 | 70.109 | 78.163 | 58.982 | 1.00 | 0.00 |
| ATOM | 2535 | CA | ASP | 183 | 69.271 | 80.064 | 58.446 | 1.00 | 16.95 |
| ATOM | 2536 | CB | ASP | 183 | 69.171 | 80.452 | 59.910 | 1.00 | 14.53 |
| ATOM | 2537 | CG | ASP | 183 | 68.165 | 79.627 | 60.721 | 1.00 | 19.32 |
| ATOM | 2538 | OD1 | ASP | 183 | 68.110 | 79.803 | 61.936 | 1.00 | 19.77 |
| ATOM | 2539 | OD2 | ASP | 183 | 67.449 | 78.788 | 60.169 | 1.00 | 21.29 |
| ATOM | 2540 | C | ASP | 183 | 69.940 | 81.239 | 57.782 | 1.00 | 17.51 |
| ATOM | 2541 | O | ASP | 183 | 69.321 | 82.281 | 57.593 | 1.00 | 21.09 |
| ATOM | 2542 | N | CYS | 184 | 71.203 | 81.075 | 57.402 | 1.00 | 17.27 |
| ATOM | 2543 | H | CYS | 184 | 71.636 | 80.240 | 57.677 | 1.00 | 0.00 |
| ATOM | 2544 | CA | CYS | 184 | 71.982 | 82.113 | 56.747 | 1.00 | 15.00 |
| ATOM | 2545 | CB | CYS | 184 | 73.427 | 81.913 | 57.039 | 1.00 | 17.60 |
| ATOM | 2546 | SG | CYS | 184 | 73.773 | 82.127 | 58.792 | 1.00 | 22.33 |
| ATOM | 2547 | C | CYS | 184 | 71.852 | 82.203 | 55.256 | 1.00 | 15.72 |
| ATOM | 2548 | O | CYS | 184 | 72.213 | 83.194 | 54.632 | 1.00 | 18.31 |
| ATOM | 2549 | N | LEU | 185 | 71.371 | 81.139 | 54.625 | 1.00 | 16.98 |
| ATOM | 2550 | H | LEU | 185 | 70.978 | 80.422 | 55.170 | 1.00 | 0.00 |
| ATOM | 2551 | CA | LEU | 185 | 71.292 | 81.068 | 53.170 | 1.00 | 14.37 |
| ATOM | 2552 | CB | LEU | 185 | 70.728 | 79.709 | 52.752 | 1.00 | 11.79 |
| ATOM | 2553 | CG | LEU | 185 | 71.611 | 78.516 | 52.858 | 1.00 | 10.34 |
| ATOM | 2554 | CD1 | LEU | 185 | 70.806 | 77.255 | 52.720 | 1.00 | 11.25 |
| ATOM | 2555 | CD2 | LEU | 185 | 72.642 | 78.588 | 51.787 | 1.00 | 9.22 |
| ATOM | 2556 | C | LEU | 185 | 70.451 | 82.162 | 52.529 | 1.00 | 16.36 |
| ATOM | 2557 | O | LEU | 185 | 69.265 | 82.337 | 52.899 | 1.00 | 15.95 |
| ATOM | 2558 | N | PRO | 186 | 71.038 | 82.896 | 51.546 | 1.00 | 17.90 |
| ATOM | 2559 | CD | PRO | 186 | 72.420 | 82.755 | 51.060 | 1.00 | 17.78 |
| ATOM | 2560 | CA | PRO | 186 | 70.316 | 83.883 | 50.752 | 1.00 | 17.18 |
| ATOM | 2561 | CB | PRO | 186 | 71.310 | 84.321 | 49.721 | 1.00 | 16.47 |
| ATOM | 2562 | CG | PRO | 186 | 72.655 | 84.078 | 50.366 | 1.00 | 16.90 |
| ATOM | 2563 | C | PRO | 186 | 69.042 | 83.287 | 50.169 | 1.00 | 20.05 |
| ATOM | 2564 | O | PRO | 186 | 68.949 | 82.110 | 49.771 | 1.00 | 23.20 |
| ATOM | 2565 | N | LEU | 187 | 67.983 | 84.069 | 50.251 | 1.00 | 21.80 |
| ATOM | 2566 | H | LEU | 187 | 68.079 | 84.938 | 50.688 | 1.00 | 0.00 |
| ATOM | 2567 | CA | LEU | 187 | 66.696 | 83.643 | 49.724 | 1.00 | 20.95 |
| ATOM | 2568 | CB | LEU | 187 | 65.603 | 84.518 | 50.361 | 1.00 | 24.13 |
| ATOM | 2569 | CG | LEU | 187 | 64.891 | 84.186 | 51.682 | 1.00 | 24.19 |
| ATOM | 2570 | CD1 | LEU | 187 | 65.625 | 83.116 | 52.454 | 1.00 | 24.21 |
| ATOM | 2571 | CD2 | LEU | 187 | 64.758 | 85.487 | 52.482 | 1.00 | 23.19 |

FIG. 1: A-44

| ATOM | 2572 | C | LEU | 187 | 66.622 | 83.725 | 48.199 | 1.00 | 20.81 |
|---|---|---|---|---|---|---|---|---|---|
| ATOM | 2573 | O | LEU | 187 | 65.910 | 82.934 | 47.581 | 1.00 | 20.82 |
| ATOM | 2574 | N | ALA | 188 | 67.369 | 84.633 | 47.551 | 1.00 | 20.12 |
| ATOM | 2575 | H | ALA | 188 | 68.006 | 85.168 | 48.064 | 1.00 | 0.00 |
| ATOM | 2576 | CA | ALA | 188 | 67.230 | 84.817 | 46.118 | 1.00 | 18.91 |
| ATOM | 2577 | CB | ALA | 188 | 66.089 | 85.760 | 45.917 | 1.00 | 21.89 |
| ATOM | 2578 | C | ALA | 188 | 68.360 | 85.285 | 45.218 | 1.00 | 19.68 |
| ATOM | 2579 | O | ALA | 188 | 69.434 | 85.621 | 45.690 | 1.00 | 22.80 |
| ATOM | 2580 | N | ALA | 189 | 68.226 | 85.363 | 43.895 | 1.00 | 16.77 |
| ATOM | 2581 | H | ALA | 189 | 67.414 | 84.984 | 43.496 | 1.00 | 0.00 |
| ATOM | 2582 | CA | ALA | 189 | 69.282 | 85.924 | 43.070 | 1.00 | 15.19 |
| ATOM | 2583 | CB | ALA | 189 | 70.197 | 84.900 | 42.417 | 1.00 | 12.32 |
| ATOM | 2584 | C | ALA | 189 | 68.807 | 86.737 | 41.906 | 1.00 | 15.83 |
| ATOM | 2585 | O | ALA | 189 | 67.953 | 86.346 | 41.141 | 1.00 | 20.26 |
| ATOM | 2586 | N | LEU | 190 | 69.250 | 87.938 | 41.748 | 1.00 | 18.42 |
| ATOM | 2587 | H | LEU | 190 | 69.711 | 88.381 | 42.480 | 1.00 | 0.00 |
| ATOM | 2588 | CA | LEU | 190 | 68.962 | 88.658 | 40.549 | 1.00 | 20.82 |
| ATOM | 2589 | CB | LEU | 190 | 68.922 | 90.130 | 40.863 | 1.00 | 17.83 |
| ATOM | 2590 | CG | LEU | 190 | 68.110 | 91.038 | 39.986 | 1.00 | 16.50 |
| ATOM | 2591 | CD1 | LEU | 190 | 68.825 | 92.366 | 40.033 | 1.00 | 15.88 |
| ATOM | 2592 | CD2 | LEU | 190 | 67.990 | 90.566 | 38.559 | 1.00 | 12.51 |
| ATOM | 2593 | C | LEU | 190 | 70.131 | 88.283 | 39.632 | 1.00 | 24.32 |
| ATOM | 2594 | O | LEU | 190 | 71.289 | 88.671 | 39.811 | 1.00 | 29.21 |
| ATOM | 2595 | N | MET | 191 | 69.867 | 87.470 | 38.635 | 1.00 | 23.81 |
| ATOM | 2596 | H | MET | 191 | 68.955 | 87.120 | 38.571 | 1.00 | 0.00 |
| ATOM | 2597 | CA | MET | 191 | 70.902 | 87.026 | 37.745 | 1.00 | 22.55 |
| ATOM | 2598 | CB | MET | 191 | 70.620 | 85.577 | 37.551 | 1.00 | 20.51 |
| ATOM | 2599 | CG | MET | 191 | 71.842 | 84.811 | 37.195 | 1.00 | 21.57 |
| ATOM | 2600 | SD | MET | 191 | 72.150 | 84.928 | 35.435 | 1.00 | 19.85 |
| ATOM | 2601 | CE | MET | 191 | 71.021 | 83.700 | 34.864 | 1.00 | 24.25 |
| ATOM | 2602 | C | MET | 191 | 70.922 | 87.837 | 36.437 | 1.00 | 24.68 |
| ATOM | 2603 | O | MET | 191 | 69.899 | 88.103 | 35.795 | 1.00 | 23.90 |
| ATOM | 2604 | N | ASN | 192 | 72.116 | 88.297 | 36.041 | 1.00 | 25.84 |
| ATOM | 2605 | H | ASN | 192 | 72.873 | 87.996 | 36.566 | 1.00 | 0.00 |
| ATOM | 2606 | CA | ASN | 192 | 72.378 | 89.096 | 34.846 | 1.00 | 26.15 |
| ATOM | 2607 | CB | ASN | 192 | 72.389 | 88.139 | 33.686 | 1.00 | 23.49 |
| ATOM | 2608 | CG | ASN | 192 | 73.226 | 88.725 | 32.601 | 1.00 | 23.02 |
| ATOM | 2609 | OD1 | ASN | 192 | 74.350 | 89.142 | 32.824 | 1.00 | 23.50 |
| ATOM | 2610 | ND2 | ASN | 192 | 72.752 | 88.831 | 31.407 | 1.00 | 23.61 |
| ATOM | 2611 | HD21 | ASN | 192 | 71.845 | 88.546 | 31.223 | 1.00 | 0.00 |
| ATOM | 2612 | HD22 | ASN | 192 | 73.364 | 89.228 | 30.765 | 1.00 | 0.00 |
| ATOM | 2613 | C | ASN | 192 | 71.448 | 90.290 | 34.546 | 1.00 | 27.11 |
| ATOM | 2614 | O | ASN | 192 | 71.046 | 90.534 | 33.412 | 1.00 | 28.53 |
| ATOM | 2615 | N | GLN | 193 | 71.040 | 91.008 | 35.606 | 1.00 | 28.08 |
| ATOM | 2616 | H | GLN | 193 | 71.441 | 90.744 | 36.457 | 1.00 | 0.00 |
| ATOM | 2617 | CA | GLN | 193 | 70.078 | 92.126 | 35.583 | 1.00 | 25.25 |
| ATOM | 2618 | CB | GLN | 193 | 70.721 | 93.298 | 34.821 | 1.00 | 27.05 |
| ATOM | 2619 | CG | GLN | 193 | 71.887 | 93.935 | 35.551 | 1.00 | 28.60 |
| ATOM | 2620 | CD | GLN | 193 | 71.440 | 94.840 | 36.681 | 1.00 | 32.33 |
| ATOM | 2621 | OE1 | GLN | 193 | 71.473 | 96.051 | 36.545 | 1.00 | 37.54 |
| ATOM | 2622 | NE2 | GLN | 193 | 70.958 | 94.476 | 37.851 | 1.00 | 33.44 |
| ATOM | 2623 | HE21 | GLN | 193 | 70.756 | 95.263 | 38.393 | 1.00 | 0.00 |
| ATOM | 2624 | HE22 | GLN | 193 | 70.811 | 93.550 | 38.090 | 1.00 | 0.00 |
| ATOM | 2625 | C | GLN | 193 | 68.712 | 91.805 | 34.990 | 1.00 | 24.06 |
| ATOM | 2626 | O | GLN | 193 | 67.984 | 92.687 | 34.571 | 1.00 | 25.42 |
| ATOM | 2627 | N | GLN | 194 | 68.336 | 90.538 | 34.904 | 1.00 | 23.26 |
| ATOM | 2628 | H | GLN | 194 | 68.944 | 89.867 | 35.272 | 1.00 | 0.00 |
| ATOM | 2629 | CA | GLN | 194 | 67.095 | 90.131 | 34.245 | 1.00 | 24.38 |
| ATOM | 2630 | CB | GLN | 194 | 67.375 | 89.964 | 32.757 | 1.00 | 25.55 |
| ATOM | 2631 | CG | GLN | 194 | 68.398 | 88.925 | 32.373 | 1.00 | 27.74 |

FIG. 1: A-45

| | | | | | | | | |
|---|---|---|---|---|---|---|---|---|
| ATOM | 2632 | CD | GLN | 194 | 69.051 | 89.051 | 30.999 | 1.00 | 29.30 |
| ATOM | 2633 | OE1 | GLN | 194 | 70.090 | 88.470 | 30.742 | 1.00 | 31.31 |
| ATOM | 2634 | NE2 | GLN | 194 | 68.610 | 89.725 | 29.976 | 1.00 | 30.09 |
| ATOM | 2635 | HE21 | GLN | 194 | 67.803 | 90.258 | 30.055 | 1.00 | 0.00 |
| ATOM | 2636 | HE22 | GLN | 194 | 69.163 | 89.617 | 29.179 | 1.00 | 0.00 |
| ATOM | 2637 | C | GLN | 194 | 66.357 | 88.883 | 34.746 | 1.00 | 24.97 |
| ATOM | 2638 | O | GLN | 194 | 65.133 | 88.743 | 34.581 | 1.00 | 25.45 |
| ATOM | 2639 | N | PHE | 195 | 67.072 | 87.917 | 35.319 | 1.00 | 24.06 |
| ATOM | 2640 | H | PHE | 195 | 68.045 | 87.998 | 35.357 | 1.00 | 0.00 |
| ATOM | 2641 | CA | PHE | 195 | 66.417 | 86.758 | 35.905 | 1.00 | 23.90 |
| ATOM | 2642 | CB | PHE | 195 | 67.159 | 85.480 | 35.543 | 1.00 | 23.27 |
| ATOM | 2643 | CG | PHE | 195 | 67.257 | 85.215 | 34.040 | 1.00 | 26.61 |
| ATOM | 2644 | CD1 | PHE | 195 | 68.378 | 85.648 | 33.319 | 1.00 | 26.80 |
| ATOM | 2645 | CD2 | PHE | 195 | 66.232 | 84.545 | 33.368 | 1.00 | 23.84 |
| ATOM | 2646 | CE1 | PHE | 195 | 68.450 | 85.411 | 31.948 | 1.00 | 26.45 |
| ATOM | 2647 | CE2 | PHE | 195 | 66.328 | 84.317 | 32.001 | 1.00 | 22.01 |
| ATOM | 2648 | CZ | PHE | 195 | 67.430 | 84.748 | 31.286 | 1.00 | 22.08 |
| ATOM | 2649 | C | PHE | 195 | 66.310 | 86.836 | 37.429 | 1.00 | 24.12 |
| ATOM | 2650 | O | PHE | 195 | 67.161 | 87.383 | 38.120 | 1.00 | 22.90 |
| ATOM | 2651 | N | LEU | 196 | 65.214 | 86.315 | 37.966 | 1.00 | 24.31 |
| ATOM | 2652 | H | LEU | 196 | 64.509 | 86.011 | 37.353 | 1.00 | 0.00 |
| ATOM | 2653 | CA | LEU | 196 | 64.986 | 86.237 | 39.399 | 1.00 | 21.88 |
| ATOM | 2654 | CB | LEU | 196 | 63.619 | 86.835 | 39.755 | 1.00 | 20.37 |
| ATOM | 2655 | CG | LEU | 196 | 63.157 | 87.218 | 41.181 | 1.00 | 21.79 |
| ATOM | 2656 | CD1 | LEU | 196 | 62.123 | 86.224 | 41.718 | 1.00 | 20.60 |
| ATOM | 2657 | CD2 | LEU | 196 | 64.380 | 87.343 | 42.062 | 1.00 | 20.97 |
| ATOM | 2658 | C | LEU | 196 | 65.016 | 84.752 | 39.670 | 1.00 | 21.57 |
| ATOM | 2659 | O | LEU | 196 | 64.315 | 83.941 | 39.052 | 1.00 | 22.21 |
| ATOM | 2660 | N | CYS | 197 | 65.957 | 84.393 | 40.519 | 1.00 | 19.86 |
| ATOM | 2661 | H | CYS | 197 | 66.563 | 85.087 | 40.848 | 1.00 | 0.00 |
| ATOM | 2662 | CA | CYS | 197 | 66.125 | 83.006 | 40.873 | 1.00 | 16.44 |
| ATOM | 2663 | CB | CYS | 197 | 67.525 | 82.555 | 40.648 | 1.00 | 16.78 |
| ATOM | 2664 | SG | CYS | 197 | 68.106 | 83.189 | 39.063 | 1.00 | 17.73 |
| ATOM | 2665 | C | CYS | 197 | 65.771 | 82.772 | 42.310 | 1.00 | 14.33 |
| ATOM | 2666 | O | CYS | 197 | 66.142 | 83.512 | 43.209 | 1.00 | 13.81 |
| ATOM | 2667 | N | VAL | 198 | 64.856 | 81.825 | 42.419 | 1.00 | 13.80 |
| ATOM | 2668 | H | VAL | 198 | 64.558 | 81.381 | 41.591 | 1.00 | 0.00 |
| ATOM | 2669 | CA | VAL | 198 | 64.311 | 81.377 | 43.688 | 1.00 | 12.53 |
| ATOM | 2670 | CB | VAL | 198 | 62.930 | 82.082 | 44.089 | 1.00 | 12.56 |
| ATOM | 2671 | CG1 | VAL | 198 | 63.222 | 83.447 | 44.758 | 1.00 | 6.32 |
| ATOM | 2672 | CG2 | VAL | 198 | 62.011 | 82.238 | 42.873 | 1.00 | 9.16 |
| ATOM | 2673 | C | VAL | 198 | 64.075 | 79.885 | 43.667 | 1.00 | 11.58 |
| ATOM | 2674 | O | VAL | 198 | 64.195 | 79.216 | 42.645 | 1.00 | 13.15 |
| ATOM | 2675 | N | HIS | 199 | 63.784 | 79.329 | 44.830 | 1.00 | 12.16 |
| ATOM | 2676 | H | HIS | 199 | 63.831 | 79.909 | 45.619 | 1.00 | 0.00 |
| ATOM | 2677 | CA | HIS | 199 | 63.508 | 77.907 | 44.927 | 1.00 | 12.11 |
| ATOM | 2678 | CB | HIS | 199 | 63.746 | 77.456 | 46.348 | 1.00 | 11.51 |
| ATOM | 2679 | CG | HIS | 199 | 63.590 | 75.964 | 46.421 | 1.00 | 8.02 |
| ATOM | 2680 | CD2 | HIS | 199 | 62.584 | 75.312 | 47.061 | 1.00 | 11.48 |
| ATOM | 2681 | ND1 | HIS | 199 | 64.347 | 75.040 | 45.870 | 1.00 | 9.86 |
| ATOM | 2682 | HD1 | HIS | 199 | 65.154 | 75.201 | 45.328 | 1.00 | 0.00 |
| ATOM | 2683 | CE1 | HIS | 199 | 63.857 | 73.864 | 46.142 | 1.00 | 9.07 |
| ATOM | 2684 | NE2 | HIS | 199 | 62.785 | 74.028 | 46.867 | 1.00 | 10.14 |
| ATOM | 2685 | HE2 | HIS | 199 | 62.352 | 73.333 | 47.407 | 1.00 | 0.00 |
| ATOM | 2686 | C | HIS | 199 | 62.084 | 77.535 | 44.514 | 1.00 | 13.91 |
| ATOM | 2687 | O | HIS | 199 | 61.940 | 76.582 | 43.762 | 1.00 | 15.34 |
| ATOM | 2688 | N | GLY | 200 | 61.045 | 78.148 | 45.112 | 1.00 | 13.57 |
| ATOM | 2689 | H | GLY | 200 | 61.231 | 78.833 | 45.787 | 1.00 | 0.00 |
| ATOM | 2690 | CA | GLY | 200 | 59.656 | 77.933 | 44.742 | 1.00 | 11.83 |
| ATOM | 2691 | C | GLY | 200 | 59.100 | 79.049 | 43.858 | 1.00 | 13.43 |

FIG. 1: A-46

| ATOM | 2692 | O | GLY | 200 | 58.607 | 78.814 | 42.755 | 1.00 | 16.49 |
|---|---|---|---|---|---|---|---|---|---|
| ATOM | 2693 | N | GLY | 201 | 59.159 | 80.310 | 44.238 | 1.00 | 11.90 |
| ATOM | 2694 | H | GLY | 201 | 59.468 | 80.541 | 45.136 | 1.00 | 0.00 |
| ATOM | 2695 | CA | GLY | 201 | 58.685 | 81.311 | 43.333 | 1.00 | 12.38 |
| ATOM | 2696 | C | GLY | 201 | 58.161 | 82.571 | 43.979 | 1.00 | 16.15 |
| ATOM | 2697 | O | GLY | 201 | 58.796 | 83.237 | 44.793 | 1.00 | 18.28 |
| ATOM | 2698 | N | LEU | 202 | 56.940 | 82.885 | 43.594 | 1.00 | 17.53 |
| ATOM | 2699 | H | LEU | 202 | 56.444 | 82.177 | 43.149 | 1.00 | 0.00 |
| ATOM | 2700 | CA | LEU | 202 | 56.304 | 84.162 | 43.887 | 1.00 | 19.34 |
| ATOM | 2701 | CB | LEU | 202 | 55.654 | 84.590 | 42.512 | 1.00 | 17.80 |
| ATOM | 2702 | CG | LEU | 202 | 56.539 | 85.360 | 41.468 | 1.00 | 18.73 |
| ATOM | 2703 | CD1 | LEU | 202 | 57.662 | 84.508 | 40.989 | 1.00 | 20.27 |
| ATOM | 2704 | CD2 | LEU | 202 | 55.788 | 85.686 | 40.207 | 1.00 | 14.12 |
| ATOM | 2705 | C | LEU | 202 | 55.333 | 84.218 | 45.098 | 1.00 | 19.75 |
| ATOM | 2706 | O | LEU | 202 | 54.912 | 83.219 | 45.702 | 1.00 | 21.48 |
| ATOM | 2707 | N | SER | 203 | 54.910 | 85.400 | 45.505 | 1.00 | 20.41 |
| ATOM | 2708 | H | SER | 203 | 55.140 | 86.188 | 44.968 | 1.00 | 0.00 |
| ATOM | 2709 | CA | SER | 203 | 54.106 | 85.583 | 46.718 | 1.00 | 22.47 |
| ATOM | 2710 | CB | SER | 203 | 55.018 | 85.912 | 47.916 | 1.00 | 20.84 |
| ATOM | 2711 | OG | SER | 203 | 54.307 | 86.081 | 49.136 | 1.00 | 21.85 |
| ATOM | 2712 | HG | SER | 203 | 54.862 | 85.699 | 49.823 | 1.00 | 0.00 |
| ATOM | 2713 | C | SER | 203 | 53.121 | 86.732 | 46.525 | 1.00 | 24.74 |
| ATOM | 2714 | O | SER | 203 | 53.504 | 87.652 | 45.790 | 1.00 | 26.97 |
| ATOM | 2715 | N | PRO | 204 | 51.887 | 86.822 | 47.067 | 1.00 | 23.67 |
| ATOM | 2716 | CD | PRO | 204 | 51.058 | 85.718 | 47.485 | 1.00 | 23.37 |
| ATOM | 2717 | CA | PRO | 204 | 51.126 | 88.055 | 47.104 | 1.00 | 23.44 |
| ATOM | 2718 | CB | PRO | 204 | 49.810 | 87.626 | 47.644 | 1.00 | 22.65 |
| ATOM | 2719 | CG | PRO | 204 | 50.093 | 86.396 | 48.429 | 1.00 | 23.05 |
| ATOM | 2720 | C | PRO | 204 | 51.758 | 89.185 | 47.889 | 1.00 | 24.01 |
| ATOM | 2721 | O | PRO | 204 | 51.617 | 90.354 | 47.565 | 1.00 | 26.26 |
| ATOM | 2722 | N | GLU | 205 | 52.536 | 88.829 | 48.897 | 1.00 | 26.00 |
| ATOM | 2723 | H | GLU | 205 | 52.673 | 87.874 | 49.051 | 1.00 | 0.00 |
| ATOM | 2724 | CA | GLU | 205 | 53.186 | 89.783 | 49.803 | 1.00 | 28.20 |
| ATOM | 2725 | CB | GLU | 205 | 53.245 | 89.119 | 51.248 | 1.00 | 31.62 |
| ATOM | 2726 | CG | GLU | 205 | 51.889 | 88.642 | 51.897 | 1.00 | 39.48 |
| ATOM | 2727 | CD | GLU | 205 | 51.852 | 87.383 | 52.819 | 1.00 | 44.65 |
| ATOM | 2728 | OE1 | GLU | 205 | 51.606 | 86.251 | 52.355 | 1.00 | 44.45 |
| ATOM | 2729 | OE2 | GLU | 205 | 52.029 | 87.532 | 54.035 | 1.00 | 47.68 |
| ATOM | 2730 | C | GLU | 205 | 54.582 | 90.206 | 49.314 | 1.00 | 26.73 |
| ATOM | 2731 | O | GLU | 205 | 55.392 | 90.767 | 50.062 | 1.00 | 26.50 |
| ATOM | 2732 | N | ILE | 206 | 54.922 | 89.854 | 48.060 | 1.00 | 26.28 |
| ATOM | 2733 | H | ILE | 206 | 54.251 | 89.382 | 47.530 | 1.00 | 0.00 |
| ATOM | 2734 | CA | ILE | 206 | 56.200 | 90.195 | 47.380 | 1.00 | 25.36 |
| ATOM | 2735 | CB | ILE | 206 | 57.145 | 88.975 | 47.033 | 1.00 | 25.09 |
| ATOM | 2736 | CG2 | ILE | 206 | 58.262 | 89.412 | 46.046 | 1.00 | 22.88 |
| ATOM | 2737 | CG1 | ILE | 206 | 57.743 | 88.381 | 48.318 | 1.00 | 24.84 |
| ATOM | 2738 | CD1 | ILE | 206 | 58.787 | 89.268 | 49.016 | 1.00 | 27.83 |
| ATOM | 2739 | C | ILE | 206 | 55.814 | 90.799 | 46.038 | 1.00 | 24.48 |
| ATOM | 2740 | O | ILE | 206 | 55.275 | 90.098 | 45.197 | 1.00 | 27.02 |
| ATOM | 2741 | N | ASN | 207 | 56.022 | 92.071 | 45.779 | 1.00 | 23.24 |
| ATOM | 2742 | H | ASN | 207 | 56.283 | 92.641 | 46.529 | 1.00 | 0.00 |
| ATOM | 2743 | CA | ASN | 207 | 55.650 | 92.627 | 44.490 | 1.00 | 24.47 |
| ATOM | 2744 | CB | ASN | 207 | 54.504 | 93.611 | 44.678 | 1.00 | 26.63 |
| ATOM | 2745 | CG | ASN | 207 | 53.357 | 93.007 | 45.487 | 1.00 | 29.48 |
| ATOM | 2746 | OD1 | ASN | 207 | 53.050 | 93.485 | 46.566 | 1.00 | 32.06 |
| ATOM | 2747 | ND2 | ASN | 207 | 52.700 | 91.908 | 45.178 | 1.00 | 31.61 |
| ATOM | 2748 | HD21 | ASN | 207 | 52.925 | 91.388 | 44.386 | 1.00 | 0.00 |
| ATOM | 2749 | HD22 | ASN | 207 | 52.033 | 91.667 | 45.856 | 1.00 | 0.00 |
| ATOM | 2750 | C | ASN | 207 | 56.778 | 93.321 | 43.746 | 1.00 | 25.50 |
| ATOM | 2751 | O | ASN | 207 | 56.651 | 93.782 | 42.619 | 1.00 | 27.51 |

FIG. 1: A-47

| ATOM | 2752 | N | THR | 208 | 57.917 | 93.422 | 44.414 | 1.00 | 26.73 |
| --- | --- | --- | --- | --- | --- | --- | --- | --- | --- |
| ATOM | 2753 | H | THR | 208 | 57.937 | 93.072 | 45.325 | 1.00 | 0.00 |
| ATOM | 2754 | CA | THR | 208 | 59.151 | 94.014 | 43.900 | 1.00 | 25.53 |
| ATOM | 2755 | CB | THR | 208 | 59.272 | 95.516 | 44.146 | 1.00 | 22.39 |
| ATOM | 2756 | OG1 | THR | 208 | 59.117 | 95.672 | 45.540 | 1.00 | 23.21 |
| ATOM | 2757 | HG1 | THR | 208 | 59.020 | 96.611 | 45.749 | 1.00 | 0.00 |
| ATOM | 2758 | CG2 | THR | 208 | 58.281 | 96.361 | 43.396 | 1.00 | 20.63 |
| ATOM | 2759 | C | THR | 208 | 60.390 | 93.404 | 44.569 | 1.00 | 27.22 |
| ATOM | 2760 | O | THR | 208 | 60.326 | 92.879 | 45.683 | 1.00 | 27.04 |
| ATOM | 2761 | N | LEU | 209 | 61.552 | 93.445 | 43.924 | 1.00 | 29.14 |
| ATOM | 2762 | H | LEU | 209 | 61.520 | 93.760 | 42.993 | 1.00 | 0.00 |
| ATOM | 2763 | CA | LEU | 209 | 62.816 | 92.957 | 44.510 | 1.00 | 30.68 |
| ATOM | 2764 | CB | LEU | 209 | 63.963 | 93.126 | 43.474 | 1.00 | 29.45 |
| ATOM | 2765 | CG | LEU | 209 | 64.186 | 92.060 | 42.366 | 1.00 | 24.80 |
| ATOM | 2766 | CD1 | LEU | 209 | 62.887 | 91.580 | 41.804 | 1.00 | 25.15 |
| ATOM | 2767 | CD2 | LEU | 209 | 64.992 | 92.659 | 41.253 | 1.00 | 21.37 |
| ATOM | 2768 | C | LEU | 209 | 63.208 | 93.631 | 45.832 | 1.00 | 32.55 |
| ATOM | 2769 | O | LEU | 209 | 63.651 | 92.907 | 46.731 | 1.00 | 33.17 |
| ATOM | 2770 | N | ASP | 210 | 62.979 | 94.965 | 46.048 | 1.00 | 35.21 |
| ATOM | 2771 | H | ASP | 210 | 62.670 | 95.494 | 45.288 | 1.00 | 0.00 |
| ATOM | 2772 | CA | ASP | 210 | 63.206 | 95.633 | 47.369 | 1.00 | 34.60 |
| ATOM | 2773 | CB | ASP | 210 | 62.881 | 97.210 | 47.457 | 1.00 | 36.36 |
| ATOM | 2774 | CG | ASP | 210 | 61.469 | 97.921 | 47.450 | 1.00 | 42.32 |
| ATOM | 2775 | OD1 | ASP | 210 | 60.416 | 97.405 | 47.880 | 1.00 | 41.10 |
| ATOM | 2776 | OD2 | ASP | 210 | 61.425 | 99.089 | 47.022 | 1.00 | 43.75 |
| ATOM | 2777 | C | ASP | 210 | 62.346 | 94.957 | 48.428 | 1.00 | 33.04 |
| ATOM | 2778 | O | ASP | 210 | 62.765 | 94.928 | 49.579 | 1.00 | 33.54 |
| ATOM | 2779 | N | ASP | 211 | 61.215 | 94.319 | 48.073 | 1.00 | 31.21 |
| ATOM | 2780 | H | ASP | 211 | 60.903 | 94.373 | 47.146 | 1.00 | 0.00 |
| ATOM | 2781 | CA | ASP | 211 | 60.403 | 93.578 | 49.050 | 1.00 | 31.60 |
| ATOM | 2782 | CB | ASP | 211 | 58.997 | 93.259 | 48.490 | 1.00 | 30.78 |
| ATOM | 2783 | CG | ASP | 211 | 58.013 | 94.453 | 48.517 | 1.00 | 34.51 |
| ATOM | 2784 | OD1 | ASP | 211 | 58.220 | 95.426 | 49.267 | 1.00 | 33.28 |
| ATOM | 2785 | OD2 | ASP | 211 | 57.018 | 94.402 | 47.781 | 1.00 | 32.68 |
| ATOM | 2786 | C | ASP | 211 | 61.000 | 92.274 | 49.563 | 1.00 | 30.20 |
| ATOM | 2787 | O | ASP | 211 | 60.552 | 91.750 | 50.573 | 1.00 | 31.80 |
| ATOM | 2788 | N | ILE | 212 | 62.012 | 91.749 | 48.864 | 1.00 | 29.16 |
| ATOM | 2789 | H | ILE | 212 | 62.204 | 92.163 | 47.997 | 1.00 | 0.00 |
| ATOM | 2790 | CA | ILE | 212 | 62.758 | 90.546 | 49.253 | 1.00 | 27.02 |
| ATOM | 2791 | CB | ILE | 212 | 63.274 | 89.747 | 48.008 | 1.00 | 25.03 |
| ATOM | 2792 | CG2 | ILE | 212 | 64.083 | 88.560 | 48.497 | 1.00 | 20.3 |
| ATOM | 2793 | CG1 | ILE | 212 | 62.102 | 89.292 | 47.111 | 1.00 | 25.73 |
| ATOM | 2794 | CD1 | ILE | 212 | 62.370 | 88.448 | 45.818 | 1.00 | 25.10 |
| ATOM | 2795 | C | ILE | 212 | 63.945 | 91.048 | 50.067 | 1.00 | 26.68 |
| ATOM | 2796 | O | ILE | 212 | 64.308 | 90.505 | 51.109 | 1.00 | 27.21 |
| ATOM | 2797 | N | ARG | 213 | 64.557 | 92.140 | 49.596 | 1.00 | 26.19 |
| ATOM | 2798 | H | ARG | 213 | 64.243 | 92.475 | 48.728 | 1.00 | 0.00 |
| ATOM | 2799 | CA | ARG | 213 | 65.650 | 92.837 | 50.288 | 1.00 | 25.75 |
| ATOM | 2800 | CB | ARG | 213 | 66.046 | 94.104 | 49.491 | 1.00 | 25.39 |
| ATOM | 2801 | CG | ARG | 213 | 66.630 | 93.747 | 48.125 | 1.00 | 24.29 |
| ATOM | 2802 | CD | ARG | 213 | 67.101 | 94.871 | 47.167 | 1.00 | 28.21 |
| ATOM | 2803 | NE | ARG | 213 | 68.025 | 94.197 | 46.250 | 1.00 | 33.55 |
| ATOM | 2804 | HE | ARG | 213 | 68.599 | 93.506 | 46.643 | 1.00 | 0.00 |
| ATOM | 2805 | CZ | ARG | 213 | 68.174 | 94.400 | 44.919 | 1.00 | 34.03 |
| ATOM | 2806 | NH1 | ARG | 213 | 69.036 | 93.605 | 44.255 | 1.00 | 34.69 |
| ATOM | 2807 | HH11 | ARG | 213 | 69.192 | 93.728 | 43.274 | 1.00 | 0.00 |
| ATOM | 2808 | HH12 | ARG | 213 | 69.547 | 92.902 | 44.754 | 1.00 | 0.00 |
| ATOM | 2809 | NH2 | ARG | 213 | 67.524 | 95.359 | 44.250 | 1.00 | 32.23 |
| ATOM | 2810 | HH21 | ARG | 213 | 66.892 | 95.959 | 44.737 | 1.00 | 0.00 |
| ATOM | 2811 | HH22 | ARG | 213 | 67.675 | 95.468 | 43.268 | 1.00 | 0.00 |

FIG. 1: A-48

| ATOM | 2812 | C | ARG | 213 | 65.229 | 93.210 | 51.715 | 1.00 | 25.40 |
|---|---|---|---|---|---|---|---|---|---|
| ATOM | 2813 | O | ARG | 213 | 65.940 | 92.934 | 52.657 | 1.00 | 24.17 |
| ATOM | 2814 | N | LYS | 214 | 64.023 | 93.735 | 51.900 | 1.00 | 26.47 |
| ATOM | 2815 | H | LYS | 214 | 63.508 | 93.960 | 51.098 | 1.00 | 0.00 |
| ATOM | 2816 | CA | LYS | 214 | 63.442 | 94.035 | 53.206 | 1.00 | 27.09 |
| ATOM | 2817 | CB | LYS | 214 | 62.242 | 94.904 | 52.988 | 1.00 | 27.14 |
| ATOM | 2818 | CG | LYS | 214 | 62.526 | 96.195 | 52.256 | 1.00 | 31.38 |
| ATOM | 2819 | CD | LYS | 214 | 61.180 | 96.895 | 52.279 | 1.00 | 39.60 |
| ATOM | 2820 | CE | LYS | 214 | 60.831 | 97.645 | 51.012 | 1.00 | 43.39 |
| ATOM | 2821 | NZ | LYS | 214 | 61.716 | 98.774 | 50.801 | 1.00 | 46.41 |
| ATOM | 2822 | HZ1 | LYS | 214 | 62.697 | 98.434 | 50.786 | 1.00 | 0.00 |
| ATOM | 2823 | HZ2 | LYS | 214 | 61.592 | 99.459 | 51.573 | 1.00 | 0.00 |
| ATOM | 2824 | HZ3 | LYS | 214 | 61.489 | 99.225 | 49.891 | 1.00 | 0.00 |
| ATOM | 2825 | C | LYS | 214 | 63.027 | 92.852 | 54.112 | 1.00 | 27.76 |
| ATOM | 2826 | O | LYS | 214 | 62.427 | 93.010 | 55.185 | 1.00 | 28.38 |
| ATOM | 2827 | N | LEU | 215 | 63.307 | 91.606 | 53.756 | 1.00 | 27.45 |
| ATOM | 2828 | H | LEU | 215 | 63.773 | 91.445 | 52.915 | 1.00 | 0.00 |
| ATOM | 2829 | CA | LEU | 215 | 62.935 | 90.505 | 54.641 | 1.00 | 27.46 |
| ATOM | 2830 | CB | LEU | 215 | 62.750 | 89.244 | 53.782 | 1.00 | 26.77 |
| ATOM | 2831 | CG | LEU | 215 | 61.651 | 89.210 | 52.723 | 1.00 | 24.92 |
| ATOM | 2832 | CD1 | LEU | 215 | 61.645 | 87.865 | 51.998 | 1.00 | 23.35 |
| ATOM | 2833 | CD2 | LEU | 215 | 60.312 | 89.424 | 53.403 | 1.00 | 21.09 |
| ATOM | 2834 | C | LEU | 215 | 63.893 | 90.198 | 55.806 | 1.00 | 26.22 |
| ATOM | 2835 | O | LEU | 215 | 65.023 | 90.671 | 55.824 | 1.00 | 28.67 |
| ATOM | 2836 | N | ASP | 216 | 63.547 | 89.485 | 56.869 | 1.00 | 26.18 |
| ATOM | 2837 | H | ASP | 216 | 62.599 | 89.363 | 57.069 | 1.00 | 0.00 |
| ATOM | 2838 | CA | ASP | 216 | 64.581 | 88.980 | 57.781 | 1.00 | 28.21 |
| ATOM | 2839 | CB | ASP | 216 | 64.208 | 89.255 | 59.256 | 1.00 | 30.34 |
| ATOM | 2840 | CG | ASP | 216 | 65.031 | 88.588 | 60.373 | 1.00 | 32.26 |
| ATOM | 2841 | OD1 | ASP | 216 | 66.155 | 88.098 | 60.194 | 1.00 | 32.70 |
| ATOM | 2842 | OD2 | ASP | 216 | 64.496 | 88.560 | 61.472 | 1.00 | 35.14 |
| ATOM | 2843 | C | ASP | 216 | 64.745 | 87.474 | 57.542 | 1.00 | 27.84 |
| ATOM | 2844 | O | ASP | 216 | 63.957 | 86.662 | 58.016 | 1.00 | 28.68 |
| ATOM | 2845 | N | ARG | 217 | 65.768 | 87.097 | 56.772 | 1.00 | 25.47 |
| ATOM | 2846 | H | ARG | 217 | 66.324 | 87.798 | 56.369 | 1.00 | 0.00 |
| ATOM | 2847 | CA | ARG | 217 | 65.996 | 85.714 | 56.387 | 1.00 | 22.69 |
| ATOM | 2848 | CB | ARG | 217 | 67.015 | 85.769 | 55.233 | 1.00 | 21.21 |
| ATOM | 2849 | CG | ARG | 217 | 68.357 | 85.015 | 55.411 | 1.00 | 22.14 |
| ATOM | 2850 | CD | ARG | 217 | 69.392 | 85.107 | 54.280 | 1.00 | 17.26 |
| ATOM | 2851 | NE | ARG | 217 | 69.782 | 86.485 | 54.173 | 1.00 | 16.50 |
| ATOM | 2852 | HE | ARG | 217 | 69.081 | 87.166 | 54.133 | 1.00 | 0.00 |
| ATOM | 2853 | CZ | ARG | 217 | 71.023 | 86.904 | 54.162 | 1.00 | 13.23 |
| ATOM | 2854 | NH1 | ARG | 217 | 71.181 | 88.217 | 54.123 | 1.00 | 15.32 |
| ATOM | 2855 | HH11 | ARG | 217 | 70.386 | 88.823 | 54.122 | 1.00 | 0.00 |
| ATOM | 2856 | HH12 | ARG | 217 | 72.101 | 88.610 | 54.140 | 1.00 | 0.00 |
| ATOM | 2857 | NH2 | ARG | 217 | 72.046 | 86.075 | 54.199 | 1.00 | 10.95 |
| ATOM | 2858 | HH21 | ARG | 217 | 71.889 | 85.089 | 54.236 | 1.00 | 0.00 |
| ATOM | 2859 | HH22 | ARG | 217 | 72.983 | 86.428 | 54.183 | 1.00 | 0.00 |
| ATOM | 2860 | C | ARG | 217 | 66.459 | 84.747 | 57.493 | 1.00 | 23.17 |
| ATOM | 2861 | O | ARG | 217 | 66.289 | 83.515 | 57.493 | 1.00 | 23.96 |
| ATOM | 2862 | N | PHE | 218 | 67.076 | 85.331 | 58.509 | 1.00 | 22.05 |
| ATOM | 2863 | H | PHE | 218 | 67.021 | 86.296 | 58.602 | 1.00 | 0.00 |
| ATOM | 2864 | CA | PHE | 218 | 67.804 | 84.519 | 59.473 | 1.00 | 18.76 |
| ATOM | 2865 | CB | PHE | 218 | 68.859 | 85.369 | 60.148 | 1.00 | 13.93 |
| ATOM | 2866 | CG | PHE | 218 | 69.866 | 85.970 | 59.189 | 1.00 | 9.96 |
| ATOM | 2867 | CD1 | PHE | 218 | 70.964 | 85.227 | 58.793 | 1.00 | 12.23 |
| ATOM | 2868 | CD2 | PHE | 218 | 69.716 | 87.278 | 58.766 | 1.00 | 9.77 |
| ATOM | 2869 | CE1 | PHE | 218 | 71.926 | 85.802 | 57.975 | 1.00 | 12.84 |
| ATOM | 2870 | CE2 | PHE | 218 | 70.674 | 87.855 | 57.949 | 1.00 | 12.20 |
| ATOM | 2871 | CZ | PHE | 218 | 71.784 | 87.121 | 57.554 | 1.00 | 14.85 |

FIG. 1: A-49

| ATOM | 2872 | C | PHE | 218 | 66.887 | 83.916 | 60.492 | 1.00 | 19.17 |
|---|---|---|---|---|---|---|---|---|---|
| ATOM | 2873 | O | PHE | 218 | 66.811 | 84.300 | 61.667 | 1.00 | 20.65 |
| ATOM | 2874 | N | LYS | 219 | 66.170 | 82.921 | 60.020 | 1.00 | 17.04 |
| ATOM | 2875 | H | LYS | 219 | 66.299 | 82.576 | 59.111 | 1.00 | 0.00 |
| ATOM | 2876 | CA | LYS | 219 | 65.200 | 82.322 | 60.901 | 1.00 | 19.42 |
| ATOM | 2877 | CB | LYS | 219 | 63.938 | 83.254 | 61.107 | 1.00 | 21.35 |
| ATOM | 2878 | CG | LYS | 219 | 63.089 | 83.464 | 59.848 | 1.00 | 22.74 |
| ATOM | 2879 | CD | LYS | 219 | 61.862 | 84.260 | 60.092 | 1.00 | 23.37 |
| ATOM | 2880 | CE | LYS | 219 | 62.157 | 85.714 | 60.404 | 1.00 | 28.16 |
| ATOM | 2881 | NZ | LYS | 219 | 60.926 | 86.466 | 60.216 | 1.00 | 29.93 |
| ATOM | 2882 | HZ1 | LYS | 219 | 61.112 | 87.480 | 60.365 | 1.00 | 0.00 |
| ATOM | 2883 | HZ2 | LYS | 219 | 60.215 | 86.136 | 60.901 | 1.00 | 0.00 |
| ATOM | 2884 | HZ3 | LYS | 219 | 60.575 | 86.314 | 59.249 | 1.00 | 0.00 |
| ATOM | 2885 | C | LYS | 219 | 64.744 | 81.018 | 60.329 | 1.00 | 18.64 |
| ATOM | 2886 | O | LYS | 219 | 65.087 | 80.654 | 59.215 | 1.00 | 22.45 |
| ATOM | 2887 | N | GLU | 220 | 64.028 | 80.263 | 61.128 | 1.00 | 18.30 |
| ATOM | 2888 | H | GLU | 220 | 63.974 | 80.497 | 62.073 | 1.00 | 0.00 |
| ATOM | 2889 | CA | GLU | 220 | 63.300 | 79.146 | 60.610 | 1.00 | 19.04 |
| ATOM | 2890 | CB | GLU | 220 | 62.788 | 78.344 | 61.763 | 1.00 | 19.96 |
| ATOM | 2891 | CG | GLU | 220 | 61.744 | 77.280 | 61.423 | 1.00 | 18.40 |
| ATOM | 2892 | CD | GLU | 220 | 62.297 | 76.022 | 60.805 | 1.00 | 20.29 |
| ATOM | 2893 | OE1 | GLU | 220 | 61.500 | 75.241 | 60.320 | 1.00 | 25.99 |
| ATOM | 2894 | OE2 | GLU | 220 | 63.494 | 75.794 | 60.811 | 1.00 | 21.68 |
| ATOM | 2895 | C | GLU | 220 | 62.136 | 79.766 | 59.811 | 1.00 | 20.14 |
| ATOM | 2896 | O | GLU | 220 | 61.368 | 80.580 | 60.345 | 1.00 | 20.27 |
| ATOM | 2897 | N | PRO | 221 | 61.957 | 79.412 | 58.539 | 1.00 | 20.99 |
| ATOM | 2898 | CD | PRO | 221 | 62.788 | 78.452 | 57.816 | 1.00 | 19.93 |
| ATOM | 2899 | CA | PRO | 221 | 60.962 | 80.048 | 57.697 | 1.00 | 21.94 |
| ATOM | 2900 | CB | PRO | 221 | 61.192 | 79.392 | 56.330 | 1.00 | 20.46 |
| ATOM | 2901 | CG | PRO | 221 | 61.989 | 78.135 | 56.584 | 1.00 | 20.82 |
| ATOM | 2902 | C | PRO | 221 | 59.542 | 79.924 | 58.256 | 1.00 | 22.07 |
| ATOM | 2903 | O | PRO | 221 | 59.186 | 78.846 | 58.727 | 1.00 | 24.17 |
| ATOM | 2904 | N | PRO | 222 | 58.745 | 80.998 | 58.309 | 1.00 | 22.36 |
| ATOM | 2905 | CD | PRO | 222 | 59.140 | 82.339 | 57.886 | 1.00 | 25.33 |
| ATOM | 2906 | CA | PRO | 222 | 57.419 | 81.080 | 58.896 | 1.00 | 22.96 |
| ATOM | 2907 | CB | PRO | 222 | 57.068 | 82.511 | 58.841 | 1.00 | 23.67 |
| ATOM | 2908 | CG | PRO | 222 | 58.383 | 83.214 | 58.868 | 1.00 | 24.85 |
| ATOM | 2909 | C | PRO | 222 | 56.338 | 80.254 | 58.245 | 1.00 | 23.63 |
| ATOM | 2910 | O | PRO | 222 | 56.477 | 79.931 | 57.076 | 1.00 | 26.60 |
| ATOM | 2911 | N | ALA | 223 | 55.239 | 79.957 | 58.954 | 1.00 | 23.49 |
| ATOM | 2912 | H | ALA | 223 | 55.238 | 80.263 | 59.879 | 1.00 | 0.00 |
| ATOM | 2913 | CA | ALA | 223 | 54.113 | 79.132 | 58.478 | 1.00 | 21.16 |
| ATOM | 2914 | CB | ALA | 223 | 53.147 | 78.984 | 59.609 | 1.00 | 22.32 |
| ATOM | 2915 | C | ALA | 223 | 53.305 | 79.554 | 57.242 | 1.00 | 19.59 |
| ATOM | 2916 | O | ALA | 223 | 52.602 | 78.816 | 56.540 | 1.00 | 17.92 |
| ATOM | 2917 | N | TYR | 224 | 53.439 | 80.838 | 57.027 | 1.00 | 16.84 |
| ATOM | 2918 | H | TYR | 224 | 54.000 | 81.343 | 57.645 | 1.00 | 0.00 |
| ATOM | 2919 | CA | TYR | 224 | 52.861 | 81.513 | 55.906 | 1.00 | 16.25 |
| ATOM | 2920 | CB | TYR | 224 | 51.418 | 81.811 | 56.204 | 1.00 | 15.17 |
| ATOM | 2921 | CG | TYR | 224 | 51.213 | 82.733 | 57.369 | 1.00 | 15.59 |
| ATOM | 2922 | CD1 | TYR | 224 | 51.032 | 84.108 | 57.174 | 1.00 | 17.87 |
| ATOM | 2923 | CE1 | TYR | 224 | 50.772 | 84.939 | 58.277 | 1.00 | 20.45 |
| ATOM | 2924 | CD2 | TYR | 224 | 51.144 | 82.186 | 58.648 | 1.00 | 18.73 |
| ATOM | 2925 | CE2 | TYR | 224 | 50.875 | 83.000 | 59.746 | 1.00 | 17.17 |
| ATOM | 2926 | CZ | TYR | 224 | 50.687 | 84.365 | 59.551 | 1.00 | 20.74 |
| ATOM | 2927 | OH | TYR | 224 | 50.371 | 85.146 | 60.639 | 1.00 | 25.58 |
| ATOM | 2928 | HH | TYR | 224 | 50.405 | 84.611 | 61.437 | 1.00 | 0.00 |
| ATOM | 2929 | C | TYR | 224 | 53.625 | 82.818 | 55.635 | 1.00 | 16.81 |
| ATOM | 2930 | O | TYR | 224 | 54.351 | 83.286 | 56.521 | 1.00 | 20.36 |
| ATOM | 2931 | N | GLY | 225 | 53.595 | 83.443 | 54.464 | 1.00 | 15.83 |

FIG. 1: A-50

| | | | | | | | | | |
|---|---|---|---|---|---|---|---|---|---|
| ATOM | 2932 | H | GLY | 225 | 53.188 | 83.009 | 53.689 | 1.00 | 0.00 |
| ATOM | 2933 | CA | GLY | 225 | 54.177 | 84.767 | 54.381 | 1.00 | 17.69 |
| ATOM | 2934 | C | GLY | 225 | 55.260 | 84.898 | 53.370 | 1.00 | 19.05 |
| ATOM | 2935 | O | GLY | 225 | 55.576 | 83.868 | 52.757 | 1.00 | 20.79 |
| ATOM | 2936 | N | PRO | 226 | 55.838 | 86.092 | 53.148 | 1.00 | 20.18 |
| ATOM | 2937 | CD | PRO | 226 | 55.449 | 87.339 | 53.812 | 1.00 | 18.41 |
| ATOM | 2938 | CA | PRO | 226 | 56.791 | 86.347 | 52.041 | 1.00 | 21.78 |
| ATOM | 2939 | CB | PRO | 226 | 57.234 | 87.813 | 52.296 | 1.00 | 21.69 |
| ATOM | 2940 | CG | PRO | 226 | 56.672 | 88.249 | 53.643 | 1.00 | 19.30 |
| ATOM | 2941 | C | PRO | 226 | 57.939 | 85.335 | 51.876 | 1.00 | 23.13 |
| ATOM | 2942 | O | PRO | 226 | 58.060 | 84.726 | 50.813 | 1.00 | 26.97 |
| ATOM | 2943 | N | MET | 227 | 58.704 | 85.026 | 52.931 | 1.00 | 23.11 |
| ATOM | 2944 | H | MET | 227 | 58.602 | 85.615 | 53.706 | 1.00 | 0.00 |
| ATOM | 2945 | CA | MET | 227 | 59.742 | 83.966 | 52.984 | 1.00 | 21.70 |
| ATOM | 2946 | CB | MET | 227 | 60.527 | 84.058 | 54.301 | 1.00 | 23.84 |
| ATOM | 2947 | CG | MET | 227 | 61.365 | 82.882 | 54.788 | 1.00 | 24.76 |
| ATOM | 2948 | SD | MET | 227 | 62.278 | 83.431 | 56.225 | 1.00 | 25.43 |
| ATOM | 2949 | CE | MET | 227 | 63.668 | 82.354 | 56.244 | 1.00 | 20.64 |
| ATOM | 2950 | C | MET | 227 | 59.284 | 82.536 | 52.854 | 1.00 | 19.77 |
| ATOM | 2951 | O | MET | 227 | 59.972 | 81.697 | 52.302 | 1.00 | 22.81 |
| ATOM | 2952 | N | CYS | 228 | 58.164 | 82.176 | 53.436 | 1.00 | 22.07 |
| ATOM | 2953 | H | CYS | 228 | 57.701 | 82.830 | 53.995 | 1.00 | 0.00 |
| ATOM | 2954 | CA | CYS | 228 | 57.592 | 80.835 | 53.230 | 1.00 | 21.95 |
| ATOM | 2955 | CB | CYS | 228 | 56.257 | 80.703 | 53.936 | 1.00 | 18.38 |
| ATOM | 2956 | SG | CYS | 228 | 55.286 | 79.254 | 53.447 | 1.00 | 26.44 |
| ATOM | 2957 | C | CYS | 228 | 57.363 | 80.616 | 51.735 | 1.00 | 21.97 |
| ATOM | 2958 | O | CYS | 228 | 57.942 | 79.731 | 51.133 | 1.00 | 21.38 |
| ATOM | 2959 | N | ASP | 229 | 56.626 | 81.556 | 51.118 | 1.00 | 22.56 |
| ATOM | 2960 | H | ASP | 229 | 56.297 | 82.296 | 51.671 | 1.00 | 0.00 |
| ATOM | 2961 | CA | ASP | 229 | 56.301 | 81.570 | 49.699 | 1.00 | 21.23 |
| ATOM | 2962 | CB | ASP | 229 | 55.491 | 82.786 | 49.395 | 1.00 | 21.67 |
| ATOM | 2963 | CG | ASP | 229 | 54.105 | 82.742 | 49.986 | 1.00 | 20.15 |
| ATOM | 2964 | OD1 | ASP | 229 | 53.629 | 83.789 | 50.389 | 1.00 | 22.44 |
| ATOM | 2965 | OD2 | ASP | 229 | 53.482 | 81.681 | 50.001 | 1.00 | 20.39 |
| ATOM | 2966 | C | ASP | 229 | 57.429 | 81.516 | 48.693 | 1.00 | 21.86 |
| ATOM | 2967 | O | ASP | 229 | 57.386 | 80.608 | 47.872 | 1.00 | 24.61 |
| ATOM | 2968 | N | ILE | 230 | 58.423 | 82.426 | 48.710 | 1.00 | 20.37 |
| ATOM | 2969 | H | ILE | 230 | 58.290 | 83.204 | 49.294 | 1.00 | 0.00 |
| ATOM | 2970 | CA | ILE | 230 | 59.663 | 82.334 | 47.913 | 1.00 | 16.29 |
| ATOM | 2971 | CB | ILE | 230 | 60.637 | 83.300 | 48.576 | 1.00 | 15.52 |
| ATOM | 2972 | CG2 | ILE | 230 | 62.059 | 83.031 | 48.118 | 1.00 | 15.46 |
| ATOM | 2973 | CG1 | ILE | 230 | 60.186 | 84.733 | 48.283 | 1.00 | 15.25 |
| ATOM | 2974 | CD1 | ILE | 230 | 61.035 | 85.828 | 48.965 | 1.00 | 10.69 |
| ATOM | 2975 | C | ILE | 230 | 60.233 | 80.904 | 47.852 | 1.00 | 18.29 |
| ATOM | 2976 | O | ILE | 230 | 60.544 | 80.342 | 46.801 | 1.00 | 19.11 |
| ATOM | 2977 | N | LEU | 231 | 60.313 | 80.290 | 49.041 | 1.00 | 20.17 |
| ATOM | 2978 | H | LEU | 231 | 60.079 | 80.827 | 49.828 | 1.00 | 0.00 |
| ATOM | 2979 | CA | LEU | 231 | 60.752 | 78.923 | 49.291 | 1.00 | 20.25 |
| ATOM | 2980 | CB | LEU | 231 | 61.175 | 78.757 | 50.761 | 1.00 | 22.81 |
| ATOM | 2981 | CG | LEU | 231 | 62.633 | 78.852 | 51.251 | 1.00 | 22.63 |
| ATOM | 2982 | CD1 | LEU | 231 | 63.391 | 80.037 | 50.704 | 1.00 | 21.65 |
| ATOM | 2983 | CD2 | LEU | 231 | 62.569 | 79.011 | 52.740 | 1.00 | 22.41 |
| ATOM | 2984 | C | LEU | 231 | 59.742 | 77.824 | 48.994 | 1.00 | 21.07 |
| ATOM | 2985 | O | LEU | 231 | 60.116 | 76.693 | 48.582 | 1.00 | 18.28 |
| ATOM | 2986 | N | TRP | 232 | 58.451 | 78.172 | 49.188 | 1.00 | 20.41 |
| ATOM | 2987 | H | TRP | 232 | 58.254 | 79.100 | 49.418 | 1.00 | 0.00 |
| ATOM | 2988 | CA | TRP | 232 | 57.372 | 77.193 | 49.007 | 1.00 | 18.64 |
| ATOM | 2989 | CB | TRP | 232 | 56.488 | 77.151 | 50.216 | 1.00 | 14.75 |
| ATOM | 2990 | CG | TRP | 232 | 57.149 | 76.285 | 51.274 | 1.00 | 17.39 |
| ATOM | 2991 | CD2 | TRP | 232 | 57.028 | 74.918 | 51.439 | 1.00 | 14.02 |

FIG. 1: A-51

| ATOM | 2992 | CE2 | TRP | 232 | 57.804 | 74.719 | 52.599 | 1.00 | 16.39 |
|---|---|---|---|---|---|---|---|---|---|
| ATOM | 2993 | CE3 | TRP | 232 | 56.396 | 73.848 | 50.819 | 1.00 | 12.32 |
| ATOM | 2994 | CD1 | TRP | 232 | 57.945 | 76.869 | 52.227 | 1.00 | 14.98 |
| ATOM | 2995 | NE1 | TRP | 232 | 58.325 | 75.889 | 53.010 | 1.00 | 17.58 |
| ATOM | 2996 | HE1 | TRP | 232 | 58.926 | 76.031 | 53.766 | 1.00 | 0.00 |
| ATOM | 2997 | CZ2 | TRP | 232 | 57.959 | 73.461 | 53.177 | 1.00 | 14.24 |
| ATOM | 2998 | CZ3 | TRP | 232 | 56.528 | 72.583 | 51.370 | 1.00 | 13.99 |
| ATOM | 2999 | CH2 | TRP | 232 | 57.299 | 72.399 | 52.539 | 1.00 | 18.88 |
| ATOM | 3000 | C | TRP | 232 | 56.430 | 77.192 | 47.829 | 1.00 | 19.17 |
| ATOM | 3001 | O | TRP | 232 | 55.985 | 76.093 | 47.504 | 1.00 | 21.89 |
| ATOM | 3002 | N | SER | 233 | 56.150 | 78.272 | 47.101 | 1.00 | 18.92 |
| ATOM | 3003 | H | SER | 233 | 56.714 | 79.062 | 47.194 | 1.00 | 0.00 |
| ATOM | 3004 | CA | SER | 233 | 55.162 | 78.255 | 46.027 | 1.00 | 18.77 |
| ATOM | 3005 | CB | SER | 233 | 54.717 | 79.672 | 45.740 | 1.00 | 19.69 |
| ATOM | 3006 | OG | SER | 233 | 55.765 | 80.555 | 45.405 | 1.00 | 24.62 |
| ATOM | 3007 | HG | SER | 233 | 55.557 | 81.451 | 45.713 | 1.00 | 0.00 |
| ATOM | 3008 | C | SER | 233 | 55.515 | 77.590 | 44.700 | 1.00 | 19.16 |
| ATOM | 3009 | O | SER | 233 | 56.643 | 77.212 | 44.411 | 1.00 | 21.40 |
| ATOM | 3010 | N | ASP | 234 | 54.472 | 77.286 | 43.952 | 1.00 | 20.13 |
| ATOM | 3011 | H | ASP | 234 | 53.600 | 77.580 | 44.291 | 1.00 | 0.00 |
| ATOM | 3012 | CA | ASP | 234 | 54.480 | 76.546 | 42.696 | 1.00 | 19.55 |
| ATOM | 3013 | CB | ASP | 234 | 53.737 | 75.248 | 42.889 | 1.00 | 20.02 |
| ATOM | 3014 | CG | ASP | 234 | 54.322 | 74.201 | 43.810 | 1.00 | 20.48 |
| ATOM | 3015 | OD1 | ASP | 234 | 53.572 | 73.363 | 44.284 | 1.00 | 24.51 |
| ATOM | 3016 | OD2 | ASP | 234 | 55.522 | 74.173 | 44.030 | 1.00 | 23.75 |
| ATOM | 3017 | C | ASP | 234 | 53.829 | 77.259 | 41.506 | 1.00 | 19.55 |
| ATOM | 3018 | O | ASP | 234 | 52.907 | 78.029 | 41.771 | 1.00 | 19.77 |
| ATOM | 3019 | N | PRO | 235 | 54.102 | 77.068 | 40.202 | 1.00 | 20.02 |
| ATOM | 3020 | CD | PRO | 235 | 55.153 | 76.224 | 39.616 | 1.00 | 20.95 |
| ATOM | 3021 | CA | PRO | 235 | 53.194 | 77.461 | 39.141 | 1.00 | 20.69 |
| ATOM | 3022 | CB | PRO | 235 | 53.957 | 77.149 | 37.877 | 1.00 | 18.45 |
| ATOM | 3023 | CG | PRO | 235 | 54.661 | 75.867 | 38.203 | 1.00 | 16.82 |
| ATOM | 3024 | C | PRO | 235 | 51.895 | 76.666 | 39.286 | 1.00 | 23.36 |
| ATOM | 3025 | O | PRO | 235 | 51.807 | 75.609 | 39.931 | 1.00 | 24.60 |
| ATOM | 3026 | N | LEU | 236 | 50.814 | 77.199 | 38.766 | 1.00 | 24.06 |
| ATOM | 3027 | H | LEU | 236 | 50.866 | 78.129 | 38.463 | 1.00 | 0.00 |
| ATOM | 3028 | CA | LEU | 236 | 49.548 | 76.475 | 38.708 | 1.00 | 26.52 |
| ATOM | 3029 | CB | LEU | 236 | 48.614 | 77.499 | 38.148 | 1.00 | 26.34 |
| ATOM | 3030 | CG | LEU | 236 | 47.281 | 77.950 | 38.581 | 1.00 | 21.41 |
| ATOM | 3031 | CD1 | LEU | 236 | 47.148 | 78.407 | 39.983 | 1.00 | 22.30 |
| ATOM | 3032 | CD2 | LEU | 236 | 47.097 | 79.140 | 37.699 | 1.00 | 23.57 |
| ATOM | 3033 | C | LEU | 236 | 49.669 | 75.214 | 37.812 | 1.00 | 28.63 |
| ATOM | 3034 | O | LEU | 236 | 50.454 | 75.244 | 36.858 | 1.00 | 31.22 |
| ATOM | 3035 | N | GLU | 237 | 48.971 | 74.080 | 37.914 | 1.00 | 30.74 |
| ATOM | 3036 | H | GLU | 237 | 48.452 | 73.927 | 38.727 | 1.00 | 0.00 |
| ATOM | 3037 | CA | GLU | 237 | 49.136 | 73.008 | 36.914 | 1.00 | 31.80 |
| ATOM | 3038 | CB | GLU | 237 | 48.343 | 71.787 | 37.345 | 1.00 | 36.38 |
| ATOM | 3039 | CG | GLU | 237 | 48.996 | 70.445 | 36.936 | 1.00 | 41.40 |
| ATOM | 3040 | CD | GLU | 237 | 48.299 | 69.605 | 35.853 | 1.00 | 42.23 |
| ATOM | 3041 | OE1 | GLU | 237 | 48.970 | 69.170 | 34.905 | 1.00 | 42.11 |
| ATOM | 3042 | OE2 | GLU | 237 | 47.093 | 69.371 | 35.969 | 1.00 | 45.28 |
| ATOM | 3043 | C | GLU | 237 | 48.715 | 73.377 | 35.486 | 1.00 | 31.63 |
| ATOM | 3044 | O | GLU | 237 | 48.954 | 72.659 | 34.529 | 1.00 | 32.35 |
| ATOM | 3045 | N | ASP | 238 | 48.084 | 74.528 | 35.291 | 1.00 | 32.10 |
| ATOM | 3046 | H | ASP | 238 | 47.913 | 75.061 | 36.087 | 1.00 | 0.00 |
| ATOM | 3047 | CA | ASP | 238 | 47.634 | 75.035 | 33.981 | 1.00 | 33.78 |
| ATOM | 3048 | CB | ASP | 238 | 46.088 | 75.066 | 33.926 | 1.00 | 38.61 |
| ATOM | 3049 | CG | ASP | 238 | 45.396 | 75.691 | 35.170 | 1.00 | 42.03 |
| ATOM | 3050 | OD1 | ASP | 238 | 44.217 | 75.401 | 35.414 | 1.00 | 44.54 |
| ATOM | 3051 | OD2 | ASP | 238 | 46.022 | 76.443 | 35.921 | 1.00 | 41.53 |

FIG. 1: A-52

| | | | | | | | | |
|---|---|---|---|---|---|---|---|---|
| ATOM | 3052 | C | ASP | 238 | 48.176 | 76.448 | 33.769 | 1.00 | 32.06 |
| ATOM | 3053 | O | ASP | 238 | 47.462 | 77.438 | 33.712 | 1.00 | 34.74 |
| ATOM | 3054 | N | PHE | 239 | 49.470 | 76.653 | 33.754 | 1.00 | 29.17 |
| ATOM | 3055 | H | PHE | 239 | 50.048 | 75.876 | 33.897 | 1.00 | 0.00 |
| ATOM | 3056 | CA | PHE | 239 | 50.045 | 77.966 | 33.570 | 1.00 | 25.52 |
| ATOM | 3057 | CB | PHE | 239 | 51.527 | 77.713 | 33.934 | 1.00 | 24.42 |
| ATOM | 3058 | CG | PHE | 239 | 52.318 | 78.929 | 34.391 | 1.00 | 17.75 |
| ATOM | 3059 | CD1 | PHE | 239 | 53.109 | 79.642 | 33.494 | 1.00 | 16.12 |
| ATOM | 3060 | CD2 | PHE | 239 | 52.202 | 79.355 | 35.693 | 1.00 | 17.03 |
| ATOM | 3061 | CE1 | PHE | 239 | 53.770 | 80.789 | 33.896 | 1.00 | 11.92 |
| ATOM | 3062 | CE2 | PHE | 239 | 52.875 | 80.504 | 36.083 | 1.00 | 17.11 |
| ATOM | 3063 | CZ | PHE | 239 | 53.650 | 81.221 | 35.190 | 1.00 | 13.27 |
| ATOM | 3064 | C | PHE | 239 | 49.789 | 78.614 | 32.183 | 1.00 | 27.25 |
| ATOM | 3065 | O | PHE | 239 | 50.498 | 79.525 | 31.770 | 1.00 | 30.77 |
| ATOM | 3066 | N | GLY | 240 | 48.776 | 78.295 | 31.371 | 1.00 | 29.28 |
| ATOM | 3067 | H | GLY | 240 | 48.078 | 77.683 | 31.682 | 1.00 | 0.00 |
| ATOM | 3068 | CA | GLY | 240 | 48.531 | 78.884 | 30.050 | 1.00 | 25.43 |
| ATOM | 3069 | C | GLY | 240 | 47.652 | 77.916 | 29.250 | 1.00 | 28.36 |
| ATOM | 3070 | O | GLY | 240 | 46.711 | 77.285 | 29.772 | 1.00 | 28.72 |
| ATOM | 3071 | CB | HIS | 247 | 46.874 | 86.745 | 40.499 | 1.00 | 23.78 |
| ATOM | 3072 | CG | HIS | 247 | 47.488 | 87.811 | 39.579 | 1.00 | 26.72 |
| ATOM | 3073 | CD2 | HIS | 247 | 48.391 | 88.741 | 40.070 | 1.00 | 26.82 |
| ATOM | 3074 | ND1 | HIS | 247 | 47.287 | 88.174 | 38.292 | 1.00 | 27.63 |
| ATOM | 3075 | HD1 | HIS | 247 | 46.703 | 87.782 | 37.610 | 1.00 | 0.00 |
| ATOM | 3076 | CE1 | HIS | 247 | 48.005 | 89.252 | 38.017 | 1.00 | 26.96 |
| ATOM | 3077 | NE2 | HIS | 247 | 48.661 | 89.578 | 39.096 | 1.00 | 26.18 |
| ATOM | 3078 | HE2 | HIS | 247 | 49.292 | 90.330 | 39.148 | 1.00 | 0.00 |
| ATOM | 3079 | C | HIS | 247 | 47.588 | 84.374 | 41.031 | 1.00 | 27.00 |
| ATOM | 3080 | O | HIS | 247 | 48.406 | 83.588 | 40.593 | 1.00 | 27.40 |
| ATOM | 3081 | HT1 | HIS | 247 | 45.284 | 83.790 | 39.870 | 1.00 | 0.00 |
| ATOM | 3082 | HT2 | HIS | 247 | 44.643 | 85.276 | 39.581 | 1.00 | 0.00 |
| ATOM | 3083 | N | HIS | 247 | 45.362 | 84.792 | 40.159 | 1.00 | 24.65 |
| ATOM | 3084 | HT3 | HIS | 247 | 44.960 | 84.795 | 41.122 | 1.00 | 0.00 |
| ATOM | 3085 | CA | HIS | 247 | 46.757 | 85.263 | 40.069 | 1.00 | 26.62 |
| ATOM | 3086 | N | PHE | 248 | 47.372 | 84.471 | 42.350 | 1.00 | 28.59 |
| ATOM | 3087 | H | PHE | 248 | 46.791 | 85.168 | 42.717 | 1.00 | 0.00 |
| ATOM | 3088 | CA | PHE | 248 | 47.942 | 83.598 | 43.398 | 1.00 | 27.05 |
| ATOM | 3089 | CB | PHE | 248 | 48.534 | 84.359 | 44.580 | 1.00 | 24.03 |
| ATOM | 3090 | CG | PHE | 248 | 49.831 | 84.984 | 44.180 | 1.00 | 19.99 |
| ATOM | 3091 | CD1 | PHE | 248 | 50.926 | 84.152 | 43.972 | 1.00 | 20.39 |
| ATOM | 3092 | CD2 | PHE | 248 | 49.881 | 86.345 | 43.933 | 1.00 | 17.41 |
| ATOM | 3093 | CE1 | PHE | 248 | 52.095 | 84.717 | 43.488 | 1.00 | 19.09 |
| ATOM | 3094 | CE2 | PHE | 248 | 51.055 | 86.895 | 43.454 | 1.00 | 15.74 |
| ATOM | 3095 | CZ | PHE | 248 | 52.153 | 86.081 | 43.227 | 1.00 | 17.56 |
| ATOM | 3096 | C | PHE | 248 | 46.799 | 82.813 | 43.977 | 1.00 | 25.16 |
| ATOM | 3097 | O | PHE | 248 | 45.832 | 83.469 | 44.360 | 1.00 | 26.87 |
| ATOM | 3098 | N | THR | 249 | 46.789 | 81.508 | 43.969 | 1.00 | 23.77 |
| ATOM | 3099 | H | THR | 249 | 47.492 | 81.007 | 43.501 | 1.00 | 0.00 |
| ATOM | 3100 | CA | THR | 249 | 45.713 | 80.779 | 44.620 | 1.00 | 25.08 |
| ATOM | 3101 | CB | THR | 249 | 44.925 | 79.957 | 43.562 | 1.00 | 27.34 |
| ATOM | 3102 | OG1 | THR | 249 | 45.782 | 79.201 | 42.709 | 1.00 | 25.14 |
| ATOM | 3103 | HG1 | THR | 249 | 45.294 | 78.405 | 42.447 | 1.00 | 0.00 |
| ATOM | 3104 | CG2 | THR | 249 | 44.143 | 80.944 | 42.699 | 1.00 | 29.87 |
| ATOM | 3105 | C | THR | 249 | 46.243 | 79.879 | 45.719 | 1.00 | 23.78 |
| ATOM | 3106 | O | THR | 249 | 47.426 | 79.605 | 45.737 | 1.00 | 24.19 |
| ATOM | 3107 | N | HIS | 250 | 45.541 | 79.370 | 46.720 | 1.00 | 25.04 |
| ATOM | 3108 | H | HIS | 250 | 44.578 | 79.535 | 46.722 | 1.00 | 0.00 |
| ATOM | 3109 | CA | HIS | 250 | 46.171 | 78.551 | 47.747 | 1.00 | 24.41 |
| ATOM | 3110 | CB | HIS | 250 | 45.232 | 78.201 | 48.940 | 1.00 | 25.37 |
| ATOM | 3111 | CG | HIS | 250 | 45.964 | 77.522 | 50.121 | 1.00 | 27.67 |

FIG. 1: A-53

| ATOM | 3112 | CD2 | HIS | 250 | 46.894 | 78.166 | 50.939 | 1.00 | 26.48 |
|---|---|---|---|---|---|---|---|---|---|
| ATOM | 3113 | ND1 | HIS | 250 | 45.886 | 76.240 | 50.545 | 1.00 | 27.34 |
| ATOM | 3114 | HD1 | HIS | 250 | 45.389 | 75.501 | 50.129 | 1.00 | 0.00 |
| ATOM | 3115 | CE1 | HIS | 250 | 46.715 | 76.085 | 51.562 | 1.00 | 26.37 |
| ATOM | 3116 | NE2 | HIS | 250 | 47.306 | 77.242 | 51.781 | 1.00 | 27.51 |
| ATOM | 3117 | HE2 | HIS | 250 | 47.921 | 77.406 | 52.523 | 1.00 | 0.00 |
| ATOM | 3118 | C | HIS | 250 | 46.678 | 77.233 | 47.202 | 1.00 | 24.13 |
| ATOM | 3119 | O | HIS | 250 | 46.002 | 76.468 | 46.540 | 1.00 | 22.54 |
| ATOM | 3120 | N | ASN | 251 | 47.925 | 76.980 | 47.530 | 1.00 | 25.29 |
| ATOM | 3121 | H | ASN | 251 | 48.455 | 77.695 | 47.929 | 1.00 | 0.00 |
| ATOM | 3122 | CA | ASN | 251 | 48.542 | 75.735 | 47.178 | 1.00 | 26.17 |
| ATOM | 3123 | CB | ASN | 251 | 50.041 | 75.857 | 47.335 | 1.00 | 23.97 |
| ATOM | 3124 | CG | ASN | 251 | 50.773 | 74.746 | 46.628 | 1.00 | 22.83 |
| ATOM | 3125 | OD1 | ASN | 251 | 50.526 | 73.556 | 46.801 | 1.00 | 17.87 |
| ATOM | 3126 | ND2 | ASN | 251 | 51.682 | 75.066 | 45.750 | 1.00 | 23.87 |
| ATOM | 3127 | HD21 | ASN | 251 | 51.894 | 76.003 | 45.590 | 1.00 | 0.00 |
| ATOM | 3128 | HD22 | ASN | 251 | 52.080 | 74.297 | 45.309 | 1.00 | 0.00 |
| ATOM | 3129 | C | ASN | 251 | 48.016 | 74.582 | 48.018 | 1.00 | 25.42 |
| ATOM | 3130 | O | ASN | 251 | 48.349 | 74.307 | 49.169 | 1.00 | 27.72 |
| ATOM | 3131 | N | THR | 252 | 47.067 | 73.934 | 47.396 | 1.00 | 27.21 |
| ATOM | 3132 | H | THR | 252 | 46.701 | 74.333 | 46.575 | 1.00 | 0.00 |
| ATOM | 3133 | CA | THR | 252 | 46.510 | 72.734 | 47.974 | 1.00 | 27.44 |
| ATOM | 3134 | CB | THR | 252 | 45.182 | 72.406 | 47.249 | 1.00 | 28.93 |
| ATOM | 3135 | OG1 | THR | 252 | 44.575 | 71.305 | 47.915 | 1.00 | 32.62 |
| ATOM | 3136 | HG1 | THR | 252 | 45.237 | 70.635 | 48.156 | 1.00 | 0.00 |
| ATOM | 3137 | CG2 | THR | 252 | 45.407 | 72.054 | 45.772 | 1.00 | 32.23 |
| ATOM | 3138 | C | THR | 252 | 47.517 | 71.591 | 47.863 | 1.00 | 26.38 |
| ATOM | 3139 | O | THR | 252 | 47.338 | 70.661 | 48.623 | 1.00 | 28.38 |
| ATOM | 3140 | N | VAL | 253 | 48.564 | 71.538 | 47.022 | 1.00 | 23.72 |
| ATOM | 3141 | H | VAL | 253 | 48.763 | 72.310 | 46.458 | 1.00 | 0.00 |
| ATOM | 3142 | CA | VAL | 253 | 49.501 | 70.402 | 47.022 | 1.00 | 23.99 |
| ATOM | 3143 | CB | VAL | 253 | 50.427 | 70.441 | 45.755 | 1.00 | 23.79 |
| ATOM | 3144 | CG1 | VAL | 253 | 51.588 | 69.463 | 45.892 | 1.00 | 19.76 |
| ATOM | 3145 | CG2 | VAL | 253 | 49.652 | 69.997 | 44.530 | 1.00 | 20.79 |
| ATOM | 3146 | C | VAL | 253 | 50.395 | 70.379 | 48.279 | 1.00 | 26.73 |
| ATOM | 3147 | O | VAL | 253 | 50.445 | 69.410 | 49.036 | 1.00 | 27.90 |
| ATOM | 3148 | N | ARG | 254 | 51.152 | 71.469 | 48.450 | 1.00 | 26.41 |
| ATOM | 3149 | H | ARG | 254 | 51.151 | 72.104 | 47.718 | 1.00 | 0.00 |
| ATOM | 3150 | CA | ARG | 254 | 52.013 | 71.761 | 49.578 | 1.00 | 25.68 |
| ATOM | 3151 | CB | ARG | 254 | 52.667 | 73.088 | 49.354 | 1.00 | 26.71 |
| ATOM | 3152 | CG | ARG | 254 | 53.497 | 73.266 | 48.119 | 1.00 | 27.49 |
| ATOM | 3153 | CD | ARG | 254 | 54.678 | 72.349 | 48.147 | 1.00 | 25.03 |
| ATOM | 3154 | NE | ARG | 254 | 55.338 | 72.428 | 46.874 | 1.00 | 21.74 |
| ATOM | 3155 | HE | ARG | 254 | 55.150 | 73.178 | 46.271 | 1.00 | 0.00 |
| ATOM | 3156 | CZ | ARG | 254 | 56.209 | 71.503 | 46.510 | 1.00 | 20.78 |
| ATOM | 3157 | NH1 | ARG | 254 | 56.755 | 71.620 | 45.295 | 1.00 | 18.66 |
| ATOM | 3158 | HH11 | ARG | 254 | 57.416 | 70.938 | 44.983 | 1.00 | 0.00 |
| ATOM | 3159 | HH12 | ARG | 254 | 56.506 | 72.385 | 44.700 | 1.00 | 0.00 |
| ATOM | 3160 | NH2 | ARG | 254 | 56.581 | 70.546 | 47.369 | 1.00 | 17.46 |
| ATOM | 3161 | HH21 | ARG | 254 | 56.203 | 70.517 | 48.294 | 1.00 | 0.00 |
| ATOM | 3162 | HH22 | ARG | 254 | 57.231 | 69.846 | 47.080 | 1.00 | 0.00 |
| ATOM | 3163 | C | ARG | 254 | 51.402 | 71.824 | 50.996 | 1.00 | 27.61 |
| ATOM | 3164 | O | ARG | 254 | 52.120 | 71.852 | 52.016 | 1.00 | 26.41 |
| ATOM | 3165 | N | GLY | 255 | 50.066 | 72.003 | 51.077 | 1.00 | 28.13 |
| ATOM | 3166 | H | GLY | 255 | 49.553 | 71.892 | 50.253 | 1.00 | 0.00 |
| ATOM | 3167 | CA | GLY | 255 | 49.386 | 72.232 | 52.358 | 1.00 | 29.13 |
| ATOM | 3168 | C | GLY | 255 | 49.709 | 73.615 | 52.965 | 1.00 | 30.08 |
| ATOM | 3169 | O | GLY | 255 | 49.234 | 74.021 | 54.011 | 1.00 | 31.93 |
| ATOM | 3170 | N | CYS | 256 | 50.550 | 74.399 | 52.319 | 1.00 | 31.22 |
| ATOM | 3171 | H | CYS | 256 | 51.120 | 73.968 | 51.656 | 1.00 | 0.00 |

FIG. 1: A-54

| ATOM | 3172 | CA | CYS | 256 | 50.912 | 75.770 | 52.656 | 1.00 | 28.71 |
|---|---|---|---|---|---|---|---|---|---|
| ATOM | 3173 | CB | CYS | 256 | 52.190 | 75.857 | 53.461 | 1.00 | 31.75 |
| ATOM | 3174 | SG | CYS | 256 | 53.555 | 74.911 | 52.727 | 1.00 | 26.89 |
| ATOM | 3175 | C | CYS | 256 | 51.196 | 76.485 | 51.345 | 1.00 | 27.09 |
| ATOM | 3176 | O | CYS | 256 | 51.315 | 75.891 | 50.279 | 1.00 | 24.12 |
| ATOM | 3177 | N | SER | 257 | 51.298 | 77.797 | 51.421 | 1.00 | 26.20 |
| ATOM | 3178 | H | SER | 257 | 51.220 | 78.204 | 52.307 | 1.00 | 0.00 |
| ATOM | 3179 | CA | SER | 257 | 51.603 | 78.655 | 50.279 | 1.00 | 24.26 |
| ATOM | 3180 | CB | SER | 257 | 52.973 | 78.281 | 49.693 | 1.00 | 25.54 |
| ATOM | 3181 | OG | SER | 257 | 53.496 | 79.326 | 48.892 | 1.00 | 20.80 |
| ATOM | 3182 | HG | SER | 257 | 54.404 | 79.092 | 48.658 | 1.00 | 0.00 |
| ATOM | 3183 | C | SER | 257 | 50.594 | 78.716 | 49.140 | 1.00 | 23.11 |
| ATOM | 3184 | O | SER | 257 | 49.402 | 78.437 | 49.364 | 1.00 | 20.03 |
| ATOM | 3185 | N | TYR | 258 | 51.087 | 79.230 | 47.994 | 1.00 | 21.07 |
| ATOM | 3186 | H | TYR | 258 | 51.968 | 79.635 | 48.013 | 1.00 | 0.00 |
| ATOM | 3187 | CA | TYR | 258 | 50.413 | 79.425 | 46.742 | 1.00 | 20.45 |
| ATOM | 3188 | CB | TYR | 258 | 50.534 | 80.898 | 46.378 | 1.00 | 23.00 |
| ATOM | 3189 | CG | TYR | 258 | 49.841 | 81.721 | 47.445 | 1.00 | 26.87 |
| ATOM | 3190 | CD1 | TYR | 258 | 50.546 | 82.189 | 48.554 | 1.00 | 26.62 |
| ATOM | 3191 | CE1 | TYR | 258 | 49.851 | 82.834 | 49.572 | 1.00 | 26.92 |
| ATOM | 3192 | CD2 | TYR | 258 | 48.459 | 81.916 | 47.361 | 1.00 | 28.03 |
| ATOM | 3193 | CE2 | TYR | 258 | 47.765 | 82.556 | 48.360 | 1.00 | 23.37 |
| ATOM | 3194 | CZ | TYR | 258 | 48.475 | 83.004 | 49.446 | 1.00 | 26.49 |
| ATOM | 3195 | OH | TYR | 258 | 47.793 | 83.694 | 50.413 | 1.00 | 32.47 |
| ATOM | 3196 | HH | TYR | 258 | 46.893 | 83.869 | 50.122 | 1.00 | 0.00 |
| ATOM | 3197 | C | TYR | 258 | 50.856 | 78.580 | 45.554 | 1.00 | 20.26 |
| ATOM | 3198 | O | TYR | 258 | 51.851 | 77.868 | 45.570 | 1.00 | 20.06 |
| ATOM | 3199 | N | PHE | 259 | 49.929 | 78.586 | 44.610 | 1.00 | 20.62 |
| ATOM | 3200 | H | PHE | 259 | 49.055 | 78.955 | 44.868 | 1.00 | 0.00 |
| ATOM | 3201 | CA | PHE | 259 | 50.040 | 78.147 | 43.232 | 1.00 | 21.61 |
| ATOM | 3202 | CB | PHE | 259 | 48.835 | 77.361 | 42.749 | 1.00 | 18.22 |
| ATOM | 3203 | CG | PHE | 259 | 48.772 | 75.886 | 43.087 | 1.00 | 15.28 |
| ATOM | 3204 | CD1 | PHE | 259 | 49.818 | 75.038 | 42.724 | 1.00 | 15.43 |
| ATOM | 3205 | CD2 | PHE | 259 | 47.660 | 75.392 | 43.746 | 1.00 | 11.29 |
| ATOM | 3206 | CE1 | PHE | 259 | 49.735 | 73.680 | 43.029 | 1.00 | 16.32 |
| ATOM | 3207 | CE2 | PHE | 259 | 47.587 | 74.045 | 44.040 | 1.00 | 11.44 |
| ATOM | 3208 | CZ | PHE | 259 | 48.614 | 73.184 | 43.687 | 1.00 | 15.70 |
| ATOM | 3209 | C | PHE | 259 | 49.987 | 79.470 | 42.481 | 1.00 | 24.53 |
| ATOM | 3210 | O | PHE | 259 | 49.055 | 80.238 | 42.749 | 1.00 | 29.71 |
| ATOM | 3211 | N | TYR | 260 | 50.884 | 79.903 | 41.607 | 1.00 | 27.18 |
| ATOM | 3212 | H | TYR | 260 | 51.671 | 79.357 | 41.443 | 1.00 | 0.00 |
| ATOM | 3213 | CA | TYR | 260 | 50.694 | 81.183 | 40.887 | 1.00 | 29.95 |
| ATOM | 3214 | CB | TYR | 260 | 51.893 | 82.145 | 41.190 | 1.00 | 30.03 |
| ATOM | 3215 | CG | TYR | 260 | 53.288 | 81.520 | 41.056 | 1.00 | 31.93 |
| ATOM | 3216 | CD1 | TYR | 260 | 53.842 | 81.377 | 39.782 | 1.00 | 30.21 |
| ATOM | 3217 | CE1 | TYR | 260 | 55.078 | 80.774 | 39.621 | 1.00 | 33.46 |
| ATOM | 3218 | CD2 | TYR | 260 | 53.976 | 81.057 | 42.184 | 1.00 | 30.07 |
| ATOM | 3219 | CE2 | TYR | 260 | 55.215 | 80.443 | 42.019 | 1.00 | 31.96 |
| ATOM | 3220 | CZ | TYR | 260 | 55.772 | 80.304 | 40.734 | 1.00 | 34.07 |
| ATOM | 3221 | OH | TYR | 260 | 57.025 | 79.729 | 40.517 | 1.00 | 31.76 |
| ATOM | 3222 | HH | TYR | 260 | 57.424 | 79.405 | 41.343 | 1.00 | 0.00 |
| ATOM | 3223 | C | TYR | 260 | 50.494 | 81.026 | 39.359 | 1.00 | 32.49 |
| ATOM | 3224 | O | TYR | 260 | 50.893 | 80.026 | 38.713 | 1.00 | 33.88 |
| ATOM | 3225 | N | SER | 261 | 49.863 | 82.039 | 38.747 | 1.00 | 32.05 |
| ATOM | 3226 | H | SER | 261 | 49.666 | 82.823 | 39.296 | 1.00 | 0.00 |
| ATOM | 3227 | CA | SER | 261 | 49.474 | 81.992 | 37.335 | 1.00 | 27.70 |
| ATOM | 3228 | CB | SER | 261 | 48.102 | 82.610 | 37.142 | 1.00 | 27.77 |
| ATOM | 3229 | OG | SER | 261 | 47.971 | 84.054 | 37.229 | 1.00 | 24.36 |
| ATOM | 3230 | HG | SER | 261 | 47.335 | 84.218 | 36.521 | 1.00 | 0.00 |
| ATOM | 3231 | C | SER | 261 | 50.394 | 82.686 | 36.361 | 1.00 | 27.85 |

FIG. 1: A-55

| ATOM | 3232 | O | SER | 261 | 51.272 | 83.440 | 36.774 | 1.00 | 27.95 |
| --- | --- | --- | --- | --- | --- | --- | --- | --- | --- |
| ATOM | 3233 | N | TYR | 262 | 50.202 | 82.489 | 35.047 | 1.00 | 28.67 |
| ATOM | 3234 | H | TYR | 262 | 49.577 | 81.783 | 34.773 | 1.00 | 0.00 |
| ATOM | 3235 | CA | TYR | 262 | 50.957 | 83.199 | 34.030 | 1.00 | 27.65 |
| ATOM | 3236 | CB | TYR | 262 | 50.671 | 82.537 | 32.702 | 1.00 | 27.21 |
| ATOM | 3237 | CG | TYR | 262 | 51.203 | 83.219 | 31.452 | 1.00 | 29.56 |
| ATOM | 3238 | CD1 | TYR | 262 | 52.566 | 83.342 | 31.193 | 1.00 | 30.15 |
| ATOM | 3239 | CE1 | TYR | 262 | 52.997 | 83.992 | 30.042 | 1.00 | 31.58 |
| ATOM | 3240 | CD2 | TYR | 262 | 50.277 | 83.738 | 30.560 | 1.00 | 30.20 |
| ATOM | 3241 | CE2 | TYR | 262 | 50.707 | 84.391 | 29.414 | 1.00 | 31.66 |
| ATOM | 3242 | CZ | TYR | 262 | 52.058 | 84.523 | 29.155 | 1.00 | 33.65 |
| ATOM | 3243 | OH | TYR | 262 | 52.430 | 85.238 | 28.017 | 1.00 | 37.67 |
| ATOM | 3244 | HH | TYR | 262 | 53.358 | 85.056 | 27.809 | 1.00 | 0.00 |
| ATOM | 3245 | C | TYR | 262 | 50.598 | 84.676 | 34.030 | 1.00 | 29.66 |
| ATOM | 3246 | O | TYR | 262 | 51.540 | 85.473 | 34.002 | 1.00 | 33.39 |
| ATOM | 3247 | N | PRO | 263 | 49.338 | 85.154 | 34.168 | 1.00 | 29.59 |
| ATOM | 3248 | CD | PRO | 263 | 48.104 | 84.466 | 33.770 | 1.00 | 28.28 |
| ATOM | 3249 | CA | PRO | 263 | 49.028 | 86.485 | 34.699 | 1.00 | 28.70 |
| ATOM | 3250 | CB | PRO | 263 | 47.575 | 86.419 | 35.038 | 1.00 | 28.27 |
| ATOM | 3251 | CG | PRO | 263 | 47.027 | 85.508 | 33.953 | 1.00 | 29.80 |
| ATOM | 3252 | C | PRO | 263 | 49.854 | 86.935 | 35.894 | 1.00 | 30.47 |
| ATOM | 3253 | O | PRO | 263 | 50.193 | 88.109 | 35.975 | 1.00 | 33.15 |
| ATOM | 3254 | N | ALA | 264 | 50.170 | 86.113 | 36.907 | 1.00 | 31.52 |
| ATOM | 3255 | H | ALA | 264 | 49.891 | 85.173 | 36.880 | 1.00 | 0.00 |
| ATOM | 3256 | CA | ALA | 264 | 51.037 | 86.569 | 37.995 | 1.00 | 29.68 |
| ATOM | 3257 | CB | ALA | 264 | 51.114 | 85.594 | 39.159 | 1.00 | 29.65 |
| ATOM | 3258 | C | ALA | 264 | 52.469 | 86.766 | 37.524 | 1.00 | 29.91 |
| ATOM | 3259 | O | ALA | 264 | 52.919 | 87.927 | 37.574 | 1.00 | 28.83 |
| ATOM | 3260 | N | VAL | 265 | 53.186 | 85.749 | 36.986 | 1.00 | 27.83 |
| ATOM | 3261 | H | VAL | 265 | 52.774 | 84.869 | 36.852 | 1.00 | 0.00 |
| ATOM | 3262 | CA | VAL | 265 | 54.586 | 86.033 | 36.666 | 1.00 | 26.54 |
| ATOM | 3263 | CB | VAL | 265 | 55.458 | 84.789 | 36.229 | 1.00 | 24.65 |
| ATOM | 3264 | CG1 | VAL | 265 | 55.113 | 83.668 | 37.156 | 1.00 | 26.80 |
| ATOM | 3265 | CG2 | VAL | 265 | 55.210 | 84.285 | 34.861 | 1.00 | 28.18 |
| ATOM | 3266 | C | VAL | 265 | 54.672 | 87.084 | 35.575 | 1.00 | 26.85 |
| ATOM | 3267 | O | VAL | 265 | 55.445 | 88.027 | 35.769 | 1.00 | 27.45 |
| ATOM | 3268 | N | CYS | 266 | 53.837 | 87.128 | 34.523 | 1.00 | 26.17 |
| ATOM | 3269 | H | CYS | 266 | 53.158 | 86.432 | 34.426 | 1.00 | 0.00 |
| ATOM | 3270 | CA | CYS | 266 | 53.991 | 88.205 | 33.536 | 1.00 | 24.92 |
| ATOM | 3271 | CB | CYS | 266 | 53.042 | 87.929 | 32.323 | 1.00 | 24.54 |
| ATOM | 3272 | SG | CYS | 266 | 53.871 | 87.357 | 30.790 | 1.00 | 27.09 |
| ATOM | 3273 | C | CYS | 266 | 53.753 | 89.587 | 34.175 | 1.00 | 23.76 |
| ATOM | 3274 | O | CYS | 266 | 54.407 | 90.553 | 33.806 | 1.00 | 26.29 |
| ATOM | 3275 | N | GLU | 267 | 52.975 | 89.740 | 35.242 | 1.00 | 23.60 |
| ATOM | 3276 | H | GLU | 267 | 52.442 | 88.968 | 35.525 | 1.00 | 0.00 |
| ATOM | 3277 | CA | GLU | 267 | 52.849 | 91.000 | 36.002 | 1.00 | 25.10 |
| ATOM | 3278 | CB | GLU | 267 | 51.648 | 90.892 | 36.943 | 1.00 | 27.58 |
| ATOM | 3279 | CG | GLU | 267 | 51.425 | 91.990 | 37.980 | 1.00 | 32.71 |
| ATOM | 3280 | CD | GLU | 267 | 51.514 | 93.403 | 37.422 | 1.00 | 36.74 |
| ATOM | 3281 | OE1 | GLU | 267 | 52.377 | 94.187 | 37.845 | 1.00 | 38.60 |
| ATOM | 3282 | OE2 | GLU | 267 | 50.720 | 93.713 | 36.544 | 1.00 | 40.70 |
| ATOM | 3283 | C | GLU | 267 | 54.090 | 91.374 | 36.830 | 1.00 | 26.56 |
| ATOM | 3284 | O | GLU | 267 | 54.514 | 92.538 | 36.909 | 1.00 | 27.89 |
| ATOM | 3285 | N | PHE | 268 | 54.703 | 90.380 | 37.478 | 1.00 | 26.49 |
| ATOM | 3286 | H | PHE | 268 | 54.265 | 89.502 | 37.429 | 1.00 | 0.00 |
| ATOM | 3287 | CA | PHE | 268 | 55.959 | 90.522 | 38.224 | 1.00 | 24.12 |
| ATOM | 3288 | CB | PHE | 268 | 56.437 | 89.184 | 38.850 | 1.00 | 24.61 |
| ATOM | 3289 | CG | PHE | 268 | 57.564 | 89.378 | 39.851 | 1.00 | 21.69 |
| ATOM | 3290 | CD1 | PHE | 268 | 57.249 | 89.900 | 41.111 | 1.00 | 19.96 |
| ATOM | 3291 | CD2 | PHE | 268 | 58.890 | 89.153 | 39.480 | 1.00 | 20.60 |

FIG. 1: A-56

| | | | | | | | | |
|---|---|---|---|---|---|---|---|---|
| ATOM | 3292 | CE1 | PHE | 268 | 58.263 | 90.228 | 41.998 | 1.00 | 17.34 |
| ATOM | 3293 | CE2 | PHE | 268 | 59.893 | 89.489 | 40.390 | 1.00 | 23.36 |
| ATOM | 3294 | CZ | PHE | 268 | 59.583 | 90.032 | 41.639 | 1.00 | 19.55 |
| ATOM | 3295 | C | PHE | 268 | 57.053 | 90.973 | 37.287 | 1.00 | 24.28 |
| ATOM | 3296 | O | PHE | 268 | 57.746 | 91.957 | 37.544 | 1.00 | 25.43 |
| ATOM | 3297 | N | LEU | 269 | 57.161 | 90.230 | 36.180 | 1.00 | 25.16 |
| ATOM | 3298 | H | LEU | 269 | 56.546 | 89.474 | 36.111 | 1.00 | 0.00 |
| ATOM | 3299 | CA | LEU | 269 | 58.124 | 90.446 | 35.090 | 1.00 | 26.95 |
| ATOM | 3300 | CB | LEU | 269 | 57.924 | 89.332 | 34.041 | 1.00 | 23.08 |
| ATOM | 3301 | CG | LEU | 269 | 58.282 | 87.949 | 34.559 | 1.00 | 17.37 |
| ATOM | 3302 | CD1 | LEU | 269 | 58.168 | 86.883 | 33.484 | 1.00 | 18.64 |
| ATOM | 3303 | CD2 | LEU | 269 | 59.726 | 87.997 | 35.034 | 1.00 | 19.21 |
| ATOM | 3304 | C | LEU | 269 | 58.035 | 91.833 | 34.431 | 1.00 | 30.69 |
| ATOM | 3305 | O | LEU | 269 | 59.029 | 92.576 | 34.400 | 1.00 | 33.53 |
| ATOM | 3306 | N | GLN | 270 | 56.846 | 92.272 | 33.985 | 1.00 | 30.63 |
| ATOM | 3307 | H | GLN | 270 | 56.099 | 91.634 | 33.952 | 1.00 | 0.00 |
| ATOM | 3308 | CA | GLN | 270 | 56.684 | 93.640 | 33.492 | 1.00 | 30.29 |
| ATOM | 3309 | CB | GLN | 270 | 55.298 | 93.833 | 32.904 | 1.00 | 32.88 |
| ATOM | 3310 | CG | GLN | 270 | 55.184 | 92.796 | 31.785 | 1.00 | 37.43 |
| ATOM | 3311 | CD | GLN | 270 | 53.952 | 92.783 | 30.912 | 1.00 | 36.41 |
| ATOM | 3312 | OE1 | GLN | 270 | 52.829 | 92.922 | 31.360 | 1.00 | 37.69 |
| ATOM | 3313 | NE2 | GLN | 270 | 54.106 | 92.587 | 29.622 | 1.00 | 37.81 |
| ATOM | 3314 | HE21 | GLN | 270 | 55.005 | 92.422 | 29.278 | 1.00 | 0.00 |
| ATOM | 3315 | HE22 | GLN | 270 | 53.273 | 92.581 | 29.123 | 1.00 | 0.00 |
| ATOM | 3316 | C | GLN | 270 | 56.893 | 94.642 | 34.618 | 1.00 | 29.71 |
| ATOM | 3317 | O | GLN | 270 | 57.685 | 95.568 | 34.465 | 1.00 | 28.91 |
| ATOM | 3318 | N | HIS | 271 | 56.330 | 94.445 | 35.817 | 1.00 | 28.81 |
| ATOM | 3319 | H | HIS | 271 | 55.769 | 93.649 | 35.940 | 1.00 | 0.00 |
| ATOM | 3320 | CA | HIS | 271 | 56.524 | 95.420 | 36.886 | 1.00 | 28.70 |
| ATOM | 3321 | CB | HIS | 271 | 55.679 | 95.063 | 38.070 | 1.00 | 30.20 |
| ATOM | 3322 | CG | HIS | 271 | 55.546 | 96.214 | 39.057 | 1.00 | 32.78 |
| ATOM | 3323 | CD2 | HIS | 271 | 56.433 | 96.536 | 40.062 | 1.00 | 33.83 |
| ATOM | 3324 | ND1 | HIS | 271 | 54.565 | 97.102 | 39.098 | 1.00 | 34.76 |
| ATOM | 3325 | HD1 | HIS | 271 | 53.777 | 97.138 | 38.516 | 1.00 | 0.00 |
| ATOM | 3326 | CE1 | HIS | 271 | 54.825 | 97.940 | 40.073 | 1.00 | 35.78 |
| ATOM | 3327 | NE2 | HIS | 271 | 55.948 | 97.595 | 40.645 | 1.00 | 33.48 |
| ATOM | 3328 | HE2 | HIS | 271 | 56.380 | 98.072 | 41.382 | 1.00 | 0.00 |
| ATOM | 3329 | C | HIS | 271 | 57.947 | 95.638 | 37.409 | 1.00 | 28.94 |
| ATOM | 3330 | O | HIS | 271 | 58.319 | 96.699 | 37.925 | 1.00 | 28.66 |
| ATOM | 3331 | N | ASN | 272 | 58.727 | 94.575 | 37.392 | 1.00 | 30.67 |
| ATOM | 3332 | H | ASN | 272 | 58.367 | 93.725 | 37.070 | 1.00 | 0.00 |
| ATOM | 3333 | CA | ASN | 272 | 60.098 | 94.685 | 37.844 | 1.00 | 29.80 |
| ATOM | 3334 | CB | ASN | 272 | 60.296 | 93.476 | 38.707 | 1.00 | 29.16 |
| ATOM | 3335 | CG | ASN | 272 | 59.481 | 93.663 | 39.990 | 1.00 | 29.43 |
| ATOM | 3336 | OD1 | ASN | 272 | 59.870 | 94.372 | 40.913 | 1.00 | 27.49 |
| ATOM | 3337 | ND2 | ASN | 272 | 58.308 | 93.094 | 40.164 | 1.00 | 26.58 |
| ATOM | 3338 | HD21 | ASN | 272 | 57.954 | 92.534 | 39.450 | 1.00 | 0.00 |
| ATOM | 3339 | HD22 | ASN | 272 | 57.879 | 93.288 | 41.023 | 1.00 | 0.00 |
| ATOM | 3340 | C | ASN | 272 | 61.148 | 94.841 | 36.729 | 1.00 | 29.95 |
| ATOM | 3341 | O | ASN | 272 | 62.320 | 95.072 | 37.012 | 1.00 | 30.29 |
| ATOM | 3342 | N | ASN | 273 | 60.696 | 94.821 | 35.456 | 1.00 | 28.09 |
| ATOM | 3343 | H | ASN | 273 | 59.726 | 94.794 | 35.332 | 1.00 | 0.00 |
| ATOM | 3344 | CA | ASN | 273 | 61.509 | 94.928 | 34.248 | 1.00 | 27.15 |
| ATOM | 3345 | CB | ASN | 273 | 62.210 | 96.314 | 34.191 | 1.00 | 29.71 |
| ATOM | 3346 | CG | ASN | 273 | 63.067 | 96.607 | 32.956 | 1.00 | 31.42 |
| ATOM | 3347 | OD1 | ASN | 273 | 62.682 | 96.337 | 31.822 | 1.00 | 31.34 |
| ATOM | 3348 | ND2 | ASN | 273 | 64.269 | 97.163 | 33.050 | 1.00 | 29.17 |
| ATOM | 3349 | HD21 | ASN | 273 | 64.643 | 97.366 | 33.925 | 1.00 | 0.00 |
| ATOM | 3350 | HD22 | ASN | 273 | 64.694 | 97.288 | 32.182 | 1.00 | 0.00 |
| ATOM | 3351 | C | ASN | 273 | 62.511 | 93.795 | 34.232 | 1.00 | 26.12 |

FIG. 1: A-57

| ATOM | 3352 | O    | ASN | 273 | 63.736 | 93.894 | 34.158 | 1.00 | 25.90 |
|------|------|------|-----|-----|--------|--------|--------|------|-------|
| ATOM | 3353 | N    | LEU | 274 | 61.871 | 92.654 | 34.356 | 1.00 | 25.36 |
| ATOM | 3354 | H    | LEU | 274 | 60.899 | 92.685 | 34.410 | 1.00 | 0.00  |
| ATOM | 3355 | CA   | LEU | 274 | 62.575 | 91.379 | 34.356 | 1.00 | 25.44 |
| ATOM | 3356 | CB   | LEU | 274 | 62.297 | 90.650 | 35.676 | 1.00 | 23.63 |
| ATOM | 3357 | CG   | LEU | 274 | 62.733 | 91.179 | 37.023 | 1.00 | 21.66 |
| ATOM | 3358 | CD1  | LEU | 274 | 62.117 | 90.271 | 38.045 | 1.00 | 17.73 |
| ATOM | 3359 | CD2  | LEU | 274 | 64.256 | 91.158 | 37.214 | 1.00 | 18.97 |
| ATOM | 3360 | C    | LEU | 274 | 62.256 | 90.420 | 33.199 | 1.00 | 22.88 |
| ATOM | 3361 | O    | LEU | 274 | 61.144 | 90.327 | 32.685 | 1.00 | 24.51 |
| ATOM | 3362 | N    | LEU | 275 | 63.204 | 89.614 | 32.767 | 1.00 | 22.83 |
| ATOM | 3363 | H    | LEU | 275 | 64.078 | 89.671 | 33.206 | 1.00 | 0.00  |
| ATOM | 3364 | CA   | LEU | 275 | 62.962 | 88.641 | 31.713 | 1.00 | 21.29 |
| ATOM | 3365 | CB   | LEU | 275 | 64.291 | 88.316 | 31.126 | 1.00 | 20.41 |
| ATOM | 3366 | CG   | LEU | 275 | 64.251 | 87.576 | 29.845 | 1.00 | 20.28 |
| ATOM | 3367 | CD1  | LEU | 275 | 63.515 | 88.416 | 28.843 | 1.00 | 23.16 |
| ATOM | 3368 | CD2  | LEU | 275 | 65.642 | 87.263 | 29.398 | 1.00 | 22.33 |
| ATOM | 3369 | C    | LEU | 275 | 62.228 | 87.332 | 32.063 | 1.00 | 22.03 |
| ATOM | 3370 | O    | LEU | 275 | 61.350 | 86.847 | 31.340 | 1.00 | 20.34 |
| ATOM | 3371 | N    | SER | 276 | 62.597 | 86.701 | 33.182 | 1.00 | 21.44 |
| ATOM | 3372 | H    | SER | 276 | 63.194 | 87.156 | 33.810 | 1.00 | 0.00  |
| ATOM | 3373 | CA   | SER | 276 | 62.039 | 85.401 | 33.526 | 1.00 | 19.63 |
| ATOM | 3374 | CB   | SER | 276 | 62.721 | 84.331 | 32.704 | 1.00 | 15.72 |
| ATOM | 3375 | OG   | SER | 276 | 62.116 | 83.052 | 32.739 | 1.00 | 16.88 |
| ATOM | 3376 | HG   | SER | 276 | 61.522 | 82.973 | 31.975 | 1.00 | 0.00  |
| ATOM | 3377 | C    | SER | 276 | 62.208 | 85.072 | 34.999 | 1.00 | 21.13 |
| ATOM | 3378 | O    | SER | 276 | 62.977 | 85.756 | 35.676 | 1.00 | 22.01 |
| ATOM | 3379 | N    | ILE | 277 | 61.478 | 84.074 | 35.523 | 1.00 | 20.71 |
| ATOM | 3380 | H    | ILE | 277 | 60.779 | 83.699 | 34.942 | 1.00 | 0.00  |
| ATOM | 3381 | CA   | ILE | 277 | 61.647 | 83.534 | 36.879 | 1.00 | 18.06 |
| ATOM | 3382 | CB   | ILE | 277 | 60.293 | 83.382 | 37.699 | 1.00 | 17.47 |
| ATOM | 3383 | CG2  | ILE | 277 | 60.617 | 82.768 | 39.051 | 1.00 | 16.09 |
| ATOM | 3384 | CG1  | ILE | 277 | 59.551 | 84.707 | 37.888 | 1.00 | 14.46 |
| ATOM | 3385 | CD1  | ILE | 277 | 60.368 | 85.947 | 38.246 | 1.00 | 16.30 |
| ATOM | 3386 | C    | ILE | 277 | 62.257 | 82.135 | 36.774 | 1.00 | 17.20 |
| ATOM | 3387 | O    | ILE | 277 | 61.589 | 81.167 | 36.375 | 1.00 | 17.80 |
| ATOM | 3388 | N    | LEU | 278 | 63.549 | 82.030 | 37.117 | 1.00 | 17.25 |
| ATOM | 3389 | H    | LEU | 278 | 63.997 | 82.831 | 37.455 | 1.00 | 0.00  |
| ATOM | 3390 | CA   | LEU | 278 | 64.232 | 80.733 | 37.145 | 1.00 | 16.64 |
| ATOM | 3391 | CB   | LEU | 278 | 65.731 | 80.753 | 36.872 | 1.00 | 17.64 |
| ATOM | 3392 | CG   | LEU | 278 | 66.328 | 81.501 | 35.707 | 1.00 | 19.09 |
| ATOM | 3393 | CD1  | LEU | 278 | 67.688 | 80.900 | 35.386 | 1.00 | 20.10 |
| ATOM | 3394 | CD2  | LEU | 278 | 65.428 | 81.391 | 34.509 | 1.00 | 19.63 |
| ATOM | 3395 | C    | LEU | 278 | 64.114 | 80.161 | 38.543 | 1.00 | 16.12 |
| ATOM | 3396 | O    | LEU | 278 | 64.436 | 80.761 | 39.560 | 1.00 | 17.50 |
| ATOM | 3397 | N    | ARG | 279 | 63.580 | 78.967 | 38.603 | 1.00 | 15.53 |
| ATOM | 3398 | H    | ARG | 279 | 63.350 | 78.492 | 37.777 | 1.00 | 0.00  |
| ATOM | 3399 | CA   | ARG | 279 | 63.251 | 78.368 | 39.872 | 1.00 | 13.35 |
| ATOM | 3400 | CB   | ARG | 279 | 61.813 | 78.741 | 40.177 | 1.00 | 10.64 |
| ATOM | 3401 | CG   | ARG | 279 | 60.836 | 78.057 | 39.257 | 1.00 | 8.14  |
| ATOM | 3402 | CD   | ARG | 279 | 59.826 | 77.608 | 40.216 | 1.00 | 13.27 |
| ATOM | 3403 | NE   | ARG | 279 | 59.390 | 76.270 | 39.952 | 1.00 | 14.83 |
| ATOM | 3404 | HE   | ARG | 279 | 59.696 | 75.807 | 39.146 | 1.00 | 0.00  |
| ATOM | 3405 | CZ   | ARG | 279 | 58.577 | 75.644 | 40.806 | 1.00 | 14.31 |
| ATOM | 3406 | NH1  | ARG | 279 | 58.227 | 74.415 | 40.504 | 1.00 | 16.84 |
| ATOM | 3407 | HH11 | ARG | 279 | 57.642 | 73.910 | 41.133 | 1.00 | 0.00  |
| ATOM | 3408 | HH12 | ARG | 279 | 58.571 | 73.986 | 39.668 | 1.00 | 0.00  |
| ATOM | 3409 | NH2  | ARG | 279 | 58.111 | 76.169 | 41.939 | 1.00 | 8.13  |
| ATOM | 3410 | HH21 | ARG | 279 | 58.375 | 77.089 | 42.211 | 1.00 | 0.00  |
| ATOM | 3411 | HH22 | ARG | 279 | 57.508 | 75.626 | 42.525 | 1.00 | 0.00  |

FIG. 1: A-58

| ATOM | 3412 | C | ARG | 279 | 63.439 | 76.861 | 39.777 | 1.00 | 14.44 |
|---|---|---|---|---|---|---|---|---|---|
| ATOM | 3413 | O | ARG | 279 | 63.702 | 76.330 | 38.686 | 1.00 | 14.64 |
| ATOM | 3414 | N | ALA | 280 | 63.267 | 76.144 | 40.883 | 1.00 | 14.07 |
| ATOM | 3415 | H | ALA | 280 | 62.978 | 76.627 | 41.683 | 1.00 | 0.00 |
| ATOM | 3416 | CA | ALA | 280 | 63.462 | 74.698 | 40.886 | 1.00 | 14.65 |
| ATOM | 3417 | CB | ALA | 280 | 64.780 | 74.472 | 41.623 | 1.00 | 7.95 |
| ATOM | 3418 | C | ALA | 280 | 62.258 | 74.009 | 41.557 | 1.00 | 16.36 |
| ATOM | 3419 | O | ALA | 280 | 61.137 | 74.159 | 41.087 | 1.00 | 18.11 |
| ATOM | 3420 | N | HIS | 281 | 62.399 | 73.167 | 42.608 | 1.00 | 18.12 |
| ATOM | 3421 | H | HIS | 281 | 63.297 | 72.817 | 42.678 | 1.00 | 0.00 |
| ATOM | 3422 | CA | HIS | 281 | 61.353 | 72.685 | 43.540 | 1.00 | 15.72 |
| ATOM | 3423 | CB | HIS | 281 | 60.577 | 73.888 | 44.014 | 1.00 | 15.93 |
| ATOM | 3424 | CG | HIS | 281 | 59.586 | 73.858 | 45.164 | 1.00 | 19.33 |
| ATOM | 3425 | CD2 | HIS | 281 | 58.487 | 74.703 | 45.165 | 1.00 | 18.95 |
| ATOM | 3426 | ND1 | HIS | 281 | 59.580 | 73.199 | 46.312 | 1.00 | 21.77 |
| ATOM | 3427 | HD1 | HIS | 281 | 59.943 | 72.307 | 46.441 | 1.00 | 0.00 |
| ATOM | 3428 | CE1 | HIS | 281 | 58.543 | 73.629 | 46.994 | 1.00 | 21.06 |
| ATOM | 3429 | NE2 | HIS | 281 | 57.899 | 74.524 | 46.294 | 1.00 | 20.13 |
| ATOM | 3430 | HE2 | HIS | 281 | 57.054 | 74.952 | 46.552 | 1.00 | 0.00 |
| ATOM | 3431 | C | HIS | 281 | 60.392 | 71.625 | 43.081 | 1.00 | 15.77 |
| ATOM | 3432 | O | HIS | 281 | 59.853 | 70.886 | 43.890 | 1.00 | 15.52 |
| ATOM | 3433 | N | GLU | 282 | 60.194 | 71.601 | 41.782 | 1.00 | 17.89 |
| ATOM | 3434 | H | GLU | 282 | 60.568 | 72.323 | 41.241 | 1.00 | 0.00 |
| ATOM | 3435 | CA | GLU | 282 | 59.370 | 70.645 | 41.091 | 1.00 | 18.03 |
| ATOM | 3436 | CB | GLU | 282 | 58.439 | 71.412 | 40.240 | 1.00 | 18.88 |
| ATOM | 3437 | CG | GLU | 282 | 57.044 | 70.972 | 40.520 | 1.00 | 22.26 |
| ATOM | 3438 | CD | GLU | 282 | 56.294 | 72.174 | 40.965 | 1.00 | 20.86 |
| ATOM | 3439 | OE1 | GLU | 282 | 56.314 | 72.405 | 42.162 | 1.00 | 27.50 |
| ATOM | 3440 | OE2 | GLU | 282 | 55.777 | 72.890 | 40.129 | 1.00 | 17.91 |
| ATOM | 3441 | C | GLU | 282 | 60.096 | 69.607 | 40.227 | 1.00 | 18.08 |
| ATOM | 3442 | O | GLU | 282 | 60.710 | 69.910 | 39.193 | 1.00 | 18.00 |
| ATOM | 3443 | N | ALA | 283 | 59.979 | 68.353 | 40.667 | 1.00 | 16.31 |
| ATOM | 3444 | H | ALA | 283 | 59.466 | 68.218 | 41.488 | 1.00 | 0.00 |
| ATOM | 3445 | CA | ALA | 283 | 60.556 | 67.221 | 39.972 | 1.00 | 15.14 |
| ATOM | 3446 | CB | ALA | 283 | 60.035 | 65.932 | 40.549 | 1.00 | 12.58 |
| ATOM | 3447 | C | ALA | 283 | 60.222 | 67.246 | 38.507 | 1.00 | 14.53 |
| ATOM | 3448 | O | ALA | 283 | 59.063 | 67.360 | 38.228 | 1.00 | 16.04 |
| ATOM | 3449 | N | GLN | 284 | 61.144 | 67.301 | 37.551 | 1.00 | 18.04 |
| ATOM | 3450 | H | GLN | 284 | 62.076 | 67.415 | 37.819 | 1.00 | 0.00 |
| ATOM | 3451 | CA | GLN | 284 | 60.813 | 67.219 | 36.136 | 1.00 | 16.76 |
| ATOM | 3452 | CB | GLN | 284 | 61.295 | 68.412 | 35.361 | 1.00 | 17.57 |
| ATOM | 3453 | CG | GLN | 284 | 60.760 | 69.776 | 35.727 | 1.00 | 19.06 |
| ATOM | 3454 | CD | GLN | 284 | 59.257 | 69.875 | 35.711 | 1.00 | 18.59 |
| ATOM | 3455 | OE1 | GLN | 284 | 58.596 | 69.756 | 34.711 | 1.00 | 20.73 |
| ATOM | 3456 | NE2 | GLN | 284 | 58.574 | 70.056 | 36.798 | 1.00 | 22.84 |
| ATOM | 3457 | HE21 | GLN | 284 | 57.614 | 70.115 | 36.647 | 1.00 | 0.00 |
| ATOM | 3458 | HE22 | GLN | 284 | 59.049 | 70.124 | 37.647 | 1.00 | 0.00 |
| ATOM | 3459 | C | GLN | 284 | 61.446 | 66.005 | 35.483 | 1.00 | 18.81 |
| ATOM | 3460 | O | GLN | 284 | 62.559 | 65.555 | 35.757 | 1.00 | 20.97 |
| ATOM | 3461 | N | ASP | 285 | 60.728 | 65.459 | 34.537 | 1.00 | 20.00 |
| ATOM | 3462 | H | ASP | 285 | 59.842 | 65.842 | 34.360 | 1.00 | 0.00 |
| ATOM | 3463 | CA | ASP | 285 | 61.171 | 64.270 | 33.830 | 1.00 | 22.02 |
| ATOM | 3464 | CB | ASP | 285 | 60.013 | 63.788 | 32.984 | 1.00 | 27.23 |
| ATOM | 3465 | CG | ASP | 285 | 60.053 | 62.290 | 32.956 | 1.00 | 32.95 |
| ATOM | 3466 | OD1 | ASP | 285 | 59.334 | 61.719 | 33.781 | 1.00 | 39.86 |
| ATOM | 3467 | OD2 | ASP | 285 | 60.823 | 61.730 | 32.159 | 1.00 | 36.01 |
| ATOM | 3468 | C | ASP | 285 | 62.420 | 64.399 | 32.970 | 1.00 | 19.72 |
| ATOM | 3469 | O | ASP | 285 | 63.255 | 63.510 | 32.967 | 1.00 | 20.36 |
| ATOM | 3470 | N | GLY | 286 | 62.497 | 65.490 | 32.197 | 1.00 | 20.09 |
| ATOM | 3471 | H | GLY | 286 | 61.683 | 66.027 | 32.121 | 1.00 | 0.00 |

FIG. 1: A-59

| ATOM | 3472 | CA | GLY | 286 | 63.678 | 65.868 | 31.432 | 1.00 | 18.31 |
|------|------|-----|-----|-----|--------|--------|--------|------|-------|
| ATOM | 3473 | C | GLY | 286 | 64.637 | 66.694 | 32.306 | 1.00 | 21.16 |
| ATOM | 3474 | O | GLY | 286 | 65.546 | 67.382 | 31.833 | 1.00 | 24.21 |
| ATOM | 3475 | N | GLY | 287 | 64.470 | 66.710 | 33.629 | 1.00 | 20.95 |
| ATOM | 3476 | H | GLY | 287 | 63.925 | 66.021 | 34.063 | 1.00 | 0.00 |
| ATOM | 3477 | CA | GLY | 287 | 65.247 | 67.581 | 34.504 | 1.00 | 17.89 |
| ATOM | 3478 | C | GLY | 287 | 64.964 | 69.062 | 34.407 | 1.00 | 14.88 |
| ATOM | 3479 | O | GLY | 287 | 65.444 | 69.775 | 35.257 | 1.00 | 15.62 |
| ATOM | 3480 | N | TYR | 288 | 64.225 | 69.588 | 33.438 | 1.00 | 14.85 |
| ATOM | 3481 | H | TYR | 288 | 63.920 | 68.986 | 32.735 | 1.00 | 0.00 |
| ATOM | 3482 | CA | TYR | 288 | 63.914 | 71.012 | 33.267 | 1.00 | 15.02 |
| ATOM | 3483 | CB | TYR | 288 | 64.950 | 71.729 | 32.364 | 1.00 | 14.57 |
| ATOM | 3484 | CG | TYR | 288 | 64.862 | 71.390 | 30.866 | 1.00 | 17.21 |
| ATOM | 3485 | CD1 | TYR | 288 | 65.262 | 70.123 | 30.388 | 1.00 | 18.76 |
| ATOM | 3486 | CE1 | TYR | 288 | 65.148 | 69.807 | 29.026 | 1.00 | 16.60 |
| ATOM | 3487 | CD2 | TYR | 288 | 64.355 | 72.340 | 29.955 | 1.00 | 17.61 |
| ATOM | 3488 | CE2 | TYR | 288 | 64.251 | 72.038 | 28.589 | 1.00 | 15.87 |
| ATOM | 3489 | CZ | TYR | 288 | 64.642 | 70.774 | 28.148 | 1.00 | 18.39 |
| ATOM | 3490 | OH | TYR | 288 | 64.505 | 70.464 | 26.807 | 1.00 | 26.73 |
| ATOM | 3491 | HH | TYR | 288 | 64.823 | 69.565 | 26.665 | 1.00 | 0.00 |
| ATOM | 3492 | C | TYR | 288 | 62.539 | 71.208 | 32.617 | 1.00 | 15.28 |
| ATOM | 3493 | O | TYR | 288 | 61.982 | 70.295 | 32.033 | 1.00 | 16.05 |
| ATOM | 3494 | N | ARG | 289 | 61.963 | 72.396 | 32.639 | 1.00 | 17.42 |
| ATOM | 3495 | H | ARG | 289 | 62.397 | 73.070 | 33.209 | 1.00 | 0.00 |
| ATOM | 3496 | CA | ARG | 289 | 60.707 | 72.739 | 31.974 | 1.00 | 17.90 |
| ATOM | 3497 | CB | ARG | 289 | 59.574 | 72.352 | 32.876 | 1.00 | 19.13 |
| ATOM | 3498 | CG | ARG | 289 | 58.238 | 72.932 | 32.508 | 1.00 | 23.08 |
| ATOM | 3499 | CD | ARG | 289 | 57.350 | 71.821 | 32.190 | 1.00 | 24.89 |
| ATOM | 3500 | NE | ARG | 289 | 56.217 | 71.817 | 33.051 | 1.00 | 27.20 |
| ATOM | 3501 | HE | ARG | 289 | 56.272 | 71.424 | 33.948 | 1.00 | 0.00 |
| ATOM | 3502 | CZ | ARG | 289 | 55.069 | 72.312 | 32.614 | 1.00 | 32.35 |
| ATOM | 3503 | NH1 | ARG | 289 | 53.980 | 72.136 | 33.385 | 1.00 | 35.22 |
| ATOM | 3504 | HH11 | ARG | 289 | 54.060 | 71.644 | 34.251 | 1.00 | 0.00 |
| ATOM | 3505 | HH12 | ARG | 289 | 53.094 | 72.498 | 33.094 | 1.00 | 0.00 |
| ATOM | 3506 | NH2 | ARG | 289 | 54.991 | 73.016 | 31.465 | 1.00 | 33.43 |
| ATOM | 3507 | HH21 | ARG | 289 | 55.802 | 73.169 | 30.903 | 1.00 | 0.00 |
| ATOM | 3508 | HH22 | ARG | 289 | 54.105 | 73.368 | 31.167 | 1.00 | 0.00 |
| ATOM | 3509 | C | ARG | 289 | 60.619 | 74.234 | 31.648 | 1.00 | 19.75 |
| ATOM | 3510 | O | ARG | 289 | 60.809 | 75.123 | 32.485 | 1.00 | 18.68 |
| ATOM | 3511 | N | MET | 290 | 60.339 | 74.560 | 30.397 | 1.00 | 22.37 |
| ATOM | 3512 | H | MET | 290 | 60.124 | 73.841 | 29.772 | 1.00 | 0.00 |
| ATOM | 3513 | CA | MET | 290 | 60.195 | 75.963 | 29.974 | 1.00 | 23.15 |
| ATOM | 3514 | CB | MET | 290 | 60.774 | 76.156 | 28.564 | 1.00 | 22.09 |
| ATOM | 3515 | CG | MET | 290 | 62.258 | 75.973 | 28.366 | 1.00 | 19.95 |
| ATOM | 3516 | SD | MET | 290 | 63.167 | 77.381 | 29.026 | 1.00 | 28.66 |
| ATOM | 3517 | CE | MET | 290 | 64.822 | 76.799 | 29.289 | 1.00 | 24.57 |
| ATOM | 3518 | C | MET | 290 | 58.697 | 76.327 | 29.973 | 1.00 | 24.22 |
| ATOM | 3519 | O | MET | 290 | 57.865 | 75.551 | 29.490 | 1.00 | 26.56 |
| ATOM | 3520 | N | TYR | 291 | 58.221 | 77.424 | 30.529 | 1.00 | 23.54 |
| ATOM | 3521 | H | TYR | 291 | 58.838 | 78.049 | 30.965 | 1.00 | 0.00 |
| ATOM | 3522 | CA | TYR | 291 | 56.780 | 77.650 | 30.511 | 1.00 | 22.89 |
| ATOM | 3523 | CB | TYR | 291 | 56.285 | 78.153 | 31.942 | 1.00 | 22.49 |
| ATOM | 3524 | CG | TYR | 291 | 56.457 | 77.112 | 33.047 | 1.00 | 18.53 |
| ATOM | 3525 | CD1 | TYR | 291 | 55.367 | 76.443 | 33.581 | 1.00 | 18.70 |
| ATOM | 3526 | CE1 | TYR | 291 | 55.594 | 75.385 | 34.467 | 1.00 | 20.79 |
| ATOM | 3527 | CD2 | TYR | 291 | 57.739 | 76.744 | 33.416 | 1.00 | 18.28 |
| ATOM | 3528 | CE2 | TYR | 291 | 57.969 | 75.697 | 34.298 | 1.00 | 18.50 |
| ATOM | 3529 | CZ | TYR | 291 | 56.897 | 75.002 | 34.827 | 1.00 | 18.93 |
| ATOM | 3530 | OH | TYR | 291 | 57.137 | 73.919 | 35.668 | 1.00 | 15.29 |
| ATOM | 3531 | HH | TYR | 291 | 58.025 | 74.010 | 36.042 | 1.00 | 0.00 |

FIG. 1: A-60

| ATOM | 3532 | C | TYR | 291 | 56.408 | 78.641 | 29.425 | 1.00 | 24.16 |
|---|---|---|---|---|---|---|---|---|---|
| ATOM | 3533 | O | TYR | 291 | 57.254 | 79.165 | 28.701 | 1.00 | 22.65 |
| ATOM | 3534 | N | ARG | 292 | 55.115 | 78.944 | 29.337 | 1.00 | 26.89 |
| ATOM | 3535 | H | ARG | 292 | 54.496 | 78.465 | 29.923 | 1.00 | 0.00 |
| ATOM | 3536 | CA | ARG | 292 | 54.599 | 79.941 | 28.404 | 1.00 | 29.05 |
| ATOM | 3537 | CB | ARG | 292 | 53.177 | 80.332 | 28.857 | 1.00 | 29.32 |
| ATOM | 3538 | CG | ARG | 292 | 52.563 | 81.057 | 27.676 | 1.00 | 27.54 |
| ATOM | 3539 | CD | ARG | 292 | 51.078 | 80.980 | 27.658 | 1.00 | 25.70 |
| ATOM | 3540 | NE | ARG | 292 | 50.636 | 81.894 | 26.629 | 1.00 | 25.94 |
| ATOM | 3541 | HE | ARG | 292 | 51.181 | 82.032 | 25.826 | 1.00 | 0.00 |
| ATOM | 3542 | CZ | ARG | 292 | 49.489 | 82.546 | 26.744 | 1.00 | 28.62 |
| ATOM | 3543 | NH1 | ARG | 292 | 49.189 | 83.398 | 25.775 | 1.00 | 32.49 |
| ATOM | 3544 | HH11 | ARG | 292 | 49.804 | 83.507 | 24.994 | 1.00 | 0.00 |
| ATOM | 3545 | HH12 | ARG | 292 | 48.321 | 83.894 | 25.805 | 1.00 | 0.00 |
| ATOM | 3546 | NH2 | ARG | 292 | 48.640 | 82.375 | 27.780 | 1.00 | 30.70 |
| ATOM | 3547 | HH21 | ARG | 292 | 48.856 | 81.738 | 28.519 | 1.00 | 0.00 |
| ATOM | 3548 | HH22 | ARG | 292 | 47.784 | 82.892 | 27.806 | 1.00 | 0.00 |
| ATOM | 3549 | C | ARG | 292 | 55.444 | 81.201 | 28.195 | 1.00 | 29.50 |
| ATOM | 3550 | O | ARG | 292 | 55.742 | 81.927 | 29.148 | 1.00 | 32.32 |
| ATOM | 3551 | N | LYS | 293 | 55.906 | 81.385 | 26.943 | 1.00 | 30.05 |
| ATOM | 3552 | H | LYS | 293 | 55.666 | 80.696 | 26.292 | 1.00 | 0.00 |
| ATOM | 3553 | CA | LYS | 293 | 56.784 | 82.501 | 26.530 | 1.00 | 28.64 |
| ATOM | 3554 | CB | LYS | 293 | 57.177 | 82.307 | 25.055 | 1.00 | 29.25 |
| ATOM | 3555 | CG | LYS | 293 | 58.234 | 81.231 | 24.898 | 1.00 | 30.03 |
| ATOM | 3556 | CD | LYS | 293 | 58.771 | 81.061 | 23.486 | 1.00 | 33.20 |
| ATOM | 3557 | CE | LYS | 293 | 59.703 | 79.813 | 23.332 | 1.00 | 37.50 |
| ATOM | 3558 | NZ | LYS | 293 | 61.127 | 79.916 | 23.684 | 1.00 | 36.16 |
| ATOM | 3559 | HZ1 | LYS | 293 | 61.220 | 80.221 | 24.675 | 1.00 | 0.00 |
| ATOM | 3560 | HZ2 | LYS | 293 | 61.585 | 80.610 | 23.060 | 1.00 | 0.00 |
| ATOM | 3561 | HZ3 | LYS | 293 | 61.587 | 78.991 | 23.568 | 1.00 | 0.00 |
| ATOM | 3562 | C | LYS | 293 | 56.217 | 83.905 | 26.730 | 1.00 | 27.12 |
| ATOM | 3563 | O | LYS | 293 | 55.001 | 84.041 | 26.813 | 1.00 | 28.76 |
| ATOM | 3564 | N | SER | 294 | 56.967 | 84.981 | 26.825 | 1.00 | 26.42 |
| ATOM | 3565 | H | SER | 294 | 57.941 | 84.885 | 26.772 | 1.00 | 0.00 |
| ATOM | 3566 | CA | SER | 294 | 56.372 | 86.281 | 27.097 | 1.00 | 26.77 |
| ATOM | 3567 | CB | SER | 294 | 57.406 | 87.292 | 27.576 | 1.00 | 26.90 |
| ATOM | 3568 | OG | SER | 294 | 57.066 | 88.648 | 27.894 | 1.00 | 21.66 |
| ATOM | 3569 | HG | SER | 294 | 56.518 | 89.078 | 27.218 | 1.00 | 0.00 |
| ATOM | 3570 | C | SER | 294 | 55.637 | 86.978 | 25.983 | 1.00 | 30.85 |
| ATOM | 3571 | O | SER | 294 | 55.229 | 88.095 | 26.276 | 1.00 | 35.97 |
| ATOM | 3572 | N | GLN | 295 | 55.334 | 86.551 | 24.740 | 1.00 | 31.67 |
| ATOM | 3573 | H | GLN | 295 | 55.555 | 85.630 | 24.514 | 1.00 | 0.00 |
| ATOM | 3574 | CA | GLN | 295 | 54.682 | 87.433 | 23.709 | 1.00 | 30.98 |
| ATOM | 3575 | CB | GLN | 295 | 53.229 | 87.875 | 24.148 | 1.00 | 29.89 |
| ATOM | 3576 | CG | GLN | 295 | 52.063 | 87.039 | 23.616 | 1.00 | 32.09 |
| ATOM | 3577 | CD | GLN | 295 | 51.743 | 87.270 | 22.137 | 1.00 | 34.28 |
| ATOM | 3578 | OE1 | GLN | 295 | 51.781 | 86.379 | 21.313 | 1.00 | 37.34 |
| ATOM | 3579 | NE2 | GLN | 295 | 51.384 | 88.406 | 21.578 | 1.00 | 37.52 |
| ATOM | 3580 | HE21 | GLN | 295 | 51.260 | 89.205 | 22.117 | 1.00 | 0.00 |
| ATOM | 3581 | HE22 | GLN | 295 | 51.236 | 88.310 | 20.619 | 1.00 | 0.00 |
| ATOM | 3582 | C | GLN | 295 | 55.484 | 88.715 | 23.363 | 1.00 | 28.54 |
| ATOM | 3583 | O | GLN | 295 | 56.154 | 88.850 | 22.356 | 1.00 | 25.42 |
| ATOM | 3584 | N | THR | 296 | 55.488 | 89.676 | 24.270 | 1.00 | 30.60 |
| ATOM | 3585 | H | THR | 296 | 54.956 | 89.492 | 25.072 | 1.00 | 0.00 |
| ATOM | 3586 | CA | THR | 296 | 56.222 | 90.946 | 24.251 | 1.00 | 32.14 |
| ATOM | 3587 | CB | THR | 296 | 55.837 | 91.725 | 25.470 | 1.00 | 34.89 |
| ATOM | 3588 | OG1 | THR | 296 | 56.395 | 91.005 | 26.582 | 1.00 | 38.56 |
| ATOM | 3589 | HG1 | THR | 296 | 56.506 | 91.496 | 27.414 | 1.00 | 0.00 |
| ATOM | 3590 | CG2 | THR | 296 | 54.297 | 91.822 | 25.643 | 1.00 | 36.02 |
| ATOM | 3591 | C | THR | 296 | 57.728 | 90.819 | 24.231 | 1.00 | 33.39 |

FIG. 1: A-61

| | | | | | | | | |
|---|---|---|---|---|---|---|---|---|
| ATOM | 3592 | O | THR | 296 | 58.465 | 91.806 | 24.195 | 1.00 | 36.52 |
| ATOM | 3593 | N | THR | 297 | 58.150 | 89.592 | 24.540 | 1.00 | 33.35 |
| ATOM | 3594 | H | THR | 297 | 57.489 | 89.033 | 24.995 | 1.00 | 0.00 |
| ATOM | 3595 | CA | THR | 297 | 59.505 | 89.055 | 24.368 | 1.00 | 32.44 |
| ATOM | 3596 | CB | THR | 297 | 60.478 | 89.035 | 25.627 | 1.00 | 32.41 |
| ATOM | 3597 | OG1 | THR | 297 | 60.317 | 87.806 | 26.346 | 1.00 | 32.84 |
| ATOM | 3598 | HG1 | THR | 297 | 60.118 | 87.979 | 27.283 | 1.00 | 0.00 |
| ATOM | 3599 | CG2 | THR | 297 | 60.263 | 90.252 | 26.511 | 1.00 | 33.29 |
| ATOM | 3600 | C | THR | 297 | 59.216 | 87.586 | 24.026 | 1.00 | 33.78 |
| ATOM | 3601 | O | THR | 297 | 58.165 | 87.035 | 24.427 | 1.00 | 35.63 |
| ATOM | 3602 | N | GLY | 298 | 60.060 | 86.841 | 23.311 | 1.00 | 30.43 |
| ATOM | 3603 | H | GLY | 298 | 60.903 | 87.215 | 22.992 | 1.00 | 0.00 |
| ATOM | 3604 | CA | GLY | 298 | 59.644 | 85.476 | 22.970 | 1.00 | 27.91 |
| ATOM | 3605 | C | GLY | 298 | 60.326 | 84.428 | 23.810 | 1.00 | 26.58 |
| ATOM | 3606 | O | GLY | 298 | 60.603 | 83.324 | 23.369 | 1.00 | 26.80 |
| ATOM | 3607 | N | PHE | 299 | 60.578 | 84.772 | 25.060 | 1.00 | 27.46 |
| ATOM | 3608 | H | PHE | 299 | 60.256 | 85.643 | 25.374 | 1.00 | 0.00 |
| ATOM | 3609 | CA | PHE | 299 | 61.333 | 83.918 | 25.984 | 1.00 | 25.78 |
| ATOM | 3610 | CB | PHE | 299 | 62.424 | 84.860 | 26.560 | 1.00 | 24.19 |
| ATOM | 3611 | CG | PHE | 299 | 63.481 | 84.089 | 27.315 | 1.00 | 22.71 |
| ATOM | 3612 | CD1 | PHE | 299 | 64.496 | 83.452 | 26.611 | 1.00 | 20.47 |
| ATOM | 3613 | CD2 | PHE | 299 | 63.407 | 83.986 | 28.699 | 1.00 | 22.01 |
| ATOM | 3614 | CE1 | PHE | 299 | 65.454 | 82.697 | 27.277 | 1.00 | 18.37 |
| ATOM | 3615 | CE2 | PHE | 299 | 64.371 | 83.229 | 29.345 | 1.00 | 22.41 |
| ATOM | 3616 | CZ | PHE | 299 | 65.393 | 82.584 | 28.644 | 1.00 | 20.57 |
| ATOM | 3617 | C | PHE | 299 | 60.443 | 83.236 | 27.070 | 1.00 | 24.34 |
| ATOM | 3618 | O | PHE | 299 | 59.445 | 83.875 | 27.449 | 1.00 | 23.78 |
| ATOM | 3619 | N | PRO | 300 | 60.640 | 82.013 | 27.632 | 1.00 | 21.90 |
| ATOM | 3620 | CD | PRO | 300 | 61.661 | 81.046 | 27.241 | 1.00 | 19.41 |
| ATOM | 3621 | CA | PRO | 300 | 59.741 | 81.424 | 28.640 | 1.00 | 21.55 |
| ATOM | 3622 | CB | PRO | 300 | 60.439 | 80.126 | 29.008 | 1.00 | 18.91 |
| ATOM | 3623 | CG | PRO | 300 | 61.077 | 79.728 | 27.722 | 1.00 | 18.30 |
| ATOM | 3624 | C | PRO | 300 | 59.456 | 82.346 | 29.843 | 1.00 | 22.51 |
| ATOM | 3625 | O | PRO | 300 | 60.422 | 82.909 | 30.377 | 1.00 | 25.12 |
| ATOM | 3626 | N | SER | 301 | 58.223 | 82.630 | 30.299 | 1.00 | 21.04 |
| ATOM | 3627 | H | SER | 301 | 57.451 | 82.263 | 29.830 | 1.00 | 0.00 |
| ATOM | 3628 | CA | SER | 301 | 58.040 | 83.519 | 31.467 | 1.00 | 21.06 |
| ATOM | 3629 | CB | SER | 301 | 56.604 | 83.918 | 31.575 | 1.00 | 16.89 |
| ATOM | 3630 | OG | SER | 301 | 55.854 | 82.730 | 31.735 | 1.00 | 20.09 |
| ATOM | 3631 | HG | SER | 301 | 55.375 | 82.580 | 30.905 | 1.00 | 0.00 |
| ATOM | 3632 | C | SER | 301 | 58.492 | 82.926 | 32.832 | 1.00 | 20.40 |
| ATOM | 3633 | O | SER | 301 | 58.873 | 83.615 | 33.783 | 1.00 | 20.81 |
| ATOM | 3634 | N | LEU | 302 | 58.537 | 81.594 | 32.876 | 1.00 | 19.95 |
| ATOM | 3635 | H | LEU | 302 | 58.153 | 81.150 | 32.098 | 1.00 | 0.00 |
| ATOM | 3636 | CA | LEU | 302 | 59.024 | 80.756 | 33.977 | 1.00 | 17.90 |
| ATOM | 3637 | CB | LEU | 302 | 57.838 | 80.182 | 34.757 | 1.00 | 14.34 |
| ATOM | 3638 | CG | LEU | 302 | 58.029 | 79.405 | 36.043 | 1.00 | 9.24 |
| ATOM | 3639 | CD1 | LEU | 302 | 58.428 | 80.277 | 37.178 | 1.00 | 7.80 |
| ATOM | 3640 | CD2 | LEU | 302 | 56.726 | 78.774 | 36.376 | 1.00 | 9.67 |
| ATOM | 3641 | C | LEU | 302 | 59.902 | 79.590 | 33.474 | 1.00 | 17.95 |
| ATOM | 3642 | O | LEU | 302 | 59.687 | 79.062 | 32.377 | 1.00 | 16.22 |
| ATOM | 3643 | N | ILE | 303 | 60.932 | 79.198 | 34.236 | 1.00 | 18.30 |
| ATOM | 3644 | H | ILE | 303 | 61.130 | 79.742 | 35.033 | 1.00 | 0.00 |
| ATOM | 3645 | CA | ILE | 303 | 61.795 | 78.050 | 33.910 | 1.00 | 15.87 |
| ATOM | 3646 | CB | ILE | 303 | 63.222 | 78.495 | 33.439 | 1.00 | 15.87 |
| ATOM | 3647 | CG2 | ILE | 303 | 64.032 | 77.285 | 33.026 | 1.00 | 15.12 |
| ATOM | 3648 | CG1 | ILE | 303 | 63.152 | 79.437 | 32.274 | 1.00 | 17.94 |
| ATOM | 3649 | CD1 | ILE | 303 | 64.492 | 79.818 | 31.610 | 1.00 | 18.32 |
| ATOM | 3650 | C | ILE | 303 | 61.974 | 77.178 | 35.169 | 1.00 | 14.97 |
| ATOM | 3651 | O | ILE | 303 | 62.303 | 77.667 | 36.237 | 1.00 | 15.82 |

FIG. 1: A-62

| ATOM | 3652 | N | THR | 304 | 61.735 | 75.885 | 35.152 | 1.00 | 14.28 |
|------|------|------|-----|-----|--------|--------|--------|------|-------|
| ATOM | 3653 | H | THR | 304 | 61.323 | 75.533 | 34.334 | 1.00 | 0.00 |
| ATOM | 3654 | CA | THR | 304 | 61.987 | 74.999 | 36.276 | 1.00 | 11.17 |
| ATOM | 3655 | CB | THR | 304 | 60.836 | 73.999 | 36.513 | 1.00 | 11.73 |
| ATOM | 3656 | OG1 | THR | 304 | 59.791 | 74.820 | 37.001 | 1.00 | 12.34 |
| ATOM | 3657 | HG1 | THR | 304 | 60.083 | 75.307 | 37.786 | 1.00 | 0.00 |
| ATOM | 3658 | CG2 | THR | 304 | 61.073 | 72.873 | 37.516 | 1.00 | 8.94 |
| ATOM | 3659 | C | THR | 304 | 63.225 | 74.202 | 35.970 | 1.00 | 12.65 |
| ATOM | 3660 | O | THR | 304 | 63.321 | 73.512 | 34.964 | 1.00 | 11.49 |
| ATOM | 3661 | N | ILE | 305 | 64.266 | 74.330 | 36.761 | 1.00 | 14.93 |
| ATOM | 3662 | H | ILE | 305 | 64.238 | 75.009 | 37.466 | 1.00 | 0.00 |
| ATOM | 3663 | CA | ILE | 305 | 65.428 | 73.462 | 36.601 | 1.00 | 15.02 |
| ATOM | 3664 | CB | ILE | 305 | 66.712 | 74.396 | 36.474 | 1.00 | 11.43 |
| ATOM | 3665 | CG2 | ILE | 305 | 66.973 | 75.287 | 37.652 | 1.00 | 9.79 |
| ATOM | 3666 | CG1 | ILE | 305 | 67.906 | 73.470 | 36.314 | 1.00 | 12.67 |
| ATOM | 3667 | CD1 | ILE | 305 | 67.897 | 72.824 | 34.915 | 1.00 | 10.15 |
| ATOM | 3668 | C | ILE | 305 | 65.478 | 72.415 | 37.758 | 1.00 | 13.96 |
| ATOM | 3669 | O | ILE | 305 | 65.106 | 72.677 | 38.892 | 1.00 | 16.32 |
| ATOM | 3670 | N | PHE | 306 | 65.806 | 71.157 | 37.546 | 1.00 | 13.27 |
| ATOM | 3671 | H | PHE | 306 | 66.053 | 70.905 | 36.632 | 1.00 | 0.00 |
| ATOM | 3672 | CA | PHE | 306 | 65.796 | 70.137 | 38.575 | 1.00 | 14.28 |
| ATOM | 3673 | CB | PHE | 306 | 64.458 | 69.329 | 38.388 | 1.00 | 12.63 |
| ATOM | 3674 | CG | PHE | 306 | 64.164 | 68.354 | 39.550 | 1.00 | 13.60 |
| ATOM | 3675 | CD1 | PHE | 306 | 64.263 | 66.959 | 39.348 | 1.00 | 11.15 |
| ATOM | 3676 | CD2 | PHE | 306 | 63.861 | 68.850 | 40.834 | 1.00 | 9.58 |
| ATOM | 3677 | CE1 | PHE | 306 | 64.075 | 66.085 | 40.411 | 1.00 | 9.70 |
| ATOM | 3678 | CE2 | PHE | 306 | 63.679 | 67.949 | 41.885 | 1.00 | 10.72 |
| ATOM | 3679 | CZ | PHE | 306 | 63.786 | 66.578 | 41.685 | 1.00 | 6.48 |
| ATOM | 3680 | C | PHE | 306 | 67.065 | 69.261 | 38.507 | 1.00 | 14.99 |
| ATOM | 3681 | O | PHE | 306 | 67.288 | 68.595 | 37.493 | 1.00 | 18.50 |
| ATOM | 3682 | N | SER | 307 | 67.934 | 69.170 | 39.528 | 1.00 | 13.71 |
| ATOM | 3683 | H | SER | 307 | 67.741 | 69.599 | 40.384 | 1.00 | 0.00 |
| ATOM | 3684 | CA | SER | 307 | 69.191 | 68.424 | 39.362 | 1.00 | 13.70 |
| ATOM | 3685 | CB | SER | 307 | 70.321 | 69.352 | 39.707 | 1.00 | 15.42 |
| ATOM | 3686 | OG | SER | 307 | 70.200 | 70.599 | 39.011 | 1.00 | 16.93 |
| ATOM | 3687 | HG | SER | 307 | 70.222 | 70.439 | 38.049 | 1.00 | 0.00 |
| ATOM | 3688 | C | SER | 307 | 69.484 | 67.072 | 40.029 | 1.00 | 16.04 |
| ATOM | 3689 | O | SER | 307 | 70.614 | 66.563 | 40.085 | 1.00 | 17.06 |
| ATOM | 3690 | N | ALA | 308 | 68.407 | 66.432 | 40.472 | 1.00 | 14.46 |
| ATOM | 3691 | H | ALA | 308 | 67.562 | 66.911 | 40.404 | 1.00 | 0.00 |
| ATOM | 3692 | CA | ALA | 308 | 68.406 | 65.117 | 41.078 | 1.00 | 13.13 |
| ATOM | 3693 | CB | ALA | 308 | 67.499 | 65.192 | 42.298 | 1.00 | 7.67 |
| ATOM | 3694 | C | ALA | 308 | 67.878 | 64.104 | 40.047 | 1.00 | 15.64 |
| ATOM | 3695 | O | ALA | 308 | 66.653 | 64.097 | 39.846 | 1.00 | 17.74 |
| ATOM | 3696 | N | PRO | 309 | 68.652 | 63.307 | 39.278 | 1.00 | 14.64 |
| ATOM | 3697 | CD | PRO | 309 | 70.089 | 63.326 | 39.201 | 1.00 | 17.47 |
| ATOM | 3698 | CA | PRO | 309 | 68.150 | 62.363 | 38.305 | 1.00 | 17.09 |
| ATOM | 3699 | CB | PRO | 309 | 69.260 | 62.195 | 37.348 | 1.00 | 15.02 |
| ATOM | 3700 | CG | PRO | 309 | 70.428 | 62.195 | 38.245 | 1.00 | 15.30 |
| ATOM | 3701 | C | PRO | 309 | 67.747 | 61.085 | 39.004 | 1.00 | 22.93 |
| ATOM | 3702 | O | PRO | 309 | 68.229 | 60.850 | 40.135 | 1.00 | 28.85 |
| ATOM | 3703 | N | ASN | 310 | 66.897 | 60.229 | 38.411 | 1.00 | 23.54 |
| ATOM | 3704 | H | ASN | 310 | 66.597 | 60.441 | 37.512 | 1.00 | 0.00 |
| ATOM | 3705 | CA | ASN | 310 | 66.327 | 59.062 | 39.093 | 1.00 | 19.53 |
| ATOM | 3706 | CB | ASN | 310 | 67.271 | 57.894 | 39.028 | 1.00 | 18.91 |
| ATOM | 3707 | CG | ASN | 310 | 66.507 | 56.654 | 39.429 | 1.00 | 21.12 |
| ATOM | 3708 | OD1 | ASN | 310 | 65.299 | 56.529 | 39.216 | 1.00 | 26.53 |
| ATOM | 3709 | ND2 | ASN | 310 | 67.091 | 55.656 | 40.051 | 1.00 | 23.09 |
| ATOM | 3710 | HD21 | ASN | 310 | 66.454 | 54.928 | 40.222 | 1.00 | 0.00 |
| ATOM | 3711 | HD22 | ASN | 310 | 68.032 | 55.681 | 40.283 | 1.00 | 0.00 |

FIG. 1: A-63

| ATOM | 3712 | C   | ASN | 310 | 65.980 | 59.364 | 40.548 | 1.00 | 19.31 |
|------|------|-----|-----|-----|--------|--------|--------|------|-------|
| ATOM | 3713 | O   | ASN | 310 | 66.414 | 58.774 | 41.536 | 1.00 | 19.31 |
| ATOM | 3714 | N   | TYR | 311 | 65.173 | 60.407 | 40.628 | 1.00 | 20.90 |
| ATOM | 3715 | H   | TYR | 311 | 64.845 | 60.760 | 39.781 | 1.00 | 0.00  |
| ATOM | 3716 | CA  | TYR | 311 | 64.705 | 61.002 | 41.862 | 1.00 | 21.59 |
| ATOM | 3717 | CB  | TYR | 311 | 63.793 | 62.168 | 41.533 | 1.00 | 22.37 |
| ATOM | 3718 | CG  | TYR | 311 | 63.407 | 63.000 | 42.721 | 1.00 | 19.95 |
| ATOM | 3719 | CD1 | TYR | 311 | 62.085 | 63.385 | 42.857 | 1.00 | 21.80 |
| ATOM | 3720 | CE1 | TYR | 311 | 61.683 | 64.114 | 43.980 | 1.00 | 23.04 |
| ATOM | 3721 | CD2 | TYR | 311 | 64.348 | 63.336 | 43.684 | 1.00 | 19.85 |
| ATOM | 3722 | CE2 | TYR | 311 | 63.955 | 64.067 | 44.806 | 1.00 | 21.14 |
| ATOM | 3723 | CZ  | TYR | 311 | 62.629 | 64.453 | 44.947 | 1.00 | 22.10 |
| ATOM | 3724 | OH  | TYR | 311 | 62.251 | 65.225 | 46.032 | 1.00 | 25.87 |
| ATOM | 3725 | HH  | TYR | 311 | 61.289 | 65.155 | 46.101 | 1.00 | 0.00  |
| ATOM | 3726 | C   | TYR | 311 | 63.985 | 60.057 | 42.784 | 1.00 | 23.03 |
| ATOM | 3727 | O   | TYR | 311 | 62.878 | 59.593 | 42.536 | 1.00 | 25.34 |
| ATOM | 3728 | N   | LEU | 312 | 64.648 | 59.879 | 43.919 | 1.00 | 24.35 |
| ATOM | 3729 | H   | LEU | 312 | 65.436 | 60.450 | 44.044 | 1.00 | 0.00  |
| ATOM | 3730 | CA  | LEU | 312 | 64.280 | 58.957 | 44.994 | 1.00 | 24.13 |
| ATOM | 3731 | CB  | LEU | 312 | 62.802 | 59.012 | 45.393 | 1.00 | 22.50 |
| ATOM | 3732 | CG  | LEU | 312 | 62.044 | 60.274 | 45.614 | 1.00 | 21.39 |
| ATOM | 3733 | CD1 | LEU | 312 | 60.605 | 59.922 | 45.809 | 1.00 | 23.61 |
| ATOM | 3734 | CD2 | LEU | 312 | 62.548 | 60.980 | 46.803 | 1.00 | 20.39 |
| ATOM | 3735 | C   | LEU | 312 | 64.541 | 57.514 | 44.581 | 1.00 | 23.98 |
| ATOM | 3736 | O   | LEU | 312 | 63.982 | 56.572 | 45.140 | 1.00 | 25.69 |
| ATOM | 3737 | N   | ASP | 313 | 65.389 | 57.316 | 43.571 | 1.00 | 24.04 |
| ATOM | 3738 | H   | ASP | 313 | 65.816 | 58.110 | 43.197 | 1.00 | 0.00  |
| ATOM | 3739 | CA  | ASP | 313 | 65.746 | 56.002 | 43.008 | 1.00 | 25.47 |
| ATOM | 3740 | CB  | ASP | 313 | 66.373 | 54.997 | 44.059 | 1.00 | 24.40 |
| ATOM | 3741 | CG  | ASP | 313 | 67.493 | 55.493 | 44.977 | 1.00 | 24.48 |
| ATOM | 3742 | OD1 | ASP | 313 | 68.443 | 56.097 | 44.494 | 1.00 | 22.06 |
| ATOM | 3743 | OD2 | ASP | 313 | 67.410 | 55.285 | 46.188 | 1.00 | 25.28 |
| ATOM | 3744 | C   | ASP | 313 | 64.534 | 55.292 | 42.408 | 1.00 | 26.13 |
| ATOM | 3745 | O   | ASP | 313 | 64.587 | 54.142 | 42.005 | 1.00 | 30.76 |
| ATOM | 3746 | N   | VAL | 314 | 63.466 | 56.046 | 42.276 | 1.00 | 25.66 |
| ATOM | 3747 | H   | VAL | 314 | 63.609 | 57.002 | 42.389 | 1.00 | 0.00  |
| ATOM | 3748 | CA  | VAL | 314 | 62.138 | 55.611 | 41.902 | 1.00 | 25.88 |
| ATOM | 3749 | CB  | VAL | 314 | 61.283 | 55.890 | 43.163 | 1.00 | 25.21 |
| ATOM | 3750 | CG1 | VAL | 314 | 59.822 | 55.917 | 42.820 | 1.00 | 29.84 |
| ATOM | 3751 | CG2 | VAL | 314 | 61.516 | 54.794 | 44.196 | 1.00 | 26.41 |
| ATOM | 3752 | C   | VAL | 314 | 61.617 | 56.307 | 40.640 | 1.00 | 25.00 |
| ATOM | 3753 | O   | VAL | 314 | 61.183 | 55.660 | 39.711 | 1.00 | 26.42 |
| ATOM | 3754 | N   | TYR | 315 | 61.525 | 57.637 | 40.590 | 1.00 | 25.47 |
| ATOM | 3755 | H   | TYR | 315 | 61.800 | 58.133 | 41.389 | 1.00 | 0.00  |
| ATOM | 3756 | CA  | TYR | 315 | 61.125 | 58.414 | 39.416 | 1.00 | 25.63 |
| ATOM | 3757 | CB  | TYR | 315 | 61.098 | 59.901 | 39.720 | 1.00 | 27.24 |
| ATOM | 3758 | CG  | TYR | 315 | 60.193 | 60.519 | 40.774 | 1.00 | 30.56 |
| ATOM | 3759 | CD1 | TYR | 315 | 59.714 | 59.881 | 41.917 | 1.00 | 32.10 |
| ATOM | 3760 | CE1 | TYR | 315 | 58.867 | 60.538 | 42.809 | 1.00 | 33.76 |
| ATOM | 3761 | CD2 | TYR | 315 | 59.826 | 61.831 | 40.530 | 1.00 | 37.13 |
| ATOM | 3762 | CE2 | TYR | 315 | 58.975 | 62.506 | 41.421 | 1.00 | 40.30 |
| ATOM | 3763 | CZ  | TYR | 315 | 58.501 | 61.859 | 42.561 | 1.00 | 37.01 |
| ATOM | 3764 | OH  | TYR | 315 | 57.694 | 62.585 | 43.419 | 1.00 | 36.31 |
| ATOM | 3765 | HH  | TYR | 315 | 57.413 | 63.396 | 42.989 | 1.00 | 0.00  |
| ATOM | 3766 | C   | TYR | 315 | 62.225 | 58.189 | 38.372 | 1.00 | 27.40 |
| ATOM | 3767 | O   | TYR | 315 | 63.358 | 58.500 | 38.730 | 1.00 | 32.40 |
| ATOM | 3768 | N   | ASN | 316 | 62.161 | 57.750 | 37.118 | 1.00 | 25.08 |
| ATOM | 3769 | H   | ASN | 316 | 61.312 | 57.440 | 36.752 | 1.00 | 0.00  |
| ATOM | 3770 | CA  | ASN | 316 | 63.444 | 57.519 | 36.428 | 1.00 | 25.17 |
| ATOM | 3771 | CB  | ASN | 316 | 63.232 | 56.190 | 35.739 | 1.00 | 26.79 |

FIG. 1: A-64

| ATOM | 3772 | CG | ASN | 316 | 64.312 | 55.908 | 34.758 | 1.00 | 29.98 |
|------|------|------|-----|-----|--------|--------|--------|------|-------|
| ATOM | 3773 | OD1 | ASN | 316 | 65.487 | 56.147 | 35.012 | 1.00 | 35.47 |
| ATOM | 3774 | ND2 | ASN | 316 | 63.965 | 55.510 | 33.552 | 1.00 | 32.83 |
| ATOM | 3775 | HD21 | ASN | 316 | 63.038 | 55.406 | 33.297 | 1.00 | 0.00 |
| ATOM | 3776 | HD22 | ASN | 316 | 64.742 | 55.390 | 32.964 | 1.00 | 0.00 |
| ATOM | 3777 | C | ASN | 316 | 63.881 | 58.684 | 35.515 | 1.00 | 25.21 |
| ATOM | 3778 | O | ASN | 316 | 64.080 | 58.633 | 34.288 | 1.00 | 23.89 |
| ATOM | 3779 | N | ASN | 317 | 64.005 | 59.826 | 36.173 | 1.00 | 24.64 |
| ATOM | 3780 | H | ASN | 317 | 63.991 | 59.808 | 37.156 | 1.00 | 0.00 |
| ATOM | 3781 | CA | ASN | 317 | 64.201 | 61.071 | 35.446 | 1.00 | 25.12 |
| ATOM | 3782 | CB | ASN | 317 | 63.456 | 62.218 | 36.169 | 1.00 | 27.83 |
| ATOM | 3783 | CG | ASN | 317 | 64.113 | 62.544 | 37.490 | 1.00 | 28.75 |
| ATOM | 3784 | OD1 | ASN | 317 | 64.313 | 61.633 | 38.284 | 1.00 | 27.24 |
| ATOM | 3785 | ND2 | ASN | 317 | 64.565 | 63.757 | 37.754 | 1.00 | 29.52 |
| ATOM | 3786 | HD21 | ASN | 317 | 64.484 | 64.445 | 37.061 | 1.00 | 0.00 |
| ATOM | 3787 | HD22 | ASN | 317 | 65.006 | 63.866 | 38.624 | 1.00 | 0.00 |
| ATOM | 3788 | C | ASN | 317 | 65.623 | 61.548 | 35.166 | 1.00 | 24.17 |
| ATOM | 3789 | O | ASN | 317 | 66.610 | 61.174 | 35.819 | 1.00 | 24.18 |
| ATOM | 3790 | N | LYS | 318 | 65.682 | 62.337 | 34.109 | 1.00 | 18.96 |
| ATOM | 3791 | H | LYS | 318 | 64.888 | 62.438 | 33.542 | 1.00 | 0.00 |
| ATOM | 3792 | CA | LYS | 318 | 66.885 | 63.047 | 33.830 | 1.00 | 17.86 |
| ATOM | 3793 | CB | LYS | 318 | 66.855 | 63.605 | 32.420 | 1.00 | 17.44 |
| ATOM | 3794 | CG | LYS | 318 | 67.219 | 62.470 | 31.513 | 1.00 | 18.88 |
| ATOM | 3795 | CD | LYS | 318 | 67.362 | 62.936 | 30.096 | 1.00 | 21.37 |
| ATOM | 3796 | CE | LYS | 318 | 68.160 | 61.856 | 29.359 | 1.00 | 22.37 |
| ATOM | 3797 | NZ | LYS | 318 | 68.251 | 62.162 | 27.938 | 1.00 | 22.60 |
| ATOM | 3798 | HZ1 | LYS | 318 | 67.287 | 62.231 | 27.549 | 1.00 | 0.00 |
| ATOM | 3799 | HZ2 | LYS | 318 | 68.762 | 61.395 | 27.453 | 1.00 | 0.00 |
| ATOM | 3800 | HZ3 | LYS | 318 | 68.750 | 63.062 | 27.793 | 1.00 | 0.00 |
| ATOM | 3801 | C | LYS | 318 | 66.964 | 64.207 | 34.815 | 1.00 | 18.82 |
| ATOM | 3802 | O | LYS | 318 | 65.973 | 64.597 | 35.453 | 1.00 | 19.70 |
| ATOM | 3803 | N | ALA | 319 | 68.167 | 64.717 | 35.009 | 1.00 | 16.81 |
| ATOM | 3804 | H | ALA | 319 | 68.944 | 64.221 | 34.675 | 1.00 | 0.00 |
| ATOM | 3805 | CA | ALA | 319 | 68.313 | 65.988 | 35.670 | 1.00 | 12.88 |
| ATOM | 3806 | CB | ALA | 319 | 69.295 | 65.955 | 36.747 | 1.00 | 14.57 |
| ATOM | 3807 | C | ALA | 319 | 68.883 | 66.942 | 34.657 | 1.00 | 16.04 |
| ATOM | 3808 | O | ALA | 319 | 69.161 | 66.594 | 33.494 | 1.00 | 13.94 |
| ATOM | 3809 | N | ALA | 320 | 69.091 | 68.179 | 35.093 | 1.00 | 17.44 |
| ATOM | 3810 | H | ALA | 320 | 68.695 | 68.470 | 35.943 | 1.00 | 0.00 |
| ATOM | 3811 | CA | ALA | 320 | 69.738 | 69.120 | 34.220 | 1.00 | 16.48 |
| ATOM | 3812 | CB | ALA | 320 | 68.732 | 69.604 | 33.152 | 1.00 | 17.51 |
| ATOM | 3813 | C | ALA | 320 | 70.268 | 70.307 | 34.988 | 1.00 | 17.51 |
| ATOM | 3814 | O | ALA | 320 | 69.780 | 70.588 | 36.084 | 1.00 | 17.34 |
| ATOM | 3815 | N | VAL | 321 | 71.315 | 70.920 | 34.422 | 1.00 | 17.83 |
| ATOM | 3816 | H | VAL | 321 | 71.729 | 70.451 | 33.665 | 1.00 | 0.00 |
| ATOM | 3817 | CA | VAL | 321 | 71.833 | 72.226 | 34.809 | 1.00 | 17.28 |
| ATOM | 3818 | CB | VAL | 321 | 73.390 | 72.343 | 35.024 | 1.00 | 18.81 |
| ATOM | 3819 | CG1 | VAL | 321 | 73.695 | 71.611 | 36.293 | 1.00 | 19.75 |
| ATOM | 3820 | CG2 | VAL | 321 | 74.239 | 71.739 | 33.931 | 1.00 | 19.58 |
| ATOM | 3821 | C | VAL | 321 | 71.520 | 73.208 | 33.690 | 1.00 | 18.87 |
| ATOM | 3822 | O | VAL | 321 | 71.438 | 72.863 | 32.503 | 1.00 | 21.36 |
| ATOM | 3823 | N | LEU | 322 | 71.368 | 74.473 | 34.022 | 1.00 | 17.74 |
| ATOM | 3824 | H | LEU | 322 | 71.485 | 74.724 | 34.964 | 1.00 | 0.00 |
| ATOM | 3825 | CA | LEU | 322 | 71.049 | 75.476 | 33.048 | 1.00 | 17.21 |
| ATOM | 3826 | CB | LEU | 322 | 69.873 | 76.122 | 33.647 | 1.00 | 16.44 |
| ATOM | 3827 | CG | LEU | 322 | 68.953 | 77.111 | 33.016 | 1.00 | 21.00 |
| ATOM | 3828 | CD1 | LEU | 322 | 67.786 | 77.356 | 33.982 | 1.00 | 22.70 |
| ATOM | 3829 | CD2 | LEU | 322 | 69.671 | 78.418 | 32.760 | 1.00 | 25.19 |
| ATOM | 3830 | C | LEU | 322 | 72.259 | 76.382 | 32.843 | 1.00 | 20.45 |
| ATOM | 3831 | O | LEU | 322 | 72.547 | 77.200 | 33.696 | 1.00 | 22.73 |

FIG. 1: A-65

| ATOM | 3832 | N | LYS | 323 | 73.025 | 76.319 | 31.755 | 1.00 | 23.33 |
|---|---|---|---|---|---|---|---|---|---|
| ATOM | 3833 | H | LYS | 323 | 72.802 | 75.628 | 31.100 | 1.00 | 0.00 |
| ATOM | 3834 | CA | LYS | 323 | 74.167 | 77.199 | 31.499 | 1.00 | 24.45 |
| ATOM | 3835 | CB | LYS | 323 | 75.215 | 76.389 | 30.781 | 1.00 | 27.34 |
| ATOM | 3836 | CG | LYS | 323 | 75.833 | 75.186 | 31.557 | 1.00 | 28.78 |
| ATOM | 3837 | CD | LYS | 323 | 76.566 | 74.422 | 30.454 | 1.00 | 34.23 |
| ATOM | 3838 | CE | LYS | 323 | 77.572 | 73.329 | 30.815 | 1.00 | 36.72 |
| ATOM | 3839 | NZ | LYS | 323 | 78.264 | 72.919 | 29.604 | 1.00 | 35.30 |
| ATOM | 3840 | HZ1 | LYS | 323 | 77.571 | 72.586 | 28.904 | 1.00 | 0.00 |
| ATOM | 3841 | HZ2 | LYS | 323 | 78.930 | 72.151 | 29.819 | 1.00 | 0.00 |
| ATOM | 3842 | HZ3 | LYS | 323 | 78.783 | 73.727 | 29.207 | 1.00 | 0.00 |
| ATOM | 3843 | C | LYS | 323 | 73.930 | 78.507 | 30.735 | 1.00 | 26.44 |
| ATOM | 3844 | O | LYS | 323 | 73.628 | 78.519 | 29.544 | 1.00 | 27.95 |
| ATOM | 3845 | N | TYR | 324 | 73.977 | 79.670 | 31.393 | 1.00 | 27.42 |
| ATOM | 3846 | H | TYR | 324 | 74.078 | 79.621 | 32.362 | 1.00 | 0.00 |
| ATOM | 3847 | CA | TYR | 324 | 73.801 | 80.958 | 30.744 | 1.00 | 25.80 |
| ATOM | 3848 | CB | TYR | 324 | 72.969 | 81.819 | 31.625 | 1.00 | 23.59 |
| ATOM | 3849 | CG | TYR | 324 | 72.399 | 83.023 | 30.899 | 1.00 | 24.11 |
| ATOM | 3850 | CD1 | TYR | 324 | 72.652 | 84.301 | 31.367 | 1.00 | 27.10 |
| ATOM | 3851 | CE1 | TYR | 324 | 72.068 | 85.414 | 30.757 | 1.00 | 30.71 |
| ATOM | 3852 | CD2 | TYR | 324 | 71.567 | 82.852 | 29.801 | 1.00 | 27.19 |
| ATOM | 3853 | CE2 | TYR | 324 | 70.974 | 83.945 | 29.169 | 1.00 | 30.24 |
| ATOM | 3854 | CZ | TYR | 324 | 71.228 | 85.229 | 29.655 | 1.00 | 31.54 |
| ATOM | 3855 | OH | TYR | 324 | 70.625 | 86.318 | 29.046 | 1.00 | 32.14 |
| ATOM | 3856 | HH | TYR | 324 | 70.736 | 87.109 | 29.589 | 1.00 | 0.00 |
| ATOM | 3857 | C | TYR | 324 | 75.081 | 81.728 | 30.398 | 1.00 | 28.35 |
| ATOM | 3858 | O | TYR | 324 | 75.760 | 82.229 | 31.292 | 1.00 | 30.60 |
| ATOM | 3859 | N | GLU | 325 | 75.411 | 81.921 | 29.113 | 1.00 | 28.11 |
| ATOM | 3860 | H | GLU | 325 | 74.792 | 81.517 | 28.460 | 1.00 | 0.00 |
| ATOM | 3861 | CA | GLU | 325 | 76.561 | 82.696 | 28.621 | 1.00 | 26.50 |
| ATOM | 3862 | CB | GLU | 325 | 77.734 | 81.781 | 28.488 | 1.00 | 25.00 |
| ATOM | 3863 | CG | GLU | 325 | 79.061 | 82.430 | 28.167 | 1.00 | 24.51 |
| ATOM | 3864 | CD | GLU | 325 | 80.288 | 81.622 | 28.553 | 1.00 | 25.96 |
| ATOM | 3865 | OE1 | GLU | 325 | 81.347 | 82.204 | 28.764 | 1.00 | 28.64 |
| ATOM | 3866 | OE2 | GLU | 325 | 80.209 | 80.410 | 28.669 | 1.00 | 23.60 |
| ATOM | 3867 | C | GLU | 325 | 76.315 | 83.384 | 27.264 | 1.00 | 29.68 |
| ATOM | 3868 | O | GLU | 325 | 75.472 | 82.942 | 26.477 | 1.00 | 31.58 |
| ATOM | 3869 | N | ASN | 326 | 77.004 | 84.479 | 26.910 | 1.00 | 29.43 |
| ATOM | 3870 | H | ASN | 326 | 77.758 | 84.730 | 27.483 | 1.00 | 0.00 |
| ATOM | 3871 | CA | ASN | 326 | 76.856 | 85.222 | 25.649 | 1.00 | 27.35 |
| ATOM | 3872 | CB | ASN | 326 | 77.858 | 84.687 | 24.601 | 1.00 | 28.21 |
| ATOM | 3873 | CG | ASN | 326 | 79.319 | 84.515 | 25.039 | 1.00 | 32.70 |
| ATOM | 3874 | OD1 | ASN | 326 | 79.717 | 84.825 | 26.144 | 1.00 | 37.70 |
| ATOM | 3875 | ND2 | ASN | 326 | 80.309 | 83.995 | 24.347 | 1.00 | 36.57 |
| ATOM | 3876 | HD21 | ASN | 326 | 80.156 | 83.665 | 23.442 | 1.00 | 0.00 |
| ATOM | 3877 | HD22 | ASN | 326 | 81.150 | 83.993 | 24.837 | 1.00 | 0.00 |
| ATOM | 3878 | C | ASN | 326 | 75.450 | 85.234 | 25.037 | 1.00 | 26.03 |
| ATOM | 3879 | O | ASN | 326 | 75.242 | 84.999 | 23.846 | 1.00 | 26.65 |
| ATOM | 3880 | N | ASN | 327 | 74.490 | 85.488 | 25.932 | 1.00 | 23.28 |
| ATOM | 3881 | H | ASN | 327 | 74.798 | 85.604 | 26.849 | 1.00 | 0.00 |
| ATOM | 3882 | CA | ASN | 327 | 73.050 | 85.630 | 25.670 | 1.00 | 24.87 |
| ATOM | 3883 | CB | ASN | 327 | 72.856 | 86.713 | 24.625 | 1.00 | 28.32 |
| ATOM | 3884 | CG | ASN | 327 | 71.489 | 87.391 | 24.657 | 1.00 | 34.63 |
| ATOM | 3885 | OD1 | ASN | 327 | 71.093 | 87.960 | 25.673 | 1.00 | 35.74 |
| ATOM | 3886 | ND2 | ASN | 327 | 70.683 | 87.393 | 23.595 | 1.00 | 34.60 |
| ATOM | 3887 | HD21 | ASN | 327 | 70.947 | 86.929 | 22.784 | 1.00 | 0.00 |
| ATOM | 3888 | HD22 | ASN | 327 | 69.858 | 87.887 | 23.756 | 1.00 | 0.00 |
| ATOM | 3889 | C | ASN | 327 | 72.240 | 84.381 | 25.268 | 1.00 | 24.91 |
| ATOM | 3890 | O | ASN | 327 | 71.083 | 84.377 | 24.810 | 1.00 | 24.50 |
| ATOM | 3891 | N | VAL | 328 | 72.876 | 83.253 | 25.518 | 1.00 | 23.09 |

FIG. 1: A-66

| ATOM | 3892 | H | VAL | 328 | 73.776 | 83.299 | 25.880 | 1.00 | 0.00 |
|---|---|---|---|---|---|---|---|---|---|
| ATOM | 3893 | CA | VAL | 328 | 72.287 | 81.958 | 25.229 | 1.00 | 22.77 |
| ATOM | 3894 | CB | VAL | 328 | 73.256 | 81.144 | 24.303 | 1.00 | 21.00 |
| ATOM | 3895 | CG1 | VAL | 328 | 72.666 | 79.807 | 23.973 | 1.00 | 18.03 |
| ATOM | 3896 | CG2 | VAL | 328 | 73.523 | 81.879 | 22.994 | 1.00 | 19.70 |
| ATOM | 3897 | C | VAL | 328 | 72.093 | 81.253 | 26.579 | 1.00 | 23.61 |
| ATOM | 3898 | O | VAL | 328 | 72.824 | 81.433 | 27.545 | 1.00 | 24.60 |
| ATOM | 3899 | N | MET | 329 | 71.052 | 80.464 | 26.683 | 1.00 | 24.83 |
| ATOM | 3900 | H | MET | 329 | 70.425 | 80.448 | 25.929 | 1.00 | 0.00 |
| ATOM | 3901 | CA | MET | 329 | 70.747 | 79.655 | 27.834 | 1.00 | 25.19 |
| ATOM | 3902 | CB | MET | 329 | 69.379 | 79.989 | 28.347 | 1.00 | 28.01 |
| ATOM | 3903 | CG | MET | 329 | 69.113 | 79.211 | 29.599 | 1.00 | 32.69 |
| ATOM | 3904 | SD | MET | 329 | 67.782 | 79.943 | 30.571 | 1.00 | 39.20 |
| ATOM | 3905 | CE | MET | 329 | 68.494 | 81.453 | 31.169 | 1.00 | 36.28 |
| ATOM | 3906 | C | MET | 329 | 70.750 | 78.232 | 27.350 | 1.00 | 25.28 |
| ATOM | 3907 | O | MET | 329 | 69.845 | 77.816 | 26.627 | 1.00 | 27.67 |
| ATOM | 3908 | N | ASN | 330 | 71.776 | 77.469 | 27.649 | 1.00 | 26.19 |
| ATOM | 3909 | H | ASN | 330 | 72.514 | 77.846 | 28.173 | 1.00 | 0.00 |
| ATOM | 3910 | CA | ASN | 330 | 71.805 | 76.092 | 27.215 | 1.00 | 27.50 |
| ATOM | 3911 | CB | ASN | 330 | 73.181 | 75.666 | 26.730 | 1.00 | 28.29 |
| ATOM | 3912 | CG | ASN | 330 | 73.151 | 74.301 | 26.043 | 1.00 | 31.11 |
| ATOM | 3913 | OD1 | ASN | 330 | 73.982 | 73.400 | 26.217 | 1.00 | 33.46 |
| ATOM | 3914 | ND2 | ASN | 330 | 72.165 | 74.059 | 25.208 | 1.00 | 29.11 |
| ATOM | 3915 | HD21 | ASN | 330 | 72.242 | 73.182 | 24.789 | 1.00 | 0.00 |
| ATOM | 3916 | HD22 | ASN | 330 | 71.472 | 74.718 | 25.043 | 1.00 | 0.00 |
| ATOM | 3917 | C | ASN | 330 | 71.425 | 75.175 | 28.355 | 1.00 | 28.52 |
| ATOM | 3918 | O | ASN | 330 | 71.839 | 75.376 | 29.497 | 1.00 | 30.94 |
| ATOM | 3919 | N | ILE | 331 | 70.580 | 74.195 | 28.078 | 1.00 | 26.45 |
| ATOM | 3920 | H | ILE | 331 | 70.137 | 74.183 | 27.210 | 1.00 | 0.00 |
| ATOM | 3921 | CA | ILE | 331 | 70.258 | 73.183 | 29.071 | 1.00 | 22.75 |
| ATOM | 3922 | CB | ILE | 331 | 68.795 | 72.744 | 28.873 | 1.00 | 20.41 |
| ATOM | 3923 | CG2 | ILE | 331 | 68.510 | 71.436 | 29.642 | 1.00 | 18.06 |
| ATOM | 3924 | CG1 | ILE | 331 | 67.897 | 73.948 | 29.184 | 1.00 | 18.27 |
| ATOM | 3925 | CD1 | ILE | 331 | 67.948 | 74.555 | 30.600 | 1.00 | 18.18 |
| ATOM | 3926 | C | ILE | 331 | 71.220 | 72.014 | 28.865 | 1.00 | 23.36 |
| ATOM | 3927 | O | ILE | 331 | 71.410 | 71.541 | 27.739 | 1.00 | 25.07 |
| ATOM | 3928 | N | ARG | 332 | 71.851 | 71.564 | 29.940 | 1.00 | 22.29 |
| ATOM | 3929 | H | ARG | 332 | 71.790 | 72.084 | 30.769 | 1.00 | 0.00 |
| ATOM | 3930 | CA | ARG | 332 | 72.684 | 70.386 | 29.886 | 1.00 | 22.25 |
| ATOM | 3931 | CB | ARG | 332 | 74.057 | 70.732 | 30.391 | 1.00 | 22.75 |
| ATOM | 3932 | CG | ARG | 332 | 74.951 | 71.441 | 29.399 | 1.00 | 23.25 |
| ATOM | 3933 | CD | ARG | 332 | 75.271 | 70.550 | 28.200 | 1.00 | 25.46 |
| ATOM | 3934 | NE | ARG | 332 | 75.946 | 69.272 | 28.465 | 1.00 | 24.91 |
| ATOM | 3935 | HE | ARG | 332 | 75.399 | 68.467 | 28.584 | 1.00 | 0.00 |
| ATOM | 3936 | CZ | ARG | 332 | 77.278 | 69.146 | 28.530 | 1.00 | 25.28 |
| ATOM | 3937 | NH1 | ARG | 332 | 77.834 | 67.965 | 28.656 | 1.00 | 26.08 |
| ATOM | 3938 | HH11 | ARG | 332 | 78.830 | 67.884 | 28.708 | 1.00 | 0.00 |
| ATOM | 3939 | HH12 | ARG | 332 | 77.262 | 67.145 | 28.701 | 1.00 | 0.00 |
| ATOM | 3940 | NH2 | ARG | 332 | 78.111 | 70.170 | 28.523 | 1.00 | 29.65 |
| ATOM | 3941 | HH21 | ARG | 332 | 79.096 | 70.009 | 28.577 | 1.00 | 0.00 |
| ATOM | 3942 | HH22 | ARG | 332 | 77.761 | 71.106 | 28.461 | 1.00 | 0.00 |
| ATOM | 3943 | C | ARG | 332 | 72.097 | 69.252 | 30.724 | 1.00 | 23.10 |
| ATOM | 3944 | O | ARG | 332 | 72.093 | 69.274 | 31.967 | 1.00 | 24.40 |
| ATOM | 3945 | N | GLN | 333 | 71.548 | 68.230 | 30.094 | 1.00 | 21.63 |
| ATOM | 3946 | H | GLN | 333 | 71.546 | 68.224 | 29.117 | 1.00 | 0.00 |
| ATOM | 3947 | CA | GLN | 333 | 70.980 | 67.116 | 30.878 | 1.00 | 20.44 |
| ATOM | 3948 | CB | GLN | 333 | 69.908 | 66.323 | 30.111 | 1.00 | 16.81 |
| ATOM | 3949 | CG | GLN | 333 | 68.871 | 67.280 | 29.603 | 1.00 | 18.88 |
| ATOM | 3950 | CD | GLN | 333 | 67.712 | 66.549 | 29.023 | 1.00 | 20.19 |
| ATOM | 3951 | OE1 | GLN | 333 | 67.869 | 65.670 | 28.219 | 1.00 | 27.23 |

FIG. 1: A-67

| ATOM | 3952 | NE2 | GLN | 333 | 66.465 | 66.729 | 29.308 | 1.00 | 23.12 |
|------|------|-----|-----|-----|--------|--------|--------|------|-------|
| ATOM | 3953 | HE21 | GLN | 333 | 66.195 | 67.363 | 29.996 | 1.00 | 0.00 |
| ATOM | 3954 | HE22 | GLN | 333 | 65.894 | 66.157 | 28.771 | 1.00 | 0.00 |
| ATOM | 3955 | C | GLN | 333 | 71.960 | 66.067 | 31.360 | 1.00 | 18.42 |
| ATOM | 3956 | O | GLN | 333 | 72.952 | 65.815 | 30.679 | 1.00 | 20.65 |
| ATOM | 3957 | N | PHE | 334 | 71.714 | 65.413 | 32.482 | 1.00 | 16.67 |
| ATOM | 3958 | H | PHE | 334 | 70.944 | 65.699 | 33.022 | 1.00 | 0.00 |
| ATOM | 3959 | CA | PHE | 334 | 72.518 | 64.272 | 32.868 | 1.00 | 14.00 |
| ATOM | 3960 | CB | PHE | 334 | 73.611 | 64.715 | 33.829 | 1.00 | 12.14 |
| ATOM | 3961 | CG | PHE | 334 | 73.250 | 65.377 | 35.176 | 1.00 | 10.69 |
| ATOM | 3962 | CD1 | PHE | 334 | 72.865 | 66.711 | 35.215 | 1.00 | 2.88 |
| ATOM | 3963 | CD2 | PHE | 334 | 73.365 | 64.635 | 36.376 | 1.00 | 10.68 |
| ATOM | 3964 | CE1 | PHE | 334 | 72.606 | 67.292 | 36.437 | 1.00 | 7.34 |
| ATOM | 3965 | CE2 | PHE | 334 | 73.100 | 65.228 | 37.615 | 1.00 | 10.68 |
| ATOM | 3966 | CZ | PHE | 334 | 72.719 | 66.569 | 37.637 | 1.00 | 10.84 |
| ATOM | 3967 | C | PHE | 334 | 71.704 | 63.129 | 33.488 | 1.00 | 17.32 |
| ATOM | 3968 | O | PHE | 334 | 70.575 | 63.273 | 33.972 | 1.00 | 18.71 |
| ATOM | 3969 | N | ASN | 335 | 72.278 | 61.937 | 33.448 | 1.00 | 19.12 |
| ATOM | 3970 | H | ASN | 335 | 73.158 | 61.864 | 33.037 | 1.00 | 0.00 |
| ATOM | 3971 | CA | ASN | 335 | 71.641 | 60.766 | 34.006 | 1.00 | 18.40 |
| ATOM | 3972 | CB | ASN | 335 | 71.775 | 59.599 | 33.056 | 1.00 | 20.12 |
| ATOM | 3973 | CG | ASN | 335 | 70.864 | 59.713 | 31.848 | 1.00 | 19.52 |
| ATOM | 3974 | OD1 | ASN | 335 | 69.968 | 60.531 | 31.716 | 1.00 | 23.77 |
| ATOM | 3975 | ND2 | ASN | 335 | 71.021 | 58.920 | 30.844 | 1.00 | 20.14 |
| ATOM | 3976 | HD21 | ASN | 335 | 71.720 | 58.244 | 30.827 | 1.00 | 0.00 |
| ATOM | 3977 | HD22 | ASN | 335 | 70.376 | 59.097 | 30.130 | 1.00 | 0.00 |
| ATOM | 3978 | C | ASN | 335 | 72.191 | 60.368 | 35.354 | 1.00 | 19.37 |
| ATOM | 3979 | O | ASN | 335 | 73.194 | 60.893 | 35.805 | 1.00 | 21.32 |
| ATOM | 3980 | N | CYS | 336 | 71.504 | 59.483 | 36.046 | 1.00 | 19.06 |
| ATOM | 3981 | H | CYS | 336 | 70.680 | 59.114 | 35.656 | 1.00 | 0.00 |
| ATOM | 3982 | CA | CYS | 336 | 71.894 | 59.127 | 37.385 | 1.00 | 18.14 |
| ATOM | 3983 | CB | CYS | 336 | 70.777 | 58.290 | 38.015 | 1.00 | 19.33 |
| ATOM | 3984 | SG | CYS | 336 | 70.713 | 56.556 | 37.490 | 1.00 | 22.43 |
| ATOM | 3985 | C | CYS | 336 | 73.206 | 58.373 | 37.481 | 1.00 | 18.52 |
| ATOM | 3986 | O | CYS | 336 | 73.627 | 57.701 | 36.537 | 1.00 | 17.86 |
| ATOM | 3987 | N | SER | 337 | 73.838 | 58.459 | 38.647 | 1.00 | 15.39 |
| ATOM | 3988 | H | SER | 337 | 73.520 | 59.074 | 39.326 | 1.00 | 0.00 |
| ATOM | 3989 | CA | SER | 337 | 75.055 | 57.713 | 38.876 | 1.00 | 15.10 |
| ATOM | 3990 | CB | SER | 337 | 76.163 | 58.661 | 39.231 | 1.00 | 13.90 |
| ATOM | 3991 | OG | SER | 337 | 76.122 | 59.834 | 38.422 | 1.00 | 16.53 |
| ATOM | 3992 | HG | SER | 337 | 76.844 | 60.416 | 38.691 | 1.00 | 0.00 |
| ATOM | 3993 | C | SER | 337 | 74.859 | 56.715 | 40.001 | 1.00 | 15.68 |
| ATOM | 3994 | O | SER | 337 | 74.095 | 56.988 | 40.933 | 1.00 | 18.01 |
| ATOM | 3995 | N | PRO | 338 | 75.464 | 55.524 | 40.021 | 1.00 | 18.06 |
| ATOM | 3996 | CD | PRO | 338 | 76.415 | 55.008 | 39.014 | 1.00 | 17.70 |
| ATOM | 3997 | CA | PRO | 338 | 75.282 | 54.558 | 41.107 | 1.00 | 17.20 |
| ATOM | 3998 | CB | PRO | 338 | 76.168 | 53.375 | 40.678 | 1.00 | 16.50 |
| ATOM | 3999 | CG | PRO | 338 | 77.224 | 53.982 | 39.779 | 1.00 | 17.15 |
| ATOM | 4000 | C | PRO | 338 | 75.598 | 55.093 | 42.508 | 1.00 | 16.33 |
| ATOM | 4001 | O | PRO | 338 | 76.332 | 56.070 | 42.685 | 1.00 | 17.24 |
| ATOM | 4002 | N | HIS | 339 | 74.981 | 54.576 | 43.545 | 1.00 | 12.58 |
| ATOM | 4003 | H | HIS | 339 | 74.295 | 53.891 | 43.391 | 1.00 | 0.00 |
| ATOM | 4004 | CA | HIS | 339 | 75.464 | 54.932 | 44.863 | 1.00 | 14.70 |
| ATOM | 4005 | CB | HIS | 339 | 74.684 | 56.046 | 45.467 | 1.00 | 12.77 |
| ATOM | 4006 | CG | HIS | 339 | 73.212 | 55.762 | 45.492 | 1.00 | 12.22 |
| ATOM | 4007 | CD2 | HIS | 339 | 72.349 | 56.375 | 44.645 | 1.00 | 11.37 |
| ATOM | 4008 | ND1 | HIS | 339 | 72.517 | 54.951 | 46.264 | 1.00 | 14.02 |
| ATOM | 4009 | HD1 | HIS | 339 | 72.851 | 54.310 | 46.933 | 1.00 | 0.00 |
| ATOM | 4010 | CE1 | HIS | 339 | 71.255 | 55.052 | 45.918 | 1.00 | 12.43 |
| ATOM | 4011 | NE2 | HIS | 339 | 71.183 | 55.916 | 44.951 | 1.00 | 11.50 |

FIG. 1: A-68

| ATOM | 4012 | HE2 | HIS | 339 | 70.381 | 56.393 | 44.664 | 1.00 | 0.00 |
|------|------|-----|-----|-----|--------|--------|--------|------|-------|
| ATOM | 4013 | C   | HIS | 339 | 75.346 | 53.746 | 45.780 | 1.00 | 15.47 |
| ATOM | 4014 | O   | HIS | 339 | 74.500 | 52.904 | 45.467 | 1.00 | 17.77 |
| ATOM | 4015 | N   | PRO | 340 | 76.063 | 53.625 | 46.901 | 1.00 | 14.63 |
| ATOM | 4016 | CD  | PRO | 340 | 77.133 | 54.509 | 47.301 | 1.00 | 13.76 |
| ATOM | 4017 | CA  | PRO | 340 | 75.832 | 52.588 | 47.901 | 1.00 | 13.39 |
| ATOM | 4018 | CB  | PRO | 340 | 76.925 | 52.780 | 48.878 | 1.00 | 13.92 |
| ATOM | 4019 | CG  | PRO | 340 | 77.161 | 54.244 | 48.776 | 1.00 | 14.72 |
| ATOM | 4020 | C   | PRO | 340 | 74.458 | 52.643 | 48.528 | 1.00 | 13.52 |
| ATOM | 4021 | O   | PRO | 340 | 73.765 | 53.670 | 48.431 | 1.00 | 12.06 |
| ATOM | 4022 | N   | TYR | 341 | 74.090 | 51.478 | 49.083 | 1.00 | 16.61 |
| ATOM | 4023 | H   | TYR | 341 | 74.789 | 50.827 | 49.243 | 1.00 | 0.00  |
| ATOM | 4024 | CA  | TYR | 341 | 72.762 | 51.193 | 49.619 | 1.00 | 15.61 |
| ATOM | 4025 | CB  | TYR | 341 | 72.264 | 49.773 | 49.234 | 1.00 | 15.84 |
| ATOM | 4026 | CG  | TYR | 341 | 70.766 | 49.479 | 49.530 | 1.00 | 14.17 |
| ATOM | 4027 | CD1 | TYR | 341 | 69.747 | 50.215 | 48.943 | 1.00 | 11.52 |
| ATOM | 4028 | CE1 | TYR | 341 | 68.422 | 50.040 | 49.316 | 1.00 | 7.77  |
| ATOM | 4029 | CD2 | TYR | 341 | 70.417 | 48.530 | 50.488 | 1.00 | 12.93 |
| ATOM | 4030 | CE2 | TYR | 341 | 69.088 | 48.350 | 50.848 | 1.00 | 12.43 |
| ATOM | 4031 | CZ  | TYR | 341 | 68.096 | 49.112 | 50.273 | 1.00 | 9.68  |
| ATOM | 4032 | OH  | TYR | 341 | 66.794 | 48.964 | 50.711 | 1.00 | 10.36 |
| ATOM | 4033 | HH  | TYR | 341 | 66.710 | 48.107 | 51.140 | 1.00 | 0.00  |
| ATOM | 4034 | C   | TYR | 341 | 72.721 | 51.299 | 51.126 | 1.00 | 17.92 |
| ATOM | 4035 | O   | TYR | 341 | 73.527 | 50.785 | 51.901 | 1.00 | 16.80 |
| ATOM | 4036 | N   | TRP | 342 | 71.736 | 52.112 | 51.478 | 1.00 | 17.70 |
| ATOM | 4037 | H   | TRP | 342 | 71.246 | 52.605 | 50.790 | 1.00 | 0.00  |
| ATOM | 4038 | CA  | TRP | 342 | 71.406 | 52.275 | 52.862 | 1.00 | 17.95 |
| ATOM | 4039 | CB  | TRP | 342 | 71.414 | 53.705 | 53.217 | 1.00 | 16.93 |
| ATOM | 4040 | CG  | TRP | 342 | 72.729 | 54.274 | 53.703 | 1.00 | 16.28 |
| ATOM | 4041 | CD2 | TRP | 342 | 73.179 | 54.203 | 54.991 | 1.00 | 17.44 |
| ATOM | 4042 | CE2 | TRP | 342 | 74.324 | 54.997 | 54.910 | 1.00 | 20.45 |
| ATOM | 4043 | CE3 | TRP | 342 | 72.807 | 53.626 | 56.198 | 1.00 | 18.13 |
| ATOM | 4044 | CD1 | TRP | 342 | 73.522 | 55.019 | 52.877 | 1.00 | 14.49 |
| ATOM | 4045 | NE1 | TRP | 342 | 74.481 | 55.454 | 53.644 | 1.00 | 19.39 |
| ATOM | 4046 | HE1 | TRP | 342 | 75.212 | 56.060 | 53.365 | 1.00 | 0.00  |
| ATOM | 4047 | CZ2 | TRP | 342 | 75.114 | 55.224 | 56.049 | 1.00 | 18.96 |
| ATOM | 4048 | CZ3 | TRP | 342 | 73.598 | 53.857 | 57.332 | 1.00 | 20.09 |
| ATOM | 4049 | CH2 | TRP | 342 | 74.740 | 54.651 | 57.261 | 1.00 | 16.19 |
| ATOM | 4050 | C   | TRP | 342 | 70.014 | 51.723 | 53.073 | 1.00 | 20.15 |
| ATOM | 4051 | O   | TRP | 342 | 69.165 | 51.936 | 52.185 | 1.00 | 22.55 |
| ATOM | 4052 | N   | LEU | 343 | 69.753 | 50.948 | 54.133 | 1.00 | 16.44 |
| ATOM | 4053 | H   | LEU | 343 | 70.482 | 50.711 | 54.749 | 1.00 | 0.00  |
| ATOM | 4054 | CA  | LEU | 343 | 68.370 | 50.550 | 54.369 | 1.00 | 16.78 |
| ATOM | 4055 | CB  | LEU | 343 | 68.315 | 49.589 | 55.552 | 1.00 | 17.45 |
| ATOM | 4056 | CG  | LEU | 343 | 68.604 | 48.128 | 55.437 | 1.00 | 14.00 |
| ATOM | 4057 | CD1 | LEU | 343 | 69.029 | 47.546 | 56.766 | 1.00 | 11.12 |
| ATOM | 4058 | CD2 | LEU | 343 | 67.373 | 47.493 | 54.893 | 1.00 | 13.70 |
| ATOM | 4059 | C   | LEU | 343 | 67.472 | 51.787 | 54.673 | 1.00 | 20.56 |
| ATOM | 4060 | O   | LEU | 343 | 67.974 | 52.903 | 54.989 | 1.00 | 19.56 |
| ATOM | 4061 | N   | PRO | 344 | 66.125 | 51.656 | 54.611 | 1.00 | 22.32 |
| ATOM | 4062 | CD  | PRO | 344 | 65.396 | 50.570 | 53.945 | 1.00 | 23.54 |
| ATOM | 4063 | CA  | PRO | 344 | 65.182 | 52.700 | 55.013 | 1.00 | 22.57 |
| ATOM | 4064 | CB  | PRO | 344 | 63.845 | 52.004 | 54.990 | 1.00 | 22.75 |
| ATOM | 4065 | CG  | PRO | 344 | 63.969 | 51.127 | 53.775 | 1.00 | 22.34 |
| ATOM | 4066 | C   | PRO | 344 | 65.543 | 53.270 | 56.357 | 1.00 | 24.22 |
| ATOM | 4067 | O   | PRO | 344 | 66.107 | 52.553 | 57.179 | 1.00 | 24.35 |
| ATOM | 4068 | N   | ASN | 345 | 65.316 | 54.560 | 56.559 | 1.00 | 26.09 |
| ATOM | 4069 | H   | ASN | 345 | 64.971 | 55.066 | 55.787 | 1.00 | 0.00  |
| ATOM | 4070 | CA  | ASN | 345 | 65.604 | 55.303 | 57.782 | 1.00 | 28.48 |
| ATOM | 4071 | CB  | ASN | 345 | 64.452 | 55.113 | 58.716 | 1.00 | 33.67 |

FIG. 1: A-69

| ATOM | 4072 | CG | ASN | 345 | 63.152 | 55.572 | 58.093 | 1.00 | 39.40 |
| --- | --- | --- | --- | --- | --- | --- | --- | --- | --- |
| ATOM | 4073 | OD1 | ASN | 345 | 62.936 | 56.712 | 57.667 | 1.00 | 41.34 |
| ATOM | 4074 | ND2 | ASN | 345 | 62.220 | 54.650 | 58.016 | 1.00 | 43.82 |
| ATOM | 4075 | HD21 | ASN | 345 | 62.377 | 53.781 | 58.432 | 1.00 | 0.00 |
| ATOM | 4076 | HD22 | ASN | 345 | 61.414 | 54.937 | 57.545 | 1.00 | 0.00 |
| ATOM | 4077 | C | ASN | 345 | 66.914 | 55.043 | 58.546 | 1.00 | 30.18 |
| ATOM | 4078 | O | ASN | 345 | 67.054 | 55.285 | 59.752 | 1.00 | 33.05 |
| ATOM | 4079 | N | PHE | 346 | 67.934 | 54.580 | 57.790 | 1.00 | 27.92 |
| ATOM | 4080 | H | PHE | 346 | 67.743 | 54.438 | 56.839 | 1.00 | 0.00 |
| ATOM | 4081 | CA | PHE | 346 | 69.275 | 54.245 | 58.260 | 1.00 | 22.26 |
| ATOM | 4082 | CB | PHE | 346 | 69.928 | 55.458 | 58.929 | 1.00 | 20.92 |
| ATOM | 4083 | CG | PHE | 346 | 70.142 | 56.553 | 57.915 | 1.00 | 15.15 |
| ATOM | 4084 | CD1 | PHE | 346 | 71.152 | 56.414 | 56.976 | 1.00 | 15.16 |
| ATOM | 4085 | CD2 | PHE | 346 | 69.301 | 57.651 | 57.911 | 1.00 | 16.25 |
| ATOM | 4086 | CE1 | PHE | 346 | 71.343 | 57.380 | 56.012 | 1.00 | 15.30 |
| ATOM | 4087 | CE2 | PHE | 346 | 69.483 | 58.626 | 56.946 | 1.00 | 18.49 |
| ATOM | 4088 | CZ | PHE | 346 | 70.501 | 58.484 | 56.000 | 1.00 | 20.86 |
| ATOM | 4089 | C | PHE | 346 | 69.289 | 53.078 | 59.218 | 1.00 | 21.21 |
| ATOM | 4090 | O | PHE | 346 | 70.279 | 52.804 | 59.884 | 1.00 | 20.07 |
| ATOM | 4091 | N | MET | 347 | 68.182 | 52.333 | 59.200 | 1.00 | 19.98 |
| ATOM | 4092 | H | MET | 347 | 67.507 | 52.541 | 58.527 | 1.00 | 0.00 |
| ATOM | 4093 | CA | MET | 347 | 67.997 | 51.182 | 60.051 | 1.00 | 20.17 |
| ATOM | 4094 | CB | MET | 347 | 66.791 | 50.327 | 59.733 | 1.00 | 23.07 |
| ATOM | 4095 | CG | MET | 347 | 65.365 | 50.801 | 59.807 | 1.00 | 24.76 |
| ATOM | 4096 | SD | MET | 347 | 64.392 | 49.281 | 59.704 | 1.00 | 24.79 |
| ATOM | 4097 | CE | MET | 347 | 64.531 | 48.910 | 57.979 | 1.00 | 24.46 |
| ATOM | 4098 | C | MET | 347 | 69.137 | 50.220 | 59.889 | 1.00 | 18.69 |
| ATOM | 4099 | O | MET | 347 | 69.698 | 50.098 | 58.792 | 1.00 | 19.17 |
| ATOM | 4100 | N | ASP | 348 | 69.449 | 49.548 | 60.981 | 1.00 | 17.35 |
| ATOM | 4101 | H | ASP | 348 | 69.012 | 49.798 | 61.816 | 1.00 | 0.00 |
| ATOM | 4102 | CA | ASP | 348 | 70.480 | 48.539 | 60.922 | 1.00 | 21.38 |
| ATOM | 4103 | CB | ASP | 348 | 71.255 | 48.491 | 62.224 | 1.00 | 20.24 |
| ATOM | 4104 | CG | ASP | 348 | 70.437 | 48.150 | 63.431 | 1.00 | 22.19 |
| ATOM | 4105 | OD1 | ASP | 348 | 69.851 | 49.072 | 63.997 | 1.00 | 24.98 |
| ATOM | 4106 | OD2 | ASP | 348 | 70.415 | 46.975 | 63.801 | 1.00 | 23.32 |
| ATOM | 4107 | C | ASP | 348 | 69.966 | 47.143 | 60.616 | 1.00 | 22.36 |
| ATOM | 4108 | O | ASP | 348 | 68.791 | 46.830 | 60.858 | 1.00 | 22.23 |
| ATOM | 4109 | N | VAL | 349 | 70.870 | 46.254 | 60.186 | 1.00 | 22.02 |
| ATOM | 4110 | H | VAL | 349 | 71.806 | 46.535 | 60.077 | 1.00 | 0.00 |
| ATOM | 4111 | CA | VAL | 349 | 70.412 | 44.927 | 59.800 | 1.00 | 22.74 |
| ATOM | 4112 | CB | VAL | 349 | 71.539 | 44.086 | 59.091 | 1.00 | 23.46 |
| ATOM | 4113 | CG1 | VAL | 349 | 71.819 | 44.835 | 57.804 | 1.00 | 21.72 |
| ATOM | 4114 | CG2 | VAL | 349 | 72.782 | 43.863 | 59.899 | 1.00 | 20.58 |
| ATOM | 4115 | C | VAL | 349 | 69.826 | 44.085 | 60.912 | 1.00 | 22.01 |
| ATOM | 4116 | O | VAL | 349 | 69.065 | 43.166 | 60.644 | 1.00 | 22.35 |
| ATOM | 4117 | N | PHE | 350 | 70.120 | 44.403 | 62.170 | 1.00 | 22.52 |
| ATOM | 4118 | H | PHE | 350 | 70.794 | 45.097 | 62.316 | 1.00 | 0.00 |
| ATOM | 4119 | CA | PHE | 350 | 69.517 | 43.678 | 63.296 | 1.00 | 20.77 |
| ATOM | 4120 | CB | PHE | 350 | 70.309 | 43.977 | 64.599 | 1.00 | 19.68 |
| ATOM | 4121 | CG | PHE | 350 | 71.687 | 43.332 | 64.606 | 1.00 | 17.12 |
| ATOM | 4122 | CD1 | PHE | 350 | 71.808 | 41.949 | 64.540 | 1.00 | 15.34 |
| ATOM | 4123 | CD2 | PHE | 350 | 72.824 | 44.128 | 64.679 | 1.00 | 17.67 |
| ATOM | 4124 | CE1 | PHE | 350 | 73.073 | 41.355 | 64.547 | 1.00 | 18.03 |
| ATOM | 4125 | CE2 | PHE | 350 | 74.083 | 43.523 | 64.686 | 1.00 | 17.42 |
| ATOM | 4126 | CZ | PHE | 350 | 74.213 | 42.140 | 64.620 | 1.00 | 16.33 |
| ATOM | 4127 | C | PHE | 350 | 68.050 | 44.095 | 63.417 | 1.00 | 19.53 |
| ATOM | 4128 | O | PHE | 350 | 67.169 | 43.251 | 63.238 | 1.00 | 21.18 |
| ATOM | 4129 | N | THR | 351 | 67.798 | 45.404 | 63.615 | 1.00 | 15.59 |
| ATOM | 4130 | H | THR | 351 | 68.553 | 45.985 | 63.818 | 1.00 | 0.00 |
| ATOM | 4131 | CA | THR | 351 | 66.466 | 46.024 | 63.622 | 1.00 | 14.70 |

FIG. 1: A-70

| | | | | | | | | |
|---|---|---|---|---|---|---|---|---|
| ATOM | 4132 | CB | THR | 351 | 66.557 | 47.549 | 63.686 | 1.00 | 12.86 |
| ATOM | 4133 | OG1 | THR | 351 | 67.311 | 47.820 | 64.829 | 1.00 | 16.10 |
| ATOM | 4134 | HG1 | THR | 351 | 66.733 | 47.904 | 65.597 | 1.00 | 0.00 |
| ATOM | 4135 | CG2 | THR | 351 | 65.287 | 48.284 | 63.879 | 1.00 | 13.58 |
| ATOM | 4136 | C | THR | 351 | 65.659 | 45.695 | 62.368 | 1.00 | 17.28 |
| ATOM | 4137 | O | THR | 351 | 64.429 | 45.637 | 62.436 | 1.00 | 22.38 |
| ATOM | 4138 | N | TRP | 352 | 66.307 | 45.524 | 61.198 | 1.00 | 15.22 |
| ATOM | 4139 | H | TRP | 352 | 67.250 | 45.764 | 61.180 | 1.00 | 0.00 |
| ATOM | 4140 | CA | TRP | 352 | 65.653 | 45.089 | 59.956 | 1.00 | 15.01 |
| ATOM | 4141 | CB | TRP | 352 | 66.626 | 45.269 | 58.776 | 1.00 | 14.13 |
| ATOM | 4142 | CG | TRP | 352 | 66.155 | 44.935 | 57.349 | 1.00 | 10.89 |
| ATOM | 4143 | CD2 | TRP | 352 | 66.867 | 44.170 | 56.484 | 1.00 | 4.33 |
| ATOM | 4144 | CE2 | TRP | 352 | 66.107 | 44.239 | 55.329 | 1.00 | 5.98 |
| ATOM | 4145 | CE3 | TRP | 352 | 68.039 | 43.464 | 56.544 | 1.00 | 2.91 |
| ATOM | 4146 | CD1 | TRP | 352 | 65.001 | 45.448 | 56.767 | 1.00 | 9.30 |
| ATOM | 4147 | NE1 | TRP | 352 | 65.003 | 44.999 | 55.535 | 1.00 | 8.92 |
| ATOM | 4148 | HE1 | TRP | 352 | 64.254 | 45.132 | 54.908 | 1.00 | 0.00 |
| ATOM | 4149 | CZ2 | TRP | 352 | 66.553 | 43.571 | 54.207 | 1.00 | 8.44 |
| ATOM | 4150 | CZ3 | TRP | 352 | 68.487 | 42.798 | 55.427 | 1.00 | 4.84 |
| ATOM | 4151 | CH2 | TRP | 352 | 67.754 | 42.847 | 54.258 | 1.00 | 7.67 |
| ATOM | 4152 | C | TRP | 352 | 65.139 | 43.645 | 59.925 | 1.00 | 13.50 |
| ATOM | 4153 | O | TRP | 352 | 63.976 | 43.337 | 59.634 | 1.00 | 11.96 |
| ATOM | 4154 | N | SER | 353 | 66.058 | 42.743 | 60.245 | 1.00 | 15.84 |
| ATOM | 4155 | H | SER | 353 | 66.937 | 43.042 | 60.562 | 1.00 | 0.00 |
| ATOM | 4156 | CA | SER | 353 | 65.793 | 41.323 | 60.211 | 1.00 | 17.23 |
| ATOM | 4157 | CB | SER | 353 | 67.083 | 40.626 | 59.898 | 1.00 | 19.08 |
| ATOM | 4158 | OG | SER | 353 | 68.056 | 40.918 | 60.889 | 1.00 | 22.82 |
| ATOM | 4159 | HG | SER | 353 | 68.819 | 41.344 | 60.481 | 1.00 | 0.00 |
| ATOM | 4160 | C | SER | 353 | 65.171 | 40.689 | 61.456 | 1.00 | 19.96 |
| ATOM | 4161 | O | SER | 353 | 64.548 | 39.625 | 61.340 | 1.00 | 20.39 |
| ATOM | 4162 | N | LEU | 354 | 65.221 | 41.286 | 62.665 | 1.00 | 21.50 |
| ATOM | 4163 | H | LEU | 354 | 65.723 | 42.122 | 62.726 | 1.00 | 0.00 |
| ATOM | 4164 | CA | LEU | 354 | 64.715 | 40.644 | 63.879 | 1.00 | 18.85 |
| ATOM | 4165 | CB | LEU | 354 | 65.228 | 41.504 | 65.066 | 1.00 | 20.93 |
| ATOM | 4166 | CG | LEU | 354 | 65.587 | 40.801 | 66.421 | 1.00 | 24.45 |
| ATOM | 4167 | CD1 | LEU | 354 | 67.082 | 40.500 | 66.536 | 1.00 | 22.48 |
| ATOM | 4168 | CD2 | LEU | 354 | 65.197 | 41.713 | 67.574 | 1.00 | 23.69 |
| ATOM | 4169 | C | LEU | 354 | 63.206 | 40.318 | 64.003 | 1.00 | 18.69 |
| ATOM | 4170 | O | LEU | 354 | 62.886 | 39.166 | 64.316 | 1.00 | 16.92 |
| ATOM | 4171 | N | PRO | 355 | 62.171 | 41.128 | 63.735 | 1.00 | 19.76 |
| ATOM | 4172 | CD | PRO | 355 | 62.240 | 42.568 | 63.623 | 1.00 | 19.97 |
| ATOM | 4173 | CA | PRO | 355 | 60.784 | 40.672 | 63.550 | 1.00 | 20.68 |
| ATOM | 4174 | CB | PRO | 355 | 60.036 | 41.933 | 63.136 | 1.00 | 20.98 |
| ATOM | 4175 | CG | PRO | 355 | 61.142 | 42.829 | 62.643 | 1.00 | 21.74 |
| ATOM | 4176 | C | PRO | 355 | 60.530 | 39.490 | 62.601 | 1.00 | 21.57 |
| ATOM | 4177 | O | PRO | 355 | 59.633 | 38.674 | 62.813 | 1.00 | 23.30 |
| ATOM | 4178 | N | PHE | 356 | 61.346 | 39.298 | 61.572 | 1.00 | 22.75 |
| ATOM | 4179 | H | PHE | 356 | 62.102 | 39.909 | 61.459 | 1.00 | 0.00 |
| ATOM | 4180 | CA | PHE | 356 | 61.232 | 38.133 | 60.697 | 1.00 | 23.52 |
| ATOM | 4181 | CB | PHE | 356 | 61.774 | 38.541 | 59.354 | 1.00 | 24.59 |
| ATOM | 4182 | CG | PHE | 356 | 61.571 | 37.484 | 58.299 | 1.00 | 25.40 |
| ATOM | 4183 | CD1 | PHE | 356 | 60.277 | 37.100 | 57.947 | 1.00 | 24.62 |
| ATOM | 4184 | CD2 | PHE | 356 | 62.686 | 36.925 | 57.679 | 1.00 | 25.81 |
| ATOM | 4185 | CE1 | PHE | 356 | 60.116 | 36.139 | 56.946 | 1.00 | 27.09 |
| ATOM | 4186 | CE2 | PHE | 356 | 62.499 | 35.971 | 56.691 | 1.00 | 27.40 |
| ATOM | 4187 | CZ | PHE | 356 | 61.223 | 35.571 | 56.315 | 1.00 | 25.41 |
| ATOM | 4188 | C | PHE | 356 | 61.955 | 36.886 | 61.245 | 1.00 | 24.71 |
| ATOM | 4189 | O | PHE | 356 | 61.581 | 35.729 | 61.015 | 1.00 | 26.29 |
| ATOM | 4190 | N | VAL | 357 | 63.050 | 37.079 | 61.972 | 1.00 | 26.15 |
| ATOM | 4191 | H | VAL | 357 | 63.501 | 37.949 | 61.941 | 1.00 | 0.00 |

FIG. 1: A-71

| ATOM | 4192 | CA | VAL | 357 | 63.650 | 35.991 | 62.737 | 1.00 | 27.41 |
|---|---|---|---|---|---|---|---|---|---|
| ATOM | 4193 | CB | VAL | 357 | 65.002 | 36.532 | 63.304 | 1.00 | 28.60 |
| ATOM | 4194 | CG1 | VAL | 357 | 65.578 | 35.574 | 64.339 | 1.00 | 26.87 |
| ATOM | 4195 | CG2 | VAL | 357 | 65.982 | 36.719 | 62.165 | 1.00 | 26.28 |
| ATOM | 4196 | C | VAL | 357 | 62.641 | 35.569 | 63.858 | 1.00 | 28.05 |
| ATOM | 4197 | O | VAL | 357 | 62.366 | 34.406 | 64.154 | 1.00 | 26.26 |
| ATOM | 4198 | N | GLY | 358 | 62.022 | 36.530 | 64.535 | 1.00 | 27.50 |
| ATOM | 4199 | H | GLY | 358 | 62.343 | 37.436 | 64.424 | 1.00 | 0.00 |
| ATOM | 4200 | CA | GLY | 358 | 61.005 | 36.228 | 65.509 | 1.00 | 29.46 |
| ATOM | 4201 | C | GLY | 358 | 59.889 | 35.379 | 64.921 | 1.00 | 30.47 |
| ATOM | 4202 | O | GLY | 358 | 59.485 | 34.332 | 65.440 | 1.00 | 30.98 |
| ATOM | 4203 | N | GLU | 359 | 59.433 | 35.830 | 63.760 | 1.00 | 31.37 |
| ATOM | 4204 | H | GLU | 359 | 59.780 | 36.685 | 63.425 | 1.00 | 0.00 |
| ATOM | 4205 | CA | GLU | 359 | 58.351 | 35.160 | 63.058 | 1.00 | 29.44 |
| ATOM | 4206 | CB | GLU | 359 | 58.017 | 35.967 | 61.863 | 1.00 | 27.90 |
| ATOM | 4207 | CG | GLU | 359 | 56.910 | 35.350 | 61.068 | 1.00 | 25.03 |
| ATOM | 4208 | CD | GLU | 359 | 56.409 | 36.359 | 60.105 | 1.00 | 26.28 |
| ATOM | 4209 | OE1 | GLU | 359 | 55.252 | 36.743 | 60.247 | 1.00 | 29.15 |
| ATOM | 4210 | OE2 | GLU | 359 | 57.184 | 36.758 | 59.247 | 1.00 | 27.05 |
| ATOM | 4211 | C | GLU | 359 | 58.488 | 33.722 | 62.619 | 1.00 | 28.39 |
| ATOM | 4212 | O | GLU | 359 | 57.698 | 32.854 | 62.964 | 1.00 | 28.95 |
| ATOM | 4213 | N | LYS | 360 | 59.454 | 33.474 | 61.783 | 1.00 | 29.66 |
| ATOM | 4214 | H | LYS | 360 | 60.058 | 34.201 | 61.503 | 1.00 | 0.00 |
| ATOM | 4215 | CA | LYS | 360 | 59.620 | 32.129 | 61.274 | 1.00 | 32.22 |
| ATOM | 4216 | CB | LYS | 360 | 60.549 | 32.214 | 60.081 | 1.00 | 31.97 |
| ATOM | 4217 | CG | LYS | 360 | 59.933 | 33.059 | 58.976 | 1.00 | 31.76 |
| ATOM | 4218 | CD | LYS | 360 | 58.850 | 32.296 | 58.266 | 1.00 | 30.70 |
| ATOM | 4219 | CE | LYS | 360 | 58.190 | 33.212 | 57.265 | 1.00 | 33.27 |
| ATOM | 4220 | NZ | LYS | 360 | 57.419 | 32.455 | 56.290 | 1.00 | 36.09 |
| ATOM | 4221 | HZ1 | LYS | 360 | 56.634 | 31.975 | 56.775 | 1.00 | 0.00 |
| ATOM | 4222 | HZ2 | LYS | 360 | 58.032 | 31.751 | 55.833 | 1.00 | 0.00 |
| ATOM | 4223 | HZ3 | LYS | 360 | 57.042 | 33.108 | 55.574 | 1.00 | 0.00 |
| ATOM | 4224 | C | LYS | 360 | 60.140 | 31.181 | 62.352 | 1.00 | 32.07 |
| ATOM | 4225 | O | LYS | 360 | 59.833 | 29.993 | 62.304 | 1.00 | 33.67 |
| ATOM | 4226 | N | VAL | 361 | 60.883 | 31.678 | 63.364 | 1.00 | 32.66 |
| ATOM | 4227 | H | VAL | 361 | 61.216 | 32.601 | 63.285 | 1.00 | 0.00 |
| ATOM | 4228 | CA | VAL | 361 | 61.289 | 30.896 | 64.550 | 1.00 | 30.72 |
| ATOM | 4229 | CB | VAL | 361 | 62.279 | 31.708 | 65.350 | 1.00 | 27.64 |
| ATOM | 4230 | CG1 | VAL | 361 | 62.399 | 31.351 | 66.800 | 1.00 | 26.98 |
| ATOM | 4231 | CG2 | VAL | 361 | 63.580 | 31.420 | 64.670 | 1.00 | 26.02 |
| ATOM | 4232 | C | VAL | 361 | 60.072 | 30.532 | 65.391 | 1.00 | 31.94 |
| ATOM | 4233 | O | VAL | 361 | 59.831 | 29.351 | 65.612 | 1.00 | 34.95 |
| ATOM | 4234 | N | THR | 362 | 59.251 | 31.489 | 65.833 | 1.00 | 32.24 |
| ATOM | 4235 | H | THR | 362 | 59.557 | 32.418 | 65.771 | 1.00 | 0.00 |
| ATOM | 4236 | CA | THR | 362 | 57.979 | 31.219 | 66.510 | 1.00 | 31.58 |
| ATOM | 4237 | CB | THR | 362 | 57.225 | 32.535 | 66.729 | 1.00 | 31.93 |
| ATOM | 4238 | OG1 | THR | 362 | 58.068 | 33.301 | 67.589 | 1.00 | 33.08 |
| ATOM | 4239 | HG1 | THR | 362 | 58.397 | 34.068 | 67.101 | 1.00 | 0.00 |
| ATOM | 4240 | CG2 | THR | 362 | 55.835 | 32.376 | 67.313 | 1.00 | 32.64 |
| ATOM | 4241 | C | THR | 362 | 57.105 | 30.273 | 65.691 | 1.00 | 31.89 |
| ATOM | 4242 | O | THR | 362 | 56.702 | 29.203 | 66.171 | 1.00 | 34.09 |
| ATOM | 4243 | N | GLU | 363 | 56.861 | 30.570 | 64.409 | 1.00 | 31.31 |
| ATOM | 4244 | H | GLU | 363 | 57.226 | 31.404 | 64.054 | 1.00 | 0.00 |
| ATOM | 4245 | CA | GLU | 363 | 56.062 | 29.688 | 63.543 | 1.00 | 29.58 |
| ATOM | 4246 | CB | GLU | 363 | 55.942 | 30.135 | 62.098 | 1.00 | 32.45 |
| ATOM | 4247 | CG | GLU | 363 | 55.131 | 31.396 | 61.767 | 1.00 | 38.02 |
| ATOM | 4248 | CD | GLU | 363 | 55.344 | 31.945 | 60.342 | 1.00 | 41.06 |
| ATOM | 4249 | OE1 | GLU | 363 | 54.820 | 33.033 | 60.052 | 1.00 | 40.10 |
| ATOM | 4250 | OE2 | GLU | 363 | 56.025 | 31.294 | 59.531 | 1.00 | 39.79 |
| ATOM | 4251 | C | GLU | 363 | 56.653 | 28.307 | 63.450 | 1.00 | 25.77 |

FIG. 1: A-72

| | | | | | | | | |
|---|---|---|---|---|---|---|---|---|
| ATOM | 4252 | O | GLU | 363 | 55.884 | 27.366 | 63.572 | 1.00 | 27.98 |
| ATOM | 4253 | N | MET | 364 | 57.978 | 28.152 | 63.341 | 1.00 | 21.88 |
| ATOM | 4254 | H | MET | 364 | 58.531 | 28.960 | 63.286 | 1.00 | 0.00 |
| ATOM | 4255 | CA | MET | 364 | 58.629 | 26.850 | 63.267 | 1.00 | 20.42 |
| ATOM | 4256 | CB | MET | 364 | 60.150 | 26.927 | 63.378 | 1.00 | 19.89 |
| ATOM | 4257 | CG | MET | 364 | 60.673 | 25.510 | 63.284 | 1.00 | 18.68 |
| ATOM | 4258 | SD | MET | 364 | 62.440 | 25.178 | 63.448 | 1.00 | 26.44 |
| ATOM | 4259 | CE | MET | 364 | 62.475 | 23.761 | 64.530 | 1.00 | 22.40 |
| ATOM | 4260 | C | MET | 364 | 58.160 | 26.012 | 64.431 | 1.00 | 23.53 |
| ATOM | 4261 | O | MET | 364 | 57.839 | 24.845 | 64.291 | 1.00 | 26.17 |
| ATOM | 4262 | N | LEU | 365 | 58.053 | 26.654 | 65.583 | 1.00 | 24.44 |
| ATOM | 4263 | H | LEU | 365 | 58.314 | 27.599 | 65.615 | 1.00 | 0.00 |
| ATOM | 4264 | CA | LEU | 365 | 57.651 | 26.003 | 66.801 | 1.00 | 24.41 |
| ATOM | 4265 | CB | LEU | 365 | 58.184 | 26.830 | 67.959 | 1.00 | 23.48 |
| ATOM | 4266 | CG | LEU | 365 | 59.646 | 26.760 | 68.160 | 1.00 | 19.19 |
| ATOM | 4267 | CD1 | LEU | 365 | 59.998 | 27.794 | 69.159 | 1.00 | 21.11 |
| ATOM | 4268 | CD2 | LEU | 365 | 60.055 | 25.399 | 68.620 | 1.00 | 19.79 |
| ATOM | 4269 | C | LEU | 365 | 56.150 | 25.787 | 66.956 | 1.00 | 25.89 |
| ATOM | 4270 | O | LEU | 365 | 55.752 | 24.769 | 67.534 | 1.00 | 22.80 |
| ATOM | 4271 | N | VAL | 366 | 55.295 | 26.728 | 66.507 | 1.00 | 25.68 |
| ATOM | 4272 | H | VAL | 366 | 55.646 | 27.566 | 66.145 | 1.00 | 0.00 |
| ATOM | 4273 | CA | VAL | 366 | 53.883 | 26.444 | 66.602 | 1.00 | 26.42 |
| ATOM | 4274 | CB | VAL | 366 | 52.986 | 27.668 | 66.202 | 1.00 | 27.47 |
| ATOM | 4275 | CG1 | VAL | 366 | 53.376 | 28.871 | 67.037 | 1.00 | 26.27 |
| ATOM | 4276 | CG2 | VAL | 366 | 53.115 | 28.031 | 64.750 | 1.00 | 31.98 |
| ATOM | 4277 | C | VAL | 366 | 53.677 | 25.253 | 65.652 | 1.00 | 28.74 |
| ATOM | 4278 | O | VAL | 366 | 53.191 | 24.220 | 66.091 | 1.00 | 32.36 |
| ATOM | 4279 | N | ASN | 367 | 54.191 | 25.217 | 64.429 | 1.00 | 28.54 |
| ATOM | 4280 | H | ASN | 367 | 54.559 | 26.043 | 64.055 | 1.00 | 0.00 |
| ATOM | 4281 | CA | ASN | 367 | 54.136 | 24.012 | 63.601 | 1.00 | 30.74 |
| ATOM | 4282 | CB | ASN | 367 | 54.847 | 24.291 | 62.297 | 1.00 | 32.99 |
| ATOM | 4283 | CG | ASN | 367 | 54.032 | 25.291 | 61.504 | 1.00 | 35.43 |
| ATOM | 4284 | OD1 | ASN | 367 | 53.257 | 26.114 | 61.987 | 1.00 | 37.16 |
| ATOM | 4285 | ND2 | ASN | 367 | 54.137 | 25.255 | 60.206 | 1.00 | 37.37 |
| ATOM | 4286 | HD21 | ASN | 367 | 53.586 | 25.928 | 59.767 | 1.00 | 0.00 |
| ATOM | 4287 | HD22 | ASN | 367 | 54.713 | 24.609 | 59.760 | 1.00 | 0.00 |
| ATOM | 4288 | C | ASN | 367 | 54.709 | 22.721 | 64.177 | 1.00 | 30.03 |
| ATOM | 4289 | O | ASN | 367 | 54.151 | 21.641 | 64.072 | 1.00 | 30.48 |
| ATOM | 4290 | N | VAL | 368 | 55.887 | 22.770 | 64.778 | 1.00 | 32.11 |
| ATOM | 4291 | H | VAL | 368 | 56.354 | 23.631 | 64.816 | 1.00 | 0.00 |
| ATOM | 4292 | CA | VAL | 368 | 56.490 | 21.572 | 65.380 | 1.00 | 30.74 |
| ATOM | 4293 | CB | VAL | 368 | 57.945 | 21.888 | 65.752 | 1.00 | 25.54 |
| ATOM | 4294 | CG1 | VAL | 368 | 58.601 | 21.044 | 66.821 | 1.00 | 25.93 |
| ATOM | 4295 | CG2 | VAL | 368 | 58.663 | 21.545 | 64.479 | 1.00 | 25.45 |
| ATOM | 4296 | C | VAL | 368 | 55.708 | 21.063 | 66.571 | 1.00 | 31.98 |
| ATOM | 4297 | O | VAL | 368 | 55.821 | 19.883 | 66.903 | 1.00 | 34.28 |
| ATOM | 4298 | N | LEU | 369 | 54.883 | 21.875 | 67.219 | 1.00 | 30.89 |
| ATOM | 4299 | H | LEU | 369 | 54.793 | 22.819 | 66.960 | 1.00 | 0.00 |
| ATOM | 4300 | CA | LEU | 369 | 54.054 | 21.321 | 68.256 | 1.00 | 31.88 |
| ATOM | 4301 | CB | LEU | 369 | 54.019 | 22.325 | 69.404 | 1.00 | 28.75 |
| ATOM | 4302 | CG | LEU | 369 | 55.313 | 22.910 | 70.012 | 1.00 | 28.06 |
| ATOM | 4303 | CD1 | LEU | 369 | 54.843 | 23.559 | 71.296 | 1.00 | 26.76 |
| ATOM | 4304 | CD2 | LEU | 369 | 56.418 | 21.918 | 70.293 | 1.00 | 21.34 |
| ATOM | 4305 | C | LEU | 369 | 52.673 | 21.034 | 67.634 | 1.00 | 34.65 |
| ATOM | 4306 | O | LEU | 369 | 51.619 | 21.499 | 68.077 | 1.00 | 38.13 |
| ATOM | 4307 | N | ALA | 370 | 52.783 | 20.108 | 66.662 | 1.00 | 35.98 |
| ATOM | 4308 | H | ALA | 370 | 53.669 | 19.712 | 66.568 | 1.00 | 0.00 |
| ATOM | 4309 | CA | ALA | 370 | 51.770 | 19.667 | 65.694 | 1.00 | 36.22 |
| ATOM | 4310 | CB | ALA | 370 | 51.850 | 18.135 | 65.554 | 1.00 | 35.48 |
| ATOM | 4311 | C | ALA | 370 | 50.310 | 20.040 | 65.859 | 1.00 | 36.80 |

FIG. 1: A-73

| ATOM | 4312 | O | ALA | 370 | 49.949 | 21.166 | 65.490 | 1.00 | 38.97 |

CALCINEURIN SUBUNIT B COORDINATES

| | | Atom Type | Residue | # | X | Y | Z | OCC | B |
|---|---|---|---|---|---|---|---|---|---|
| ATOM | 4313 | CB | ALA | 5 | 68.996 | 3.990 | 78.300 | 1.00 | 43.20 |
| ATOM | 4314 | C | ALA | 5 | 67.752 | 4.521 | 80.411 | 1.00 | 39.74 |
| ATOM | 4315 | O | ALA | 5 | 66.721 | 4.569 | 81.082 | 1.00 | 40.79 |
| ATOM | 4316 | HT1 | ALA | 5 | 66.618 | 5.263 | 78.122 | 1.00 | 0.00 |
| ATOM | 4317 | HT2 | ALA | 5 | 65.668 | 4.153 | 78.943 | 1.00 | 0.00 |
| ATOM | 4318 | N | ALA | 5 | 66.506 | 4.238 | 78.330 | 1.00 | 41.36 |
| ATOM | 4319 | HT3 | ALA | 5 | 66.360 | 3.716 | 77.445 | 1.00 | 0.00 |
| ATOM | 4320 | CA | ALA | 5 | 67.668 | 3.763 | 79.084 | 1.00 | 42.01 |
| ATOM | 4321 | N | TYR | 6 | 68.839 | 5.165 | 80.828 | 1.00 | 36.60 |
| ATOM | 4322 | H | TYR | 6 | 69.646 | 5.223 | 80.283 | 1.00 | 0.00 |
| ATOM | 4323 | CA | TYR | 6 | 68.818 | 5.871 | 82.111 | 1.00 | 35.13 |
| ATOM | 4324 | CB | TYR | 6 | 70.279 | 6.251 | 82.455 | 1.00 | 32.03 |
| ATOM | 4325 | CG | TYR | 6 | 71.066 | 4.978 | 82.586 | 1.00 | 26.50 |
| ATOM | 4326 | CD1 | TYR | 6 | 70.872 | 4.159 | 83.688 | 1.00 | 25.62 |
| ATOM | 4327 | CE1 | TYR | 6 | 71.551 | 2.961 | 83.769 | 1.00 | 28.52 |
| ATOM | 4328 | CD2 | TYR | 6 | 71.925 | 4.634 | 81.561 | 1.00 | 26.37 |
| ATOM | 4329 | CE2 | TYR | 6 | 72.607 | 3.430 | 81.637 | 1.00 | 28.83 |
| ATOM | 4330 | CZ | TYR | 6 | 72.422 | 2.604 | 82.739 | 1.00 | 28.22 |
| ATOM | 4331 | OH | TYR | 6 | 73.172 | 1.456 | 82.844 | 1.00 | 30.10 |
| ATOM | 4332 | HH | TYR | 6 | 74.065 | 1.601 | 82.505 | 1.00 | 0.00 |
| ATOM | 4333 | C | TYR | 6 | 67.891 | 7.101 | 82.151 | 1.00 | 32.47 |
| ATOM | 4334 | O | TYR | 6 | 67.321 | 7.471 | 81.100 | 1.00 | 31.50 |
| ATOM | 4335 | N | PRO | 7 | 67.662 | 7.710 | 83.321 | 1.00 | 30.37 |
| ATOM | 4336 | CD | PRO | 7 | 68.018 | 7.204 | 84.631 | 1.00 | 27.64 |
| ATOM | 4337 | CA | PRO | 7 | 66.867 | 8.931 | 83.429 | 1.00 | 30.75 |
| ATOM | 4338 | CB | PRO | 7 | 66.845 | 9.236 | 84.903 | 1.00 | 29.60 |
| ATOM | 4339 | CG | PRO | 7 | 66.948 | 7.851 | 85.476 | 1.00 | 30.15 |
| ATOM | 4340 | C | PRO | 7 | 67.430 | 10.072 | 82.599 | 1.00 | 30.04 |
| ATOM | 4341 | O | PRO | 7 | 68.551 | 9.995 | 82.073 | 1.00 | 32.39 |
| ATOM | 4342 | N | LEU | 8 | 66.678 | 11.131 | 82.395 | 1.00 | 28.53 |
| ATOM | 4343 | H | LEU | 8 | 65.747 | 11.108 | 82.710 | 1.00 | 0.00 |
| ATOM | 4344 | CA | LEU | 8 | 67.231 | 12.265 | 81.676 | 1.00 | 27.91 |
| ATOM | 4345 | CB | LEU | 8 | 66.347 | 12.612 | 80.505 | 1.00 | 30.34 |
| ATOM | 4346 | CG | LEU | 8 | 65.873 | 11.530 | 79.554 | 1.00 | 32.13 |
| ATOM | 4347 | CD1 | LEU | 8 | 64.748 | 12.129 | 78.747 | 1.00 | 31.79 |
| ATOM | 4348 | CD2 | LEU | 8 | 67.011 | 11.011 | 78.669 | 1.00 | 32.09 |
| ATOM | 4349 | C | LEU | 8 | 67.292 | 13.459 | 82.607 | 1.00 | 26.46 |
| ATOM | 4350 | O | LEU | 8 | 66.285 | 13.681 | 83.271 | 1.00 | 28.90 |
| ATOM | 4351 | N | GLU | 9 | 68.352 | 14.227 | 82.805 | 1.00 | 24.83 |
| ATOM | 4352 | H | GLU | 9 | 69.210 | 13.979 | 82.407 | 1.00 | 0.00 |
| ATOM | 4353 | CA | GLU | 9 | 68.204 | 15.449 | 83.579 | 1.00 | 25.20 |
| ATOM | 4354 | CB | GLU | 9 | 69.413 | 15.727 | 84.527 | 1.00 | 27.85 |
| ATOM | 4355 | CG | GLU | 9 | 70.848 | 15.880 | 83.980 | 1.00 | 32.21 |
| ATOM | 4356 | CD | GLU | 9 | 71.375 | 17.231 | 83.462 | 1.00 | 33.39 |
| ATOM | 4357 | OE1 | GLU | 9 | 72.445 | 17.228 | 82.826 | 1.00 | 33.56 |
| ATOM | 4358 | OE2 | GLU | 9 | 70.754 | 18.271 | 83.699 | 1.00 | 33.78 |
| ATOM | 4359 | C | GLU | 9 | 68.085 | 16.586 | 82.570 | 1.00 | 25.53 |
| ATOM | 4360 | O | GLU | 9 | 68.608 | 16.510 | 81.452 | 1.00 | 22.83 |
| ATOM | 4361 | N | MET | 10 | 67.355 | 17.638 | 82.985 | 1.00 | 25.63 |
| ATOM | 4362 | H | MET | 10 | 66.913 | 17.531 | 83.857 | 1.00 | 0.00 |
| ATOM | 4363 | CA | MET | 10 | 67.072 | 18.850 | 82.195 | 1.00 | 22.21 |
| ATOM | 4364 | CB | MET | 10 | 65.962 | 18.576 | 81.153 | 1.00 | 20.45 |
| ATOM | 4365 | CG | MET | 10 | 64.683 | 17.900 | 81.644 | 1.00 | 18.85 |
| ATOM | 4366 | SD | MET | 10 | 63.637 | 17.395 | 80.263 | 1.00 | 23.92 |

FIG. 1: A-74

| | | | | | | | | |
|---|---|---|---|---|---|---|---|---|
| ATOM | 4367 | CE | MET | 10 | 64.421 | 15.895 | 79.759 | 1.00 | 19.95 |
| ATOM | 4368 | C | MET | 10 | 66.611 | 20.034 | 83.037 | 1.00 | 21.86 |
| ATOM | 4369 | O | MET | 10 | 66.121 | 19.892 | 84.163 | 1.00 | 22.80 |
| ATOM | 4370 | N | CYS | 11 | 66.659 | 21.232 | 82.498 | 1.00 | 21.34 |
| ATOM | 4371 | H | CYS | 11 | 67.032 | 21.331 | 81.596 | 1.00 | 0.00 |
| ATOM | 4372 | CA | CYS | 11 | 66.130 | 22.399 | 83.210 | 1.00 | 20.10 |
| ATOM | 4373 | CB | CYS | 11 | 67.313 | 23.297 | 83.616 | 1.00 | 20.74 |
| ATOM | 4374 | SG | CYS | 11 | 66.808 | 24.872 | 84.345 | 1.00 | 22.79 |
| ATOM | 4375 | C | CYS | 11 | 65.117 | 23.174 | 82.356 | 1.00 | 18.00 |
| ATOM | 4376 | O | CYS | 11 | 65.406 | 23.571 | 81.242 | 1.00 | 17.85 |
| ATOM | 4377 | N | SER | 12 | 63.914 | 23.453 | 82.797 | 1.00 | 18.58 |
| ATOM | 4378 | H | SER | 12 | 63.704 | 23.255 | 83.738 | 1.00 | 0.00 |
| ATOM | 4379 | CA | SER | 12 | 62.912 | 24.124 | 81.966 | 1.00 | 19.13 |
| ATOM | 4380 | CB | SER | 12 | 62.112 | 23.169 | 81.167 | 1.00 | 19.31 |
| ATOM | 4381 | OG | SER | 12 | 61.608 | 22.112 | 81.995 | 1.00 | 20.90 |
| ATOM | 4382 | HG | SER | 12 | 61.163 | 22.351 | 82.830 | 1.00 | 0.00 |
| ATOM | 4383 | C | SER | 12 | 61.861 | 24.912 | 82.718 | 1.00 | 21.25 |
| ATOM | 4384 | O | SER | 12 | 61.743 | 24.772 | 83.921 | 1.00 | 23.67 |
| ATOM | 4385 | N | HIS | 13 | 60.998 | 25.708 | 82.078 | 1.00 | 22.81 |
| ATOM | 4386 | H | HIS | 13 | 61.113 | 25.793 | 81.114 | 1.00 | 0.00 |
| ATOM | 4387 | CA | HIS | 13 | 59.879 | 26.365 | 82.760 | 1.00 | 20.37 |
| ATOM | 4388 | CB | HIS | 13 | 59.517 | 27.589 | 82.042 | 1.00 | 19.47 |
| ATOM | 4389 | CG | HIS | 13 | 60.525 | 28.699 | 82.196 | 1.00 | 20.32 |
| ATOM | 4390 | CD2 | HIS | 13 | 61.291 | 29.195 | 81.170 | 1.00 | 19.77 |
| ATOM | 4391 | ND1 | HIS | 13 | 60.783 | 29.430 | 83.274 | 1.00 | 20.82 |
| ATOM | 4392 | HD1 | HIS | 13 | 60.411 | 29.335 | 84.180 | 1.00 | 0.00 |
| ATOM | 4393 | CE1 | HIS | 13 | 61.660 | 30.357 | 82.954 | 1.00 | 18.39 |
| ATOM | 4394 | NE2 | HIS | 13 | 61.951 | 30.194 | 81.688 | 1.00 | 19.37 |
| ATOM | 4395 | HE2 | HIS | 13 | 62.549 | 30.804 | 81.193 | 1.00 | 0.00 |
| ATOM | 4396 | C | HIS | 13 | 58.610 | 25.524 | 82.868 | 1.00 | 21.27 |
| ATOM | 4397 | O | HIS | 13 | 57.573 | 25.933 | 83.381 | 1.00 | 23.84 |
| ATOM | 4398 | N | PHE | 14 | 58.667 | 24.308 | 82.371 | 1.00 | 20.73 |
| ATOM | 4399 | H | PHE | 14 | 59.536 | 23.905 | 82.200 | 1.00 | 0.00 |
| ATOM | 4400 | CA | PHE | 14 | 57.495 | 23.461 | 82.292 | 1.00 | 21.21 |
| ATOM | 4401 | CB | PHE | 14 | 57.585 | 22.520 | 81.042 | 1.00 | 19.24 |
| ATOM | 4402 | CG | PHE | 14 | 57.839 | 23.228 | 79.712 | 1.00 | 18.18 |
| ATOM | 4403 | CD1 | PHE | 14 | 58.947 | 22.858 | 78.936 | 1.00 | 19.31 |
| ATOM | 4404 | CD2 | PHE | 14 | 57.045 | 24.310 | 79.299 | 1.00 | 16.17 |
| ATOM | 4405 | CE1 | PHE | 14 | 59.245 | 23.592 | 77.769 | 1.00 | 19.07 |
| ATOM | 4406 | CE2 | PHE | 14 | 57.350 | 25.026 | 78.146 | 1.00 | 8.90 |
| ATOM | 4407 | CZ | PHE | 14 | 58.439 | 24.676 | 77.390 | 1.00 | 14.37 |
| ATOM | 4408 | C | PHE | 14 | 57.247 | 22.598 | 83.529 | 1.00 | 22.84 |
| ATOM | 4409 | O | PHE | 14 | 58.135 | 22.050 | 84.191 | 1.00 | 21.43 |
| ATOM | 4410 | N | ASP | 15 | 55.958 | 22.477 | 83.805 | 1.00 | 24.44 |
| ATOM | 4411 | H | ASP | 15 | 55.343 | 23.099 | 83.374 | 1.00 | 0.00 |
| ATOM | 4412 | CA | ASP | 15 | 55.495 | 21.517 | 84.786 | 1.00 | 25.80 |
| ATOM | 4413 | CB | ASP | 15 | 54.174 | 22.042 | 85.359 | 1.00 | 25.64 |
| ATOM | 4414 | CG | ASP | 15 | 52.939 | 22.084 | 84.464 | 1.00 | 30.17 |
| ATOM | 4415 | OD1 | ASP | 15 | 52.643 | 21.102 | 83.775 | 1.00 | 33.16 |
| ATOM | 4416 | OD2 | ASP | 15 | 52.232 | 23.097 | 84.486 | 1.00 | 31.52 |
| ATOM | 4417 | C | ASP | 15 | 55.342 | 20.120 | 84.158 | 1.00 | 24.87 |
| ATOM | 4418 | O | ASP | 15 | 55.504 | 19.960 | 82.953 | 1.00 | 27.40 |
| ATOM | 4419 | N | ALA | 16 | 54.914 | 19.082 | 84.865 | 1.00 | 27.40 |
| ATOM | 4420 | H | ALA | 16 | 54.813 | 19.226 | 85.828 | 1.00 | 0.00 |
| ATOM | 4421 | CA | ALA | 16 | 54.759 | 17.716 | 84.338 | 1.00 | 25.44 |
| ATOM | 4422 | CB | ALA | 16 | 54.488 | 16.782 | 85.461 | 1.00 | 27.16 |
| ATOM | 4423 | C | ALA | 16 | 53.724 | 17.412 | 83.278 | 1.00 | 26.54 |
| ATOM | 4424 | O | ALA | 16 | 53.877 | 16.410 | 82.580 | 1.00 | 27.26 |
| ATOM | 4425 | N | ASP | 17 | 52.640 | 18.183 | 83.100 | 1.00 | 27.46 |
| ATOM | 4426 | H | ASP | 17 | 52.336 | 18.733 | 83.846 | 1.00 | 0.00 |

FIG. 1: A-75

| ATOM | 4427 | CA | ASP | 17 | 51.791 | 17.989 | 81.901 | 1.00 | 29.39 |
| --- | --- | --- | --- | --- | --- | --- | --- | --- | --- |
| ATOM | 4428 | CB | ASP | 17 | 50.487 | 18.742 | 81.835 | 1.00 | 33.94 |
| ATOM | 4429 | CG | ASP | 17 | 49.555 | 18.585 | 83.005 | 1.00 | 38.23 |
| ATOM | 4430 | OD1 | ASP | 17 | 49.450 | 17.485 | 83.587 | 1.00 | 37.82 |
| ATOM | 4431 | OD2 | ASP | 17 | 48.937 | 19.612 | 83.289 | 1.00 | 40.00 |
| ATOM | 4432 | C | ASP | 17 | 52.468 | 18.540 | 80.654 | 1.00 | 28.81 |
| ATOM | 4433 | O | ASP | 17 | 52.475 | 17.909 | 79.587 | 1.00 | 26.82 |
| ATOM | 4434 | N | GLU | 18 | 53.089 | 19.727 | 80.860 | 1.00 | 25.40 |
| ATOM | 4435 | H | GLU | 18 | 53.020 | 20.126 | 81.745 | 1.00 | 0.00 |
| ATOM | 4436 | CA | GLU | 18 | 53.802 | 20.411 | 79.783 | 1.00 | 22.90 |
| ATOM | 4437 | CB | GLU | 18 | 54.403 | 21.701 | 80.171 | 1.00 | 20.45 |
| ATOM | 4438 | CG | GLU | 18 | 53.327 | 22.510 | 80.807 | 1.00 | 23.40 |
| ATOM | 4439 | CD | GLU | 18 | 53.580 | 23.991 | 80.803 | 1.00 | 27.53 |
| ATOM | 4440 | OE1 | GLU | 18 | 52.814 | 24.682 | 80.141 | 1.00 | 29.77 |
| ATOM | 4441 | OE2 | GLU | 18 | 54.527 | 24.456 | 81.442 | 1.00 | 31.72 |
| ATOM | 4442 | C | GLU | 18 | 54.932 | 19.573 | 79.301 | 1.00 | 22.97 |
| ATOM | 4443 | O | GLU | 18 | 55.052 | 19.417 | 78.094 | 1.00 | 25.32 |
| ATOM | 4444 | N | ILE | 19 | 55.704 | 18.938 | 80.196 | 1.00 | 22.77 |
| ATOM | 4445 | H | ILE | 19 | 55.631 | 19.158 | 81.148 | 1.00 | 0.00 |
| ATOM | 4446 | CA | ILE | 19 | 56.737 | 18.044 | 79.704 | 1.00 | 20.13 |
| ATOM | 4447 | CB | ILE | 19 | 57.718 | 17.616 | 80.809 | 1.00 | 17.46 |
| ATOM | 4448 | CG2 | ILE | 19 | 58.753 | 16.592 | 80.315 | 1.00 | 12.45 |
| ATOM | 4449 | CG1 | ILE | 19 | 58.413 | 18.866 | 81.270 | 1.00 | 14.53 |
| ATOM | 4450 | CD1 | ILE | 19 | 59.419 | 18.623 | 82.367 | 1.00 | 14.67 |
| ATOM | 4451 | C | ILE | 19 | 56.087 | 16.834 | 79.121 | 1.00 | 21.16 |
| ATOM | 4452 | O | ILE | 19 | 56.491 | 16.416 | 78.058 | 1.00 | 25.31 |
| ATOM | 4453 | N | ALA | 20 | 55.050 | 16.247 | 79.678 | 1.00 | 25.11 |
| ATOM | 4454 | H | ALA | 20 | 54.704 | 16.581 | 80.530 | 1.00 | 0.00 |
| ATOM | 4455 | CA | ALA | 20 | 54.464 | 15.046 | 79.084 | 1.00 | 28.76 |
| ATOM | 4456 | CB | ALA | 20 | 53.342 | 14.610 | 80.026 | 1.00 | 26.76 |
| ATOM | 4457 | C | ALA | 20 | 53.940 | 15.208 | 77.629 | 1.00 | 31.53 |
| ATOM | 4458 | O | ALA | 20 | 54.259 | 14.483 | 76.664 | 1.00 | 29.66 |
| ATOM | 4459 | N | ARG | 21 | 53.174 | 16.286 | 77.452 | 1.00 | 33.34 |
| ATOM | 4460 | H | ARG | 21 | 53.024 | 16.870 | 78.214 | 1.00 | 0.00 |
| ATOM | 4461 | CA | ARG | 21 | 52.546 | 16.561 | 76.171 | 1.00 | 34.72 |
| ATOM | 4462 | CB | ARG | 21 | 51.484 | 17.625 | 76.382 | 1.00 | 37.21 |
| ATOM | 4463 | CG | ARG | 21 | 50.508 | 17.344 | 77.576 | 1.00 | 42.09 |
| ATOM | 4464 | CD | ARG | 21 | 49.773 | 15.990 | 77.888 | 1.00 | 44.07 |
| ATOM | 4465 | NE | ARG | 21 | 49.126 | 16.029 | 79.210 | 1.00 | 43.55 |
| ATOM | 4466 | HE | ARG | 21 | 49.431 | 15.387 | 79.884 | 1.00 | 0.00 |
| ATOM | 4467 | CZ | ARG | 21 | 48.130 | 16.891 | 79.565 | 1.00 | 40.96 |
| ATOM | 4468 | NH1 | ARG | 21 | 47.607 | 16.877 | 80.795 | 1.00 | 39.06 |
| ATOM | 4469 | HH11 | ARG | 21 | 47.945 | 16.220 | 81.470 | 1.00 | 0.00 |
| ATOM | 4470 | HH12 | ARG | 21 | 46.874 | 17.511 | 81.038 | 1.00 | 0.00 |
| ATOM | 4471 | NH2 | ARG | 21 | 47.585 | 17.757 | 78.723 | 1.00 | 39.24 |
| ATOM | 4472 | HH21 | ARG | 21 | 47.897 | 17.806 | 77.775 | 1.00 | 0.00 |
| ATOM | 4473 | HH22 | ARG | 21 | 46.857 | 18.363 | 79.042 | 1.00 | 0.00 |
| ATOM | 4474 | C | ARG | 21 | 53.578 | 16.976 | 75.137 | 1.00 | 34.10 |
| ATOM | 4475 | O | ARG | 21 | 53.572 | 16.540 | 73.982 | 1.00 | 36.49 |
| ATOM | 4476 | N | LEU | 22 | 54.592 | 17.689 | 75.594 | 1.00 | 32.79 |
| ATOM | 4477 | H | LEU | 22 | 54.554 | 18.021 | 76.518 | 1.00 | 0.00 |
| ATOM | 4478 | CA | LEU | 22 | 55.742 | 18.014 | 74.753 | 1.00 | 31.82 |
| ATOM | 4479 | CB | LEU | 22 | 56.576 | 19.022 | 75.547 | 1.00 | 31.09 |
| ATOM | 4480 | CG | LEU | 22 | 57.371 | 20.172 | 74.976 | 1.00 | 30.54 |
| ATOM | 4481 | CD1 | LEU | 22 | 56.600 | 21.072 | 74.038 | 1.00 | 25.60 |
| ATOM | 4482 | CD2 | LEU | 22 | 57.751 | 20.993 | 76.155 | 1.00 | 25.45 |
| ATOM | 4483 | C | LEU | 22 | 56.505 | 16.724 | 74.404 | 1.00 | 31.42 |
| ATOM | 4484 | O | LEU | 22 | 57.049 | 16.559 | 73.309 | 1.00 | 34.16 |
| ATOM | 4485 | N | GLY | 23 | 56.508 | 15.713 | 75.266 | 1.00 | 30.31 |
| ATOM | 4486 | H | GLY | 23 | 56.151 | 15.866 | 76.166 | 1.00 | 0.00 |

FIG. 1: A-76

| ATOM | 4487 | CA | GLY | 23 | 57.120 | 14.426 | 74.949 | 1.00 | 30.03 |
| --- | --- | --- | --- | --- | --- | --- | --- | --- | --- |
| ATOM | 4488 | C | GLY | 23 | 56.283 | 13.631 | 73.940 | 1.00 | 31.87 |
| ATOM | 4489 | O | GLY | 23 | 56.802 | 12.832 | 73.149 | 1.00 | 33.29 |
| ATOM | 4490 | N | ALA | 24 | 54.951 | 13.828 | 73.931 | 1.00 | 31.23 |
| ATOM | 4491 | H | ALA | 24 | 54.570 | 14.353 | 74.665 | 1.00 | 0.00 |
| ATOM | 4492 | CA | ALA | 24 | 54.059 | 13.195 | 72.941 | 1.00 | 28.78 |
| ATOM | 4493 | CB | ALA | 24 | 52.620 | 13.561 | 73.295 | 1.00 | 28.27 |
| ATOM | 4494 | C | ALA | 24 | 54.380 | 13.632 | 71.493 | 1.00 | 28.51 |
| ATOM | 4495 | O | ALA | 24 | 54.628 | 12.821 | 70.568 | 1.00 | 27.58 |
| ATOM | 4496 | N | ARG | 25 | 54.457 | 14.971 | 71.328 | 1.00 | 24.88 |
| ATOM | 4497 | H | ARG | 25 | 54.180 | 15.536 | 72.083 | 1.00 | 0.00 |
| ATOM | 4498 | CA | ARG | 25 | 54.969 | 15.532 | 70.078 | 1.00 | 22.10 |
| ATOM | 4499 | CB | ARG | 25 | 55.001 | 17.023 | 70.186 | 1.00 | 16.85 |
| ATOM | 4500 | CG | ARG | 25 | 53.679 | 17.556 | 70.634 | 1.00 | 17.34 |
| ATOM | 4501 | CD | ARG | 25 | 53.907 | 18.813 | 71.436 | 1.00 | 16.25 |
| ATOM | 4502 | NE | ARG | 25 | 52.799 | 19.693 | 71.198 | 1.00 | 20.00 |
| ATOM | 4503 | HE | ARG | 25 | 52.500 | 19.811 | 70.272 | 1.00 | 0.00 |
| ATOM | 4504 | CZ | ARG | 25 | 52.131 | 20.359 | 72.139 | 1.00 | 25.33 |
| ATOM | 4505 | NH1 | ARG | 25 | 51.151 | 21.166 | 71.710 | 1.00 | 25.36 |
| ATOM | 4506 | HH11 | ARG | 25 | 50.942 | 21.226 | 70.734 | 1.00 | 0.00 |
| ATOM | 4507 | HH12 | ARG | 25 | 50.601 | 21.674 | 72.372 | 1.00 | 0.00 |
| ATOM | 4508 | NH2 | ARG | 25 | 52.374 | 20.245 | 73.465 | 1.00 | 27.50 |
| ATOM | 4509 | HH21 | ARG | 25 | 53.101 | 19.639 | 73.785 | 1.00 | 0.00 |
| ATOM | 4510 | HH22 | ARG | 25 | 51.836 | 20.774 | 74.121 | 1.00 | 0.00 |
| ATOM | 4511 | C | ARG | 25 | 56.392 | 14.997 | 69.779 | 1.00 | 23.93 |
| ATOM | 4512 | O | ARG | 25 | 56.583 | 14.399 | 68.724 | 1.00 | 25.12 |
| ATOM | 4513 | N | PHE | 26 | 57.425 | 15.031 | 70.644 | 1.00 | 26.26 |
| ATOM | 4514 | H | PHE | 26 | 57.287 | 15.482 | 71.506 | 1.00 | 0.00 |
| ATOM | 4515 | CA | PHE | 26 | 58.765 | 14.508 | 70.296 | 1.00 | 27.68 |
| ATOM | 4516 | CB | PHE | 26 | 59.687 | 14.541 | 71.498 | 1.00 | 27.32 |
| ATOM | 4517 | CG | PHE | 26 | 61.142 | 14.205 | 71.185 | 1.00 | 24.72 |
| ATOM | 4518 | CD1 | PHE | 26 | 62.020 | 15.232 | 70.805 | 1.00 | 24.07 |
| ATOM | 4519 | CD2 | PHE | 26 | 61.617 | 12.886 | 71.279 | 1.00 | 23.51 |
| ATOM | 4520 | CE1 | PHE | 26 | 63.368 | 14.950 | 70.518 | 1.00 | 21.75 |
| ATOM | 4521 | CE2 | PHE | 26 | 62.959 | 12.620 | 70.991 | 1.00 | 21.50 |
| ATOM | 4522 | CZ | PHE | 26 | 63.838 | 13.646 | 70.610 | 1.00 | 18.22 |
| ATOM | 4523 | C | PHE | 26 | 58.782 | 13.085 | 69.769 | 1.00 | 29.91 |
| ATOM | 4524 | O | PHE | 26 | 59.440 | 12.738 | 68.784 | 1.00 | 29.09 |
| ATOM | 4525 | N | ALA | 27 | 58.017 | 12.248 | 70.469 | 1.00 | 34.66 |
| ATOM | 4526 | H | ALA | 27 | 57.592 | 12.567 | 71.294 | 1.00 | 0.00 |
| ATOM | 4527 | CA | ALA | 27 | 57.798 | 10.865 | 70.034 | 1.00 | 37.38 |
| ATOM | 4528 | CB | ALA | 27 | 57.023 | 10.092 | 71.128 | 1.00 | 34.12 |
| ATOM | 4529 | C | ALA | 27 | 57.033 | 10.817 | 68.688 | 1.00 | 38.26 |
| ATOM | 4530 | O | ALA | 27 | 57.488 | 10.061 | 67.818 | 1.00 | 38.75 |
| ATOM | 4531 | N | LYS | 28 | 55.990 | 11.643 | 68.388 | 1.00 | 37.68 |
| ATOM | 4532 | H | LYS | 28 | 55.680 | 12.266 | 69.076 | 1.00 | 0.00 |
| ATOM | 4533 | CA | LYS | 28 | 55.353 | 11.623 | 67.046 | 1.00 | 37.22 |
| ATOM | 4534 | CB | LYS | 28 | 54.191 | 12.618 | 66.904 | 1.00 | 36.44 |
| ATOM | 4535 | CG | LYS | 28 | 52.900 | 12.336 | 67.687 | 1.00 | 36.78 |
| ATOM | 4536 | CD | LYS | 28 | 52.030 | 13.587 | 67.836 | 1.00 | 35.42 |
| ATOM | 4537 | CE | LYS | 28 | 51.016 | 13.576 | 69.004 | 1.00 | 34.61 |
| ATOM | 4538 | NZ | LYS | 28 | 50.402 | 14.899 | 69.149 | 1.00 | 28.68 |
| ATOM | 4539 | HZ1 | LYS | 28 | 49.693 | 14.860 | 69.909 | 1.00 | 0.00 |
| ATOM | 4540 | HZ2 | LYS | 28 | 49.930 | 15.152 | 68.257 | 1.00 | 0.00 |
| ATOM | 4541 | HZ3 | LYS | 28 | 51.122 | 15.611 | 69.379 | 1.00 | 0.00 |
| ATOM | 4542 | C | LYS | 28 | 56.331 | 11.966 | 65.925 | 1.00 | 38.00 |
| ATOM | 4543 | O | LYS | 28 | 56.240 | 11.494 | 64.796 | 1.00 | 40.42 |
| ATOM | 4544 | N | LEU | 29 | 57.318 | 12.781 | 66.261 | 1.00 | 38.23 |
| ATOM | 4545 | H | LEU | 29 | 57.290 | 13.164 | 67.164 | 1.00 | 0.00 |
| ATOM | 4546 | CA | LEU | 29 | 58.371 | 13.179 | 65.348 | 1.00 | 38.73 |

FIG. 1: A-77

| ATOM | 4547 | CB | LEU | 29 | 58.956 | 14.536 | 65.726 | 1.00 | 37.72 |
|---|---|---|---|---|---|---|---|---|---|
| ATOM | 4548 | CG | LEU | 29 | 58.235 | 15.868 | 65.747 | 1.00 | 35.83 |
| ATOM | 4549 | CD1 | LEU | 29 | 58.906 | 16.782 | 66.772 | 1.00 | 35.68 |
| ATOM | 4550 | CD2 | LEU | 29 | 58.271 | 16.484 | 64.373 | 1.00 | 33.58 |
| ATOM | 4551 | C | LEU | 29 | 59.574 | 12.250 | 65.244 | 1.00 | 40.44 |
| ATOM | 4552 | O | LEU | 29 | 60.290 | 12.311 | 64.244 | 1.00 | 42.13 |
| ATOM | 4553 | N | ASP | 30 | 59.926 | 11.433 | 66.241 | 1.00 | 42.58 |
| ATOM | 4554 | H | ASP | 30 | 59.384 | 11.435 | 67.060 | 1.00 | 0.00 |
| ATOM | 4555 | CA | ASP | 30 | 61.185 | 10.651 | 66.185 | 1.00 | 42.30 |
| ATOM | 4556 | CB | ASP | 30 | 61.405 | 9.946 | 67.540 | 1.00 | 43.54 |
| ATOM | 4557 | CG | ASP | 30 | 62.812 | 9.482 | 67.936 | 1.00 | 44.15 |
| ATOM | 4558 | OD1 | ASP | 30 | 62.936 | 8.960 | 69.053 | 1.00 | 44.88 |
| ATOM | 4559 | OD2 | ASP | 30 | 63.774 | 9.624 | 67.171 | 1.00 | 43.78 |
| ATOM | 4560 | C | ASP | 30 | 61.403 | 9.623 | 65.076 | 1.00 | 41.27 |
| ATOM | 4561 | O | ASP | 30 | 62.575 | 9.342 | 64.812 | 1.00 | 41.73 |
| ATOM | 4562 | N | LEU | 31 | 60.381 | 9.048 | 64.397 | 1.00 | 39.76 |
| ATOM | 4563 | H | LEU | 31 | 59.489 | 9.303 | 64.708 | 1.00 | 0.00 |
| ATOM | 4564 | CA | LEU | 31 | 60.487 | 8.107 | 63.243 | 1.00 | 36.87 |
| ATOM | 4565 | CB | LEU | 31 | 60.409 | 8.876 | 61.929 | 1.00 | 33.02 |
| ATOM | 4566 | CG | LEU | 31 | 59.229 | 9.805 | 61.651 | 1.00 | 30.30 |
| ATOM | 4567 | CD1 | LEU | 31 | 59.542 | 10.513 | 60.367 | 1.00 | 27.67 |
| ATOM | 4568 | CD2 | LEU | 31 | 57.890 | 9.069 | 61.548 | 1.00 | 30.35 |
| ATOM | 4569 | C | LEU | 31 | 61.679 | 7.141 | 63.111 | 1.00 | 36.93 |
| ATOM | 4570 | O | LEU | 31 | 61.462 | 5.954 | 62.946 | 1.00 | 38.62 |
| ATOM | 4571 | N | ASP | 32 | 62.955 | 7.481 | 63.139 | 1.00 | 36.31 |
| ATOM | 4572 | H | ASP | 32 | 63.184 | 8.429 | 63.146 | 1.00 | 0.00 |
| ATOM | 4573 | CA | ASP | 32 | 63.975 | 6.453 | 63.287 | 1.00 | 39.61 |
| ATOM | 4574 | CB | ASP | 32 | 65.355 | 7.007 | 62.836 | 1.00 | 41.25 |
| ATOM | 4575 | CG | ASP | 32 | 65.512 | 7.129 | 61.301 | 1.00 | 45.97 |
| ATOM | 4576 | OD1 | ASP | 32 | 64.963 | 8.080 | 60.706 | 1.00 | 47.73 |
| ATOM | 4577 | OD2 | ASP | 32 | 66.186 | 6.269 | 60.702 | 1.00 | 44.58 |
| ATOM | 4578 | C | ASP | 32 | 64.048 | 5.950 | 64.750 | 1.00 | 41.47 |
| ATOM | 4579 | O | ASP | 32 | 64.851 | 5.091 | 65.123 | 1.00 | 42.13 |
| ATOM | 4580 | N | ASN | 33 | 63.213 | 6.448 | 65.671 | 1.00 | 42.53 |
| ATOM | 4581 | H | ASN | 33 | 62.543 | 7.091 | 65.364 | 1.00 | 0.00 |
| ATOM | 4582 | CA | ASN | 33 | 63.236 | 6.130 | 67.111 | 1.00 | 42.93 |
| ATOM | 4583 | CB | ASN | 33 | 62.403 | 4.893 | 67.366 | 1.00 | 42.09 |
| ATOM | 4584 | CG | ASN | 33 | 60.983 | 5.238 | 66.960 | 1.00 | 43.57 |
| ATOM | 4585 | OD1 | ASN | 33 | 60.641 | 6.390 | 66.680 | 1.00 | 43.22 |
| ATOM | 4586 | ND2 | ASN | 33 | 60.075 | 4.304 | 66.810 | 1.00 | 43.38 |
| ATOM | 4587 | HD21 | ASN | 33 | 60.321 | 3.372 | 66.936 | 1.00 | 0.00 |
| ATOM | 4588 | HD22 | ASN | 33 | 59.201 | 4.657 | 66.555 | 1.00 | 0.00 |
| ATOM | 4589 | C | ASN | 33 | 64.569 | 5.983 | 67.823 | 1.00 | 43.78 |
| ATOM | 4590 | O | ASN | 33 | 64.752 | 5.368 | 68.880 | 1.00 | 45.36 |
| ATOM | 4591 | N | SER | 34 | 65.475 | 6.789 | 67.272 | 1.00 | 44.51 |
| ATOM | 4592 | H | SER | 34 | 65.227 | 7.281 | 66.463 | 1.00 | 0.00 |
| ATOM | 4593 | CA | SER | 34 | 66.853 | 6.941 | 67.757 | 1.00 | 44.38 |
| ATOM | 4594 | CB | SER | 34 | 67.671 | 7.741 | 66.746 | 1.00 | 45.95 |
| ATOM | 4595 | OG | SER | 34 | 66.852 | 8.737 | 66.109 | 1.00 | 46.88 |
| ATOM | 4596 | HG | SER | 34 | 66.714 | 9.521 | 66.662 | 1.00 | 0.00 |
| ATOM | 4597 | C | SER | 34 | 66.979 | 7.644 | 69.097 | 1.00 | 42.56 |
| ATOM | 4598 | O | SER | 34 | 68.050 | 7.729 | 69.714 | 1.00 | 42.02 |
| ATOM | 4599 | N | GLY | 35 | 65.847 | 8.199 | 69.538 | 1.00 | 39.70 |
| ATOM | 4600 | H | GLY | 35 | 65.011 | 7.996 | 69.078 | 1.00 | 0.00 |
| ATOM | 4601 | CA | GLY | 35 | 65.850 | 8.998 | 70.742 | 1.00 | 38.72 |
| ATOM | 4602 | C | GLY | 35 | 66.148 | 10.399 | 70.278 | 1.00 | 38.78 |
| ATOM | 4603 | O | GLY | 35 | 65.267 | 11.241 | 70.328 | 1.00 | 38.52 |
| ATOM | 4604 | N | SER | 36 | 67.359 | 10.679 | 69.756 | 1.00 | 37.34 |
| ATOM | 4605 | H | SER | 36 | 68.051 | 9.988 | 69.819 | 1.00 | 0.00 |
| ATOM | 4606 | CA | SER | 36 | 67.611 | 11.971 | 69.129 | 1.00 | 33.09 |

FIG. 1: A-78

| ATOM | 4607 | CB | SER | 36 | 68.969 | 12.027 | 68.564 | 1.00 | 32.13 |
| --- | --- | --- | --- | --- | --- | --- | --- | --- | --- |
| ATOM | 4608 | OG | SER | 36 | 69.912 | 12.565 | 69.472 | 1.00 | 33.95 |
| ATOM | 4609 | HG | SER | 36 | 69.963 | 13.526 | 69.386 | 1.00 | 0.00 |
| ATOM | 4610 | C | SER | 36 | 66.653 | 12.227 | 67.988 | 1.00 | 33.28 |
| ATOM | 4611 | O | SER | 36 | 66.100 | 11.269 | 67.472 | 1.00 | 36.15 |
| ATOM | 4612 | N | LEU | 37 | 66.380 | 13.471 | 67.603 | 1.00 | 33.98 |
| ATOM | 4613 | H | LEU | 37 | 66.635 | 14.189 | 68.217 | 1.00 | 0.00 |
| ATOM | 4614 | CA | LEU | 37 | 65.519 | 13.861 | 66.476 | 1.00 | 31.74 |
| ATOM | 4615 | CB | LEU | 37 | 64.579 | 14.905 | 67.038 | 1.00 | 30.55 |
| ATOM | 4616 | CG | LEU | 37 | 63.206 | 15.137 | 66.562 | 1.00 | 29.82 |
| ATOM | 4617 | CD1 | LEU | 37 | 62.397 | 13.891 | 66.759 | 1.00 | 32.01 |
| ATOM | 4618 | CD2 | LEU | 37 | 62.573 | 16.218 | 67.398 | 1.00 | 31.36 |
| ATOM | 4619 | C | LEU | 37 | 66.347 | 14.405 | 65.301 | 1.00 | 32.42 |
| ATOM | 4620 | O | LEU | 37 | 66.976 | 15.461 | 65.371 | 1.00 | 30.47 |
| ATOM | 4621 | N | GLY | 38 | 66.429 | 13.696 | 64.175 | 1.00 | 37.35 |
| ATOM | 4622 | H | GLY | 38 | 65.894 | 12.874 | 64.157 | 1.00 | 0.00 |
| ATOM | 4623 | CA | GLY | 38 | 67.269 | 14.061 | 62.995 | 1.00 | 37.14 |
| ATOM | 4624 | C | GLY | 38 | 66.775 | 15.204 | 62.106 | 1.00 | 37.17 |
| ATOM | 4625 | O | GLY | 38 | 65.563 | 15.430 | 62.038 | 1.00 | 39.62 |
| ATOM | 4626 | N | VAL | 39 | 67.642 | 15.934 | 61.383 | 1.00 | 35.67 |
| ATOM | 4627 | H | VAL | 39 | 68.591 | 15.799 | 61.578 | 1.00 | 0.00 |
| ATOM | 4628 | CA | VAL | 39 | 67.209 | 17.033 | 60.480 | 1.00 | 35.70 |
| ATOM | 4629 | CB | VAL | 39 | 68.392 | 17.525 | 59.588 | 1.00 | 36.97 |
| ATOM | 4630 | CG1 | VAL | 39 | 67.933 | 18.850 | 58.978 | 1.00 | 36.00 |
| ATOM | 4631 | CG2 | VAL | 39 | 69.722 | 17.650 | 60.328 | 1.00 | 36.41 |
| ATOM | 4632 | C | VAL | 39 | 66.037 | 16.725 | 59.501 | 1.00 | 36.52 |
| ATOM | 4633 | O | VAL | 39 | 65.116 | 17.515 | 59.220 | 1.00 | 33.21 |
| ATOM | 4634 | N | GLY | 40 | 66.158 | 15.496 | 58.944 | 1.00 | 38.25 |
| ATOM | 4635 | H | GLY | 40 | 66.985 | 15.014 | 59.131 | 1.00 | 0.00 |
| ATOM | 4636 | CA | GLY | 40 | 65.171 | 14.910 | 58.037 | 1.00 | 37.84 |
| ATOM | 4637 | C | GLY | 40 | 63.731 | 15.020 | 58.555 | 1.00 | 37.95 |
| ATOM | 4638 | O | GLY | 40 | 62.882 | 15.643 | 57.922 | 1.00 | 39.33 |
| ATOM | 4639 | N | GLU | 41 | 63.477 | 14.523 | 59.770 | 1.00 | 38.27 |
| ATOM | 4640 | H | GLU | 41 | 64.241 | 14.224 | 60.300 | 1.00 | 0.00 |
| ATOM | 4641 | CA | GLU | 41 | 62.140 | 14.479 | 60.394 | 1.00 | 37.37 |
| ATOM | 4642 | CB | GLU | 41 | 62.206 | 13.756 | 61.714 | 1.00 | 40.29 |
| ATOM | 4643 | CG | GLU | 41 | 62.421 | 12.263 | 61.445 | 1.00 | 42.63 |
| ATOM | 4644 | CD | GLU | 41 | 63.051 | 11.431 | 62.557 | 1.00 | 44.09 |
| ATOM | 4645 | OE1 | GLU | 41 | 63.188 | 11.893 | 63.690 | 1.00 | 44.47 |
| ATOM | 4646 | OE2 | GLU | 41 | 63.407 | 10.288 | 62.275 | 1.00 | 44.86 |
| ATOM | 4647 | C | GLU | 41 | 61.520 | 15.823 | 60.644 | 1.00 | 35.58 |
| ATOM | 4648 | O | GLU | 41 | 60.311 | 16.021 | 60.623 | 1.00 | 35.78 |
| ATOM | 4649 | N | PHE | 42 | 62.405 | 16.777 | 60.904 | 1.00 | 36.39 |
| ATOM | 4650 | H | PHE | 42 | 63.335 | 16.526 | 61.061 | 1.00 | 0.00 |
| ATOM | 4651 | CA | PHE | 42 | 61.985 | 18.169 | 61.032 | 1.00 | 35.52 |
| ATOM | 4652 | CB | PHE | 42 | 63.214 | 19.013 | 61.495 | 1.00 | 34.46 |
| ATOM | 4653 | CG | PHE | 42 | 63.469 | 19.084 | 63.010 | 1.00 | 33.27 |
| ATOM | 4654 | CD1 | PHE | 42 | 62.569 | 19.771 | 63.852 | 1.00 | 33.16 |
| ATOM | 4655 | CD2 | PHE | 42 | 64.634 | 18.537 | 63.554 | 1.00 | 32.67 |
| ATOM | 4656 | CE1 | PHE | 42 | 62.838 | 19.917 | 65.210 | 1.00 | 29.54 |
| ATOM | 4657 | CE2 | PHE | 42 | 64.891 | 18.692 | 64.919 | 1.00 | 30.12 |
| ATOM | 4658 | CZ | PHE | 42 | 63.998 | 19.378 | 65.742 | 1.00 | 27.83 |
| ATOM | 4659 | C | PHE | 42 | 61.446 | 18.625 | 59.667 | 1.00 | 35.00 |
| ATOM | 4660 | O | PHE | 42 | 60.273 | 18.979 | 59.444 | 1.00 | 33.42 |
| ATOM | 4661 | N | MET | 43 | 62.352 | 18.439 | 58.702 | 1.00 | 36.19 |
| ATOM | 4662 | H | MET | 43 | 63.210 | 18.028 | 58.935 | 1.00 | 0.00 |
| ATOM | 4663 | CA | MET | 43 | 62.067 | 18.765 | 57.322 | 1.00 | 35.94 |
| ATOM | 4664 | CB | MET | 43 | 63.380 | 18.565 | 56.578 | 1.00 | 36.20 |
| ATOM | 4665 | CG | MET | 43 | 64.344 | 19.722 | 56.917 | 1.00 | 37.04 |
| ATOM | 4666 | SD | MET | 43 | 63.563 | 21.344 | 56.618 | 1.00 | 34.77 |

FIG. 1: A-79

| ATOM | 4667 | CE   | MET | 43 | 63.748 | 21.469 | 54.860 | 1.00 | 40.60 |
| ---- | ---- | ---- | --- | -- | ------ | ------ | ------ | ---- | ----- |
| ATOM | 4668 | C    | MET | 43 | 60.891 | 17.994 | 56.713 | 1.00 | 36.44 |
| ATOM | 4669 | O    | MET | 43 | 60.256 | 18.568 | 55.843 | 1.00 | 37.44 |
| ATOM | 4670 | N    | SER | 44 | 60.488 | 16.768 | 57.116 | 1.00 | 37.83 |
| ATOM | 4671 | H    | SER | 44 | 61.071 | 16.277 | 57.728 | 1.00 | 0.00  |
| ATOM | 4672 | CA   | SER | 44 | 59.219 | 16.162 | 56.645 | 1.00 | 38.34 |
| ATOM | 4673 | CB   | SER | 44 | 59.127 | 14.653 | 56.891 | 1.00 | 37.41 |
| ATOM | 4674 | OG   | SER | 44 | 59.265 | 14.146 | 58.207 | 1.00 | 35.40 |
| ATOM | 4675 | HG   | SER | 44 | 58.681 | 14.602 | 58.827 | 1.00 | 0.00  |
| ATOM | 4676 | C    | SER | 44 | 57.903 | 16.718 | 57.213 | 1.00 | 38.60 |
| ATOM | 4677 | O    | SER | 44 | 56.810 | 16.177 | 57.029 | 1.00 | 37.90 |
| ATOM | 4678 | N    | LEU | 45 | 57.931 | 17.820 | 57.949 | 1.00 | 39.42 |
| ATOM | 4679 | H    | LEU | 45 | 58.802 | 18.163 | 58.235 | 1.00 | 0.00  |
| ATOM | 4680 | CA   | LEU | 45 | 56.696 | 18.456 | 58.405 | 1.00 | 40.35 |
| ATOM | 4681 | CB   | LEU | 45 | 57.044 | 19.103 | 59.765 | 1.00 | 38.21 |
| ATOM | 4682 | CG   | LEU | 45 | 57.237 | 18.335 | 61.092 | 1.00 | 33.06 |
| ATOM | 4683 | CD1  | LEU | 45 | 58.179 | 19.066 | 62.019 | 1.00 | 31.72 |
| ATOM | 4684 | CD2  | LEU | 45 | 55.934 | 18.313 | 61.850 | 1.00 | 30.96 |
| ATOM | 4685 | C    | LEU | 45 | 56.166 | 19.484 | 57.366 | 1.00 | 42.87 |
| ATOM | 4686 | O    | LEU | 45 | 56.802 | 19.669 | 56.318 | 1.00 | 43.28 |
| ATOM | 4687 | N    | PRO | 46 | 55.098 | 20.292 | 57.517 | 1.00 | 44.08 |
| ATOM | 4688 | CD   | PRO | 46 | 53.855 | 19.898 | 58.172 | 1.00 | 45.04 |
| ATOM | 4689 | CA   | PRO | 46 | 54.927 | 21.541 | 56.732 | 1.00 | 43.45 |
| ATOM | 4690 | CB   | PRO | 46 | 53.444 | 21.797 | 56.823 | 1.00 | 45.31 |
| ATOM | 4691 | CG   | PRO | 46 | 52.844 | 20.427 | 57.153 | 1.00 | 46.26 |
| ATOM | 4692 | C    | PRO | 46 | 55.792 | 22.728 | 57.199 | 1.00 | 43.68 |
| ATOM | 4693 | O    | PRO | 46 | 55.362 | 23.885 | 57.285 | 1.00 | 43.00 |
| ATOM | 4694 | N    | ALA | 47 | 57.061 | 22.398 | 57.522 | 1.00 | 42.63 |
| ATOM | 4695 | H    | ALA | 47 | 57.329 | 21.500 | 57.252 | 1.00 | 0.00  |
| ATOM | 4696 | CA   | ALA | 47 | 58.099 | 23.288 | 58.077 | 1.00 | 41.49 |
| ATOM | 4697 | CB   | ALA | 47 | 58.938 | 22.537 | 59.178 | 1.00 | 38.87 |
| ATOM | 4698 | C    | ALA | 47 | 59.052 | 23.785 | 56.985 | 1.00 | 39.96 |
| ATOM | 4699 | O    | ALA | 47 | 59.359 | 24.966 | 56.867 | 1.00 | 37.48 |
| ATOM | 4700 | N    | ALA | 48 | 59.526 | 22.835 | 56.169 | 1.00 | 42.03 |
| ATOM | 4701 | H    | ALA | 48 | 59.291 | 21.912 | 56.393 | 1.00 | 0.00  |
| ATOM | 4702 | CA   | ALA | 48 | 60.314 | 23.056 | 54.930 | 1.00 | 42.00 |
| ATOM | 4703 | CB   | ALA | 48 | 60.096 | 21.883 | 53.961 | 1.00 | 41.89 |
| ATOM | 4704 | C    | ALA | 48 | 60.018 | 24.332 | 54.125 | 1.00 | 40.63 |
| ATOM | 4705 | O    | ALA | 48 | 58.877 | 24.820 | 54.128 | 1.00 | 39.97 |
| ATOM | 4706 | N    | GLN | 49 | 60.969 | 24.918 | 53.397 | 1.00 | 38.82 |
| ATOM | 4707 | H    | GLN | 49 | 61.847 | 24.490 | 53.377 | 1.00 | 0.00  |
| ATOM | 4708 | CA   | GLN | 49 | 60.741 | 26.195 | 52.694 | 1.00 | 39.31 |
| ATOM | 4709 | CB   | GLN | 49 | 59.652 | 25.955 | 51.580 | 1.00 | 43.04 |
| ATOM | 4710 | CG   | GLN | 49 | 58.662 | 27.003 | 51.064 | 1.00 | 46.76 |
| ATOM | 4711 | CD   | GLN | 49 | 57.230 | 26.821 | 51.578 | 1.00 | 49.15 |
| ATOM | 4712 | OE1  | GLN | 49 | 56.257 | 27.247 | 50.971 | 1.00 | 50.46 |
| ATOM | 4713 | NE2  | GLN | 49 | 56.877 | 26.201 | 52.673 | 1.00 | 50.49 |
| ATOM | 4714 | HE21 | GLN | 49 | 57.513 | 25.768 | 53.264 | 1.00 | 0.00  |
| ATOM | 4715 | HE22 | GLN | 49 | 55.910 | 26.242 | 52.789 | 1.00 | 0.00  |
| ATOM | 4716 | C    | GLN | 49 | 60.385 | 27.381 | 53.600 | 1.00 | 37.90 |
| ATOM | 4717 | O    | GLN | 49 | 60.813 | 28.491 | 53.303 | 1.00 | 36.12 |
| ATOM | 4718 | N    | ALA | 50 | 59.652 | 27.283 | 54.715 | 1.00 | 39.42 |
| ATOM | 4719 | H    | ALA | 50 | 59.242 | 26.437 | 54.981 | 1.00 | 0.00  |
| ATOM | 4720 | CA   | ALA | 50 | 59.455 | 28.415 | 55.625 | 1.00 | 39.87 |
| ATOM | 4721 | CB   | ALA | 50 | 58.321 | 28.188 | 56.622 | 1.00 | 43.11 |
| ATOM | 4722 | C    | ALA | 50 | 60.713 | 28.701 | 56.442 | 1.00 | 38.16 |
| ATOM | 4723 | O    | ALA | 50 | 61.117 | 28.175 | 57.465 | 1.00 | 35.76 |
| ATOM | 4724 | N    | ASN | 51 | 61.367 | 29.569 | 55.701 | 1.00 | 39.25 |
| ATOM | 4725 | H    | ASN | 51 | 60.965 | 29.761 | 54.825 | 1.00 | 0.00  |
| ATOM | 4726 | CA   | ASN | 51 | 62.639 | 30.147 | 55.959 | 1.00 | 35.30 |

FIG. 1: A-80

| ATOM | 4727 | CB   | ASN | 51 | 62.416 | 31.139 | 56.990 | 1.00 | 37.03 |
|------|------|------|-----|----|--------|--------|--------|------|-------|
| ATOM | 4728 | CG   | ASN | 51 | 63.428 | 32.174 | 56.681 | 1.00 | 40.09 |
| ATOM | 4729 | OD1  | ASN | 51 | 64.610 | 32.006 | 56.925 | 1.00 | 42.52 |
| ATOM | 4730 | ND2  | ASN | 51 | 63.077 | 33.246 | 56.040 | 1.00 | 44.40 |
| ATOM | 4731 | HD21 | ASN | 51 | 63.831 | 33.847 | 55.881 | 1.00 | 0.00  |
| ATOM | 4732 | HD22 | ASN | 51 | 62.155 | 33.379 | 55.763 | 1.00 | 0.00  |
| ATOM | 4733 | C    | ASN | 51 | 63.772 | 29.209 | 56.308 | 1.00 | 35.77 |
| ATOM | 4734 | O    | ASN | 51 | 63.649 | 28.061 | 56.727 | 1.00 | 33.32 |
| ATOM | 4735 | N    | PRO | 52 | 64.953 | 29.684 | 55.976 | 1.00 | 37.71 |
| ATOM | 4736 | CD   | PRO | 52 | 65.255 | 30.167 | 54.609 | 1.00 | 43.47 |
| ATOM | 4737 | CA   | PRO | 52 | 66.182 | 29.192 | 56.555 | 1.00 | 38.05 |
| ATOM | 4738 | CB   | PRO | 52 | 67.256 | 29.796 | 55.696 | 1.00 | 41.31 |
| ATOM | 4739 | CG   | PRO | 52 | 66.676 | 29.631 | 54.303 | 1.00 | 43.68 |
| ATOM | 4740 | C    | PRO | 52 | 66.446 | 29.379 | 58.010 | 1.00 | 36.65 |
| ATOM | 4741 | O    | PRO | 52 | 67.588 | 29.238 | 58.494 | 1.00 | 38.33 |
| ATOM | 4742 | N    | LEU | 53 | 65.336 | 29.657 | 58.704 | 1.00 | 33.10 |
| ATOM | 4743 | H    | LEU | 53 | 64.614 | 30.123 | 58.249 | 1.00 | 0.00  |
| ATOM | 4744 | CA   | LEU | 53 | 65.366 | 29.609 | 60.154 | 1.00 | 28.71 |
| ATOM | 4745 | CB   | LEU | 53 | 64.289 | 30.519 | 60.722 | 1.00 | 24.11 |
| ATOM | 4746 | CG   | LEU | 53 | 64.727 | 32.007 | 60.528 | 1.00 | 23.96 |
| ATOM | 4747 | CD1  | LEU | 53 | 63.753 | 32.993 | 61.136 | 1.00 | 18.97 |
| ATOM | 4748 | CD2  | LEU | 53 | 66.087 | 32.193 | 61.157 | 1.00 | 19.94 |
| ATOM | 4749 | C    | LEU | 53 | 65.246 | 28.202 | 60.679 | 1.00 | 28.10 |
| ATOM | 4750 | O    | LEU | 53 | 65.829 | 27.975 | 61.723 | 1.00 | 29.34 |
| ATOM | 4751 | N    | VAL | 54 | 64.697 | 27.174 | 60.016 | 1.00 | 28.55 |
| ATOM | 4752 | H    | VAL | 54 | 64.172 | 27.372 | 59.208 | 1.00 | 0.00  |
| ATOM | 4753 | CA   | VAL | 54 | 64.735 | 25.797 | 60.549 | 1.00 | 29.15 |
| ATOM | 4754 | CB   | VAL | 54 | 63.950 | 24.806 | 59.660 | 1.00 | 27.63 |
| ATOM | 4755 | CG1  | VAL | 54 | 64.220 | 23.283 | 59.776 | 1.00 | 24.44 |
| ATOM | 4756 | CG2  | VAL | 54 | 62.567 | 25.015 | 60.236 | 1.00 | 27.84 |
| ATOM | 4757 | C    | VAL | 54 | 66.073 | 25.141 | 60.827 | 1.00 | 29.87 |
| ATOM | 4758 | O    | VAL | 54 | 66.279 | 24.627 | 61.933 | 1.00 | 33.39 |
| ATOM | 4759 | N    | GLN | 55 | 67.033 | 25.101 | 59.922 | 1.00 | 29.85 |
| ATOM | 4760 | H    | GLN | 55 | 66.856 | 25.434 | 59.021 | 1.00 | 0.00  |
| ATOM | 4761 | CA   | GLN | 55 | 68.304 | 24.482 | 60.291 | 1.00 | 29.88 |
| ATOM | 4762 | CB   | GLN | 55 | 69.043 | 24.300 | 59.000 | 1.00 | 32.95 |
| ATOM | 4763 | CG   | GLN | 55 | 70.414 | 23.622 | 59.011 | 1.00 | 35.84 |
| ATOM | 4764 | CD   | GLN | 55 | 70.436 | 22.287 | 59.693 | 1.00 | 36.37 |
| ATOM | 4765 | OE1  | GLN | 55 | 71.135 | 22.093 | 60.666 | 1.00 | 39.75 |
| ATOM | 4766 | NE2  | GLN | 55 | 69.698 | 21.299 | 59.277 | 1.00 | 34.96 |
| ATOM | 4767 | HE21 | GLN | 55 | 69.126 | 21.380 | 58.498 | 1.00 | 0.00  |
| ATOM | 4768 | HE22 | GLN | 55 | 69.827 | 20.512 | 59.838 | 1.00 | 0.00  |
| ATOM | 4769 | C    | GLN | 55 | 69.066 | 25.309 | 61.346 | 1.00 | 28.98 |
| ATOM | 4770 | O    | GLN | 55 | 69.689 | 24.740 | 62.236 | 1.00 | 30.91 |
| ATOM | 4771 | N    | ARG | 56 | 69.003 | 26.647 | 61.338 | 1.00 | 27.89 |
| ATOM | 4772 | H    | ARG | 56 | 68.622 | 27.089 | 60.552 | 1.00 | 0.00  |
| ATOM | 4773 | CA   | ARG | 56 | 69.486 | 27.499 | 62.441 | 1.00 | 26.72 |
| ATOM | 4774 | CB   | ARG | 56 | 69.007 | 28.936 | 62.282 | 1.00 | 26.41 |
| ATOM | 4775 | CG   | ARG | 56 | 69.659 | 29.756 | 61.192 | 1.00 | 24.38 |
| ATOM | 4776 | CD   | ARG | 56 | 70.952 | 30.345 | 61.758 | 1.00 | 29.01 |
| ATOM | 4777 | NE   | ARG | 56 | 72.034 | 29.380 | 61.906 | 1.00 | 29.18 |
| ATOM | 4778 | HE   | ARG | 56 | 72.154 | 28.707 | 61.203 | 1.00 | 0.00  |
| ATOM | 4779 | CZ   | ARG | 56 | 72.884 | 29.362 | 62.926 | 1.00 | 27.05 |
| ATOM | 4780 | NH1  | ARG | 56 | 73.800 | 28.411 | 62.935 | 1.00 | 29.23 |
| ATOM | 4781 | HH11 | ARG | 56 | 74.454 | 28.362 | 63.690 | 1.00 | 0.00  |
| ATOM | 4782 | HH12 | ARG | 56 | 73.838 | 27.739 | 62.196 | 1.00 | 0.00  |
| ATOM | 4783 | NH2  | ARG | 56 | 72.860 | 30.249 | 63.905 | 1.00 | 25.94 |
| ATOM | 4784 | HH21 | ARG | 56 | 72.172 | 30.974 | 63.902 | 1.00 | 0.00  |
| ATOM | 4785 | HH22 | ARG | 56 | 73.517 | 30.189 | 64.656 | 1.00 | 0.00  |
| ATOM | 4786 | C    | ARG | 56 | 68.973 | 27.022 | 63.807 | 1.00 | 26.27 |

FIG. 1: A-81

| | | | | | | | | |
|---|---|---|---|---|---|---|---|---|
| ATOM | 4787 | O | ARG | 56 | 69.749 | 26.616 | 64.665 | 1.00 | 24.82 |
| ATOM | 4788 | N | VAL | 57 | 67.640 | 26.938 | 63.952 | 1.00 | 26.24 |
| ATOM | 4789 | H | VAL | 57 | 67.091 | 27.206 | 63.184 | 1.00 | 0.00 |
| ATOM | 4790 | CA | VAL | 57 | 66.972 | 26.481 | 65.160 | 1.00 | 25.79 |
| ATOM | 4791 | CB | VAL | 57 | 65.466 | 26.552 | 64.962 | 1.00 | 28.37 |
| ATOM | 4792 | CG1 | VAL | 57 | 64.787 | 26.100 | 66.254 | 1.00 | 32.19 |
| ATOM | 4793 | CG2 | VAL | 57 | 65.003 | 27.996 | 64.675 | 1.00 | 27.17 |
| ATOM | 4794 | C | VAL | 57 | 67.360 | 25.076 | 65.581 | 1.00 | 25.61 |
| ATOM | 4795 | O | VAL | 57 | 67.585 | 24.871 | 66.768 | 1.00 | 25.38 |
| ATOM | 4796 | N | ILE | 58 | 67.479 | 24.096 | 64.678 | 1.00 | 27.36 |
| ATOM | 4797 | H | ILE | 58 | 67.162 | 24.279 | 63.769 | 1.00 | 0.00 |
| ATOM | 4798 | CA | ILE | 58 | 68.045 | 22.768 | 65.012 | 1.00 | 27.73 |
| ATOM | 4799 | CB | ILE | 58 | 68.134 | 21.810 | 63.770 | 1.00 | 29.70 |
| ATOM | 4800 | CG2 | ILE | 58 | 68.673 | 20.428 | 64.164 | 1.00 | 29.51 |
| ATOM | 4801 | CG1 | ILE | 58 | 66.753 | 21.608 | 63.187 | 1.00 | 30.90 |
| ATOM | 4802 | CD1 | ILE | 58 | 66.655 | 20.797 | 61.890 | 1.00 | 29.63 |
| ATOM | 4803 | C | ILE | 58 | 69.465 | 22.918 | 65.574 | 1.00 | 27.65 |
| ATOM | 4804 | O | ILE | 58 | 69.786 | 22.424 | 66.658 | 1.00 | 27.43 |
| ATOM | 4805 | N | ASP | 59 | 70.323 | 23.692 | 64.915 | 1.00 | 29.50 |
| ATOM | 4806 | H | ASP | 59 | 70.048 | 24.070 | 64.051 | 1.00 | 0.00 |
| ATOM | 4807 | CA | ASP | 59 | 71.690 | 23.908 | 65.399 | 1.00 | 30.63 |
| ATOM | 4808 | CB | ASP | 59 | 72.453 | 24.726 | 64.337 | 1.00 | 30.52 |
| ATOM | 4809 | CG | ASP | 59 | 72.600 | 23.878 | 63.070 | 1.00 | 32.62 |
| ATOM | 4810 | OD1 | ASP | 59 | 72.680 | 22.653 | 63.173 | 1.00 | 34.14 |
| ATOM | 4811 | OD2 | ASP | 59 | 72.628 | 24.416 | 61.968 | 1.00 | 33.24 |
| ATOM | 4812 | C | ASP | 59 | 71.800 | 24.556 | 66.773 | 1.00 | 31.09 |
| ATOM | 4813 | O | ASP | 59 | 72.611 | 24.136 | 67.612 | 1.00 | 31.17 |
| ATOM | 4814 | N | ILE | 60 | 70.909 | 25.520 | 67.064 | 1.00 | 29.67 |
| ATOM | 4815 | H | ILE | 60 | 70.326 | 25.835 | 66.342 | 1.00 | 0.00 |
| ATOM | 4816 | CA | ILE | 60 | 70.895 | 26.107 | 68.397 | 1.00 | 27.03 |
| ATOM | 4817 | CB | ILE | 60 | 70.127 | 27.412 | 68.330 | 1.00 | 23.72 |
| ATOM | 4818 | CG2 | ILE | 60 | 70.031 | 28.087 | 69.695 | 1.00 | 24.77 |
| ATOM | 4819 | CG1 | ILE | 60 | 70.870 | 28.320 | 67.401 | 1.00 | 17.79 |
| ATOM | 4820 | CD1 | ILE | 60 | 70.019 | 29.539 | 67.147 | 1.00 | 16.29 |
| ATOM | 4821 | C | ILE | 60 | 70.302 | 25.155 | 69.449 | 1.00 | 27.91 |
| ATOM | 4822 | O | ILE | 60 | 70.821 | 25.104 | 70.576 | 1.00 | 29.66 |
| ATOM | 4823 | N | PHE | 61 | 69.264 | 24.362 | 69.086 | 1.00 | 25.45 |
| ATOM | 4824 | H | PHE | 61 | 68.884 | 24.483 | 68.190 | 1.00 | 0.00 |
| ATOM | 4825 | CA | PHE | 61 | 68.691 | 23.356 | 69.986 | 1.00 | 22.23 |
| ATOM | 4826 | CB | PHE | 61 | 67.411 | 22.746 | 69.423 | 1.00 | 19.37 |
| ATOM | 4827 | CG | PHE | 61 | 66.106 | 23.532 | 69.583 | 1.00 | 17.84 |
| ATOM | 4828 | CD1 | PHE | 61 | 64.901 | 22.822 | 69.552 | 1.00 | 18.49 |
| ATOM | 4829 | CD2 | PHE | 61 | 66.076 | 24.930 | 69.737 | 1.00 | 20.62 |
| ATOM | 4830 | CE1 | PHE | 61 | 63.677 | 23.477 | 69.662 | 1.00 | 17.14 |
| ATOM | 4831 | CE2 | PHE | 61 | 64.853 | 25.598 | 69.855 | 1.00 | 20.70 |
| ATOM | 4832 | CZ | PHE | 61 | 63.656 | 24.866 | 69.811 | 1.00 | 21.06 |
| ATOM | 4833 | C | PHE | 61 | 69.676 | 22.234 | 70.223 | 1.00 | 22.94 |
| ATOM | 4834 | O | PHE | 61 | 69.684 | 21.569 | 71.241 | 1.00 | 23.72 |
| ATOM | 4835 | N | ASP | 62 | 70.574 | 22.052 | 69.285 | 1.00 | 25.47 |
| ATOM | 4836 | H | ASP | 62 | 70.508 | 22.617 | 68.488 | 1.00 | 0.00 |
| ATOM | 4837 | CA | ASP | 62 | 71.628 | 21.052 | 69.310 | 1.00 | 27.41 |
| ATOM | 4838 | CB | ASP | 62 | 72.160 | 20.886 | 67.898 | 1.00 | 27.53 |
| ATOM | 4839 | CG | ASP | 62 | 72.771 | 19.532 | 67.656 | 1.00 | 28.86 |
| ATOM | 4840 | OD1 | ASP | 62 | 73.945 | 19.322 | 67.915 | 1.00 | 28.91 |
| ATOM | 4841 | OD2 | ASP | 62 | 72.036 | 18.665 | 67.211 | 1.00 | 31.95 |
| ATOM | 4842 | C | ASP | 62 | 72.786 | 21.374 | 70.236 | 1.00 | 28.90 |
| ATOM | 4843 | O | ASP | 62 | 73.952 | 21.277 | 69.835 | 1.00 | 30.31 |
| ATOM | 4844 | N | THR | 63 | 72.565 | 21.674 | 71.513 | 1.00 | 29.59 |
| ATOM | 4845 | H | THR | 63 | 71.649 | 21.615 | 71.856 | 1.00 | 0.00 |
| ATOM | 4846 | CA | THR | 63 | 73.693 | 22.108 | 72.357 | 1.00 | 31.16 |

FIG. 1: A-82

| ATOM | 4847 | CB | THR | 63 | 73.268 | 22.306 | 73.802 | 1.00 | 27.05 |
| --- | --- | --- | --- | --- | --- | --- | --- | --- | --- |
| ATOM | 4848 | OG1 | THR | 63 | 72.814 | 21.073 | 74.311 | 1.00 | 30.92 |
| ATOM | 4849 | HG1 | THR | 63 | 72.455 | 21.222 | 75.196 | 1.00 | 0.00 |
| ATOM | 4850 | CG2 | THR | 63 | 72.188 | 23.329 | 73.891 | 1.00 | 25.87 |
| ATOM | 4851 | C | THR | 63 | 74.942 | 21.234 | 72.386 | 1.00 | 32.49 |
| ATOM | 4852 | O | THR | 63 | 76.047 | 21.741 | 72.206 | 1.00 | 32.96 |
| ATOM | 4853 | N | ASP | 64 | 74.836 | 19.906 | 72.459 | 1.00 | 36.46 |
| ATOM | 4854 | H | ASP | 64 | 73.938 | 19.531 | 72.560 | 1.00 | 0.00 |
| ATOM | 4855 | CA | ASP | 64 | 76.055 | 19.065 | 72.483 | 1.00 | 38.79 |
| ATOM | 4856 | CB | ASP | 64 | 75.769 | 17.732 | 73.135 | 1.00 | 41.46 |
| ATOM | 4857 | CG | ASP | 64 | 75.061 | 16.776 | 72.202 | 1.00 | 42.82 |
| ATOM | 4858 | OD1 | ASP | 64 | 74.103 | 17.209 | 71.590 | 1.00 | 40.12 |
| ATOM | 4859 | OD2 | ASP | 64 | 75.502 | 15.632 | 72.077 | 1.00 | 48.32 |
| ATOM | 4860 | C | ASP | 64 | 76.742 | 18.753 | 71.155 | 1.00 | 37.76 |
| ATOM | 4861 | O | ASP | 64 | 77.508 | 17.789 | 71.001 | 1.00 | 38.18 |
| ATOM | 4862 | N | GLY | 65 | 76.347 | 19.492 | 70.131 | 1.00 | 37.16 |
| ATOM | 4863 | H | GLY | 65 | 75.662 | 20.185 | 70.252 | 1.00 | 0.00 |
| ATOM | 4864 | CA | GLY | 65 | 77.007 | 19.332 | 68.846 | 1.00 | 36.17 |
| ATOM | 4865 | C | GLY | 65 | 76.661 | 18.095 | 68.052 | 1.00 | 33.75 |
| ATOM | 4866 | O | GLY | 65 | 77.073 | 18.089 | 66.912 | 1.00 | 35.07 |
| ATOM | 4867 | N | ASN | 66 | 75.871 | 17.075 | 68.424 | 1.00 | 35.08 |
| ATOM | 4868 | H | ASN | 66 | 75.559 | 17.024 | 69.349 | 1.00 | 0.00 |
| ATOM | 4869 | CA | ASN | 66 | 75.719 | 15.929 | 67.494 | 1.00 | 33.84 |
| ATOM | 4870 | CB | ASN | 66 | 75.561 | 14.608 | 68.335 | 1.00 | 36.20 |
| ATOM | 4871 | CG | ASN | 66 | 74.281 | 14.223 | 69.056 | 1.00 | 37.54 |
| ATOM | 4872 | OD1 | ASN | 66 | 73.841 | 14.864 | 69.989 | 1.00 | 40.92 |
| ATOM | 4873 | ND2 | ASN | 66 | 73.595 | 13.148 | 68.747 | 1.00 | 38.66 |
| ATOM | 4874 | HD21 | ASN | 66 | 73.879 | 12.590 | 68.005 | 1.00 | 0.00 |
| ATOM | 4875 | HD22 | ASN | 66 | 72.830 | 12.994 | 69.334 | 1.00 | 0.00 |
| ATOM | 4876 | C | ASN | 66 | 74.699 | 15.913 | 66.349 | 1.00 | 29.58 |
| ATOM | 4877 | O | ASN | 66 | 74.259 | 14.863 | 65.859 | 1.00 | 30.26 |
| ATOM | 4878 | N | GLY | 67 | 74.323 | 17.082 | 65.864 | 1.00 | 24.27 |
| ATOM | 4879 | H | GLY | 67 | 74.772 | 17.877 | 66.216 | 1.00 | 0.00 |
| ATOM | 4880 | CA | GLY | 67 | 73.398 | 17.170 | 64.742 | 1.00 | 22.85 |
| ATOM | 4881 | C | GLY | 67 | 71.898 | 16.881 | 64.907 | 1.00 | 23.84 |
| ATOM | 4882 | O | GLY | 67 | 71.041 | 17.499 | 64.260 | 1.00 | 23.40 |
| ATOM | 4883 | N | GLY | 68 | 71.499 | 15.921 | 65.730 | 1.00 | 25.27 |
| ATOM | 4884 | H | GLY | 68 | 72.184 | 15.345 | 66.126 | 1.00 | 0.00 |
| ATOM | 4885 | CA | GLY | 68 | 70.076 | 15.679 | 65.960 | 1.00 | 24.34 |
| ATOM | 4886 | C | GLY | 68 | 69.609 | 16.327 | 67.254 | 1.00 | 26.00 |
| ATOM | 4887 | O | GLY | 68 | 70.302 | 16.371 | 68.263 | 1.00 | 24.97 |
| ATOM | 4888 | N | VAL | 69 | 68.426 | 16.864 | 67.356 | 1.00 | 27.40 |
| ATOM | 4889 | H | VAL | 69 | 67.863 | 16.916 | 66.552 | 1.00 | 0.00 |
| ATOM | 4890 | CA | VAL | 69 | 67.996 | 17.404 | 68.640 | 1.00 | 28.53 |
| ATOM | 4891 | CB | VAL | 69 | 66.939 | 18.488 | 68.317 | 1.00 | 28.35 |
| ATOM | 4892 | CG1 | VAL | 69 | 66.562 | 19.169 | 69.597 | 1.00 | 30.00 |
| ATOM | 4893 | CG2 | VAL | 69 | 67.485 | 19.554 | 67.365 | 1.00 | 25.07 |
| ATOM | 4894 | C | VAL | 69 | 67.485 | 16.310 | 69.609 | 1.00 | 29.91 |
| ATOM | 4895 | O | VAL | 69 | 66.398 | 15.784 | 69.419 | 1.00 | 30.66 |
| ATOM | 4896 | N | ASP | 70 | 68.206 | 15.810 | 70.627 | 1.00 | 31.42 |
| ATOM | 4897 | H | ASP | 70 | 69.149 | 16.073 | 70.660 | 1.00 | 0.00 |
| ATOM | 4898 | CA | ASP | 70 | 67.650 | 14.846 | 71.607 | 1.00 | 30.14 |
| ATOM | 4899 | CB | ASP | 70 | 68.795 | 14.348 | 72.562 | 1.00 | 32.22 |
| ATOM | 4900 | CG | ASP | 70 | 69.533 | 15.249 | 73.573 | 1.00 | 32.20 |
| ATOM | 4901 | OD1 | ASP | 70 | 70.745 | 15.127 | 73.730 | 1.00 | 36.10 |
| ATOM | 4902 | OD2 | ASP | 70 | 68.921 | 16.048 | 74.261 | 1.00 | 33.14 |
| ATOM | 4903 | C | ASP | 70 | 66.449 | 15.301 | 72.474 | 1.00 | 30.31 |
| ATOM | 4904 | O | ASP | 70 | 66.166 | 16.495 | 72.491 | 1.00 | 33.09 |
| ATOM | 4905 | N | PHE | 71 | 65.688 | 14.512 | 73.259 | 1.00 | 27.47 |
| ATOM | 4906 | H | PHE | 71 | 65.814 | 13.545 | 73.187 | 1.00 | 0.00 |

FIG. 1: A-83

| ATOM | 4907 | CA | PHE | 71 | 64.583 | 15.045 | 74.055 | 1.00 | 23.77 |
|---|---|---|---|---|---|---|---|---|---|
| ATOM | 4908 | CB | PHE | 71 | 63.841 | 13.896 | 74.725 | 1.00 | 22.90 |
| ATOM | 4909 | CG | PHE | 71 | 62.600 | 14.336 | 75.496 | 1.00 | 22.35 |
| ATOM | 4910 | CD1 | PHE | 71 | 62.548 | 14.144 | 76.884 | 1.00 | 22.82 |
| ATOM | 4911 | CD2 | PHE | 71 | 61.548 | 14.982 | 74.839 | 1.00 | 21.06 |
| ATOM | 4912 | CE1 | PHE | 71 | 61.462 | 14.598 | 77.629 | 1.00 | 19.30 |
| ATOM | 4913 | CE2 | PHE | 71 | 60.462 | 15.433 | 75.583 | 1.00 | 21.43 |
| ATOM | 4914 | CZ | PHE | 71 | 60.419 | 15.244 | 76.972 | 1.00 | 22.04 |
| ATOM | 4915 | C | PHE | 71 | 64.985 | 16.078 | 75.111 | 1.00 | 25.41 |
| ATOM | 4916 | O | PHE | 71 | 64.254 | 17.059 | 75.269 | 1.00 | 26.02 |
| ATOM | 4917 | N | LYS | 72 | 66.102 | 15.989 | 75.858 | 1.00 | 25.13 |
| ATOM | 4918 | H | LYS | 72 | 66.612 | 15.154 | 75.841 | 1.00 | 0.00 |
| ATOM | 4919 | CA | LYS | 72 | 66.501 | 17.096 | 76.760 | 1.00 | 24.45 |
| ATOM | 4920 | CB | LYS | 72 | 67.846 | 16.833 | 77.420 | 1.00 | 24.51 |
| ATOM | 4921 | CG | LYS | 72 | 68.596 | 18.006 | 78.023 | 1.00 | 21.28 |
| ATOM | 4922 | CD | LYS | 72 | 69.876 | 17.542 | 78.703 | 1.00 | 25.45 |
| ATOM | 4923 | CE | LYS | 72 | 70.655 | 18.784 | 79.080 | 1.00 | 27.81 |
| ATOM | 4924 | NZ | LYS | 72 | 71.497 | 18.588 | 80.248 | 1.00 | 28.70 |
| ATOM | 4925 | HZ1 | LYS | 72 | 72.017 | 19.466 | 80.448 | 1.00 | 0.00 |
| ATOM | 4926 | HZ2 | LYS | 72 | 72.174 | 17.821 | 80.060 | 1.00 | 0.00 |
| ATOM | 4927 | HZ3 | LYS | 72 | 70.914 | 18.340 | 81.073 | 1.00 | 0.00 |
| ATOM | 4928 | C | LYS | 72 | 66.624 | 18.432 | 76.046 | 1.00 | 25.42 |
| ATOM | 4929 | O | LYS | 72 | 66.121 | 19.470 | 76.490 | 1.00 | 28.71 |
| ATOM | 4930 | N | GLU | 73 | 67.269 | 18.380 | 74.890 | 1.00 | 23.15 |
| ATOM | 4931 | H | GLU | 73 | 67.559 | 17.513 | 74.569 | 1.00 | 0.00 |
| ATOM | 4932 | CA | GLU | 73 | 67.446 | 19.553 | 74.065 | 1.00 | 21.70 |
| ATOM | 4933 | CB | GLU | 73 | 68.391 | 19.308 | 72.971 | 1.00 | 25.79 |
| ATOM | 4934 | CG | GLU | 73 | 69.833 | 18.977 | 73.327 | 1.00 | 26.84 |
| ATOM | 4935 | CD | GLU | 73 | 70.626 | 18.572 | 72.099 | 1.00 | 27.35 |
| ATOM | 4936 | OE1 | GLU | 73 | 70.021 | 18.046 | 71.161 | 1.00 | 27.09 |
| ATOM | 4937 | OE2 | GLU | 73 | 71.846 | 18.787 | 72.089 | 1.00 | 29.72 |
| ATOM | 4938 | C | GLU | 73 | 66.160 | 19.989 | 73.406 | 1.00 | 19.96 |
| ATOM | 4939 | O | GLU | 73 | 65.998 | 21.171 | 73.133 | 1.00 | 23.87 |
| ATOM | 4940 | N | PHE | 74 | 65.218 | 19.110 | 73.133 | 1.00 | 15.49 |
| ATOM | 4941 | H | PHE | 74 | 65.428 | 18.158 | 73.190 | 1.00 | 0.00 |
| ATOM | 4942 | CA | PHE | 74 | 63.931 | 19.531 | 72.645 | 1.00 | 16.50 |
| ATOM | 4943 | CB | PHE | 74 | 63.149 | 18.268 | 72.256 | 1.00 | 19.77 |
| ATOM | 4944 | CG | PHE | 74 | 61.725 | 18.509 | 71.737 | 1.00 | 22.83 |
| ATOM | 4945 | CD1 | PHE | 74 | 61.519 | 18.992 | 70.432 | 1.00 | 23.10 |
| ATOM | 4946 | CD2 | PHE | 74 | 60.626 | 18.280 | 72.584 | 1.00 | 21.59 |
| ATOM | 4947 | CE1 | PHE | 74 | 60.212 | 19.250 | 69.988 | 1.00 | 24.60 |
| ATOM | 4948 | CE2 | PHE | 74 | 59.337 | 18.541 | 72.133 | 1.00 | 21.78 |
| ATOM | 4949 | CZ | PHE | 74 | 59.122 | 19.027 | 70.838 | 1.00 | 24.23 |
| ATOM | 4950 | C | PHE | 74 | 63.212 | 20.361 | 73.716 | 1.00 | 17.83 |
| ATOM | 4951 | O | PHE | 74 | 62.683 | 21.433 | 73.406 | 1.00 | 16.95 |
| ATOM | 4952 | N | ILE | 75 | 63.212 | 19.892 | 74.990 | 1.00 | 19.54 |
| ATOM | 4953 | H | ILE | 75 | 63.585 | 18.995 | 75.112 | 1.00 | 0.00 |
| ATOM | 4954 | CA | ILE | 75 | 62.664 | 20.597 | 76.172 | 1.00 | 18.64 |
| ATOM | 4955 | CB | ILE | 75 | 62.690 | 19.628 | 77.407 | 1.00 | 19.68 |
| ATOM | 4956 | CG2 | ILE | 75 | 62.228 | 20.312 | 78.718 | 1.00 | 19.97 |
| ATOM | 4957 | CG1 | ILE | 75 | 61.751 | 18.486 | 77.132 | 1.00 | 16.06 |
| ATOM | 4958 | CD1 | ILE | 75 | 60.285 | 18.853 | 76.886 | 1.00 | 13.75 |
| ATOM | 4959 | C | ILE | 75 | 63.354 | 21.916 | 76.561 | 1.00 | 18.00 |
| ATOM | 4960 | O | ILE | 75 | 62.736 | 22.965 | 76.749 | 1.00 | 16.91 |
| ATOM | 4961 | N | GLU | 76 | 64.662 | 21.855 | 76.764 | 1.00 | 20.17 |
| ATOM | 4962 | H | GLU | 76 | 65.079 | 20.976 | 76.786 | 1.00 | 0.00 |
| ATOM | 4963 | CA | GLU | 76 | 65.473 | 23.046 | 77.028 | 1.00 | 21.98 |
| ATOM | 4964 | CB | GLU | 76 | 66.930 | 22.608 | 77.076 | 1.00 | 23.44 |
| ATOM | 4965 | CG | GLU | 76 | 67.491 | 22.815 | 78.450 | 1.00 | 27.67 |
| ATOM | 4966 | CD | GLU | 76 | 68.336 | 21.682 | 78.998 | 1.00 | 29.76 |

FIG. 1: A-84

| ATOM | 4967 | OE1 | GLU | 76 | 69.556 | 21.760 | 78.940 | 1.00 | 30.95 |
|---|---|---|---|---|---|---|---|---|---|
| ATOM | 4968 | OE2 | GLU | 76 | 67.773 | 20.731 | 79.529 | 1.00 | 33.60 |
| ATOM | 4969 | C | GLU | 76 | 65.253 | 24.130 | 75.958 | 1.00 | 22.04 |
| ATOM | 4970 | O | GLU | 76 | 64.851 | 25.255 | 76.278 | 1.00 | 22.30 |
| ATOM | 4971 | N | GLY | 77 | 65.403 | 23.719 | 74.671 | 1.00 | 20.48 |
| ATOM | 4972 | H | GLY | 77 | 65.743 | 22.811 | 74.545 | 1.00 | 0.00 |
| ATOM | 4973 | CA | GLY | 77 | 65.169 | 24.550 | 73.494 | 1.00 | 16.85 |
| ATOM | 4974 | C | GLY | 77 | 63.773 | 25.164 | 73.406 | 1.00 | 17.32 |
| ATOM | 4975 | O | GLY | 77 | 63.625 | 26.356 | 73.179 | 1.00 | 17.28 |
| ATOM | 4976 | N | VAL | 78 | 62.677 | 24.425 | 73.544 | 1.00 | 19.21 |
| ATOM | 4977 | H | VAL | 78 | 62.787 | 23.453 | 73.650 | 1.00 | 0.00 |
| ATOM | 4978 | CA | VAL | 78 | 61.347 | 25.048 | 73.495 | 1.00 | 20.86 |
| ATOM | 4979 | CB | VAL | 78 | 60.237 | 23.985 | 73.330 | 1.00 | 20.81 |
| ATOM | 4980 | CG1 | VAL | 78 | 58.905 | 24.671 | 73.036 | 1.00 | 18.46 |
| ATOM | 4981 | CG2 | VAL | 78 | 60.589 | 23.043 | 72.204 | 1.00 | 22.50 |
| ATOM | 4982 | C | VAL | 78 | 61.034 | 25.884 | 74.748 | 1.00 | 23.71 |
| ATOM | 4983 | O | VAL | 78 | 60.215 | 26.801 | 74.621 | 1.00 | 25.45 |
| ATOM | 4984 | N | MET | 79 | 61.628 | 25.597 | 75.950 | 1.00 | 24.32 |
| ATOM | 4985 | H | MET | 79 | 62.192 | 24.793 | 75.985 | 1.00 | 0.00 |
| ATOM | 4986 | CA | MET | 79 | 61.510 | 26.409 | 77.174 | 1.00 | 24.58 |
| ATOM | 4987 | CB | MET | 79 | 62.340 | 25.751 | 78.300 | 1.00 | 29.49 |
| ATOM | 4988 | CG | MET | 79 | 62.811 | 26.609 | 79.487 | 1.00 | 36.70 |
| ATOM | 4989 | SD | MET | 79 | 64.621 | 26.923 | 79.690 | 1.00 | 48.09 |
| ATOM | 4990 | CE | MET | 79 | 64.794 | 27.963 | 81.145 | 1.00 | 41.05 |
| ATOM | 4991 | C | MET | 79 | 61.949 | 27.867 | 77.009 | 1.00 | 22.64 |
| ATOM | 4992 | O | MET | 79 | 61.413 | 28.721 | 77.705 | 1.00 | 20.32 |
| ATOM | 4993 | N | GLN | 80 | 62.952 | 28.226 | 76.180 | 1.00 | 23.59 |
| ATOM | 4994 | H | GLN | 80 | 63.527 | 27.497 | 75.851 | 1.00 | 0.00 |
| ATOM | 4995 | CA | GLN | 80 | 63.276 | 29.634 | 75.906 | 1.00 | 24.86 |
| ATOM | 4996 | CB | GLN | 80 | 64.369 | 29.815 | 74.865 | 1.00 | 24.27 |
| ATOM | 4997 | CG | GLN | 80 | 65.557 | 28.925 | 74.812 | 1.00 | 23.03 |
| ATOM | 4998 | CD | GLN | 80 | 66.095 | 28.678 | 76.189 | 1.00 | 26.50 |
| ATOM | 4999 | OE1 | GLN | 80 | 65.893 | 27.629 | 76.783 | 1.00 | 27.80 |
| ATOM | 5000 | NE2 | GLN | 80 | 66.802 | 29.603 | 76.801 | 1.00 | 28.20 |
| ATOM | 5001 | HE21 | GLN | 80 | 67.022 | 30.435 | 76.329 | 1.00 | 0.00 |
| ATOM | 5002 | HE22 | GLN | 80 | 67.134 | 29.324 | 77.676 | 1.00 | 0.00 |
| ATOM | 5003 | C | GLN | 80 | 62.084 | 30.432 | 75.342 | 1.00 | 27.04 |
| ATOM | 5004 | O | GLN | 80 | 61.949 | 31.635 | 75.516 | 1.00 | 28.64 |
| ATOM | 5005 | N | PHE | 81 | 61.162 | 29.742 | 74.688 | 1.00 | 29.96 |
| ATOM | 5006 | H | PHE | 81 | 61.265 | 28.768 | 74.648 | 1.00 | 0.00 |
| ATOM | 5007 | CA | PHE | 81 | 59.979 | 30.303 | 74.064 | 1.00 | 30.84 |
| ATOM | 5008 | CB | PHE | 81 | 59.758 | 29.641 | 72.711 | 1.00 | 32.21 |
| ATOM | 5009 | CG | PHE | 81 | 60.998 | 29.760 | 71.850 | 1.00 | 35.32 |
| ATOM | 5010 | CD1 | PHE | 81 | 61.971 | 28.759 | 71.888 | 1.00 | 34.31 |
| ATOM | 5011 | CD2 | PHE | 81 | 61.143 | 30.874 | 71.018 | 1.00 | 36.97 |
| ATOM | 5012 | CE1 | PHE | 81 | 63.089 | 28.871 | 71.082 | 1.00 | 32.83 |
| ATOM | 5013 | CE2 | PHE | 81 | 62.269 | 30.977 | 70.217 | 1.00 | 34.22 |
| ATOM | 5014 | CZ | PHE | 81 | 63.226 | 29.977 | 70.254 | 1.00 | 34.39 |
| ATOM | 5015 | C | PHE | 81 | 58.743 | 30.112 | 74.897 | 1.00 | 30.57 |
| ATOM | 5016 | O | PHE | 81 | 57.886 | 29.352 | 74.504 | 1.00 | 33.66 |
| ATOM | 5017 | N | VAL | 82 | 58.537 | 30.740 | 76.042 | 1.00 | 32.34 |
| ATOM | 5018 | H | VAL | 82 | 59.243 | 31.346 | 76.337 | 1.00 | 0.00 |
| ATOM | 5019 | CA | VAL | 82 | 57.307 | 30.550 | 76.793 | 1.00 | 31.03 |
| ATOM | 5020 | CB | VAL | 82 | 57.423 | 29.149 | 77.500 | 1.00 | 31.67 |
| ATOM | 5021 | CG1 | VAL | 82 | 58.097 | 29.216 | 78.845 | 1.00 | 31.98 |
| ATOM | 5022 | CG2 | VAL | 82 | 56.019 | 28.571 | 77.610 | 1.00 | 34.97 |
| ATOM | 5023 | C | VAL | 82 | 57.102 | 31.726 | 77.740 | 1.00 | 31.27 |
| ATOM | 5024 | O | VAL | 82 | 55.963 | 32.098 | 78.089 | 1.00 | 32.61 |
| ATOM | 5025 | CB | LYS | 84 | 56.980 | 30.500 | 81.933 | 1.00 | 21.43 |
| ATOM | 5026 | CG | LYS | 84 | 55.808 | 30.277 | 82.848 | 1.00 | 21.83 |

FIG. 1: A-85

| ATOM | 5027 | CD | LYS | 84 | 55.648 | 28.776 | 83.111 | 1.00 | 27.02 |
|---|---|---|---|---|---|---|---|---|---|
| ATOM | 5028 | CE | LYS | 84 | 55.174 | 27.866 | 81.945 | 1.00 | 32.18 |
| ATOM | 5029 | NZ | LYS | 84 | 56.055 | 27.700 | 80.787 | 1.00 | 32.47 |
| ATOM | 5030 | HZ1 | LYS | 84 | 56.953 | 27.274 | 81.095 | 1.00 | 0.00 |
| ATOM | 5031 | HZ2 | LYS | 84 | 56.240 | 28.630 | 80.363 | 1.00 | 0.00 |
| ATOM | 5032 | HZ3 | LYS | 84 | 55.604 | 27.084 | 80.084 | 1.00 | 0.00 |
| ATOM | 5033 | C | LYS | 84 | 58.631 | 32.084 | 81.041 | 1.00 | 24.32 |
| ATOM | 5034 | O | LYS | 84 | 59.415 | 31.883 | 81.960 | 1.00 | 27.07 |
| ATOM | 5035 | HT1 | LYS | 84 | 55.117 | 32.236 | 81.158 | 1.00 | 0.00 |
| ATOM | 5036 | HT2 | LYS | 84 | 55.865 | 31.551 | 79.810 | 1.00 | 0.00 |
| ATOM | 5037 | N | LYS | 84 | 55.999 | 32.231 | 80.593 | 1.00 | 24.15 |
| ATOM | 5038 | HT3 | LYS | 84 | 56.079 | 33.155 | 80.120 | 1.00 | 0.00 |
| ATOM | 5039 | CA | LYS | 84 | 57.147 | 31.913 | 81.449 | 1.00 | 23.63 |
| ATOM | 5040 | N | GLY | 85 | 59.176 | 32.422 | 79.854 | 1.00 | 22.00 |
| ATOM | 5041 | H | GLY | 85 | 58.610 | 32.700 | 79.110 | 1.00 | 0.00 |
| ATOM | 5042 | CA | GLY | 85 | 60.616 | 32.702 | 79.704 | 1.00 | 22.40 |
| ATOM | 5043 | C | GLY | 85 | 60.918 | 34.213 | 79.650 | 1.00 | 23.71 |
| ATOM | 5044 | O | GLY | 85 | 59.958 | 34.897 | 79.289 | 1.00 | 25.16 |
| ATOM | 5045 | N | ASP | 86 | 62.051 | 34.906 | 79.944 | 1.00 | 26.27 |
| ATOM | 5046 | H | ASP | 86 | 62.857 | 34.419 | 80.208 | 1.00 | 0.00 |
| ATOM | 5047 | CA | ASP | 86 | 62.070 | 36.392 | 79.799 | 1.00 | 27.84 |
| ATOM | 5048 | CB | ASP | 86 | 62.359 | 37.112 | 81.179 | 1.00 | 29.81 |
| ATOM | 5049 | CG | ASP | 86 | 62.103 | 38.651 | 81.276 | 1.00 | 33.67 |
| ATOM | 5050 | OD1 | ASP | 86 | 63.002 | 39.403 | 81.679 | 1.00 | 34.79 |
| ATOM | 5051 | OD2 | ASP | 86 | 61.011 | 39.131 | 80.938 | 1.00 | 35.92 |
| ATOM | 5052 | C | ASP | 86 | 63.023 | 37.000 | 78.757 | 1.00 | 26.96 |
| ATOM | 5053 | O | ASP | 86 | 63.932 | 36.353 | 78.259 | 1.00 | 28.38 |
| ATOM | 5054 | N | LYS | 87 | 62.812 | 38.270 | 78.398 | 1.00 | 26.64 |
| ATOM | 5055 | H | LYS | 87 | 62.032 | 38.684 | 78.814 | 1.00 | 0.00 |
| ATOM | 5056 | CA | LYS | 87 | 63.515 | 39.038 | 77.389 | 1.00 | 26.57 |
| ATOM | 5057 | CB | LYS | 87 | 63.348 | 40.521 | 77.837 | 1.00 | 28.92 |
| ATOM | 5058 | CG | LYS | 87 | 64.160 | 41.790 | 77.479 | 1.00 | 29.28 |
| ATOM | 5059 | CD | LYS | 87 | 65.313 | 41.972 | 78.516 | 1.00 | 35.56 |
| ATOM | 5060 | CE | LYS | 87 | 64.873 | 42.020 | 80.040 | 1.00 | 38.72 |
| ATOM | 5061 | NZ | LYS | 87 | 65.921 | 41.646 | 81.009 | 1.00 | 34.40 |
| ATOM | 5062 | HZ1 | LYS | 87 | 66.703 | 42.330 | 80.971 | 1.00 | 0.00 |
| ATOM | 5063 | HZ2 | LYS | 87 | 66.287 | 40.698 | 80.783 | 1.00 | 0.00 |
| ATOM | 5064 | HZ3 | LYS | 87 | 65.530 | 41.630 | 81.971 | 1.00 | 0.00 |
| ATOM | 5065 | C | LYS | 87 | 64.932 | 38.576 | 77.181 | 1.00 | 27.53 |
| ATOM | 5066 | O | LYS | 87 | 65.257 | 38.130 | 76.091 | 1.00 | 31.48 |
| ATOM | 5067 | N | GLU | 88 | 65.727 | 38.403 | 78.223 | 1.00 | 27.03 |
| ATOM | 5068 | H | GLU | 88 | 65.370 | 38.570 | 79.114 | 1.00 | 0.00 |
| ATOM | 5069 | CA | GLU | 88 | 67.122 | 37.986 | 78.035 | 1.00 | 27.90 |
| ATOM | 5070 | CB | GLU | 88 | 67.854 | 38.078 | 79.344 | 1.00 | 29.77 |
| ATOM | 5071 | CG | GLU | 88 | 69.367 | 37.905 | 79.198 | 1.00 | 28.70 |
| ATOM | 5072 | CD | GLU | 88 | 70.077 | 37.855 | 80.525 | 1.00 | 26.54 |
| ATOM | 5073 | OE1 | GLU | 88 | 69.643 | 38.470 | 81.496 | 1.00 | 23.30 |
| ATOM | 5074 | OE2 | GLU | 88 | 71.067 | 37.150 | 80.563 | 1.00 | 27.08 |
| ATOM | 5075 | C | GLU | 88 | 67.428 | 36.612 | 77.456 | 1.00 | 26.23 |
| ATOM | 5076 | O | GLU | 88 | 68.353 | 36.488 | 76.669 | 1.00 | 26.81 |
| ATOM | 5077 | N | GLN | 89 | 66.750 | 35.537 | 77.823 | 1.00 | 27.26 |
| ATOM | 5078 | H | GLN | 89 | 66.034 | 35.646 | 78.485 | 1.00 | 0.00 |
| ATOM | 5079 | CA | GLN | 89 | 67.013 | 34.242 | 77.178 | 1.00 | 30.08 |
| ATOM | 5080 | CB | GLN | 89 | 66.408 | 33.032 | 77.972 | 1.00 | 30.56 |
| ATOM | 5081 | CG | GLN | 89 | 64.892 | 32.963 | 78.354 | 1.00 | 31.83 |
| ATOM | 5082 | CD | GLN | 89 | 64.524 | 31.740 | 79.202 | 1.00 | 26.96 |
| ATOM | 5083 | OE1 | GLN | 89 | 63.788 | 31.804 | 80.172 | 1.00 | 25.64 |
| ATOM | 5084 | NE2 | GLN | 89 | 64.990 | 30.550 | 78.922 | 1.00 | 24.46 |
| ATOM | 5085 | HE21 | GLN | 89 | 64.716 | 29.817 | 79.491 | 1.00 | 0.00 |
| ATOM | 5086 | HE22 | GLN | 89 | 65.566 | 30.460 | 78.142 | 1.00 | 0.00 |

FIG. 1: A-86

| ATOM | 5087 | C | GLN | 89 | 66.423 | 34.265 | 75.763 | 1.00 | 29.96 |
| ATOM | 5088 | O | GLN | 89 | 67.042 | 33.791 | 74.816 | 1.00 | 29.12 |
| ATOM | 5089 | N | LYS | 90 | 65.265 | 34.910 | 75.581 | 1.00 | 30.48 |
| ATOM | 5090 | H | LYS | 90 | 64.799 | 35.277 | 76.364 | 1.00 | 0.00 |
| ATOM | 5091 | CA | LYS | 90 | 64.694 | 35.126 | 74.255 | 1.00 | 29.75 |
| ATOM | 5092 | CB | LYS | 90 | 63.320 | 35.762 | 74.376 | 1.00 | 28.54 |
| ATOM | 5093 | CG | LYS | 90 | 62.330 | 34.820 | 75.060 | 1.00 | 27.21 |
| ATOM | 5094 | CD | LYS | 90 | 60.987 | 35.544 | 75.221 | 1.00 | 28.59 |
| ATOM | 5095 | CE | LYS | 90 | 59.938 | 34.674 | 75.882 | 1.00 | 25.81 |
| ATOM | 5096 | NZ | LYS | 90 | 59.737 | 33.456 | 75.124 | 1.00 | 27.36 |
| ATOM | 5097 | HZ1 | LYS | 90 | 59.436 | 33.727 | 74.168 | 1.00 | 0.00 |
| ATOM | 5098 | HZ2 | LYS | 90 | 59.003 | 32.870 | 75.570 | 1.00 | 0.00 |
| ATOM | 5099 | HZ3 | LYS | 90 | 60.624 | 32.921 | 75.060 | 1.00 | 0.00 |
| ATOM | 5100 | C | LYS | 90 | 65.598 | 36.025 | 73.421 | 1.00 | 28.62 |
| ATOM | 5101 | O | LYS | 90 | 65.580 | 35.939 | 72.194 | 1.00 | 29.68 |
| ATOM | 5102 | N | LEU | 91 | 66.470 | 36.844 | 74.020 | 1.00 | 28.09 |
| ATOM | 5103 | H | LEU | 91 | 66.352 | 37.028 | 74.969 | 1.00 | 0.00 |
| ATOM | 5104 | CA | LEU | 91 | 67.441 | 37.611 | 73.218 | 1.00 | 30.27 |
| ATOM | 5105 | CB | LEU | 91 | 67.594 | 39.011 | 73.790 | 1.00 | 30.59 |
| ATOM | 5106 | CG | LEU | 91 | 66.581 | 39.966 | 73.185 | 1.00 | 31.11 |
| ATOM | 5107 | CD1 | LEU | 91 | 66.497 | 41.228 | 73.992 | 1.00 | 32.24 |
| ATOM | 5108 | CD2 | LEU | 91 | 67.006 | 40.274 | 71.750 | 1.00 | 32.70 |
| ATOM | 5109 | C | LEU | 91 | 68.825 | 36.986 | 73.033 | 1.00 | 30.77 |
| ATOM | 5110 | O | LEU | 91 | 69.498 | 37.172 | 72.010 | 1.00 | 31.76 |
| ATOM | 5111 | N | ARG | 92 | 69.250 | 36.179 | 74.000 | 1.00 | 28.76 |
| ATOM | 5112 | H | ARG | 92 | 68.840 | 36.250 | 74.881 | 1.00 | 0.00 |
| ATOM | 5113 | CA | ARG | 92 | 70.355 | 35.271 | 73.787 | 1.00 | 27.29 |
| ATOM | 5114 | CB | ARG | 92 | 70.659 | 34.407 | 74.994 | 1.00 | 28.38 |
| ATOM | 5115 | CG | ARG | 92 | 71.140 | 35.124 | 76.222 | 1.00 | 29.93 |
| ATOM | 5116 | CD | ARG | 92 | 72.641 | 34.866 | 76.362 | 1.00 | 35.29 |
| ATOM | 5117 | NE | ARG | 92 | 73.286 | 35.926 | 77.133 | 1.00 | 37.73 |
| ATOM | 5118 | HE | ARG | 92 | 73.942 | 36.498 | 76.686 | 1.00 | 0.00 |
| ATOM | 5119 | CZ | ARG | 92 | 73.045 | 36.119 | 78.430 | 1.00 | 37.81 |
| ATOM | 5120 | NH1 | ARG | 92 | 73.600 | 37.160 | 79.045 | 1.00 | 36.85 |
| ATOM | 5121 | HH11 | ARG | 92 | 74.196 | 37.786 | 78.540 | 1.00 | 0.00 |
| ATOM | 5122 | HH12 | ARG | 92 | 73.407 | 37.322 | 80.013 | 1.00 | 0.00 |
| ATOM | 5123 | NH2 | ARG | 92 | 72.293 | 35.267 | 79.131 | 1.00 | 38.94 |
| ATOM | 5124 | HH21 | ARG | 92 | 72.106 | 35.443 | 80.097 | 1.00 | 0.00 |
| ATOM | 5125 | HH22 | ARG | 92 | 71.878 | 34.476 | 78.682 | 1.00 | 0.00 |
| ATOM | 5126 | C | ARG | 92 | 69.935 | 34.308 | 72.676 | 1.00 | 27.47 |
| ATOM | 5127 | O | ARG | 92 | 70.797 | 33.868 | 71.916 | 1.00 | 31.19 |
| ATOM | 5128 | N | PHE | 93 | 68.658 | 33.920 | 72.481 | 1.00 | 25.84 |
| ATOM | 5129 | H | PHE | 93 | 67.987 | 34.190 | 73.141 | 1.00 | 0.00 |
| ATOM | 5130 | CA | PHE | 93 | 68.328 | 33.003 | 71.377 | 1.00 | 25.52 |
| ATOM | 5131 | CB | PHE | 93 | 66.854 | 32.505 | 71.412 | 1.00 | 26.81 |
| ATOM | 5132 | CG | PHE | 93 | 66.586 | 31.324 | 70.444 | 1.00 | 28.33 |
| ATOM | 5133 | CD1 | PHE | 93 | 66.825 | 30.006 | 70.853 | 1.00 | 27.70 |
| ATOM | 5134 | CD2 | PHE | 93 | 66.073 | 31.546 | 69.149 | 1.00 | 27.39 |
| ATOM | 5135 | CE1 | PHE | 93 | 66.545 | 28.941 | 69.984 | 1.00 | 26.87 |
| ATOM | 5136 | CE2 | PHE | 93 | 65.801 | 30.481 | 68.297 | 1.00 | 24.09 |
| ATOM | 5137 | CZ | PHE | 93 | 66.034 | 29.178 | 68.711 | 1.00 | 25.45 |
| ATOM | 5138 | C | PHE | 93 | 68.554 | 33.719 | 70.050 | 1.00 | 25.02 |
| ATOM | 5139 | O | PHE | 93 | 69.344 | 33.283 | 69.207 | 1.00 | 23.28 |
| ATOM | 5140 | N | ALA | 94 | 67.886 | 34.876 | 69.942 | 1.00 | 24.06 |
| ATOM | 5141 | H | ALA | 94 | 67.254 | 35.095 | 70.660 | 1.00 | 0.00 |
| ATOM | 5142 | CA | ALA | 94 | 67.999 | 35.787 | 68.823 | 1.00 | 21.59 |
| ATOM | 5143 | CB | ALA | 94 | 67.399 | 37.102 | 69.249 | 1.00 | 22.43 |
| ATOM | 5144 | C | ALA | 94 | 69.458 | 35.965 | 68.435 | 1.00 | 21.63 |
| ATOM | 5145 | O | ALA | 94 | 69.840 | 35.697 | 67.294 | 1.00 | 25.22 |
| ATOM | 5146 | N | PHE | 95 | 70.315 | 36.313 | 69.395 | 1.00 | 20.00 |

FIG. 1: A-87

| ATOM | 5147 | H | PHE | 95 | 69.946 | 36.556 | 70.269 | 1.00 | 0.00 |
|------|------|------|-----|----|--------|--------|--------|------|-------|
| ATOM | 5148 | CA | PHE | 95 | 71.770 | 36.403 | 69.185 | 1.00 | 18.95 |
| ATOM | 5149 | CB | PHE | 95 | 72.535 | 36.539 | 70.518 | 1.00 | 15.37 |
| ATOM | 5150 | CG | PHE | 95 | 73.996 | 36.878 | 70.267 | 1.00 | 17.36 |
| ATOM | 5151 | CD1 | PHE | 95 | 74.331 | 38.166 | 69.875 | 1.00 | 17.17 |
| ATOM | 5152 | CD2 | PHE | 95 | 74.989 | 35.906 | 70.379 | 1.00 | 17.58 |
| ATOM | 5153 | CE1 | PHE | 95 | 75.639 | 38.480 | 69.592 | 1.00 | 17.94 |
| ATOM | 5154 | CE2 | PHE | 95 | 76.307 | 36.232 | 70.092 | 1.00 | 16.57 |
| ATOM | 5155 | CZ | PHE | 95 | 76.639 | 37.518 | 69.696 | 1.00 | 19.91 |
| ATOM | 5156 | C | PHE | 95 | 72.357 | 35.192 | 68.473 | 1.00 | 17.92 |
| ATOM | 5157 | O | PHE | 95 | 73.104 | 35.281 | 67.509 | 1.00 | 17.70 |
| ATOM | 5158 | N | ARG | 96 | 71.939 | 34.031 | 68.944 | 1.00 | 21.05 |
| ATOM | 5159 | H | ARG | 96 | 71.293 | 34.038 | 69.682 | 1.00 | 0.00 |
| ATOM | 5160 | CA | ARG | 96 | 72.400 | 32.767 | 68.431 | 1.00 | 21.58 |
| ATOM | 5161 | CB | ARG | 96 | 71.943 | 31.717 | 69.408 | 1.00 | 23.33 |
| ATOM | 5162 | CG | ARG | 96 | 72.804 | 31.854 | 70.655 | 1.00 | 28.61 |
| ATOM | 5163 | CD | ARG | 96 | 72.487 | 30.914 | 71.809 | 1.00 | 37.68 |
| ATOM | 5164 | NE | ARG | 96 | 72.542 | 29.455 | 71.555 | 1.00 | 47.07 |
| ATOM | 5165 | HE | ARG | 96 | 71.771 | 28.940 | 71.864 | 1.00 | 0.00 |
| ATOM | 5166 | CZ | ARG | 96 | 73.530 | 28.737 | 70.933 | 1.00 | 49.16 |
| ATOM | 5167 | NH1 | ARG | 96 | 73.378 | 27.389 | 70.893 | 1.00 | 50.86 |
| ATOM | 5168 | HH11 | ARG | 96 | 72.564 | 26.966 | 71.295 | 1.00 | 0.00 |
| ATOM | 5169 | HH12 | ARG | 96 | 74.074 | 26.821 | 70.451 | 1.00 | 0.00 |
| ATOM | 5170 | NH2 | ARG | 96 | 74.606 | 29.290 | 70.313 | 1.00 | 45.62 |
| ATOM | 5171 | HH21 | ARG | 96 | 75.302 | 28.702 | 69.902 | 1.00 | 0.00 |
| ATOM | 5172 | HH22 | ARG | 96 | 74.723 | 30.283 | 70.302 | 1.00 | 0.00 |
| ATOM | 5173 | C | ARG | 96 | 71.968 | 32.476 | 67.003 | 1.00 | 22.27 |
| ATOM | 5174 | O | ARG | 96 | 72.678 | 31.758 | 66.288 | 1.00 | 23.11 |
| ATOM | 5175 | N | ILE | 97 | 70.887 | 33.100 | 66.519 | 1.00 | 21.62 |
| ATOM | 5176 | H | ILE | 97 | 70.360 | 33.638 | 67.144 | 1.00 | 0.00 |
| ATOM | 5177 | CA | ILE | 97 | 70.479 | 32.941 | 65.129 | 1.00 | 21.50 |
| ATOM | 5178 | CB | ILE | 97 | 69.098 | 33.653 | 64.922 | 1.00 | 22.99 |
| ATOM | 5179 | CG2 | ILE | 97 | 68.778 | 33.789 | 63.411 | 1.00 | 23.49 |
| ATOM | 5180 | CG1 | ILE | 97 | 67.953 | 32.830 | 65.609 | 1.00 | 23.98 |
| ATOM | 5181 | CD1 | ILE | 97 | 67.588 | 31.445 | 64.978 | 1.00 | 21.89 |
| ATOM | 5182 | C | ILE | 97 | 71.552 | 33.492 | 64.181 | 1.00 | 21.60 |
| ATOM | 5183 | O | ILE | 97 | 71.857 | 32.888 | 63.147 | 1.00 | 23.87 |
| ATOM | 5184 | N | TYR | 98 | 72.204 | 34.609 | 64.490 | 1.00 | 19.64 |
| ATOM | 5185 | H | TYR | 98 | 71.977 | 35.050 | 65.334 | 1.00 | 0.00 |
| ATOM | 5186 | CA | TYR | 98 | 73.222 | 35.154 | 63.592 | 1.00 | 18.71 |
| ATOM | 5187 | CB | TYR | 98 | 73.235 | 36.671 | 63.671 | 1.00 | 17.53 |
| ATOM | 5188 | CG | TYR | 98 | 71.907 | 37.415 | 63.622 | 1.00 | 15.18 |
| ATOM | 5189 | CD1 | TYR | 98 | 71.378 | 37.780 | 62.398 | 1.00 | 15.27 |
| ATOM | 5190 | CE1 | TYR | 98 | 70.158 | 38.471 | 62.354 | 1.00 | 18.26 |
| ATOM | 5191 | CD2 | TYR | 98 | 71.217 | 37.734 | 64.802 | 1.00 | 17.20 |
| ATOM | 5192 | CE2 | TYR | 98 | 69.997 | 38.418 | 64.765 | 1.00 | 17.93 |
| ATOM | 5193 | CZ | TYR | 98 | 69.471 | 38.790 | 63.529 | 1.00 | 18.96 |
| ATOM | 5194 | OH | TYR | 98 | 68.286 | 39.504 | 63.448 | 1.00 | 20.27 |
| ATOM | 5195 | HH | TYR | 98 | 68.161 | 39.835 | 62.547 | 1.00 | 0.00 |
| ATOM | 5196 | C | TYR | 98 | 74.627 | 34.630 | 63.944 | 1.00 | 21.68 |
| ATOM | 5197 | O | TYR | 98 | 75.573 | 34.573 | 63.149 | 1.00 | 20.70 |
| ATOM | 5198 | N | ASP | 99 | 74.820 | 34.226 | 65.199 | 1.00 | 23.41 |
| ATOM | 5199 | H | ASP | 99 | 74.060 | 34.272 | 65.816 | 1.00 | 0.00 |
| ATOM | 5200 | CA | ASP | 99 | 76.097 | 33.724 | 65.699 | 1.00 | 24.89 |
| ATOM | 5201 | CB | ASP | 99 | 76.070 | 33.929 | 67.212 | 1.00 | 23.81 |
| ATOM | 5202 | CG | ASP | 99 | 77.255 | 33.499 | 68.044 | 1.00 | 23.56 |
| ATOM | 5203 | OD1 | ASP | 99 | 78.296 | 33.216 | 67.459 | 1.00 | 24.89 |
| ATOM | 5204 | OD2 | ASP | 99 | 77.116 | 33.443 | 69.274 | 1.00 | 24.46 |
| ATOM | 5205 | C | ASP | 99 | 76.397 | 32.266 | 65.325 | 1.00 | 27.31 |
| ATOM | 5206 | O | ASP | 99 | 76.675 | 31.422 | 66.175 | 1.00 | 27.53 |

FIG. 1: A-88

| ATOM | 5207 | N | MET | 100 | 76.454 | 31.959 | 64.022 | 1.00 | 28.62 |
|------|------|---|-----|-----|--------|--------|--------|------|-------|
| ATOM | 5208 | H | MET | 100 | 76.263 | 32.694 | 63.401 | 1.00 | 0.00 |
| ATOM | 5209 | CA | MET | 100 | 76.682 | 30.597 | 63.526 | 1.00 | 26.59 |
| ATOM | 5210 | CB | MET | 100 | 77.091 | 30.731 | 62.098 | 1.00 | 26.12 |
| ATOM | 5211 | CG | MET | 100 | 75.785 | 31.000 | 61.402 | 1.00 | 31.98 |
| ATOM | 5212 | SD | MET | 100 | 76.010 | 31.405 | 59.660 | 1.00 | 38.98 |
| ATOM | 5213 | CE | MET | 100 | 76.583 | 29.831 | 59.099 | 1.00 | 42.31 |
| ATOM | 5214 | C | MET | 100 | 77.608 | 29.594 | 64.227 | 1.00 | 25.05 |
| ATOM | 5215 | O | MET | 100 | 77.166 | 28.590 | 64.787 | 1.00 | 24.37 |
| ATOM | 5216 | N | ASP | 101 | 78.902 | 29.828 | 64.348 | 1.00 | 25.72 |
| ATOM | 5217 | H | ASP | 101 | 79.244 | 30.669 | 63.992 | 1.00 | 0.00 |
| ATOM | 5218 | CA | ASP | 101 | 79.796 | 28.879 | 65.013 | 1.00 | 24.96 |
| ATOM | 5219 | CB | ASP | 101 | 81.206 | 29.256 | 64.642 | 1.00 | 22.87 |
| ATOM | 5220 | CG | ASP | 101 | 81.575 | 30.678 | 65.026 | 1.00 | 25.13 |
| ATOM | 5221 | OD1 | ASP | 101 | 82.463 | 31.246 | 64.388 | 1.00 | 25.82 |
| ATOM | 5222 | OD2 | ASP | 101 | 80.998 | 31.203 | 65.973 | 1.00 | 22.31 |
| ATOM | 5223 | C | ASP | 101 | 79.653 | 28.809 | 66.537 | 1.00 | 26.32 |
| ATOM | 5224 | O | ASP | 101 | 80.592 | 28.528 | 67.268 | 1.00 | 29.18 |
| ATOM | 5225 | N | LYS | 102 | 78.539 | 29.207 | 67.113 | 1.00 | 27.26 |
| ATOM | 5226 | H | LYS | 102 | 77.767 | 29.447 | 66.559 | 1.00 | 0.00 |
| ATOM | 5227 | CA | LYS | 102 | 78.350 | 29.242 | 68.540 | 1.00 | 27.19 |
| ATOM | 5228 | CB | LYS | 102 | 78.439 | 27.813 | 69.076 | 1.00 | 27.51 |
| ATOM | 5229 | CG | LYS | 102 | 77.554 | 26.775 | 68.350 | 1.00 | 29.02 |
| ATOM | 5230 | CD | LYS | 102 | 76.021 | 26.870 | 68.504 | 1.00 | 25.52 |
| ATOM | 5231 | CE | LYS | 102 | 75.456 | 25.549 | 67.973 | 1.00 | 24.57 |
| ATOM | 5232 | NZ | LYS | 102 | 74.903 | 24.699 | 69.015 | 1.00 | 23.47 |
| ATOM | 5233 | HZ1 | LYS | 102 | 74.653 | 23.771 | 68.620 | 1.00 | 0.00 |
| ATOM | 5234 | HZ2 | LYS | 102 | 74.044 | 25.154 | 69.385 | 1.00 | 0.00 |
| ATOM | 5235 | HZ3 | LYS | 102 | 75.590 | 24.580 | 69.785 | 1.00 | 0.00 |
| ATOM | 5236 | C | LYS | 102 | 79.293 | 30.156 | 69.320 | 1.00 | 29.06 |
| ATOM | 5237 | O | LYS | 102 | 78.839 | 30.643 | 70.345 | 1.00 | 33.70 |
| ATOM | 5238 | N | ASP | 103 | 80.517 | 30.567 | 68.964 | 1.00 | 29.06 |
| ATOM | 5239 | H | ASP | 103 | 80.883 | 30.235 | 68.125 | 1.00 | 0.00 |
| ATOM | 5240 | CA | ASP | 103 | 81.388 | 31.371 | 69.836 | 1.00 | 28.78 |
| ATOM | 5241 | CB | ASP | 103 | 82.680 | 31.540 | 69.072 | 1.00 | 32.33 |
| ATOM | 5242 | CG | ASP | 103 | 82.821 | 32.599 | 67.985 | 1.00 | 33.75 |
| ATOM | 5243 | OD1 | ASP | 103 | 83.771 | 32.486 | 67.203 | 1.00 | 37.00 |
| ATOM | 5244 | OD2 | ASP | 103 | 82.020 | 33.526 | 67.906 | 1.00 | 36.62 |
| ATOM | 5245 | C | ASP | 103 | 81.121 | 32.710 | 70.568 | 1.00 | 29.40 |
| ATOM | 5246 | O | ASP | 103 | 82.051 | 33.319 | 71.121 | 1.00 | 28.70 |
| ATOM | 5247 | N | GLY | 104 | 79.902 | 33.258 | 70.608 | 1.00 | 29.83 |
| ATOM | 5248 | H | GLY | 104 | 79.165 | 32.702 | 70.282 | 1.00 | 0.00 |
| ATOM | 5249 | CA | GLY | 104 | 79.644 | 34.534 | 71.293 | 1.00 | 30.15 |
| ATOM | 5250 | C | GLY | 104 | 79.781 | 35.855 | 70.507 | 1.00 | 29.23 |
| ATOM | 5251 | O | GLY | 104 | 79.377 | 36.907 | 70.998 | 1.00 | 30.73 |
| ATOM | 5252 | N | TYR | 105 | 80.311 | 35.889 | 69.286 | 1.00 | 28.10 |
| ATOM | 5253 | H | TYR | 105 | 80.593 | 35.038 | 68.902 | 1.00 | 0.00 |
| ATOM | 5254 | CA | TYR | 105 | 80.485 | 37.110 | 68.497 | 1.00 | 27.18 |
| ATOM | 5255 | CB | TYR | 105 | 81.962 | 37.463 | 68.307 | 1.00 | 27.91 |
| ATOM | 5256 | CG | TYR | 105 | 82.662 | 37.746 | 69.600 | 1.00 | 31.20 |
| ATOM | 5257 | CD1 | TYR | 105 | 82.574 | 39.042 | 70.084 | 1.00 | 33.04 |
| ATOM | 5258 | CE1 | TYR | 105 | 83.001 | 39.313 | 71.373 | 1.00 | 35.53 |
| ATOM | 5259 | CD2 | TYR | 105 | 83.213 | 36.705 | 70.363 | 1.00 | 31.78 |
| ATOM | 5260 | CE2 | TYR | 105 | 83.641 | 36.976 | 71.663 | 1.00 | 32.77 |
| ATOM | 5261 | CZ | TYR | 105 | 83.514 | 38.284 | 72.165 | 1.00 | 35.60 |
| ATOM | 5262 | OH | TYR | 105 | 83.757 | 38.589 | 73.496 | 1.00 | 35.29 |
| ATOM | 5263 | HH | TYR | 105 | 84.025 | 37.791 | 73.960 | 1.00 | 0.00 |
| ATOM | 5264 | C | TYR | 105 | 79.921 | 36.995 | 67.083 | 1.00 | 26.94 |
| ATOM | 5265 | O | TYR | 105 | 80.333 | 36.077 | 66.384 | 1.00 | 26.80 |
| ATOM | 5266 | N | ILE | 106 | 79.023 | 37.837 | 66.567 | 1.00 | 25.40 |

FIG. 1: A-89

| ATOM | 5267 | H    | ILE | 106 | 78.583 | 38.437 | 67.194 | 1.00 | 0.00  |
|------|------|------|-----|-----|--------|--------|--------|------|-------|
| ATOM | 5268 | CA   | ILE | 106 | 78.561 | 37.816 | 65.172 | 1.00 | 21.05 |
| ATOM | 5269 | CB   | ILE | 106 | 77.168 | 38.456 | 65.050 | 1.00 | 18.84 |
| ATOM | 5270 | CG2  | ILE | 106 | 76.774 | 38.343 | 63.589 | 1.00 | 16.28 |
| ATOM | 5271 | CG1  | ILE | 106 | 76.131 | 37.804 | 65.961 | 1.00 | 13.65 |
| ATOM | 5272 | CD1  | ILE | 106 | 75.030 | 38.763 | 66.314 | 1.00 | 8.95  |
| ATOM | 5273 | C    | ILE | 106 | 79.501 | 38.543 | 64.202 | 1.00 | 22.56 |
| ATOM | 5274 | O    | ILE | 106 | 79.582 | 39.773 | 64.075 | 1.00 | 20.04 |
| ATOM | 5275 | N    | SER | 107 | 80.182 | 37.700 | 63.450 | 1.00 | 22.11 |
| ATOM | 5276 | H    | SER | 107 | 80.017 | 36.748 | 63.589 | 1.00 | 0.00  |
| ATOM | 5277 | CA   | SER | 107 | 81.109 | 38.170 | 62.444 | 1.00 | 22.53 |
| ATOM | 5278 | CB   | SER | 107 | 82.038 | 37.070 | 61.957 | 1.00 | 20.87 |
| ATOM | 5279 | OG   | SER | 107 | 81.323 | 36.165 | 61.126 | 1.00 | 21.98 |
| ATOM | 5280 | HG   | SER | 107 | 81.566 | 35.264 | 61.383 | 1.00 | 0.00  |
| ATOM | 5281 | C    | SER | 107 | 80.370 | 38.666 | 61.228 | 1.00 | 23.39 |
| ATOM | 5282 | O    | SER | 107 | 79.307 | 38.133 | 60.930 | 1.00 | 25.31 |
| ATOM | 5283 | N    | ASN | 108 | 80.947 | 39.610 | 60.468 | 1.00 | 26.13 |
| ATOM | 5284 | H    | ASN | 108 | 81.713 | 40.073 | 60.868 | 1.00 | 0.00  |
| ATOM | 5285 | CA   | ASN | 108 | 80.413 | 40.103 | 59.176 | 1.00 | 26.33 |
| ATOM | 5286 | CB   | ASN | 108 | 81.525 | 40.974 | 58.555 | 1.00 | 24.46 |
| ATOM | 5287 | CG   | ASN | 108 | 81.168 | 41.683 | 57.256 | 1.00 | 29.73 |
| ATOM | 5288 | OD1  | ASN | 108 | 80.364 | 41.233 | 56.441 | 1.00 | 30.26 |
| ATOM | 5289 | ND2  | ASN | 108 | 81.729 | 42.807 | 56.896 | 1.00 | 27.31 |
| ATOM | 5290 | HD21 | ASN | 108 | 82.394 | 43.273 | 57.425 | 1.00 | 0.00  |
| ATOM | 5291 | HD22 | ASN | 108 | 81.370 | 43.083 | 56.021 | 1.00 | 0.00  |
| ATOM | 5292 | C    | ASN | 108 | 79.948 | 38.972 | 58.229 | 1.00 | 26.85 |
| ATOM | 5293 | O    | ASN | 108 | 78.846 | 38.967 | 57.676 | 1.00 | 27.81 |
| ATOM | 5294 | N    | GLY | 109 | 80.743 | 37.901 | 58.210 | 1.00 | 26.08 |
| ATOM | 5295 | H    | GLY | 109 | 81.530 | 37.934 | 58.786 | 1.00 | 0.00  |
| ATOM | 5296 | CA   | GLY | 109 | 80.511 | 36.717 | 57.378 | 1.00 | 25.57 |
| ATOM | 5297 | C    | GLY | 109 | 79.237 | 35.974 | 57.679 | 1.00 | 26.47 |
| ATOM | 5298 | O    | GLY | 109 | 78.487 | 35.629 | 56.763 | 1.00 | 29.73 |
| ATOM | 5299 | N    | GLU | 110 | 78.988 | 35.765 | 58.974 | 1.00 | 26.38 |
| ATOM | 5300 | H    | GLU | 110 | 79.655 | 36.085 | 59.621 | 1.00 | 0.00  |
| ATOM | 5301 | CA   | GLU | 110 | 77.759 | 35.166 | 59.502 | 1.00 | 22.46 |
| ATOM | 5302 | CB   | GLU | 110 | 77.819 | 34.952 | 60.921 | 1.00 | 23.04 |
| ATOM | 5303 | CG   | GLU | 110 | 78.834 | 33.892 | 61.116 | 1.00 | 25.08 |
| ATOM | 5304 | CD   | GLU | 110 | 79.326 | 33.780 | 62.528 | 1.00 | 26.42 |
| ATOM | 5305 | OE1  | GLU | 110 | 79.206 | 34.755 | 63.275 | 1.00 | 24.76 |
| ATOM | 5306 | OE2  | GLU | 110 | 79.843 | 32.703 | 62.841 | 1.00 | 29.02 |
| ATOM | 5307 | C    | GLU | 110 | 76.594 | 36.097 | 59.336 | 1.00 | 24.39 |
| ATOM | 5308 | O    | GLU | 110 | 75.506 | 35.634 | 58.969 | 1.00 | 23.48 |
| ATOM | 5309 | N    | LEU | 111 | 76.851 | 37.413 | 59.542 | 1.00 | 22.30 |
| ATOM | 5310 | H    | LEU | 111 | 77.722 | 37.690 | 59.889 | 1.00 | 0.00  |
| ATOM | 5311 | CA   | LEU | 111 | 75.786 | 38.363 | 59.324 | 1.00 | 22.27 |
| ATOM | 5312 | CB   | LEU | 111 | 76.193 | 39.809 | 59.646 | 1.00 | 20.27 |
| ATOM | 5313 | CG   | LEU | 111 | 75.298 | 40.576 | 60.676 | 1.00 | 18.88 |
| ATOM | 5314 | CD1  | LEU | 111 | 75.591 | 42.042 | 60.509 | 1.00 | 16.83 |
| ATOM | 5315 | CD2  | LEU | 111 | 73.790 | 40.354 | 60.476 | 1.00 | 15.28 |
| ATOM | 5316 | C    | LEU | 111 | 75.320 | 38.311 | 57.879 | 1.00 | 23.14 |
| ATOM | 5317 | O    | LEU | 111 | 74.129 | 38.062 | 57.638 | 1.00 | 24.07 |
| ATOM | 5318 | N    | PHE | 112 | 76.208 | 38.453 | 56.888 | 1.00 | 23.90 |
| ATOM | 5319 | H    | PHE | 112 | 77.116 | 38.730 | 57.106 | 1.00 | 0.00  |
| ATOM | 5320 | CA   | PHE | 112 | 75.786 | 38.314 | 55.499 | 1.00 | 23.26 |
| ATOM | 5321 | CB   | PHE | 112 | 77.001 | 38.563 | 54.577 | 1.00 | 20.22 |
| ATOM | 5322 | CG   | PHE | 112 | 76.625 | 38.492 | 53.090 | 1.00 | 20.57 |
| ATOM | 5323 | CD1  | PHE | 112 | 76.684 | 37.272 | 52.396 | 1.00 | 17.93 |
| ATOM | 5324 | CD2  | PHE | 112 | 76.202 | 39.635 | 52.426 | 1.00 | 18.72 |
| ATOM | 5325 | CE1  | PHE | 112 | 76.314 | 37.225 | 51.059 | 1.00 | 20.01 |
| ATOM | 5326 | CE2  | PHE | 112 | 75.836 | 39.569 | 51.083 | 1.00 | 19.54 |

FIG. 1: A-90

| ATOM | 5327 | CZ | PHE | 112 | 75.887 | 38.370 | 50.393 | 1.00 | 18.60 |
|------|------|------|-----|-----|--------|--------|--------|------|-------|
| ATOM | 5328 | C | PHE | 112 | 75.166 | 36.918 | 55.252 | 1.00 | 24.79 |
| ATOM | 5329 | O | PHE | 112 | 74.034 | 36.842 | 54.773 | 1.00 | 26.07 |
| ATOM | 5330 | N | GLN | 113 | 75.791 | 35.790 | 55.583 | 1.00 | 24.77 |
| ATOM | 5331 | H | GLN | 113 | 76.688 | 35.870 | 55.963 | 1.00 | 0.00 |
| ATOM | 5332 | CA | GLN | 113 | 75.172 | 34.484 | 55.393 | 1.00 | 27.20 |
| ATOM | 5333 | CB | GLN | 113 | 76.102 | 33.455 | 56.031 | 1.00 | 30.75 |
| ATOM | 5334 | CG | GLN | 113 | 76.849 | 32.498 | 55.082 | 1.00 | 41.23 |
| ATOM | 5335 | CD | GLN | 113 | 77.974 | 33.041 | 54.163 | 1.00 | 47.37 |
| ATOM | 5336 | OE1 | GLN | 113 | 78.070 | 32.719 | 52.971 | 1.00 | 49.20 |
| ATOM | 5337 | NE2 | GLN | 113 | 78.934 | 33.844 | 54.596 | 1.00 | 47.87 |
| ATOM | 5338 | HE21 | GLN | 113 | 78.923 | 34.151 | 55.521 | 1.00 | 0.00 |
| ATOM | 5339 | HE22 | GLN | 113 | 79.595 | 34.054 | 53.909 | 1.00 | 0.00 |
| ATOM | 5340 | C | GLN | 113 | 73.723 | 34.319 | 55.940 | 1.00 | 26.35 |
| ATOM | 5341 | O | GLN | 113 | 72.783 | 33.907 | 55.251 | 1.00 | 26.56 |
| ATOM | 5342 | N | VAL | 114 | 73.468 | 34.689 | 57.183 | 1.00 | 23.35 |
| ATOM | 5343 | H | VAL | 114 | 74.206 | 35.048 | 57.714 | 1.00 | 0.00 |
| ATOM | 5344 | CA | VAL | 114 | 72.148 | 34.576 | 57.782 | 1.00 | 24.03 |
| ATOM | 5345 | CB | VAL | 114 | 72.376 | 34.747 | 59.309 | 1.00 | 22.75 |
| ATOM | 5346 | CG1 | VAL | 114 | 71.049 | 34.755 | 60.092 | 1.00 | 21.95 |
| ATOM | 5347 | CG2 | VAL | 114 | 73.257 | 33.596 | 59.764 | 1.00 | 20.17 |
| ATOM | 5348 | C | VAL | 114 | 71.080 | 35.552 | 57.208 | 1.00 | 26.11 |
| ATOM | 5349 | O | VAL | 114 | 69.885 | 35.257 | 57.033 | 1.00 | 24.79 |
| ATOM | 5350 | N | LEU | 115 | 71.471 | 36.783 | 56.885 | 1.00 | 25.17 |
| ATOM | 5351 | H | LEU | 115 | 72.390 | 37.059 | 57.105 | 1.00 | 0.00 |
| ATOM | 5352 | CA | LEU | 115 | 70.536 | 37.692 | 56.257 | 1.00 | 24.36 |
| ATOM | 5353 | CB | LEU | 115 | 71.154 | 39.054 | 56.146 | 1.00 | 20.53 |
| ATOM | 5354 | CG | LEU | 115 | 71.517 | 39.664 | 57.440 | 1.00 | 16.89 |
| ATOM | 5355 | CD1 | LEU | 115 | 72.199 | 40.949 | 57.068 | 1.00 | 17.86 |
| ATOM | 5356 | CD2 | LEU | 115 | 70.322 | 39.841 | 58.362 | 1.00 | 16.11 |
| ATOM | 5357 | C | LEU | 115 | 70.196 | 37.190 | 54.866 | 1.00 | 26.20 |
| ATOM | 5358 | O | LEU | 115 | 69.033 | 37.091 | 54.485 | 1.00 | 27.73 |
| ATOM | 5359 | N | LYS | 116 | 71.243 | 36.831 | 54.114 | 1.00 | 28.62 |
| ATOM | 5360 | H | LYS | 116 | 72.130 | 36.924 | 54.526 | 1.00 | 0.00 |
| ATOM | 5361 | CA | LYS | 116 | 71.152 | 36.314 | 52.752 | 1.00 | 29.48 |
| ATOM | 5362 | CB | LYS | 116 | 72.539 | 35.834 | 52.374 | 1.00 | 31.44 |
| ATOM | 5363 | CG | LYS | 116 | 72.703 | 35.307 | 50.970 | 1.00 | 37.30 |
| ATOM | 5364 | CD | LYS | 116 | 74.023 | 34.507 | 50.970 | 1.00 | 42.94 |
| ATOM | 5365 | CE | LYS | 116 | 74.476 | 34.118 | 49.547 | 1.00 | 45.49 |
| ATOM | 5366 | NZ | LYS | 116 | 74.645 | 35.290 | 48.696 | 1.00 | 47.17 |
| ATOM | 5367 | HZ1 | LYS | 116 | 75.356 | 35.926 | 49.109 | 1.00 | 0.00 |
| ATOM | 5368 | HZ2 | LYS | 116 | 73.739 | 35.794 | 48.612 | 1.00 | 0.00 |
| ATOM | 5369 | HZ3 | LYS | 116 | 74.957 | 34.994 | 47.750 | 1.00 | 0.00 |
| ATOM | 5370 | C | LYS | 116 | 70.121 | 35.192 | 52.613 | 1.00 | 28.92 |
| ATOM | 5371 | O | LYS | 116 | 69.254 | 35.251 | 51.743 | 1.00 | 27.83 |
| ATOM | 5372 | N | MET | 117 | 70.171 | 34.230 | 53.568 | 1.00 | 28.75 |
| ATOM | 5373 | H | MET | 117 | 70.908 | 34.288 | 54.214 | 1.00 | 0.00 |
| ATOM | 5374 | CA | MET | 117 | 69.274 | 33.071 | 53.626 | 1.00 | 25.77 |
| ATOM | 5375 | CB | MET | 117 | 69.756 | 32.049 | 54.623 | 1.00 | 24.82 |
| ATOM | 5376 | CG | MET | 117 | 69.583 | 32.128 | 56.127 | 1.00 | 25.63 |
| ATOM | 5377 | SD | MET | 117 | 70.092 | 30.532 | 56.857 | 1.00 | 28.13 |
| ATOM | 5378 | CE | MET | 117 | 71.867 | 30.610 | 56.986 | 1.00 | 16.67 |
| ATOM | 5379 | C | MET | 117 | 67.828 | 33.347 | 53.954 | 1.00 | 25.30 |
| ATOM | 5380 | O | MET | 117 | 66.941 | 32.556 | 53.643 | 1.00 | 26.93 |
| ATOM | 5381 | N | MET | 118 | 67.595 | 34.493 | 54.564 | 1.00 | 22.91 |
| ATOM | 5382 | H | MET | 118 | 68.351 | 34.989 | 54.937 | 1.00 | 0.00 |
| ATOM | 5383 | CA | MET | 118 | 66.252 | 34.967 | 54.760 | 1.00 | 22.57 |
| ATOM | 5384 | CB | MET | 118 | 66.037 | 35.670 | 56.092 | 1.00 | 25.13 |
| ATOM | 5385 | CG | MET | 118 | 66.079 | 34.897 | 57.408 | 1.00 | 24.54 |
| ATOM | 5386 | SD | MET | 118 | 66.018 | 36.098 | 58.769 | 1.00 | 25.16 |

FIG. 1: A-91

| ATOM | 5387 | CE | MET | 118 | 67.755 | 36.223 | 59.060 | 1.00 | 25.97 |
|---|---|---|---|---|---|---|---|---|---|
| ATOM | 5388 | C | MET | 118 | 65.888 | 35.995 | 53.715 | 1.00 | 23.77 |
| ATOM | 5389 | O | MET | 118 | 64.701 | 36.294 | 53.611 | 1.00 | 25.11 |
| ATOM | 5390 | N | VAL | 119 | 66.800 | 36.635 | 52.960 | 1.00 | 23.41 |
| ATOM | 5391 | H | VAL | 119 | 67.749 | 36.483 | 53.142 | 1.00 | 0.00 |
| ATOM | 5392 | CA | VAL | 119 | 66.369 | 37.638 | 51.982 | 1.00 | 24.25 |
| ATOM | 5393 | CB | VAL | 119 | 67.341 | 38.853 | 52.175 | 1.00 | 25.42 |
| ATOM | 5394 | CG1 | VAL | 119 | 68.631 | 38.676 | 51.416 | 1.00 | 25.15 |
| ATOM | 5395 | CG2 | VAL | 119 | 66.683 | 40.106 | 51.652 | 1.00 | 25.73 |
| ATOM | 5396 | C | VAL | 119 | 66.248 | 37.181 | 50.498 | 1.00 | 24.97 |
| ATOM | 5397 | O | VAL | 119 | 65.598 | 37.774 | 49.606 | 1.00 | 23.28 |
| ATOM | 5398 | N | GLY | 120 | 66.934 | 36.060 | 50.276 | 1.00 | 24.64 |
| ATOM | 5399 | H | GLY | 120 | 67.466 | 35.709 | 51.020 | 1.00 | 0.00 |
| ATOM | 5400 | CA | GLY | 120 | 67.008 | 35.385 | 49.003 | 1.00 | 25.51 |
| ATOM | 5401 | C | GLY | 120 | 67.590 | 36.309 | 47.958 | 1.00 | 27.72 |
| ATOM | 5402 | O | GLY | 120 | 68.688 | 36.861 | 48.107 | 1.00 | 29.69 |
| ATOM | 5403 | N | ALA | 121 | 66.800 | 36.539 | 46.907 | 1.00 | 26.98 |
| ATOM | 5404 | H | ALA | 121 | 65.935 | 36.089 | 46.869 | 1.00 | 0.00 |
| ATOM | 5405 | CA | ALA | 121 | 67.240 | 37.444 | 45.848 | 1.00 | 24.75 |
| ATOM | 5406 | CB | ALA | 121 | 67.026 | 36.808 | 44.486 | 1.00 | 24.87 |
| ATOM | 5407 | C | ALA | 121 | 66.517 | 38.776 | 45.862 | 1.00 | 24.77 |
| ATOM | 5408 | O | ALA | 121 | 66.257 | 39.403 | 44.837 | 1.00 | 26.11 |
| ATOM | 5409 | N | ASN | 122 | 66.060 | 39.227 | 47.021 | 1.00 | 24.49 |
| ATOM | 5410 | H | ASN | 122 | 66.125 | 38.670 | 47.829 | 1.00 | 0.00 |
| ATOM | 5411 | CA | ASN | 122 | 65.411 | 40.531 | 47.008 | 1.00 | 27.02 |
| ATOM | 5412 | CB | ASN | 122 | 64.306 | 40.528 | 48.033 | 1.00 | 29.77 |
| ATOM | 5413 | CG | ASN | 122 | 63.137 | 39.647 | 47.603 | 1.00 | 30.83 |
| ATOM | 5414 | OD1 | ASN | 122 | 62.419 | 39.279 | 48.502 | 1.00 | 34.34 |
| ATOM | 5415 | ND2 | ASN | 122 | 62.733 | 39.220 | 46.404 | 1.00 | 24.59 |
| ATOM | 5416 | HD21 | ASN | 122 | 63.205 | 39.493 | 45.593 | 1.00 | 0.00 |
| ATOM | 5417 | HD22 | ASN | 122 | 61.959 | 38.630 | 46.468 | 1.00 | 0.00 |
| ATOM | 5418 | C | ASN | 122 | 66.312 | 41.744 | 47.211 | 1.00 | 24.73 |
| ATOM | 5419 | O | ASN | 122 | 65.921 | 42.896 | 47.086 | 1.00 | 23.26 |
| ATOM | 5420 | N | LEU | 123 | 67.559 | 41.400 | 47.466 | 1.00 | 23.48 |
| ATOM | 5421 | H | LEU | 123 | 67.782 | 40.448 | 47.456 | 1.00 | 0.00 |
| ATOM | 5422 | CA | LEU | 123 | 68.642 | 42.327 | 47.653 | 1.00 | 25.00 |
| ATOM | 5423 | CB | LEU | 123 | 69.137 | 42.239 | 49.111 | 1.00 | 21.46 |
| ATOM | 5424 | CG | LEU | 123 | 68.840 | 43.139 | 50.310 | 1.00 | 20.78 |
| ATOM | 5425 | CD1 | LEU | 123 | 69.527 | 44.456 | 50.114 | 1.00 | 20.56 |
| ATOM | 5426 | CD2 | LEU | 123 | 67.364 | 43.383 | 50.479 | 1.00 | 24.04 |
| ATOM | 5427 | C | LEU | 123 | 69.764 | 41.885 | 46.673 | 1.00 | 26.76 |
| ATOM | 5428 | O | LEU | 123 | 69.943 | 40.686 | 46.416 | 1.00 | 26.82 |
| ATOM | 5429 | N | LYS | 124 | 70.466 | 42.801 | 45.986 | 1.00 | 26.51 |
| ATOM | 5430 | H | LYS | 124 | 70.064 | 43.686 | 45.881 | 1.00 | 0.00 |
| ATOM | 5431 | CA | LYS | 124 | 71.730 | 42.456 | 45.306 | 1.00 | 26.94 |
| ATOM | 5432 | CB | LYS | 124 | 72.308 | 43.651 | 44.548 | 1.00 | 27.43 |
| ATOM | 5433 | CG | LYS | 124 | 71.342 | 44.313 | 43.579 | 1.00 | 28.59 |
| ATOM | 5434 | CD | LYS | 124 | 71.425 | 45.859 | 43.624 | 1.00 | 31.32 |
| ATOM | 5435 | CE | LYS | 124 | 71.448 | 46.587 | 45.017 | 1.00 | 28.42 |
| ATOM | 5436 | NZ | LYS | 124 | 70.391 | 46.172 | 45.913 | 1.00 | 22.71 |
| ATOM | 5437 | HZ1 | LYS | 124 | 70.417 | 46.737 | 46.786 | 1.00 | 0.00 |
| ATOM | 5438 | HZ2 | LYS | 124 | 70.496 | 45.162 | 46.133 | 1.00 | 0.00 |
| ATOM | 5439 | HZ3 | LYS | 124 | 69.490 | 46.329 | 45.417 | 1.00 | 0.00 |
| ATOM | 5440 | C | LYS | 124 | 72.783 | 42.039 | 46.368 | 1.00 | 26.26 |
| ATOM | 5441 | O | LYS | 124 | 72.773 | 42.611 | 47.480 | 1.00 | 24.46 |
| ATOM | 5442 | N | ASP | 125 | 73.737 | 41.121 | 46.143 | 1.00 | 23.51 |
| ATOM | 5443 | H | ASP | 125 | 73.707 | 40.597 | 45.319 | 1.00 | 0.00 |
| ATOM | 5444 | CA | ASP | 125 | 74.631 | 40.788 | 47.243 | 1.00 | 22.27 |
| ATOM | 5445 | CB | ASP | 125 | 75.458 | 39.523 | 46.875 | 1.00 | 25.75 |
| ATOM | 5446 | CG | ASP | 125 | 74.742 | 38.143 | 47.036 | 1.00 | 31.78 |

FIG. 1: A-92

| ATOM | 5447 | OD1 | ASP | 125 | 73.764 | 38.015 | 47.779 | 1.00 | 38.34 |
|---|---|---|---|---|---|---|---|---|---|
| ATOM | 5448 | OD2 | ASP | 125 | 75.150 | 37.143 | 46.437 | 1.00 | 33.84 |
| ATOM | 5449 | C | ASP | 125 | 75.509 | 41.977 | 47.604 | 1.00 | 21.69 |
| ATOM | 5450 | O | ASP | 125 | 75.797 | 42.193 | 48.769 | 1.00 | 24.74 |
| ATOM | 5451 | N | THR | 126 | 75.898 | 42.861 | 46.689 | 1.00 | 21.93 |
| ATOM | 5452 | H | THR | 126 | 75.812 | 42.593 | 45.755 | 1.00 | 0.00 |
| ATOM | 5453 | CA | THR | 126 | 76.608 | 44.122 | 46.995 | 1.00 | 22.45 |
| ATOM | 5454 | CB | THR | 126 | 76.903 | 44.862 | 45.683 | 1.00 | 22.69 |
| ATOM | 5455 | OG1 | THR | 126 | 78.079 | 44.158 | 45.255 | 1.00 | 25.91 |
| ATOM | 5456 | HG1 | THR | 126 | 78.320 | 44.511 | 44.392 | 1.00 | 0.00 |
| ATOM | 5457 | CG2 | THR | 126 | 77.111 | 46.361 | 45.728 | 1.00 | 21.49 |
| ATOM | 5458 | C | THR | 126 | 75.867 | 45.044 | 47.937 | 1.00 | 22.36 |
| ATOM | 5459 | O | THR | 126 | 76.425 | 45.613 | 48.864 | 1.00 | 23.73 |
| ATOM | 5460 | N | ALA | 127 | 74.564 | 45.168 | 47.781 | 1.00 | 24.20 |
| ATOM | 5461 | H | ALA | 127 | 74.125 | 44.663 | 47.072 | 1.00 | 0.00 |
| ATOM | 5462 | CA | ALA | 127 | 73.768 | 45.946 | 48.734 | 1.00 | 26.05 |
| ATOM | 5463 | CB | ALA | 127 | 72.320 | 46.127 | 48.267 | 1.00 | 29.30 |
| ATOM | 5464 | C | ALA | 127 | 73.717 | 45.234 | 50.078 | 1.00 | 23.90 |
| ATOM | 5465 | O | ALA | 127 | 74.159 | 45.842 | 51.042 | 1.00 | 26.67 |
| ATOM | 5466 | N | LEU | 128 | 73.295 | 43.975 | 50.236 | 1.00 | 21.72 |
| ATOM | 5467 | H | LEU | 128 | 72.988 | 43.465 | 49.455 | 1.00 | 0.00 |
| ATOM | 5468 | CA | LEU | 128 | 73.376 | 43.343 | 51.554 | 1.00 | 21.95 |
| ATOM | 5469 | CB | LEU | 128 | 73.023 | 41.872 | 51.498 | 1.00 | 20.57 |
| ATOM | 5470 | CG | LEU | 128 | 72.784 | 41.168 | 52.844 | 1.00 | 17.44 |
| ATOM | 5471 | CD1 | LEU | 128 | 71.685 | 41.813 | 53.677 | 1.00 | 18.03 |
| ATOM | 5472 | CD2 | LEU | 128 | 72.314 | 39.775 | 52.533 | 1.00 | 18.82 |
| ATOM | 5473 | C | LEU | 128 | 74.751 | 43.450 | 52.204 | 1.00 | 23.70 |
| ATOM | 5474 | O | LEU | 128 | 74.797 | 43.830 | 53.376 | 1.00 | 27.84 |
| ATOM | 5475 | N | GLN | 129 | 75.881 | 43.243 | 51.510 | 1.00 | 21.77 |
| ATOM | 5476 | H | GLN | 129 | 75.809 | 42.922 | 50.588 | 1.00 | 0.00 |
| ATOM | 5477 | CA | GLN | 129 | 77.195 | 43.471 | 52.112 | 1.00 | 21.94 |
| ATOM | 5478 | CB | GLN | 129 | 78.325 | 43.093 | 51.174 | 1.00 | 22.64 |
| ATOM | 5479 | CG | GLN | 129 | 79.715 | 43.171 | 51.843 | 1.00 | 26.48 |
| ATOM | 5480 | CD | GLN | 129 | 79.947 | 42.357 | 53.139 | 1.00 | 27.97 |
| ATOM | 5481 | OE1 | GLN | 129 | 80.415 | 42.866 | 54.160 | 1.00 | 29.15 |
| ATOM | 5482 | NE2 | GLN | 129 | 79.738 | 41.059 | 53.252 | 1.00 | 25.04 |
| ATOM | 5483 | HE21 | GLN | 129 | 79.442 | 40.510 | 52.511 | 1.00 | 0.00 |
| ATOM | 5484 | HE22 | GLN | 129 | 79.917 | 40.780 | 54.178 | 1.00 | 0.00 |
| ATOM | 5485 | C | GLN | 129 | 77.456 | 44.920 | 52.537 | 1.00 | 22.72 |
| ATOM | 5486 | O | GLN | 129 | 78.132 | 45.155 | 53.551 | 1.00 | 21.00 |
| ATOM | 5487 | N | GLN | 130 | 76.908 | 45.906 | 51.804 | 1.00 | 21.99 |
| ATOM | 5488 | H | GLN | 130 | 76.429 | 45.663 | 50.981 | 1.00 | 0.00 |
| ATOM | 5489 | CA | GLN | 130 | 77.056 | 47.325 | 52.174 | 1.00 | 19.29 |
| ATOM | 5490 | CB | GLN | 130 | 76.427 | 48.229 | 51.168 | 1.00 | 18.57 |
| ATOM | 5491 | CG | GLN | 130 | 77.360 | 48.359 | 49.975 | 1.00 | 18.83 |
| ATOM | 5492 | CD | GLN | 130 | 76.750 | 49.098 | 48.794 | 1.00 | 16.25 |
| ATOM | 5493 | OE1 | GLN | 130 | 75.556 | 49.312 | 48.617 | 1.00 | 14.76 |
| ATOM | 5494 | NE2 | GLN | 130 | 77.522 | 49.541 | 47.858 | 1.00 | 17.88 |
| ATOM | 5495 | HE21 | GLN | 130 | 78.487 | 49.430 | 47.943 | 1.00 | 0.00 |
| ATOM | 5496 | HE22 | GLN | 130 | 77.049 | 49.908 | 47.085 | 1.00 | 0.00 |
| ATOM | 5497 | C | GLN | 130 | 76.445 | 47.658 | 53.497 | 1.00 | 16.83 |
| ATOM | 5498 | O | GLN | 130 | 77.116 | 48.189 | 54.371 | 1.00 | 17.31 |
| ATOM | 5499 | N | ILE | 131 | 75.204 | 47.234 | 53.683 | 1.00 | 17.34 |
| ATOM | 5500 | H | ILE | 131 | 74.741 | 46.822 | 52.919 | 1.00 | 0.00 |
| ATOM | 5501 | CA | ILE | 131 | 74.520 | 47.419 | 54.961 | 1.00 | 16.07 |
| ATOM | 5502 | CB | ILE | 131 | 72.985 | 47.305 | 54.713 | 1.00 | 18.21 |
| ATOM | 5503 | CG2 | ILE | 131 | 72.643 | 48.288 | 53.570 | 1.00 | 10.00 |
| ATOM | 5504 | CG1 | ILE | 131 | 72.538 | 45.872 | 54.413 | 1.00 | 19.32 |
| ATOM | 5505 | CD1 | ILE | 131 | 71.024 | 45.818 | 54.149 | 1.00 | 21.77 |
| ATOM | 5506 | C | ILE | 131 | 75.001 | 46.464 | 56.069 | 1.00 | 16.80 |

FIG. 1: A-93

| ATOM | 5507 | O | ILE | 131 | 74.929 | 46.737 | 57.266 | 1.00 | 16.97 |
|---|---|---|---|---|---|---|---|---|---|
| ATOM | 5508 | N | VAL | 132 | 75.562 | 45.295 | 55.757 | 1.00 | 20.04 |
| ATOM | 5509 | H | VAL | 132 | 75.472 | 44.965 | 54.837 | 1.00 | 0.00 |
| ATOM | 5510 | CA | VAL | 132 | 76.244 | 44.475 | 56.757 | 1.00 | 17.43 |
| ATOM | 5511 | CB | VAL | 132 | 76.663 | 43.165 | 56.156 | 1.00 | 16.54 |
| ATOM | 5512 | CG1 | VAL | 132 | 77.656 | 42.512 | 57.052 | 1.00 | 18.19 |
| ATOM | 5513 | CG2 | VAL | 132 | 75.475 | 42.230 | 56.029 | 1.00 | 13.84 |
| ATOM | 5514 | C | VAL | 132 | 77.455 | 45.289 | 57.163 | 1.00 | 19.71 |
| ATOM | 5515 | O | VAL | 132 | 77.566 | 45.643 | 58.329 | 1.00 | 24.60 |
| ATOM | 5516 | N | ASP | 133 | 78.327 | 45.730 | 56.270 | 1.00 | 21.28 |
| ATOM | 5517 | H | ASP | 133 | 78.243 | 45.443 | 55.344 | 1.00 | 0.00 |
| ATOM | 5518 | CA | ASP | 133 | 79.437 | 46.577 | 56.676 | 1.00 | 20.22 |
| ATOM | 5519 | CB | ASP | 133 | 80.245 | 47.013 | 55.491 | 1.00 | 24.55 |
| ATOM | 5520 | CG | ASP | 133 | 80.918 | 45.901 | 54.714 | 1.00 | 25.28 |
| ATOM | 5521 | OD1 | ASP | 133 | 81.603 | 45.076 | 55.302 | 1.00 | 28.10 |
| ATOM | 5522 | OD2 | ASP | 133 | 80.766 | 45.867 | 53.502 | 1.00 | 27.72 |
| ATOM | 5523 | C | ASP | 133 | 79.074 | 47.840 | 57.448 | 1.00 | 20.60 |
| ATOM | 5524 | O | ASP | 133 | 79.735 | 48.099 | 58.457 | 1.00 | 22.11 |
| ATOM | 5525 | N | LYS | 134 | 78.044 | 48.638 | 57.132 | 1.00 | 19.05 |
| ATOM | 5526 | H | LYS | 134 | 77.565 | 48.473 | 56.290 | 1.00 | 0.00 |
| ATOM | 5527 | CA | LYS | 134 | 77.795 | 49.813 | 57.955 | 1.00 | 16.85 |
| ATOM | 5528 | CB | LYS | 134 | 76.853 | 50.720 | 57.264 | 1.00 | 14.20 |
| ATOM | 5529 | CG | LYS | 134 | 77.506 | 51.297 | 56.012 | 1.00 | 13.44 |
| ATOM | 5530 | CD | LYS | 134 | 76.582 | 52.210 | 55.171 | 1.00 | 18.59 |
| ATOM | 5531 | CE | LYS | 134 | 76.709 | 51.735 | 53.717 | 1.00 | 19.89 |
| ATOM | 5532 | NZ | LYS | 134 | 75.946 | 52.516 | 52.776 | 1.00 | 19.69 |
| ATOM | 5533 | HZ1 | LYS | 134 | 76.248 | 53.507 | 52.820 | 1.00 | 0.00 |
| ATOM | 5534 | HZ2 | LYS | 134 | 74.936 | 52.454 | 53.011 | 1.00 | 0.00 |
| ATOM | 5535 | HZ3 | LYS | 134 | 76.103 | 52.150 | 51.817 | 1.00 | 0.00 |
| ATOM | 5536 | C | LYS | 134 | 77.264 | 49.458 | 59.309 | 1.00 | 18.93 |
| ATOM | 5537 | O | LYS | 134 | 77.717 | 50.010 | 60.297 | 1.00 | 23.74 |
| ATOM | 5538 | N | THR | 135 | 76.449 | 48.402 | 59.435 | 1.00 | 21.95 |
| ATOM | 5539 | H | THR | 135 | 76.215 | 47.929 | 58.607 | 1.00 | 0.00 |
| ATOM | 5540 | CA | THR | 135 | 75.872 | 47.935 | 60.723 | 1.00 | 20.19 |
| ATOM | 5541 | CB | THR | 135 | 74.942 | 46.665 | 60.601 | 1.00 | 18.29 |
| ATOM | 5542 | OG1 | THR | 135 | 73.734 | 47.074 | 59.954 | 1.00 | 15.58 |
| ATOM | 5543 | HG1 | THR | 135 | 73.947 | 47.172 | 59.009 | 1.00 | 0.00 |
| ATOM | 5544 | CG2 | THR | 135 | 74.541 | 46.069 | 61.952 | 1.00 | 16.61 |
| ATOM | 5545 | C | THR | 135 | 76.942 | 47.563 | 61.716 | 1.00 | 21.35 |
| ATOM | 5546 | O | THR | 135 | 76.856 | 47.769 | 62.923 | 1.00 | 23.55 |
| ATOM | 5547 | N | ILE | 136 | 77.986 | 46.949 | 61.199 | 1.00 | 23.01 |
| ATOM | 5548 | H | ILE | 136 | 77.968 | 46.688 | 60.251 | 1.00 | 0.00 |
| ATOM | 5549 | CA | ILE | 136 | 79.108 | 46.566 | 62.049 | 1.00 | 22.07 |
| ATOM | 5550 | CB | ILE | 136 | 79.802 | 45.406 | 61.318 | 1.00 | 16.58 |
| ATOM | 5551 | CG2 | ILE | 136 | 81.171 | 45.192 | 61.857 | 1.00 | 18.53 |
| ATOM | 5552 | CG1 | ILE | 136 | 78.877 | 44.200 | 61.415 | 1.00 | 13.96 |
| ATOM | 5553 | CD1 | ILE | 136 | 79.432 | 42.881 | 60.976 | 1.00 | 11.84 |
| ATOM | 5554 | C | ILE | 136 | 79.970 | 47.809 | 62.286 | 1.00 | 24.21 |
| ATOM | 5555 | O | ILE | 136 | 80.316 | 48.103 | 63.422 | 1.00 | 26.21 |
| ATOM | 5556 | N | ILE | 137 | 80.208 | 48.676 | 61.307 | 1.00 | 25.73 |
| ATOM | 5557 | H | ILE | 137 | 79.864 | 48.475 | 60.412 | 1.00 | 0.00 |
| ATOM | 5558 | CA | ILE | 137 | 81.002 | 49.881 | 61.512 | 1.00 | 26.77 |
| ATOM | 5559 | CB | ILE | 137 | 81.065 | 50.657 | 60.157 | 1.00 | 29.17 |
| ATOM | 5560 | CG2 | ILE | 137 | 81.584 | 52.090 | 60.319 | 1.00 | 32.32 |
| ATOM | 5561 | CG1 | ILE | 137 | 81.970 | 49.916 | 59.227 | 1.00 | 27.13 |
| ATOM | 5562 | CD1 | ILE | 137 | 81.801 | 50.473 | 57.816 | 1.00 | 30.89 |
| ATOM | 5563 | C | ILE | 137 | 80.399 | 50.739 | 62.621 | 1.00 | 27.48 |
| ATOM | 5564 | O | ILE | 137 | 81.083 | 51.353 | 63.431 | 1.00 | 28.74 |
| ATOM | 5565 | N | ASN | 138 | 79.078 | 50.742 | 62.704 | 1.00 | 28.53 |
| ATOM | 5566 | H | ASN | 138 | 78.559 | 50.260 | 62.027 | 1.00 | 0.00 |

FIG. 1: A-94

| ATOM | 5567 | CA | ASN | 138 | 78.433 | 51.574 | 63.700 | 1.00 | 28.82 |
| ATOM | 5568 | CB | ASN | 138 | 77.175 | 52.186 | 63.115 | 1.00 | 28.01 |
| ATOM | 5569 | CG | ASN | 138 | 77.523 | 53.174 | 62.029 | 1.00 | 29.44 |
| ATOM | 5570 | OD1 | ASN | 138 | 76.931 | 53.157 | 60.969 | 1.00 | 31.71 |
| ATOM | 5571 | ND2 | ASN | 138 | 78.477 | 54.078 | 62.144 | 1.00 | 31.58 |
| ATOM | 5572 | HD21 | ASN | 138 | 79.024 | 54.144 | 62.946 | 1.00 | 0.00 |
| ATOM | 5573 | HD22 | ASN | 138 | 78.535 | 54.652 | 61.357 | 1.00 | 0.00 |
| ATOM | 5574 | C | ASN | 138 | 78.084 | 50.977 | 65.031 | 1.00 | 27.02 |
| ATOM | 5575 | O | ASN | 138 | 77.640 | 51.665 | 65.941 | 1.00 | 29.38 |
| ATOM | 5576 | N | ALA | 139 | 78.294 | 49.704 | 65.188 | 1.00 | 27.24 |
| ATOM | 5577 | H | ALA | 139 | 78.608 | 49.178 | 64.423 | 1.00 | 0.00 |
| ATOM | 5578 | CA | ALA | 139 | 77.893 | 49.078 | 66.445 | 1.00 | 27.48 |
| ATOM | 5579 | CB | ALA | 139 | 76.752 | 48.071 | 66.155 | 1.00 | 29.87 |
| ATOM | 5580 | C | ALA | 139 | 79.035 | 48.385 | 67.146 | 1.00 | 26.61 |
| ATOM | 5581 | O | ALA | 139 | 78.986 | 48.018 | 68.308 | 1.00 | 25.14 |
| ATOM | 5582 | N | ASP | 140 | 80.102 | 48.214 | 66.385 | 1.00 | 26.29 |
| ATOM | 5583 | H | ASP | 140 | 80.026 | 48.430 | 65.433 | 1.00 | 0.00 |
| ATOM | 5584 | CA | ASP | 140 | 81.354 | 47.695 | 66.853 | 1.00 | 28.92 |
| ATOM | 5585 | CB | ASP | 140 | 82.131 | 47.323 | 65.614 | 1.00 | 30.11 |
| ATOM | 5586 | CG | ASP | 140 | 83.550 | 46.817 | 65.744 | 1.00 | 31.44 |
| ATOM | 5587 | OD1 | ASP | 140 | 84.353 | 47.143 | 64.861 | 1.00 | 33.77 |
| ATOM | 5588 | OD2 | ASP | 140 | 83.836 | 46.100 | 66.704 | 1.00 | 31.14 |
| ATOM | 5589 | C | ASP | 140 | 82.069 | 48.740 | 67.708 | 1.00 | 30.84 |
| ATOM | 5590 | O | ASP | 140 | 83.160 | 49.269 | 67.447 | 1.00 | 31.44 |
| ATOM | 5591 | N | LYS | 141 | 81.454 | 48.938 | 68.862 | 1.00 | 31.24 |
| ATOM | 5592 | H | LYS | 141 | 80.671 | 48.387 | 69.065 | 1.00 | 0.00 |
| ATOM | 5593 | CA | LYS | 141 | 81.891 | 49.906 | 69.844 | 1.00 | 32.18 |
| ATOM | 5594 | CB | LYS | 141 | 80.645 | 50.242 | 70.663 | 1.00 | 28.42 |
| ATOM | 5595 | CG | LYS | 141 | 79.860 | 51.332 | 69.912 | 1.00 | 25.33 |
| ATOM | 5596 | CD | LYS | 141 | 78.420 | 51.077 | 70.202 | 1.00 | 25.80 |
| ATOM | 5597 | CE | LYS | 141 | 77.577 | 52.338 | 70.218 | 1.00 | 27.06 |
| ATOM | 5598 | NZ | LYS | 141 | 77.420 | 52.934 | 68.910 | 1.00 | 29.36 |
| ATOM | 5599 | HZ1 | LYS | 141 | 78.349 | 53.228 | 68.550 | 1.00 | 0.00 |
| ATOM | 5600 | HZ2 | LYS | 141 | 76.785 | 53.754 | 68.978 | 1.00 | 0.00 |
| ATOM | 5601 | HZ3 | LYS | 141 | 77.004 | 52.225 | 68.272 | 1.00 | 0.00 |
| ATOM | 5602 | C | LYS | 141 | 83.081 | 49.480 | 70.700 | 1.00 | 33.83 |
| ATOM | 5603 | O | LYS | 141 | 83.297 | 49.916 | 71.819 | 1.00 | 37.14 |
| ATOM | 5604 | N | ASP | 142 | 83.962 | 48.732 | 70.078 | 1.00 | 34.38 |
| ATOM | 5605 | H | ASP | 142 | 83.852 | 48.667 | 69.113 | 1.00 | 0.00 |
| ATOM | 5606 | CA | ASP | 142 | 85.114 | 48.118 | 70.680 | 1.00 | 38.14 |
| ATOM | 5607 | CB | ASP | 142 | 84.662 | 47.119 | 71.744 | 1.00 | 44.30 |
| ATOM | 5608 | CG | ASP | 142 | 85.514 | 45.862 | 71.774 | 1.00 | 49.24 |
| ATOM | 5609 | OD1 | ASP | 142 | 85.004 | 44.826 | 71.336 | 1.00 | 50.65 |
| ATOM | 5610 | OD2 | ASP | 142 | 86.689 | 45.943 | 72.164 | 1.00 | 55.31 |
| ATOM | 5611 | C | ASP | 142 | 85.640 | 47.431 | 69.437 | 1.00 | 38.64 |
| ATOM | 5612 | O | ASP | 142 | 85.179 | 46.369 | 69.015 | 1.00 | 41.61 |
| ATOM | 5613 | N | GLY | 143 | 86.581 | 48.109 | 68.829 | 1.00 | 37.15 |
| ATOM | 5614 | H | GLY | 143 | 86.941 | 48.879 | 69.314 | 1.00 | 0.00 |
| ATOM | 5615 | CA | GLY | 143 | 87.139 | 47.821 | 67.505 | 1.00 | 34.98 |
| ATOM | 5616 | C | GLY | 143 | 87.433 | 46.436 | 66.930 | 1.00 | 33.25 |
| ATOM | 5617 | O | GLY | 143 | 88.196 | 46.419 | 65.963 | 1.00 | 34.86 |
| ATOM | 5618 | N | ASP | 144 | 86.914 | 45.278 | 67.359 | 1.00 | 31.48 |
| ATOM | 5619 | H | ASP | 144 | 86.360 | 45.258 | 68.159 | 1.00 | 0.00 |
| ATOM | 5620 | CA | ASP | 144 | 87.240 | 44.033 | 66.683 | 1.00 | 29.20 |
| ATOM | 5621 | CB | ASP | 144 | 87.109 | 42.897 | 67.669 | 1.00 | 30.85 |
| ATOM | 5622 | CG | ASP | 144 | 85.749 | 42.672 | 68.301 | 1.00 | 31.31 |
| ATOM | 5623 | OD1 | ASP | 144 | 85.684 | 42.000 | 69.325 | 1.00 | 31.28 |
| ATOM | 5624 | OD2 | ASP | 144 | 84.758 | 43.140 | 67.760 | 1.00 | 33.44 |
| ATOM | 5625 | C | ASP | 144 | 86.459 | 43.688 | 65.424 | 1.00 | 28.83 |
| ATOM | 5626 | O | ASP | 144 | 86.713 | 42.672 | 64.783 | 1.00 | 30.85 |

FIG. 1: A-95

| ATOM | 5627 | N | GLY | 145 | 85.436 | 44.431 | 65.032 | 1.00 | 27.19 |
|------|------|------|-----|-----|--------|--------|--------|------|-------|
| ATOM | 5628 | H | GLY | 145 | 85.274 | 45.238 | 65.539 | 1.00 | 0.00 |
| ATOM | 5629 | CA | GLY | 145 | 84.759 | 44.143 | 63.760 | 1.00 | 26.86 |
| ATOM | 5630 | C | GLY | 145 | 83.762 | 42.996 | 63.736 | 1.00 | 27.14 |
| ATOM | 5631 | O | GLY | 145 | 83.224 | 42.589 | 62.714 | 1.00 | 26.66 |
| ATOM | 5632 | N | ARG | 146 | 83.519 | 42.432 | 64.897 | 1.00 | 28.83 |
| ATOM | 5633 | H | ARG | 146 | 84.093 | 42.684 | 65.642 | 1.00 | 0.00 |
| ATOM | 5634 | CA | ARG | 146 | 82.516 | 41.396 | 65.105 | 1.00 | 29.27 |
| ATOM | 5635 | CB | ARG | 146 | 83.278 | 40.085 | 65.388 | 1.00 | 27.24 |
| ATOM | 5636 | CG | ARG | 146 | 84.075 | 39.993 | 66.666 | 1.00 | 27.75 |
| ATOM | 5637 | CD | ARG | 146 | 84.829 | 38.690 | 66.538 | 1.00 | 33.54 |
| ATOM | 5638 | NE | ARG | 146 | 85.126 | 38.056 | 67.825 | 1.00 | 36.79 |
| ATOM | 5639 | HE | ARG | 146 | 84.507 | 37.382 | 68.167 | 1.00 | 0.00 |
| ATOM | 5640 | CZ | ARG | 146 | 86.250 | 38.261 | 68.509 | 1.00 | 37.51 |
| ATOM | 5641 | NH1 | ARG | 146 | 86.421 | 37.656 | 69.678 | 1.00 | 39.08 |
| ATOM | 5642 | HH11 | ARG | 146 | 85.706 | 37.055 | 70.037 | 1.00 | 0.00 |
| ATOM | 5643 | HH12 | ARG | 146 | 87.265 | 37.800 | 70.194 | 1.00 | 0.00 |
| ATOM | 5644 | NH2 | ARG | 146 | 87.228 | 39.029 | 68.026 | 1.00 | 41.44 |
| ATOM | 5645 | HH21 | ARG | 146 | 87.136 | 39.454 | 67.125 | 1.00 | 0.00 |
| ATOM | 5646 | HH22 | ARG | 146 | 88.069 | 39.152 | 68.553 | 1.00 | 0.00 |
| ATOM | 5647 | C | ARG | 146 | 81.534 | 41.794 | 66.246 | 1.00 | 29.45 |
| ATOM | 5648 | O | ARG | 146 | 81.954 | 42.379 | 67.252 | 1.00 | 33.12 |
| ATOM | 5649 | N | ILE | 147 | 80.219 | 41.568 | 66.196 | 1.00 | 27.05 |
| ATOM | 5650 | H | ILE | 147 | 79.853 | 41.106 | 65.413 | 1.00 | 0.00 |
| ATOM | 5651 | CA | ILE | 147 | 79.350 | 42.048 | 67.266 | 1.00 | 23.37 |
| ATOM | 5652 | CB | ILE | 147 | 78.032 | 42.505 | 66.619 | 1.00 | 20.25 |
| ATOM | 5653 | CG2 | ILE | 147 | 77.082 | 43.082 | 67.648 | 1.00 | 20.76 |
| ATOM | 5654 | CG1 | ILE | 147 | 78.341 | 43.548 | 65.539 | 1.00 | 18.36 |
| ATOM | 5655 | CD1 | ILE | 147 | 79.319 | 44.725 | 65.821 | 1.00 | 13.61 |
| ATOM | 5656 | C | ILE | 147 | 79.105 | 41.071 | 68.401 | 1.00 | 24.21 |
| ATOM | 5657 | O | ILE | 147 | 78.742 | 39.916 | 68.236 | 1.00 | 22.85 |
| ATOM | 5658 | N | SER | 148 | 79.376 | 41.511 | 69.629 | 1.00 | 27.21 |
| ATOM | 5659 | H | SER | 148 | 79.798 | 42.385 | 69.707 | 1.00 | 0.00 |
| ATOM | 5660 | CA | SER | 148 | 79.142 | 40.708 | 70.846 | 1.00 | 25.93 |
| ATOM | 5661 | CB | SER | 148 | 80.107 | 41.136 | 71.927 | 1.00 | 26.53 |
| ATOM | 5662 | OG | SER | 148 | 79.858 | 42.475 | 72.360 | 1.00 | 29.92 |
| ATOM | 5663 | HG | SER | 148 | 80.719 | 42.904 | 72.473 | 1.00 | 0.00 |
| ATOM | 5664 | C | SER | 148 | 77.742 | 40.798 | 71.436 | 1.00 | 24.32 |
| ATOM | 5665 | O | SER | 148 | 77.006 | 41.742 | 71.157 | 1.00 | 26.85 |
| ATOM | 5666 | N | PHE | 149 | 77.258 | 39.947 | 72.312 | 1.00 | 23.12 |
| ATOM | 5667 | H | PHE | 149 | 77.774 | 39.140 | 72.523 | 1.00 | 0.00 |
| ATOM | 5668 | CA | PHE | 149 | 75.902 | 40.122 | 72.852 | 1.00 | 24.59 |
| ATOM | 5669 | CB | PHE | 149 | 75.658 | 38.981 | 73.838 | 1.00 | 21.83 |
| ATOM | 5670 | CG | PHE | 149 | 74.232 | 38.862 | 74.283 | 1.00 | 18.19 |
| ATOM | 5671 | CD1 | PHE | 149 | 73.931 | 39.002 | 75.632 | 1.00 | 23.47 |
| ATOM | 5672 | CD2 | PHE | 149 | 73.242 | 38.669 | 73.337 | 1.00 | 18.74 |
| ATOM | 5673 | CE1 | PHE | 149 | 72.593 | 38.961 | 76.046 | 1.00 | 22.69 |
| ATOM | 5674 | CE2 | PHE | 149 | 71.917 | 38.629 | 73.733 | 1.00 | 20.23 |
| ATOM | 5675 | CZ | PHE | 149 | 71.594 | 38.777 | 75.083 | 1.00 | 24.07 |
| ATOM | 5676 | C | PHE | 149 | 75.541 | 41.470 | 73.513 | 1.00 | 27.54 |
| ATOM | 5677 | O | PHE | 149 | 74.413 | 41.945 | 73.401 | 1.00 | 27.21 |
| ATOM | 5678 | N | GLU | 150 | 76.508 | 42.116 | 74.202 | 1.00 | 32.20 |
| ATOM | 5679 | H | GLU | 150 | 77.361 | 41.647 | 74.251 | 1.00 | 0.00 |
| ATOM | 5680 | CA | GLU | 150 | 76.359 | 43.403 | 74.910 | 1.00 | 32.39 |
| ATOM | 5681 | CB | GLU | 150 | 77.673 | 43.736 | 75.663 | 1.00 | 36.29 |
| ATOM | 5682 | CG | GLU | 150 | 77.501 | 44.714 | 76.866 | 1.00 | 45.20 |
| ATOM | 5683 | CD | GLU | 150 | 78.738 | 45.309 | 77.610 | 1.00 | 49.03 |
| ATOM | 5684 | OE1 | GLU | 150 | 78.846 | 45.174 | 78.842 | 1.00 | 50.92 |
| ATOM | 5685 | OE2 | GLU | 150 | 79.583 | 45.957 | 76.985 | 1.00 | 50.03 |
| ATOM | 5686 | C | GLU | 150 | 76.053 | 44.465 | 73.844 | 1.00 | 32.49 |

FIG. 1: A-96

| ATOM | 5687 | O | GLU | 150 | 75.160 | 45.309 | 73.968 | 1.00 | 34.18 |
|---|---|---|---|---|---|---|---|---|---|
| ATOM | 5688 | N | GLU | 151 | 76.743 | 44.318 | 72.708 | 1.00 | 30.06 |
| ATOM | 5689 | H | GLU | 151 | 77.392 | 43.587 | 72.659 | 1.00 | 0.00 |
| ATOM | 5690 | CA | GLU | 151 | 76.582 | 45.179 | 71.538 | 1.00 | 27.95 |
| ATOM | 5691 | CB | GLU | 151 | 77.722 | 45.024 | 70.655 | 1.00 | 27.41 |
| ATOM | 5692 | CG | GLU | 151 | 78.974 | 45.560 | 71.223 | 1.00 | 26.99 |
| ATOM | 5693 | CD | GLU | 151 | 80.085 | 45.380 | 70.236 | 1.00 | 26.59 |
| ATOM | 5694 | OE1 | GLU | 151 | 80.079 | 44.421 | 69.458 | 1.00 | 27.15 |
| ATOM | 5695 | OE2 | GLU | 151 | 80.972 | 46.212 | 70.282 | 1.00 | 31.01 |
| ATOM | 5696 | C | GLU | 151 | 75.358 | 44.947 | 70.671 | 1.00 | 27.92 |
| ATOM | 5697 | O | GLU | 151 | 74.765 | 45.906 | 70.202 | 1.00 | 30.21 |
| ATOM | 5698 | N | PHE | 152 | 75.038 | 43.684 | 70.344 | 1.00 | 25.50 |
| ATOM | 5699 | H | PHE | 152 | 75.739 | 43.012 | 70.455 | 1.00 | 0.00 |
| ATOM | 5700 | CA | PHE | 152 | 73.759 | 43.283 | 69.783 | 1.00 | 21.63 |
| ATOM | 5701 | CB | PHE | 152 | 73.720 | 41.779 | 69.829 | 1.00 | 22.89 |
| ATOM | 5702 | CG | PHE | 152 | 72.399 | 41.129 | 69.437 | 1.00 | 20.92 |
| ATOM | 5703 | CD1 | PHE | 152 | 71.626 | 40.509 | 70.424 | 1.00 | 18.72 |
| ATOM | 5704 | CD2 | PHE | 152 | 71.983 | 41.131 | 68.095 | 1.00 | 20.98 |
| ATOM | 5705 | CE1 | PHE | 152 | 70.435 | 39.886 | 70.069 | 1.00 | 17.93 |
| ATOM | 5706 | CE2 | PHE | 152 | 70.792 | 40.507 | 67.744 | 1.00 | 21.29 |
| ATOM | 5707 | CZ | PHE | 152 | 70.024 | 39.887 | 68.737 | 1.00 | 20.25 |
| ATOM | 5708 | C | PHE | 152 | 72.644 | 43.891 | 70.637 | 1.00 | 21.29 |
| ATOM | 5709 | O | PHE | 152 | 71.799 | 44.665 | 70.208 | 1.00 | 20.17 |
| ATOM | 5710 | N | CYS | 153 | 72.712 | 43.613 | 71.926 | 1.00 | 20.84 |
| ATOM | 5711 | H | CYS | 153 | 73.368 | 42.951 | 72.214 | 1.00 | 0.00 |
| ATOM | 5712 | CA | CYS | 153 | 71.802 | 44.196 | 72.895 | 1.00 | 21.20 |
| ATOM | 5713 | CB | CYS | 153 | 72.170 | 43.733 | 74.276 | 1.00 | 24.94 |
| ATOM | 5714 | SG | CYS | 153 | 71.713 | 41.998 | 74.483 | 1.00 | 33.11 |
| ATOM | 5715 | C | CYS | 153 | 71.696 | 45.697 | 72.935 | 1.00 | 19.20 |
| ATOM | 5716 | O | CYS | 153 | 70.617 | 46.210 | 73.160 | 1.00 | 22.83 |
| ATOM | 5717 | N | ALA | 154 | 72.791 | 46.432 | 72.793 | 1.00 | 19.00 |
| ATOM | 5718 | H | ALA | 154 | 73.652 | 45.973 | 72.872 | 1.00 | 0.00 |
| ATOM | 5719 | CA | ALA | 154 | 72.785 | 47.878 | 72.648 | 1.00 | 15.82 |
| ATOM | 5720 | CB | ALA | 154 | 74.155 | 48.374 | 72.404 | 1.00 | 16.16 |
| ATOM | 5721 | C | ALA | 154 | 71.950 | 48.417 | 71.498 | 1.00 | 15.52 |
| ATOM | 5722 | O | ALA | 154 | 71.420 | 49.518 | 71.488 | 1.00 | 15.51 |
| ATOM | 5723 | N | VAL | 155 | 71.894 | 47.596 | 70.469 | 1.00 | 18.52 |
| ATOM | 5724 | H | VAL | 155 | 72.416 | 46.770 | 70.534 | 1.00 | 0.00 |
| ATOM | 5725 | CA | VAL | 155 | 71.172 | 47.871 | 69.225 | 1.00 | 17.99 |
| ATOM | 5726 | CB | VAL | 155 | 71.965 | 47.161 | 68.084 | 1.00 | 16.45 |
| ATOM | 5727 | CG1 | VAL | 155 | 71.214 | 47.283 | 66.807 | 1.00 | 17.16 |
| ATOM | 5728 | CG2 | VAL | 155 | 73.330 | 47.780 | 67.875 | 1.00 | 11.33 |
| ATOM | 5729 | C | VAL | 155 | 69.717 | 47.402 | 69.286 | 1.00 | 21.28 |
| ATOM | 5730 | O | VAL | 155 | 68.735 | 48.109 | 69.058 | 1.00 | 22.50 |
| ATOM | 5731 | N | VAL | 156 | 69.538 | 46.155 | 69.666 | 1.00 | 24.07 |
| ATOM | 5732 | H | VAL | 156 | 70.266 | 45.705 | 70.129 | 1.00 | 0.00 |
| ATOM | 5733 | CA | VAL | 156 | 68.252 | 45.542 | 69.561 | 1.00 | 25.57 |
| ATOM | 5734 | CB | VAL | 156 | 68.660 | 44.133 | 69.129 | 1.00 | 26.17 |
| ATOM | 5735 | CG1 | VAL | 156 | 68.115 | 42.990 | 69.964 | 1.00 | 27.90 |
| ATOM | 5736 | CG2 | VAL | 156 | 68.219 | 44.101 | 67.676 | 1.00 | 27.18 |
| ATOM | 5737 | C | VAL | 156 | 67.329 | 45.686 | 70.759 | 1.00 | 30.00 |
| ATOM | 5738 | O | VAL | 156 | 67.655 | 45.593 | 71.951 | 1.00 | 33.12 |
| ATOM | 5739 | N | GLY | 157 | 66.117 | 46.035 | 70.304 | 1.00 | 33.79 |
| ATOM | 5740 | H | GLY | 157 | 66.058 | 46.207 | 69.344 | 1.00 | 0.00 |
| ATOM | 5741 | CA | GLY | 157 | 64.924 | 46.329 | 71.116 | 1.00 | 31.89 |
| ATOM | 5742 | C | GLY | 157 | 63.636 | 46.240 | 70.286 | 1.00 | 30.99 |
| ATOM | 5743 | O | GLY | 157 | 63.611 | 46.477 | 69.069 | 1.00 | 27.08 |
| ATOM | 5744 | N | GLY | 158 | 62.634 | 45.808 | 71.081 | 1.00 | 34.53 |
| ATOM | 5745 | H | GLY | 158 | 62.886 | 45.728 | 72.022 | 1.00 | 0.00 |
| ATOM | 5746 | CA | GLY | 158 | 61.231 | 45.491 | 70.731 | 1.00 | 36.54 |

FIG. 1: A-97

| ATOM | 5747 | C | GLY | 158 | 60.684 | 44.030 | 70.842 | 1.00 | 39.33 |
|---|---|---|---|---|---|---|---|---|---|
| ATOM | 5748 | O | GLY | 158 | 59.901 | 43.668 | 71.721 | 1.00 | 39.57 |
| ATOM | 5749 | N | LEU | 159 | 61.172 | 43.118 | 69.982 | 1.00 | 40.34 |
| ATOM | 5750 | H | LEU | 159 | 61.961 | 43.412 | 69.675 | 1.00 | 0.00 |
| ATOM | 5751 | CA | LEU | 159 | 60.601 | 41.790 | 68.579 | 1.00 | 38.06 |
| ATOM | 5752 | CB | LEU | 159 | 61.516 | 41.243 | 67.966 | 1.00 | 40.75 |
| ATOM | 5753 | CG | LEU | 159 | 61.120 | 39.907 | 67.136 | 1.00 | 43.73 |
| ATOM | 5754 | CD1 | LEU | 159 | 59.831 | 40.061 | 67.178 | 1.00 | 46.41 |
| ATOM | 5755 | CD2 | LEU | 159 | 62.295 | 39.381 | 70.582 | 1.00 | 44.55 |
| ATOM | 5756 | C | LEU | 159 | 60.195 | 40.607 | 70.356 | 1.00 | 35.89 |
| ATOM | 5757 | O | LEU | 159 | 59.153 | 39.983 | 71.531 | 1.00 | 35.30 |
| ATOM | 5758 | N | ASP | 160 | 61.033 | 40.175 | 71.564 | 1.00 | 33.06 |
| ATOM | 5759 | H | ASP | 160 | 61.897 | 40.627 | 72.483 | 1.00 | 0.00 |
| ATOM | 5760 | CA | ASP | 160 | 60.810 | 39.090 | 73.761 | 1.00 | 29.19 |
| ATOM | 5761 | CB | ASP | 160 | 61.578 | 39.452 | 74.536 | 1.00 | 26.00 |
| ATOM | 5762 | CG | ASP | 160 | 61.161 | 40.719 | 74.115 | 1.00 | 25.71 |
| ATOM | 5763 | OD1 | ASP | 160 | 61.451 | 41.837 | 75.602 | 1.00 | 20.07 |
| ATOM | 5764 | OD2 | ASP | 160 | 60.553 | 40.592 | 72.794 | 1.00 | 26.80 |
| ATOM | 5765 | C | ASP | 160 | 59.351 | 38.776 | 72.720 | 1.00 | 30.59 |
| ATOM | 5766 | O | ASP | 160 | 58.890 | 37.657 | 72.942 | 1.00 | 31.37 |
| ATOM | 5767 | N | ILE | 161 | 58.564 | 39.839 | 72.906 | 1.00 | 33.02 |
| ATOM | 5768 | H | ILE | 161 | 59.029 | 40.696 | 73.216 | 1.00 | 0.00 |
| ATOM | 5769 | CA | ILE | 161 | 57.126 | 39.841 | 73.220 | 1.00 | 32.58 |
| ATOM | 5770 | CB | ILE | 161 | 56.651 | 41.350 | 74.547 | 1.00 | 32.12 |
| ATOM | 5771 | CG2 | ILE | 161 | 57.032 | 41.993 | 72.088 | 1.00 | 29.49 |
| ATOM | 5772 | CG1 | ILE | 161 | 57.291 | 42.177 | 70.699 | 1.00 | 32.98 |
| ATOM | 5773 | CD1 | ILE | 161 | 56.608 | 42.094 | 72.317 | 1.00 | 33.32 |
| ATOM | 5774 | C | ILE | 161 | 56.232 | 38.985 | 72.593 | 1.00 | 34.77 |
| ATOM | 5775 | O | ILE | 161 | 55.045 | 38.765 | 71.164 | 1.00 | 37.09 |
| ATOM | 5776 | N | HIS | 162 | 56.725 | 38.533 | 70.924 | 1.00 | 35.02 |
| ATOM | 5777 | H | HIS | 162 | 57.627 | 38.835 | 70.302 | 1.00 | 0.00 |
| ATOM | 5778 | CA | HIS | 162 | 55.965 | 37.616 | 68.880 | 1.00 | 36.29 |
| ATOM | 5779 | CB | HIS | 162 | 55.836 | 38.218 | 68.725 | 1.00 | 40.48 |
| ATOM | 5780 | CG | HIS | 162 | 54.691 | 39.234 | 67.588 | 1.00 | 44.88 |
| ATOM | 5781 | CD2 | HIS | 162 | 54.484 | 40.006 | 69.607 | 1.00 | 44.78 |
| ATOM | 5782 | ND1 | HIS | 162 | 53.743 | 39.592 | 70.530 | 1.00 | 46.57 |
| ATOM | 5783 | HD1 | HIS | 162 | 53.651 | 39.252 | 69.058 | 1.00 | 0.00 |
| ATOM | 5784 | CE1 | HIS | 162 | 52.993 | 40.537 | 67.843 | 1.00 | 46.67 |
| ATOM | 5785 | NE2 | HIS | 162 | 53.452 | 40.778 | 67.230 | 1.00 | 44.72 |
| ATOM | 5786 | HE2 | HIS | 162 | 53.101 | 41.459 | 70.171 | 1.00 | 0.00 |
| ATOM | 5787 | C | HIS | 162 | 56.493 | 36.172 | 69.576 | 1.00 | 35.01 |
| ATOM | 5788 | O | HIS | 162 | 55.838 | 35.311 | 70.757 | 1.00 | 33.83 |
| ATOM | 5789 | N | LYS | 163 | 57.663 | 35.876 | 71.281 | 1.00 | 33.97 |
| ATOM | 5790 | H | LYS | 163 | 58.088 | 36.584 | 70.760 | 1.00 | 0.00 |
| ATOM | 5791 | CA | LYS | 163 | 58.308 | 34.558 | 70.819 | 1.00 | 32.59 |
| ATOM | 5792 | CB | LYS | 163 | 59.839 | 34.739 | 69.572 | 1.00 | 30.49 |
| ATOM | 5793 | CG | LYS | 163 | 60.573 | 35.263 | 70.072 | 1.00 | 26.88 |
| ATOM | 5794 | CD | LYS | 163 | 61.790 | 36.039 | 69.068 | 1.00 | 21.67 |
| ATOM | 5795 | CE | LYS | 163 | 62.862 | 36.009 | 68.947 | 1.00 | 18.25 |
| ATOM | 5796 | NZ | LYS | 163 | 63.204 | 34.609 | 68.264 | 1.00 | 17.76 |
| ATOM | 5797 | HZ1 | LYS | 163 | 63.985 | 34.514 | 68.603 | 1.00 | 0.00 |
| ATOM | 5798 | HZ2 | LYS | 163 | 62.389 | 34.060 | 69.873 | 1.00 | 0.00 |
| ATOM | 5799 | HZ3 | LYS | 163 | 63.502 | 34.242 | 71.924 | 1.00 | 0.00 |
| ATOM | 5800 | C | LYS | 163 | 57.871 | 33.655 | 72.580 | 1.00 | 33.37 |
| ATOM | 5801 | O | LYS | 163 | 58.708 | 33.051 | 72.251 | 1.00 | 33.07 |
| ATOM | 5802 | N | LYS | 164 | 56.580 | 33.543 | 71.681 | 1.00 | 35.22 |
| ATOM | 5803 | H | LYS | 164 | 55.934 | 34.005 | 73.333 | 1.00 | 0.00 |
| ATOM | 5804 | CA | LYS | 164 | 56.106 | 32.685 | 74.392 | 1.00 | 38.57 |
| ATOM | 5805 | CB | LYS | 164 | 55.379 | 33.518 | 73.964 | 1.00 | 37.49 |
| ATOM | 5806 | CG | LYS | 164 | 54.138 | 34.269 | 73.964 | 1.00 | 42.53 |

FIG. 1: A-98

| | | | | | | | | |
|---|---|---|---|---|---|---|---|---|
| ATOM | 5807 | CD | LYS | 164 | 52.997 | 34.316 | 75.009 | 1.00 | 44.45 |
| ATOM | 5808 | CE | LYS | 164 | 52.266 | 32.967 | 75.240 | 1.00 | 46.00 |
| ATOM | 5809 | NZ | LYS | 164 | 51.084 | 33.183 | 76.077 | 1.00 | 47.57 |
| ATOM | 5810 | HZ1 | LYS | 164 | 51.378 | 33.543 | 77.009 | 1.00 | 0.00 |
| ATOM | 5811 | HZ2 | LYS | 164 | 50.558 | 32.296 | 76.209 | 1.00 | 0.00 |
| ATOM | 5812 | HZ3 | LYS | 164 | 50.460 | 33.887 | 75.632 | 1.00 | 0.00 |
| ATOM | 5813 | C | LYS | 164 | 55.190 | 31.515 | 72.910 | 1.00 | 40.59 |
| ATOM | 5814 | O | LYS | 164 | 54.225 | 31.654 | 72.146 | 1.00 | 42.71 |
| ATOM | 5815 | N | MET | 165 | 55.495 | 30.305 | 73.391 | 1.00 | 40.41 |
| ATOM | 5816 | H | MET | 165 | 56.236 | 30.230 | 74.026 | 1.00 | 0.00 |
| ATOM | 5817 | CA | MET | 165 | 54.790 | 29.072 | 73.038 | 1.00 | 37.43 |
| ATOM | 5818 | CB | MET | 165 | 55.700 | 27.828 | 72.980 | 1.00 | 37.04 |
| ATOM | 5819 | CG | MET | 165 | 56.543 | 27.686 | 71.753 | 1.00 | 37.02 |
| ATOM | 5820 | SD | MET | 165 | 55.493 | 28.100 | 70.348 | 1.00 | 36.83 |
| ATOM | 5821 | CE | MET | 165 | 56.186 | 29.671 | 69.934 | 1.00 | 38.85 |
| ATOM | 5822 | C | MET | 165 | 53.698 | 28.650 | 73.970 | 1.00 | 36.35 |
| ATOM | 5823 | O | MET | 165 | 53.962 | 28.401 | 75.151 | 1.00 | 38.21 |
| ATOM | 5824 | N | VAL | 166 | 52.463 | 28.529 | 73.503 | 1.00 | 34.39 |
| ATOM | 5825 | H | VAL | 166 | 52.252 | 28.886 | 72.618 | 1.00 | 0.00 |
| ATOM | 5826 | CA | VAL | 166 | 51.486 | 27.857 | 74.360 | 1.00 | 31.34 |
| ATOM | 5827 | CB | VAL | 166 | 50.005 | 28.382 | 74.046 | 1.00 | 29.33 |
| ATOM | 5828 | CG1 | VAL | 166 | 49.857 | 29.784 | 74.646 | 1.00 | 29.16 |
| ATOM | 5829 | CG2 | VAL | 166 | 49.702 | 28.591 | 72.595 | 1.00 | 29.78 |
| ATOM | 5830 | C | VAL | 166 | 51.658 | 26.328 | 74.190 | 1.00 | 30.34 |
| ATOM | 5831 | O | VAL | 166 | 51.548 | 25.696 | 73.146 | 1.00 | 30.68 |
| ATOM | 5832 | N | VAL | 167 | 52.240 | 25.746 | 75.226 | 1.00 | 32.14 |
| ATOM | 5833 | H | VAL | 167 | 52.589 | 26.342 | 75.924 | 1.00 | 0.00 |
| ATOM | 5834 | CA | VAL | 167 | 52.487 | 24.299 | 75.323 | 1.00 | 32.77 |
| ATOM | 5835 | CB | VAL | 167 | 53.798 | 24.001 | 76.086 | 1.00 | 31.39 |
| ATOM | 5836 | CG1 | VAL | 167 | 54.120 | 22.534 | 75.991 | 1.00 | 27.50 |
| ATOM | 5837 | CG2 | VAL | 167 | 54.936 | 24.840 | 75.525 | 1.00 | 32.03 |
| ATOM | 5838 | C | VAL | 167 | 51.325 | 23.693 | 76.096 | 1.00 | 34.62 |
| ATOM | 5839 | O | VAL | 167 | 50.818 | 24.299 | 77.049 | 1.00 | 33.51 |
| ATOM | 5840 | N | ASP | 168 | 50.946 | 22.484 | 75.683 | 1.00 | 38.07 |
| ATOM | 5841 | H | ASP | 168 | 51.445 | 22.056 | 74.968 | 1.00 | 0.00 |
| ATOM | 5842 | CA | ASP | 168 | 49.756 | 21.833 | 76.249 | 1.00 | 41.94 |
| ATOM | 5843 | CB | ASP | 168 | 48.730 | 21.605 | 75.091 | 1.00 | 44.80 |
| ATOM | 5844 | CG | ASP | 168 | 48.444 | 22.859 | 74.240 | 1.00 | 47.71 |
| ATOM | 5845 | OD1 | ASP | 168 | 49.087 | 23.064 | 73.198 | 1.00 | 46.53 |
| ATOM | 5846 | OD2 | ASP | 168 | 47.580 | 23.644 | 74.644 | 1.00 | 51.45 |
| ATOM | 5847 | C | ASP | 168 | 49.988 | 20.519 | 76.999 | 1.00 | 39.97 |
| ATOM | 5848 | O | ASP | 168 | 49.580 | 20.378 | 78.158 | 1.00 | 37.61 |

FK506 COORDINATES

| | | Atom Type | Residue # | X | Y | Z | OCC | B |
|---|---|---|---|---|---|---|---|---|
| ATOM | 5849 | O | 506 | 908 | 57.006 | 42.568 | 53.877 | 1.00 | 32.39 |
| ATOM | 5850 | C | 506 | 908 | 55.721 | 42.785 | 53.515 | 1.00 | 31.77 |
| ATOM | 5851 | O1 | 506 | 908 | 54.818 | 42.061 | 53.809 | 1.00 | 33.81 |
| ATOM | 5852 | C1 | 506 | 908 | 55.441 | 43.968 | 52.579 | 1.00 | 30.46 |
| ATOM | 5853 | H1 | 506 | 908 | 54.576 | 44.440 | 53.053 | 1.00 | 0.00 |
| ATOM | 5854 | C2 | 506 | 908 | 54.901 | 43.424 | 51.284 | 1.00 | 26.34 |
| ATOM | 5855 | H3 | 506 | 908 | 54.501 | 44.271 | 50.747 | 1.00 | 0.00 |
| ATOM | 5856 | H2 | 506 | 908 | 54.043 | 42.763 | 51.433 | 1.00 | 0.00 |
| ATOM | 5857 | C3 | 506 | 908 | 56.009 | 42.734 | 50.498 | 1.00 | 26.65 |
| ATOM | 5858 | H5 | 506 | 908 | 55.609 | 42.444 | 49.529 | 1.00 | 0.00 |
| ATOM | 5859 | H4 | 506 | 908 | 56.246 | 41.774 | 50.964 | 1.00 | 0.00 |
| ATOM | 5860 | C4 | 506 | 908 | 57.301 | 43.539 | 50.324 | 1.00 | 26.47 |

FIG. 1: A-99

| | | | | | | | | | |
|---|---|---|---|---|---|---|---|---|---|
| ATOM | 5861 | H7 | 506 | 908 | 57.489 | 43.710 | 49.260 | 1.00 | 0.00 |
| ATOM | 5862 | H6 | 506 | 908 | 58.164 | 42.961 | 50.648 | 1.00 | 0.00 |
| ATOM | 5863 | C5 | 506 | 908 | 57.335 | 44.869 | 51.050 | 1.00 | 26.33 |
| ATOM | 5864 | H9 | 506 | 908 | 57.016 | 45.648 | 50.351 | 1.00 | 0.00 |
| ATOM | 5865 | H8 | 506 | 908 | 58.385 | 45.080 | 51.284 | 1.00 | 0.00 |
| ATOM | 5866 | N | 506 | 908 | 56.487 | 44.987 | 52.276 | 1.00 | 28.84 |
| ATOM | 5867 | C6 | 506 | 908 | 56.575 | 46.057 | 53.127 | 1.00 | 29.05 |
| ATOM | 5868 | O2 | 506 | 908 | 55.820 | 46.118 | 54.126 | 1.00 | 24.92 |
| ATOM | 5869 | C7 | 506 | 908 | 57.518 | 47.092 | 52.828 | 1.00 | 29.84 |
| ATOM | 5870 | O3 | 506 | 908 | 57.399 | 47.792 | 51.799 | 1.00 | 29.45 |
| ATOM | 5871 | C8 | 506 | 908 | 58.776 | 47.296 | 53.794 | 1.00 | 30.12 |
| ATOM | 5872 | O5 | 506 | 908 | 59.237 | 48.653 | 53.803 | 1.00 | 28.06 |
| ATOM | 5873 | H67 | 506 | 908 | 59.972 | 48.639 | 53.191 | 1.00 | 0.00 |
| ATOM | 5874 | C9 | 506 | 908 | 58.568 | 46.879 | 55.311 | 1.00 | 28.47 |
| ATOM | 5875 | H10 | 506 | 908 | 58.033 | 45.932 | 55.372 | 1.00 | 0.00 |
| ATOM | 5876 | C33 | 506 | 908 | 57.701 | 47.870 | 56.097 | 1.00 | 30.64 |
| ATOM | 5877 | H39 | 506 | 908 | 57.575 | 47.587 | 57.141 | 1.00 | 0.00 |
| ATOM | 5878 | H40 | 506 | 908 | 56.699 | 47.959 | 55.678 | 1.00 | 0.00 |
| ATOM | 5879 | H41 | 506 | 908 | 58.121 | 48.875 | 56.061 | 1.00 | 0.00 |
| ATOM | 5880 | C10 | 506 | 908 | 59.875 | 46.599 | 56.007 | 1.00 | 28.45 |
| ATOM | 5881 | H12 | 506 | 908 | 59.692 | 46.253 | 57.023 | 1.00 | 0.00 |
| ATOM | 5882 | H11 | 506 | 908 | 60.433 | 47.531 | 56.105 | 1.00 | 0.00 |
| ATOM | 5883 | C11 | 506 | 908 | 60.708 | 45.610 | 55.189 | 1.00 | 29.13 |
| ATOM | 5884 | H13 | 506 | 908 | 60.124 | 44.708 | 55.027 | 1.00 | 0.00 |
| ATOM | 5885 | O6 | 506 | 908 | 61.920 | 45.333 | 55.880 | 1.00 | 29.99 |
| ATOM | 5886 | C41 | 506 | 908 | 61.855 | 44.360 | 56.903 | 1.00 | 31.23 |
| ATOM | 5887 | H58 | 506 | 908 | 61.027 | 43.658 | 56.820 | 1.00 | 0.00 |
| ATOM | 5888 | H59 | 506 | 908 | 61.822 | 44.849 | 57.877 | 1.00 | 0.00 |
| ATOM | 5889 | H60 | 506 | 908 | 62.757 | 43.763 | 56.888 | 1.00 | 0.00 |
| ATOM | 5890 | O4 | 506 | 908 | 59.819 | 46.574 | 53.125 | 1.00 | 29.88 |
| ATOM | 5891 | C12 | 506 | 908 | 61.031 | 46.219 | 53.802 | 1.00 | 29.70 |
| ATOM | 5892 | H14 | 506 | 908 | 61.564 | 47.152 | 53.988 | 1.00 | 0.00 |
| ATOM | 5893 | C13 | 506 | 908 | 61.922 | 45.377 | 52.799 | 1.00 | 27.30 |
| ATOM | 5894 | H15 | 506 | 908 | 61.756 | 45.824 | 51.815 | 1.00 | 0.00 |
| ATOM | 5895 | O7 | 506 | 908 | 63.316 | 45.448 | 53.141 | 1.00 | 25.83 |
| ATOM | 5896 | C42 | 506 | 908 | 64.083 | 46.477 | 52.562 | 1.00 | 23.93 |
| ATOM | 5897 | H61 | 506 | 908 | 63.983 | 46.504 | 51.474 | 1.00 | 0.00 |
| ATOM | 5898 | H62 | 506 | 908 | 65.137 | 46.303 | 52.771 | 1.00 | 0.00 |
| ATOM | 5899 | H63 | 506 | 908 | 63.822 | 47.453 | 52.969 | 1.00 | 0.00 |
| ATOM | 5900 | C14 | 506 | 908 | 61.458 | 43.880 | 52.648 | 1.00 | 25.37 |
| ATOM | 5901 | H17 | 506 | 908 | 60.404 | 43.898 | 52.356 | 1.00 | 0.00 |
| ATOM | 5902 | H16 | 506 | 908 | 61.429 | 43.395 | 53.619 | 1.00 | 0.00 |
| ATOM | 5903 | C15 | 506 | 908 | 62.206 | 42.903 | 51.713 | 1.00 | 24.18 |
| ATOM | 5904 | H18 | 506 | 908 | 61.518 | 42.062 | 51.580 | 1.00 | 0.00 |
| ATOM | 5905 | C34 | 506 | 908 | 62.425 | 43.409 | 50.268 | 1.00 | 23.52 |
| ATOM | 5906 | H42 | 506 | 908 | 62.607 | 42.595 | 49.568 | 1.00 | 0.00 |
| ATOM | 5907 | H43 | 506 | 908 | 63.285 | 44.077 | 50.194 | 1.00 | 0.00 |
| ATOM | 5908 | H44 | 506 | 908 | 61.560 | 43.954 | 49.884 | 1.00 | 0.00 |
| ATOM | 5909 | C16 | 506 | 908 | 63.484 | 42.279 | 52.346 | 1.00 | 24.84 |
| ATOM | 5910 | H20 | 506 | 908 | 64.056 | 43.041 | 52.867 | 1.00 | 0.00 |
| ATOM | 5911 | H19 | 506 | 908 | 64.182 | 41.992 | 51.558 | 1.00 | 0.00 |
| ATOM | 5912 | C17 | 506 | 908 | 63.259 | 41.071 | 53.273 | 1.00 | 22.00 |
| ATOM | 5913 | C35 | 506 | 908 | 63.210 | 39.698 | 52.605 | 1.00 | 20.86 |
| ATOM | 5914 | H45 | 506 | 908 | 63.668 | 38.913 | 53.203 | 1.00 | 0.00 |
| ATOM | 5915 | H46 | 506 | 908 | 63.715 | 39.687 | 51.637 | 1.00 | 0.00 |
| ATOM | 5916 | H47 | 506 | 908 | 62.187 | 39.406 | 52.375 | 1.00 | 0.00 |
| ATOM | 5917 | C18 | 506 | 908 | 63.140 | 41.323 | 54.598 | 1.00 | 23.11 |
| ATOM | 5918 | H21 | 506 | 908 | 63.113 | 42.365 | 54.899 | 1.00 | 0.00 |
| ATOM | 5919 | C19 | 506 | 908 | 63.054 | 40.416 | 55.795 | 1.00 | 22.06 |
| ATOM | 5920 | H22 | 506 | 908 | 63.286 | 39.385 | 55.521 | 1.00 | 0.00 |

FIG. 1: A-100

| | | | | | | | | | |
|---|---|---|---|---|---|---|---|---|---|
| ATOM | 5921 | C36 | 506 | 908 | 64.081 | 40.804 | 56.856 | 1.00 | 17.62 |
| ATOM | 5922 | H49 | 506 | 908 | 63.842 | 40.306 | 57.799 | 1.00 | 0.00 |
| ATOM | 5923 | H48 | 506 | 908 | 64.057 | 41.864 | 57.091 | 1.00 | 0.00 |
| ATOM | 5924 | C37 | 506 | 908 | 65.480 | 40.426 | 56.448 | 1.00 | 15.36 |
| ATOM | 5925 | H29 | 506 | 908 | 65.917 | 41.028 | 55.666 | 1.00 | 0.00 |
| ATOM | 5926 | C38 | 506 | 908 | 66.184 | 39.400 | 56.946 | 1.00 | 14.87 |
| ATOM | 5927 | H51 | 506 | 908 | 67.219 | 39.234 | 56.671 | 1.00 | 0.00 |
| ATOM | 5928 | H50 | 506 | 908 | 65.787 | 38.674 | 57.642 | 1.00 | 0.00 |
| ATOM | 5929 | C20 | 506 | 908 | 61.588 | 40.446 | 56.252 | 1.00 | 27.35 |
| ATOM | 5930 | O8 | 506 | 908 | 61.209 | 41.104 | 57.239 | 1.00 | 27.85 |
| ATOM | 5931 | C21 | 506 | 908 | 60.673 | 39.568 | 55.372 | 1.00 | 29.21 |
| ATOM | 5932 | H24 | 506 | 908 | 60.886 | 38.543 | 55.625 | 1.00 | 0.00 |
| ATOM | 5933 | H23 | 506 | 908 | 61.036 | 39.599 | 54.367 | 1.00 | 0.00 |
| ATOM | 5934 | C22 | 506 | 908 | 59.157 | 39.795 | 55.322 | 1.00 | 30.04 |
| ATOM | 5935 | H25 | 506 | 908 | 58.784 | 39.884 | 56.344 | 1.00 | 0.00 |
| ATOM | 5936 | O9 | 506 | 908 | 58.608 | 38.580 | 54.834 | 1.00 | 31.55 |
| ATOM | 5937 | H68 | 506 | 908 | 57.730 | 38.790 | 54.486 | 1.00 | 0.00 |
| ATOM | 5938 | C23 | 506 | 908 | 58.716 | 40.921 | 54.358 | 1.00 | 29.65 |
| ATOM | 5939 | H26 | 506 | 908 | 59.431 | 41.742 | 54.479 | 1.00 | 0.00 |
| ATOM | 5940 | C39 | 506 | 908 | 58.818 | 40.537 | 52.863 | 1.00 | 30.32 |
| ATOM | 5941 | H52 | 506 | 908 | 59.662 | 39.921 | 52.569 | 1.00 | 0.00 |
| ATOM | 5942 | H53 | 506 | 908 | 58.870 | 41.429 | 52.245 | 1.00 | 0.00 |
| ATOM | 5943 | H54 | 506 | 908 | 57.931 | 39.990 | 52.529 | 1.00 | 0.00 |
| ATOM | 5944 | C24 | 506 | 908 | 57.313 | 41.440 | 54.729 | 1.00 | 31.11 |
| ATOM | 5945 | H27 | 506 | 908 | 56.623 | 40.615 | 54.503 | 1.00 | 0.00 |
| ATOM | 5946 | C25 | 506 | 908 | 57.116 | 41.838 | 56.199 | 1.00 | 30.22 |
| ATOM | 5947 | C40 | 506 | 908 | 57.930 | 43.041 | 56.591 | 1.00 | 27.36 |
| ATOM | 5948 | H55 | 506 | 908 | 58.327 | 43.569 | 55.735 | 1.00 | 0.00 |
| ATOM | 5949 | H56 | 506 | 908 | 58.758 | 42.755 | 57.237 | 1.00 | 0.00 |
| ATOM | 5950 | H57 | 506 | 908 | 57.313 | 43.778 | 57.098 | 1.00 | 0.00 |
| ATOM | 5951 | C26 | 506 | 908 | 56.257 | 41.190 | 57.047 | 1.00 | 29.03 |
| ATOM | 5952 | H28 | 506 | 908 | 55.642 | 40.397 | 56.634 | 1.00 | 0.00 |
| ATOM | 5953 | C27 | 506 | 908 | 56.057 | 41.427 | 58.546 | 1.00 | 29.20 |
| ATOM | 5954 | H30 | 506 | 908 | 56.334 | 42.444 | 58.816 | 1.00 | 0.00 |
| ATOM | 5955 | C28 | 506 | 908 | 54.577 | 41.285 | 58.979 | 1.00 | 31.12 |
| ATOM | 5956 | H32 | 506 | 908 | 54.163 | 40.368 | 58.549 | 1.00 | 0.00 |
| ATOM | 5957 | H31 | 506 | 908 | 53.981 | 42.073 | 58.521 | 1.00 | 0.00 |
| ATOM | 5958 | C29 | 506 | 908 | 54.328 | 41.257 | 60.513 | 1.00 | 31.05 |
| ATOM | 5959 | H33 | 506 | 908 | 54.606 | 42.228 | 60.938 | 1.00 | 0.00 |
| ATOM | 5960 | O10 | 506 | 908 | 52.926 | 40.974 | 60.723 | 1.00 | 32.76 |
| ATOM | 5961 | C43 | 506 | 908 | 52.128 | 42.001 | 61.313 | 1.00 | 33.01 |
| ATOM | 5962 | H64 | 506 | 908 | 52.200 | 42.943 | 60.764 | 1.00 | 0.00 |
| ATOM | 5963 | H65 | 506 | 908 | 52.408 | 42.175 | 62.354 | 1.00 | 0.00 |
| ATOM | 5964 | H66 | 506 | 908 | 51.075 | 41.714 | 61.296 | 1.00 | 0.00 |
| ATOM | 5965 | C30 | 506 | 908 | 55.256 | 40.175 | 61.170 | 1.00 | 28.01 |
| ATOM | 5966 | H34 | 506 | 908 | 54.901 | 39.182 | 60.895 | 1.00 | 0.00 |
| ATOM | 5967 | O11 | 506 | 908 | 55.282 | 40.173 | 62.571 | 1.00 | 22.17 |
| ATOM | 5968 | H69 | 506 | 908 | 54.354 | 40.168 | 62.831 | 1.00 | 0.00 |
| ATOM | 5969 | C31 | 506 | 908 | 56.725 | 40.385 | 60.820 | 1.00 | 29.05 |
| ATOM | 5970 | H36 | 506 | 908 | 57.303 | 39.549 | 61.232 | 1.00 | 0.00 |
| ATOM | 5971 | H35 | 506 | 908 | 57.115 | 41.270 | 61.327 | 1.00 | 0.00 |
| ATOM | 5972 | C32 | 506 | 908 | 56.974 | 40.475 | 59.316 | 1.00 | 29.10 |
| ATOM | 5973 | H37 | 506 | 908 | 58.023 | 40.699 | 59.116 | 1.00 | 0.00 |
| ATOM | 5974 | H38 | 506 | 908 | 56.837 | 39.473 | 58.896 | 1.00 | 0.00 |

FIG. 1: A-101

CALCIUM ION COORDINATES

| | | Atom Type | Residue | # | X | Y | Z | OCC | B |
|---|---|---|---|---|---|---|---|---|---|
| ATOM | 5975 | CAL | CAL | 901 | 65.324 | 10.388 | 64.524 | 1.00 | 47.05 |
| ATOM | 5976 | CAL | CAL | 902 | 72.311 | 17.145 | 69.723 | 1.00 | 31.70 |
| ATOM | 5977 | CAL | CAL | 903 | 80.363 | 33.691 | 65.529 | 1.00 | 30.20 |
| ATOM | 5978 | CAL | CAL | 904 | 82.785 | 44.562 | 68.903 | 1.00 | 26.23 |

FERRIC ION COORDINATE

| | | Atom Type | Residue | # | X | Y | Z | OCC | B |
|---|---|---|---|---|---|---|---|---|---|
| ATOM | 5979 | FE | FE | 905 | 61.528 | 72.037 | 47.242 | 1.00 | 23.55 |

ZINC ION COORDINATE

| | | Atom Type | Residue | # | X | Y | Z | OCC | B |
|---|---|---|---|---|---|---|---|---|---|
| ATOM | 5980 | ZN | ZN | 906 | 62.726 | 69.501 | 46.374 | 1.00 | 30.32 |

PHOPHATE ION COORDINATES

| | | Atom Type | Residue | # | X | Y | Z | OCC | B |
|---|---|---|---|---|---|---|---|---|---|
| ATOM | 5981 | O1P | PO4 | 907 | 61.107 | 68.299 | 48.125 | 1.00 | 37.73 |
| ATOM | 5982 | P | PO4 | 907 | 59.922 | 69.174 | 48.160 | 1.00 | 30.85 |
| ATOM | 5983 | O2P | PO4 | 907 | 58.966 | 68.627 | 47.138 | 1.00 | 35.23 |
| ATOM | 5984 | O3P | PO4 | 907 | 60.371 | 70.557 | 47.823 | 1.00 | 28.17 |
| ATOM | 5985 | O4P | PO4 | 907 | 59.294 | 69.129 | 49.519 | 1.00 | 34.45 |

WATER MOLECULE COORDINATES

| | | Atom Type | Residue | # | X | Y | Z | OCC | B |
|---|---|---|---|---|---|---|---|---|---|
| ATOM | 5986 | OH2 | TIP3 | 1 | 47.336 | 80.672 | 34.273 | 1.00 | 23.34 |
| ATOM | 5987 | H1 | TIP3 | 1 | 47.265 | 79.709 | 34.372 | 1.00 | 0.00 |
| ATOM | 5988 | H2 | TIP3 | 1 | 46.921 | 80.786 | 33.410 | 1.00 | 0.00 |
| ATOM | 5989 | OH2 | TIP3 | 3 | 71.494 | 62.927 | 28.830 | 1.00 | 16.40 |
| ATOM | 5990 | H1 | TIP3 | 3 | 71.733 | 63.680 | 29.374 | 1.00 | 0.00 |
| ATOM | 5991 | H2 | TIP3 | 3 | 70.619 | 62.690 | 29.142 | 1.00 | 0.00 |
| ATOM | 5992 | OH2 | TIP3 | 4 | 60.670 | 28.930 | 59.843 | 1.00 | 26.01 |
| ATOM | 5993 | H1 | TIP3 | 4 | 60.551 | 28.181 | 59.250 | 1.00 | 0.00 |
| ATOM | 5994 | H2 | TIP3 | 4 | 60.213 | 28.690 | 60.652 | 1.00 | 0.00 |
| ATOM | 5995 | OH2 | TIP3 | 5 | 102.239 | 64.992 | 56.010 | 1.00 | 33.43 |
| ATOM | 5996 | H1 | TIP3 | 5 | 102.312 | 64.823 | 55.068 | 1.00 | 0.00 |
| ATOM | 5997 | H2 | TIP3 | 5 | 102.779 | 64.294 | 56.401 | 1.00 | 0.00 |
| ATOM | 5998 | OH2 | TIP3 | 6 | 85.259 | 82.104 | 37.937 | 1.00 | 23.58 |
| ATOM | 5999 | H1 | TIP3 | 6 | 85.871 | 81.703 | 38.558 | 1.00 | 0.00 |
| ATOM | 6000 | H2 | TIP3 | 6 | 84.816 | 82.779 | 38.459 | 1.00 | 0.00 |
| ATOM | 6001 | OH2 | TIP3 | 7 | 54.673 | 85.588 | 58.504 | 1.00 | 20.86 |
| ATOM | 6002 | H1 | TIP3 | 7 | 53.881 | 86.128 | 58.460 | 1.00 | 0.00 |
| ATOM | 6003 | H2 | TIP3 | 7 | 54.519 | 84.890 | 57.857 | 1.00 | 0.00 |
| ATOM | 6004 | OH2 | TIP3 | 8 | 67.239 | 82.097 | 55.155 | 1.00 | 34.16 |
| ATOM | 6005 | H1 | TIP3 | 8 | 67.193 | 82.312 | 56.094 | 1.00 | 0.00 |
| ATOM | 6006 | H2 | TIP3 | 8 | 68.160 | 81.883 | 55.004 | 1.00 | 0.00 |
| ATOM | 6007 | OH2 | TIP3 | 9 | 55.449 | 36.212 | 66.550 | 1.00 | 36.02 |
| ATOM | 6008 | H1 | TIP3 | 9 | 55.279 | 35.669 | 65.776 | 1.00 | 0.00 |
| ATOM | 6009 | H2 | TIP3 | 9 | 55.498 | 35.567 | 67.272 | 1.00 | 0.00 |

FIG. 1: A-102

| ATOM | 6010 | OH2 | TIP3 | 10 | 76.857 | 57.127 | 53.471 | 1.00 | 28.54 |
|---|---|---|---|---|---|---|---|---|---|
| ATOM | 6011 | H1 | TIP3 | 10 | 77.389 | 57.371 | 54.232 | 1.00 | 0.00 |
| ATOM | 6012 | H2 | TIP3 | 10 | 77.230 | 57.653 | 52.760 | 1.00 | 0.00 |
| ATOM | 6013 | OH2 | TIP3 | 11 | 86.599 | 72.139 | 70.201 | 1.00 | 34.06 |
| ATOM | 6014 | H1 | TIP3 | 11 | 87.019 | 72.238 | 71.056 | 1.00 | 0.00 |
| ATOM | 6015 | H2 | TIP3 | 11 | 87.324 | 71.904 | 69.613 | 1.00 | 0.00 |
| ATOM | 6016 | OH2 | TIP3 | 12 | 71.575 | 59.398 | 46.514 | 1.00 | 19.65 |
| ATOM | 6017 | H1 | TIP3 | 12 | 71.074 | 59.185 | 47.317 | 1.00 | 0.00 |
| ATOM | 6018 | H2 | TIP3 | 12 | 70.891 | 59.346 | 45.826 | 1.00 | 0.00 |
| ATOM | 6019 | OH2 | TIP3 | 13 | 54.038 | 57.492 | 27.211 | 1.00 | 41.30 |
| ATOM | 6020 | H1 | TIP3 | 13 | 54.405 | 58.331 | 27.488 | 1.00 | 0.00 |
| ATOM | 6021 | H2 | TIP3 | 13 | 53.954 | 56.984 | 28.016 | 1.00 | 0.00 |
| ATOM | 6022 | OH2 | TIP3 | 14 | 82.496 | 86.387 | 58.952 | 1.00 | 24.40 |
| ATOM | 6023 | H1 | TIP3 | 14 | 82.026 | 86.463 | 59.787 | 1.00 | 0.00 |
| ATOM | 6024 | H2 | TIP3 | 14 | 81.755 | 86.335 | 58.334 | 1.00 | 0.00 |
| ATOM | 6025 | OH2 | TIP3 | 15 | 67.353 | 59.318 | 46.216 | 1.00 | 21.55 |
| ATOM | 6026 | H1 | TIP3 | 15 | 67.280 | 60.286 | 46.204 | 1.00 | 0.00 |
| ATOM | 6027 | H2 | TIP3 | 15 | 67.000 | 59.110 | 47.092 | 1.00 | 0.00 |
| ATOM | 6028 | OH2 | TIP3 | 16 | 75.668 | 89.508 | 45.560 | 1.00 | 45.41 |
| ATOM | 6029 | H1 | TIP3 | 16 | 76.007 | 90.340 | 45.214 | 1.00 | 0.00 |
| ATOM | 6030 | H2 | TIP3 | 16 | 76.407 | 88.905 | 45.432 | 1.00 | 0.00 |
| ATOM | 6031 | OH2 | TIP3 | 17 | 82.467 | 61.005 | 62.613 | 1.00 | 26.38 |
| ATOM | 6032 | H1 | TIP3 | 17 | 82.793 | 61.380 | 61.790 | 1.00 | 0.00 |
| ATOM | 6033 | H2 | TIP3 | 17 | 81.589 | 60.669 | 62.394 | 1.00 | 0.00 |
| ATOM | 6034 | OH2 | TIP3 | 19 | 59.392 | 90.450 | 30.502 | 1.00 | 27.76 |
| ATOM | 6035 | H1 | TIP3 | 19 | 59.469 | 89.491 | 30.423 | 1.00 | 0.00 |
| ATOM | 6036 | H2 | TIP3 | 19 | 59.997 | 90.640 | 31.230 | 1.00 | 0.00 |
| ATOM | 6037 | OH2 | TIP3 | 20 | 53.326 | 32.656 | 82.561 | 1.00 | 26.20 |
| ATOM | 6038 | H1 | TIP3 | 20 | 53.200 | 32.792 | 83.507 | 1.00 | 0.00 |
| ATOM | 6039 | H2 | TIP3 | 20 | 52.428 | 32.774 | 82.228 | 1.00 | 0.00 |
| ATOM | 6040 | OH2 | TIP3 | 21 | 63.402 | 40.149 | 85.242 | 1.00 | 42.97 |
| ATOM | 6041 | H1 | TIP3 | 21 | 62.817 | 40.907 | 85.172 | 1.00 | 0.00 |
| ATOM | 6042 | H2 | TIP3 | 21 | 64.255 | 40.554 | 85.419 | 1.00 | 0.00 |
| ATOM | 6043 | OH2 | TIP3 | 22 | 64.770 | 35.375 | 81.326 | 1.00 | 18.63 |
| ATOM | 6044 | H1 | TIP3 | 22 | 64.285 | 35.235 | 82.148 | 1.00 | 0.00 |
| ATOM | 6045 | H2 | TIP3 | 22 | 65.674 | 35.478 | 81.636 | 1.00 | 0.00 |
| ATOM | 6046 | OH2 | TIP3 | 24 | 76.447 | 74.507 | 27.377 | 1.00 | 12.88 |
| ATOM | 6047 | H1 | TIP3 | 24 | 76.839 | 73.630 | 27.295 | 1.00 | 0.00 |
| ATOM | 6048 | H2 | TIP3 | 24 | 75.615 | 74.310 | 26.930 | 1.00 | 0.00 |
| ATOM | 6049 | OH2 | TIP3 | 25 | 61.766 | 59.700 | 54.342 | 1.00 | 37.89 |
| ATOM | 6050 | H1 | TIP3 | 25 | 61.774 | 59.672 | 55.326 | 1.00 | 0.00 |
| ATOM | 6051 | H2 | TIP3 | 25 | 60.891 | 59.331 | 54.181 | 1.00 | 0.00 |
| ATOM | 6052 | OH2 | TIP3 | 26 | 44.430 | 76.748 | 42.682 | 1.00 | 23.66 |
| ATOM | 6053 | H1 | TIP3 | 26 | 45.012 | 76.038 | 42.960 | 1.00 | 0.00 |
| ATOM | 6054 | H2 | TIP3 | 26 | 43.649 | 76.278 | 42.374 | 1.00 | 0.00 |
| ATOM | 6055 | OH2 | TIP3 | 28 | 83.290 | 62.478 | 38.959 | 1.00 | 20.79 |
| ATOM | 6056 | H1 | TIP3 | 28 | 83.774 | 63.127 | 38.444 | 1.00 | 0.00 |
| ATOM | 6057 | H2 | TIP3 | 28 | 83.567 | 62.659 | 39.861 | 1.00 | 0.00 |
| ATOM | 6058 | OH2 | TIP3 | 29 | 97.210 | 69.561 | 60.063 | 1.00 | 40.13 |
| ATOM | 6059 | H1 | TIP3 | 29 | 96.883 | 70.343 | 60.508 | 1.00 | 0.00 |
| ATOM | 6060 | H2 | TIP3 | 29 | 96.445 | 69.294 | 59.548 | 1.00 | 0.00 |
| ATOM | 6061 | OH2 | TIP3 | 30 | 68.288 | 98.497 | 47.783 | 1.00 | 31.72 |
| ATOM | 6062 | H1 | TIP3 | 30 | 69.165 | 98.560 | 48.161 | 1.00 | 0.00 |
| ATOM | 6063 | H2 | TIP3 | 30 | 68.430 | 98.184 | 46.891 | 1.00 | 0.00 |
| ATOM | 6064 | OH2 | TIP3 | 31 | 73.508 | 90.298 | 55.446 | 1.00 | 32.42 |
| ATOM | 6065 | H1 | TIP3 | 31 | 73.285 | 89.395 | 55.172 | 1.00 | 0.00 |
| ATOM | 6066 | H2 | TIP3 | 31 | 74.153 | 90.542 | 54.776 | 1.00 | 0.00 |
| ATOM | 6067 | OH2 | TIP3 | 32 | 48.818 | 41.586 | 57.942 | 1.00 | 19.71 |
| ATOM | 6068 | H1 | TIP3 | 32 | 49.303 | 42.308 | 58.367 | 1.00 | 0.00 |
| ATOM | 6069 | H2 | TIP3 | 32 | 48.286 | 41.256 | 58.672 | 1.00 | 0.00 |

FIG. 1: A-103

| | | | | | | | | |
|---|---|---|---|---|---|---|---|---|
| ATOM | 6070 | OH2 | TIP3 | 33 | 61.533 | 59.497 | 57.050 | 1.00 | 35.49 |
| ATOM | 6071 | H1 | TIP3 | 33 | 61.851 | 58.711 | 57.519 | 1.00 | 0.00 |
| ATOM | 6072 | H2 | TIP3 | 33 | 61.713 | 60.219 | 57.674 | 1.00 | 0.00 |
| ATOM | 6073 | OH2 | TIP3 | 34 | 71.997 | 26.621 | 79.347 | 1.00 | 36.22 |
| ATOM | 6074 | H1 | TIP3 | 34 | 72.824 | 26.282 | 79.701 | 1.00 | 0.00 |
| ATOM | 6075 | H2 | TIP3 | 34 | 71.648 | 25.877 | 78.847 | 1.00 | 0.00 |
| ATOM | 6076 | OH2 | TIP3 | 35 | 69.385 | 58.585 | 44.506 | 1.00 | 13.50 |
| ATOM | 6077 | H1 | TIP3 | 35 | 69.182 | 59.121 | 43.730 | 1.00 | 0.00 |
| ATOM | 6078 | H2 | TIP3 | 35 | 68.618 | 58.795 | 45.086 | 1.00 | 0.00 |
| ATOM | 6079 | OH2 | TIP3 | 36 | 66.224 | 81.111 | 17.801 | 1.00 | 27.45 |
| ATOM | 6080 | H1 | TIP3 | 36 | 65.543 | 80.610 | 18.261 | 1.00 | 0.00 |
| ATOM | 6081 | H2 | TIP3 | 36 | 66.001 | 82.021 | 18.019 | 1.00 | 0.00 |
| ATOM | 6082 | OH2 | TIP3 | 37 | 74.716 | 49.003 | 46.186 | 1.00 | 33.20 |
| ATOM | 6083 | H1 | TIP3 | 37 | 73.953 | 49.452 | 46.550 | 1.00 | 0.00 |
| ATOM | 6084 | H2 | TIP3 | 37 | 75.067 | 48.561 | 46.963 | 1.00 | 0.00 |
| ATOM | 6085 | OH2 | TIP3 | 38 | 98.702 | 67.424 | 27.542 | 1.00 | 43.66 |
| ATOM | 6086 | H1 | TIP3 | 38 | 98.839 | 66.509 | 27.295 | 1.00 | 0.00 |
| ATOM | 6087 | H2 | TIP3 | 38 | 98.110 | 67.761 | 26.868 | 1.00 | 0.00 |
| ATOM | 6088 | OH2 | TIP3 | 39 | 84.094 | 69.567 | 41.374 | 1.00 | 27.40 |
| ATOM | 6089 | H1 | TIP3 | 39 | 84.499 | 68.714 | 41.194 | 1.00 | 0.00 |
| ATOM | 6090 | H2 | TIP3 | 39 | 83.608 | 69.753 | 40.567 | 1.00 | 0.00 |
| ATOM | 6091 | OH2 | TIP3 | 40 | 70.180 | 58.008 | 48.682 | 1.00 | 21.85 |
| ATOM | 6092 | H1 | TIP3 | 40 | 69.504 | 57.319 | 48.683 | 1.00 | 0.00 |
| ATOM | 6093 | H2 | TIP3 | 40 | 70.954 | 57.541 | 49.024 | 1.00 | 0.00 |
| ATOM | 6094 | OH2 | TIP3 | 41 | 55.401 | 51.983 | 36.066 | 1.00 | 34.21 |
| ATOM | 6095 | H1 | TIP3 | 41 | 54.937 | 52.813 | 36.166 | 1.00 | 0.00 |
| ATOM | 6096 | H2 | TIP3 | 41 | 54.836 | 51.472 | 35.483 | 1.00 | 0.00 |
| ATOM | 6097 | OH2 | TIP3 | 42 | 74.315 | 31.715 | 78.991 | 1.00 | 36.80 |
| ATOM | 6098 | H1 | TIP3 | 42 | 73.565 | 32.297 | 79.111 | 1.00 | 0.00 |
| ATOM | 6099 | H2 | TIP3 | 42 | 73.874 | 30.881 | 78.727 | 1.00 | 0.00 |
| ATOM | 6100 | OH2 | TIP3 | 43 | 85.548 | 64.644 | 68.987 | 1.00 | 32.11 |
| ATOM | 6101 | H1 | TIP3 | 43 | 85.017 | 63.973 | 69.418 | 1.00 | 0.00 |
| ATOM | 6102 | H2 | TIP3 | 43 | 85.450 | 65.412 | 69.553 | 1.00 | 0.00 |
| ATOM | 6103 | OH2 | TIP3 | 44 | 59.703 | 35.882 | 48.430 | 1.00 | 35.51 |
| ATOM | 6104 | H1 | TIP3 | 44 | 59.495 | 36.585 | 47.802 | 1.00 | 0.00 |
| ATOM | 6105 | H2 | TIP3 | 44 | 60.283 | 36.318 | 49.059 | 1.00 | 0.00 |
| ATOM | 6106 | OH2 | TIP3 | 45 | 69.533 | 30.112 | 73.068 | 1.00 | 19.29 |
| ATOM | 6107 | H1 | TIP3 | 45 | 69.460 | 29.151 | 73.037 | 1.00 | 0.00 |
| ATOM | 6108 | H2 | TIP3 | 45 | 70.170 | 30.291 | 72.371 | 1.00 | 0.00 |
| ATOM | 6109 | OH2 | TIP3 | 46 | 65.652 | 55.503 | 30.633 | 1.00 | 45.26 |
| ATOM | 6110 | H1 | TIP3 | 46 | 66.178 | 56.301 | 30.703 | 1.00 | 0.00 |
| ATOM | 6111 | H2 | TIP3 | 46 | 65.257 | 55.595 | 29.743 | 1.00 | 0.00 |
| ATOM | 6112 | OH2 | TIP3 | 47 | 51.206 | 6.734 | 74.457 | 1.00 | 37.94 |
| ATOM | 6113 | H1 | TIP3 | 47 | 51.203 | 6.199 | 73.665 | 1.00 | 0.00 |
| ATOM | 6114 | H2 | TIP3 | 47 | 51.988 | 6.455 | 74.933 | 1.00 | 0.00 |
| ATOM | 6115 | OH2 | TIP3 | 48 | 47.698 | 78.013 | 70.445 | 1.00 | 23.79 |
| ATOM | 6116 | H1 | TIP3 | 48 | 47.689 | 78.841 | 70.927 | 1.00 | 0.00 |
| ATOM | 6117 | H2 | TIP3 | 48 | 47.787 | 78.283 | 69.529 | 1.00 | 0.00 |
| ATOM | 6118 | OH2 | TIP3 | 49 | 99.764 | 74.702 | 51.666 | 1.00 | 35.48 |
| ATOM | 6119 | H1 | TIP3 | 49 | 99.927 | 74.946 | 50.754 | 1.00 | 0.00 |
| ATOM | 6120 | H2 | TIP3 | 49 | 98.816 | 74.552 | 51.690 | 1.00 | 0.00 |
| ATOM | 6121 | OH2 | TIP3 | 50 | 84.183 | 83.179 | 34.005 | 1.00 | 29.62 |
| ATOM | 6122 | H1 | TIP3 | 50 | 84.731 | 82.576 | 33.503 | 1.00 | 0.00 |
| ATOM | 6123 | H2 | TIP3 | 50 | 84.458 | 83.027 | 34.915 | 1.00 | 0.00 |
| ATOM | 6124 | OH2 | TIP3 | 51 | 56.439 | 88.980 | 57.676 | 1.00 | 19.78 |
| ATOM | 6125 | H1 | TIP3 | 51 | 56.675 | 89.558 | 58.404 | 1.00 | 0.00 |
| ATOM | 6126 | H2 | TIP3 | 51 | 56.251 | 88.141 | 58.111 | 1.00 | 0.00 |
| ATOM | 6127 | OH2 | TIP3 | 52 | 59.712 | 86.020 | 29.324 | 1.00 | 15.48 |
| ATOM | 6128 | H1 | TIP3 | 52 | 60.169 | 86.110 | 30.165 | 1.00 | 0.00 |
| ATOM | 6129 | H2 | TIP3 | 52 | 59.830 | 85.091 | 29.110 | 1.00 | 0.00 |

FIG. 1: A-104

| | | | | | | | | |
|---|---|---|---|---|---|---|---|---|
| ATOM | 6130 | OH2 | TIP3 | 53 | 101.595 | 65.098 | 51.161 | 1.00 | 29.28 |
| ATOM | 6131 | H1 | TIP3 | 53 | 100.988 | 65.799 | 51.408 | 1.00 | 0.00 |
| ATOM | 6132 | H2 | TIP3 | 53 | 102.158 | 65.500 | 50.496 | 1.00 | 0.00 |
| ATOM | 6133 | OH2 | TIP3 | 54 | 53.851 | 37.912 | 57.213 | 1.00 | 26.35 |
| ATOM | 6134 | H1 | TIP3 | 54 | 54.009 | 37.054 | 56.806 | 1.00 | 0.00 |
| ATOM | 6135 | H2 | TIP3 | 54 | 53.176 | 38.292 | 56.646 | 1.00 | 0.00 |
| ATOM | 6136 | OH2 | TIP3 | 55 | 73.558 | 52.054 | 42.842 | 1.00 | 19.98 |
| ATOM | 6137 | H1 | TIP3 | 55 | 73.695 | 51.858 | 43.781 | 1.00 | 0.00 |
| ATOM | 6138 | H2 | TIP3 | 55 | 73.672 | 51.190 | 42.439 | 1.00 | 0.00 |
| ATOM | 6139 | OH2 | TIP3 | 56 | 87.767 | 64.791 | 40.527 | 1.00 | 26.39 |
| ATOM | 6140 | H1 | TIP3 | 56 | 88.462 | 64.141 | 40.419 | 1.00 | 0.00 |
| ATOM | 6141 | H2 | TIP3 | 56 | 88.068 | 65.338 | 41.255 | 1.00 | 0.00 |
| ATOM | 6142 | OH2 | TIP3 | 57 | 71.089 | 22.668 | 81.876 | 1.00 | 22.04 |
| ATOM | 6143 | H1 | TIP3 | 57 | 70.983 | 22.552 | 82.830 | 1.00 | 0.00 |
| ATOM | 6144 | H2 | TIP3 | 57 | 71.331 | 23.596 | 81.815 | 1.00 | 0.00 |
| ATOM | 6145 | OH2 | TIP3 | 58 | 100.862 | 69.035 | 30.631 | 1.00 | 38.85 |
| ATOM | 6146 | H1 | TIP3 | 58 | 100.635 | 68.105 | 30.608 | 1.00 | 0.00 |
| ATOM | 6147 | H2 | TIP3 | 58 | 100.492 | 69.373 | 29.815 | 1.00 | 0.00 |
| ATOM | 6148 | OH2 | TIP3 | 59 | 61.515 | 89.197 | 61.611 | 1.00 | 6.25 |
| ATOM | 6149 | H1 | TIP3 | 59 | 61.974 | 88.358 | 61.543 | 1.00 | 0.00 |
| ATOM | 6150 | H2 | TIP3 | 59 | 61.209 | 89.229 | 62.517 | 1.00 | 0.00 |
| ATOM | 6151 | OH2 | TIP3 | 60 | 81.007 | 61.049 | 38.051 | 1.00 | 16.14 |
| ATOM | 6152 | H1 | TIP3 | 60 | 81.397 | 60.192 | 37.880 | 1.00 | 0.00 |
| ATOM | 6153 | H2 | TIP3 | 60 | 81.775 | 61.577 | 38.343 | 1.00 | 0.00 |
| ATOM | 6154 | OH2 | TIP3 | 61 | 72.599 | 42.973 | 39.044 | 1.00 | 37.14 |
| ATOM | 6155 | H1 | TIP3 | 61 | 72.184 | 43.583 | 39.660 | 1.00 | 0.00 |
| ATOM | 6156 | H2 | TIP3 | 61 | 71.909 | 42.804 | 38.400 | 1.00 | 0.00 |
| ATOM | 6157 | OH2 | TIP3 | 62 | 77.614 | 26.247 | 72.486 | 1.00 | 45.60 |
| ATOM | 6158 | H1 | TIP3 | 62 | 78.497 | 25.899 | 72.359 | 1.00 | 0.00 |
| ATOM | 6159 | H2 | TIP3 | 62 | 77.052 | 25.650 | 71.987 | 1.00 | 0.00 |
| ATOM | 6160 | OH2 | TIP3 | 63 | 60.866 | 40.457 | 35.935 | 1.00 | 34.04 |
| ATOM | 6161 | H1 | TIP3 | 63 | 61.119 | 40.947 | 35.152 | 1.00 | 0.00 |
| ATOM | 6162 | H2 | TIP3 | 63 | 61.678 | 40.028 | 36.211 | 1.00 | 0.00 |
| ATOM | 6163 | OH2 | TIP3 | 64 | 94.127 | 73.432 | 48.710 | 1.00 | 57.63 |
| ATOM | 6164 | H1 | TIP3 | 64 | 94.313 | 73.250 | 49.633 | 1.00 | 0.00 |
| ATOM | 6165 | H2 | TIP3 | 64 | 93.293 | 73.907 | 48.733 | 1.00 | 0.00 |
| ATOM | 6166 | OH2 | TIP3 | 65 | 86.747 | 56.747 | 66.031 | 1.00 | 46.69 |
| ATOM | 6167 | H1 | TIP3 | 65 | 87.003 | 56.047 | 65.429 | 1.00 | 0.00 |
| ATOM | 6168 | H2 | TIP3 | 65 | 86.083 | 57.241 | 65.549 | 1.00 | 0.00 |
| ATOM | 6169 | OH2 | TIP3 | 66 | 64.991 | 52.254 | 70.196 | 1.00 | 42.84 |
| ATOM | 6170 | H1 | TIP3 | 66 | 65.020 | 51.298 | 70.269 | 1.00 | 0.00 |
| ATOM | 6171 | H2 | TIP3 | 66 | 65.902 | 52.519 | 70.326 | 1.00 | 0.00 |
| ATOM | 6172 | OH2 | TIP3 | 67 | 72.332 | 21.577 | 79.746 | 1.00 | 31.43 |
| ATOM | 6173 | H1 | TIP3 | 67 | 72.669 | 20.747 | 80.081 | 1.00 | 0.00 |
| ATOM | 6174 | H2 | TIP3 | 67 | 71.794 | 21.901 | 80.496 | 1.00 | 0.00 |
| ATOM | 6175 | OH2 | TIP3 | 68 | 56.953 | 90.848 | 29.332 | 1.00 | 29.80 |
| ATOM | 6176 | H1 | TIP3 | 68 | 56.811 | 89.908 | 29.185 | 1.00 | 0.00 |
| ATOM | 6177 | H2 | TIP3 | 68 | 57.854 | 90.826 | 29.719 | 1.00 | 0.00 |
| ATOM | 6178 | OH2 | TIP3 | 69 | 69.360 | 53.403 | 49.577 | 1.00 | 28.09 |
| ATOM | 6179 | H1 | TIP3 | 69 | 68.683 | 52.964 | 49.053 | 1.00 | 0.00 |
| ATOM | 6180 | H2 | TIP3 | 69 | 69.156 | 53.064 | 50.465 | 1.00 | 0.00 |
| ATOM | 6181 | OH2 | TIP3 | 70 | 69.319 | 29.836 | 80.545 | 1.00 | 21.16 |
| ATOM | 6182 | H1 | TIP3 | 70 | 69.614 | 29.982 | 81.445 | 1.00 | 0.00 |
| ATOM | 6183 | H2 | TIP3 | 70 | 69.082 | 28.903 | 80.529 | 1.00 | 0.00 |
| ATOM | 6184 | OH2 | TIP3 | 71 | 51.153 | 76.464 | 56.574 | 1.00 | 27.83 |
| ATOM | 6185 | H1 | TIP3 | 71 | 51.959 | 75.941 | 56.522 | 1.00 | 0.00 |
| ATOM | 6186 | H2 | TIP3 | 71 | 51.498 | 77.354 | 56.689 | 1.00 | 0.00 |
| ATOM | 6187 | OH2 | TIP3 | 72 | 71.680 | 50.506 | 56.619 | 1.00 | 14.84 |
| ATOM | 6188 | H1 | TIP3 | 72 | 72.230 | 51.082 | 57.156 | 1.00 | 0.00 |
| ATOM | 6189 | H2 | TIP3 | 72 | 70.973 | 50.277 | 57.244 | 1.00 | 0.00 |

FIG. 1: A-105

| | | | | | | | | |
|---|---|---|---|---|---|---|---|---|
| ATOM | 6190 | OH2 | TIP3 | 73 | 72.642 | 29.649 | 78.390 | 1.00 | 29.75 |
| ATOM | 6191 | H1 | TIP3 | 73 | 71.723 | 29.924 | 78.306 | 1.00 | 0.00 |
| ATOM | 6192 | H2 | TIP3 | 73 | 72.543 | 28.726 | 78.670 | 1.00 | 0.00 |
| ATOM | 6193 | OH2 | TIP3 | 74 | 72.204 | 57.547 | 27.111 | 1.00 | 22.34 |
| ATOM | 6194 | H1 | TIP3 | 74 | 71.935 | 56.625 | 26.988 | 1.00 | 0.00 |
| ATOM | 6195 | H2 | TIP3 | 74 | 73.153 | 57.487 | 27.217 | 1.00 | 0.00 |
| ATOM | 6196 | OH2 | TIP3 | 75 | 68.263 | 22.615 | 73.589 | 1.00 | 17.94 |
| ATOM | 6197 | H1 | TIP3 | 75 | 67.446 | 22.413 | 73.123 | 1.00 | 0.00 |
| ATOM | 6198 | H2 | TIP3 | 75 | 68.932 | 22.356 | 72.942 | 1.00 | 0.00 |
| ATOM | 6199 | OH2 | TIP3 | 76 | 43.037 | 84.119 | 40.245 | 1.00 | 41.44 |
| ATOM | 6200 | H1 | TIP3 | 76 | 42.447 | 83.926 | 40.996 | 1.00 | 0.00 |
| ATOM | 6201 | H2 | TIP3 | 76 | 42.408 | 83.958 | 39.518 | 1.00 | 0.00 |
| ATOM | 6202 | OH2 | TIP3 | 77 | 41.149 | 73.038 | 39.924 | 1.00 | 47.77 |
| ATOM | 6203 | H1 | TIP3 | 77 | 41.325 | 72.558 | 39.113 | 1.00 | 0.00 |
| ATOM | 6204 | H2 | TIP3 | 77 | 40.323 | 73.492 | 39.755 | 1.00 | 0.00 |
| ATOM | 6205 | OH2 | TIP3 | 78 | 95.575 | 76.386 | 42.861 | 1.00 | 18.01 |
| ATOM | 6206 | H1 | TIP3 | 78 | 95.552 | 75.639 | 43.462 | 1.00 | 0.00 |
| ATOM | 6207 | H2 | TIP3 | 78 | 96.237 | 76.966 | 43.238 | 1.00 | 0.00 |
| ATOM | 6208 | OH2 | TIP3 | 79 | 68.587 | 58.986 | 35.774 | 1.00 | 23.95 |
| ATOM | 6209 | H1 | TIP3 | 79 | 68.116 | 58.193 | 35.488 | 1.00 | 0.00 |
| ATOM | 6210 | H2 | TIP3 | 79 | 67.924 | 59.677 | 35.615 | 1.00 | 0.00 |
| ATOM | 6211 | OH2 | TIP3 | 80 | 75.155 | 46.288 | 42.156 | 1.00 | 39.10 |
| ATOM | 6212 | H1 | TIP3 | 80 | 75.466 | 46.322 | 41.247 | 1.00 | 0.00 |
| ATOM | 6213 | H2 | TIP3 | 80 | 74.886 | 47.192 | 42.341 | 1.00 | 0.00 |
| ATOM | 6214 | OH2 | TIP3 | 81 | 51.611 | 46.003 | 74.162 | 1.00 | 33.51 |
| ATOM | 6215 | H1 | TIP3 | 81 | 51.866 | 46.875 | 73.862 | 1.00 | 0.00 |
| ATOM | 6216 | H2 | TIP3 | 81 | 50.656 | 46.036 | 74.216 | 1.00 | 0.00 |
| ATOM | 6217 | OH2 | TIP3 | 82 | 63.400 | 57.477 | 53.365 | 1.00 | 31.46 |
| ATOM | 6218 | H1 | TIP3 | 82 | 62.980 | 58.320 | 53.635 | 1.00 | 0.00 |
| ATOM | 6219 | H2 | TIP3 | 82 | 62.632 | 56.973 | 53.081 | 1.00 | 0.00 |
| ATOM | 6220 | OH2 | TIP3 | 83 | 84.384 | 73.896 | 65.092 | 1.00 | 28.52 |
| ATOM | 6221 | H1 | TIP3 | 83 | 84.574 | 73.410 | 65.896 | 1.00 | 0.00 |
| ATOM | 6222 | H2 | TIP3 | 83 | 84.548 | 74.810 | 65.325 | 1.00 | 0.00 |
| ATOM | 6223 | OH2 | TIP3 | 84 | 51.883 | 14.856 | 83.841 | 1.00 | 20.94 |
| ATOM | 6224 | H1 | TIP3 | 84 | 52.591 | 14.902 | 83.191 | 1.00 | 0.00 |
| ATOM | 6225 | H2 | TIP3 | 84 | 51.545 | 13.965 | 83.770 | 1.00 | 0.00 |
| ATOM | 6226 | OH2 | TIP3 | 85 | 71.836 | 48.721 | 27.742 | 1.00 | 38.58 |
| ATOM | 6227 | H1 | TIP3 | 85 | 72.488 | 48.176 | 28.180 | 1.00 | 0.00 |
| ATOM | 6228 | H2 | TIP3 | 85 | 71.250 | 48.091 | 27.319 | 1.00 | 0.00 |
| ATOM | 6229 | OH2 | TIP3 | 86 | 68.232 | 87.507 | 20.055 | 1.00 | 54.49 |
| ATOM | 6230 | H1 | TIP3 | 86 | 68.018 | 86.691 | 19.577 | 1.00 | 0.00 |
| ATOM | 6231 | H2 | TIP3 | 86 | 68.243 | 87.147 | 20.962 | 1.00 | 0.00 |
| ATOM | 6232 | OH2 | TIP3 | 87 | 68.285 | 31.411 | 75.213 | 1.00 | 31.00 |
| ATOM | 6233 | H1 | TIP3 | 87 | 68.779 | 30.910 | 74.528 | 1.00 | 0.00 |
| ATOM | 6234 | H2 | TIP3 | 87 | 68.130 | 32.243 | 74.755 | 1.00 | 0.00 |
| ATOM | 6235 | OH2 | TIP3 | 88 | 64.547 | 55.874 | 28.138 | 1.00 | 39.17 |
| ATOM | 6236 | H1 | TIP3 | 88 | 64.379 | 55.222 | 27.451 | 1.00 | 0.00 |
| ATOM | 6237 | H2 | TIP3 | 88 | 63.806 | 56.482 | 28.050 | 1:00 | 0.00 |
| ATOM | 6238 | OH2 | TIP3 | 89 | 59.857 | 46.342 | 29.666 | 1.00 | 41.24 |
| ATOM | 6239 | H1 | TIP3 | 89 | 59.873 | 45.826 | 28.859 | 1.00 | 0.00 |
| ATOM | 6240 | H2 | TIP3 | 89 | 59.300 | 45.838 | 30.258 | 1.00 | 0.00 |
| ATOM | 6241 | OH2 | TIP3 | 90 | 74.066 | 89.861 | 58.071 | 1.00 | 40.33 |
| ATOM | 6242 | H1 | TIP3 | 90 | 74.429 | 89.034 | 57.744 | 1.00 | 0.00 |
| ATOM | 6243 | H2 | TIP3 | 90 | 73.725 | 90.226 | 57.232 | 1.00 | 0.00 |
| ATOM | 6244 | OH2 | TIP3 | 91 | 78.426 | 56.927 | 35.957 | 1.00 | 25.80 |
| ATOM | 6245 | H1 | TIP3 | 91 | 77.517 | 56.670 | 35.781 | 1.00 | 0.00 |
| ATOM | 6246 | H2 | TIP3 | 91 | 78.387 | 57.886 | 35.903 | 1.00 | 0.00 |

FIG. 1: A-106

MYRISTATE COORDINATES

| | | Atom Type | Residue | # | X | Y | Z | OCC | B |
|---|---|---|---|---|---|---|---|---|---|
| ATOM | 6247 | CA | MYR | 500 | 61.798 | 10.612 | 74.237 | 1.00 | 30.58 |
| ATOM | 6248 | C | MYR | 500 | 62.880 | 9.515 | 74.260 | 1.00 | 29.59 |
| ATOM | 6249 | C3 | MYR | 500 | 61.342 | 10.943 | 75.657 | 1.00 | 33.83 |
| ATOM | 6250 | C4 | MYR | 500 | 59.857 | 10.578 | 75.854 | 1.00 | 36.65 |
| ATOM | 6251 | C5 | MYR | 500 | 59.053 | 11.719 | 76.522 | 1.00 | 36.89 |
| ATOM | 6252 | C6 | MYR | 500 | 58.349 | 11.351 | 77.862 | 1.00 | 36.76 |
| ATOM | 6253 | C7 | MYR | 500 | 58.416 | 12.451 | 78.960 | 1.00 | 33.84 |
| ATOM | 6254 | C8 | MYR | 500 | 57.432 | 12.222 | 80.114 | 1.00 | 29.21 |
| ATOM | 6255 | C9 | MYR | 500 | 57.749 | 13.185 | 81.256 | 1.00 | 26.86 |
| ATOM | 6256 | C10 | MYR | 500 | 56.668 | 13.397 | 82.334 | 1.00 | 22.32 |
| ATOM | 6257 | C11 | MYR | 500 | 57.032 | 14.557 | 83.258 | 1.00 | 20.60 |
| ATOM | 6258 | C12 | MYR | 500 | 58.395 | 14.314 | 83.870 | 1.00 | 20.64 |
| ATOM | 6259 | C13 | MYR | 500 | 59.209 | 15.557 | 84.220 | 1.00 | 25.12 |
| ATOM | 6260 | C14 | MYR | 500 | 58.677 | 16.418 | 85.390 | 1.00 | 23.56 |

MOLECULES COMPRISING A CALCINEURIN-LIKE BINDING POCKET AND ENCODED DATA STORAGE MEDIUM CAPABLE OF GRAPHICALLY DISPLAYING THEM

This application is a divisional application of U.S. application Ser. No. 08/512,815, filed Aug. 9, 1995, now U.S. Pat. No. 5,978,740.

TECHNICAL FIELD OF INVENTION

The present invention relates to crystallized molecules and molecular complexes which comprise the active site binding pocket or the FKBP12/FK506 binding pocket of calcineurin or close structural homologues to either binding pocket. This invention also relates to a data storage medium encoded with the corresponding structure coordinates of those crystallized molecules or molecular complexes. Such data storage material is capable of displaying such molecules and molecular complexes as a graphical three-dimensional representation on a computer screen. In addition, this invention relates to methods of using the structure coordinates of those molecules or molecular complexes to solve the structure of homologous proteins. This invention also relates to methods of using the structure coordinates to screen and design compounds that bind to calcineurin or homologues thereof.

BACKGROUND OF THE INVENTION

FK506 is an immunosuppressant that inhibits T-cell activation and proliferation (B. E. Bierer et al., *Current Opinions in Immunology* 5, pp. 763–773 (1993)]. Immunosuppressants, such as FK506, are useful drugs in the treatment of transplant rejection and the prevention of autoimmune diseases. Furthermore, such compounds are useful tools in immune system research.

FK506 is a more recently discovered and more potent immunosuppressant than cyclosporin. Unfortunately, FK506 is characterized by undesirable pharmacological properties, such as toxicity and poor bioavailability [P. Neuhaus et al., *Lancet*, 344, pp. 423–428 (1994)]. Therefore, there remains a need for potent immunosuppressants with improved pharmacological properties.

FK506 acts as an immunosuppressant by inhibiting T-cell signal transduction pathways that control lymphokine transcription factors. As a result, gene activation of various lymphokines, including IL-2, is prevented. This in turn leads to an inhibition of T-cells, and therefore, immunosuppression.

FK506 exerts these effects in a step-wise process. Initially, FK506 binds to a peptidyl prolyl isomerase, FK506 Binding Protein ("FKBP12"). This complex then binds to, and inhibits, calcineurin. Subsequent events inhibit signal transduction pathways, inhibit lymphokine gene transcription, and ultimately, reduce production of lymphokines, such as IL-2.

Calcineurin is a $Ca^{2+}$ L-dependent serine/threonine phosphatase. It is a heterodimer composed of 2 subunits: calcineurin A ("CnA"), a 59 kDa catalytic subunit and calcineurin B ("CnB"), a 19 kDa subunit. CnA contains a phosphatase active site and an autoinhibitory region as well as binding sites for calmodulin and CnB. Binding of FKBP12/FK506 inhibits the phosphatase activity of calcineurin against physiological substrates. FKBP12/FK506 does not, however, bind at the phosphatase active site.

Thus, a compound may inhibit calcineurin by binding to the phosphatase active site ("active site"), by binding to an accessory binding site, such as the FKBP12/FK506 binding site, or by binding to both sites simultaneously. Such compounds may interact directly with calcineurin or, alternatively, may bind to FKBP12, or a FKBP12 homologue, prior to binding to calcineurin.

FKBP12 has been characterized by its cDNA and amino acid sequences. The crystal structures of FKBP12, and of FKBP12 bound to FK506, have been reported. However, this structural information has not proven useful in the design of calcineurin inhibitors [M. V. Caffrey et al., *Bioorg. Med. Chem. Lett.*, 21, pp. 2507–2510 (1994)].

Rat calcineurin has been characterized by its amino acid sequences and its cDNA. Human calcineurin has been characterized by its amino acid sequences and its cDNA [Guerini et al., *Proc. Natl. Acad. Sci. USA*, 86, pp. 9183–87 (1989)]. Knowledge of the primary structure, i.e., amino acid sequence, of calcineurin, however, does not allow prediction of its tertiary structure. Nor does it afford an understanding of the structural, conformational, and chemical interactions of calcineurin with FKBP12/FK506 or other compounds or inhibitors.

The crystal structure of calcineurin has not been reported. Nor has the crystal structure of a calcineurin homologue or a calcineurin co-complex been reported. The need, therefore, exists for determining the crystal structure of calcineurin to provide a more accurate description of the structure of calcineurin to aid in the design of improved inhibitors of calcineurin activity. The crystal structure of a complex comprising calcineurin A, calcineurin B, FKBP12, and FK506 would provide such a description.

Calcineurin inhibitors, such as FK506, have therapeutic potential as immunosuppressants. Specifically, such compounds may be used in the treatment of transplant rejection and autoimmune diseases, such as rheumatoid arthritis, multiple sclerosis, juvenile diabetes, asthma, inflammatory bowel disease, and other autoimmune diseases.

SUMMARY OF THE INVENTION

Applicants have solved this problem by achieving, for the first time, the crystallization and three-dimensional structure determination of a calcineurin/FKBP12/FK506 complex and have solved the three-dimensional structure of that complex. This has allowed applicants to determine the key structural features of calcineurin, particularly the shape of its FKBP12/FK506 binding pocket and its phosphatase active site binding pocket.

Thus, the present invention provides molecules or molecular complexes that comprise either one or both of these binding pockets or homologues of either binding pocket that have similar three-dimensional shapes.

The invention also provides machine readable storage medium which comprises the structural coordinates of either one or both of these calcineurin binding pockets, or similarly shaped, homologous binding pockets. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which bind to the aforementioned binding pockets. Such compounds are potential inhibitors of calcineurin or its homologues.

The invention also provides a method for determining at least a portion of the three-dimensional structure of molecules or molecular complexes which contain at least some structurally similar features to calcineurin. This is achieved by using at least some of the structural information obtained for the calcineurin complex.

The invention also provides a method for crystallizing a calcineurin/FKBP12/FK506 complex and related complexes by removing the C-terminal portion of calcineurin subunit A.

BRIEF DESCRIPTION OF THE FIGURES

FIG. 1 lists the atomic structure coordinates for a bovine brain CnA/CnB/FKBP12/FK506 complex as derived by X-ray diffraction from a crystal of that complex. The following abbreviations are used in FIG. 1:
"Atom type" refers to the element whose coordinates are measured. The first letter in the column defines the element.
"X, Y, Z" crystallographically define the atomic position of the element measured.
"B" is a thermal factor that measures movement of the atom around its atomic center.
"Occ" is an occupancy factor that refers to the fraction of the molecules in which each atom occupies the position specified by the coordinates.
A value of "1" indicates that each atom has the same conformation, i.e., the same position, in all molecules of the crystal.

DETAILED DESCRIPTION OF THE INVENTION

Figure 2:
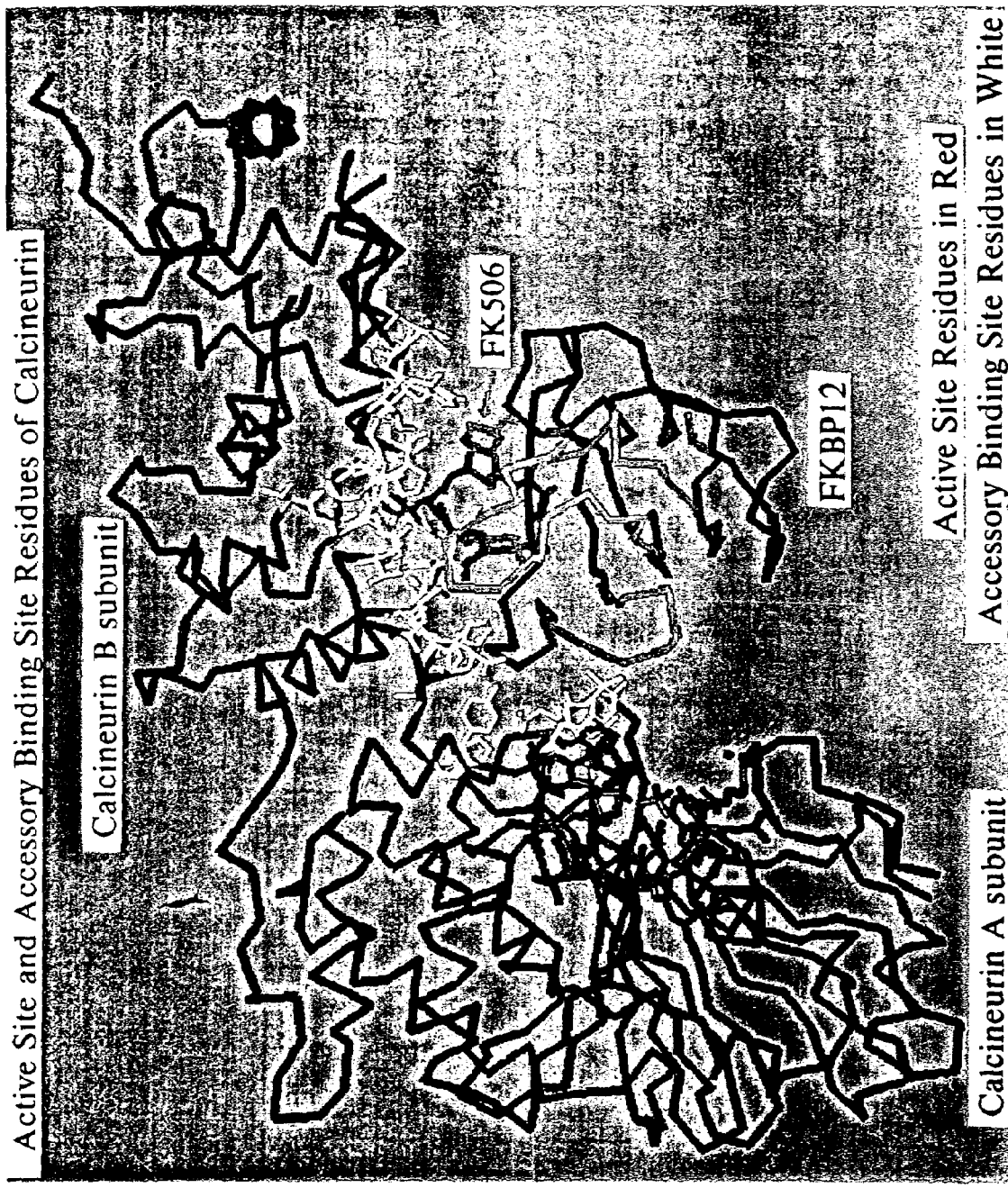
FIG. 2 depicts the structure of the calcineurin A, calcineurin B, FKBP12, and FK506 co-complex as determined from x-ray crystallography.

The following abbreviations are used throughout the application:

| A = | Ala = | Alanine | T = | Thr = | Threonine |
| V = | Val = | Valine | C = | Cys = | Cysteine |
| L = | Leu = | Leucine | Y = | Tyr = | Tyrosine |
| I = | Ile = | Isoleucine | N = | Asn = | Asparagine |
| P = | Pro = | Proline | Q = | Gln = | Glutamine |
| F = | Phe = | Phenylalanine | D = | Asp = | Aspartic Acid |
| W = | Trp = | Tryptophan | E = | Glu = | Glutamic Acid |
| M = | Met = | Methionine | K = | Lys = | Lysine |
| C = | Gly = | Glycine | R = | Arg = | Arginine |
| S = | Ser = | Serine | H = | His = | Histidine |

CnA = calcineurin subunit A
CnB = calcineurin subunit B

Additional definitions are set forth in the specification where necessary.

In order that the invention described herein may be more fully understood, the following detailed description is set forth.

Applicants have solved the three-dimensional structure of a calcineurin/FKBP12/FK506 complex using high resolution X-ray crystallography. Importantly, this has provided, for the first time, the information about the shape and structure of both the calcineurin active site binding pocket and the auxiliary FKBP12/FK506 binding pocket.

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. An understanding of such associations will help lead to the design of drugs having more favorable associations with their target receptor or enzyme, and thus, improved biological effects. Therefore, this information is crucial in designing potential inhibitors of calcineurin-like binding pockets.

The term "binding pocket", as used herein, refers to a region of a molecule or molecular complex, that, as a result of its shape, favorably associates with another chemical entity or compound.

The term "calcineurin-like binding pocket" refers to a portion of a molecule whose shape is sufficiently similar to either the active site binding pocket or FKBP12/FK506 binding pocket as to bind common ligands. This commonality of shape is defined by a root mean square deviation from the structure coordinates of the backbone atoms of the amino acids that make up that binding pocket in calcineurin (as set forth in FIG. 1) of not more than 1.5 Å. How this calculation is obtained is described below.

The "active site binding pocket" or "active site" of calcineurin refers to the site where dephosphorylation of a substrate occurs. In resolving the crystal structure of bovine brain calcineurin applicants have determined that calcineurin subunit A amino acids 90, 91, 92, 118, 120, 121, 122, 150, 151, 156, 160, 199, 232, 253, 254, 256, 281, 282, 283, 284, 306, 311, 312, and 317 are situated close enough to a phosphate molecule present in the active site (within 8 Å) to interact with it. It will be readily apparent to those of skill in the art that the numbering of amino acids in other isoforms of calcineurin may be different than that isolated from bovine brain.

Each of those amino acids is defined by a set of structure coordinates as set forth in FIG. 1. The term "structure coordinates" refers to Cartesian coordinates derived from mathematical equations related to the patterns obtained on diffraction of a monochromatic beam of X-rays by the atoms (scattering centers) of a calcineurin complex in crystal form. The diffraction data are used to calculate an electron density map of the repeating unit of the crystal. The electron density maps are used to establish the positions of the individual atoms within the unit cell of the crystal.

Those of skill in the art understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations caused by acceptable errors in the individual coordinates will have little, if any, effect on overall shape. In terms of binding pockets, these acceptable variations would not be expected to alter the nature of ligands that could associate with those pockets.

The term "associating with" refers to a condition of proximity between a chemical entity or compound, or portions thereof, and a calcineurin molecule or portions thereof. The association may be non-covalent—wherein the juxtaposition is energetically favored by hydrogen bonding or van der Waals or electrostatic interactions—or it may be covalent.

The variations discussed above may be generated because of mathematical manipulations of the CnA/CnB/FK506/FKBP12 structure coordinates. For example, the structure coordinates set forth in FIG. 1 could be manipulated by crystallographic permutations of the raw structure coordinates, fractionalization of the raw structure coordinates, integer additions or subtractions to sets of the raw structure coordinates, inversion of the raw structure coordinates or any combination of the above.

Alternatively, modifications in the crystal structure due to mutations, additions and deletions of amino acids in any of the components that make up the crystal could also account for variations in structure coordinates. If such variations are within an acceptable standard error as compared to the original coordinates, the resulting three-dimensional shape is considered to be the same. Thus, for example, a ligand that bound to the active site binding pocket of calcineurin would also be expected to bind to another binding pocket whose structure coordinates defined a shape that fell within the acceptable error. Such modified complexes or the binding pocket(s) thereof are also within the scope of this invention.

A third possible variant is an unrelated molecule or molecular complex which contains a binding pocket that has a similar shape as a calcineurin binding pocket. The binding pocket of that unrelated molecule would also be expected to bind ligands that are capable of binding to the calcineurin binding pocket.

Various computational analyses are therefore necessary to determine whether a molecule or the binding pocket portion thereof is sufficiently similar to either of the two calcineurin binding pockets described above. Such analyses may be carried out in current software applications, such as the Molecular Similarity application of QUANTA (Molecular Simulations Inc., Waltham, Mass.) version 3.3, and as described in the accompanying User's Guide, Volume 3 pgs. 134–135.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, C$\alpha$, C and O) for all conserved residues between the two structures being compared. We will also consider only rigid fitting operations.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any set of structure coordinates of a molecule or molecular complex or a binding pocket thereof that has a root mean square deviation of conserved residue backbone atoms (N, C$\alpha$, C, O) of less than 1.5 Å when superimposed—using backbone atoms—on the relevant structure coordinates listed in FIG. 1 are considered identical. More preferably, the root mean square deviation is less than 1.0 Å. Most preferably, the root mean square deviation is less than 0.5 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of calcineurin or a binding pocket portion thereof, as defined by the structure coordinates of calcineurin described herein.

The term "least squares" refers to a method based on the principle that the best estimate of a value is that in which the sum of the squares of the deviations of observed values is a minimum.

Therefore, according to one embodiment, the present invention provides a crystallized molecule or molecular complex comprising a binding pocket defined by structure coordinates of CnA amino acids 90, 91, 92, 118, 120, 121, 122, 150, 151, 156, 160, 199, 232, 253, 254, 256, 281, 282, 283, 284, 306, 311, 312, and 317 according to FIG. 1, or a homologue of said molecule or molecular complex comprising a binding pocket that has a root mean square deviation from the backbone atoms of said amino acids of not more than 1.5 Å.

Preferably, the crystallized molecule or molecular complex comprises a binding pocket that is defined by structure coordinates of those CnA amino acids that are situated within 5 Å of the phosphate molecule in the crystal, i.e., amino acids 90, 91, 92, 118, 120, 121, 122, 150, 151, 156, 160, 281, 282, 283, 306, 311, 199, 232, and 254 according to FIG. 1, or a binding pocket, wherein that has a root mean square deviation from the backbone atoms of those amino acids of not more than 1.5 Å.

Applicants' elucidation of the calcineurin/FKBP12/FK506 crystal structure has also revealed the details about the FKBP12/FK506 binding pocket. An FKBP12/FK506 complex is capable of binding to calcineurin at a site separate from the active site. Because the binding of that complex inhibits calcineurin-mediated activities, the elucidation of the binding site provides a second area on which new inhibitors may be modelled. The crystal structure revealed a subset of calcineurin amino acids that were close enough to interact with the bound FKBP12/FK506 complex.

Therefore, according to an alternate embodiment, the invention provides a crystallized molecule or molecular complex comprising a binding pocket defined by structure coordinates of CnA 122, 124, 159, 160, 310, 312, 313, 314, 339, 341, 343, 344, 345, 347, 351, 352, 353, 354, 355, 356, 359, 360, and 363, and CnB amino acids 49, 50, 114, 115, 118, 119, 121, 122, 123, 124, 157, 158, 159, 161, and 162 amino acids according to FIG. 1, or a homologue of said molecule or molecular complex comprising a binding pocket that has a root mean square deviation from the backbone atoms of said amino acids of not more than 1.5 Å.

According to a more preferred embodiment, the molecule or molecular complex comprises two binding pockets. One is defined by the structure coordinates of the amino acids that make up the calcineurin active site binding pocket±a root mean square deviation from the backbone atoms of those amino acids of not more than 1.5 Å. The other is defined by the structure coordinates of the amino acids that make up the calcineurin FKBP12/FK506 binding pocket±a root mean square deviation from the backbone atoms of those amino acids of not more than 1.5 Å.

Even more preferred are molecules or molecular complexes that are defined by the entire set of structure coordinates in FIG. 1±a root mean square deviation from the backbone atoms of those amino acids of not more than 1.5 Å. An alternative more preferred embodiment of this invention is a molecular complex that comprises amino acids 17–392 of CnA, amino acids 5–169 of CnB, FKBP12 and FK506.

In order to use the structure coordinates generated for the CnA/CnB/FKBP12/FK506 complex or one of its binding pockets or homologues thereof, it is necessary to convert them into a three-dimensional shape. This is achieved through the use of commercially available software that is capable of generating three-dimensional graphical representations of molecules or portions thereof from a set of structure coordinates.

Therefore, according to another embodiment of this invention is provided a machine-readable storage medium comprising a data storage material encoded with machine readable data which, when using a machine programmed with instructions for using said data, is capable of displaying a graphical three-dimensional representation of any of the molecule or molecular complexes of this invention that have been described above.

According to one embodiment, the machine-readable storage medium is capable of displaying a graphical three-dimensional representation of a molecule or molecular complex comprising a binding pocket defined by structure coordinates of CnA amino acids 90, 91, 92, 118, 120, 121, 122, 150, 151, 156, 160, 199, 232, 253, 254, 256, 281, 282, 283, 284, 306, 311, 312, and 317 according to FIG. 1, or a homologue of said molecule or molecular complex, wherein said homologue comprises a binding pocket that has a root mean square deviation from the backbone atoms of said amino acids of not more than 1.5 Å. More preferably, the binding pocket is defined by structure coordinates of CnA amino acids 90, 91, 92, 118, 120, 121, 122, 150, 151, 156, 160, 199, 281, 282, 283, 306, 311, 232 and 254, according to FIG. 1±a root mean square deviation from the backbone atoms of said amino acids of not more than 1.5 Å.

According to another embodiment, the machine-readable storage medium is capable of displaying a graphical three-dimensional representation of a molecule or molecular complex comprising a binding pocket defined by structure coordinates of CnA amino acids 122, 124, 159, 160, 310, 312, 313, 314, 339, 341, 343, 344, 345, 347, 351, 352, 353, 354, 355, 356, 359, 360, and 363; and CnB amino acids 49, 50, 114, 115, 118, 119, 121, 122, 123, 124, 157, 158, 159, 161, and 162 or a homologue of said molecule or molecular complex, wherein said homologue comprises a binding pocket that has a root mean square deviation from the backbone atoms of said amino acids of not more than 1.5 Å.

More preferably, the computer-readable storage medium is capable of displaying a graphical three-dimensional representation of a molecule or molecular complex that comprises two binding pockets. One binding pocket is defined by the structure coordinates of the amino acids that make up the calcineurin active site binding pocket±a root mean square deviation from the backbone atoms of those amino acids of not more than 1.5 Å. The other is defined by the structure coordinates of the amino acids that make up the calcineurin FKBP12/FK506 binding pocket±a root mean square deviation from the backbone atoms of those amino acids of not more than 1.5 Å.

Even more preferred is a machine-readable data storage medium that is capable of displaying a graphical three-dimensional representation of a molecule or molecular complex that is defined by the structure coordinates of all of the amino acids in FIG. 1±a root mean square deviation from the backbone atoms of those amino acids of not more than 1.5 Å.

According to an alternate embodiment, the machine-readable data storage medium comprises a data storage material encoded with a first set of machine readable data which comprises the Fourier transform of the structural coordinates set forth in FIG. 1, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

Figure 3:
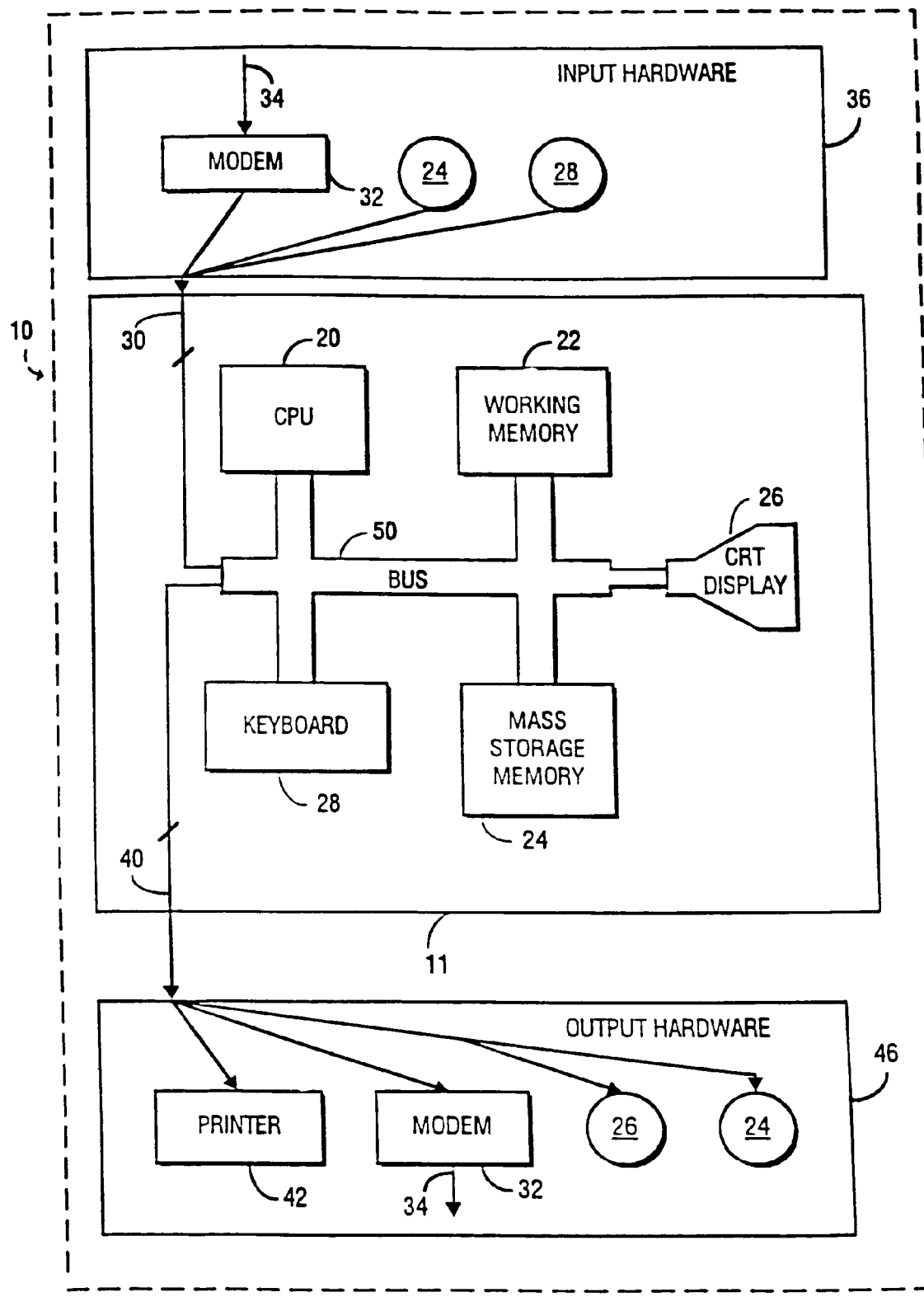
FIG. 3 shows a diagram of a system used to carry out the instructions encoded by the storage medium of FIGS. 4 and 5.

FIG. 3 demonstrates one version of these embodiments. System 10 includes a computer 11 comprising a central processing unit ("CPU") 20, a working memory 22 which may be, e.g, RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

Figure 4:
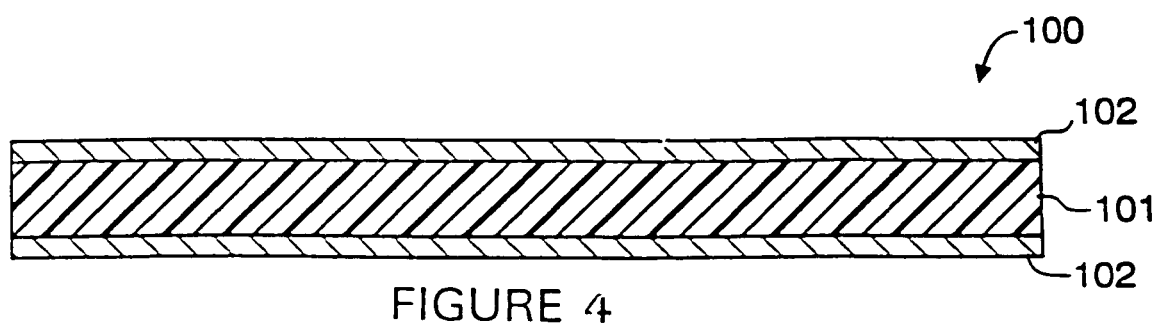
FIG. 4 shows a cross section of a magnetic storage medium.

FIG. 4 shows a cross section of a magnetic data storage medium 100 which can be encoded with a machine-readable data that can be carried out by a system such as system 10 of FIG. 3. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 10 of FIG. 3.

Figure 5:
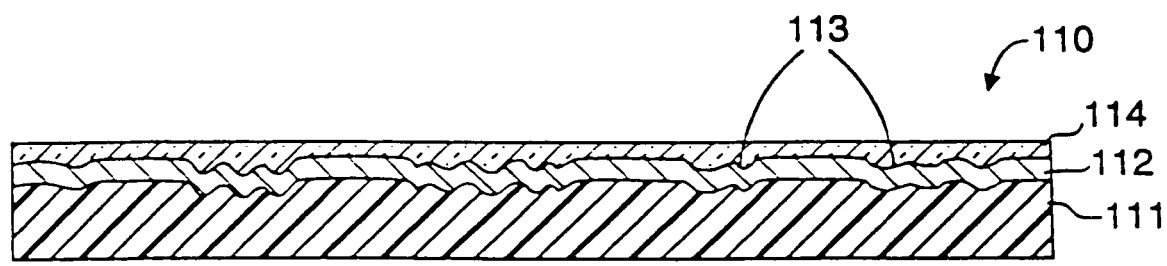
FIG. 5 shows a cross section of a optically-readable data storage medium.

FIG. 5 shows a cross section of an optically-readable data storage medium 110 which also can be encoded with such a machine-readable data, or set of instructions, which can be carried out by a system such as system 10 of FIG. 3. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

Thus, in accordance with the present invention, data capable of displaying the three dimensional structure of calcineurin and portions thereof and their structurally similar homologues is stored in a machine-readable storage medium, which is capable of displaying a graphical three-dimensional representation of the structure. Such data may be used for a variety of purposes, such as drug discovery.

For example, the structure encoded by the data may be computationally evaluated for its ability to associate with chemical entities. This provides insight into calcineurin's ability to associate with the chemical entities. Chemical entities that are capable of associating with calcineurin may inhibit calcineurin. Such chemical entities are potential drug candidates. Alternatively, the structure encoded by the data may be displayed in a graphical format. This allows visual inspection of the structure, as well as visual inspection of the structure's association with chemical entities.

Thus, according to another embodiment, the invention provides a method for evaluating the ability of a chemical entity to associate with any of the molecules or molecular complexes set forth above. This method comprises the steps of: a) employing computational means to perform a fitting operation between the chemical entity and a binding pocket of the molecule or molecular complex; and b) analyzing the results of said fitting operation to quantify the association between the chemical entity and the binding pocket. The term "chemical entity", as used herein, refers to chemical compounds, complexes of at least two chemical compounds, and fragments of such compounds or complexes.

For the first time, the present invention permits the use of molecular design techniques to design, select and synthesize chemical entities, including inhibitory compounds, capable of binding to calcineurin-like binding pockets. Such chemical entities may interact directly with such pockets, in areas adjacent to those pockets or, alternatively, may interact with FKBP12, or a homologue or mutant of FKBP12, and the resulting complex may interact with the binding pocket. Such chemical entities and compounds, optionally bound to FKBP12, may interact with either or both calcineurin-like binding pockets, in whole or in part. Preferably, if the entity binds to FKBP12, the resulting complex interacts with the calcineurin-like binding pocket that corresponds to the FKBP12/FK506 binding site on calcineurin.

Portions of both FKBP12 and FK506 participate in the binding of that complex to the FKBP12/FK506 binding site of calcineurin. Therefore, inhibitors that bind to a corresponding calcineurin-like binding site may be designed to mimic the interactions of that entire complex with the binding site. Alternatively, if the inhibitor is capable of complexing with FKBP12, it need only mimic the interactions of the FK506 portion of the FKBP12/FK506 complex with the binding site.

The crystal structure of the FKBP12/FK506 complex has been solved and has aided in the design of new compounds that bind to FKBP12 [D. A. Holt et al., *J. Am. Chem. Soc.*, 115, pp. 9925–38 (1993)]. However, none of those compounds when bound to FKBP12 have been satisfactory in inhibiting calcineurin [M. V. Caffrey et al., *Bioorg. Med. Chem. Letts.*, 4, pp. 2507–10 (1994)]. Accordingly, applicants' elucidation of the FKBP12/FK506 binding site on calcineurin provides the necessary information for designing compounds that when bound to FKBP12 are able to bind to the corresponding calcineurin-like binding site.

Throughout this section, discussions about the ability of an entity to bind to, associate with or inhibit a calcineurin-like binding pocket refers to features of the entity alone, or as part of a complex with FKBP12 or naturally occurring FKBP12 isoforms and homologues. Assays to determine if a compound binds to FKBP12 are well known in the art [M. W. Harding et al., *Nature*, 341, pp. 758–60 (1989); J. J. Siekierka et al., *Nature*, 341, pp. 755–57 (1989)].

The design of compounds that bind to or inhibit calcineurin-like binding pockets according to this invention generally involves consideration of two factors. First, the entity must be capable of physically and structurally associating with the calcineurin-like binding pocket. Non-covalent molecular interactions important in this association include hydrogen bonding, van der Waals interactions, hydrophobic interactions and electrostatic interactions.

Second, the entity must be able to assume a conformation that allows it to associate with the calcineurin-like binding pocket directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the calcineurin-like binding pocket or FKBP12 or homologues thereof.

The potential inhibitory or binding effect of a chemical entity on a calcineurin-like binding pocket may be analyzed prior to its actual synthesis and testing by the use of computer modelling techniques. If the theoretical structure of the given entity suggests insufficient interaction and association between it and the calcineurin-like binding pocket testing of the entity is obviated. However, if computer modelling indicates a strong interaction, the molecule may then be synthesized and tested for its ability to bind to a calcineurin-like binding pocket. This may be achieved by testing the ability of the molecule to inhibit calcineurin using the assays described in Examples 6 and 7. In this manner, synthesis of inoperative compounds may be avoided.

A potential inhibitor of a calcineurin-like binding pocket may be computationally evaluated and designed by means of a series of steps in which chemical entities or fragments are screened and selected for their ability to associate with the calcineurin-like binding pockets.

One skilled in the art may use one of several methods to screen chemical entities or fragments for their ability to associate with a calcineurin-like binding pocket. This process may begin by visual inspection of, for example, a calcineurin-like binding pocket on the computer screen based on the calcineurin coordinates in FIG. 1 or other coordinates which define a similar shape generated from the machine-readable storage medium. Selected fragments or chemical entities may then be positioned in a variety of orientations, or docked, within that binding pocket as defined supra. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:
1. GRID (P. J. Goodford, "A Computational Procedure for Determining Energetically Favorable Binding Sites on Biologically Important Macromolecules", *J. Med. Chem.*, 28, pp. 849–857 (1985)). GRID is available from Oxford University, Oxford, UK.
2. MCSS (A. Miranker et al., "Functionality Maps of Binding Sites: A Multiple Copy Simultaneous Search Method." *Proteins: Structure, Function and Genetics*, 11, pp. 29–34 (1991)). MCSS is available from Molecular Simulations, Burlington, Mass.
3. AUTODOCK (D. S. Goodsell et al., "Automated Docking of Substrates to Proteins by Simulated Annealing", *Proteins: Structure, Function, and Genetics*, 8, pp. 195–202 (1990)). AUTODOCK is available from Scripps Research Institute, La Jolla, Calif.
4. DOCK (I. D. Kuntz et al., "A Geometric Approach to Macromolecule-Ligand Interactions", *J. Mol. Biol.*, 161, pp. 269–288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of calcineurin. This would be followed by manual model building using software such as Quanta or Sybyl.

Useful programs to aid one of skill in the art in connecting the individual chemical entities or fragments include:
1. CAVEAT (P. A. Bartlett et al, "CAVEAT: A Program to Facilitate the Structure-Derived Design of Biologically Active Molecules". In *Molecular Recognition in Chemical and Biological Problems*", Special Pub., Royal Chem. Soc., 78, pp. 182–196 (1989)). CAVEAT is available from the University of California, Berkeley, Calif.
2. 3D Database systems such as MACCS-3D (MDL Information Systems, San Leandro, Calif.). This area is reviewed in Y. C. Martin, "3D Database Searching in Drug Design", *J. Med. Chem.*, 35, pp. 2145–2154 (1992).
3. HOOK (available from Molecular Simulations, Burlington, Mass.).

Instead of proceeding to build an inhibitor of a calcineurin-like binding pocket in a step-wise fashion one fragment or chemical entity at a time as described above, inhibitory or other calcineurin binding compounds may be designed as a whole or "de novo" using either an empty binding site or optionally including some portion(s) of a known inhibitor(s). These methods include:
1. LUDI (H.-J. Bohm, "The Computer Program LUDI: A New Method for the De Novo Design of Enzyme Inhibitors", *J. Comp. Aid. Molec. Design*, 6, pp. 61–78 (1992)). LUDI is available from Biosym Technologies, San Diego, Calif.
2. LEGEND (Y. Nishibata et al., *Tetrahedron*, 47, p. 8985 (1991)). LEGEND is available from Molecular Simulations, Burlington, Mass.
3. LeapFrog (available from Tripos Associates, St. Louis, Mo.).

Other molecular modelling techniques may also be employed in accordance with this invention. See, e.g., N. C. Cohen et al., "Molecular Modeling Software and Methods for Medicinal Chemistry, *J. Med. Chem.*, 33, pp. 883–894 (1990). See also, M. A. Navia et al., "The Use of Structural Information in Drug Design", *Current Opinions in Structural Biology*, 2, pp. 202–210 (1992).

Once a compound has been designed or selected by the above methods, the efficiency with which that entity may bind to a calcineurin-like binding pocket may be tested and optimized by computational evaluation. For example, an effective calcineurin-like binding pocket inhibitor must preferably demonstrate a relatively small difference in energy between its bound and free states (i.e., a small deformation energy of binding). Thus, the most efficient calcineurin-like binding pocket inhibitors should preferably be designed with a deformation energy of binding of not greater than about 10 kcal/mole, preferably, not greater than 7 kcal/mole. Calcineurin-like binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to a calcineurin-like binding pocket may be further computationally optimized so that in its bound state it would preferably lack repulsive electrostatic interaction with the target enzyme. Such non-complementary (e.g., electrostatic) interactions include repulsive charge—charge, dipole—dipole and charge-dipole interactions. Specifically, the sum of all electrostatic interactions between the inhibitor and the protein when the inhibitor is bound to FKBP12 or a calcineurin-like binding pocket, preferably make a neutral or favorable contribution to the enthalpy of binding.

Specific computer software is available in the art to evaluate compound deformation energy and electrostatic interaction. Examples of programs designed for such uses include: Gaussian 92, revision C [M. J. Frisch, Gaussian, Inc., Pittsburgh, Pa. ©1992]; AMBER, version 4.0 [P. A. Kollman, University of California at San Francisco, ©1994]; QUANTA/CHARMM [Molecular Simulations, Inc., Burlington, Mass. ©1994]; and Insight II/Discover (Biosysm Technologies Inc., San Diego, Calif. ©1994). These programs may be implemented, for instance, using a Silicon Graphics workstation, IRIS 4D/35 or IBM RISC/6000 workstation model 550. Other hardware systems and software packages will be known to those skilled in the art.

Once the calcineurin binding-pocket inhibitory entity has been optimally selected or designed, as described above, substitutions may then be made in some of its atoms or side groups in order to improve or modify its binding properties.

Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to a calcineurin-like binding pocket by the same computer methods described in detail, above.

Another approach made possible and enabled by this invention, is the computational screening of small molecule data bases for chemical entities or compounds that can bind in whole, or in part, to a calcineurin-like binding pocket. In this screening, the quality of fit of such entities to the binding site may be judged either by shape complementarity or by estimated interaction energy. E. C. Meng et al., *J. Comp. Chem.*, 13, pp. 505–524 (1992).

The structure coordinates set forth in FIG. 1 can also be used to aid in obtaining structural information about another crystallized molecule or molecular complex. This may be achieved by any of a number of well-known techniques, including molecular replacement.

Therefore, in another embodiment this invention provides a method of utilizing molecular replacement to obtain structural information about a molecule or molecular complex comprising the steps of:

a) crystallizing said molecule or molecular complex;
b) generating an X-ray diffraction pattern from said crystallized molecule or molecular complex; and
c) applying at least a portion of the structure coordinates set forth in FIG. 1 to the X-ray diffraction pattern to generate a three-dimensional electron density map of the molecule or molecular complex.

By using molecular replacement, all or part of the structure coordinates of the CnA/CnB/FKBP12/FK506 complex as provided by this invention (and set forth in FIG. 1) can provide an accurate structure determination for all or part of an unknown crystallized molecule or molecular complex more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide an accurate estimate of the phases for the unknown structure.

Thus, this method involves generating a preliminary model of a molecule or molecular complex whose structure coordinates are unknown, by orienting and positioning the relevant portion of the CnA/CnB/FKBP12/FK506 complex according to FIG. 1 within the unit cell of the unknown molecule or molecular complex so as best to account for the observed X-ray diffraction pattern of the unknown crystal. Phases can then be calculated from this model and combined with the observed X-ray diffraction pattern amplitudes to give an approximate Fourier synthesis of the structure whose coordinates are unknown. This, in turn, can be subjected to any well-known refinement technique to provide a final, accurate structure of the unknown crystal. E. Lattman, "Use of the Rotation and Translation Functions", in *Meth. Enzymol.*, 115, pp. 55–77 (1985); M. G. Rossmann, ed., "The Molecular Replacement Method", *Int. Sci. Rev. Ser.*, No. 13, Gordon & Breach, New York, (1972).

The structure of any portion of any crystallized molecule or molecular complex that is sufficiently homologous to a portion of the CnA/CnB/FKBP12/FK506 can be resolved by this method.

In a preferred embodiment, the method of molecular replacement is utilized to obtain structural information about a molecule or molecular complex, wherein the complex comprises at least one catalytically functional calcineurin A subunit. The term "catalytically functional calcineurin A subunit refers" to calcineurin A, as well as fragments and structural homologues thereof which retain their phosphatase activity.

The structure coordinates of calcineurin as provided by this invention are particularly useful in solving the structure of other crystal forms of the CnA/CnB/FKBP12/FK506 complex.

Furthermore, the structure coordinates of calcineurin as provided by this invention are useful in solving the structure of calcineurin mutants, which may optionally be crystallized in co-complex with a chemical entity. The crystal structures of a series of such complexes may then be solved by molecular replacement and compared with that of wild-type calcineurin. Potential sites for modification within the various binding sites of the enzyme may thus be identified. This information provides an additional tool for determining the most efficient binding interactions, for example, increased hydrophobic interactions, between calcineurin and a chemical entity or compound.

The structure coordinates are also particularly useful to solve the structure of crystals of calcineurin or calcineurin homologues co-complexed with a variety of chemical entities. This approach enables the determination of the optimal sites for interaction between chemical entities, including candidate calcineurin inhibitors and calcineurin. For example, high resolution X-ray diffraction data collected from crystals saturated with solvent allows the determination of where each type of solvent molecule resides. Small molecules that bind tightly to those sites can then be designed and synthesized and tested for their calcineurin inhibition activity.

All of the complexes referred to above may be studied using well-known X-ray diffraction techniques and may be refined versus 2–3 Å resolution X-ray data to an R value of about 0.20 or less using computer software, such as X-PLOR (Yale University, ©1992, distributed by Molecular Simulations, Inc.). See, e.g., Blundell & Johnson, supra; *Meth. Enzymol.*, vol. 114 & 115, H. W. Wyckoff et al., eds., Academic Press (1985). This information may thus be used to optimize known calcineurin inhibitors, and more importantly, to design and synthesize new calcineurin inhibitors.

In another embodiment of this invention is provided a method for preparing a CnA/CnB/FKBP12/FK506 crystal comprising the steps of forming a molecular complex between FKBP12, FK506, calcineurin A and calcineurin B; digesting the molecular complex with a protease that removes the calmodulin binding site and the autoinhibitory domain of calcineurin A; and crystallizing the digested complex.

In another embodiment of this invention is provided a method for preparing a CnA/CnB/FKBP12/FK506 crystal comprising the steps of forming a molecular complex between FKBP12, FK506, calcineurin A and calcineurin B; wherein calcineurin A lacks a calmodulin binding domain and an autoinhibitory domain; and crystallizing the complex.

The autoinhibitory domain of CnA has been mapped to the C-terminal 4 kDa of that polypeptide. The calmodulin binding domain is located adjacent to the autoinhibitory domain and occupies up to 14 kDa. Thus, an N-terminal 43 kDa fragment of CnA lacks both domains [M. J. Hubbard et al., *Biochemistry*, 28, pp. 1868–74 (1989)]. Removal of the calmodulin binding domain and the autoinhibitory domain does not appear to affect the active site or FKBP12/FK506 binding sites, nor the ability of CnA to bind to CnB. Removal of the calmodulin binding site and the autoinhibitory site does, however, provide a complex that provides stable crystals, suitable for analysis by X-ray crystallography.

The removal of the autoinhibitory and calmodulin domains may be carried out either before or after calcineurin is bound to the FKBP12/FK506 complex. Removal of these domains is preferably achieved by proteolytic digestion or through recombinant DNA techniques.

Preferably, the protease is selected from the group consisting of clostripain, trypsin, endoproteinase Lys-C, endoproteinase Asp-N, endoproteinase Glu-C, elastase, enterokinase, restriction protease Factor Xa, thermolysin (Altus Biologics, Cambridge, Mass.), Il-1 beta converting enzyme or HIV-1 protease. Most preferably, the protease is clostripain.

Preferably, the processed CnA subunit in the crystallized complex has a molecular weight of about 42 kDa.

In order that the invention described herein may be more fully understood, the following examples are set forth. It should be understood that these examples are for illustrative purposes only and are not to be construed as limiting this invention in any manner.

EXAMPLE 1

Purification of Calcineurin A/Calcineurin B

Bovine calcineurin was isolated from calf brains (1 year old, or less), essentially as described by Sharma and Wang. (R. K. Sharma et al., *J. Biol. Chem.* 261, pp. 1322–1328 (1986)). This procedure yields a mixed population of calcineurin isozymes and a small proportion of non-calcineurin contaminants. Most of the non-calcineurin contaminants were removed by anion exchange chromatography. The crude calcineurin fraction was exchanged into buffer A (20 mM Tris-HCl, 2 mM β-mercaptoethanol, 1 mM magnesium acetate, 1 mM imidazole, 0.1 mM EGTA, 0.1 mM PMSF, pH 7.6 at 4° C.), by dialysis or ultrafiltration, at a protein concentration of 0.5–2 mg/ml. The protein was loaded onto a column (2.5×20–30 cm) of DEAE-Sepharose (Pharmacia) that had been pre-equilibrated, at 4° C., in the same buffer. After loading the protein, the column was washed with 2–5 column volumes of buffer A, and then the bound proteins were eluted from the column with a linear gradient of 0–300 mM NaCl (10 column volumes), in the same buffer system, at 4° C. The calcineurin, eluting as the main peak, was then fractionated into numerous isoforms by hydrophobic interaction chromatography. The protein was exchanged into buffer B (50 mm Tris-HCl, 1.4 M ammonium sulfate, 5% (v/v) glycerol, 2 mM β-mercaptoethanol, 1 mM EGTA, pH 7.5 at 20° C.), and loaded onto a Hydropore-HIC (Rainin) column (2.0×30 cm) pre-equilibrated in the same buffer. The calcineurin isozymes were eluted at 20° C. with a linear gradient (8 column volumes) from 1.4 M to 0 M ammonium sulfate, keeping the other buffer components constant. The first peak representing about 60% of the total was designated as the "major isoform." The A and B subunits were of this major isoform were separated by reversed phase HPLC and SDS PAGE. Peptide mapping of the fractionated subunits, followed by amino acid sequence analysis of the peptide products, generated internal sequence data for both subunits. When compared with independently determined cDNA sequences (and the deduced amino acid sequences) the experimentally obtained protein sequences indicated that this major isoform consisted of intact, myristoylated calcineurin B, and intact calcineurin A. This protein was concentrated by ultrafiltration and dialyzed into buffer C (25 mM Tris-HCl, 0.1 mM $MnCl_2$, 0.1 mM $CaCl_2$, 2 mM β-mercaptoethanol, pH 8.0 at 4° C.).

EXAMPLE 2

Crystallization of Calcineurin A/Calcineurin B/FKBP12/FK506

A binary complex of recombinant bovine FKBP12 and FK506 was prepared, essentially as described previously [K. P. Wilson et al., *Acta Crystallography*, in press (1995)]. This complex was exchanged into buffer C (25 mM Tris-HCl, 0.1 mM $MnCl_2$, 0.1 mM $CaCl_2$, 2 mM β-mercaptoethanol, pH 8.0 at 4° C.), and then combined with the pure calcineurin major isoform at a molar ratio of 1:1.3 (calcineurin:FKBP/FK506 complex) and a final total protein concentration of 1–2 mg/ml. The calcineurin/FKBP12/FK506 complex was allowed to equilibrate for 1 hour at 4° C., before the addition of clostripain (IUB:4.4.22.8; Worthington) at 3 mg of clostripain per 100 mg of complex. Proteolytic digestion of the complex was allowed to proceed for 3–4 days at 4° C., before the protein was concentrated to 15–20 mg/ml (50–100 mg total protein) by ultrafiltration, and then size-fractionated at 4° C. on a column system of Sephacryl S-300 HR (2.6×100 cm×3) equilibrated in the same buffer (buffer C). The central 90% of the main peak, eluting soon after the void volume, was pooled. The pooled material was analyzed by SDS-polyacrylamide gel electrophoresis, reversed phase HPLC, UV absorption spectroscopy and electrospray mass spectroscopy. In addition, direct N-terminal amino acid sequence analyses were performed on each of the polypeptide components present, and on HPLC-purified peptides from additional proteolytic mapping experiments which generated a range of internally truncated peptides. These analyses indicated that pooled material consisted, predominantly, of intact complex, containing (in approximately 1:1:1:1 stoichiometry):

a) N- and C-terminally truncated calcineurin A (residues 17–392);
b) intact, myristoylated calcineurin B (residues 1–169);
c) intact FKBP12; and
d) FK506.

The added clostripain, unbound FKBP-12/FK506 complex, and the small peptide fragments (generated by clostripain-proteolysis of the calcineurin) eluted later from the size-exclusion column and were discarded.

The proteolytic processing of the complex under these conditions does not give single pure products for either the calcineurin A or the calcineurin B. The product initiation and termination points are all extremely similar, but not identical. For the A chain, cleavage at the N-terminus results in about 95%+of the products beginning at residue 17. Approximately 5% of the products begin at residue 20. The majority of the C-terminal cleavage leaves products that appear to terminate at residue 392, since no evidence was found for other C-terminal termination points. For the calcineurin B, the majority of the products remain N-terminally blocked and, therefore, are still myristoylated, as demonstrated by the crystal structure. A small proportion (perhaps up to 25%) appears to be cleaved between residues 4 (Ala) and 5 (Ser). No evidence was found for C-terminal cleavage of the calcineurin B.

The purified complex was concentrated by ultrafiltration to 25–55 mg/ml, and centrifuged at 40,000×g for 10–15 minutes. Crystals were obtained from these solutions, using hanging drops (initially 8 µL total, 25% precipitant) suspended over a precipitant reservoir of 8% PEG 8000, 0.1 M potassium phosphate, 20 mM β-mercaptoethanol. Crystals appeared within 3–4 days at 4° C., and reached maximal size in about 2–3 weeks. SDS PAGE analysis of the redissolved crystals showed essentially identical protein composition as the original complex solution.

Those of skill in the art will appreciate that the aforesaid crystallization conditions can be varied. Such variations may be used alone or in combination, and include final protein/inhibitor complex concentrations between 5 mg/ml and 35 mg/ml; all combinations of calcineurin/FKBP12/FK506 to precipitant ratios; citrate concentrations between 1 mM and 200 mM; DTT concentrations between 0 mM and 10 mM; and any concentration of β-mercaptoethanol; pH ranges between 5.5 and 9.5; PEG concentrations between 10% and 25% (g/100 ml); PEG weights between 2000 and 8000; $LiSO_4$ concentrations between 50 and 750 mM; HEPES concentrations between 5 and 395 mM; and any concentration or type of detergent; any temperature between −5° C. and 30° C.; and crystallization of calcineurin/FKBP12/FK506 complexes by batch, liquid bridge, or dialysis method using these conditions or variations thereof.

EXAMPLE 3

Crystal Structure of Calcineurin A/Calcineurin B/FKBP12/FK506

Initial heavy atom searches were carried out with crystals stabilized in 50 mM HEPES, pH 7.5, and 12% PEG 8000. Native and heavy atom derivatized crystals were transferred to 50 mM HEPES, pH 7.5, 12% PEG 8000, and 22% glycerol (w/v), and frozen at approximately −165° C. in a dry nitrogen gas stream for data collection. This stabilization process changed the unit cell dimensions to a=89.3 Å, b=92.1 Å, and c=118.5 Å. Two derivatives were obtained under these conditions using di-Ω-iodobis(ethylenediamine)-di-platinum (II) nitrate (PIP), and $Pb(NO_3)_2$, the latter on crystals which had been treated with EGTA to remove $Ca^{++}$ from the metal binding sites on calcineurin B. Native and derivative data sets were collected on frozen crystals by oscillation photography on a Rigaku R-AXIS IIC phosphor imaging area detector mounted on a Rigaku RU200 rotating anode generator (Molecular Structure Corp., Houston, Tex.), operating at 50 kV and 100 mA. Measured intensities were integrated, scaled, and merged using the HKL software package (Z. Otwinowski and W. Minor, personal communication). The native data set was denoted native1 and the two derivative data sets denoted calc 106 (PIP) and calc__149 ($Pb(NO_3)_2$).

Heavy atom positions were located by inspection or with RSPS (Knight, S. Thesis, Swedish Unv. Agricultural Sciences (1989)) and confirmed with difference Fourier syntheses using PHASES (W. Furey et al., *S. Am. Cryst. Assoc. Mtg. Summ.* 18, p. 73 (1990)). Heavy atom parameters were refined with HEAVY (T. C. Terwilliger et al., *Acta Crystallogr.*, *A*39, pp. 813–817 (1983)), and phases computed using either HEAVY or MLPHARE (Z. Otwinowski, ML-PHARE CCP4 Proc. 80–88 (Daresbury Laboratory, Warrington, UK, 1991)). MIR phases were improved and extended by cycles of solvent flattening (B. C. Wang, *Meth. Enzym.* 115, pp. 90–112 (1985)), phase combination using SIGMAA (R. J. Reed, *Acta Crystallogr.*, *A*42, pp. 140–149 (1986), and histogram matching combined with Sayre's equation (K. Y. J. Zhang et al., *Acta Crystallogr.*, *A*46, pp. 377–381 (1990) using the CCP4 crystallographic package (CCP4 (1986), *A Suite of Programs for Protein Crystalloaraphy*, SERC Daresbury Laboratory, Warrington WA4 4WD, England). The molecular model was built into electron density maps using QUANTA (*Quanta version* 4.1, Molecular Simulations Inc., Burlington Mass., 1995), and the model refined with XPLOR-3.1 (A. T. Brunger, *X-PLOR* (*Version* 3.1), Yale Univ., New Haven, (1993)).

Refinement of the PIP and $Pb(NO_3)_2$ derivatives, including the anomalous contribution from the $Pb(NO_3)_2$ derivative gave a figure of merit of 0.53 to 4.6 Å. The resulting MIRAS map was subjected to cycles of solvent flattening, phase combination, and phase extension to produce an electron density map at 4.0 Å. A partial model for calcineurin A and calcineurin B was built into this map, and FKBP12 was positioned into the density as a rigid body. The partial structure was refined against the native1 data, and then refined as a rigid body against a new native data set (denoted native2), from crystals stabilized in 0.1M potassium phosphate, pH 7.5, 12% PEG 8000, and cryoprotected with 0.1M potassium phosphate, pH 7.5, 9% PEG 8000, and 23% ethylene glycol. These conditions yielded yet another cell, with dimensions a=91.3 Å, b=94.4 Å, and c=116.8. Three new derivatives soaked and cryoprotected under the same conditions as native2 were obtained with $HgCl_2$ (calc__158), $Pb(NO_3)_2$ (calc__171), and $K_2PtCl_4$ (calc__170). Heavy atom parameter refinement for these three derivatives against native2 to 3.3 Å gave a final figure of merit of 0.58, including the $Pb(NO_3)_2$ anomalous data. This MIRAS map was again subjected to cycles of solvent flattening/phase extension, and multiple electron density maps were calculated ranging from 3.6 to 2.6 Å resolution. The resulting maps were used to build in approximately 80% of CnA and CnB chains as polyalanine, beginning with the previous model. Multiple rounds of model building, positional refinement, phase combination, and phase extension gave improved electron density maps into which a nearly complete model was built. The positions of the lead, mercury, and platinum heavy atom sites were used to confirm the register of the sequence during building of loops and side chains in the latter stages of model building. A nearly complete model of the CnA/CnB/FKBP12/FK506 complex was subjected to simulated annealing refinement, followed by positional and temperature factor refinement at 2.6 Å. The remainder of the model along with well ordered water molecules was built into $2|F_o|-|F_c|$ and $|F_o|-|F_c|$ difference fourier maps. The current model contains residues 24–240 and 247–370 of calcineurin A, residues 5–82 and 84–168 of calcineurin B, an N-terminal myristoyl group associated with calcineurin B, residues 1–107 of FKBP12, FK506, 4 $Ca^{++}$ ions in the calcineurin B $Ca^{++}$ binding sites, 1 $PO_4^{--}$ group, 1 $Fe^{++}$ ion, and 1 $Zn^{++}$ ion in the calcineurin A active site, and 87 waters. It has been refined using data between 6.0 and 2.5 Å.

EXAMPLE 4

Structural Features of the CnA/CnB/FKBP12/FK506 Crystal

The crystals had an orthorhombic space group symmetry $P_{12_12_1}$. The crystals also had a rectangular shaped unit cell, each unit cell having the dimensions a=90±5 Å, b=94±6 Å, and c=117±5 γ. The crystal comprised four complexes per unit cell, wherein CnA interacts with CnB, FKBP12, and FK506; CnB interacts with CnA, FKBP12, and FK506; FKBP12 interacts with CnA, CnB, and FK506; and FK506 interacts with CnA, CnB, and FKBP12.

The CnA subunit contained a series of amino acids within 8 Å of a phosphate group and two metal ions bound to the active site. These were amino acids 90, 91, 92, 118, 120, 121, 122, 150, 151, 156, 160, 199, 232, 253, 254, 256, 281, 282, 283, 284, 306, 311, 312, and 317, according to FIG. 1. A subset of these, amino acids 90, 91, 92, 118, 120, 121, 122, 150, 151, 156, 160, 281, 282, 283, 306, 311, 199, 232, and 254, where within 5 Å.

The crystal further contained a FKBP12/FK506 binding site made up of CnA amino acids 122, 124, 159, 160, 310, 312, 313, 314, 339, 341, 343, 344, 345, 347, 351, 352, 353, 354, 355, 356, 359, 360, and 363 and CnB amino acids 49, 50, 114, 115, 118, 119, 121, 122, 123, 124, 157, 158, 159, 161, and 162.

The components of the quarternary complex that make up the crystal associated to form a roughly rectangular structure with overall dimensions of 87×61×37 Å. CnA was the largest component of the complex and consisted mainly of a globular domain which contains the phosphatase site. This phosphatase-containing domain was characterized by a β-sandwich motif which formed the core of the enzyme. Perhaps the most striking feature of the quarternary complex was a 22 residue α-helix which extended nearly 40 Å away from the surface of the phosphatase-containing domain and contained the CnB binding helix (BBH). CnB comprised two calmodulin-like domains that, taken together, formed a hydrophobic groove which interacted with the upper surface of the calcineurin binding helix, leaving the underside completely exposed. It is to this exposed region of the BBH that the FKBP12-FK506 complex bound.

Architecture of Calcineurin A

The CnA fragment used in this study contained only the phosphatase domain and the CnB binding region (residues 17–392). Missing from this fragment were the calmodulin binding domain and the autoinhibitory regions. The phosphatase domain formed a compact α/β sandwich while the CnB binding region consisted of a short linker followed by a single α-helix that protruded from the phosphatase domain.

Phosphatase Domain

The phosphatase domain of CnA formed an ellipsoid with approximate dimensions 35 Å×35 Å×45 Å. The core of the domain consisted of two mixed β-sheets, termed sheet 1 and sheet 2, which were flanked on one side by a mixed α/β structure and on the other side by an all α structure. The two central β-sheets formed a distorted β-sandwich which contains an open and closed end. At the closed end of the β-sandwich sheet 2 extended above sheet 1, giving the β-sandwich an overall appearance similar to the greek letter λ. The two sheets formed an angle of approximately 30°, resulting in their gradual separation from closed to open end. The inner core of the β-sandwich was filled almost exclusively with hydrophobic residues, with smaller side chains residing at the closed end of the core and larger, more bulky side chains filling the open end. Strands β6, β10, and β12 from sheet 1 were parallel and ran in the direction of the closed end of the sandwich, as did strands β4, β3, β2, and β14 in sheet 2. Following β14, the sequence formed an extended region covering approximately 24 residues before the start of the BBH. Residues 340–348, while still part of the phosphatase core, participated in multiple contacts with CnB and thus can be considered as part of the CnB binding region. Additional contacts between CnA and CnB occurred at the N-terminus of CnA and in loop L1 where a salt bridge is formed between Glu-53 of CnA and Lys-134 of CnB. These interactions appeared to help stabilize the extended CnB/BBH structure.

The phosphatase active site was located above the closed end of the β-sandwich, formed by the convergence of several loops and by a portion of sheet 2 which extends above the β-sandwich. Residues that formed part of the active site were located in loops L2, L3, L4, and L6 and at the C-termini of strands β2 and β3. The somewhat shallow active site pocket was located in the middle of a larger, curved channel that runs along the top of sheet 1 and helix α9. This channel should accommodate access to the active site by larger, phosphorylated substrates and may help provide specificity through interactions with residues surrounding the phosphorylated side chain of the substrate.

The active site contained two metal ion sites that are modelled as $Zn^{2+}$ and $Fe^{3+}$, as well as a single phosphate ion, whose presence in the structure may be the result of including 100 mM potassium phosphate buffer in the crystallization conditions.

The $Zn^{2+}$ and $Fe^{3+}$ atoms were separated by approximately 3.0 Å in CnA and were identified in the active site on the basis of their interactions with surrounding ligands. The zinc was coordinated by the side chains Asp-118(Oδ2), Asn-150(Oδ1), His-199(Nε2) and His-281(Nδ1), and by a phosphate oxygen. The iron was coordinated by Asp-90 (Oδ1), His-92(Nε2), Asp-118(Oδ2), a phosphate oxygen, and a water molecule.

The bound phosphate, in addition to coordinating both metals, was stabilized by interactions with the guanidinium groups of Arg-122 and Arg-254, and with the Nε2 of His-151. Arg-254 extended down from loop L5, which is fully 8.5 Å away from the phosphate group, and was stabilized through a bidentate interaction with the carboxylate of Asp-234. His-151 was situated in the active site within hydrogen bonding distance of the most solvent exposed phosphate oxygen. Its side chain position was stabilized by a hydrogen bond to Asp-121, while the main chain conformation was stabilized by the next residue, Glu-152, which makes a pair of hydrogen bonds to main chain nitrogens surrounding the metal-bridging ligand, Asp-118.

Calcineurin B Binding Helix

The BBH was a five turn amphipathic α-helix (residues 350–370) to which both CnB and the binary FKBP12-FK506 complex bound. The top half of the BBH was completely non-polar and formed a complementary surface to the hydrophobic groove formed by CnB (see below). The tip of the BBH abutted the N-terminal helix of CnB, which lay perpendicular to the axis of BBH and caps the end of the BBH binding groove. The lower half of the BBH helix was polar except for a small hydrophobic patch near its N-terminus. This patch formed part of the contact surface with the FKBP12-FK506 complex.

Architecture of Calcineurin B

The structure of CnB consisted of two globular calcium-binding domains flanked by a long C-terminal β-strand.

Each calcium-binding domain contained two Ca$^{2+}$-binding EF-hand motifs. Domain 1 (residues 1 to 84) connected to domain 2 (residues 86 to 155) via an α-helix that was kinked at Gly-85. Domains 1 and 2 were arranged linearly along the BBH and, together with the amphipathic C-terminal strand, forms a 33 Å long hydrophobic groove into which the top half of the BBH was embedded.

The three-dimensional structure of each of the pairs of EF-hands (EF1 and EF2 in domain 1, and EF3 and EF4 in domain 2) in CnB was highly conserved with those of other members of the super-family; the intra-domain calcium—calcium distances in CnB were nearly identical to those found in calmodulin, for example. In all four EF hands the Ca$^{2+}$ ion was coordinated by five ligands. These are Asp-30, Asp-32, Ser-34, Glu-41, and the Ser-36 carbonyl oxygen for EF1, Asp-62, Asp-64, Asn-66, Glu-73, and the Gly-68 carbonyl oxygen for EF2, Asp-99, Asp-101, Asp-103, Glu-110 and the Tyr-105 carbonyl oxygen for EF3, and Asp-140, Asp-142, Asp-144, Glu-151 and the Arg-146 carbonyl oxygen for EF4.

The N-terminal glycine of CnB was covalently linked to myristate, a 14 carbon saturated fatty acid. The myristate group was located at the extreme end of the calcineurin complex, near the end of the BBH (FIG. 2). It was connected to the N-terminal helix by a 15 residue loop, and lay against and ran parallel to the N-terminal helix of CnB, which was itself hydrophobic.

Structure of FKBP12-FK506

The conformation of FKBP12 in the ternary complex was nearly identical to that found in the structure of the FKBP12-FK506 binary complex (van Duyne et al., 1991a; Becker et al., 1993; Wilson et al., in press). Superposition of FKBP12 from the ternary and binary complexes gave a root-mean-square (rms) deviation of 0.59 Å for Cα atoms. Similarly, the conformations of FK506 were almost identical in the two complexes, with an rms difference of 0.21 Å for all non-hydrogen atoms, excluding those from the highly flexible C21 allyl group. However, the relative position of FK506 to FKBP12 differed in the ternary and binary complexes. In the ternary complex FK506 was rotated by about 80 from the body of FKBP12, resulting in a displacement of 1.7 Å for the C21 carbon at the base of the allyl group. A concomitant displacement of the His-87 to Ile-90 loop in FKBP12 was observed as well. This rotation allowed the allyl, and to a lesser extent, cyclohexyl moieties of FK506 to more intimately contact the BBH. One consequence of this rotation was the loss of a hydrogen bond between the Glu-54 carbonyl oxygen of FKBP12 and the C24 hydroxyl group of FK506 in the ternary complex.

FKBP12-FK506 Binding to Calcineurin

The FKBP12-FK506 complex bound to calcineurin at the base of the BBH making contacts with the BBH, CnB, and the phosphatase domain of CnA. The solvent accessible surface area lost to each component upon FKBP12-FK506 binding was 320 Å$^2$, 479%$^2$, and 512 Å$^2$. The FKBP12-calcineurin contacts surrounded the FK506 ligand and clustered to three distinct regions of the FKBP12 sequence: His-87 to Ile-90, Asp-37 to Asp-41, and Arg-42 to Phe-46. These regions contacted the BBH, the phosphatase domain, and CnB, respectively.

The principal site of interaction between FK506 and calcineurin was a predominantly hydrophobic cleft located at the interface of CnB and the BBH. Side chains that formed the cleft came from residues Leu-343, Pro-344, Trp-352, Ser-353 (Cβ), and Phe-356 on the BBH and residues Leu-115, Met-118, Val-119 and Leu-123 from CnB. This binding cleft was approximately 8 Å long, and had surface properties complementary to the C15–C21 region of FK506. The majority of contacts made by FK506 were from C15 through C17 and the C21 allyl group. The allyl group extended into a deep pocket within the hydrophobic cleft, making a number of favorable van der Waals contacts with main chain and side chain atoms. The FK506-calcineurin interaction was further stabilized by an unusual bifurcated hydrogen bond between Nε1 of Trp-352 and the C13 and C15 methoxy oxygens of FK506.

FIG. 2 depicts the structure of the calcineurin A, calcineurin B, FKBP12, and FK506 subunits as determined by x-ray crystallography.

EXAMPLE 5

Use of Calcineurin A/Calcineurin B/FKBP12/FK506

The coordinates in FIG. 1 are used to design compounds, including inhibitory compounds, that associate with calcineurin or homologues of calcineurin, directly or through prior complexation with FKBP12 or a FKBP12 homologue. This process may be aided by using a machine-readable data storage medium encoded with a set of machine-executable instructions, wherein the recorded instructions are capable of displaying a three-dimensional representation of the CnA/CnB/FKBP12/FK506 complex or a portion thereof. The graphical representation is used according to the methods described herein to design compounds, including an inhibitory compound, that bind to calcineurin. Such compounds may associate with calcineurin at the active site, the FKBP12/FK506 binding site, or both sites or at adjacent area to either or both of these sites.

FKBP12/FK506 Binding Site Inhibitors

The process outlined above is used to design a compound that inhibit calcineurin by associating with the FKBP12/FK506 binding site. Such a compound binds first to FKBP12 or a variant of FKBP12 and then associates with the FKBP12/FK506 binding site. This compound consists of a hydrophobic moiety capable of making van der Waal's contact with one or more of the following residues on FKBP12: Trp59, Phe46, Tyr26, Val55, Phe99, and Ile56. Substituted onto this hydrophobic core is a hydrogen bond acceptor capable of forming a hydrogen bond with Ile56 on FKBP12 and a second hydrogen bond acceptor or a hydrogen bond donor that can form a hydrogen bond with Tyr82 on FKBP12. The binding core also contains a linker that projects a hydrophobic moiety 10–14 Å from the center of the binding core to make van der Waal's contact with one or more of the following residues: Leu115, Val119, Met118 of CnB and Trp352, Ser353, Phe356 and Val357 on CnA. The binding core also contains a second linker that projects a moiety 7–11 Å from the center of the binding core to make van der Waal's contact with one or more of the following residues: Leu123 on CnB and Leu343, Tyr341, Pro344 and Trp352 on CnA and may optionally act as a hydrogen bond acceptor with Trp352 and/or a hydrogen bond donor or acceptor with Tyr341. The binding core contains a third linker that projects a moiety 8–12 Å from the center of the binding core to make van der Waal's contact with one or more of the following residues: Pro355 and Phe356 and may optionally act as a hydrogen bond donor with Glu359 on CnA. This third linker will also make van der Waal contact with Tyr82, Ile56 and His87 on FKBP12. This molecule contains fewer than three secondary amide bonds and has a molecular weight of less than 1000.

Active Site Inhibitors

In another example, the process outlined above is used to design compounds that inhibit calcineurin by associating directly with the phosphatase active site. Such compounds will contain either a phosphate residue or a surrogate for a phosphate residue and additional functionality that imparts affinity for calcineurin.

The process outlined above could also be used to design compounds that inhibit calcineurin by blocking access to the active site. Examples of clefts in the enzyme that may be blocked are described by the following groups of CnA amino acids, as set forth in FIG. 1:

a) Arg122, Phe125, Asp313, His339, Pro340, Tyr341, Trp342, Phe346, Tyr124, Thr161, Pro344, Phe160 and Asn345;

b) Trp232, Leu231, Pro221, His155, Glu220, Leu156, Cys153, Asn150, Pro222, Cys256, Gly255 and Arg148; and c) Leu302, Pro235, Glu282, Phe239, Tyr291, Gln284, Thr304, Phe259, Leu236, Glu237, Val253, Ala283 and Asp234.

Compounds that make contact primarily with any of these three sets of residues would be active site inhibitors.

EXAMPLE 6

Calcineurin Inhibition Assay

The calcineurin assay is performed essentially as described by Klee and Cohen [C. V. Klee et al., *Mol. Aspects Cell. Regul.*, 5, pp. 225–248 (1988)].

A commercial preparation of bovine brain calcineurin is used (Sigma, Cat# C-1907, specific activity=16 nmol/min/mg under the conditions of the assay). Radiolabeled phosphorylated peptide substrate, derived from the serine phosphorylation site sequence of the RII subunit of cAMP-dependent protein kinase, is prepared as described previously [R. A. Aldape et al., *J. Biol. Chem.* 267, pp. 16029–16032 (1992)].

The serine phosphatase assay is performed in 60 µl buffer containing 20 mM Tris, pH 8.0, 0.1M NaCl, 6 mM $MgCl_2$, 0.1 mM $CaCl_2$, 0.5 mM dithiothreitol, and 0.1 mg/ml bovine serum albumin (C. V. Klee et al, supra). The following ordered additions are made for the assays: 5 nM–15 µM FKBP, 5 nM–15 µM FK506, 160 nM bovine calmodulin (Sigma, Cat# P-277) and 40 nM bovine brain calcineurin. [$^{32}P$]-phosphorylated peptide is added to 1–2 µM final concentration, followed by a 15 min incubation at 30° C. Reactions are quenched with 540 µl 0.1M potassium phosphate/5% trichloracetic acid (w/v). Cation exchange columns (Dowex AG1-X8, 0.6 ml) are used for separation of free [$^{32}P$]-$P_i$ (M. J. Hubbard et al., in *Molecular Neurobiology: A Practical Approach*, J. Chad et al., Eds. (Oxford University Press, Oxford, England) pp. 135–149, 1991). The quenched reaction mixtures (0.6 ml) are applied to the columns, followed by a 0.6 ml $H_2O$ wash, and the effluents are collected in scintillation vials and counted with 5 ml of scintillation cocktail (Beckmann Liquiscint). All assays are performed in duplicate.

Affinity of the FKBP-test ligand complexes for calcineurin is determined by varying the concentrations of FKBP and test ligand at 30° C., using a drug:FKBP ratio of 1.35:1. FK506:test ligand ratios are increased appropriately for the lower affinity ligands to ensure saturation of the FKBP with test ligand.

Data Analysis

The inhibition constant for calcineurin by the FKBP/test ligand complexes ($K_{ic}$) is calculated by computer-fitting the fractional inhibition data as a function of concentration of free FKBP and test ligand to an the equilibrium equation derived by Liu et al [J. Liu, et al., *Biochemistry*, 31, pp. 3896–3901 (1992)]. Quadratic equations are first used to calculate the free concentrations of these reaction components from the concentrations of calcineurin, FKBP and test ligand in the experiment, as well as the $K_i$ of the FKBP for test ligand. The calcineurin affinity of the FKBP/test ligand complex is calculated using the equation: $I/(1-I)=[TestLigand]_{free}[FKBP12]_{free}/(K_i K_{ic})$, where I is the fractional inhibition of calcineurin and (1-I) is the fractional activity remaining. $K_{ic}$ and the associated standard deviation are calculated from the linear regressions performed on MiniTab (Addison-Wesley).

EXAMPLE 7

Immunosuppression (Mitogenesis) Assays Cell Source and Culture

Fresh peripheral blood lymphocytes (PBLs) from Leuko-Pak cells or whole blood from random normal blood donors (tested HIV-negative and hepatitis negative) are isolated and separated by density centrifugation over Histopaque 1077 (Sigma Chemical Co., St. Louis, Mo.). The murine CTLL cytotoxic T cell line and the human Jurkat T cell line are available from ATCC (CTLL-2 ATCC TIB214, JURKAT CLONE E6-1 ATCC TIB152). The human allogeneic B cell lines used for activation of the fresh PBLs are EBV-transformed lymphocytes from normal healthy adult donors with two completely different HLA haplotypes. All cell lines are routinely tested for the presence of Mycoplasma contamination using the Gibco Mycotect test kit and found to be Mycoplasma-free. Culture medium consisted of RPMI 1640 (Gibco, Grand Island, N.Y.) containing penicillin (50 U/ml) and streptomycin (50 µg/ml), L-glutamine 2 mM, 2 mer-captoethanol ($5 \times 10^{-5}$), 10% heat-inactivated FCS and 10 mM HEPES.

Compound Solutions and Titrations

All chemical stocks are dissolved in DMSO. Titrations of compounds are made into the medium the individual assay are carried out in, i.e., complete RPMI or HB 104 for final diluted concentrations, using multiple three-fold dilutions from 1 µM or 10 µM stock solutions.

Mitogenesis Assays ("PMA" and "OKT3")

The inhibitory effect of test compounds on the proliferation of human PBLs in response to mitogens (W. K. Waithe et al., *Handbook of Experimental Immunology*, 3d Ed., Blackwell Scientific Publications, Oxford (1978); B. B. Mishell et al., *Selected Methods in Cellular Immunology*, W. H. Freeman and Co., San Francisco, Calif. (1980)) are assessed by stimulation of $5 \times 10^4$ cells with OKT3 ($10^{-4}$ dilution final) or PMA (10 ng/ml) plus ionomycin (250 ng/ml) in the presence or absence of different concentrations of test compounds and control drugs (CsA, FK506, rapamycin) in final volume of 200 µl per well in 96 well round bottomed plates. After 48 h incubation (37° C., 5% $CO_2$), cells are pulsed with 1 µCi of $^3H$-Leucine, harvested 24 h later with a Tom Tek cell harvester, and counted in LKB β-scintillation counter. Results (cpm) are compared with controls with medium alone, and concentrations causing 50% reduction in counts ($IC_{50}$) are calculated.

While we have described a number of embodiments of this invention, it is apparent that our basic examples may be altered to provide other embodiments which utilize the products and processes of this invention. Therefore, it will be appreciated that the scope of this invention is to be defined by the appended claims rather than by the specific embodiments which have been represented by way of example.

We claim:

1. A method of using a computer for selecting at least one of a plurality of chemical entities based on its ability to associate with all or part of a molecule or molecular complex comprising a calcineurin A (CnA) binding pocket defined by structure coordinates of CnA amino acids 90, 91, 92, 118, 120, 121, 122, 150, 151, 156, 160, 199, 232, 253, 254, 256, 281, 282, 283, 284, 306, 311, 312, and 317 according to FIG. 1;

wherein said computer comprises a machine-readable data storage medium comprising a data storage material encoded with said structure coordinates and wherein said method comprises the steps of:

a) producing a crystal of a molecular complex comprising amino acids 17–392 of CnA and amino acids 1–169 of CnB; intact FKBP12; and FK506;

b) determining the three-dimensional structure coordinates of the molecular complex by X-ray diffraction of the crystal;

c) identifying the structural coordinates of a CnA binding pocket of said molecular complex of CnA amino acids 90, 91, 92, 118, 120, 121, 122, 150, 151, 156, 160, 199, 232, 253, 254, 256, 281, 282, 283, 284, 306, 311, 312, and 317, which coordinates fall within the range of those recited in FIG. 1±a root mean square deviation from the backbone atoms of said amino acids of 1.5 Å and encoding those coordinates on a data storage material;

d) utilizing said structure coordinates defining said CnA binding pocket and the structure coordinates of one of said plurality of chemical entities to position a chemical entity within all or part of the CnA binding pocket;

e) docking said chemical entity with all or part of the CnA binding pocket by employing computational means which utilize said structure coordinates defining said CnA binding pocket and the chemical entity, wherein said docking utilizes energy minimization;

f) analyzing the results of said docking to quantify the association between said chemical entity and all or part of the CnA binding pocket;

g) optionally repeating steps d) through f) with another of said plurality of chemical entities; and h) selecting at least one of said plurality of chemical entities that associates with all or part of the CnA binding pocket based on said quantified association of said chemical entity.

2. A method of using a computer for selecting at least one of a plurality of chemical entities based on its ability to associate with all or part of a molecule or molecular complex comprising a calcineurin A (CnA) binding pocket defined by structure coordinates of CnA amino acids 90, 91, 92, 118, 120, 121, 122, 150, 151, 156, 160, 199, 281, 282, 283, 306, 311, 232, and 254 according to FIG. 1; wherein said computer comprises a machine-readable data storage medium comprising a data storage material encoded with said structure coordinates and wherein said method comprises the steps of:

a) producing a crystal of a molecular complex comprising amino acids 17–392 of CnA and amino acids 1–169 of CnB; intact FKBP12; and FK506;

b) determining the three-dimensional structure coordinates of the molecule or molecular complex by X-ray diffraction of the crystal;

c) identifying a CnA binding pocket of said molecule or molecular complex defined by structure coordinates of CnA amino acids 90, 91, 92, 118, 120, 121, 122, 150, 151, 156, 160, 199, 281, 282, 283, 306, 311, 232, and 254, which coordinates fall within the range of those recited in FIG. 1±a root mean square deviation from the backbone atoms of said amino acids of 1.5 Å and encoding those coordinates on a data storage material;

d) utilizing said structure coordinates defining said CnA binding pocket and the structure coordinates of one of said plurality of chemical entities to position a chemical entity within all or part of the CnA binding pocket;

e) docking said chemical entity with all or part of the CnA binding pocket by employing computational means which utilize said structure coordinates defining said CnA binding pocket and the chemical entity, wherein said docking utilizes energy minimization;

f) analyzing the results of said docking to quantify the association between said chemical entity and all or part of the CnA binding pocket;

g) optionally repeating steps d) through f) with another of said plurality of chemical entities; and h) selecting at least one of said plurality of chemical entities that associates with all or part of the CnA binding pocket based on said quantified association of said chemical entity.

3. A method of using a computer for selecting at least one of a plurality of chemical entities based on its ability to associate with all or part of a molecule or molecular complex comprising a CnA/CnB binding pocket defined by structure coordinates of CnA amino acids 122, 124, 159, 160, 310, 312, 313, 314, 339, 341, 343, 344, 345, 347, 351, 352, 353, 354, 355, 356, 359, 360, and 363; and calcineurin B (CnB) amino acids 49, 50, 114, 115, 118, 119, 121, 122, 123, 124, 157, 158, 159, 161, and 162 according to FIG. 1;

wherein said computer comprises a machine-readable data storage medium comprising a data storage material encoded with said structure coordinates and wherein said method comprises the steps of:

a) producing a crystal of a molecular complex comprising amino acids 17–392 of CnA and amino acids 1–169 of CnB; intact FKBP12; and FK506;

b) determining the three-dimensional structure coordinates of the molecule or molecular complex by X-ray diffraction of the crystal;

c) identifying a CnA/CnB binding pocket of said molecule or molecular complex defined by structure coordinates of CnA amino acids 122, 124, 159, 160, 310, 312, 313, 314, 339, 341, 343, 344, 345, 347, 351, 352, 353, 354, 355, 356, 359, 360, and 363; and calcineurin B (CnB) amino acids 49, 50, 114, 115, 118, 119, 121, 122, 123, 124, 157, 158, 159, 161, and 162, which coordinates fall within the range of those recited in FIG. 1±a root mean square deviation from the backbone atoms of said amino acids of 1.5 Å and encoding those coordinates on a data storage material;

d) utilizing said structure coordinates defining said CnA/CnB binding pocket and the structure coordinates of one of said plurality of chemical entities to position a chemical entity within all or part of the CnA/CnB binding pocket;

e) docking said chemical entity with all or part of the CnA/CnB binding pocket by employing computational means which utilize said structure coordinates defining said CnA/CnB binding pocket and the chemical entity, wherein said docking utilizes energy minimization;
f) analyzing the results of said docking to quantify the association between said chemical entity and all or part of the CnA/CnB binding pocket;
g) optionally repeating steps d) through f) with another of said plurality of chemical entities; and
h) selecting at least one of said plurality of chemical entities that associates with all or part of the CnA/CnB binding pocket based on said quantified association of said chemical entity.

4. A method of using a computer for selecting at least one of a plurality of chemical entities based on its ability to associate with all or part of a molecule or molecular complex comprising a CnA/CnB binding pocket defined by structure coordinates of CnA amino acids 90, 91, 92, 118, 120, 121, 122, 124, 150, 151, 156, 159, 160, 199, 232, 253, 254, 256, 281, 282, 283, 284, 306, 310, 311, 312, 313, 314, 317, 339, 341, 343, 344, 345, 347, 351, 352, 353, 354, 355, 356, 359, 360, and 363; and CnB amino acids 49, 50, 114, 115, 118, 119, 121, 122, 123, 124, 157, 158, 159, 161, and 162 according to Figure;
wherein said computer comprises a machine-readable data storage medium comprising a data storage material encoded with said structure coordinates and wherein said method comprises the steps of:
a) producing a crystal of a molecular complex comprising amino acids 17–392 of CnA and amino acids 1–169 of CnB; intact FKBP12; and FK506;
b) determining the three-dimensional structure coordinates of the molecule or molecular complex by X-ray diffraction of the crystal;
c) identifying a CnA/CnB binding pocket of said molecule or molecular complex defined by structure coordinates of CnA amino acids 90, 91, 92, 118, 120, 121, 122, 124, 150, 151, 156, 159, 160, 199, 232, 253, 254, 256, 281, 282, 283, 284, 306, 310, 311, 312, 313, 314, 317, 339, 341, 343, 344, 345, 347, 351, 352, 353, 354, 355, 356, 359, 360, and 363; and CnB amino acids 49, 50, 114, 115, 118, 119, 121, 122, 123, 124, 157, 158, 159, 161, and 162, which coordinates fall within the range of those recited in FIG. 1±a root mean square deviation from the backbone atoms of said amino acids of 1.5 Å and encoding those coordinates on a data storage material;
d) utilizing said structure coordinates defining said CnA/CnB binding pocket and the structure coordinates of one of said plurality of chemical entities to position a chemical entity within all or part of the CnA/CnB binding pocket;
e) docking said chemical entity with all or part of the CnA/CnB binding pocket by employing computational means which utilize said structure coordinates defining said CnA/CnB binding pocket or structure coordinates of the chemical entity, wherein said docking utilizes energy minimization;
f) analyzing the results of said docking to quantify the association between said chemical entity and all or part of the CnA/CnB binding pocket;
g) optionally repeating steps d) through f) with another of said plurality of chemical entities; and
h) selecting at least one of said plurality of chemical entities that associates with all or part of the CnA/CnB binding pocket based on said quantified association of said chemical entity.

5. The method according to any one of claims 1–4, further comprising the steps of:
i) contacting the selected chemical entity with said molecule or molecular complex; and
j) monitoring the association of the molecule or molecular complex with the selected chemical entity.

6. The method according to any one of claims 1–4, wherein the docking utilizes shape complementarity or is followed by molecular dynamics.

7. The method according to any one of claims 1–4, wherein the docking is performed through visual inspection on a computer screen using a computer program capable of generating a three-dimensional graphical representation of said structure coordinates and structure coordinates of said chemical entity.

8. The method according to any one of claims 1–4, further comprising the steps of:
i) repeating steps d) to h) with a second set of a plurality of chemical entities that associate with all or another part of the binding pocket;
j) optionally, visually inspecting the relationship of the selected first and second chemical entities to each other in relation to the binding pocket on a computer screen using the three-dimensional graphical representation of the binding pocket and said selected first and second chemical entity; and
k) assembling the first and second chemical entities into a compound or complex that associates with all or part of said binding pocket by model building.

* * * * *